United States Patent
Jones et al.

(10) Patent No.: US 11,149,087 B2
(45) Date of Patent: *Oct. 19, 2021

(54) METHODS AND COMPOSITIONS FOR COMBINATION IMMUNOTHERAPY

(71) Applicant: Etubics Corporation, Seattle, WA (US)

(72) Inventors: Frank R. Jones, Seattle, WA (US); Elizabeth Gabitzsch, Seattle, WA (US); Yvette Latchman, Seattle, WA (US); Adrian Rice, Seattle, WA (US)

(73) Assignee: Etubics Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/564,413

(22) PCT Filed: Apr. 20, 2016

(86) PCT No.: PCT/US2016/028496
§ 371 (c)(1),
(2) Date: Oct. 4, 2017

(87) PCT Pub. No.: WO2016/172249
PCT Pub. Date: Oct. 27, 2016

(65) Prior Publication Data
US 2018/0344832 A1    Dec. 6, 2018

Related U.S. Application Data

(63) Continuation-in-part of application No. PCT/US2016/012496, filed on Jan. 7, 2016.

(60) Provisional application No. 62/150,236, filed on Apr. 20, 2015.

(51) Int. Cl.
| | | |
|---|---|---|
| C12N 15/86 | (2006.01) |
| A61K 39/395 | (2006.01) |
| C07K 16/28 | (2006.01) |
| C07K 16/08 | (2006.01) |
| C07K 16/30 | (2006.01) |
| A61K 39/29 | (2006.01) |
| A61K 39/00 | (2006.01) |
| A61K 31/282 | (2006.01) |
| A61K 31/513 | (2006.01) |
| A61K 31/519 | (2006.01) |
| A61K 38/17 | (2006.01) |
| A61K 39/12 | (2006.01) |

(52) U.S. Cl.
CPC ........ *C07K 16/2818* (2013.01); *A61K 31/282* (2013.01); *A61K 31/513* (2013.01); *A61K 31/519* (2013.01); *A61K 38/177* (2013.01); *A61K 38/1774* (2013.01); *A61K 39/00117* (2018.08); *A61K 39/001182* (2018.08); *A61K 39/292* (2013.01); *A61K 39/3955* (2013.01); *C07K 16/081* (2013.01); *C07K 16/3007* (2013.01); *C12N 15/86* (2013.01); *A61K 39/0011* (2013.01); *A61K 39/12* (2013.01); *A61K 2039/505* (2013.01); *A61K 2039/5256* (2013.01); *A61K 2039/545* (2013.01); *A61K 2039/572* (2013.01); *A61K 2039/575* (2013.01); *C07K 2317/76* (2013.01); *C12N 2710/10034* (2013.01); *C12N 2710/10041* (2013.01); *C12N 2710/10043* (2013.01); *C12N 2710/20034* (2013.01); *Y02A 50/30* (2018.01)

(58) Field of Classification Search
CPC combination set(s) only.
See application file for complete search history.

(56) References Cited

U.S. PATENT DOCUMENTS

| | | |
|---|---|---|
| 6,045,802 A | 4/2000 | Schlom et al. |
| 6,057,158 A | 5/2000 | Chamberlain et al. |
| 6,063,622 A | 5/2000 | Chamberlain et al. |
| 6,083,750 A | 7/2000 | Chamberlain et al. |
| 6,348,450 B1 | 2/2002 | Tang et al. |
| 6,451,596 B1 | 9/2002 | Chamberlain et al. |
| 6,544,947 B2 | 4/2003 | Holaday et al. |
| 6,706,693 B1 | 3/2004 | Tang et al. |
| 6,716,823 B1 | 4/2004 | Tang et al. |
| 6,756,038 B1 | 6/2004 | Schlom et al. |
| 7,211,569 B2 | 5/2007 | Neeper et al. |
| 7,410,758 B2 | 8/2008 | Sastry et al. |
| 7,488,482 B2 | 2/2009 | Balloul et al. |
| 7,547,681 B2 | 6/2009 | Scholler et al. |
| 7,662,586 B2 | 2/2010 | Monaci et al. |
| 7,723,096 B2 | 5/2010 | Schlom et al. |
| 7,771,715 B2 | 8/2010 | Schlom et al. |

(Continued)

FOREIGN PATENT DOCUMENTS

| | | |
|---|---|---|
| EP | 1017810 B1 | 5/2004 |
| EP | 1447414 B1 | 6/2007 |

(Continued)

OTHER PUBLICATIONS

Philips et al., "Therapeutic uses of anti-PD-1 and anti-PD-L 1 antibodies", International Immunology, 2015, vol. 27, Iss. 1, pp. 39-46.

(Continued)

*Primary Examiner* — Mindy G Brown
(74) *Attorney, Agent, or Firm* — Sheridan Ross P.C.

(57) ABSTRACT

Methods and compositions for generating immune responses using adenovirus vectors that allow multiple vaccinations or in combination with other therapy and vaccinations in individuals with preexisting immunity to adenovirus are provided.

25 Claims, 63 Drawing Sheets

Specification includes a Sequence Listing.

(56) References Cited

U.S. PATENT DOCUMENTS

| | | | |
|---|---|---|---|
| 7,786,278 | B2 | 8/2010 | Parrington et al. |
| 7,999,071 | B2 | 8/2011 | Schlom et al. |
| 8,012,468 | B2 | 9/2011 | Kim et al. |
| 8,017,590 | B1 | 9/2011 | Berinstein et al. |
| 8,188,244 | B2 | 5/2012 | La et al. |
| 8,207,314 | B2 | 6/2012 | Berinstein et al. |
| 8,298,549 | B2 | 10/2012 | Balint et al. |
| 8,609,395 | B2 | 12/2013 | Schlom et al. |
| 9,248,177 | B2 | 2/2016 | Tang et al. |
| 9,605,276 | B2 | 3/2017 | Jones et al. |
| 2004/0091995 | A1 | 5/2004 | Schlom et al. |
| 2004/0265274 | A1 | 12/2004 | Wei et al. |
| 2005/0037439 | A1 | 2/2005 | Bourner et al. |
| 2006/0104986 | A1 | 5/2006 | Duke et al. |
| 2007/0104685 | A1 | 5/2007 | La et al. |
| 2007/0249043 | A1 | 10/2007 | Mayall |
| 2009/0148400 | A1* | 6/2009 | Singh ............... A61K 39/0011 424/85.1 |
| 2010/0055069 | A1 | 3/2010 | Rooke et al. |
| 2010/0209386 | A1 | 8/2010 | Schlom et al. |
| 2010/0260807 | A1 | 10/2010 | Berinstein et al. |
| 2010/0285065 | A1 | 11/2010 | Parrington et al. |
| 2011/0086061 | A1 | 4/2011 | Robertson et al. |
| 2011/0217332 | A1 | 9/2011 | Colloca et al. |
| 2012/0107347 | A1 | 5/2012 | Hodge et al. |
| 2013/0224144 | A1 | 8/2013 | Balint et al. |
| 2013/0251741 | A1 | 9/2013 | Pietersz et al. |
| 2013/0315941 | A1 | 11/2013 | Franzusoff et al. |
| 2013/0323249 | A1* | 12/2013 | Zhou ............... C07K 16/2818 424/135.1 |
| 2014/0220056 | A1 | 8/2014 | Shishido et al. |
| 2014/0377294 | A1* | 12/2014 | Fueyo-Margareto ............... C07K 14/4748 424/185.1 |
| 2015/0182621 | A1 | 7/2015 | Wu et al. |
| 2015/0232525 | A1 | 8/2015 | Durrant et al. |
| 2015/0352198 | A1 | 12/2015 | Berinstein et al. |
| 2015/0374790 | A1 | 12/2015 | Liu et al. |
| 2016/0076053 | A1 | 3/2016 | Jones et al. |
| 2016/0102122 | A1* | 4/2016 | Sun ............... A61K 38/12 424/278.1 |
| 2016/0159905 | A1* | 6/2016 | Abdiche ............... A61K 39/3955 424/139.1 |
| 2016/0304610 | A1* | 10/2016 | Sazinsky ............... C07K 16/2818 |
| 2016/0317637 | A1 | 11/2016 | Agrawal et al. |
| 2017/0065693 | A1 | 3/2017 | Balint et al. |
| 2017/0065706 | A1 | 3/2017 | Balint et al. |
| 2017/0165341 | A1 | 6/2017 | Jones et al. |
| 2017/0226219 | A1* | 8/2017 | Chang ............... A61K 39/39558 |
| 2018/0187211 | A1 | 7/2018 | Jones et al. |

FOREIGN PATENT DOCUMENTS

| | | |
|---|---|---|
| EP | 1227837 B1 | 5/2008 |
| EP | 1015035 B1 | 1/2009 |
| EP | 2465520 A2 | 6/2012 |
| JP | 2007-518414 | 7/2007 |
| WO | WO-9614876 A1 | 5/1996 |
| WO | WO-0034494 A1 | 6/2000 |
| WO | WO-0208436 A2 | 1/2002 |
| WO | WO-03008649 A1 | 1/2003 |
| WO | WO-2004058157 A2 | 7/2004 |
| WO | WO-2005012527 A1 | 2/2005 |
| WO | WO-2005051991 A2 | 6/2005 |
| WO | WO-2005058937 A2 | 6/2005 |
| WO | WO-2005058950 A2 | 6/2005 |
| WO | WO-2006033672 A2 | 3/2006 |
| WO | WO-2006044923 A2 | 4/2006 |
| WO | WO-2006033672 A3 | 6/2006 |
| WO | WO-2007008780 A2 | 1/2007 |
| WO | WO-2007008780 A3 | 3/2007 |
| WO | WO-2009006479 A2 | 1/2009 |
| WO | WO-2009006479 A3 | 3/2009 |
| WO | WO-2010121180 A1 | 10/2010 |
| WO | WO-2011032119 A1 | 3/2011 |
| WO | WO-2011115914 A1 | 9/2011 |
| WO | WO 2012/019127 | 2/2012 |
| WO | WO 2012/125998 | 9/2012 |
| WO | WO-2013025972 A1 | 2/2013 |
| WO | WO 2014/003853 | 1/2014 |
| WO | WO-2014031178 A1 | 2/2014 |
| WO | WO-2014043518 A1 | 3/2014 |
| WO | WO-2015061416 A2 | 4/2015 |
| WO | WO-2015103602 A1 | 7/2015 |
| WO | WO 2015/123532 | 8/2015 |
| WO | WO-2015127027 A1 | 8/2015 |
| WO | WO-2015157639 A1 | 10/2015 |
| WO | WO-2016007499 A1 | 1/2016 |
| WO | WO-2016112195 A1 | 7/2016 |
| WO | WO-2016172249 A1 | 10/2016 |

OTHER PUBLICATIONS

Extended European Search Report for European Patent Application No. 16783793.9 dated Aug. 29, 2018, 8 pages.

Official Action for U.S. Appl. No. 15/542,005 dated May 22, 2018, 8 pages.

Official Action for U.S. Appl. No. 15/542,005 dated Oct. 29, 2018, 11 pages.

Amalfitano, A. Use of multiply deleted adenovirus vectors to probe adenovirus vector performance and toxicities. Curr Opin Mol Ther. Aug. 2003;5(4):362-6.

Amalfitano, et al. Separating fact from fiction: assessing the potential of modified adenovirus vectors for use in human gene therapy. Curr Gene Ther 2:111-133 (2002).

Amara, et al. A new generation of HIV vaccines. Trends Mol Med 8;489-95 (2002).

Appledorn, et al. (2008) Adenovirus vector-induced innate inflammatory mediators, MAPK signaling, as well as adaptive immune responses are dependent upon both TLR2 and TLR9 in vivo. J Immunol. 181:2134-2144.

Appledorn, et al. (2008) Wild-type adenoviruses from groups A-F evoke unique innate immune responses, of which HAd3 and SAd23 are partially complement dependent. Gene Ther. 15:885-901.

Balint, et al. Extended evaluation of a phase 1/2 trial on dosing, safety, immunogenicity, and overall survival after immunizations with an advanced-generation Ad5 [E1-, E2b-]-CEA (6D) vaccine in late-stage colorectal cancer. Cancer Immunology, Immunotherapy 64.8 (2015): 977-987.

Bangari, et al. (2006) Development of nonhuman adenoviruses as vaccine vectors. Vaccine 24:849-862.

Bangari, et al. Current strategies and future directions for eluding adenoviral vector immunity. Curr Gene Ther. Apr. 2006; 6(2):215-226.

Barjot, et al. Gutted adenoviral vector growth using E1/E2b/E3-deleted helper viruses. J Gene Med 4;480-9 (2002).

Barouch, et al. (2011) International seroepidemiology of adenovirus serotypes 5, 26, 35, and 48 in pediatric and adult populations. Vaccine 29:5203-5209.

Barouch, et al. Adenovirus vector-based vaccines for human immunodeficiency virus type 1. Hum Gene Ther. 16:149-156 (2005).

Barouch, et al. Plasmid chemokines and colony-stimulating factors enhance the immunogenicity of DNA priming-viral vector boosting human immunodeficiency virus type 1 vaccines. J Virol. Aug. 2003;77(16):8729-35.

Barratt-Boyes, et al. Broad cellular immunity with robust memory responses to simian immunodeficiency virus following serial vaccination with adenovirus 5- and 35-based vectors. J Gen Virol 87:.Pt 1 139-149 (2006).

Berinstein, Neil L. Carcinoembryonic antigen as a target for therapeutic anticancer vaccines: a review. Journal of Clinical Oncology, J Clin Oncol. Apr. 15, 2002;20(8):2197-207.

Bewig, et al. (2000) Accelerated titering of adenoviruses. BioTechniques 28:871-873.

Brave, et al. Vaccine delivery methods using viral vectors. Mol Pharm 4:.1 18-32 (2007).

(56) References Cited

OTHER PUBLICATIONS

Campos, et al. (2007) Current advances and future challenges in adenoviral vector biology and targeting. Curr Gene Ther 7:189-204.
Casimiro, et al. Comparative immunogenicity in rhesus monkeys of DNA plasmid, recombinant vaccinia virus, and replication-defective adenovirus vectors expressing a human immunodeficiency virus type 1 gag gene. J Virol. Jun. 2003;77(11):6305-13.
Chamberlain, et al. Packaging cell lines for generating replication-defective and gutted adenoviral vectors. Methods Mol Med 76;153-66 (2003).
Conry, et al. 2000. Human autoantibodies to carcinoembryonic antigen (CEA) induced by a vaccinia-CEA vaccine. Clin Cancer Res 6:34-41.
Co-Pending U.S. Appl. No. 15/542,005, filed Jul. 6, 2017.
Dellorusso, et al. Functional correction of adult mdx mouse muscle using gutted adenoviral vectors expressing full-length dystrophin. Proc Natl Acad Sci U S A. Oct. 1, 2002;99(20):12979-84. Epub Sep. 23, 2002.
Ding, et al. Long-term efficacy after [E1-, polymerase-] adenovirus-mediated transfer of human acid-alpha-glucosidase gene into glycogen storage disease type II knockout mice. Hum Gene Ther 12;955-65 (2001).
Eo, et al. Prime-boost immunization with DNA vaccine: mucosal route of administration changes the rules. J Immunol 166;5473-9 (2001).
European Application No. 16153921.8-1412 Extended Search report dated Jun. 22, 2016.
European search report dated Mar. 28, 2013 for EP Application No. 08781241.8.
Evans, et al. Development of stable liquid formulations for adenovirus-based vaccines. J Pharm Sci. Oct. 2004;93(10):2458-75.
Everett, et al. Liver toxicities typically induced by first-generation adenoviral vectors can be reduced by use of E1, E2b-deleted adenoviral vectors. Hum Gene Ther, 2003. 14(18): p. 1715-26.
Everett, et al. Strain-specific rate of shutdown of CMV enhancer activity in murine liver confirmed by use of persistent [E1(-), E2b(-)] adenoviral vectors. Virology. Jul. 20, 2004; 325(1):96-105.
Fernando, et al. (2010) The T-box transcription factor Brachyury promotes epithelial-mesenchymal transition in human tumor cells. J Clin Invest. 120:533-544.
Gabaglia CR, Sercarz EE, Diaz-De-Durana Y, Hitt M, Graham FL, Gauldie J, and Braciak TA. Life-long systemic protection in mice vaccinated with L. major and adenovirus IL-12 vector requires active infection, macrophages and intact lymph nodes. Vaccine 23:.2 247-257 (2004).
Gabitzch et al. Induction and comparison of SIV immunity in Ad5 naïve and Ad5 immune non-human primates using an Ad5 [E1-, E2b-] based vaccine. Vaccine. Oct. 19, 2011; 29(45):8101-7.
Gabitzsch, et al. (2009) Novel adenovirus type 5 vaccine platform induces cellular immunity aginst HIV-Gag, Pol, Nef despite the presence of Ad5 immunity. Vaccine 27:6394-6398.
Gabitzsch, et al. (2010) Anti-tumor immunity despite immunity to adenovirus using a novel adenoviral vector Ad5 [E1-, E2b-]-CEA. Cancer Immunol Immunother 59:1131-1135.
Gabitzsch, et al. (2011) Induction and Comparison of SIV immunity in Ad5 Naïve and Ad5 Immune Non-human Primates using an Ad5 [E1-, E2b-] based vaccine. Vaccine 29:8101-8107.
Gabitzsch, et al. (2011) New Recombinant Ad5 Vector Overcomes Ad5 Immunity Allowing for Multiple Safe, Homologous Immunizations. J Clin Cell Immunol. S4:001. doi:10.4172/2155-9899.S4-001.
Gabitzsch, et al. (2012) Control of SIV infection and subsequent induction of pandemic H1N1 immunity in rhesus macaques using an Ad5 [E1-, E2b-] vector platform. Vaccine 2012; 30:7265-7270.
Gabitzsch, et al. A preliminary and comparative evaluation of a novel Ad5 [E1-, E2b-] recombinant-based vaccine used to induce cell mediated immune responses. Immunol Lett. Jan. 29, 2009;122(1):44-51. doi: 10.1016/j.imlet.2008.11.003. Epub Dec. 13, 2008.
Gabitzsch, et al. An Ad5 [E1-, E2b-]-HER2/neu vector induces immune responses and inhibits HER2/neu expressing tumor progression in Ad5 immune mice. Cancer Gene Ther. May 2011; 18(5):326-335.
Gabitzsch, et al. New Recombinant Ad5 Vector Overcomes Ad5 Immunity Allowing for Multiple Safe, Homologous Immunizations. J Clin Cell Immunol. 2011; S4-001.
Gabitzsch, et al. The generation and analyses of a novel combination of recombinant adenovirus vaccines targeting three tumor antigens as an immunotherapeutic. Oncotarget. Oct. 13, 2015; 6(31): 31344-31359.
Gao et al. Protection of mice and poultry from lethal H5N1 avian influenza virus through adenovirus-based immunization. J Virol, 2006. 80(4): p. 1959-64.
Garnett, et al. TRICOM vector based cancer vaccines. Curr Pharm Des. 2006;12(3):351-61.
Gomez-Roman, et al. Adenoviruses as vectors for HIV vaccines. AIDS Rev 5;178-85 (2003).
Gulley, et al. (2008) Pilot study of vaccination with recombinant CEA-MUC-1-TRICOM poxviral-based vaccines in patients with metastatic carcinoma. Clin Cancer Res. 14:3060-3069.
Haglund, et al. Robust recall and long-term memory T-cell responses induced by prime-boost regimens with heterologous live viral vectors expressing human immunodeficiency virus type 1 Gag and Env proteins. J Virol 76;7506-17 (2002).
Hamilton, et al. (2012) Cancer vaccines targeting the epithelial mesenchymal transition: Tissue distribution of Brachyury and other drivers of the mesenchymal-like phenotype of carcinomas. Sem Oncol. 39:358-366.
Harris, et al. (2002) Acute Regression of Advanced and Retardation of Early Aortic Atheroma in Immunocompetent Apolipoprotein-E (Apoe) Deficient Mice by Administration of a Second Generation [E1 (-), E3(-), Polymerase(-)] Adenovirus Vector Expressing Human Apoe. Human Molecular Genetics 11:43-58.
Hartigan-O'Connor, et al. Developments in gene therapy for muscular dystrophy. Microsc Res Tech 48;223-38 (2000).
Hartigan-O'Connor, et al. Efficient rescue of gutted adenovirus genomes allows rapid production of concentrated stocks without negative selection. Hum Gene Ther. Mar. 1, 2002;13(4):519-31.
Hartigan-O'Connor, et al. Generation and growth of gutted adenoviral vectors. Methods Enzymol 346;224-46 (2002).
Hartigan-O'Connor, et al. Immune evasion by muscle-specific gene expression in dystrophic muscle. Mol Ther. Dec. 2001;4(6):525-33.
Hartman, et al. (2008) Adenovirus vector induced innate immune responses: impact upon efficacy and toxicity in gene therapy and vaccine applications. Virus Res 132:1-14.
Hartman, et al. Adenoviral infection induces a multi-faceted innate cellular immune response that is mediated by the toll-like receptor pathway in A549 cells. Virology. Feb. 20, 2007;358(2):357-72. Epub Oct. 5, 2006.
Hartman, et al. Adenovirus infection triggers a rapid, MyD88-regulated transcriptome response critical to acute-phase and adaptive immune responses in vivo. J Virol. Feb. 2007;81(4):1796-812. Epub Nov. 22, 2006.
Harui, et al. 2004. Vaccination with helper-dependent adenovirus enhances the generation of transgene-specific CTL. Gene Ther 11:1617-1626.
Hauser, et al. Analysis of muscle creatine kinase regulatory elements in recombinant adenoviral vectors. Mol Ther 2;16-25 (2000).
Heery, et al. (2014) NCI experience using yeast-Brachyury vaccine (GI-6301) in patients with advanced chordoma. J Clin Oncol. 32:abstract 3081.
Heery, et al. Phase I trial of a yeast-based therapeutic cancer vaccine (GI-6301) targeting the transcription factor brachyury. Cancer Immunol Res. Nov. 2015; 3(11): 1248-1256.
Hirschowitz, et al. 2000. Murine dendritic cells infected with adenovirus vectors show signs of activation. Gene Ther 7:1112-1120.
Hodges, et al. (2000) Multiply deleted [E1, polymerase-, and pTP-] adenovirus vector persists despite deletion of the preterminal protein. J Gene Med 2:250-259.

(56) References Cited

OTHER PUBLICATIONS

Hodges, et al. Adenovirus vectors with the 100K gene deleted and their potential for multiple gene therapy applications. J Virol. Jul. 2001;75(13):5913-20.
Hoelscher, et al. Development of adenoviral-vector-based pandemic influenza vaccine against antigenically distinct human H5N1 strains in mice. Lancet, 2006. 367(9509): p. 475-81.
Hollingsworth, et al. (2004) Mucins in cancer: protection and control of the cell surface. Nat Rev Cancer 4:45-60.
Horig, et al. 2000. Phase I clinical trial of a recombinant canarypoxvirus (ALVAC) vaccine expressing human carcinoembryonic antigen and the B7.1 co-stimulatory molecule. Cancer Immunol Immunother 49:504-514.
Huang Chun-Ming et al. A differential proteome in tumors suppressed by an adenovirus-based skin patch vaccine encoding human carcinoembryonic antigen. Proteomics, 5(4); 1013-1023 (Mar. 2005).
International Application No. PCT/US2016/012496 International Search Report and Written Opinion dated Apr. 12, 2016.
International preliminary report on patentability dated Oct. 24, 2017 for PCT Application No. PCT/US2016/028496.
International search report and written opinion dated Jan. 7, 2014 for PCT Application No. US2013/032688.
International search report and written opinion dated Oct. 3, 2016 for PCT Application No. PCT/US16/28496.
International search report and written opinion dated Dec. 29, 2008 for PCT/US2008/068924.
Jochems, et al. (2013) Identification and characterization of agonist epitopes of the MUC1-C oncoprotein. Cancer Immunol Immunother. 63:161-174.
Jones, et al. Prevention of influenza virus shedding and protection from lethal H1N1 challenge using a consensus 2009 H1N1 HA and NA adenovirus vector vaccine. Vaccine. Sep. 16, 2011; 29(40): 7020-7026.
Jonuleit, et al. 2000. Efficient transduction of mature CD83+ dendritic cells using recombinant adenovirus suppressed T cell stimulatory capacity. Gene Ther 7:249-254.
Joshi, et al. (2009) Adenovirus DNA polymerase is recognized by human CD8+ T cells. J Gen Virol 90:84-94.
Kaufman, et al. (2004) Phase II randomized study of vaccine treatment of advanced prostate cancer (E7897): A trial of the Eastern Cooperative Oncology Group. J Clin Oncol 22:2122-2132.
Kawano, et al. (2007) MUC1 oncoprotein regulates Bcr-Abl stability and pathogenesis in chronic myelogenous leukemia cells. Cancer Res. 67:11576-11584.
Khanam, et al. An adenovirus prime/plasmid boost strategy for induction of equipotent immune responses to two dengue virus serotypes. BMC Biotechnol 7:.1-11 (2007).
Kiang et al. Fully deleted Ad persistently expressing GAA accomplishes long-term skeletal muscle glycogen correction in tolerant and nontolerant GSD-II mice. Mol Ther, 2006. 13(1):127.
Kiang, et al. Multiple innate inflammatory responses induced after systemic adenovirus vector delivery depend on a functional complement system. Mol Ther. Oct. 2006;14(4):588-98. Epub Jun. 2, 2006.
Kilic, et al. (2011) Brachyury expression predicts poor prognosis at early stages of colorectal cancer. Eur J Cancer 47:1080-1085.
Kirk, et al. Gene-modified dendritic cells for use in tumor vaccines. Hum Gene Ther 11;797-806 (2000).
Kong, et al. Immunogenicity of multiple gene and clade human immunodeficiency virus type 1 DNA vaccines. J Virol. 77:12764-72 (2003).
Kufe, DW. (2009) Functional targeting of the MUC1 oncogene in human cancers. Cancer Biol Ther. 8:1197-1203.
Lauer, et al. Natural variation among human adenoviruses: genome sequence and annotation of human adenovirus serotype 1. J Gen Virol. Sep. 2004;85(Pt 9):2615-25.
Lemiale et al., Enhanced mucosal immunoglobulin A response of intranasal adenoviral vector human immunodeficiency virus vaccine and localization in the central nervous system. J Virol., 77 (2003): 10078-87.

Letvin, et al. Heterologous envelope immunogens contribute to AIDS vaccine protection in rhesus monkeys. J Virol. 78;7490-7 (2004).
Limacher, et al. (2012) TG4010: A therapeutic vaccine against MUC1 expressing tumors. OncoImmunology 1:791-792.
Lozier, et al. Toxicity of a first-generation adenoviral vector in rhesus macaques. Hum Gene Ther 13;113-24 (2002).
Lubaroff, et al. Clinical protocol: phase I study of an adenovirus/prostate-specific antigen vaccine in men with metastatic prostate cancer. Hum Gene Ther. 17:220-229 (2006).
Luebke, et al. (2001) A Modified Adenovirus Can Transfect Cochlear Hair Cells In Vivo Without Compromising Cochlear Function. Gene Ther. 8:789-794.
Maione, et al. An improved helper-dependent adenoviral vector allows persistent gene expression after intramuscular delivery and overcomes preexisting immunity to adenovirus. Proc Natl Acad Sci U S A. May 22, 2001;98(11):5986-91. Epub May 15, 2001.
Maione, et al. Prolonged expression and effective readministration of erythropoietin delivered with a fully deleted adenoviral vector. Hum Gene Ther. Apr. 10, 2000;11(6):859-68.
Marshall, et al. 2000. Phase I study in advanced cancer patients of a diversified prime-and-boost vaccination protocol using recombinant vaccinia virus and recombinant nonreplicating avipox virus to elicit anti-carcinoembryonic antigen immune responses. J Clin Oncol 18:3964-3973.
Marshall, et al. Phase I study of sequential vaccinations with fowlpox-CEA(6D)-TRICOM alone and sequentially with vaccinia-CEA(6D)-TRICOM, with and without granulocyte-macrophage colony-stimulating factor, in patients with carcinoembryonic antigen-expressing carcinomas. J Clin Oncol. Feb. 1, 2005;23(4):720-31. Epub Dec. 21, 2004.
McCoy, et al. Effect of preexisting immunity to adenovirus human serotype 5 antigens on the immune responses of nonhuman primates to vaccine regimens based on human- or chimpanzee-derived adenovirus vectors. J Virol. Jun. 2007;81(12):6594-604. Epub Apr. 11, 2007.
McDermott, et al. Cytotoxic T-Lymphocyte Escape Does Not Always Explain the Transient Control of Simian Immunodeficiency Virus SIVmac239 Viremia in Adenovirus-Boosted and DNA-Primed Mamu-A*01-Positive Rhesus Macaques. J Virol. 79:15556-66 (2005).
Miller, et al. 2000. Intratumoral administration of adenoviral interleukin 7 gene-modified dendritic cells augments specific antitumor immunity and achieves tumor eradication. Hum Gene Ther 11:53-65.
Mohebtash, et al. A pilot study of MUC-1/CEA/TRICOM poxviral-based vaccine in patients with metastatic breast and ovarian cancer. Clin Cancer Res. Nov. 15, 2011;17(22):7164-73. doi: 10.1158/1078-0432.CCR-11-0649. Epub Nov. 8, 2011.
Moore, et al. Progress in DNA-based heterologous prime-boost immunization strategies for malaria. Immunol Rev. 199:126-143 (2004).
Moore, et al. Effects of antigen and genetic adjuvants on immune responses to human immunodeficiency virus DNA vaccines in mice. J Virol 76;243-50 (2002).
Morelli, et al. 2000. Recombinant adenovirus induces maturation of dendritic cells via an NF-kappaB-dependent pathway. J Virol 74:9617-9628.
Morral, et al. Lethal toxicity, severe endothelial injury, and a threshold effect with high doses of an adenoviral vector in baboons. Hum Gene Ther 13;143-54 (2002).
Morse, et al. (2005) Phase I study of immunization with dendritic cells modified with recombinant fowlpox encoding carcinoembryonic antigen and the triad of costimulatory molecules CD54, CD58, and CD80 in patients with advanced malignancies. Clin Cancer Res 11:3017-3024.
Morse, et al. (2013) A randomized Phase II study of immunization with dendritic cells modified with poxvectors encoding CEA and MUC1 compared with the same poxvectors plus GM-CSF for resected metastatic colorectal cancer. Ann Surg. 258:879-886.
Morse, et al. (2013) Novel Adenoviral Vector Induces T Cell Responses Despite Anti-Adenoviral Neutralizing Antibodies in Colorectal Cancer Patients. Cancer Immunol Immunother. 62:1293-1301.
Morse, et al. Effect of the vaccine Ad5 [E1-, E2b-]-CEA(6D) on CEA-directed CMI responses in patients with advanced CEA-

(56) References Cited

OTHER PUBLICATIONS expressing malignancies in a phase I/II clinical trial. Etubics Corporation, Seattle, WA. Poster. 2012. http://www.etubics.com/pdf/ASCO%202012.pdf.
Nazir, et al. Innate immune response to adenovirus. J Investig Med. Sep. 2005;53(6):292-304.
Nemunaitis, et al. Pilot trial of intravenous infusion of a replication-selective adenovirus (ONYX-015) in combination with chemotherapy or IL-2 treatment in refractory cancer patients. Cancer Gene Ther. 10:341-352 (2003).
Nwanegbo, et al. (2004) Prevalence of neutralizing antibodies to adenoviral serotypes 5 and 35 in the adult populations of The Gambia, South Africa, and the United States. Clin Diagn Lab Immunol 11:351-357.
Oh, et al. Dendritic cells transduced with recombinant adenoviruses induce more efficient anti-tumor immunity than dendritic cells pulsed with peptide. Vaccine, 24; 2860-2868 (2006).
Ojima et al. Successful cancer vaccine therapy for carcinoembryonic antigen (CEA)-expressing colon cancer using genetically modified dendritic cells that express CEA and T helper-type 1 cytokines in CEA transgenic mice, International Journal of Cancer 120(3), 585-593 (2006).
Osada, et al. (2009) Optimization of vaccine responses with an E1, E2b and E3-deleted Ad5 vector circumvents pre-existing anti-vector immunity. Cancer Gene Ther 16:673-682.
Osada, et al. Optimization of vaccine responses with an E1, E2b and E3-deleted Ad5 vector circumvents pre-existing anti-vector immunity. Cancer Gene Ther.vol. 16, Issue No. 9, pp. 673-682 (Sep. 2009).
Palena, et al. (2007) The human T-box mesodermal transcription factor brachyury is a candidate target for T-cell mediated cancer immunotherapy. Clin Cancer Res. 13:2471-2478.
Perkins, et al. Boosting with an adenovirus-based vaccine improves protective efficacy against Venezuelan equine encephalitis virus following DNA vaccination. Vaccine. 2006; 24:3440-5.
Etubics press release. Etubics and Duke Cancer Institute report positive phase I/II results for colorectal cancer immunotherapy. Etubics corporation. Seattle (May 16, 2012). URL:<http://etubics.com/etubics-and-duke-cancer-institute-report-positive-phase-iii-results-for-colorectal-cancer-immunotherapy/>.
Phillpotts, et al. Intranasal immunization with defective adenovirus serotype 5 expressing the Venezuelan equine encephalitis virus E2 glycoprotein protects against airborne challenge with virulent virus. Vaccine 23:1615-1623. (2005).
Qualikene, et al. Protease-deleted adenovirus vectors and complementing cell lines: potential applications of single-round replication mutants for vaccination and gene therapy. Human Gene Therapy Jun. 10, 2000;11(9):1341-53.
Ramlau, et al. (2008) A phase II study of Tg4010 (Mva-Muc1-II2) in association with chemotherapy in patients with stage III/IV Non-small cell lung cancer. J Thorac Oncol. 3:735-744.
Reddy, et al. Sustained human factor VIII expression in hemophilia A mice following systemic delivery of a gutless adenoviral vector. Mol Ther. Jan. 2002;5(1):63-73.
Rice, et al. An HPV-E6/E7 immunotherapy plus PD-1 checkpoint inhibition results in tumor regression and reduction in PD-L1 expression. Cancer Gene Therapy 22, 454-462 (Sep. 2015).
Roberts, et al. Hexon-chimaeric adenovirus serotype 5 vectors circumvent pre-existing anti-vector immunity. Nature, 2006. 441(7090):239-43.
Sandig, et al. Optimization of the helper-dependent adenovirus system for production and potency in vivo. Proc Natl Acad Sci U S A. Feb. 1, 2000;97(3):1002-7.
Santosuosso, et al. Mucosal luminal manipulation of T cell geography switches on protective efficacy by otherwise ineffective parenteral genetic immunization. J Immunol 178:.4 2387-395 (2007).
Sarkar, et al. (2012) BRACHYURY confers cancer stem cell characteristics on colorectal cancer cells. Int J Cancer 130:328-337.
Schaack, et al. E1A and E1B proteins inhibit inflammation induced by adenovirus. Proc Natl Acad Sci U S A. Mar. 2, 2004;101(9):3124-9. Epub Feb. 19, 2004.
Schaack. Induction and inhibition of innate inflammatory responses by adenovirus early region proteins. Viral Immunol. 2005;18(1):79-88.
Scott, et al. Gutted adenoviral vectors for gene transfer to muscle. Methods Mol Biol 219;19-28 (2003).
Scott et al. Viral vectors for gene transfer of micro-, mini-, or full-length dystrophin. Neuromuscul. Disord. 12(Suppl 1):S23-9 (2002).
Seregin, et al. (2009) Overcoming pre-existing Adenovirus immunity by genetic engineering of Adenovirus-based vectors. Expert Opin Biol Ther 9(12): 1521-1531.
Shiver, et al. Recent advances in the development of HIV-1 vaccines using replication-incompetent adenovirus vectors. Annu Rev Med. 55;355-72 (2004).
Shiver, et al. 2002. Replication-incompetent adenoviral vaccine vector elicits effective anti-immunodeficiency-virus immunity. Nature 415:331-335.
Slack, et al. 2001. Association between CEA-specific T cell responses following treatment wiht vaccinia CEA and survival in patients with CEA bearing cancers (abstr 1086). In Proc Am Soc Clin Oncol 272a.
Morse, et al. Synergism from combined immunologic and pharmacologic inhibition of HER2 in vivo. Int J Cancer 126(12):2893-2903 (2010). First published online Oct. 23, 2009. URL:<https://doi.org/10.1002/ijc.24995>.
Rice, et al. An HPV-E6/E7 immunotherapy plus PD-1 checkpoint inhibition results in tumor regression and reduction in PD-L1 expression (Poster Presentation). Journal for ImmunoTherapy of Cancer 3(Suppl 2):P449 (2015).
Steel, et al. Interleukin-15 and its Receptor Augment Dendritic Cell Vaccination Against the neu Oncogene Through the Induction of Antibodies Partially Independent of CD4-help. Cancer Res. Feb. 1, 2010; 70(3): 1072.
Sullivan, et al. Development of a preventive vaccine for Ebola virus infection in primates. Nature 408;605-9 (2000).
Sumida, et al. Neutralizing antibodies and CD8+ T lymphocytes both contribute to immunity to adenovirus serotype 5 vaccine vectors. J Virol. Mar. 2004;78(6):2666-73.
Tatsis, et al. (2004) Adenoviruses as vaccine vectors. Molecular Ther 10:616-629.
Tatsis, et al. A CD46-binding Chimpanzee Adenovirus Vector as a Vaccine Carrier. Mol Ther (2007).
Thomas, et al. Peripheral infection with adenovirus causes unexpected long-term brain inflammation in animals injected intracranially with first-generation, but not with high-capacity, adenovirus vectors: toward realistic long-term neurological gene therapy for chronic diseases. Proc Natl Acad Sci U S A 97;7482-7 (2000).
Thorner, et al. Immunogenicity of heterologous recombinant adenovirus prime-boost vaccine regimens is enhanced by circumventing vector cross-reactivity. J Virol. Dec. 2006;80(24):12009-16. Epub Oct. 11, 2006.
Tillman, et al. 2000. Adenoviral vectors targeted to CD40 enhance the efficacy of dendritic cell-based vaccination against human papillomavirus 16-induced tumor cells in a murine model. Cancer Res 60:5456-5463.
Tsang, et al. (2004) A human cytotoxic T-lymphocyte epitope and its agonist epitope from the nonvariable number of tandem repeat sequence of MUC-1. Clin Cancer Res. 10:2139-2149.
Tucker, et al. (2014) Identification and characterization of a cytotoxic T-lymphocyte agonist epitope of brachyury, a transcription factor involved in epithelial to mesenchymal transition and metastasis. Cancer Immunol Immunother. 63:1307-1317.
Van Cutsem, et al. (2007) Open-label Phase III trial of panitumumab plus best supportive care compared with best supportive care alone in patients with chemotherapy-refractory metastatic colorectal cancer. J Clin Oncol 25:1658-1664.
Van Kampen, et al. Safety and immunogenicity of adenovirus-vectored nasal and epicutaneous influenza vaccines in humans. Vaccine, 2005. 23(8): p. 1029-36.

(56) References Cited

OTHER PUBLICATIONS

Varnavski, et al. Evaluation of toxicity from high-dose systemic administration of recombinant adenovirus vector in vector-naive and pre-immunized mice. Gene Ther 12:.5 427-436.(2005).
VaxGen I. VaxGen Announces Initial Results of its Phase III AIDS Vaccine Trial. http://www.corporate-ir.net/ireye/ir_site.zhtml?ticker=VXGN&script=410&layout=-6&item_id=385014. Accessed Jul. 14, 2003.
Vergati, et al. (2010) Strategies for cancer vaccine development. J Biomed Biotechnol 2010. pii: 596432.
Von Mehren, et al. 2000. Phase I study of vaccine therapy with ALVAC-CEA B7.1 and GM-CSF in patients with advanced CEA-expressing cancers (abstr 1883). In Proc Am Soc Clin Oncol 480a.
Von Mehren, et al. 2000. Pilot study of a dual gene recombinant avipox vaccine containing both carcinoembryonic antigen (CEA) and B7.1 transgenes in patients with recurrent CEA-expressing adenocarcinomas. Clin Cancer Res 6:2219-2228.
Von Mehren, et al. 2001. The influence of granulocyte macrophage colony-stimulating factor and prior chemotherapy on the immunological response to a vaccine (ALVAC-CEA B7.1) in patients with metastatic carcinoma. Clin Cancer Res 7:1181-1191.
Wang, et al. Episomal segregation of the adenovirus enhancer sequence by conditional genome rearrangement abrogates late viral gene expression. J Virol. 2000; 74:11296-303.
Ward, et al. *E. coli* expression and purification of human and cynomolgus IL-15. Protein Expr Purif. Nov. 2009;68(1):42-8. doi: 10.1016/j.pep.2009.05.004. Epub May 10, 2009.
Weaver, et al. Comparison of replication-competent, first generation, and helper-dependent adenoviral vaccines. PLoS One. 2009;4(3):e5059. doi: 10.1371/journal.pone.0005059. Epub Mar. 31, 2009.
Wieking, et al. (2012) A non-oncogenic HPV 16 E6/E7 vaccine enhances treatment of HPV expressing tumors. Cancer Gene Ther. 2012; 19:667-674.
Yang, et al. Overcoming immunity to a viral vaccine by DNA priming before vector boosting. J Virol. Jan. 2003; 77(1): 799-803.
Yin, et al. (2010) Survival of human multiple myeloma cells is dependent on MUC1 C-terminal transmembrane subunit oncoprotein function. Mol Pharmacol. 78:166-174.
Yin, et al. (2011) MUC1-C Oncoprotein Blocks Terminal Differentiation of Chronic Myelogenous Leukemia Cells by a ROS-Mediated Mechanism. Genes Cancer 2:56-64.
Zhao, et al. Enhanced cellular immunity to SIV Gag following co-administration of adenoviruses encoding wild-type or mutant HIV Tat and SIV Gag. Virology 342:.1 1-12 (2005).
Zhi, et al. Efficacy of severe acute respiratory syndrome vaccine based on a nonhuman primate adenovirus in the presence of immunity against human adenovirus. Hum Gene Ther 17:.5 500-06 (2006).
Zhu, et al. (2000) Specific cytolytic T-cell responses to human CEA from patients immunized with recombinant avipox-CEA vaccine. Clin. Cancer Res. 6:24-33.
EP16735415.8 Extended European Search Report dated May 14, 2018.
Tanaka et al., "Adenovirus-mediated Prodrug Gene Therapy for Carcinoembryonic Antigen-producing Human Gastric Carcinoma Cells in Vitro," Cancer Research, 1996, vol. 56, Iss. 6, pp. 1341-1345.
Official Action for U.S. Appl. No. 15/542,005 dated Mar. 8, 2019, 11 pages.
Official Action for U.S. Appl. No. 15/542,005 dated Sep. 5, 2019, 12 pages.
Official Action for European Patent Application No. 16783793.9 dated Oct. 1, 2019, 4 pages.
Hamilton et al., "Immunological targeting of tumor cells undergoing an epithelial-mesenchymal transition via a recombinant brachyury-yeast vaccine", Oncotarget, 2013, vol. 4, No. 10, pp. 1777-1790.
Official Action (with English translation) for Chinese Patent Application No. 201680014846.8 dated Feb. 21, 2020, 21 pages.
Official Action (with English translation) for Korean Patent Application No. 10-2017-7022200 dated May 13, 2020, 8 pages.
Official Action for U.S. Appl. No. 15/542,005 dated Dec. 12, 2019, 11 pages.
Examiner's Answer for U.S. Appl. No. 15/542,005 dated Jul. 2, 2020, 12 pages.
Official Action (with English translation) for Israeli Patent Application No. 253341 dated Apr. 28, 2021 9 pages.
Official Action for Canadian Patent Application No. 2,974,237 dated Mar. 30, 2021, 4 pages.
Official Action for European Patent Application No. 16735415.8 dated Jul. 28, 2020, 4 pages.
Official Action (with English translation) for Israeli Patent Application No. 253341 dated Jul. 28, 2020. 7 pages.
Official Action (with English translation) for Australian Patent Application No. 2016205215 dated Feb. 9, 2021, 4 pages.
Official Action (with English translation) for Chinese Patent Application No. 201680014846.8 dated Nov. 6, 2020, 19 pages.
Notice of Allowance (with English machine translation) for Korean Patent Application No. 10-2017-7022200 dated Sep. 29, 2020, 10 pages.
Official Action for European Patent Application No. 16783793.9 dated Jul. 28, 2020, 4 pages.
Official Action for European Patent Application No. 16735415.8 dated Apr. 21, 2021, 3 pages.
Official Action for European Patent Application No. 16783793.9 dated Apr. 23, 2021, 7 pages.
Official Action for European Patent Application No. 16735415.8 dated Sep. 30, 2019, 5 pages.
Decision on Appeal for U.S. Appl. No. 15/542,005 dated Aug. 12, 2021, 10 pages.

* cited by examiner

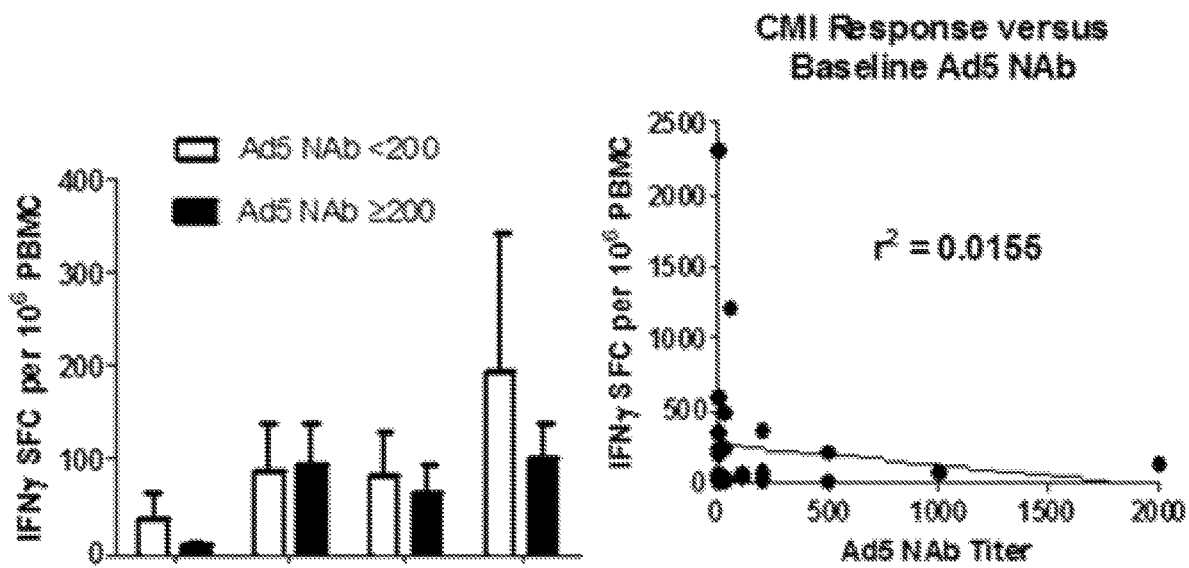
FIG. 17A
FIG. 17B
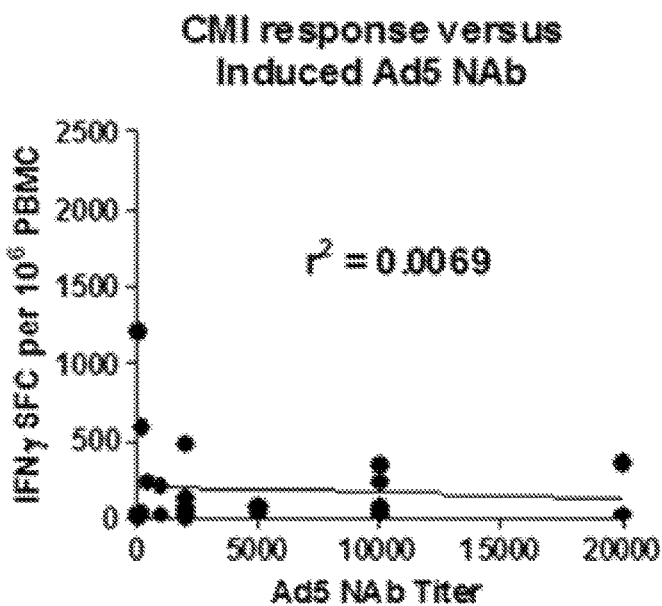
FIG. 17C

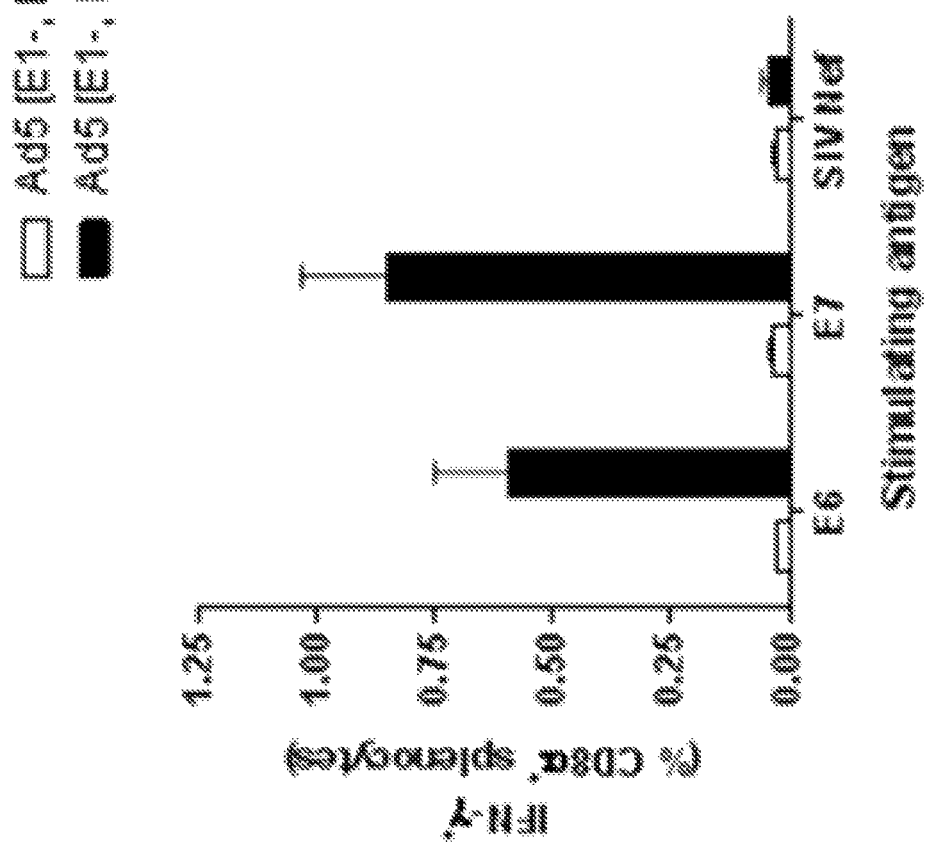
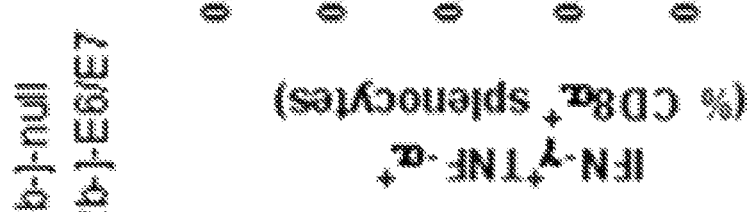
FIG. 37A
FIG. 37B

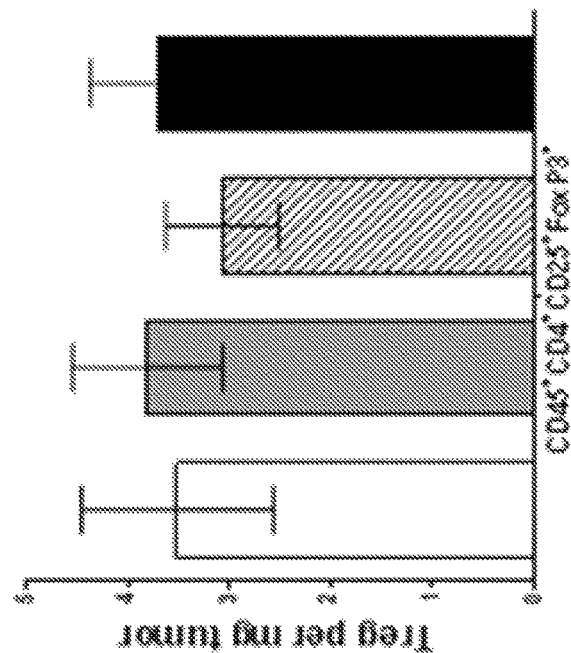
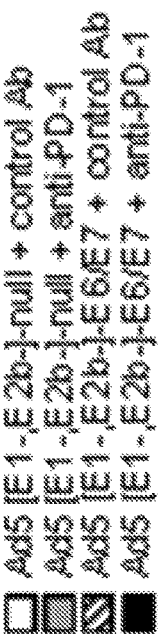
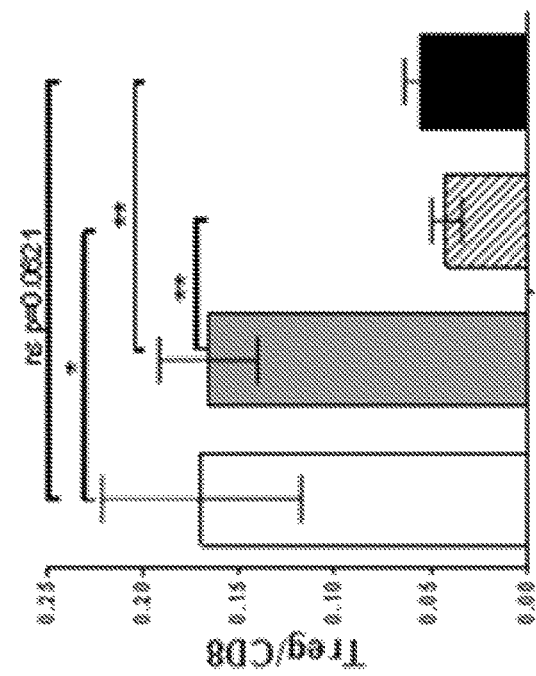
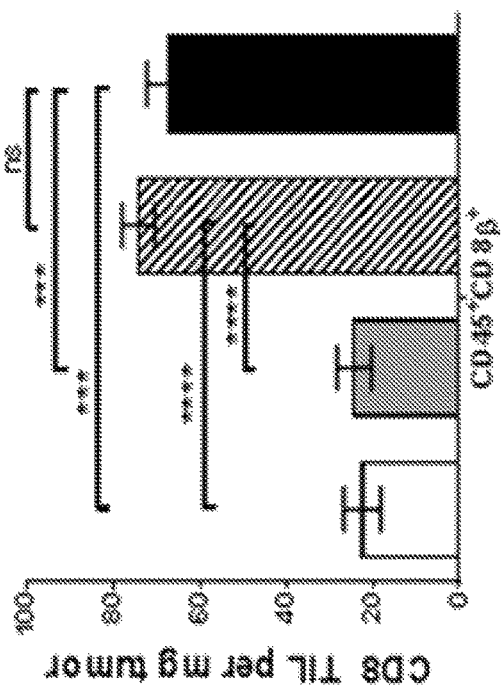
FIG. 43A
FIG. 43B
FIG. 43C

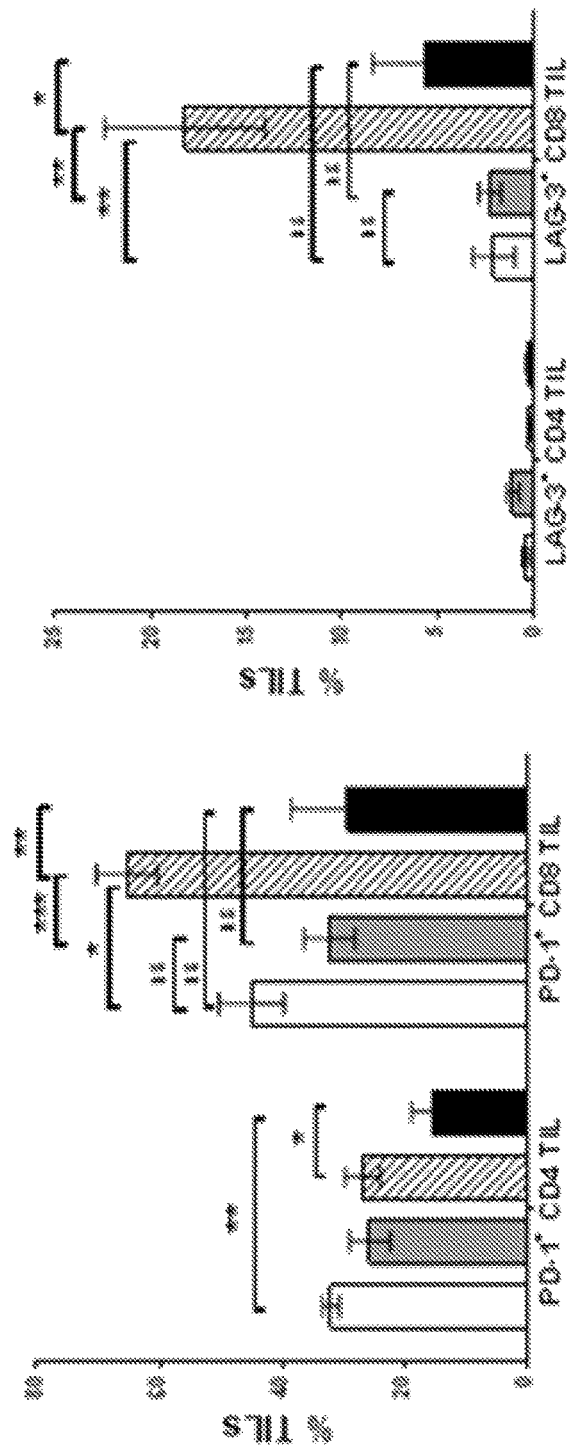
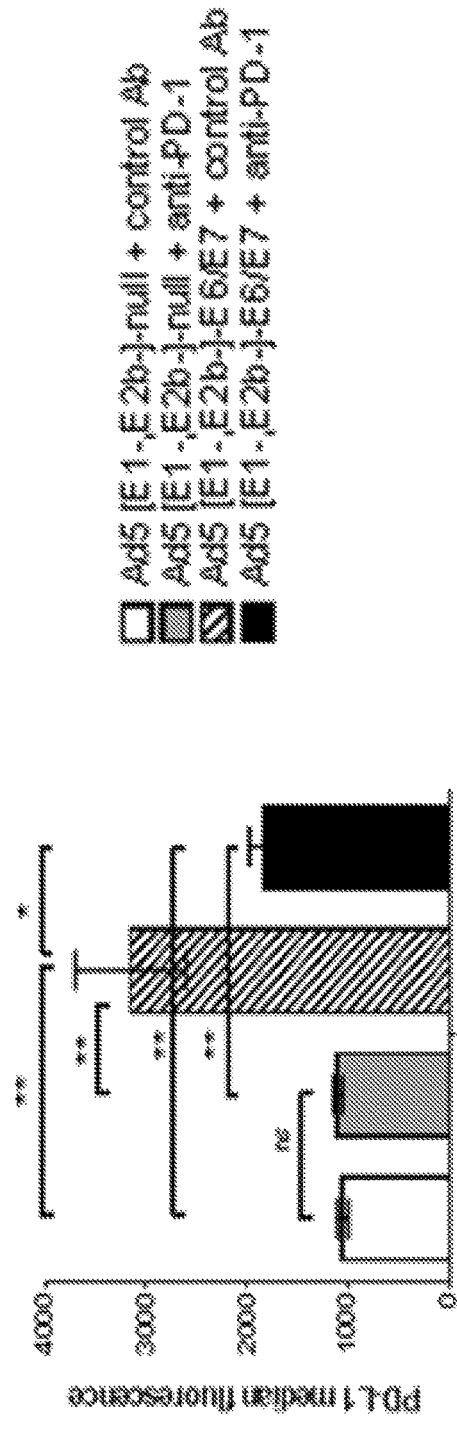
FIG. 44A
FIG. 44B
FIG. 44C

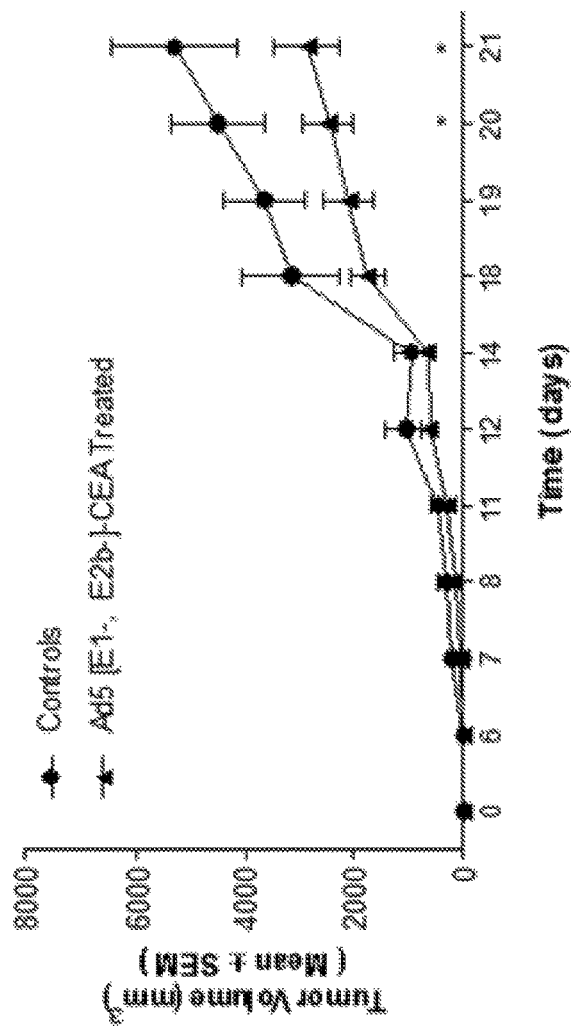
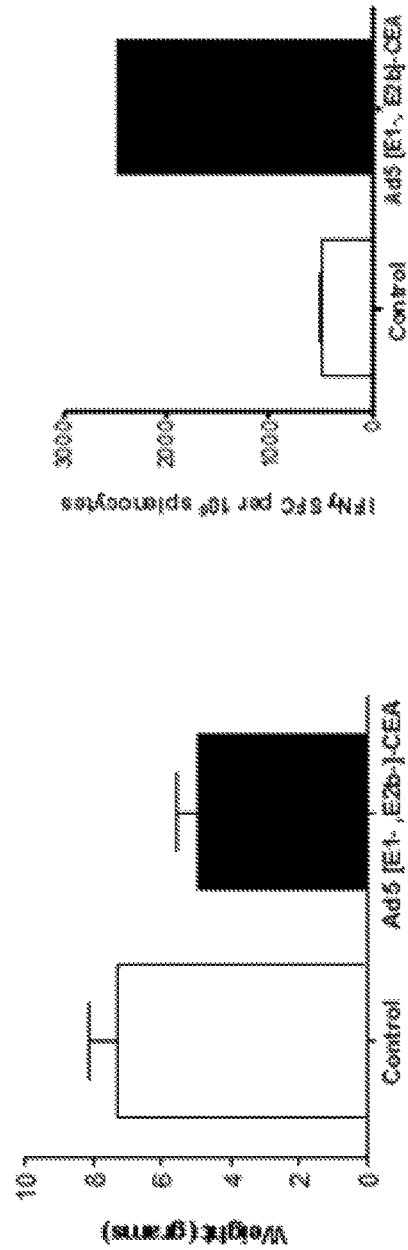
FIG. 48A
FIG. 48B
FIG. 48C

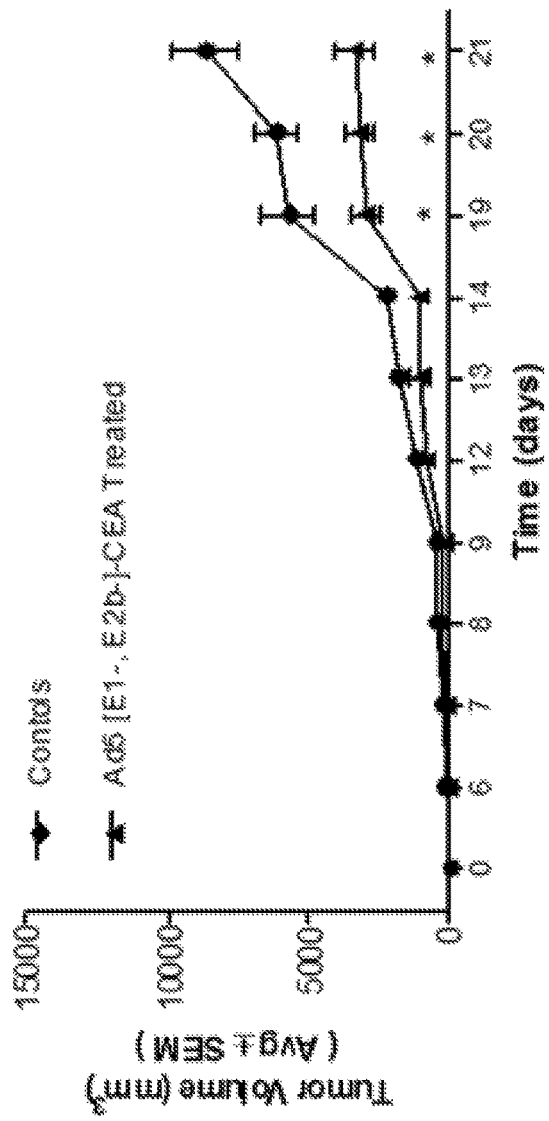
FIG. 49A
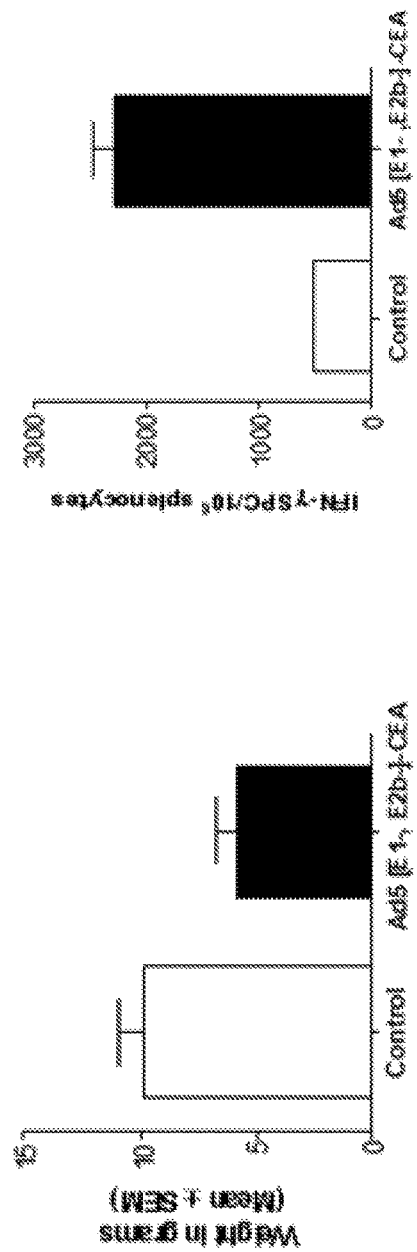
FIG. 49B
FIG. 49C

METHODS AND COMPOSITIONS FOR COMBINATION IMMUNOTHERAPY

CROSS-REFERENCE

This application is a U.S. National Phase Application under U.S.C. § 371 of International Application No. PCT/US2016/028496, filed Apr. 20, 2016, which is a continuation-in-part of International Application No. PCT/US2016/012496, filed Jan. 7, 2016, both of which claim the benefit of U.S. Provisional Application No. 62/150,236, filed Apr. 20, 2015, which are incorporated herein by reference in their entirety.

STATEMENT AS TO FEDERALLY SPONSORED RESEARCH

This invention was made with government support under Contract No. HHSN 261200900059C, awarded by the National Cancer Institute (NCI); and Contract No. HHSN 261201100097C, awarded by the NCI; Grant No. 1R43CA134063, awarded by the NCI; Grant No. 2R44CA134063 awarded by the NCI; Grant No. 1R43CA186357 awarded by the NCI; Grant No. 1R43DE021973 awarded by the National Institute of Dental and Craniofacial Research (NIDCR); and Grant No. 2R44DE021973 awarded by the NIDCR. The government may have certain rights in the invention.

SEQUENCE LISTING

The instant application contains a Sequence Listing which has been submitted electronically in ASCII text format and is hereby incorporated by reference in its entirety pursuant to 37 CFR 1.52(e)(5). Said ASCII copy, created on Oct. 23, 2020, is named 8774ETU-13-P2-PUS.txt and is 210,000 bytes in size.

SUMMARY

Disclosed herein include methods of enhancing an immune response in an individual in need thereof, the method comprising administering to the individual a first replication-defective vector comprising a first nucleic acid sequence encoding an HPV antigen, and administering to the individual an immune checkpoint inhibitor. In particular embodiments, the antigen used herein is a wild-type HPV antigen or a modified HPV antigen. For example, the modified HPV antigen a non-oncogenic HPV antigen or a modified HPV antigen that has reduced oncogenicity as compared with a wild-type HPV. For example, the antigen used herein is a modified HPV E6 antigen having an amino acid sequence set forth in SEQ ID NO:17, a modified HPV E7 antigen having an amino acid sequence set forth in SEQ ID NO:18, or a combination thereof. In further embodiments, the antigen used herein is a modified HPV E6 antigen that has one or more mutations at positions 26, 98, or 106 of SEQ ID NO:17, a modified HPV E7 antigen that a mutation at position 86 of SEQ ID NO:18, or a combination thereof. In particular embodiments, the nucleotide sequence of the antigen has a region at least 50%, 60%, 65%, 70%, 75%, 80%, 85%, 90%, 95%, 98%, 99%, 99.5%, 99.9%, 100% identical to positions 123-545 of SEQ ID NO:19, positions 602-895 of SEQ ID NO:9, or a combination thereof. For example, the nucleic acid sequence has at least 80% identity to SEQ ID NO:19 (the nucleotide sequence of a HPV E6 and E7 fusion protein). In further embodiments, the nucleic acid sequence has at least 50%, 60%, 65%, 70%, 75%, 80%, 85%, 90%, 95%, 98%, 99%, 99.5%, 99.9%, 100% identity to any portion of or full-length to SEQ ID NO:20 (the predicted sequence of an adenovirus vector expressing HPV E6 and E7), such as positions 1033 to 2179 of SEQ ID NO:20. In certain embodiments, the method may be further defined as treating an HPV infection or an HPV-associated disease, such as an HPV-associated cancer, including, but not limited to, head and neck squamous cell carcinoma (HNSCC), oropharyngeal and tonsillar cancer, anal cancer or cervical cancer.

In certain embodiments, the method may further comprise administering to the individual an immune checkpoint inhibitor, such as an immune checkpoint inhibitor that targets PD1, PDL1, PDL2, CD28, CD80, CD86, CTLA4, B7RPI, ICOS, B7RPI, B7-H3, B7-H4, BTLA, HVEM, KIR, TCR, LAG3, CD137, CD137L, OX40, OX40L, CD27, CD70, CD40, CD40L, TIM3, GALS, ADORA, CD276, VTCN1, IDO1, KIR3DL1, HAVCR2, VISTA, or CD244. In particular embodiments, the immune checkpoint inhibitor targets PD1 or PDL1, such as anti-PD-1 or anti-PD-L1 antibody, or more particularly, avelumab. In certain embodiments, the method may further comprise administering to the individual chemotherapy, radiation, or a combination thereof. The chemotherapy may be alkylating agents such as cisplatin.

In certain embodiments, the method is further defined as a method of treating a HPV-associated disease, comprising: administering to the individual a first pharmaceutical composition comprising a replication-defective adenovirus vector comprising a nucleic acid sequence encoding an HPV antigen; and administering to the individual an immune checkpoint inhibitor, a chemotherapy, radiation or a combination thereof.

In certain embodiment, there may be provided a method of enhancing an immune response in an individual in need thereof, the method comprising: administering to the individual a pharmaceutical composition comprising a replication-defective adenovirus vector comprising a nucleic acid sequence encoding an HPV antigen, wherein the administering comprises one or more of the following: i) the administration is repeated at every three weeks; ii) the pharmaceutical composition comprises at least $10^{11}$ adenovirus vectors; iii) the individual is a human; and iv) the individual has, head and neck squamous cell carcinoma (HNSCC), oropharyngeal and tonsillar cancer, anal cancer or cervical cancer.

In certain embodiments, the replication-defective adenovirus vector has a deletion in an early 2b (E2b) gene region. In further embodiments, the replication-defective adenoviral vector further comprises a deletion in an early 1 (E1) gene region, a deletion in an early 3 (E3) gene region, a deletion in an early 4 (E4) gene region, or a combination thereof. In certain embodiments, the CEA, Brachyury or MUC1 antigen has been modified to increase immunogenicity.

Disclosed herein include methods of enhancing an immune response in an individual in need thereof, the method comprising administering to the individual a first replication-defective vector comprising a first nucleic acid sequence encoding a CEA antigen, a second replication-defective vector comprising a second nucleic acid sequence encoding a Brachyury antigen, a third replication-defective vector comprising a third nucleic acid sequence encoding a MUC1 antigen.

In certain embodiments, the CEA antigen used herein is a wild-type CEA antigen or a modified CEA antigen having a least a mutation in YLSGANLNL (SEQ ID NO:4), a CAP1 epitope of CEA. The mutation can be conservative or non-conservative, substitution, addition, or deletion. In certain embodiments, the CEA antigen used herein has an amino acid sequence set forth in YLSGADLNL (SEQ ID NO:10), a mutated CAP1 epitope. In further embodiments, the first replication-defective vector or a replication-defective vector that express CEA has a nucleotide sequence at least 50%, 60%, 65%, 70%, 75%, 80%, 85%, 90%, 95%, 98%, 99%, 99.5%, 99.9%, 100% identical to any portion of SEQ ID NO:3 (the predicted sequence of an adenovirus vector express a modified CEA antigen), such as positions 1057 to 3165 of SEQ ID NO:3 or full-length SEQ ID NO:3.

In certain embodiments, the Brachyury antigen used herein is a wild-type antigen or a modified antigen. In certain embodiments, the Brachyury antigen binds to HLA-A2. In further embodiments, the Brachyury antigen is a modified Brachyury antigen having an amino acid sequence set forth in WLLPGTSTV (SEQ ID NO:22), a HLA-A2 epitope of Brachyury. In further embodiments, the Brachyury antigen is a modified Brachyury antigen having an amino acid sequence at least 50%, 60%, 65%, 70%, 75%, 80%, 85%, 90%, 95%, 98%, 99%, 99.5%, 99.9%, 100% identical to SEQ ID NO:21, a modified Brachyury protein sequence. In certain embodiments, the replication-defective vector has a nucleotide sequence at least 50%, 60%, 65%, 70%, 75%, 80%, 85%, 90%, 95%, 98%, 99%, 99.5%, 99.9%, 100% identical to SEQ ID NO:8 or positions 1033 to 2283 of SEQ ID NO:16. In further embodiments, the second replication-defective vector has a nucleotide sequence at least 50%, 60%, 65%, 70%, 75%, 80%, 85%, 90%, 95%, 98%, 99%, 99.5%, 99.9%, 100% identical to any portion or full-length of SEQ ID NO:16 (the predicted sequence of an adenovirus vector express a modified Brachyury antigen), such as positions 1033 to 2283 of SEQ ID NO:16. In some embodiments, the Brachyury antigen is a modified Brachyury antigen having an amino acid sequence at least 50%, 60%, 65%, 70%, 75%, 80%, 85%, 90%, 95%, 98%, 99%, 99.5%, 99.9%, 100% identical to SEQ ID NO:15 (another mutated Brachyury protein sequence). In certain embodiments, the second replication-defective vector or a replication-defective vector that express Brachyury has a nucleotide sequence at least 50%, 60%, 65%, 70%, 75%, 80%, 85%, 90%, 95%, 98%, 99%, 99.5%, 99.9%, 100% identical to positions 520-1824 of SEQ ID NO:7 (wild-type Brachyury), SEQ ID NO:7, or SEQ ID NO:8.

In certain embodiments, the MUC1 antigen used herein is a wild-type MUC1 antigen or a modified MUC1 antigen. In certain embodiments, the modified MUC1 antigen has at least 50%, 60%, 65%, 70%, 75%, 80%, 85%, 90%, 95%, 98%, 99%, 99.5%, 99.9%, 100% identity to SEQ ID NO:9 (a mutated MUC1 protein sequence). In certain embodiments, the MUC-1 antigen is a modified antigen having one or more mutations at positions 93, 141-142, 149-151, 392, 404, 406, 422, 430-431, 444-445, or 460 of SEQ ID NO:9. The mutation can be conservative or non-conservative, substitution, addition, or deletion. In further embodiments, the MUC-1 antigen binds to HLA-A2, HLA-A3, HLA-A24, or a combination thereof. In certain embodiments, the third replication-defective vector or a replication-defective vector that express MUC1 has a nucleotide sequence at least 50%, 60%, 65%, 70%, 75%, 80%, 85%, 90%, 95%, 98%, 99%, 99.5%, 99.9%, 100% identical to SEQ ID NO:5 (MUC_1 wild-type nucleotide sequence). In further embodiments, the third replication-defective vector or a replication-defective vector that express MUC1 has a nucleotide sequence at least 50%, 60%, 65%, 70%, 75%, 80%, 85%, 90%, 95%, 98%, 99%, 99.5%, 99.9%, 100% identical to SEQ ID NO:6 (a mutated MUC1 nucleotide sequence). In certain embodiments, the third replication-defective vector or a replication-defective vector that express MUC1 has a nucleotide sequence at least 50%, 60%, 65%, 70%, 75%, 80%, 85%, 90%, 95%, 98%, 99%, 99.5%, 99.9%, 100% identical to any portion of or full-length SEQ ID NO:14 (the predicted sequence of an adenovirus vector express a modified CEA antigen), such as positions 1033-2858 of SEQ ID NO:14.

In certain embodiments, there is a provided a composition comprising replication-defective vectors comprising nucleotide sequences encoding a CEA antigen that is a modified CEA antigen having an amino acid sequence set forth in YLSGADLNL (SEQ ID NO:10), encoding a Brachyury antigen that is a modified Brachyury antigen having an amino acid sequence set forth in WLLPGTSTV (SEQ ID NO:22), and encoding a MUC1 antigen that is a modified antigen having one or more mutations at positions 93, 141-142, 149-151, 392, 404, 406, 422, 430-431, 444-445, or 460 of SEQ ID NO:9. In further embodiments, two or more of the first, second, and third, or even more replication-defective vectors are the same vector or in separate vectors.

In certain embodiments, the method may further comprise administering to the individual an immune checkpoint inhibitor, such as an immune checkpoint inhibitor that targets PD1, PDL1, PDL2, CD28, CD80, CD86, CTLA4, B7RPI, ICOS, B7RPI, B7-H3, B7-H4, BTLA, HVEM, KIR, TCR, LAG3, CD137, CD137L, OX40, OX40L, CD27, CD70, CD40, CD40L, TIM3, GALS, ADORA, CD276, VTCN1, IDO1, KIR3DL1, HAVCR2, VISTA, or CD244. In particular embodiments, the immune checkpoint inhibitor targets PD1 or PDL1, such as anti-PD-1 or anti-PD-L1 antibody, or more particularly, avelumab.

In further embodiments, the first, second, and third replication-defective vectors are mixed at a 1:1:1 ratio, or any suitable ratios. In certain embodiments, one or more of the replication-defective vectors disclosed herein, such as the first, second, or third replication-defective vector is a replication-defective adenovirus vector. For example, the replication-defective adenovirus vector has a deletion in an early 2b (E2b) gene region. In further embodiments, the replication-defective adenoviral vector further comprises a deletion in an early 1 (E1) gene region, a deletion in an early 3 (E3) gene region, a deletion in an early 4 (E4) gene region, or a combination thereof. In certain embodiments, the CEA, Brachyury or MUC1 antigen has been modified to increase immunogenicity.

In certain embodiments, methods provided herein may be further defined as treating a cancer that expresses CEA, Brachyury, or MUC1 in an individual in need thereof. In certain embodiments, the cancer to be treated or the individual in need thereof may have breast cancer, lung cancer, head and neck cancer, prostate cancer, gastric cancer, pancreatic cancer, liver cancer, ovarian, cancer, cervical cancer, or gastrointestinal cancer.

In certain embodiments, any compositions or vectors may be administered to an individual in need thereof sequentially or at the same time. For example, the first, second, or third replication-defective vector is administered to the individual sequentially. In some other embodiments, the first, second, or third replication-defective vector is administered to the individual at the same time.

In certain embodiments, there is provided a pharmaceutical composition comprising a first replication-defective vector comprising a first nucleic acid sequence encoding a CEA antigen, a second replication-defective vector comprising a second nucleic acid sequence encoding a Brachyury antigen, and a third replication-defective vector comprising a third nucleic acid sequence encoding a MUC1 antigen. Any of the antigens may be wild-type or modified as described as above or throughout the specification.

Disclosed herein is a method of enhancing an immune response in an individual in need thereof, the method comprising: administering to the individual a first pharmaceutical composition comprising a replication-defective adenovirus vector comprising a nucleic acid sequence encoding an antigen; and administering to the individual an immune checkpoint inhibitor. In certain embodiments, the antigen is CEA, Brachyury, MUC1, an HPV antigen, such as HPV E6 and/or E7, or a combination thereof. In particular embodiments, the antigen used herein is a wild-type HPV antigen or a modified HPV antigen. For example, the modified HPV antigen a non-oncogenic HPV antigen or a modified HPV antigen that has reduced oncogenicity as compared with a wild-type HPV. For example, the antigen used herein is a modified HPV E6 antigen having an amino acid sequence set forth in SEQ ID NO:17, a modified HPV E7 antigen having an amino acid sequence set forth in SEQ ID NO:18, or a combination thereof. In further embodiments, the antigen used herein is a modified HPV E6 antigen that has one or more mutations at positions 26, 98, or 106 of SEQ ID NO:17, a modified HPV E7 antigen that a mutation at position 86 of SEQ ID NO:18, or a combination thereof. In particular embodiments, the nucleotide sequence of the antigen has a region at least 50%, 60%, 65%, 70%, 75%, 80%, 85%, 90%, 95%, 98%, 99%, 99.5%, 99.9%, 100% identical to positions 123-545 of SEQ ID NO:19, positions 602-895 of SEQ ID NO:9, or a combination thereof. For example, the nucleic acid sequence has at least 50%, 60%, 65%, 70%, 75%, 80%, 85%, 90%, 95%, 98%, 99%, 99.5%, 99.9%, 100% identity to SEQ ID NO:19 (the nucleotide sequence of a HPV E6 and E7 fusion protein). In further embodiments, the nucleic acid sequence has at least 50%, 60%, 65%, 70%, 75%, 80%, 85%, 90%, 95%, 98%, 99%, 99.5%, 99.9%, 100% identity to any portion of or full-length to SEQ ID NO:20 (the predicted sequence of an adenovirus vector expressing HPV E6 and E7), such as positions 1033 to 2179 of SEQ ID NO:20. In certain embodiments, the method may be further defined as treating an HPV infection or an HPV-associated disease, such as an HPV-associated cancer, including, but not limited to, head and neck squamous cell carcinoma (HNSCC), oropharyngeal and tonsillar cancer, anal cancer or cervical cancer.

In certain embodiments, the method may further comprise administering to the individual an immune checkpoint inhibitor, such as an immune checkpoint inhibitor that targets PD1, PDL1, PDL2, CD28, CD80, CD86, CTLA4, B7RPI, ICOS, B7RPI, B7-H3, B7-H4, BTLA, HVEM, KIR, TCR, LAG3, CD137, CD137L, OX40, OX40L, CD27, CD70, CD40, CD40L, TIM3, GALS, ADORA, CD276, VTCN1, IDO1, KIR3DL1, HAVCR2, VISTA, or CD244. In particular embodiments, the immune checkpoint inhibitor targets PD1 or PDL1, such as anti-PD-1 or anti-PD-L1 antibody, or more particularly, avelumab.

In certain embodiments, the method may further comprise administering to the individual an immune checkpoint inhibitor, chemotherapy, radiation, or a combination thereof. The chemotherapy may be alkylating agents such as cisplatin. In certain embodiments, the method is further defined as a method of treating a HPV-associated disease, comprising: administering to the individual a first pharmaceutical composition comprising a replication-defective adenovirus vector comprising a nucleic acid sequence encoding an HPV antigen; and administering to the individual an immune checkpoint inhibitor, a chemotherapy, radiation or a combination thereof.

In certain embodiments, the replication-defective adenovirus vector has a deletion in an early 2b (E2b) gene region. In further embodiments, the replication-defective adenoviral vector further comprises a deletion in an early 1 (E1) gene region, a deletion in an early 3 (E3) gene region, a deletion in an early 4 (E4) gene region, or a combination thereof. In certain embodiments, the CEA, Brachyury or MUC1 antigen has been modified to increase immunogenicity.

In certain embodiments, the vectors have nucleotide sequences encoding one or more of modified CEA, Brachyury or MUC1 antigen. The modified antigens may have insertions, deletions or substitutions, or have been modified to increase immunogenicity. In certain embodiments, the vectors may have nucleotide sequences encoding CEA, Brachyury, MUC1, or a combination thereof. In certain embodiments, two or more antigen-encoding nucleic acids may be comprised in separate vectors or in the same vector.

In certain embodiments, there is provided a method of treating a CEA-expression cancer in an individual in need thereof, the method comprising: administering to the individual a first pharmaceutical composition comprising a replication-defective vector comprising a nucleic acid sequence encoding a CEA antigen or any suitable antigen; and administering to the individual an immune checkpoint inhibitor. The method may further comprise administering to the individual a VEGF inhibitor, chemotherapy, or a combination thereof.

In certain embodiments, the individual is a human. In certain embodiments, the method is further defined as comprising: administering to the individual a first pharmaceutical composition comprising a replication-defective vector comprising a nucleic acid sequence encoding a CEA antigen; and administering to the individual an immune checkpoint inhibitor. In certain embodiments, the method is further defined as comprising: administering to the individual a first pharmaceutical composition comprising a replication-defective vector comprising a nucleic acid sequence encoding a CEA antigen; and administering to the individual a chemotherapy. In certain embodiments, the method is further defined as comprising: administering to the individual a first pharmaceutical composition comprising a replication-defective vector comprising a nucleic acid sequence encoding a CEA antigen; administering to the individual an immune checkpoint inhibitor; and administering to the individual a chemotherapy. In certain embodiments, the method is further defined as comprising: administering to the individual a first pharmaceutical composition comprising a replication-defective vector comprising a nucleic acid sequence encoding a CEA antigen; administering to the individual an immune checkpoint inhibitor; administering to the individual a chemotherapy; and administering to the individual a VEGF inhibitor.

In certain embodiments, the CEA antigen is a modified CEA antigen comprising an amino acid sequence set forth in YLSGADLNL (SEQ ID NO:10). The replication-defective vector comprising a nucleotide sequence encoding a CEA antigen may be provided as described above.

In certain embodiments, the chemotherapy used herein is capecitabine, leucovorin, fluorouracil, oxaliplatin, fluoropyrimidine, irinotecan, mitomycin, regorafenib, cetuximab, panitumumab, acetinophen, or a combination thereof. In particular embodiments, the chemotherapy used herein is FOLFOX (leucovorin, fluorouracil and oxaliplatin) or capecitabine. In certain embodiments, the immune checkpoint inhibitor is an anti-PD-1 or anti-PD-L1 antibody, such as avelumab. In certain embodiments, the VEGF inhibitor is an anti-VEGF antibody, such as bevacizumab.

In certain embodiments, the method is further defined as comprising: administering to the individual a first pharmaceutical composition comprising a replication-defective vector comprising a nucleic acid sequence encoding a CEA antigen; administering to the individual an anti-PD-1 or anti-PD-L1 antibody; administering to the individual capecitabine, leucovorin, fluorouracil, oxaliplatin, or a combination thereof; and administering to the individual an anti-VEGF antibody.

In certain embodiments, the method is further defined as comprising: administering to the individual a first pharmaceutical composition comprising a replication-defective vector comprising a nucleic acid sequence encoding a CEA antigen; administering to the individual avelumab; administering to the individual capecitabine or FOLFOX (leucovorin, fluorouracil and oxaliplatin); and administering to the individual bevacizumab.

In certain embodiments, the method is further defined as comprising: a first treatment phase comprising: administering to the individual a first pharmaceutical composition comprising a replication-defective vector comprising a nucleic acid sequence encoding a CEA antigen; administering to the individual avelumab; administering to the individual FOLFOX (leucovorin, fluorouracil and oxaliplatin); and administering to the individual bevacizumab; followed by a second treatment phase, comprising: administered to the individual the first pharmaceutical composition; administering to the individual avelumab; administering to the individual capecitabine; and administering to the individual bevacizumab.

In certain embodiments, the first pharmaceutical composition, a pharmaceutical composition or a vector disclosed herein is administered intravenously, subcutaneously, intramuscularly or intradermally.

In certain embodiments, the first pharmaceutical composition, a pharmaceutical composition or a vector disclosed herein is administered every two weeks, every four weeks, or every 12 weeks. In certain embodiments, the first pharmaceutical composition, a pharmaceutical composition or a vector disclosed herein is administered every two weeks, followed by subsequent administration of every four weeks. In certain embodiments, the first pharmaceutical composition, a pharmaceutical composition or a vector disclosed herein is administered every 12 weeks. In certain embodiments, the first pharmaceutical composition, a pharmaceutical composition or a vector disclosed herein is administered every two weeks, followed by subsequent administration of every four weeks, and followed by a second subsequent administration of every 12 weeks.

In certain embodiments, the first pharmaceutical composition is administered in a treatment phase of up to 24 weeks, wherein the treatment plan further comprises administering to the individual avelumab, FOLFOX, and bevacizumab. In certain embodiments, the first pharmaceutical composition is administered in a treatment phase of up to 24 weeks, wherein the treatment phase further comprises administering to the individual avelumab, FOLFOX, and bevacizumab every two weeks. In certain embodiments, the first pharmaceutical composition comprises at least $10^9$ vectors, at least $10^{10}$ vectors or at least $10^{11}$ vectors.

In certain embodiments, the replication-defective vector is a replication-defective adenovirus vector. In certain embodiments, the replication-defective adenovirus vector has a deletion in an early 2b (E2b) gene region or further comprises a deletion in an early 1 (E1) gene region, a deletion in an early 3 (E3) gene region, a deletion in an early 4 (E4) gene region, or a combination thereof.

In certain embodiments, the first pharmaceutical composition further comprises an immune adjuvant. In certain embodiments, the CEA antigen has been modified to increase immunogenicity.

In certain embodiments, the first pharmaceutical composition further comprises a vector encoding an antigen selected from the group consisting of Her2/neu, Her3, Brachyury, Brachyury (TIVS7-2, polymorphism), Brachyury (IVS7 T/C polymorphism), T Brachyury, T, PSA, PSCA, PSM (i.e., PSMA), HPV E6, HPV E7, MUC1, MUC1c, MUC1n, MUC2, p53, BRCA1, MAGE-A1, MAGE-A2, MAGE-A3, MAGE-A4, MAGE-A6, MAGE-A10, MAGE-A12, BAGE, DAM-6, -10, GAGE-1, -2, -8, GAGE-3, -4, -5, -6, -7B, NA88-A, NY-ESO-1, MART-1, MC1R, Gp100, PAP, Tyrosinase, TRP-1, TRP-2, ART-4, CAMEL, Cyp-B, hTERT, hTRT, iCE, PRAIVIE, P15, RU1, RU2, SART-1, SART-3, WT1, AFP, 13-catenin/m, Caspase-8/m, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mber-abl, ETV6/AML, LDLR/FUT, Pml/RARa, and TEL/AML1, or a modified tumor antigen or a modified infectious antigen, a splice variant, a functional epitope of a tumor antigen or an infectious antigen, an epitope agonist, or a combination thereof. In particular embodiments, the first pharmaceutical composition further comprises a vector encoding an antigen selected from the group consisting of HPV E6, HPV E7, Her2/neu, MUC1, Her3, Brachyury, PSA, PSM (i.e., PSMA), or a combination thereof.

In certain embodiments, the pharmaceutical composition is administered before or concurrently with administering to the individual chemotherapy. In certain embodiments, the first pharmaceutical composition is previously frozen.

In certain embodiments, the individual has previously been administered antihistamine or a pain reliever before administering the immune checkpoint inhibitor. In certain embodiments, the individual has tumor cells that overexpress CEA as compared with a baseline level in a non-tumor cell. In certain embodiments, the individual has pre-existing immunity to Ad5. In certain embodiments, the individual has cancer of the colon, rectum, breast, lung, pancreas, prostate, gastrointestinal tract, ovary, or a combination thereof. In certain embodiments, the individual has previously been determined to overexpress CEA as compared with a baseline level in a non-tumor cell. In certain embodiments, the individual is or has been determined to have pre-existing immunity to adenoviruses.

In certain embodiments, the pharmaceutical composition further comprises a vector comprising a nucleic acid sequence encoding a costimulatory molecule. In certain embodiments, the replication-defective vector in the first pharmaceutical composition further comprises a nucleic acid sequence encoding a costimulatory molecule. In certain embodiments, the costimulatory molecule comprises B7, ICAM-1, LFA-3, or a combination thereof.

In certain embodiments, the method is further defined as a method of enhancing an immune response in an individual in need thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 17A exemplifies CEA-specific immunity in patients receiving immunizations with Ad5 [E1-, E2b-]-CEA(6D)

vaccine and comparisons with Ad5 immunity. The mean CEA specific immune responses in patients (n=19) who received $1 \times 10^{11}$ VP of Ad5 [E1-, E2b-]-CEA(6D) as measured by IFN-γ secretion of PBMC in patients with none to low pre-existing Ad5 immunity (NAb<200) is shown compared to the CEA specific immune response of patients with high pre-existing Ad5 immunity (NAb≥200) prior to the initiation of treatment with Ad5 [E1-, E2b-]-CEA(6D). There was no significant difference between the two groups at any time point tested (p>0.4, Mann-Whitney test)

FIG. 17B exemplifies a plot of the correlation between pre-existing Ad5 NAb activity and the highest levels of induced CEA CMI responses. The $r^2$ value (0.0155) indicates there is no correlation between pre-existing Ad5 NAb activity and CEA CMI ELISpot responses.

FIG. 17C exemplifies a plot of the correlation between vector induced Ad5 NAb activity and CEA CMI responses. The $r^2$ value (0.0069) indicates there is no correlation between vector-induced Ad5 NAb activity and CEA CMI ELISpot responses.

Figure 18:
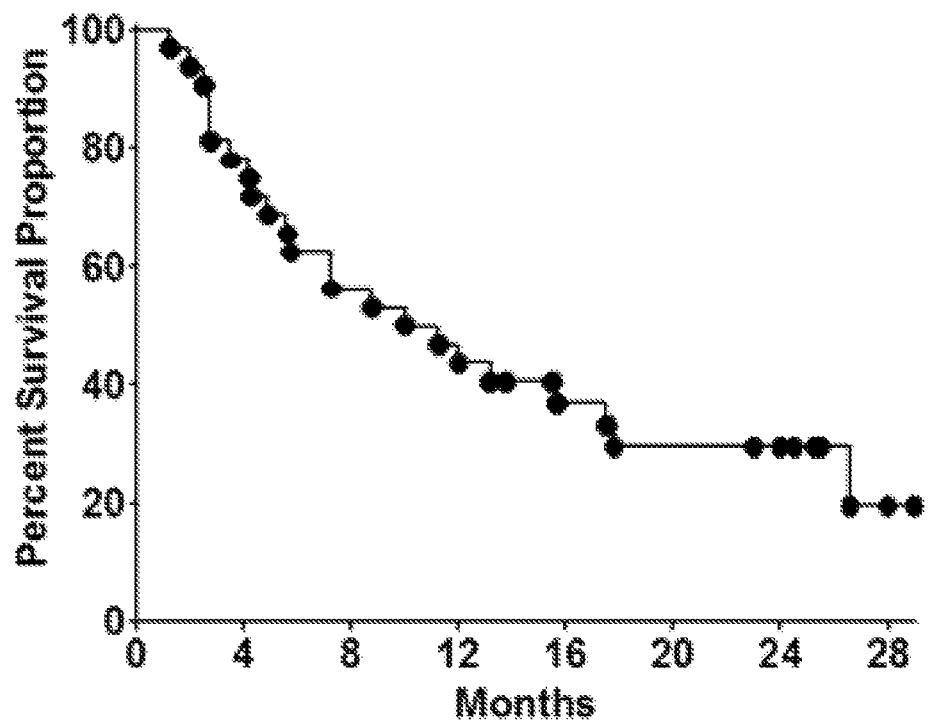

FIG. 18 exemplifies a Kaplan-Meier plot demonstrating the effect of Ad5 [E1-, E2b-]-CEA(6D) immunotherapy in 32 metastatic colorectal cancer patients (mCRC) patients treated with Ad5 [E1-, E2b-]-CEA(6D).

Figure 19:
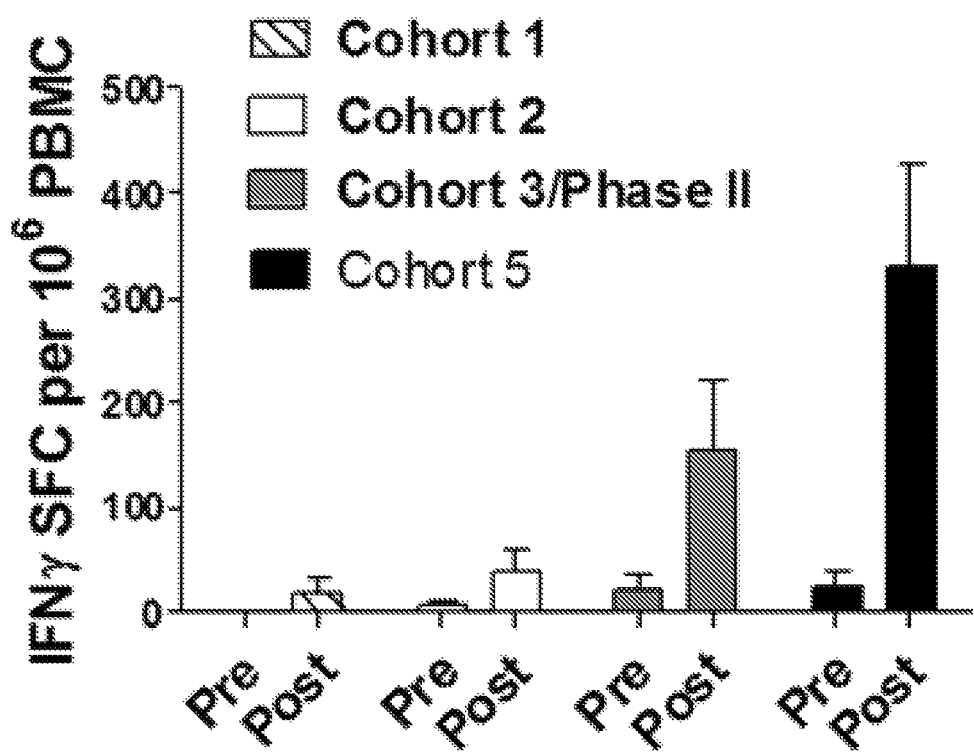

FIG. 19 exemplifies CMI responses (IFN-γ secretion) at baseline (Pre-immunized) and after administrations of Ad5 [E1-, E2b-]-CEA(6D) (Post-immunized) in mCRC patients. The highest CMI responses (regardless of time point) observed in the patients after treatment revealed a dose response. The highest CMI levels occurred in patients receiving the highest dose (Cohort 5) and were significantly elevated (p<0.02; Mann-Whitney test). Response specificity is shown by lack of reactivity with irrelevant antigens β-galactosidase and HIV-gag. For positive controls, PBMCs were exposed to Con A.

Figure 20:
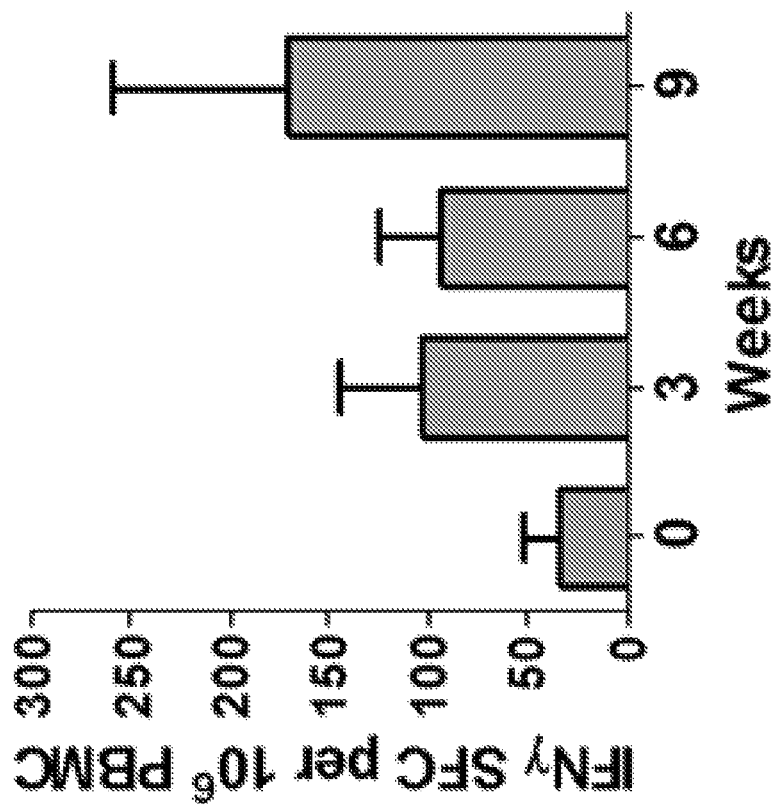

FIG. 20 exemplifies CMI responses (ELISpot IFN-γ SFCs) in immunized mCRC patients assessed at weeks 0, 3, 6, and 9. CMI responses increased during immunizations.

Figure 21:
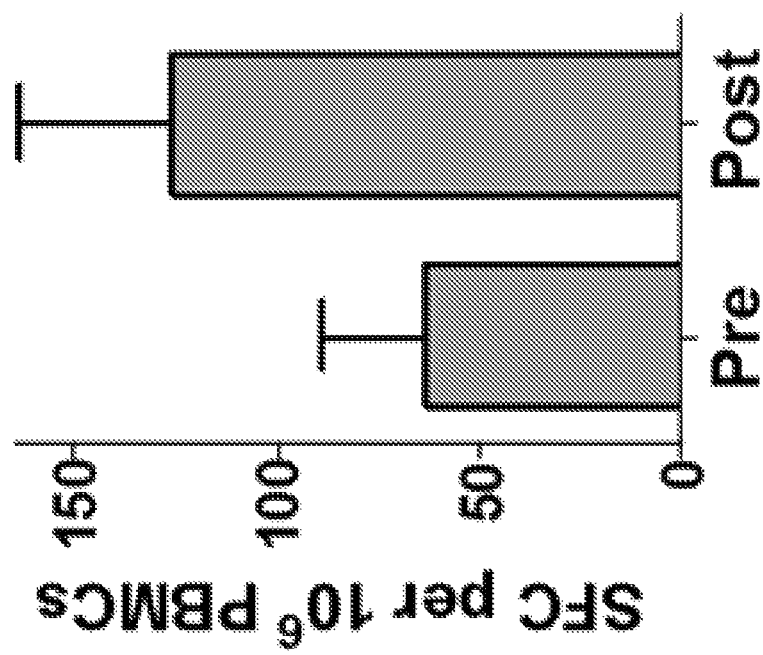

FIG. 21 exemplifies cytotoxic T-cell (CTL) mediated cytotoxicity responses (ELISpot granzyme B secreting SFCs) assessed for pre-immunized (week 0) and post-immunized (weeks 6-9) treatments. Responses increased after immunizations (P<0.05, Wilcoxon test).

Figure 22:
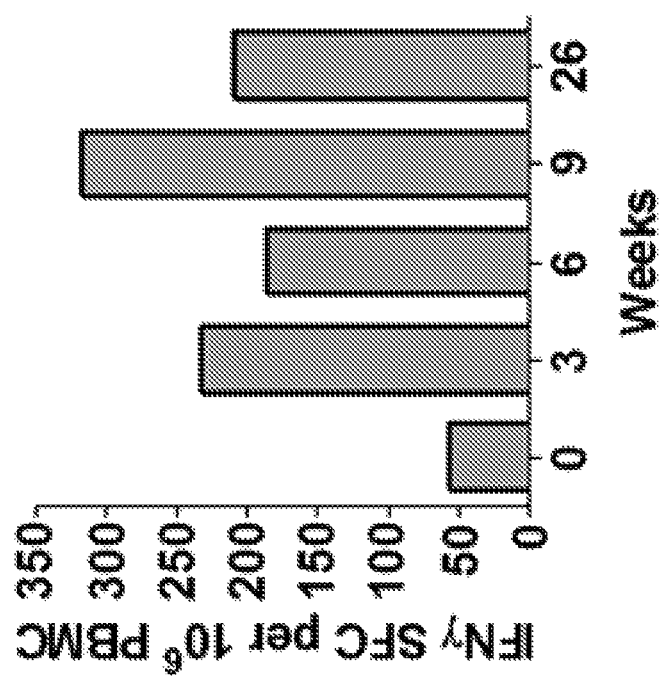

FIG. 22 exemplifies CMI responses in follow-up PBMC samples from 5 immunized mCRC patients as assessed by ELISpot IFN-γ SFCs. CMI responses peaked at week 9 and decreased by week 26 after treatment was stopped.

Figure 23:
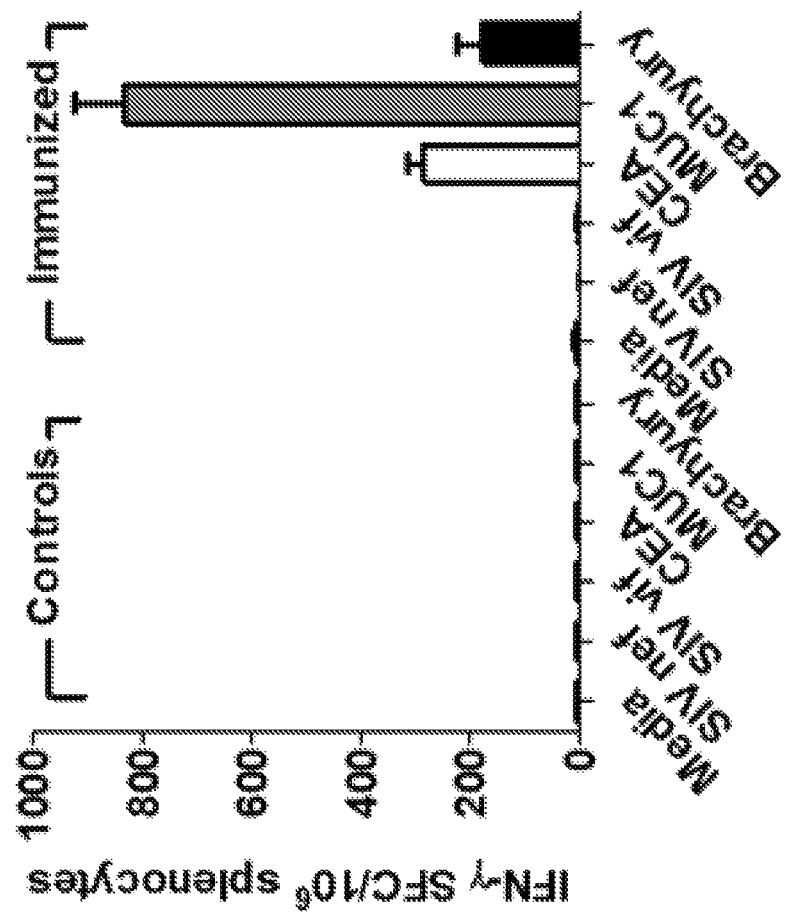

FIG. 23 exemplifies CMI responses in mice immunized against CEA, MUC1, and Brachyury as assessed by ELISpot assays for IFN-γ secretion from splenocytes (IFN-γ SFCs). IFN-γ SFCs were detected in multi-targeted immunized mice (CEA(6D), mMUC1-C, and Brachyury) but not control mice injected with Ad5-Null (empty vector). Response specificity of the ELISpot assay was confirmed by lack of reactivity to irrelevant SIV-nef or SIV-vif peptide antigens. A positive control included cells exposed to Con A.

Figure 24A:
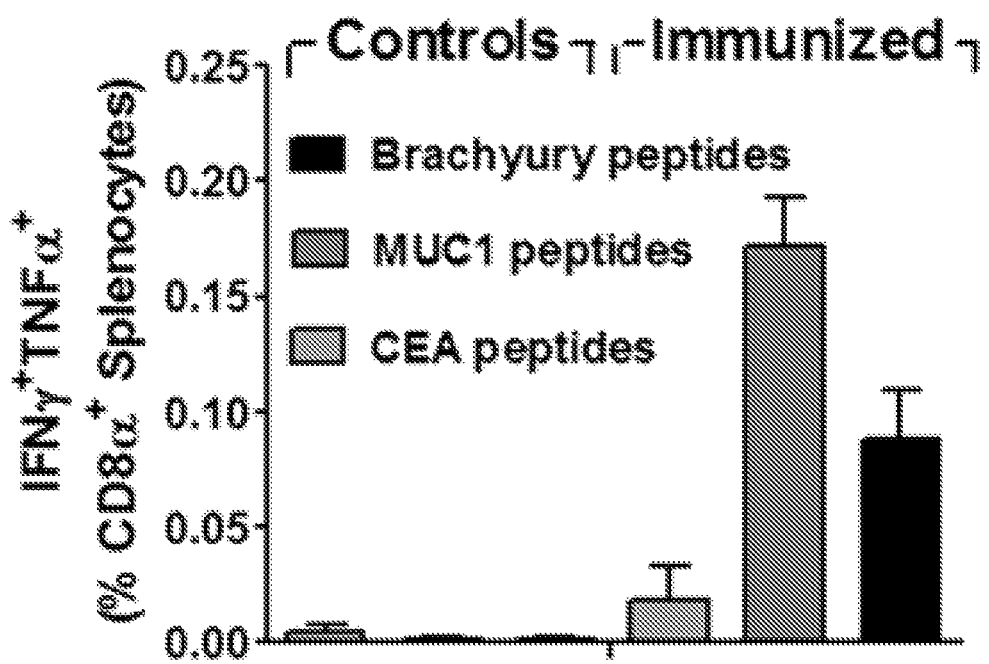

FIG. 24A exemplifies a bar graph of results from flow cytometry on polyfunctional CD8α+ splenocyte cells expressing IFN-γ and TNF-α in mice immunized with CEA(6D), mMUC1-C, and Brachyury, but not in controls injected with Ad5-null. Specificity of the responses was confirmed by lack of reactivity to media alone or irrelevant SIV-nef or SIV-vif peptides.

Figure 24B:
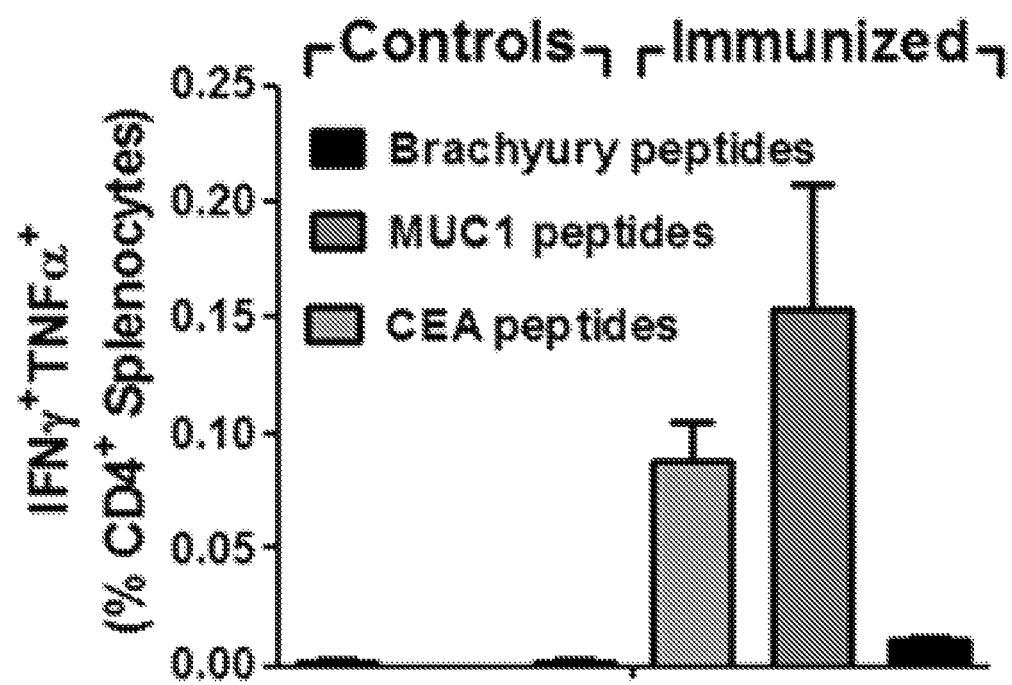

FIG. 24B exemplifies a bar graph of results from flow cytometry on polyfunctional CD4+ splenocyte cells expressing IFN-γ and TNF-α in mice immunized with CEA(6D), mMUC1-C, and Brachyury, but not in controls injected with Ad5-null. Specificity of the responses was confirmed by lack of reactivity to media alone or irrelevant SIV-nef or SIV-vif peptides.

Figures 25A, 25B:
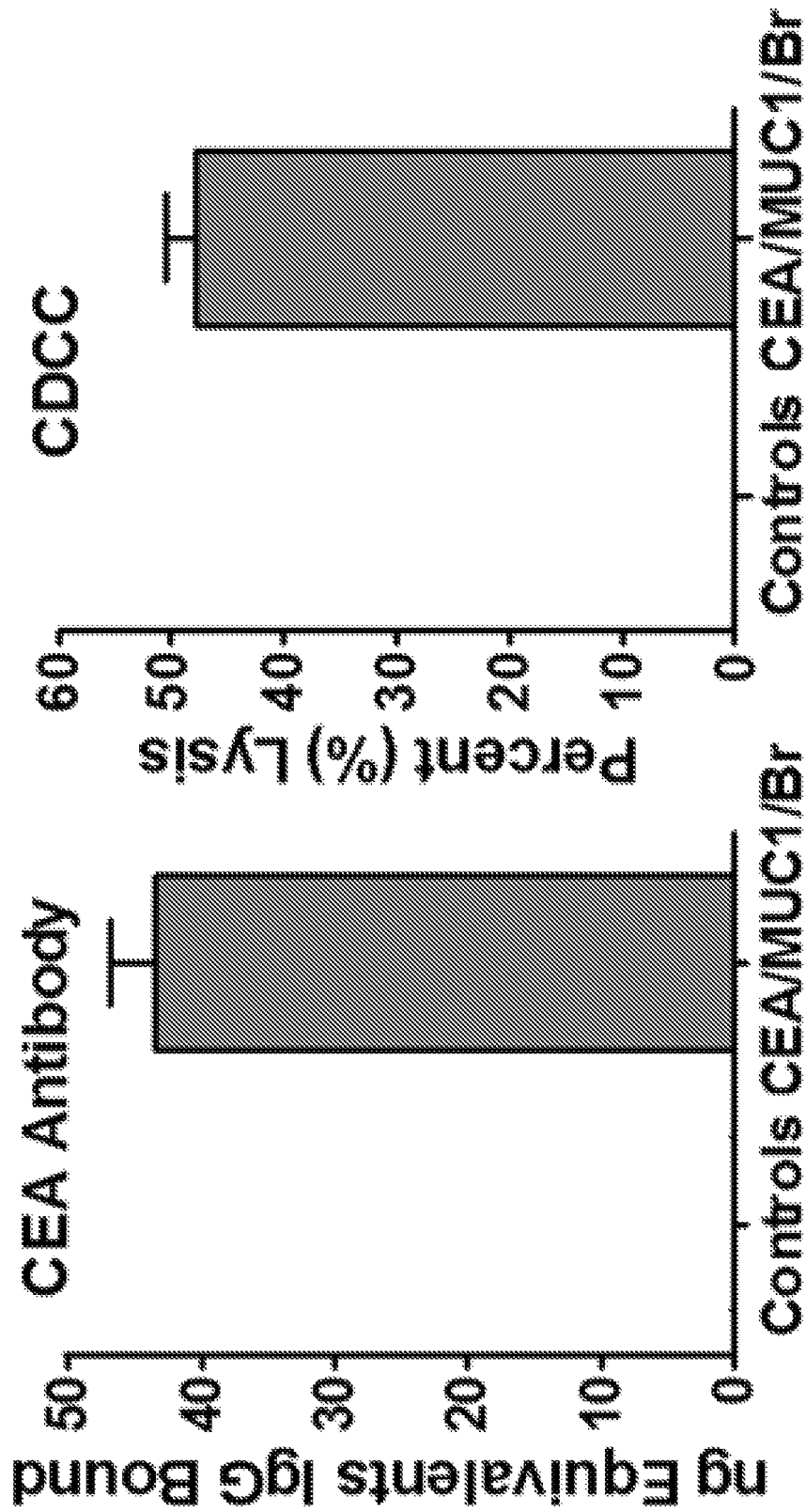

FIG. 25A exemplifies a bar graph showing statistical significance (p<0.0001) of CEA antibody-dependent cellular cytotoxicity (ADCC) responses induced in mice immunized with CEA(6D), mMUC1-C, and Brachyury, but not in control mice.

FIG. 25B exemplifies a bar graph showing statistical significance (p<0.0001) of CEA complement-dependent cellular cytotoxicity (CDCC) responses induced in mice immunized with CEA(6D), mMUC1-C, and Brachyury, but not in control mice.

Figure 26A:
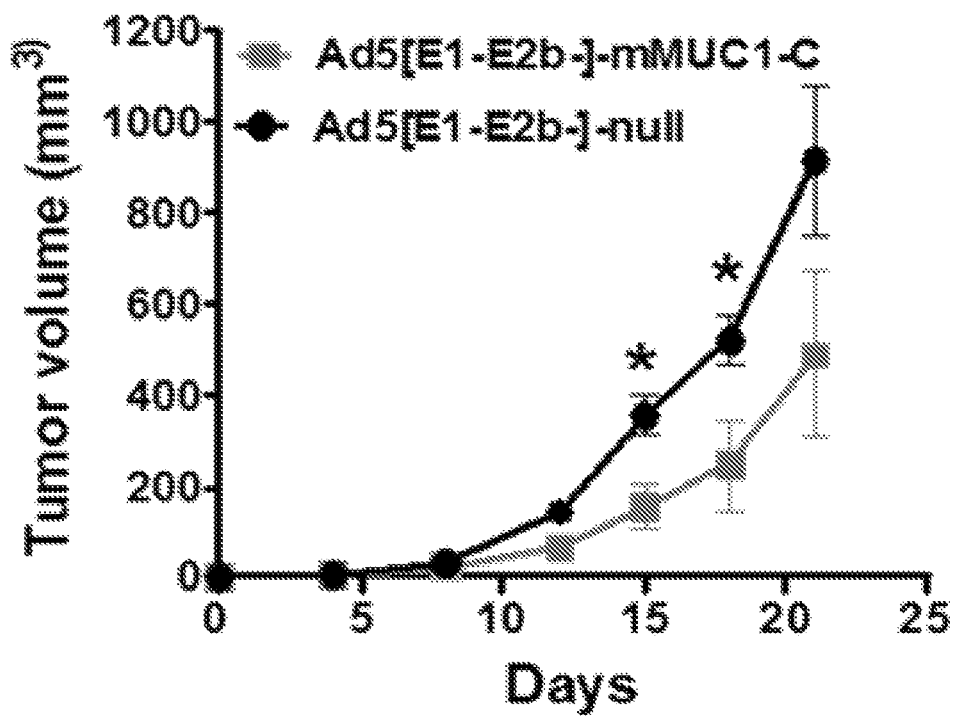

FIG. 26A exemplifies results from C57Bl/6 mice (n=7/group) subcutaneously inoculated in the left flank with MC38 tumor cells expressing MUC1 tumor cells and administered $1 \times 10^{10}$ Ad5-null VPs or $1 \times 10^{10}$ Ad5 [E1-, E2b-]-mMUC1-C VPs in the right flank on days 0, 7, 14. Mice treated with Ad5 [E1-, E2b-]-mMUC1-C had significantly (p<0.05) smaller tumors on days 15 and 18 compared to controls and significantly longer survival. Experiments were terminated on day 36.

Figure 26B:
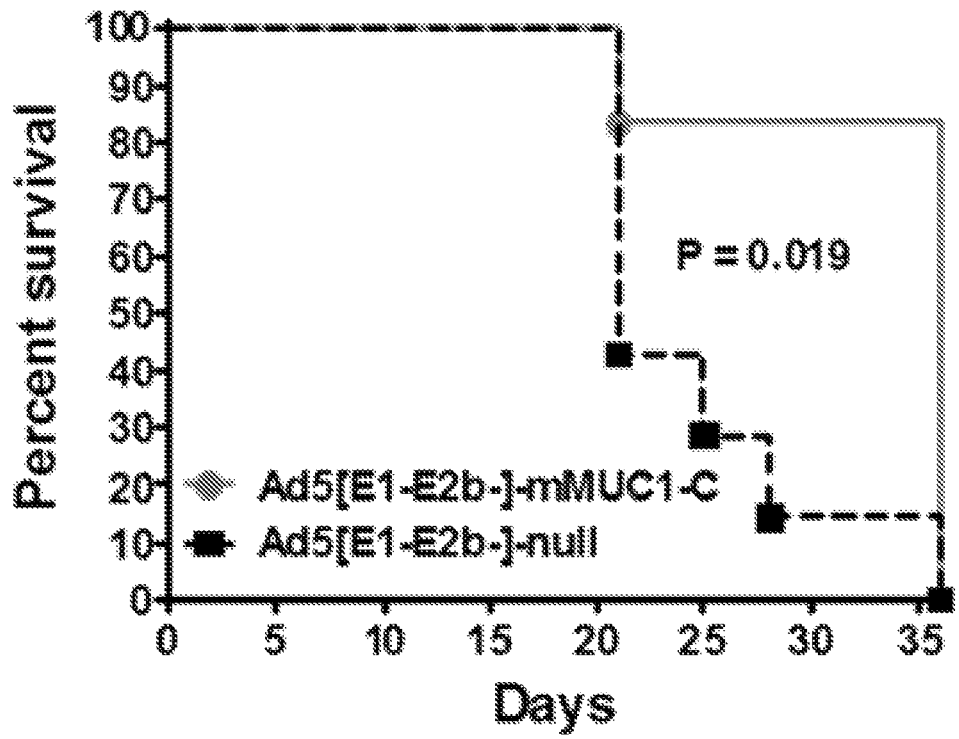

FIG. 26B exemplifies that the mice treated with Ad5 [E1-, E2b-]-mMUC1-C as described for FIG. 26A had significantly (p<0.05) longer survival on days 15 and 18 compared to controls.

Figure 27:
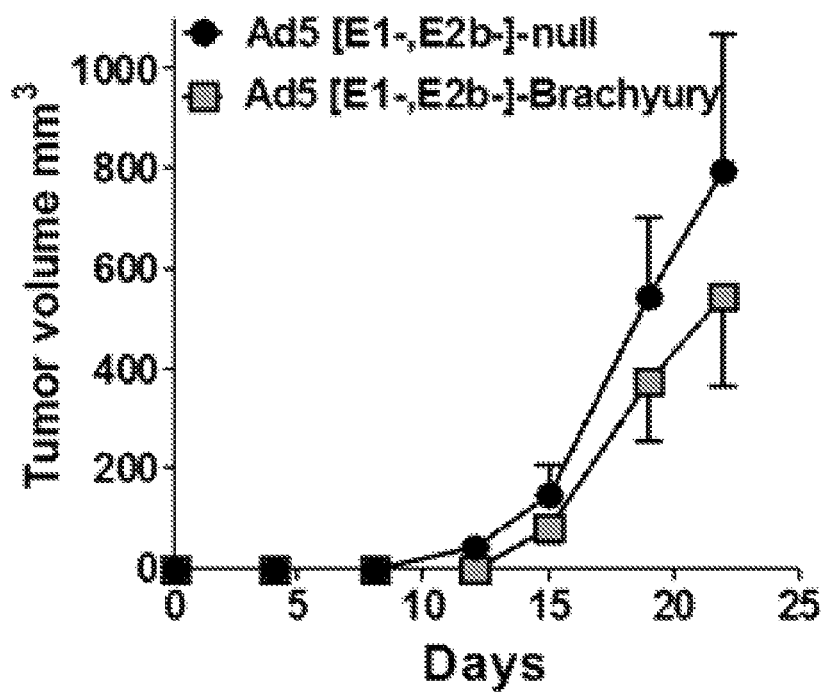

FIG. 27 exemplifies results from C57Bl/6 mice subcutaneously inoculated in the left flank with MC38 tumor cells expressing Brachyury and administered $1 \times 10^{10}$ Ad5-null VPs (n=4) or $1 \times 10^{10}$ Ad5 [E1-, E2b-]-Brachyury VPs (n=5) in the right flank on days 5, 11, and 17. Tumors were smaller in treated mice on days 15, 19, and 22.

Figure 28:
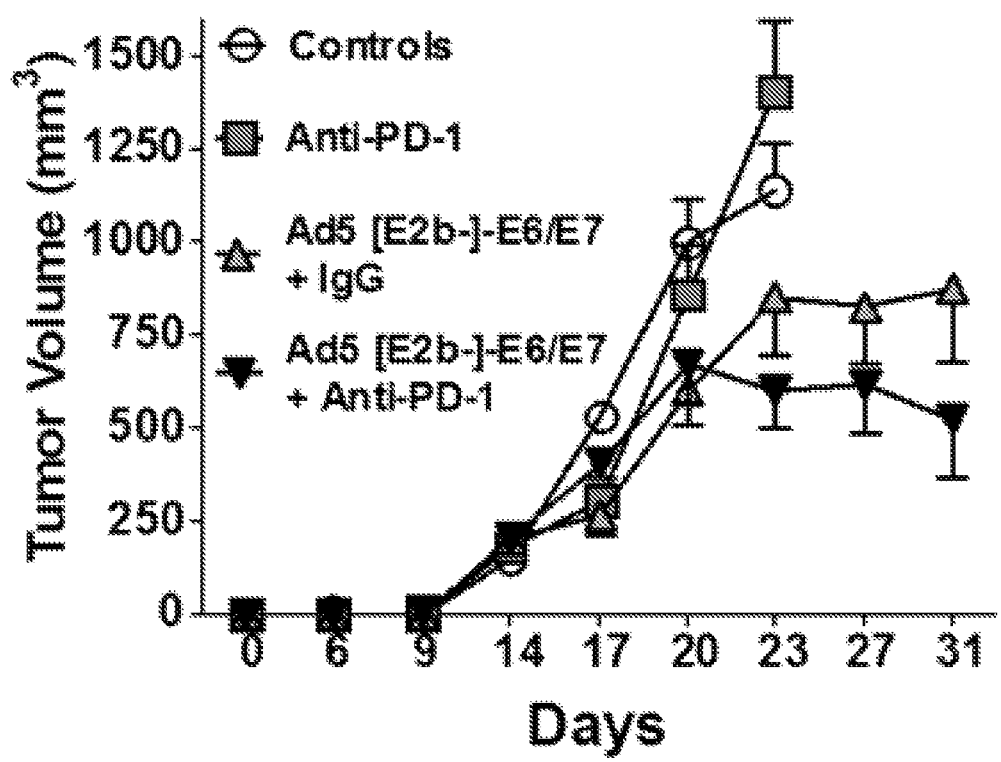

FIG. 28 exemplifies the effects of HPV immunotherapy in C57Bl/6 mice (n=7/group) implanted with HPV-E6/E7 expressing TC-1 tumor cells (day 0) and treated by immunotherapy on days 10, 17, 24 with $1 \times 10^{10}$ Ad5-null VPs plus 100 μg control IgG (intraperitoneal), $1 \times 10^{10}$ Ad5-null VPs plus 100 μg anti-PD1, $1 \times 10^{10}$ Ad5 [E1-, E2b-]-HPV-E6/E7 VPs plus 100 μg mouse IgG, or $1 \times 10^{10}$ Ad5 [E1-, E2b-]-HPV-E6/E7 VPs plus 100 μg anti-PD1. Immunotherapy with or without anti-PD1 resulted in significant inhibition of tumor growth by day 23 (p<0.05). All control mice were terminated by day 23 due to tumor mass.

Figure 29:
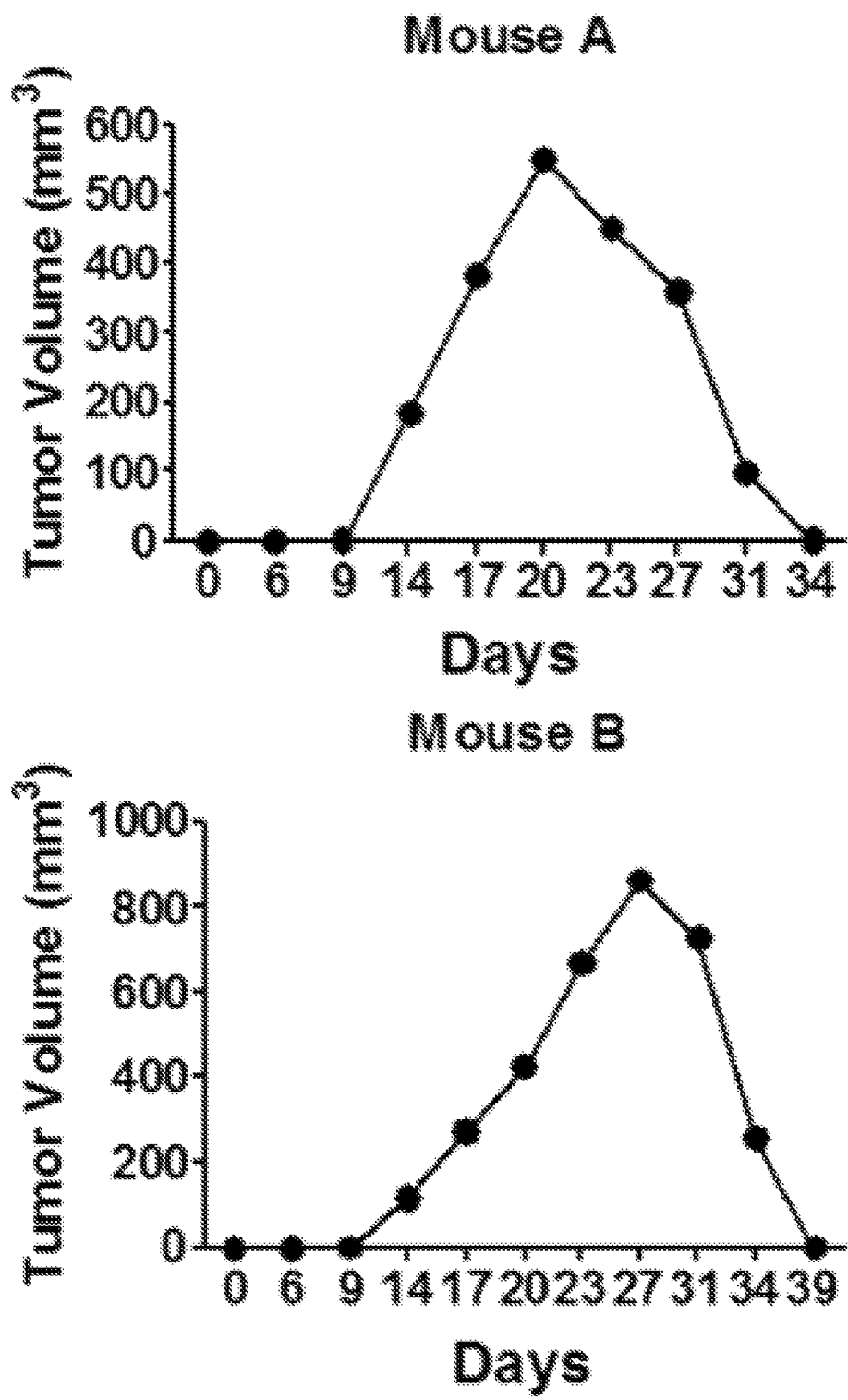

FIG. 29 exemplifies combination multi-targeted HPV immunotherapy effects on tumor growth and regression in 2 mice treated by immunotherapy with anti-PD1 injections in FIG. 28. Tumor growth peaked on days 20 and 27, respectively, and then regressed thereafter.

Figure 30A:
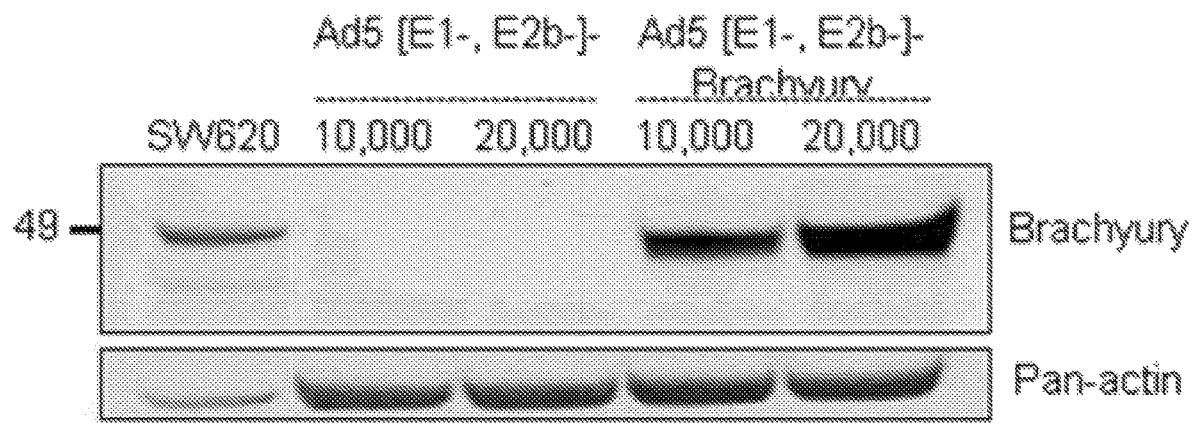

FIG. 30A exemplifies expression of Brachyury protein in human dendritic cells (DCs) infected with Ad5 [E1-, E2b-]-Brachyury. SW620 tumor cells were used as positive control. Actin was used as a loading control. Expression of Brachyury was robust in DCs infected with Ad5 [E1-, E2b-]-Brachyury.

Figure 30B:
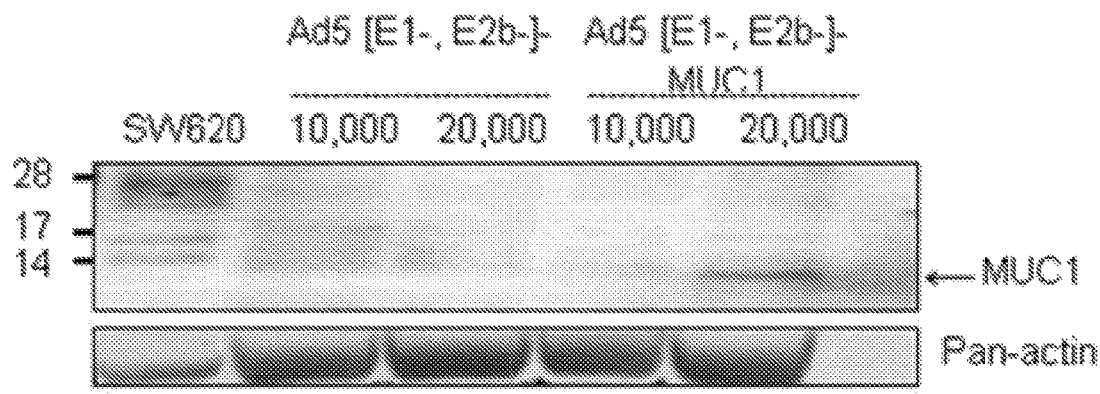

FIG. 30B exemplifies expression of MUC1 protein in human DCs infected with Ad5 [E1-, E2b-]-MUC1. SW620 tumor cells were used as positive control. Actin was used as a loading control. MUC1 expression was observed in human DCs infected with Ad5 [E1-, E2b-]-MUC1 vector as compared to DCs infected with Ad5 [E1-, E2b-]-null.

Figures 31A, 31B:
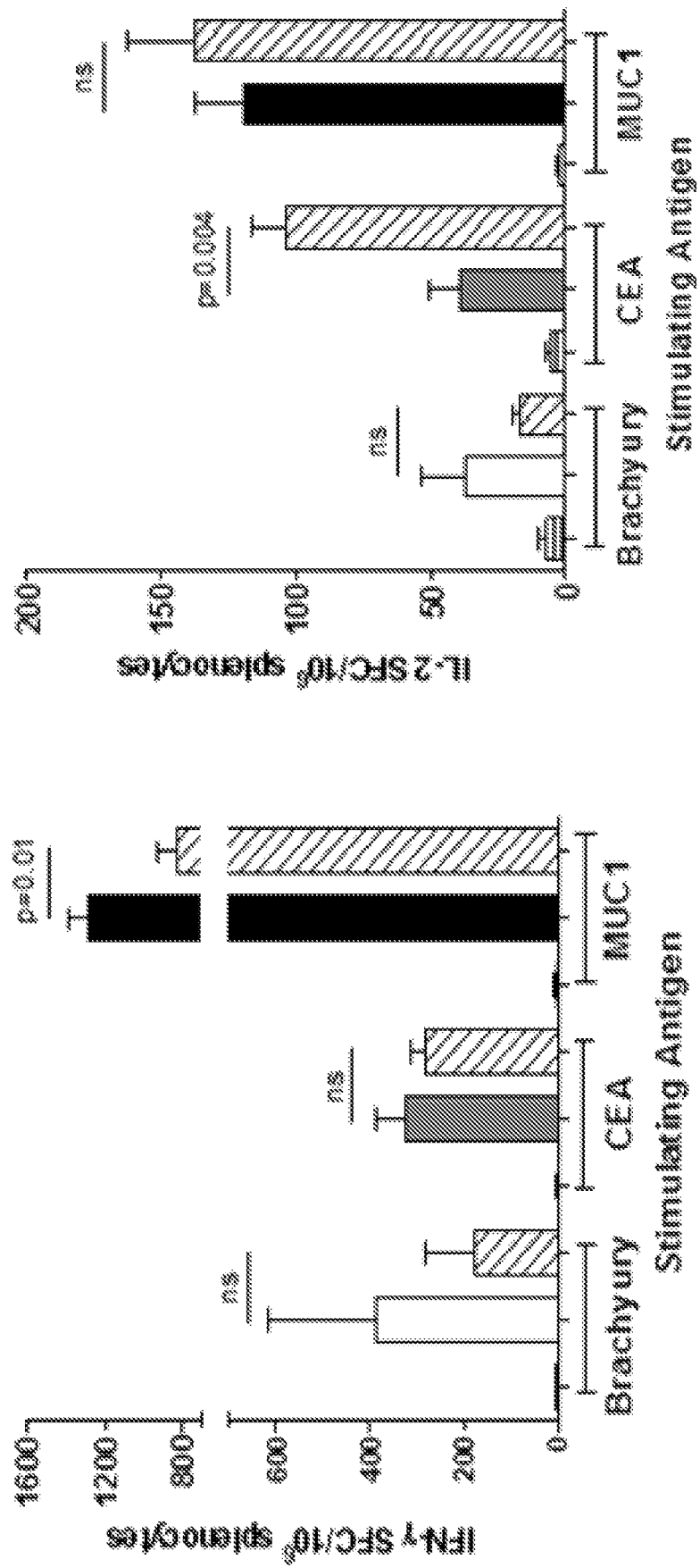

FIG. 31A exemplifies analyses of IFN-γ secreted from splenocytes from C57Bl/6 mice (n=5/group) vaccinated three times at 2-week intervals with $1 \times 10^{10}$ Ad5 [E1-, E2b-]-Brachyury VPs, $1 \times 10^{10}$ Ad5 [E1-, E2b-]-CEA VPs, $1 \times 10^{10}$ Ad5 [E1-, E2b-]-MUC1 VPs, or Tri-Ad5 (1:1:1 mixture of $1 \times 10^{10}$ Ad5 [E1-, E2b-]-Brachyury VPs, $1 \times 10^{10}$ Ad5 [E1-, E2b-]-CEA VPs, and $1 \times 10^{10}$ Ad5 [E1-, E2b-]-

MUC1 VPs). Controls received $3 \times 10^{10}$ Ad5-null VPs. Splenocytes were collected 14 days after the final vaccination and assessed for IFN-γ secretion by ELISpot assay. Positive control splenocytes were exposed to Con A. Significant differences (p<0.05) between columns are reported in p-values. Not significant=ns.

FIG. 31B exemplifies analyses of IL-2 secreted from splenocytes from the vaccinated mice described in FIG. 31A. Splenocytes were assessed for IL-2 secretion by ELISpot assay.

Figures 32A, 32B:
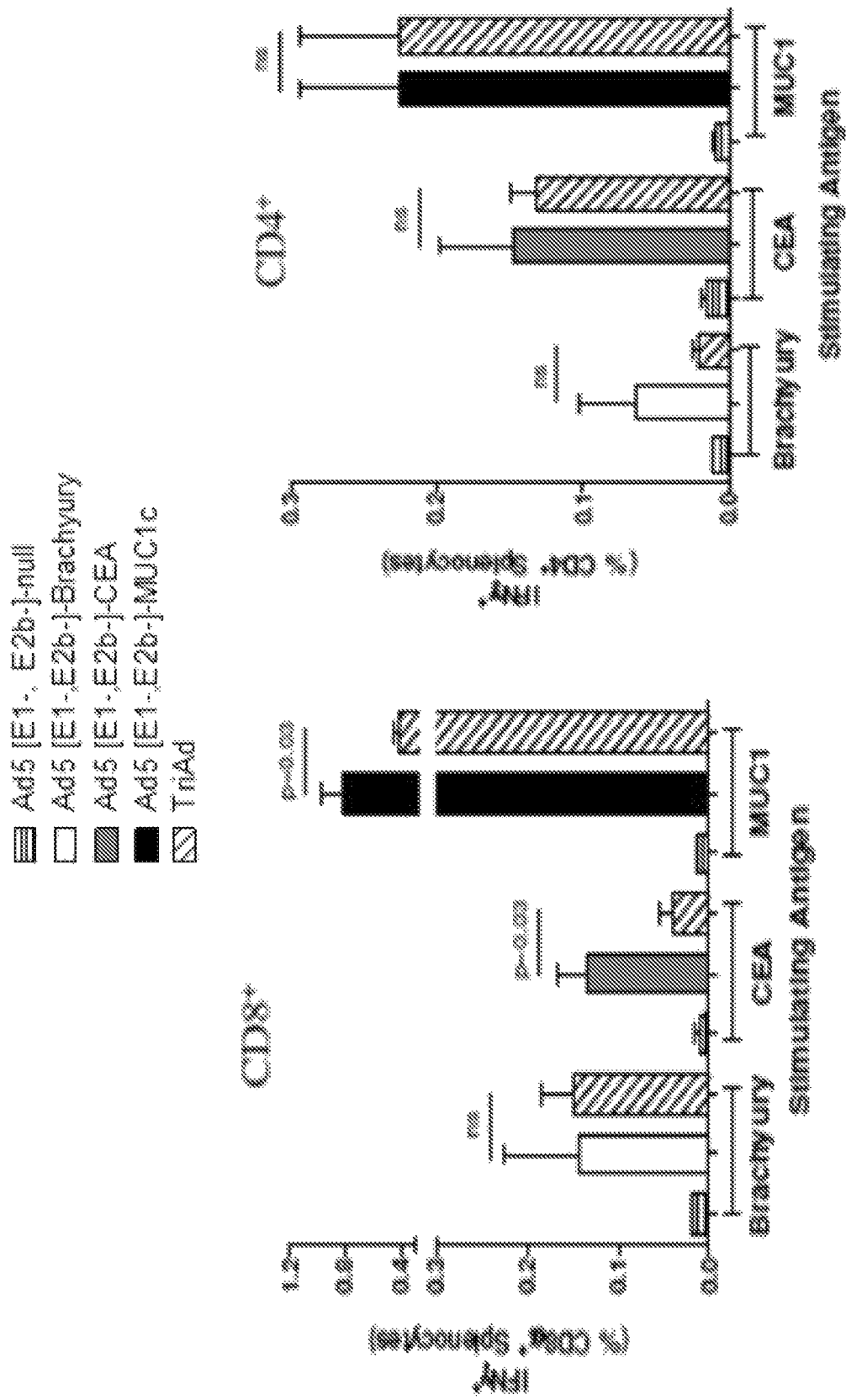

FIG. 32A exemplifies a graph of analyses of CD8+ and multifunctional cellular populations following vaccination of C57Bl/6 mice (n=5/group) vaccinated three times at 2-week intervals with $1 \times 10^{10}$ Ad5 [E1-, E2b-]-Brachyury VPs, $1 \times 10^{10}$ Ad5 [E1-, E2b-]-CEA VPs, $1 \times 10^{10}$ Ad5 [E1-, E2b-]-MUC1 VPs or Tri-Ad5 (1:1:1 mixture of $1 \times 10^{10}$ Ad5 [E1-, E2b-]-Brachyury VPs, $1 \times 10^{10}$ Ad5 [E1-, E2b-]-CEA VPs, and $1 \times 10^{10}$ Ad5 [E1-, E2b-]-MUC1 VPs). Controls received $3 \times 10^{10}$ Ad5 [E1-, E2b-]-null VPs. Splenocytes were collected 14 days after the final vaccination and were assessed by FACS for CD8α+ cells secreting IFN-γ and TNF-α. Positive control splenocytes were exposed to Con A.

FIG. 32B exemplifies a graph of FACS analyses of CD4+ cells and multifunctional cellular populations from the vaccinated mice described in FIG. 32A.

Figures 32C, 32D:
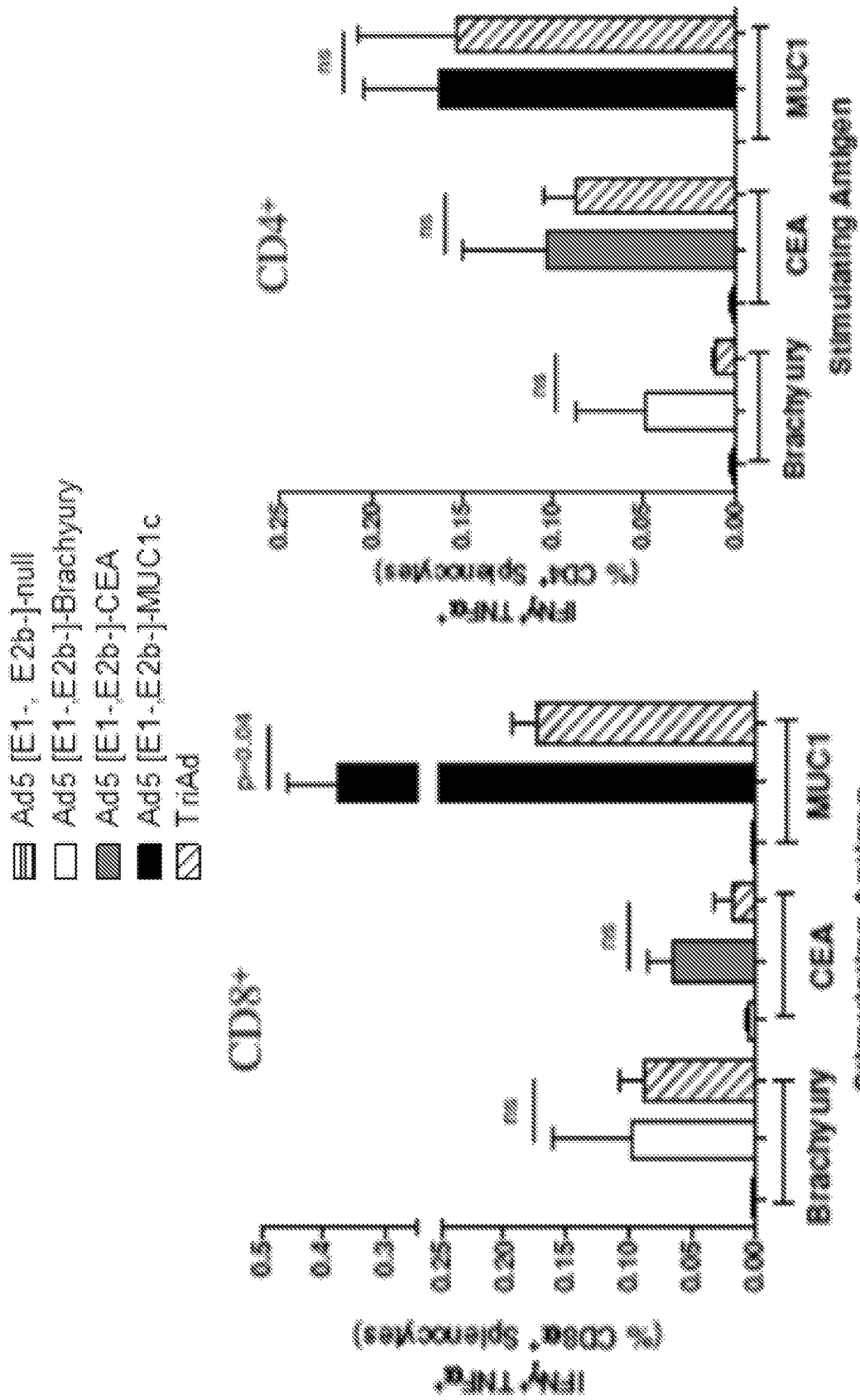

FIG. 32C exemplifies a graph of FACS analyses of CD8α+ cells secreting IFN-γ and TNF-α from the vaccinated mice described in FIG. 32A.

FIG. 32D exemplifies a graph of FACS analyses of CD4+ cells secreting IFN-γ and TNF-α from the vaccinated mice described in FIG. 32A.

Figure 33A:
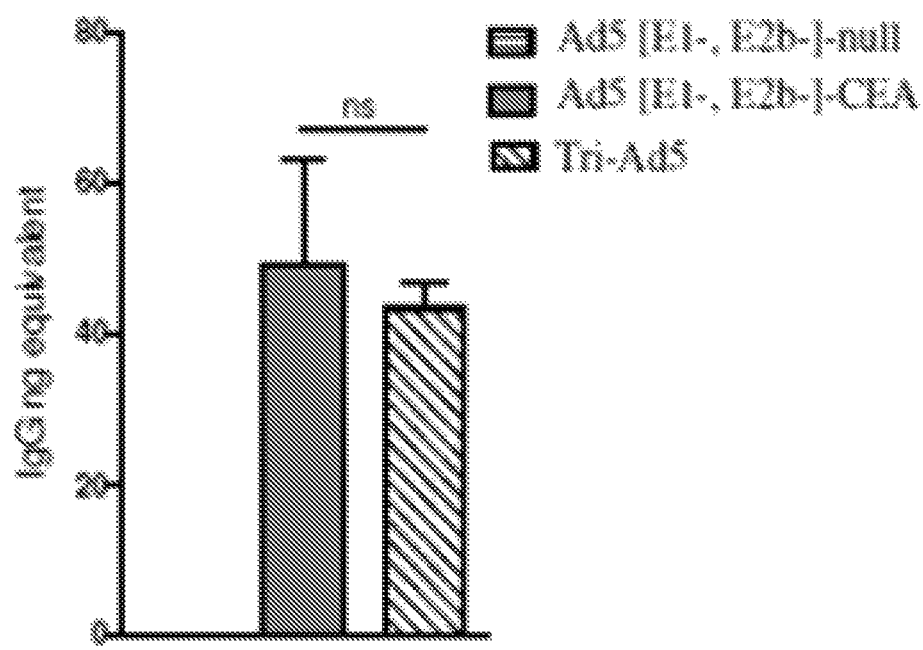

FIG. 33A exemplifies an ELISA analysis of CEA IgG levels in mice vaccinated three times with $1 \times 10^{10}$ Ad5 [E1-, E2b-]-CEA VPs, Tri-Ad5 (1:1:1 mixture of $1 \times 10^{10}$ Ad5 [E1-, E2b-]-Brachyury VPs, $1 \times 10^{10}$ Ad5 [E1-, E2b-]-CEA VPs, and $1 \times 10^{10}$ Ad5 [E1-, E2b-]-MUC1 VPs), or $3 \times 10^{10}$ Ad5 [E1-, E2b-]-null VPs.

Figure 33B:
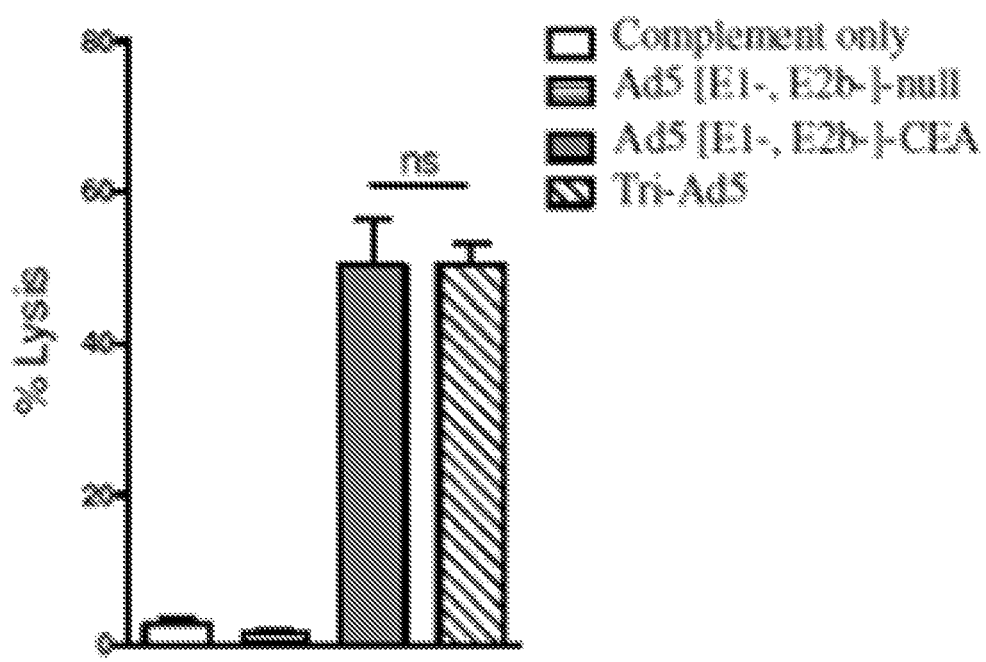

FIG. 33B exemplifies a CDC assay against MC38-CEA2 cells using the mice described in FIG. 33A.

Figure 34:
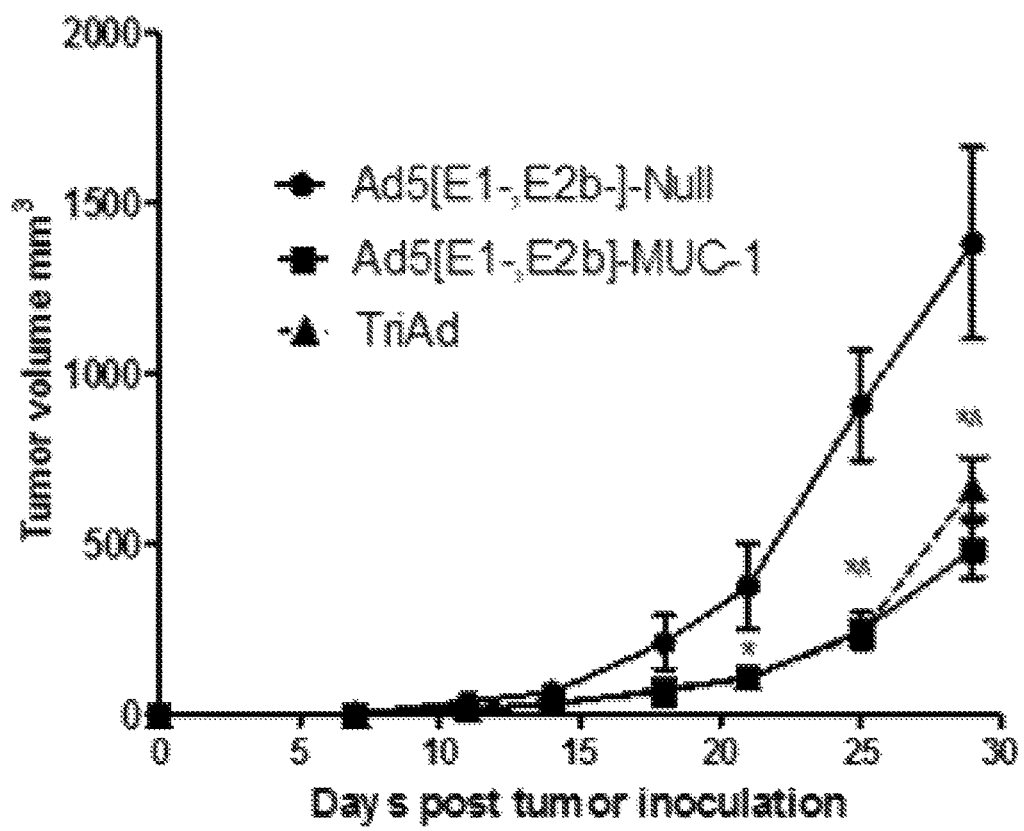

FIG. 34 exemplifies effects of immunotherapy on tumor volume in C57Bl/6 mice (n=7/group) inoculated subcutaneously in the left flank with $1 \times 10^{6}$ MC-38-MUC1 cells and $1 \times 10^{10}$ Ad5 [E1-, E2b-]-MUC1 VPs or Tri-Ad5 (1:1:1 mixture of $1 \times 10^{10}$ Ad5 [E1-, E2b-]-CEA VPs, $1 \times 10^{10}$ Ad5 [E1-, E2b-]-MUC1 VPs, and $1 \times 10^{10}$ Ad5 [E1-, E2b-]-Brachyury VPs ($3 \times 10^{10}$ VP total)). Control mice received $3 \times 10^{10}$ Ad5 [E1-, E2b-]-null VPs. (*) indicates days when Ad5 [E1-, E2b-]-MUC1 treated mice had significantly smaller (p<0.05) tumors than control mice and (^) indicates days when Tri-Ad5-treated mice had significantly smaller (p<0.05) tumors than control mice. No significant difference (p>0.1) between Ad5 [E1-, E2b-]-MUC1 and Tri-Ad5-treated mice was seen.

Figure 35:
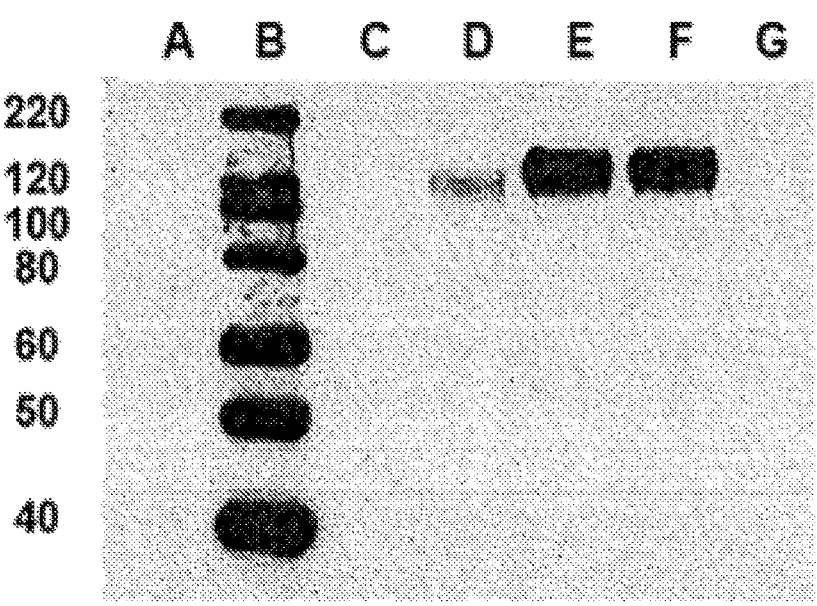

FIG. 35 exemplifies an immunoblot showing expression of CEA in A549 cells infected with Ad5 [E1-, E2b-]-CEA. (A) Negative Control. (B) Protein molecular weight marker. (C) Negative. (D) CEA Reference Material (30 ng). (E) Ad5 [E1-, E2b-]-CEA lysate (20 μL). (F) Ad5 [E1-, E2b-]-CEA lysate (20 μL). (G) Negative A549 cells. Recombinant CEA was used as a positive control and uninfected A549 cells served as a negative control.

Figure 36:
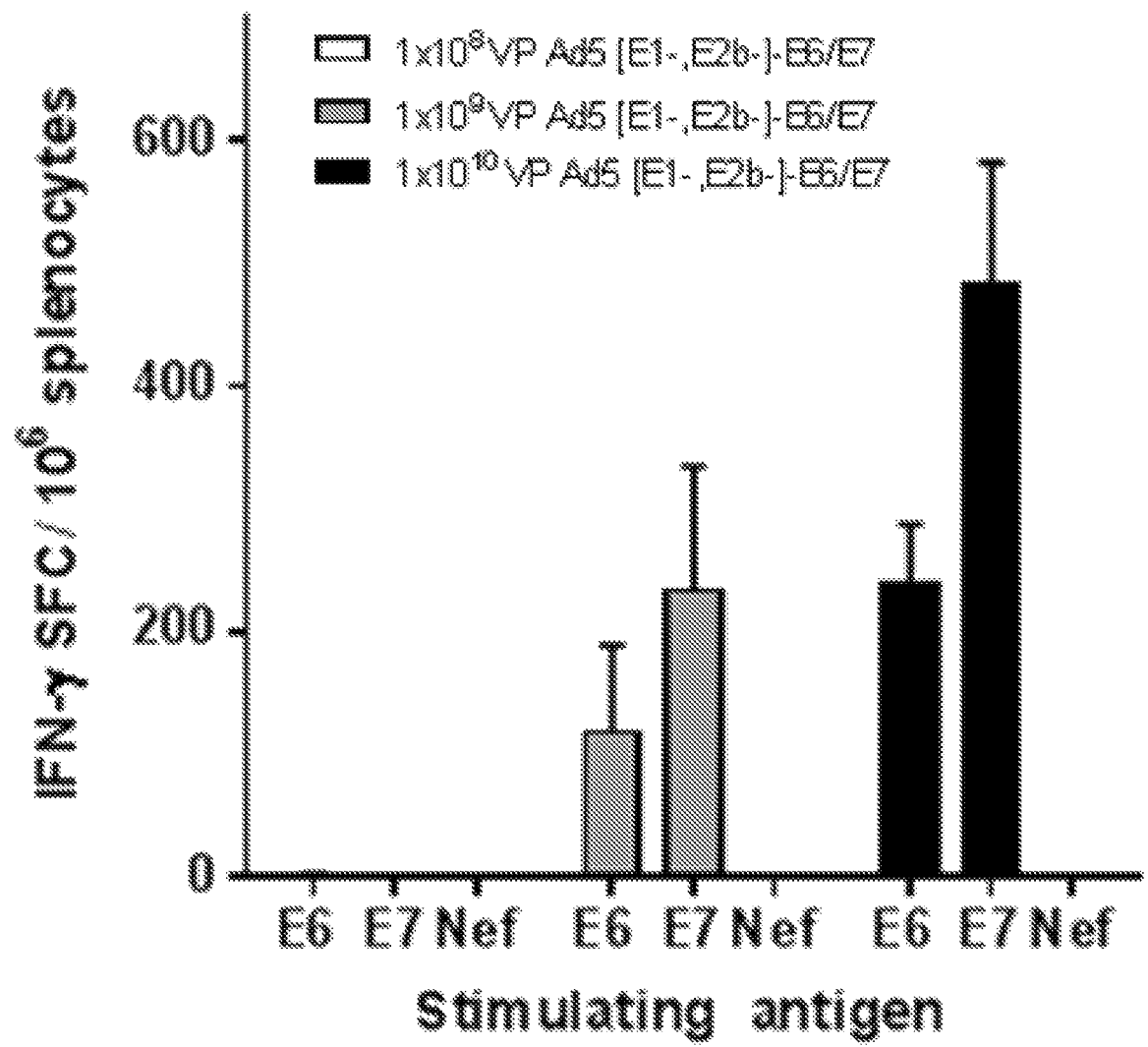

FIG. 36 exemplifies CMI dose responses as measured by ELISpot of splenocytes from C57BL/6 mice (n=5/group) immunized three times at 14-day intervals with doses of $1 \times 10^{8}$, $1 \times 10^{9}$ or $1 \times 10^{10}$ Ad5 [E1-, E2b-]-E6/E7 VPs and assessed 14 days after the final immunization. The greatest induction of CMI was achieved with the $1 \times 10^{10}$ VP dose. Positive control splenocytes were exposed to Con A.

FIG. 37A exemplifies activation of CD8-α+/IFN-γ+ splenocytes after immunization of C57BL/6 mice (n=5/group) immunized three times at two week intervals with $1 \times 10^{10}$ VP Ad5 [E1-, E2b-]-E6/E7 VPs. Controls received $1 \times 10^{10}$ Ad5 [E1-, E2b-]-null VPs. Splenocytes collected 14 days after the final immunization were assessed by flow cytometry for. For positive controls, splenocytes were exposed to PMA/ionomycin.

FIG. 37B exemplifies activation of CD8-α+/IFN-γ+/TNF-α+ splenocytes after immunization of mice as described in FIG. 37A.

Figure 38A:
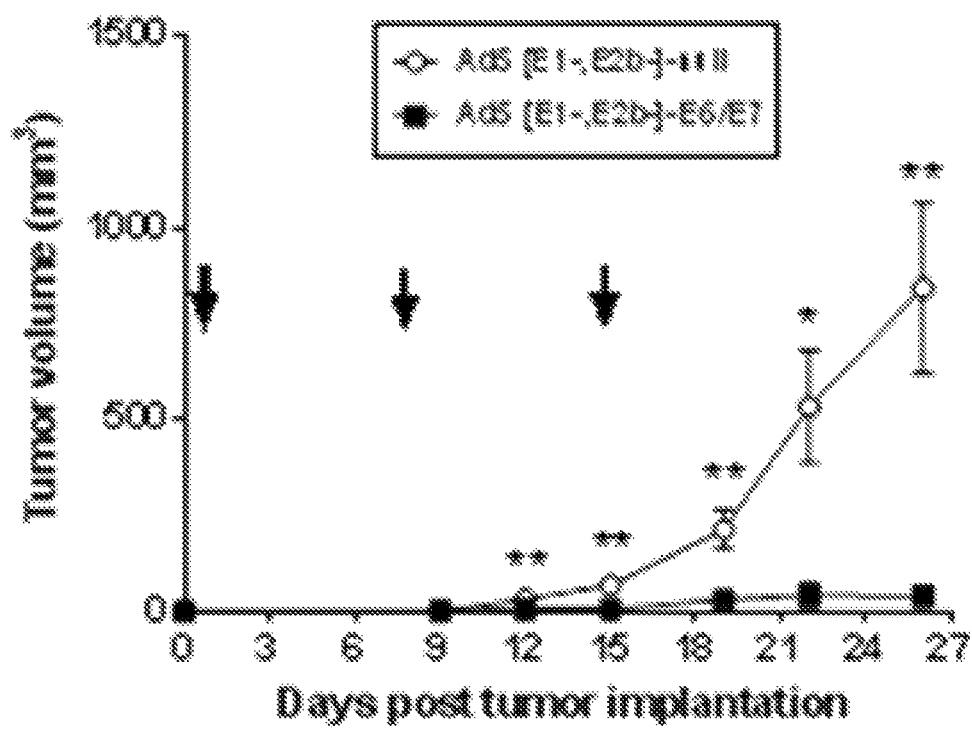

FIG. 38A exemplifies changes in tumor size from immunotherapy of C57BL/6 mice (n=5/group) implanted on day 0 with $2 \times 10^{5}$ non-palpable HPV-E6/E7 TC-1 tumor cells and administered $1 \times 10^{10}$ Ad5 [E1-, E2b-]-null VPs or $1 \times 10^{10}$ Ad5 [E1-, E2b-]-E6/E7 VPs on days 1, 8 and 15. Tumor size was determined and volumes calculated according to the formula $V=(a^2 \times b)/2$. Analysis of significance was performed between experimental and vector control groups using unpaired t-tests and significance is denoted by * (p<0.05) and ** (p<0.01).

Figure 38B:
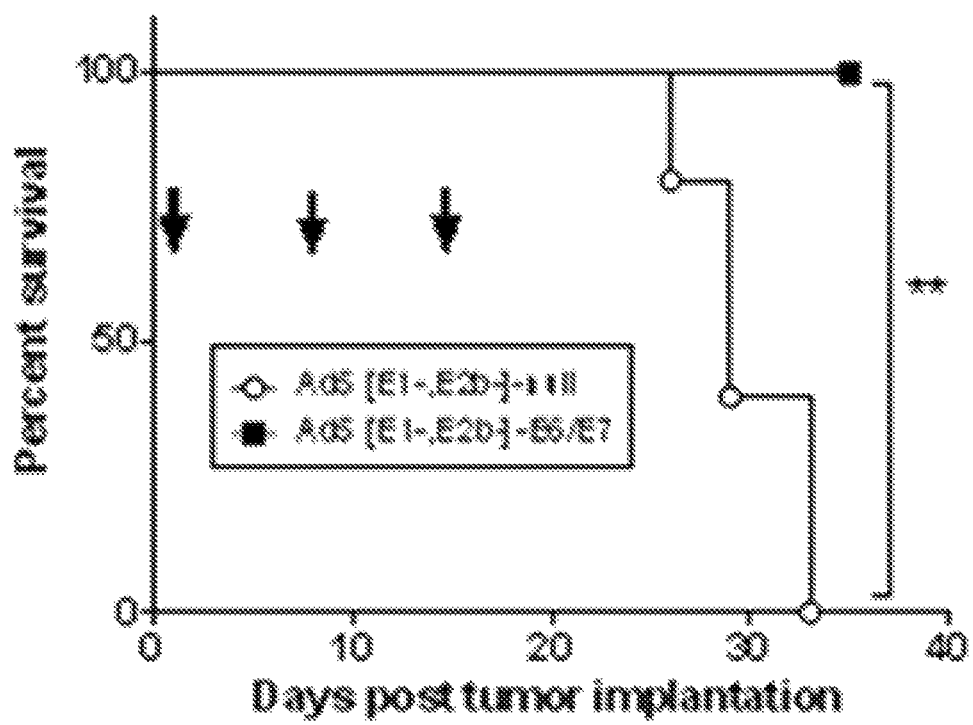

FIG. 38B exemplifies a survival curve of the mice as described in FIG. 38A that was plotted and compared using the Mantel-Cox test. Significance is denoted by ** (p<0.01).

Figure 39A:
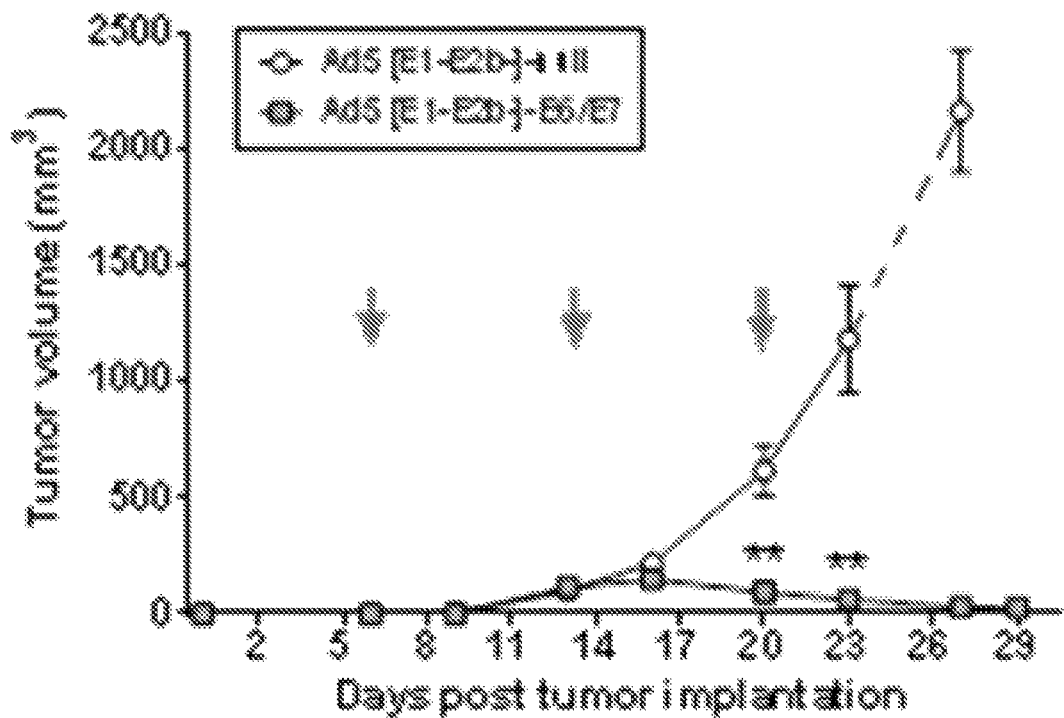

FIG. 39A exemplifies changes in tumor size from immunotherapy of C57BL/6 mice (n=4/group) implanted on day 0 with $2 \times 10^{5}$ small palpable HPV-E6/E7 TC-1 tumor cells and administered $1 \times 10^{10}$ Ad5 [E1-, E2b-]-null VPs or $1 \times 10^{10}$ Ad5 [E1-, E2b-]-E6/E7 VPs on days 6, 13 and 20. Tumor size was determined and volumes calculated according to the formula $V=(a^2 \times b)/2$. Analysis of significance was performed between experimental and vector control groups using unpaired t-tests and significance is denoted by ** (p<0.01).

Figure 39B:
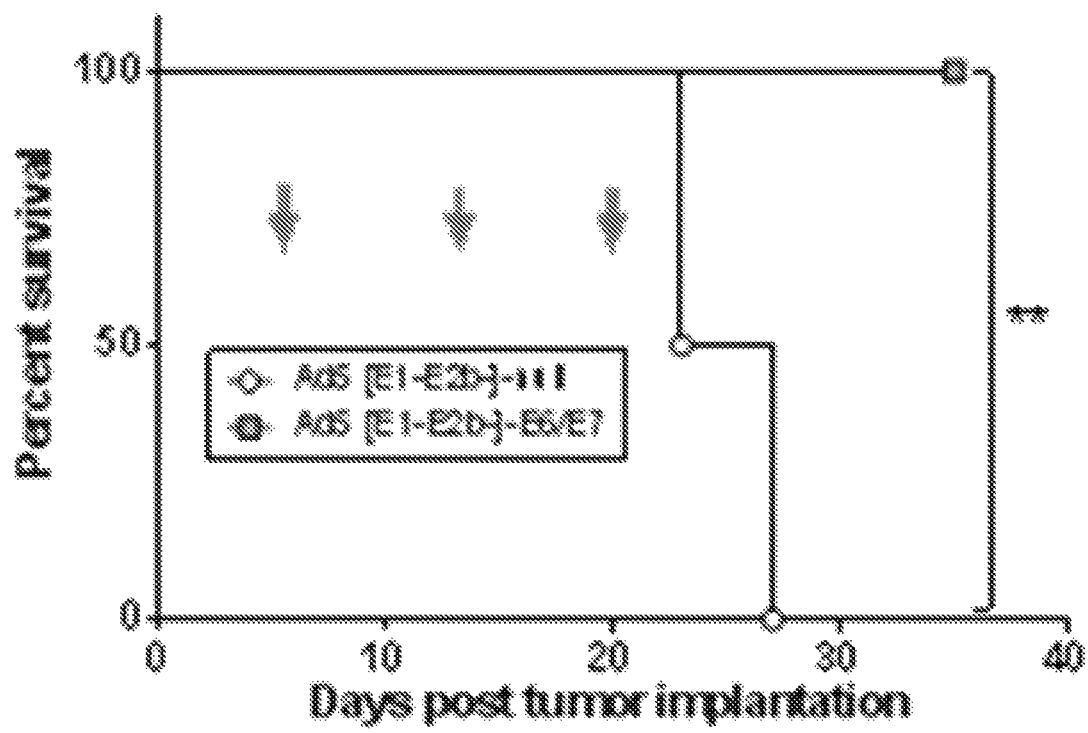

FIG. 39B exemplifies a survival curve of the mice as described in FIG. 39A that was plotted and compared using the Mantel-Cox test. Significance is denoted by ** (p<0.01).

Figure 40A:
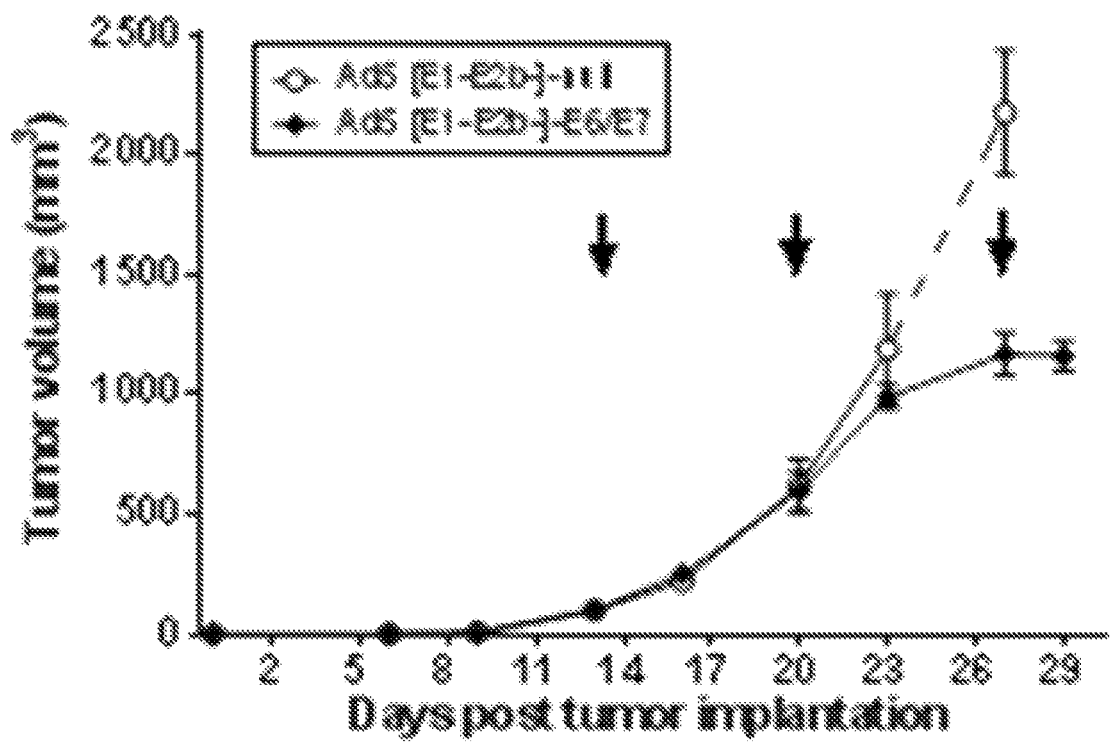

FIG. 40A exemplifies changes in tumor size from immunotherapy of C57BL/6 mice (n=4/group) implanted on day 0 with $2 \times 10^{5}$ large established HPV-E6/E7 TC-1 tumor cells and administered $1 \times 10^{10}$ Ad5 [E1-, E2b-]-null VPs or $1 \times 10^{10}$ Ad5 [E1-, E2b-]-E6/E7 VPs on days 13, 20 and 27. Tumor size was determined and volumes calculated according to the formula $V=(a^2 \times b)/2$. Analysis of significance was performed between experimental and vector control groups using unpaired t-tests and significance is denoted by ** (p<0.01).

Figure 40B:
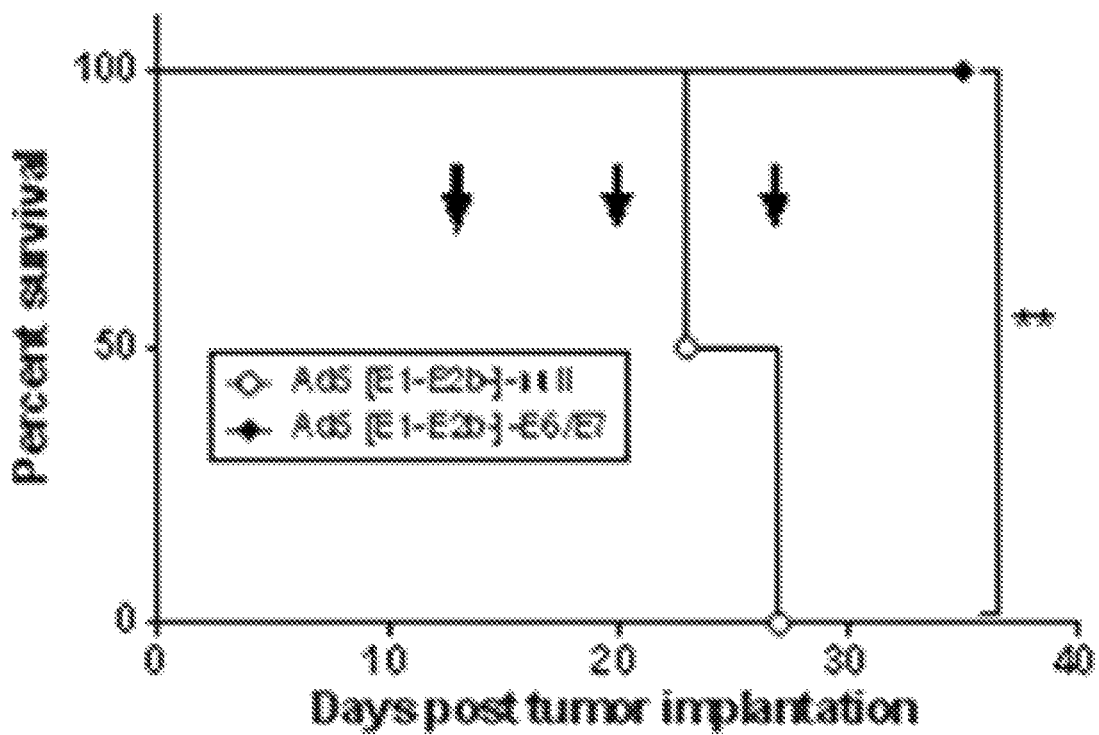

FIG. 40B exemplifies a survival curve of the mice as described in FIG. 40A that was plotted and compared using the Mantel-Cox test. Significance is denoted by ** (p<0.01).

Figure 41A:
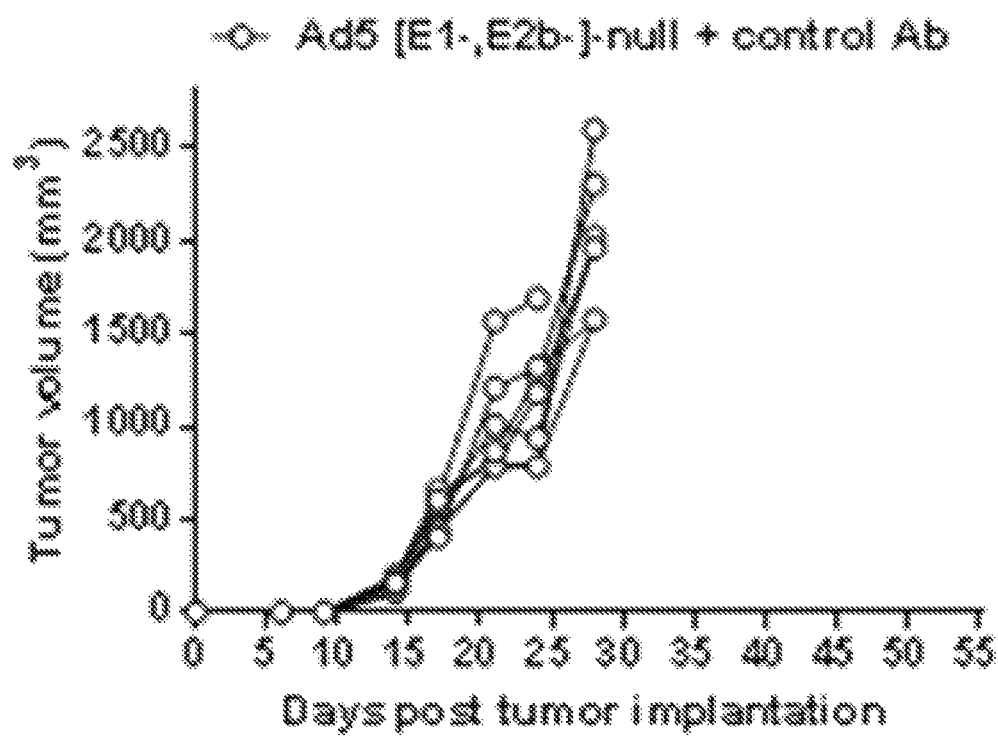

FIG. 41A exemplifies changes in tumor size from C57BL/6 mice (n=7/group) inoculated on day 0 with $2 \times 10^{5}$ TC-1 tumor cells and administered treatments on days 10, 17, and 24 with $1 \times 10^{10}$ Ad5 [E1-, E2b-]-null VPs plus 100 μg of isotype control rat IgG. Tumor size was determined and volumes calculated according to the formula $V=(a^2 \times b)/2$. Tumor growth kinetics represents individual mice in each group.

Figure 41B:
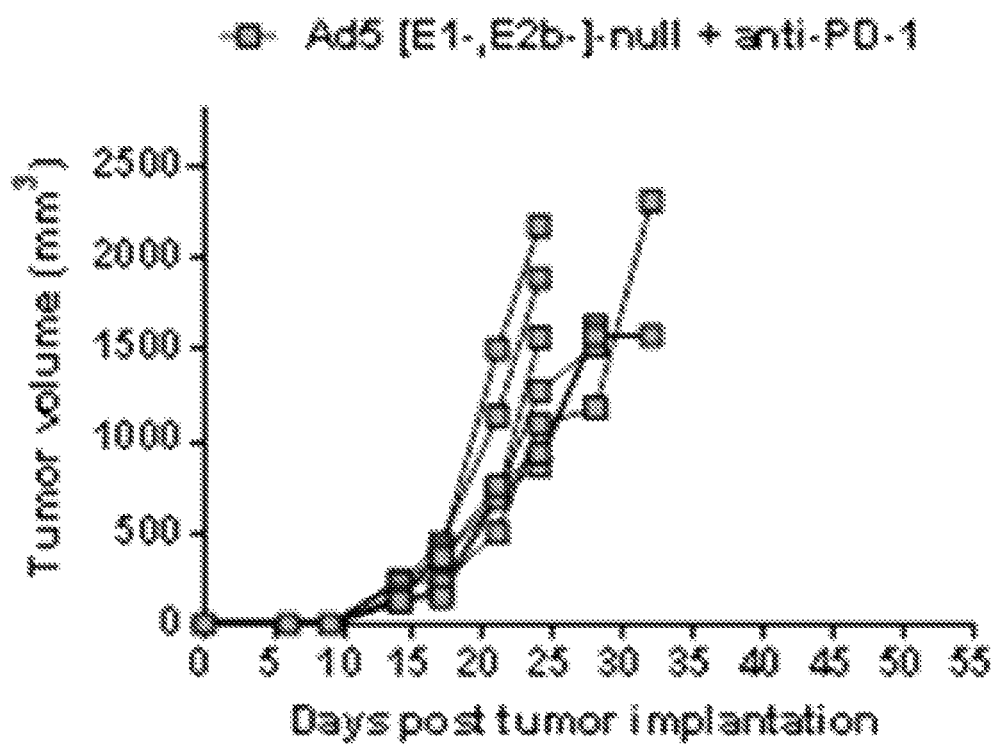

FIG. 41B exemplifies changes in tumor size from C57BL/6 mice (n=7/group) inoculated on day 0 with $2 \times 10^{5}$ TC-1 tumor cells and administered treatments on days 10, 17, and 24 with $1 \times 10^{10}$ Ad5 [E1-, E2b-]-null VPs plus 100 μg anti-PD1 antibody.

Figure 41C:
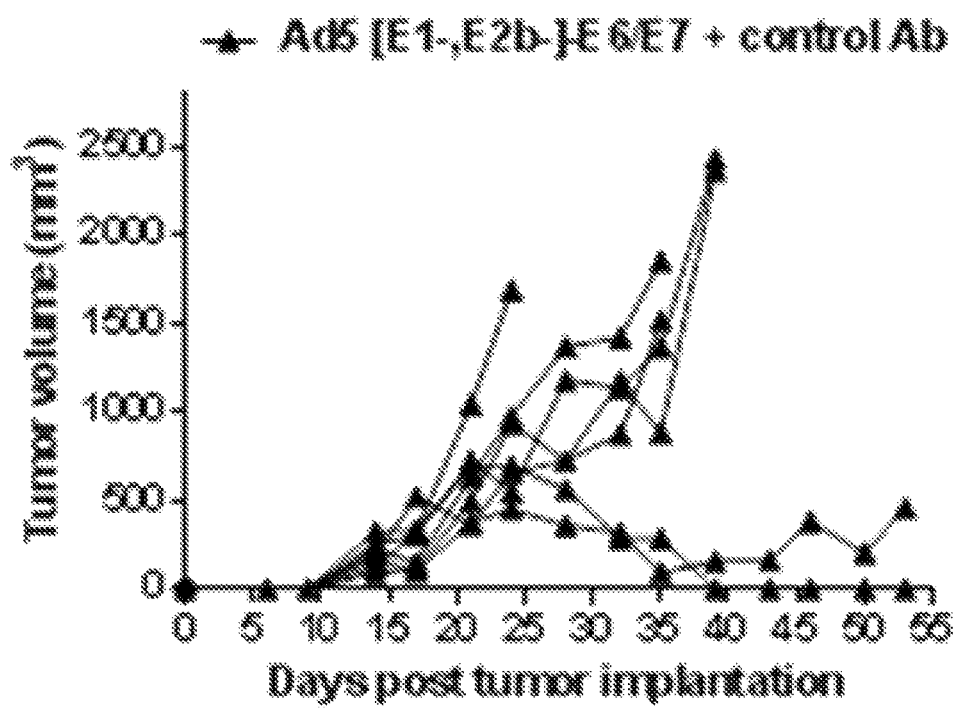

FIG. 41C exemplifies changes in tumor size from C57BL/6 mice (n=7/group) inoculated on day 0 with $2 \times 10^{5}$ TC-1 tumor cells and administered treatments on days 10, 17, and 24 with 1×10$^{10}$ Ad5 [E1-, E2b-]-E6/E7 VPs plus 100 µg isotype control rat IgG.

Figure 41D:
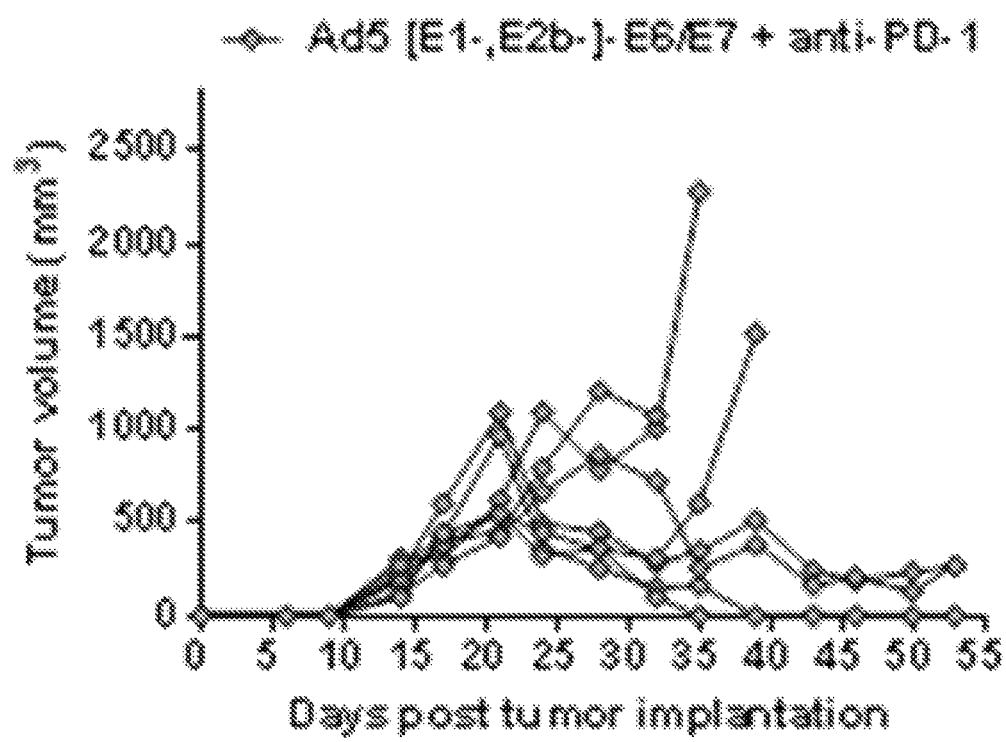

FIG. 41D exemplifies changes in tumor size from C57BL/6 mice (n=7/group) inoculated on day 0 with 2×10$^5$ TC-1 tumor cells and administered treatments on days 10, 17, and 24 with 1×10$^{10}$ Ad5 [E1-, E2b-]-E6/E7 VPs plus 100 µg anti-PD1.

Figure 42:
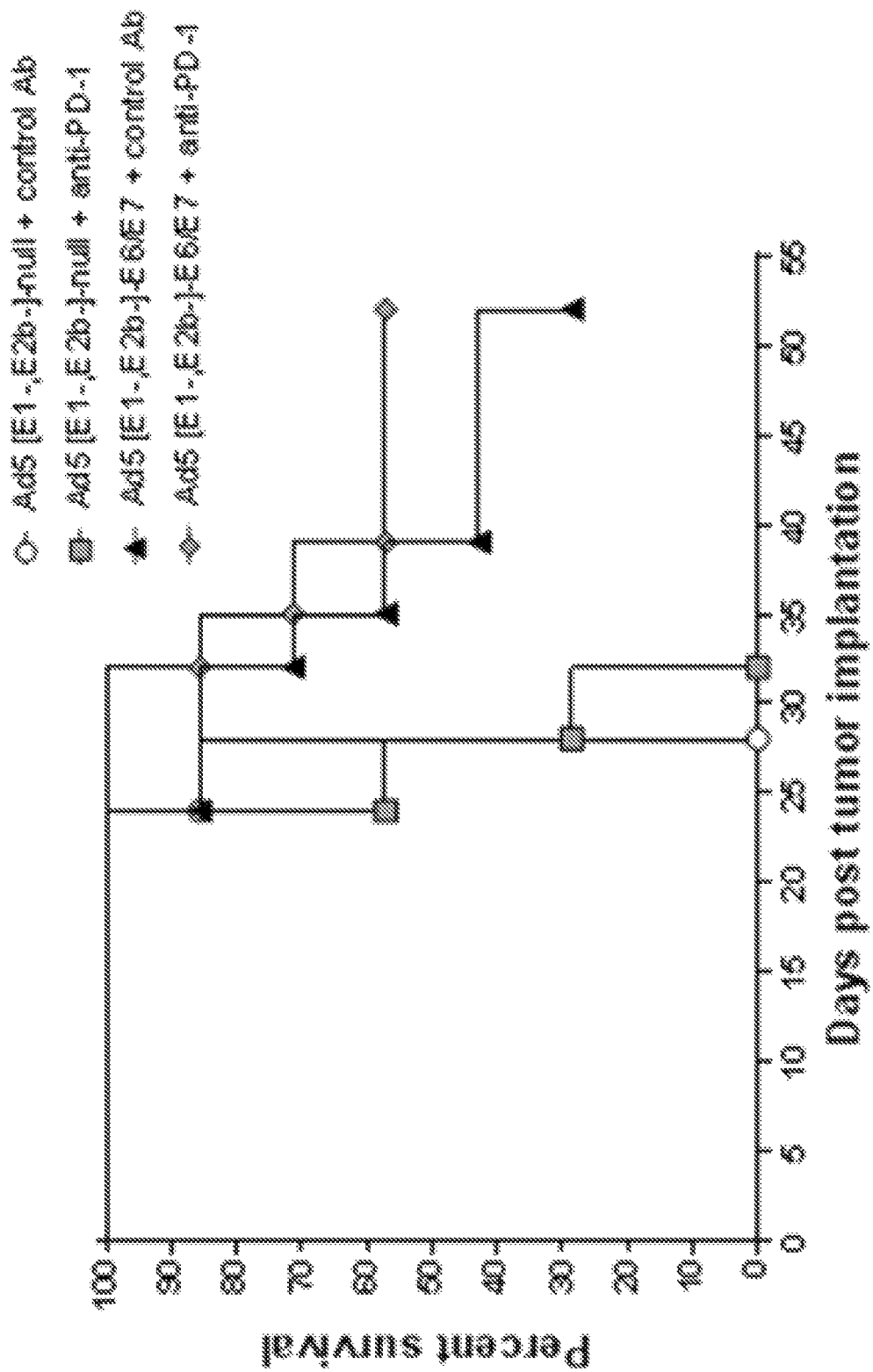

FIG. 42 exemplifies a survival curve for C57BL/6 mice (n=7/group) treated as those in FIGS. 41A-D. The experiment was terminated on day 52 following tumor implantation. Mice treated with Ad5 [E1-, E2b-]-E6/E7 and control antibody exhibited significantly (p<0.008) longer survival compared to both groups of control mice (Ad5 [E1-, E2b-]-null and control antibody or Ad5 [E1-, E2b-]-null and anti-PD1 antibody). 2 of 7 (29%) Ad5 [E1-, E2b-]-E6/E7 and control antibody treated mice remained alive at day 52. Mice treated with Ad5 [E1-, E2b-]-E6/E7 plus anti PD1 antibody exhibited significantly (p<0.0006) longer survival as compared to both groups of controls. 4 of 7 (57%) Ad5 [E1-, E2b-]-E6/E7 plus anti-PD1 antibody treated mice remained alive at day 52.

FIG. 43A exemplifies that Ad5 [E1-, E2b-]-E6/E7 promotes the recruitment of CD8+ tumor-infiltrating lymphocytes (TILs) into TC-1 tumors. C57BL/6 mice (n=5/group) were implanted with 2×105 TC-1 tumor cells. Twelve days after implantation mice began treatment with Ad5 [E1-, E2b-]-null empty vector plus control IgG, Ad5 [E1-, E2b-]-null plus anti-PD1, Ad5 [E1-, E2b-]-E6/E7 plus control IgG, or Ad5 [E1-, E2b-]-E6/E7 plus anti-P-1. Vaccine was administered subcutaneously weekly and anti-PD1 antibodies were administered via intraparietal injection every 3-4 days and tumors were analyzed on day 27. Ad5 [E1-, E2b-]-E6/E7 treatment significantly decreases the ratio of Treg/CD8+ TILs. Analysis of significance was performed using unpaired t-tests and significance is denoted by ns (p>0.05), * (p<0.05),  (p<0.01), * (p<0.001), or **** (p<0.0001).

FIG. 43B exemplifies that the reduction in the ratio of Treg/CD8+ TILs of FIG. 43A reduction is not driven by a reduction in the number of Tregs.

FIG. 43C exemplifies that the reduction in the ratio of Treg/CD8+ TILs of FIG. 43A is driven through an increase in the number of CD8+ TILs.

FIG. 44A exemplifies that Ad5 [E1-, E2b-]-E6/E7 plus anti-PD1 antibody combination therapy promotes a pro-inflammatory tumor microenvironment. C57BL/6 mice (n=5/group) were tumor implanted, treated, and tumors were analyzed as in FIGS. 43A-C. The frequency of PD1$^+$ CD4$^+$ and CD8$^+$ TILs is increased in tumors from mice treated with Ad5 [E1-, E2b-]-E6/E7. Tumors from mice treated with a combination of Ad5 [E1-, E2b-]-E6/E7 and anti-PD1 have a significantly lower frequency of PD1$^+$ CD4$^+$ and CD8$^+$ TILs (A), LAG-3$^+$ CD8$^+$ TILs (B), and (C). Analysis of significance was performed using unpaired t-tests and significance is denoted by ns (p>0.05), * (p<0.05),  (p<0.01), or * (p<0.001).

FIG. 44B exemplifies that tumors from mice treated with a combination of Ad5 [E1-, E2b-]-E6/E7 and anti-PD1 as in FIG. 44A have a significantly lower frequency of LAG-3$^+$ CD8$^+$ TILs bringing these levels more in line with tumors from control mice.

FIG. 44C exemplifies that tumors from mice treated with a combination of Ad5 [E1-, E2b-]-E6/E7 and anti-PD1 as in FIG. 44A have a significantly reduced expression level of PDL1.

Figure 45A:
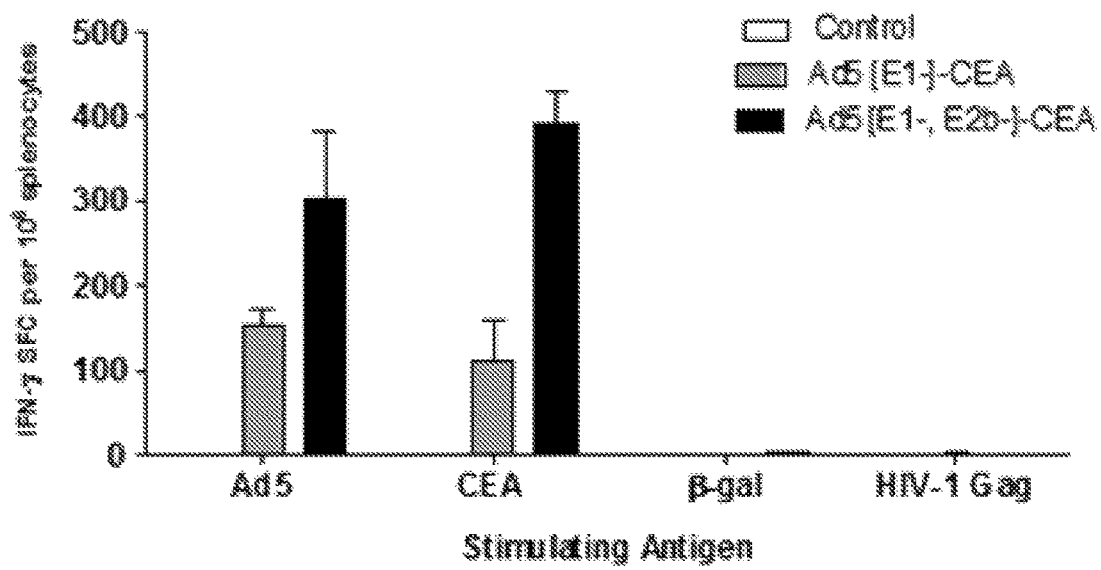

FIG. 45A exemplifies a bar graph showing INF-γ levels secreted from splenocytes from Ad5-naive mice immunized with Ad5 [E1-]-CEA(6D), Ad5 [E1-, E2b-]-CEA(6D), or injection buffer alone (control). Splenocytes were also assessed for non-specific INF-γ secreting T-cells by stimulation with the non-immunizing antigens β-galactosidase (β-gal) and HIV-1 Gag. A significantly elevated response is shown in the Ad5 [E1-, E2b-]-CEA(6D) immunized group. The errors bars depict the SEM.

Figure 45B:
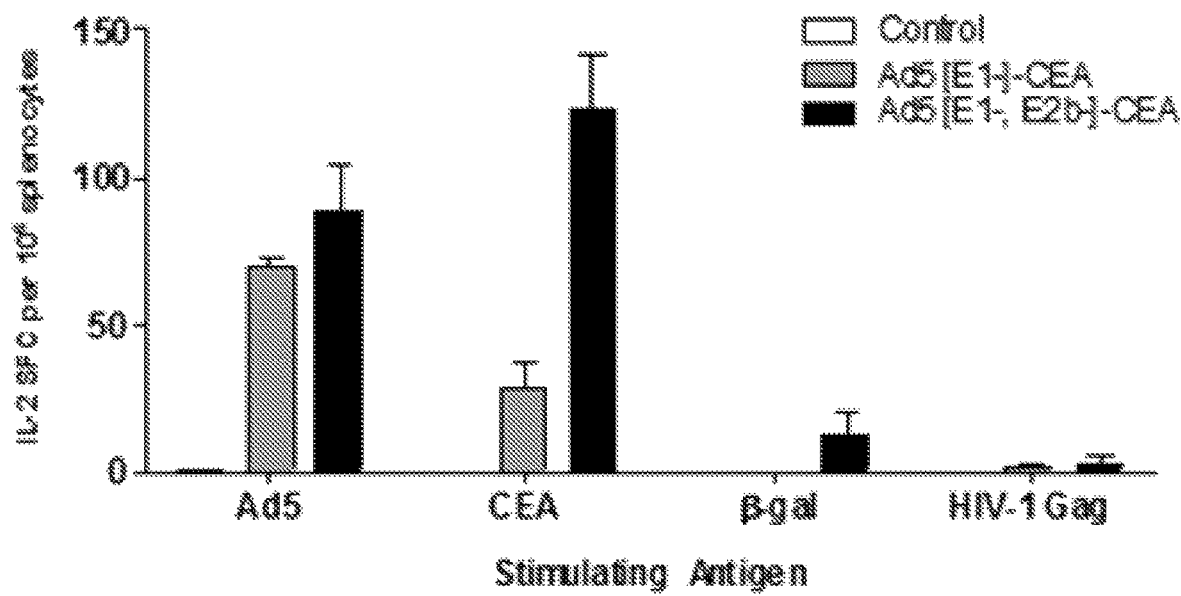

FIG. 45B exemplifies a bar graph showing IL-2 levels secreted from splenocytes from Ad5-naive mice immunized with Ad5 [E1-]-CEA(6D), Ad5 [E1-, E2b-]-CEA(6D), or injection buffer alone (control). Splenocytes were also assessed for non-specific IL-2 secreting T-cells by stimulation with the non-immunizing antigens β-galactosidase (β-gal) and HIV-1 Gag. A significantly elevated response is shown in the Ad5 [E1-, E2b-]-CEA(6D) immunized group. The errors bars depict the SEM.

Figure 46A:
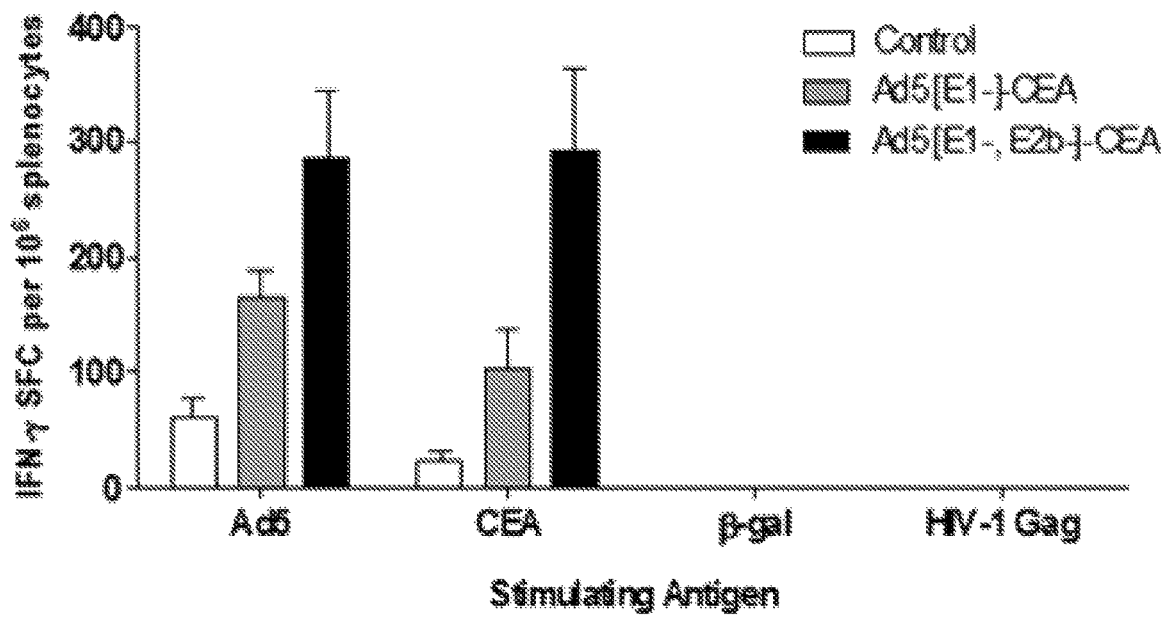

FIG. 46A exemplifies a bar graph showing INF-γ levels secreted from splenocytes from Ad5-immune mice immunized with Ad5 [E1-]-CEA(6D), Ad5 [E1-, E2b-]-CEA(6D), or injection buffer alone (control). Splenocytes were also assessed for non-specific INF-γ secreting T-cells by stimulation with the non-immunizing antigens β-galactosidase (β-gal) and HIV-1 Gag. A significantly elevated response is shown in the Ad5 [E1-, E2b-]-CEA(6D) immunized group. The errors bars depict the SEM.

Figure 46B:
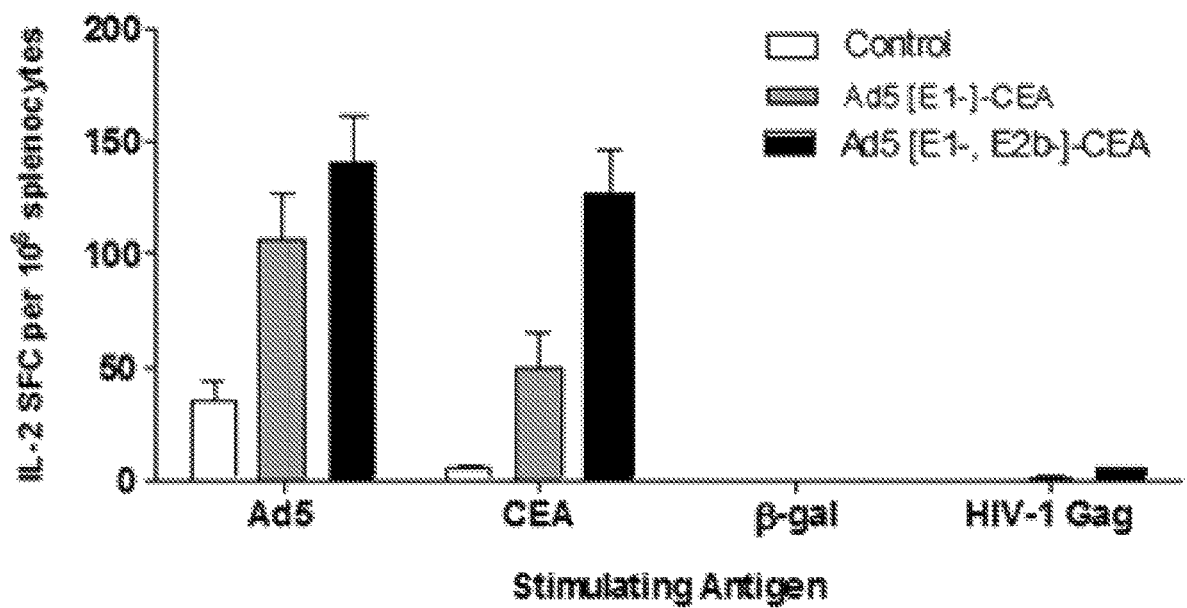

FIG. 46B exemplifies a bar graph showing IL-2 levels secreted from splenocytes from Ad5-immune mice immunized with Ad5 [E1-]-CEA(6D), Ad5 [E1-, E2b-]-CEA(6D), or injection buffer alone (control). Splenocytes were also assessed for non-specific IL-2 secreting T-cells by stimulation with the non-immunizing antigens β-galactosidase (β-gal) and HIV-1 Gag. A significantly elevated response is shown in the Ad5 [E1-, E2b-]-CEA(6D) immunized group. The errors bars depict the SEM.

Figure 47:
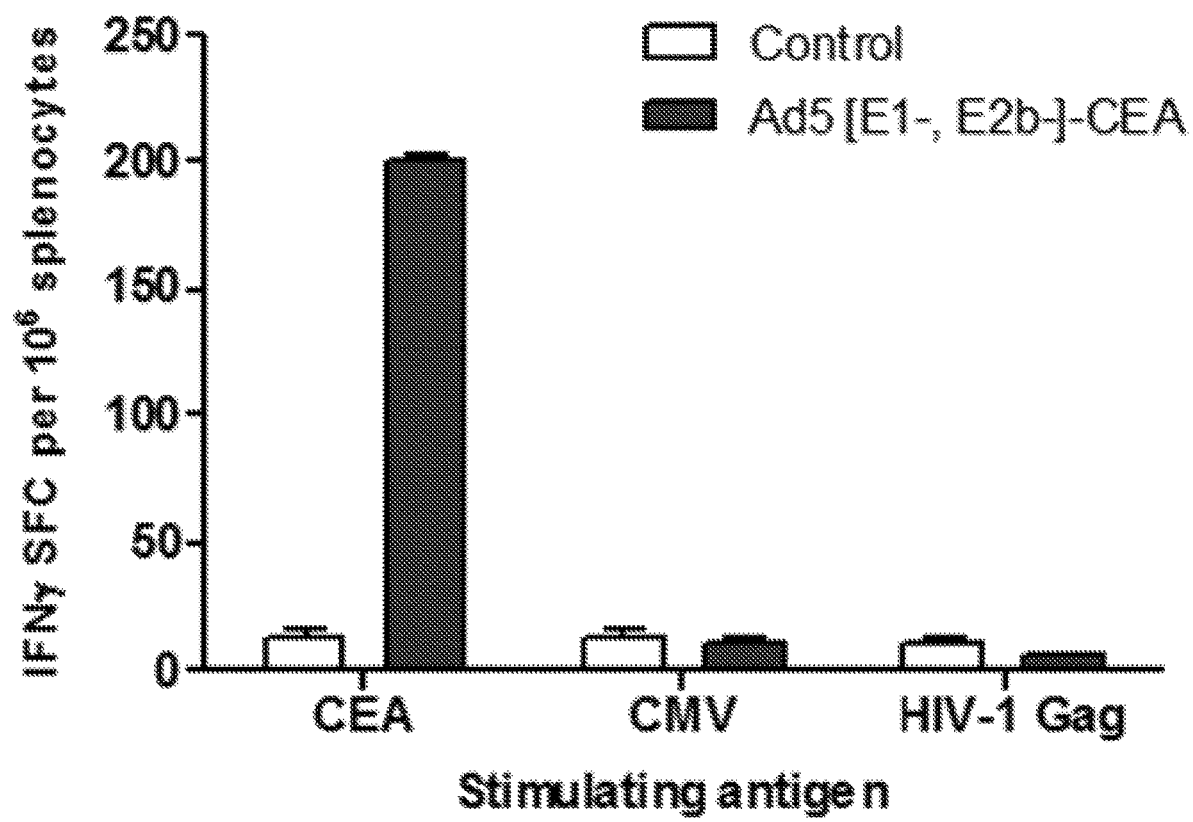

FIG. 47 exemplifies a bar graph showing INF-γ levels secreted from splenocytes from CEA transgenic mice immunized with Ad5 [E1-, E2b-]-CEA(6D), or injection buffer alone (control). Elevated levels of IFN-γ secreting splenocytes specific for CEA and not for control antigens such as CMV or HIV-1 Gag is shown. The error bars depict the SEM.

FIG. 48A exemplifies a line graph showing tumor volume over time in Ad5-naïve C57Bl/6 mice injected with MC-38 CEA-expressing tumor cells and subsequently treated with Ad5 [E1-, E2b-]-CEA vaccine. Tumor size is shown to be significantly reduced by days 20-21 compared to untreated tumor-bearing mice. * Indicates a significant difference in the value of the means on that day. Values represent Mean±SEM.

FIG. 48B exemplifies a graph showing tumor weight from 7 treated and 7 untreated Ad5-naive MC38 tumor-bearing mice. A significant (p<0.05) reduction in tumor weight in mice treated with Ad5 [E1-, E2b-]-CEA is shown. Values represent Mean±SEM.

FIG. 48C exemplifies a bar graph showing INF-γ levels secreted from splenocytes from Ad5-naive mice immunized with Ad5 [E1-, E2b-]-CEA(6D), or injection buffer alone (control). A significantly (p<0.05) elevated response is shown in the Ad5 [E1-, E2b-]-CEA(6D) immunized group. Values represent Mean±SEM.

FIG. 49A exemplifies a line graph showing tumor volume over time in Ad5-immune C57Bl/6 mice injected with MC-38 CEA-expressing tumor cells and subsequently treated with Ad5 [E1-, E2b-]-CEA vaccine. Tumor size is shown to be significantly reduced by days 19-21 compared to untreated tumor-bearing mice. * Indicates a significant difference in the value of the means on that day. Values represent Mean±SEM.

FIG. 49B exemplifies a graph showing tumor weight from 7 treated and 7 untreated Ad5-immune MC38 tumor-bearing mice. A significant (p<0.05) reduction in tumor weight in mice treated with Ad5 [E1-, E2b-]-CEA is shown. Values represent Mean±SEM.

FIG. 49C exemplifies a bar graph showing INF-γ levels secreted from splenocytes from Ad5-immune mice immunized with Ad5 [E1-, E2b-]-CEA(6D), or injection buffer alone (control). A significantly (p<0.05) elevated response is shown in the Ad5 [E1-, E2b-]-CEA(6D) immunized group. Values represent Mean±SEM.

Figure 50:
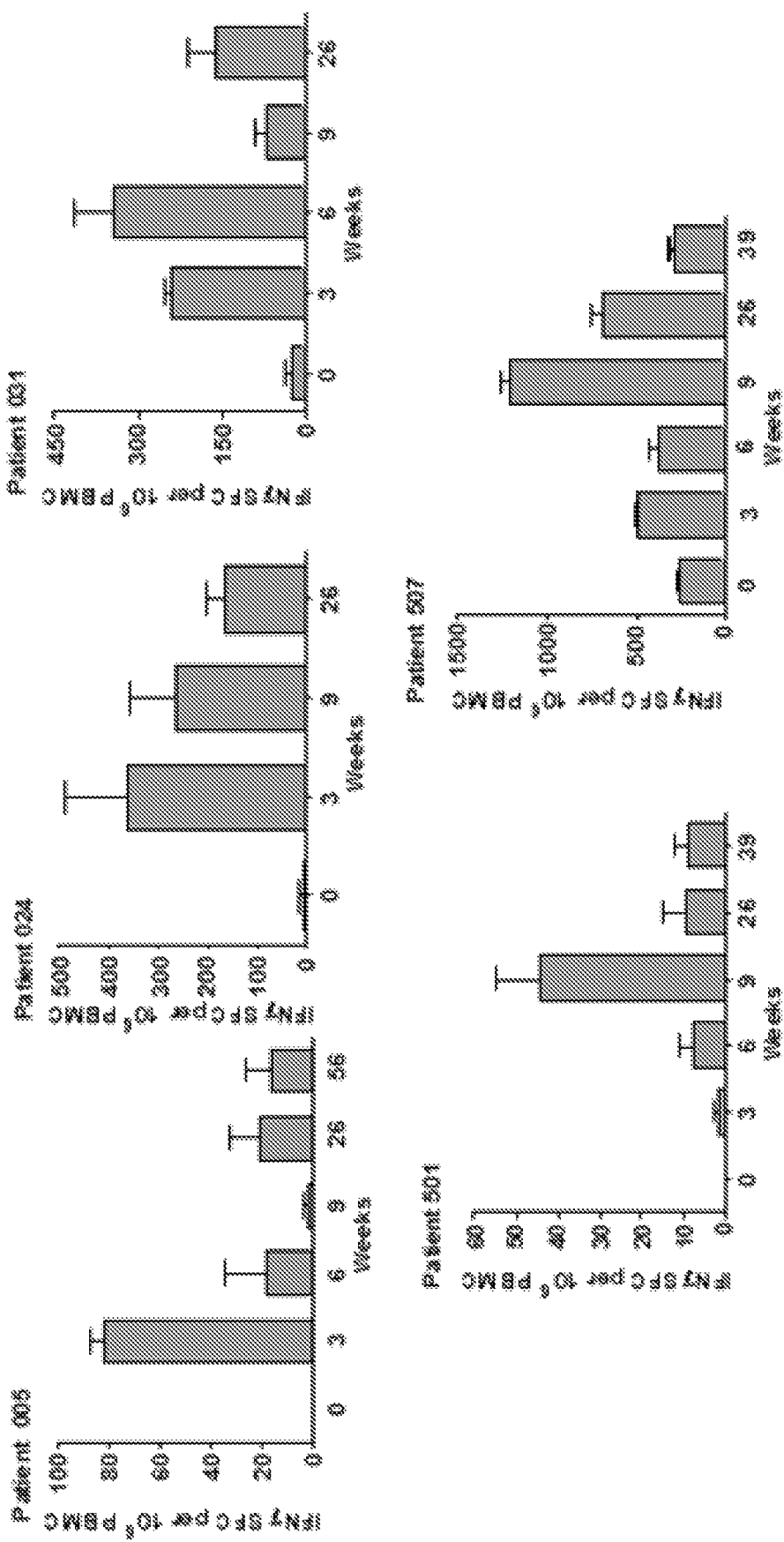

FIG. 50 exemplifies bar graphs showing profiles of CEA directed CMI responses in 5 mCRC patients during and after the course of immunotherapy. A decrease in CMI response from their peak values after immunizations ended was shown. Values are Mean±SEM.

Figure 51A:
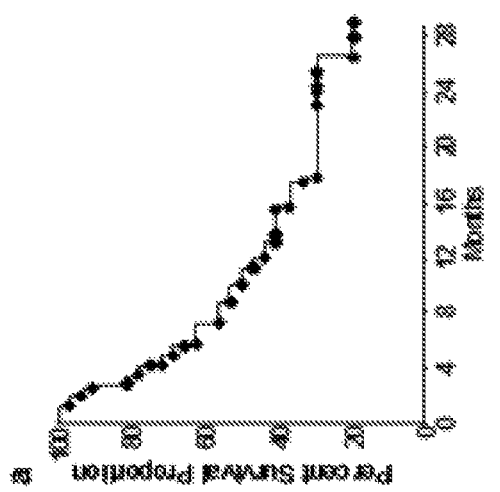

FIG. 51A exemplifies Kaplan-Meier survival plot on long-term overall survival of treated mCRC patients. Panel represents all treated patients. There were 23 events during the study.

Figure 51B:
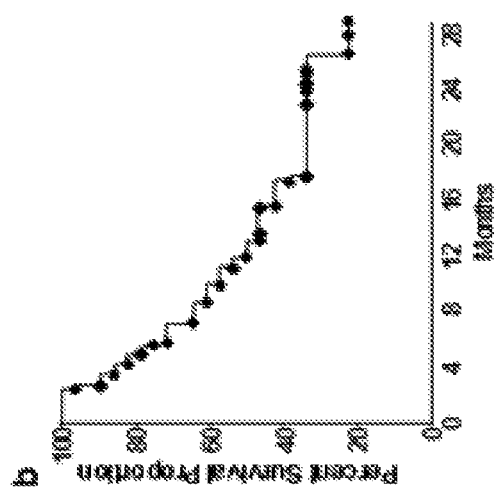

FIG. 51B exemplifies Kaplan-Meier survival plot on long-term overall survival of treated mCRC patients. Panel represents patients that received all 3 treatments. There were 23 events during the study.

Figure 51C:
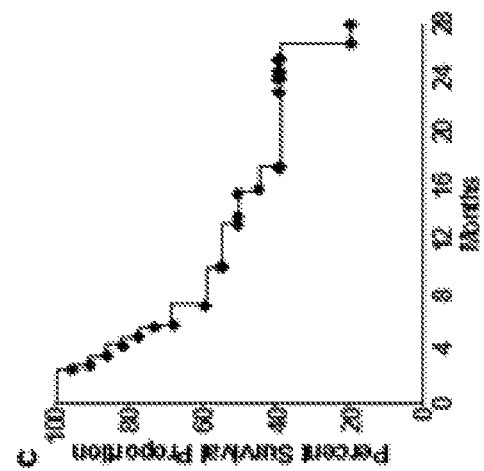

FIG. 51C exemplifies Kaplan-Meier survival plot on long-term overall survival of treated mCRC patients. Panel represents patients immunized 3 times with the 2 highest doses of vaccine. There were 23 events during the study.

Figure 52:
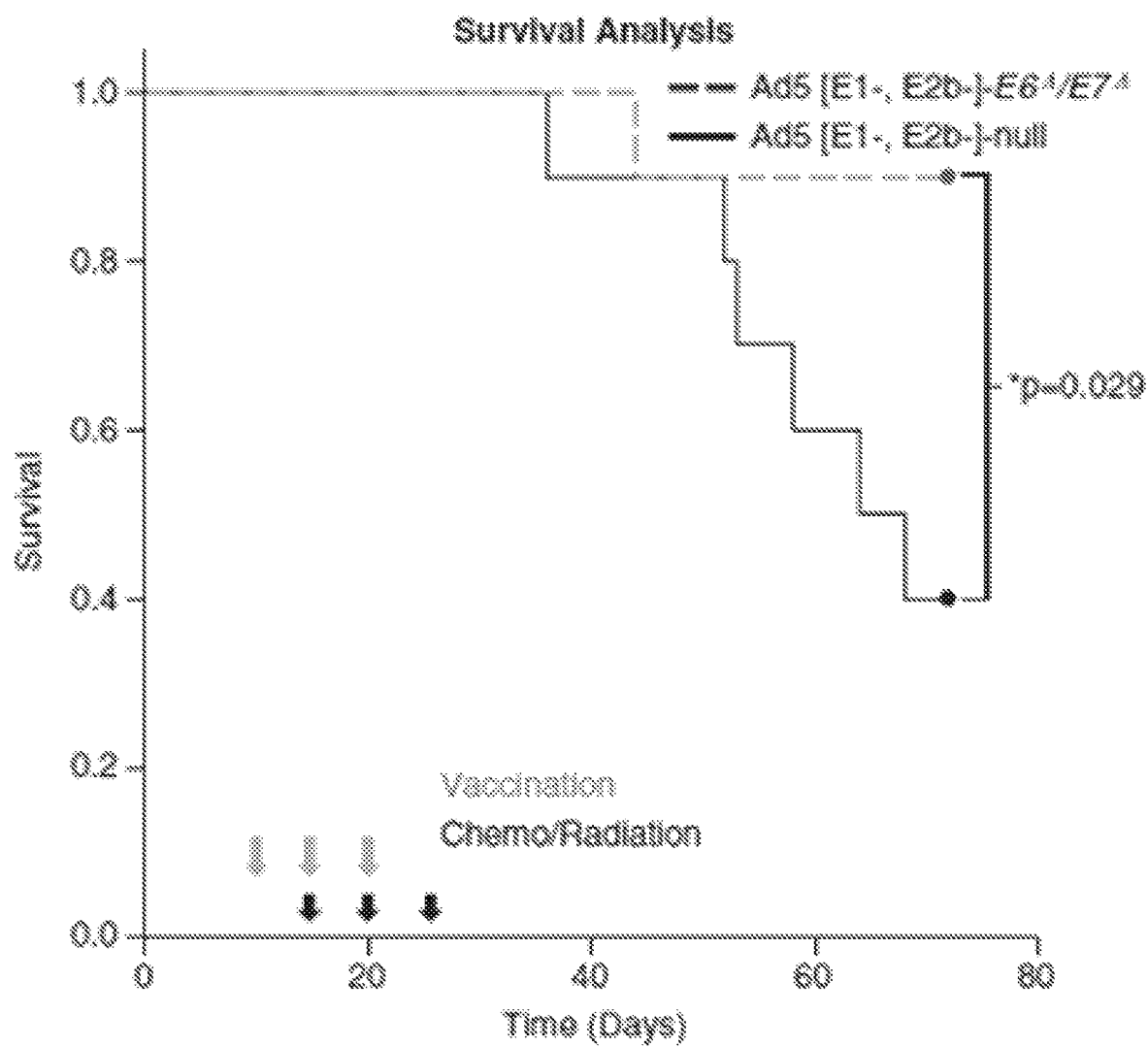

FIG. 52 exemplifies immunotherapy combined with chemotherapy/radiation treatment of established HPV-E6/E7 expressing tumors. Established HPV-E6/E7 expressing tumors were treated by immunotherapy on days 7, 14, & 21 combined with cisplatin/radiation treatment on days 13, 20, & 27. Control tumor bearing mice were treated by injections with Ad-null combined with cisplatin/radiation treatment.

Figure 53:
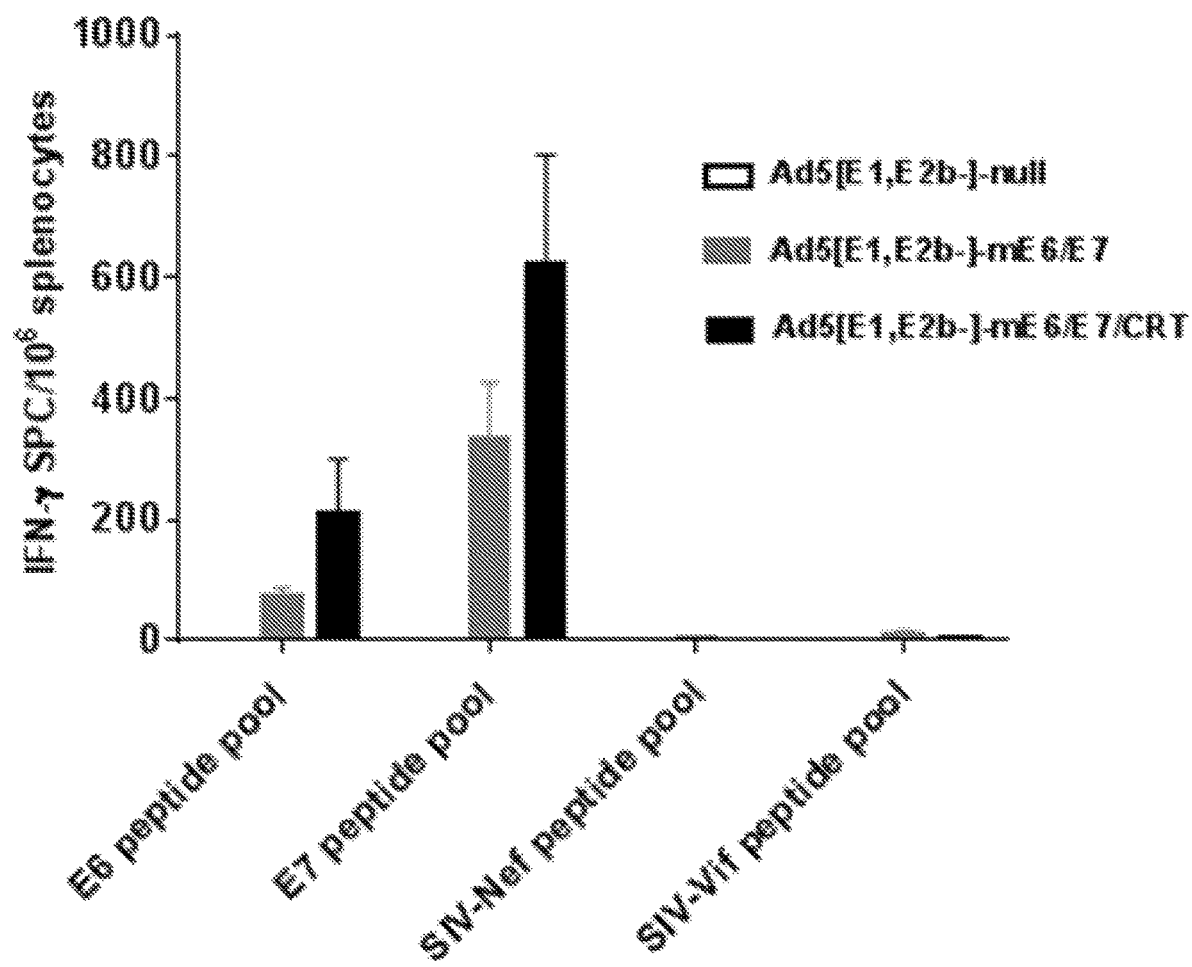

FIG. 53 exemplifies bar graph for CMI responses in mice treated with combination therapy. Non-tumor bearing mice were treated as described in FIG. 44. Two weeks after the last treatment, mice were assessed for CMI activity as determined by ELISpot assays for IFN-γ secreting splenocytes. Increased CMI responses in mice treated with combination therapy (Ad5 [E1-, E2b-]-mE6/E7/CRT) was shown.

Figure 54:
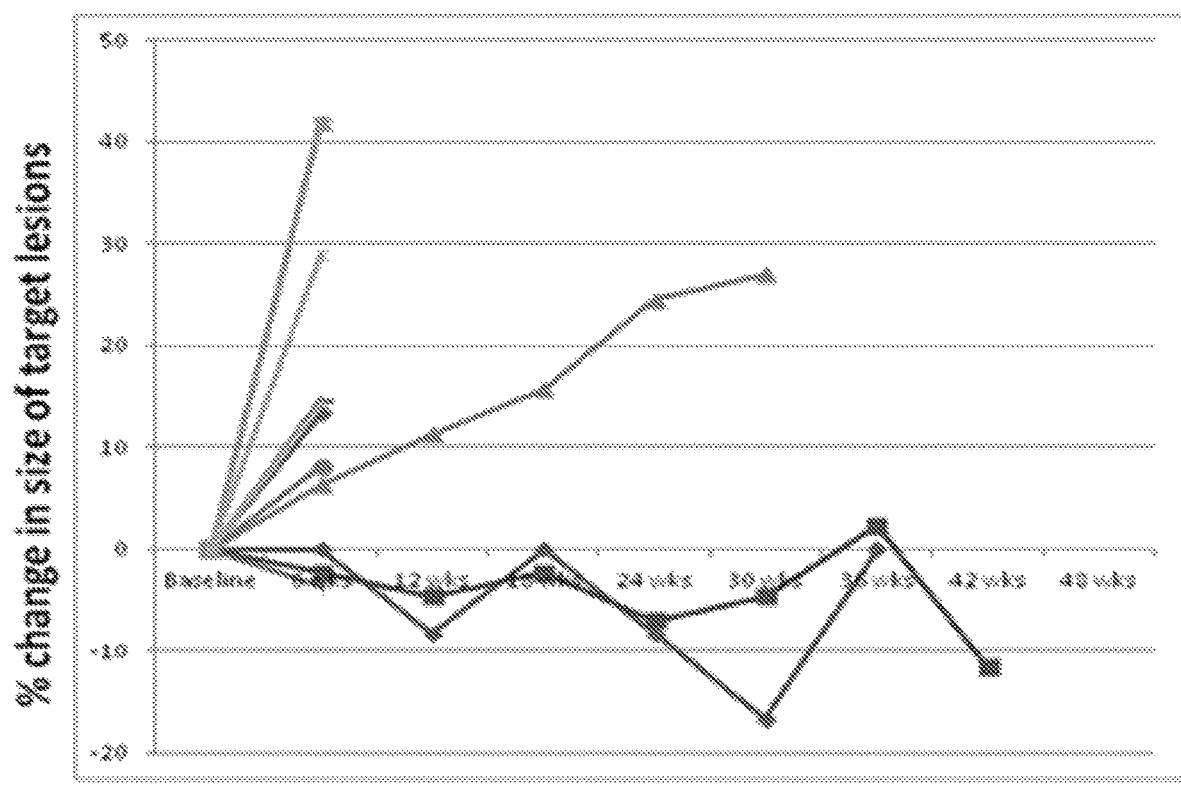

FIG. 54 exemplifies clinical outcomes for colorectal cancer patients with avelumab by RECIST criteria.

Figure 55:
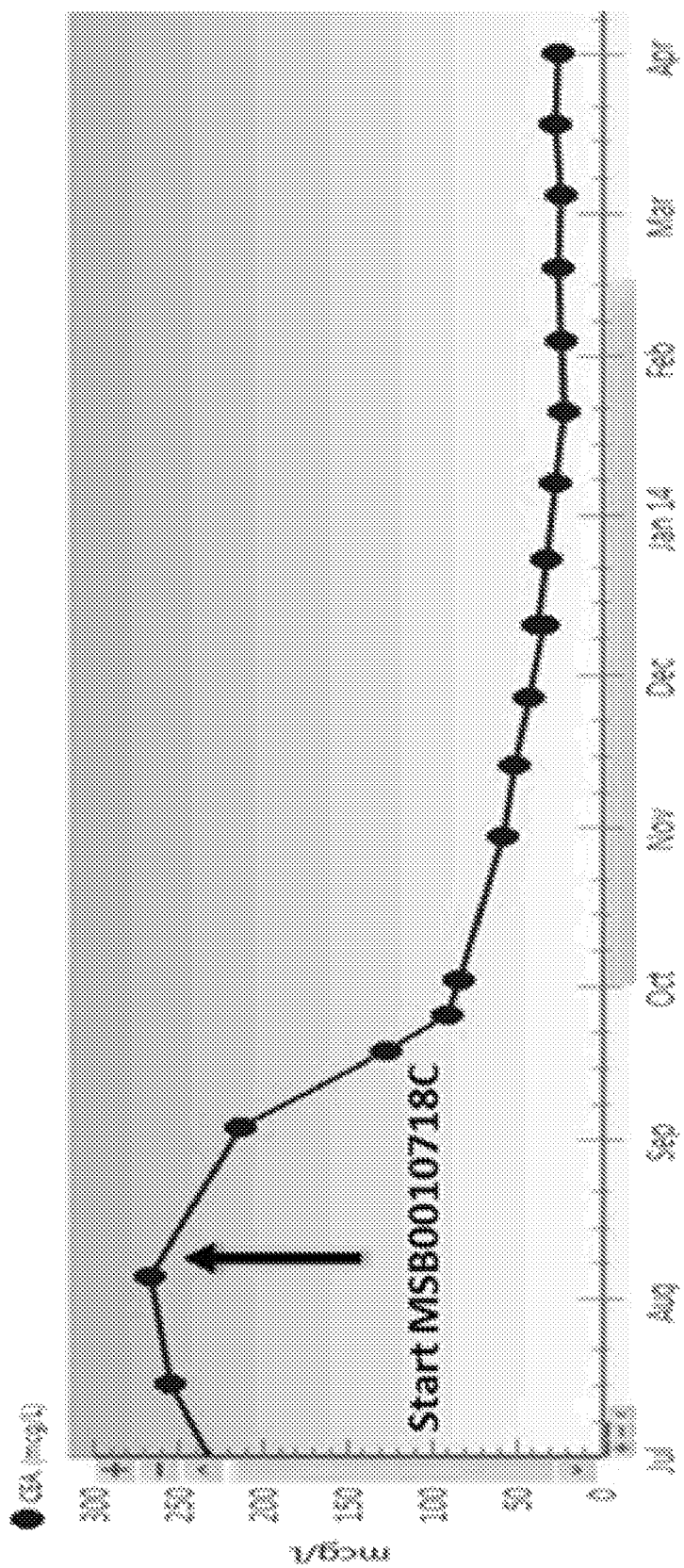

FIG. 55 exemplifies CEA change in patient with mCRC receiving single agent avelumab (MSB0010718C).

Figure 56:
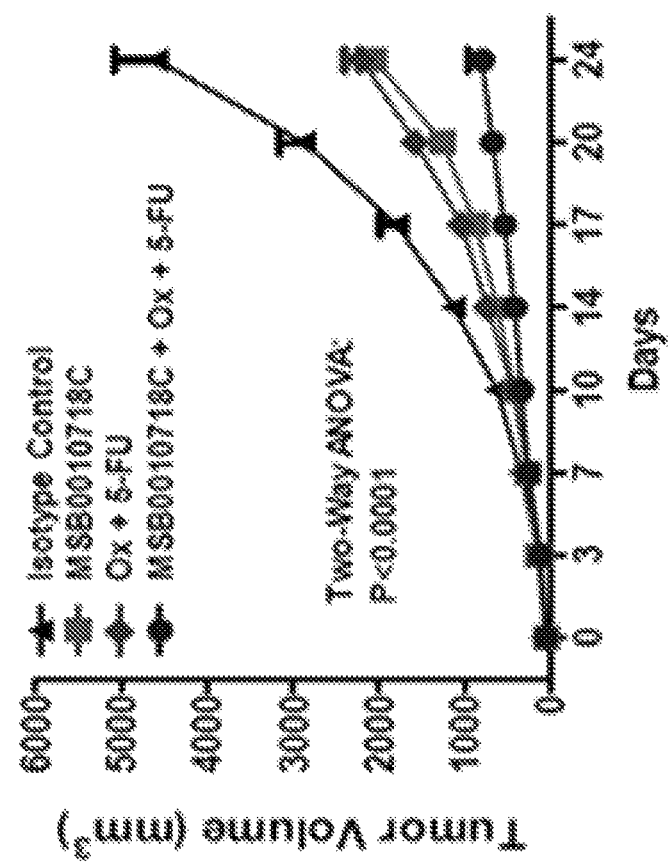
Figure 56:
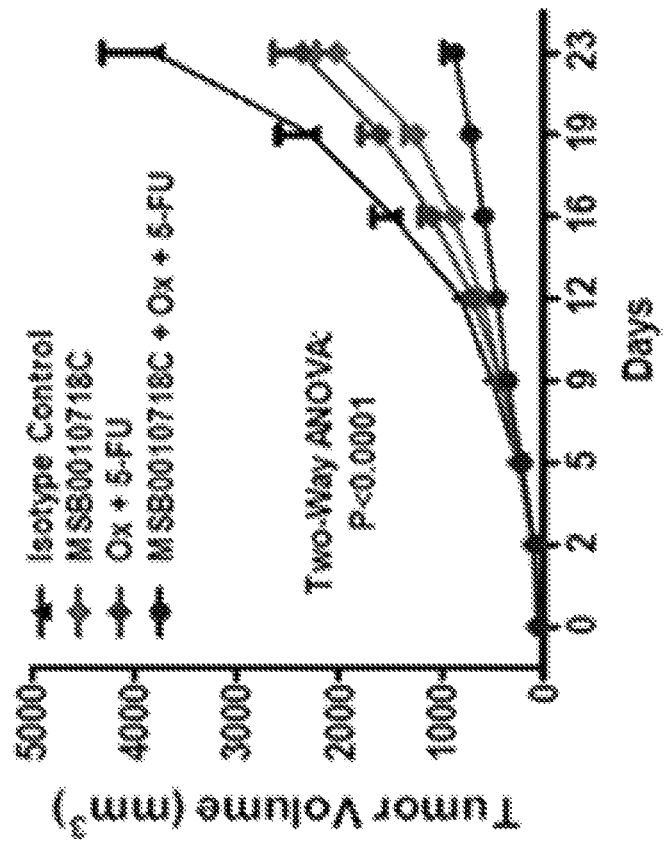

FIG. 56 exemplifies MC 38 Tumor Growth Inhibition in Mice Receiving Avelumab (Anti-PD-L1) in Combination with Oxaliplatin and 5-FU. Female C57BL/6 mice were inoculated in the right subcutaneous flank with 1×106 MC38 colon carcinoma cells. When tumors reached a mean volume of ~50 mm3, mice were sorted into treatment groups (N=10). 5-FU (60 mg/kg by i.v.injection) and OX (5 mg/kg by i.p. injection) were administered on days 0 and 14. MSB0010718C (400 μg by i.v.injection) was given on days 3, 6, and 9. Tumor volumes were measured twice weekly via calipers. Data are mean±SEM.

Figure 57:
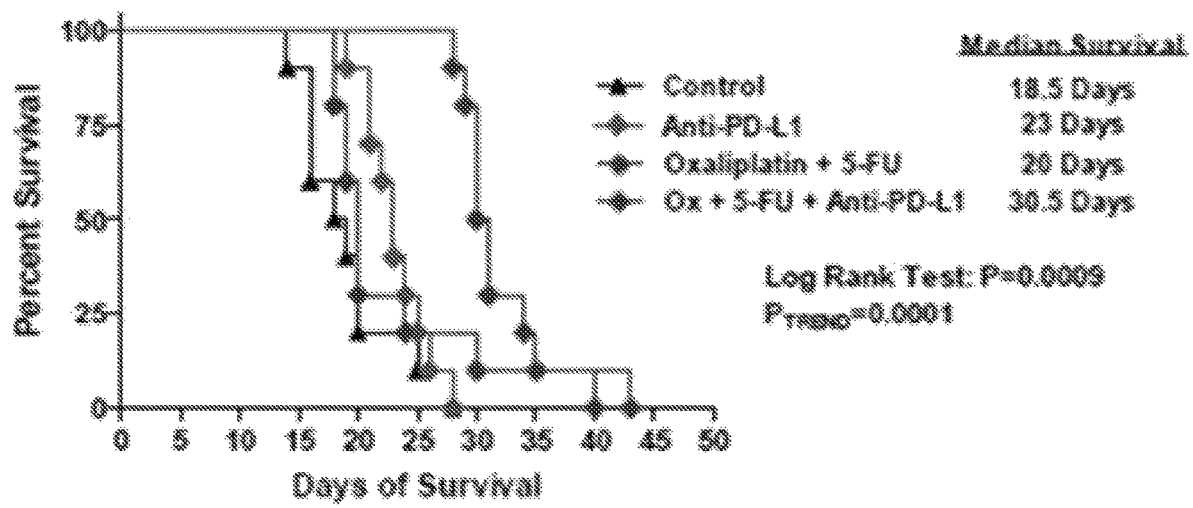
Figure 57:
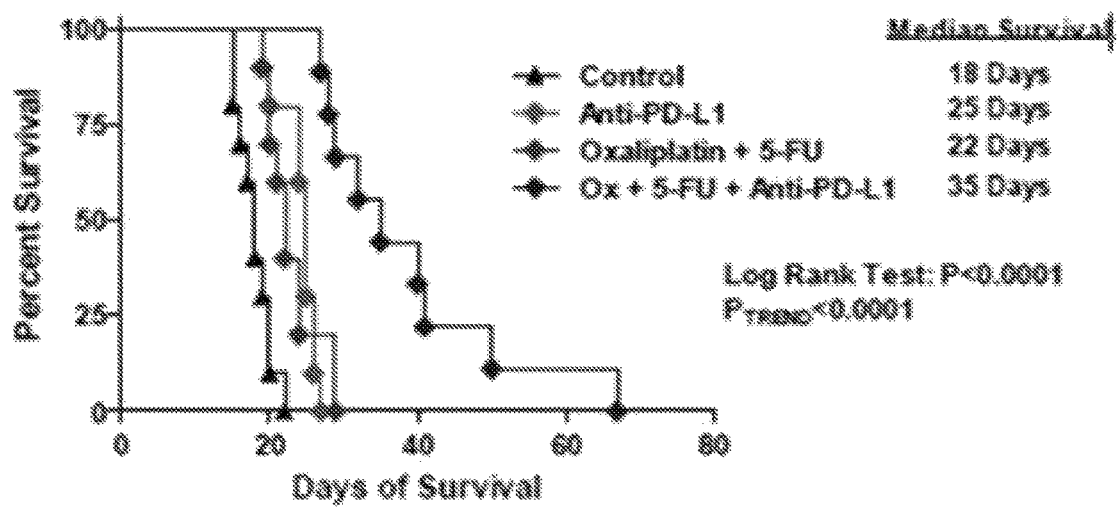

FIG. 57 exemplifies survival of MC38 Tumor-Bearing Mice Receiving Avelumab (Anti-PD-L1) in Combination with Oxaliplatin and 5-FU. Female C57BL/6 mice were inoculated in the right subcutaneous flank with 1×10$^6$ MC38 colon carcinoma cells. When tumors reached a mean volume of ~50 mm3, mice were sorted into treatment groups (N=10). 5-FU (60 mg/kg by i.v. injection) and OX (5 mg/kg by i.p. injection) were administered on days 0 and 14. MSB0010718C (400 μg by i.v. injection) was given on days 3, 6, and 9. Kaplan-Meier plots and Log Rank statistics were used to calculate survival differences between groups. Survival was censored at the time tumor volumes reached 2000 mm3. Data are expressed as median survival time in days.

Figure 58:
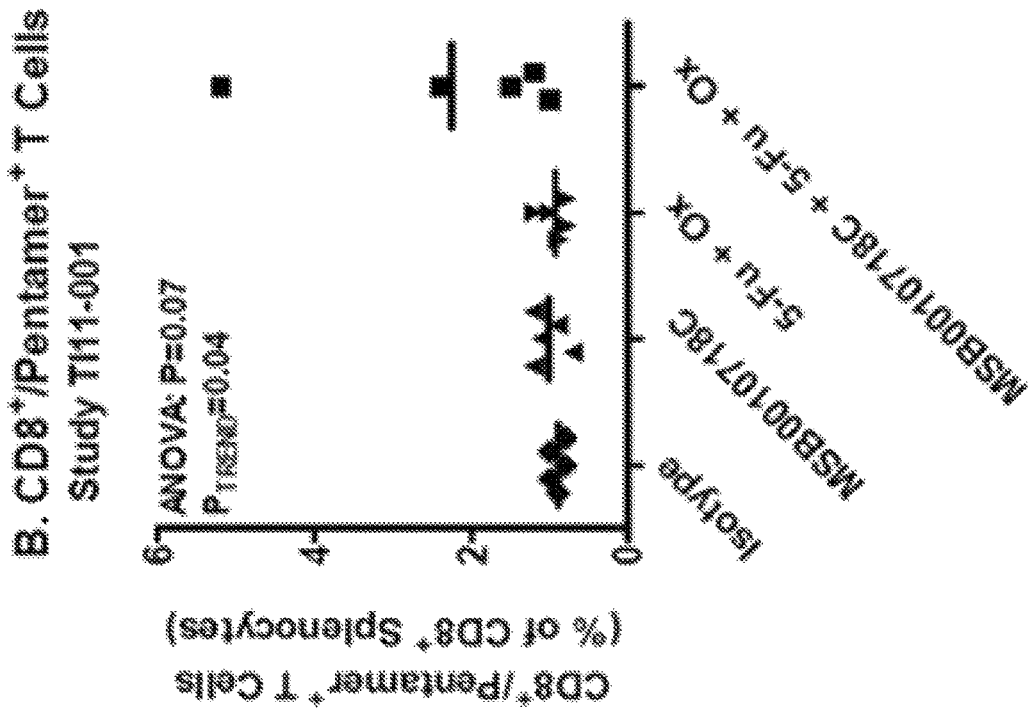
Figure 58:
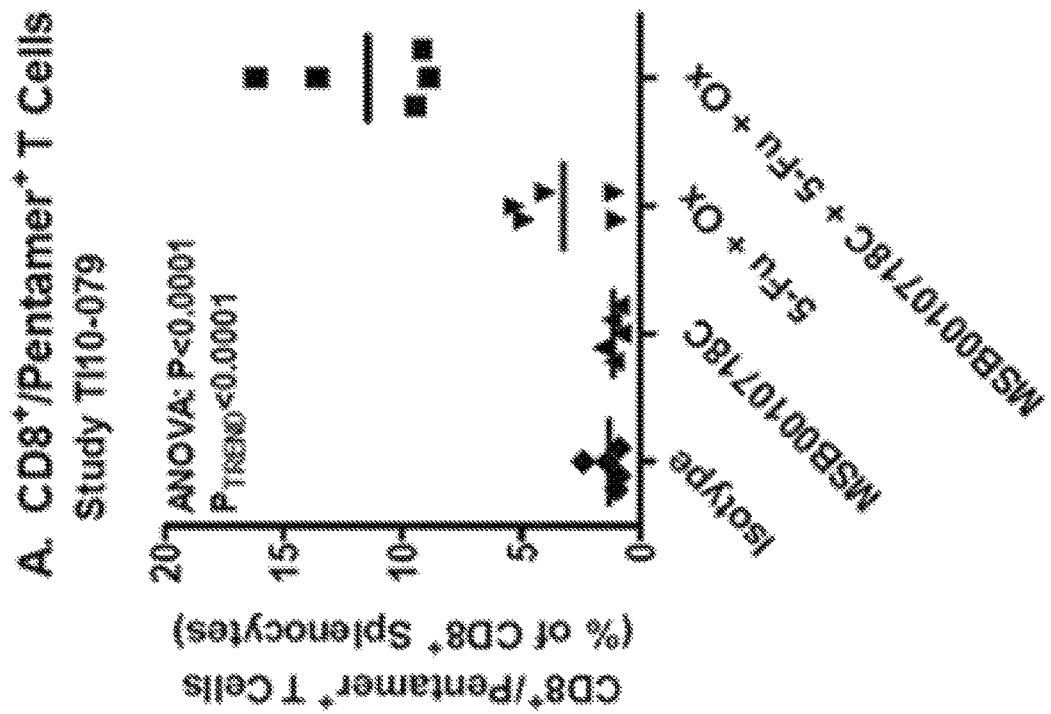

FIG. 58 exemplifies Pentamer Analysis of Tumor-Antigen Specific T Cells. Subsets of 5 animals from each study group were sacrificed on study day 21 for FACS-based detection of p15E specific T cells using a fluorescently-labeled synthetic MHC class I pentamer loaded with a p15E-derived antigenic peptide epitope. The spleen from each animal was dissociated into single cell suspensions and subsequently stained with an anti-CD8 antibody and the p15E pentamer. From the total splenocyte gate, the percentage of cells positive for both CD8 and the pentamer was determined. Data were acquired using a BD LSR II flow cytometer.

Figure 59:
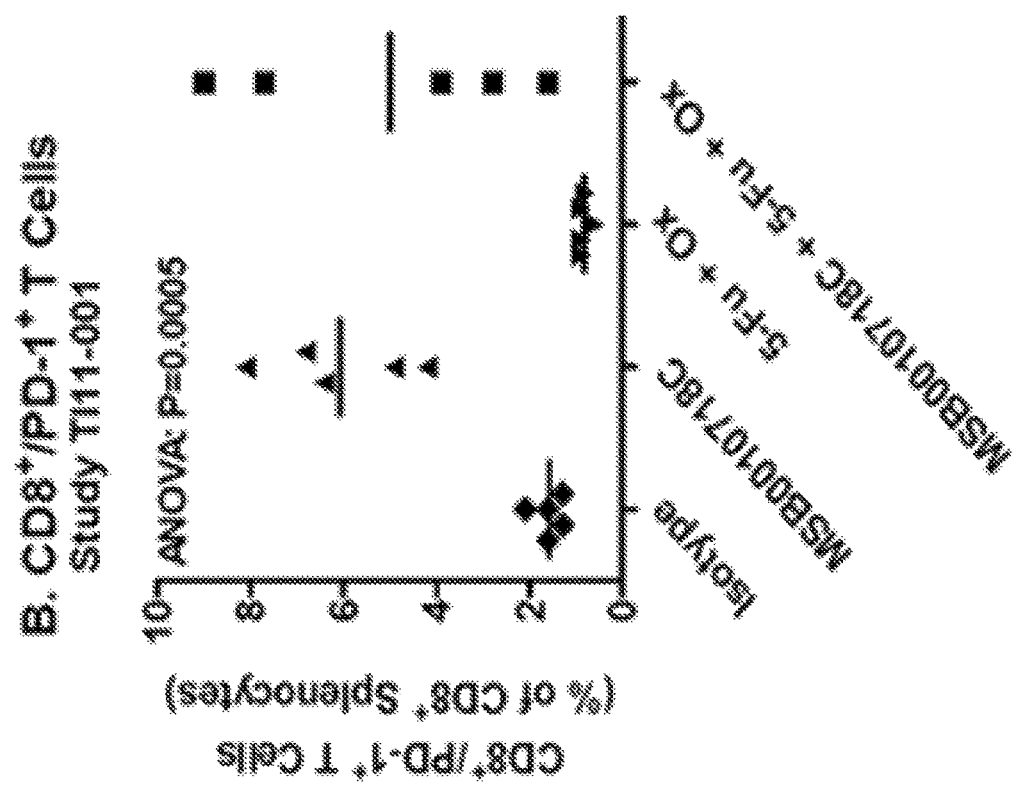
Figure 59:
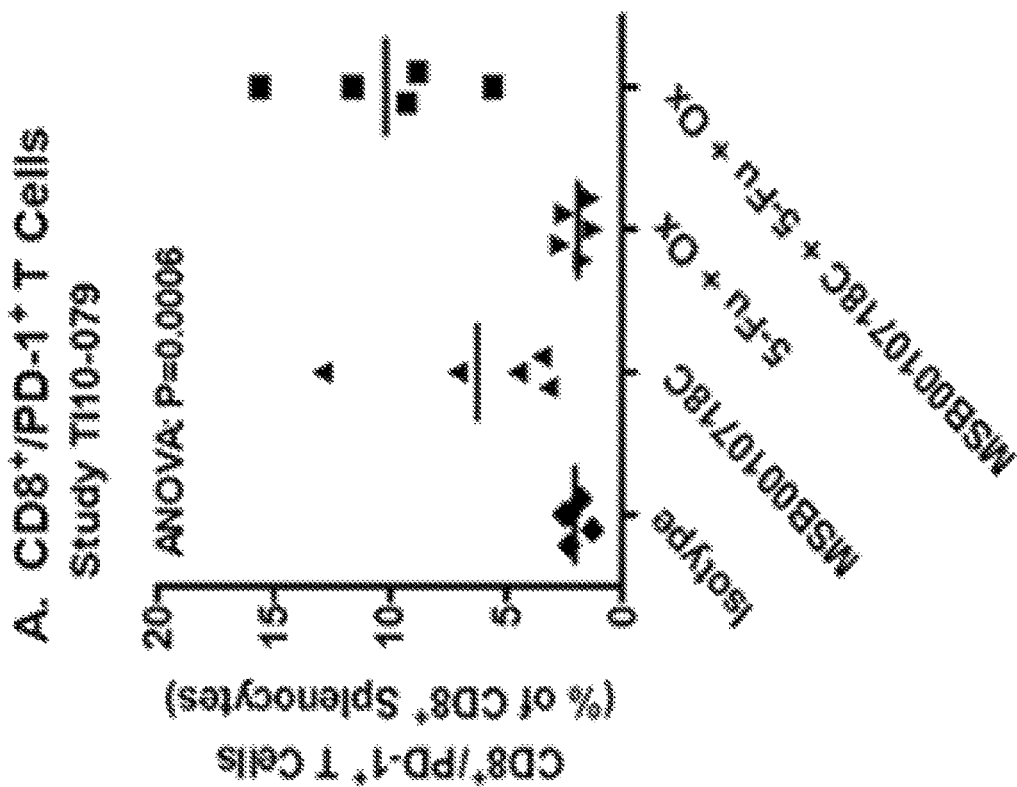

FIG. 59 exemplifies Splenic CD8+/PD-1+ T cell Counts. Subsets of 5 animals from each group were sacrificed for FACS-based immunophenotyping on day 21 after the start of treatment. Spleens were harvested and dissociated into single cell suspensions by mechanical disruption. Suspensions were then stained with fluorescently-labeled antibodies specific for relevant T cell surface markers (i.e. CD8, PD-1, CD44, CD62L) and data were acquired on a BD LSR II flow cytometer.

Figure 60:
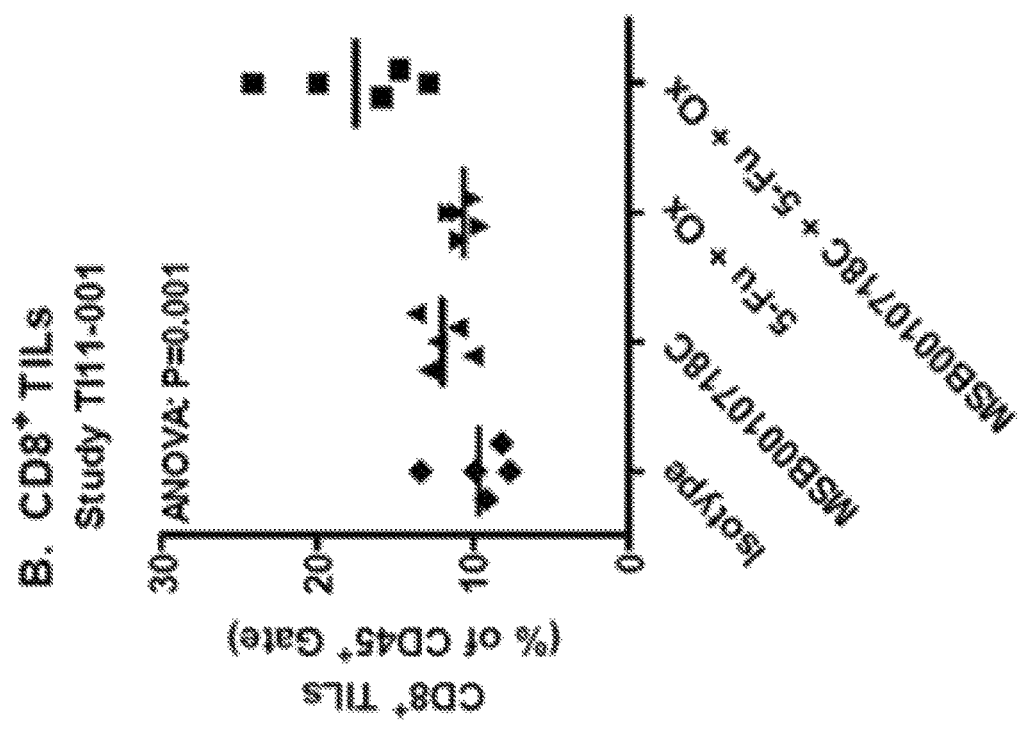
Figure 60:
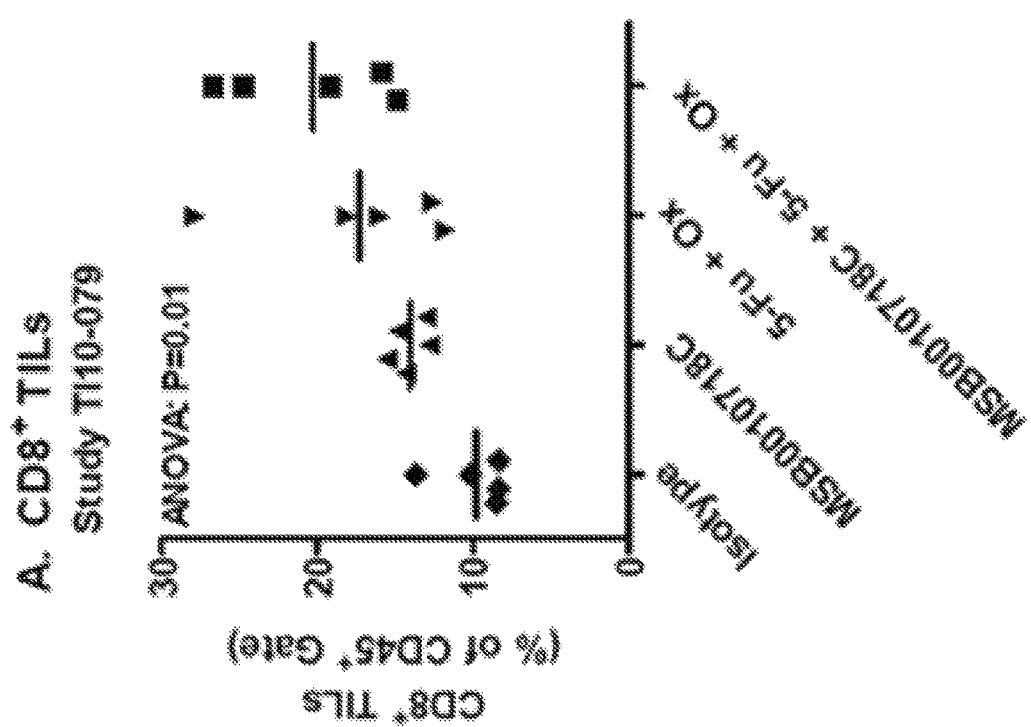

FIG. 60 exemplifies CD8+ Tumor-Infiltrating Lymphocyte Levels. Subsets of 5 animals from each group were sacrificed for FACS-based immunophenotyping analysis on day 21 following the start of treatment. Tumors were harvested and dissociated into single cell suspensions by enzymatic digestion (collagenase) and mechanical disruption. Suspensions were then stained with a fluorescently-labeled antibodies specific for the NK1.1 surface marker and data were acquired using a BD LSR II flow cytometer.

Figure 61:
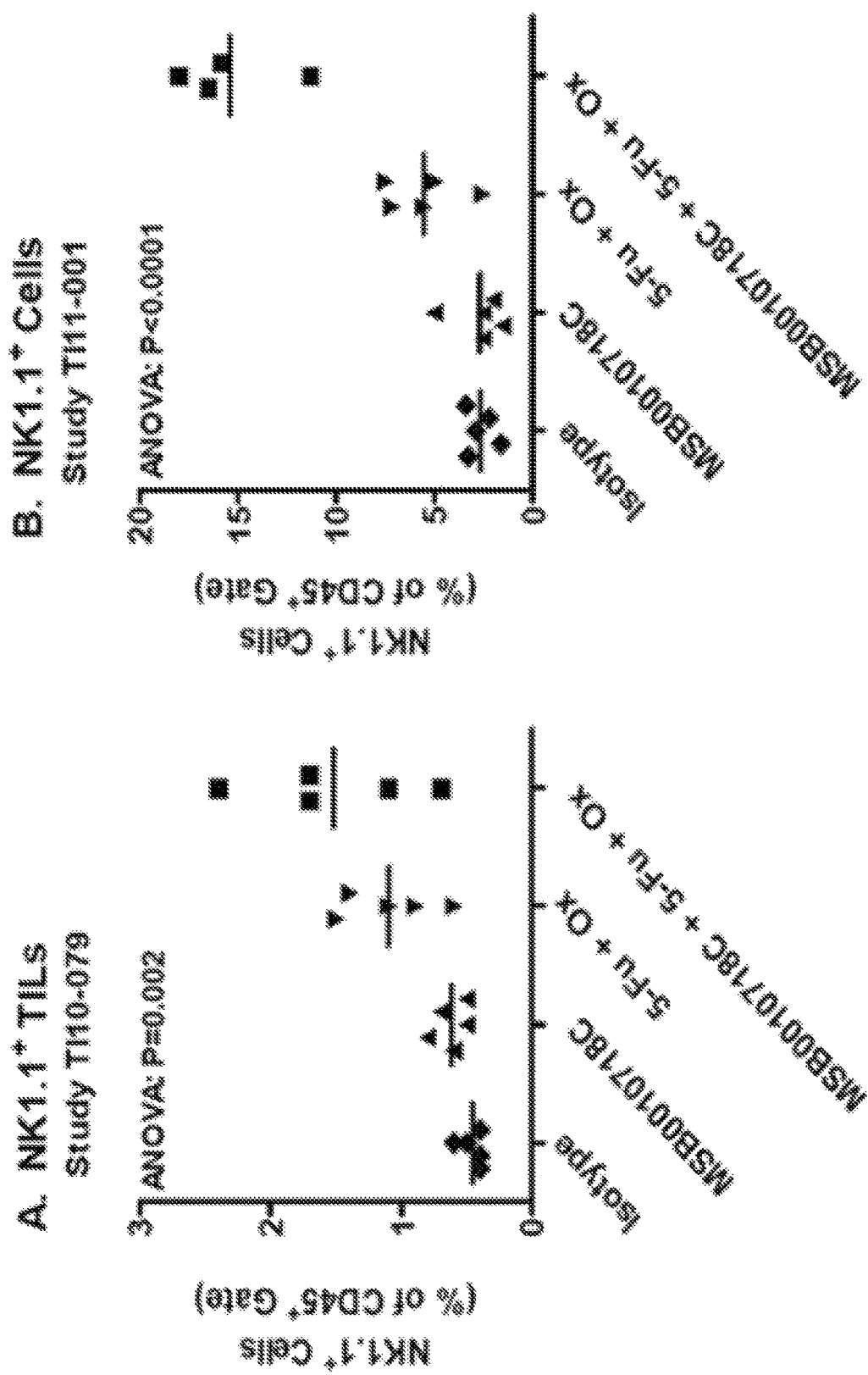

FIG. 61 exemplifies Tumor-Infiltrating NK Cell Levels. Subsets of 5 animals from each group were sacrificed for FACS-based immunophenotyping analysis on day 21 following the start of treatment. Tumors were harvested and dissociated into single cell suspensions by enzymatic digestion (collagenase) and mechanical disruption. Suspensions were then stained with a fluorescently-labeled antibodies specific for the NK1.1 surface marker and data were acquired using a BD LSR II flow cytometer.

Figure 62:
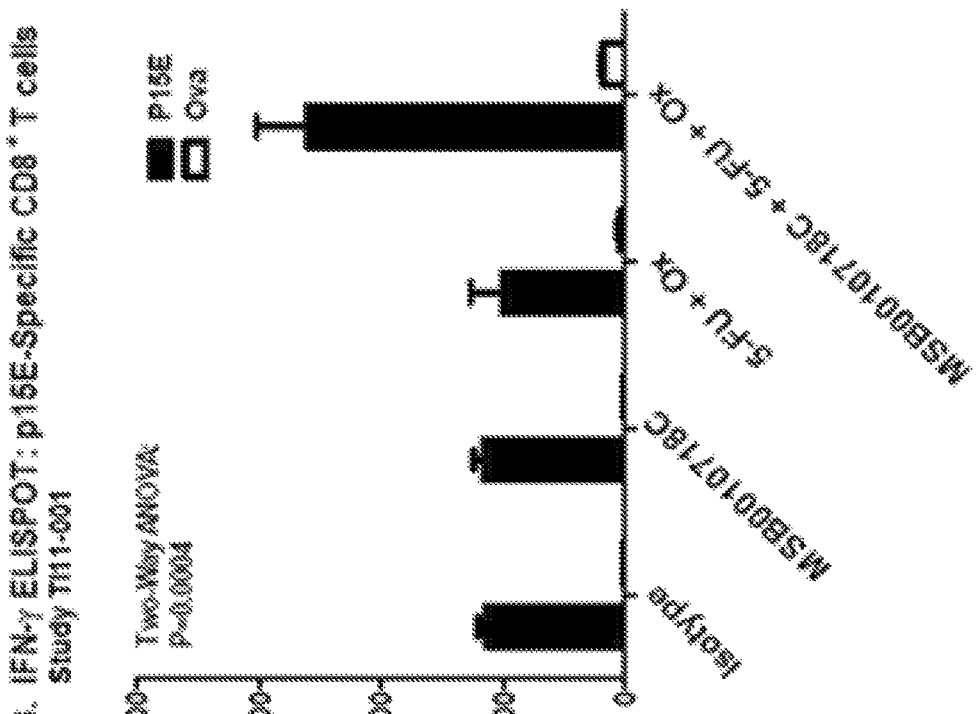
Figure 62:
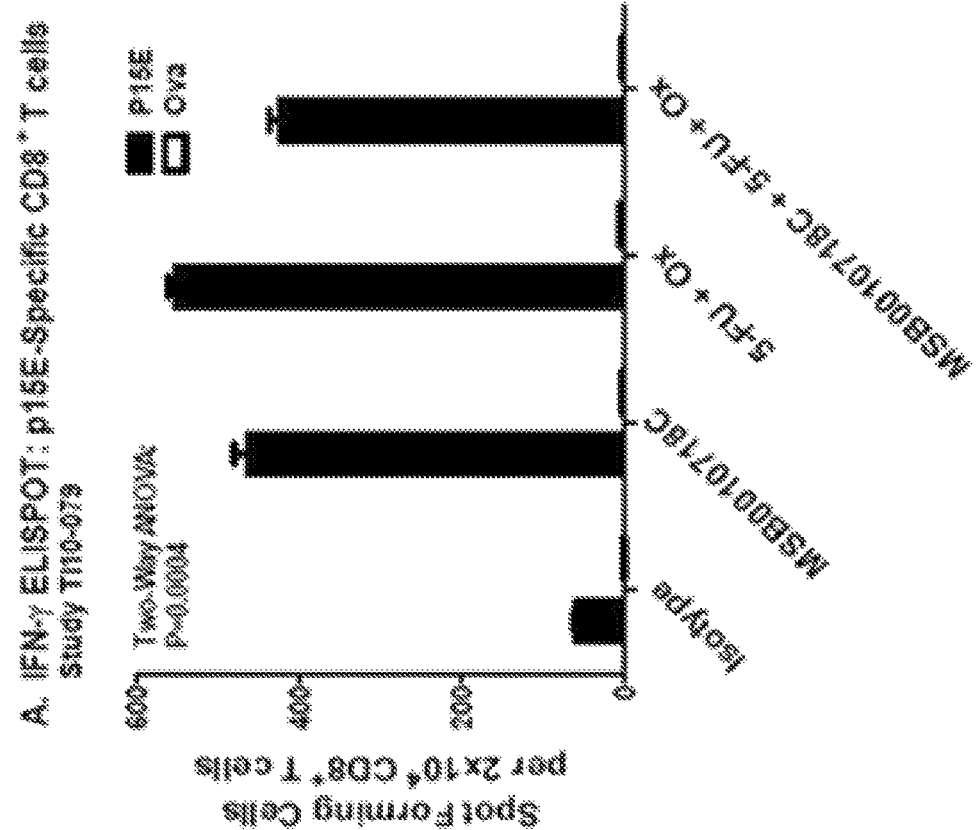

FIG. 62 exemplifies Combination of Avelumab (MSB0010718C) with 5-FU and Oxaliplatin: ELISPOT Measurement of Tumor Antigen Specific CD8+ T cells. For the ELISPOT assay, spleens from treated animals were harvested on day 21 after the start of treatment and processed into single cells suspensions (splenocytes from 5 mice from each group were pooled). The splenocytes were cultured for six days in the presence of a p15E-derived peptide antigen epitope (amino acid sequence KSPWFTTL) in order to stimulate expansion of antigen-specific CD8+ T cells. As a control for non-specific activation, the assay was run in parallel using an irrelevant peptide derived from chicken ovalbumin (OVA). Following the six day period of in vitro antigen stimulation, the CD8+ T cells were isolated from the cultures and placed in co-culture with antigen presenting cells (APCs) loaded with the same p15E antigenic peptide or OVA as a control. The cocultures were prepared in ELISPOT assay plates coated with an antibody that captured secreted IFN-γ. Following assay plate development, each IFN-γ positive "spot" represented a CD8+ T cell that had become activated by p15E-specific stimulation.

Figure 63:
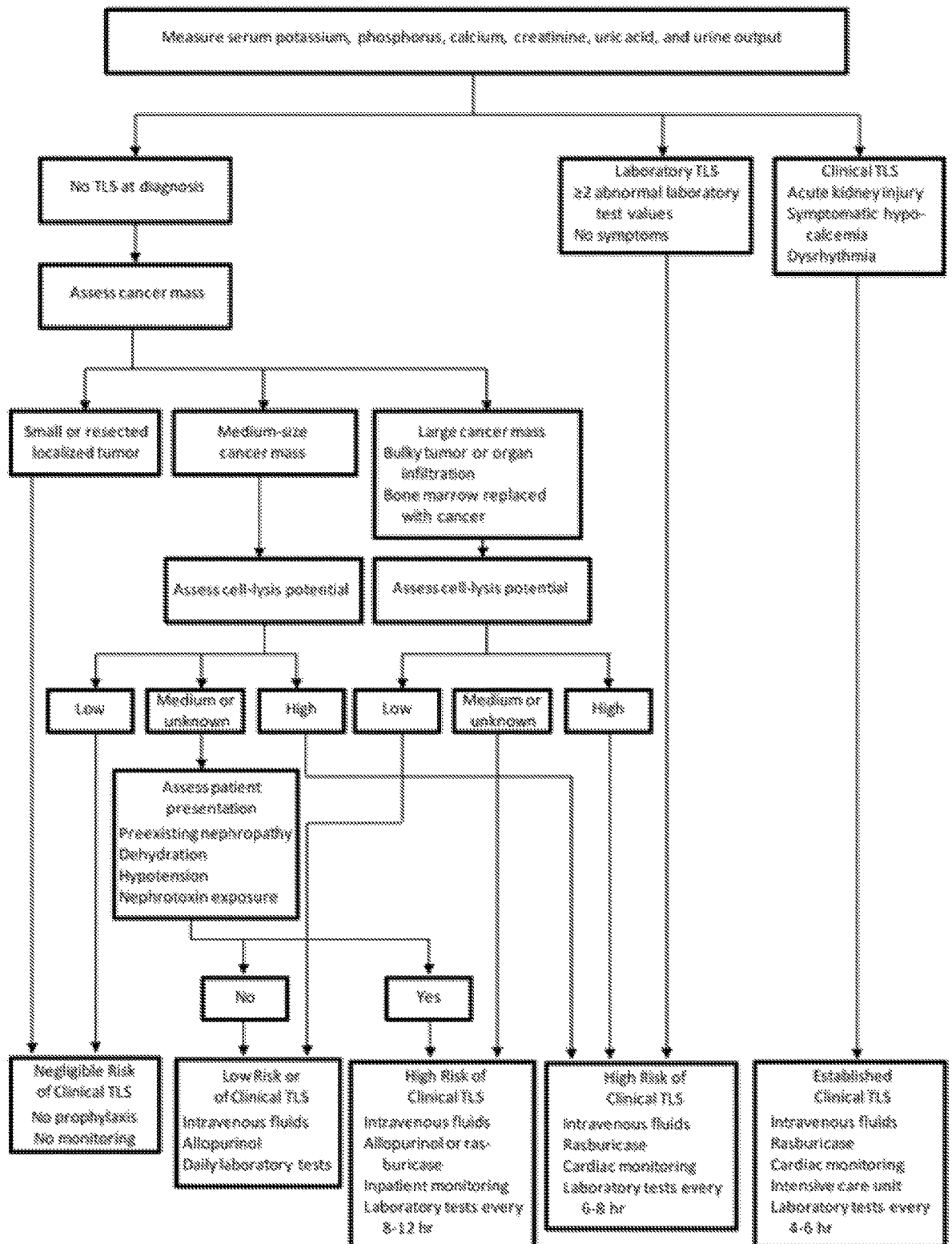

FIG. 63 exemplifies Assessment and Initial Management of Tumor Lysis Syndrome (TLS).

Figure 64A:
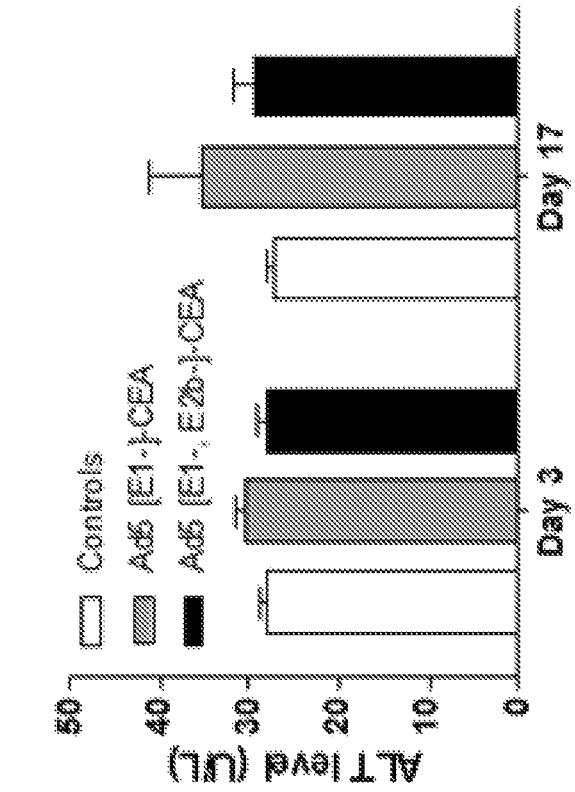

FIG. 64A exemplifies adverse effects in Ad5 naïve mice following immunization with Ad5 [E1]-CEA(6D) or Ad5 [E1-, E2b-]-CEA(6D). Adverse effects were determined by evaluation of the liver enzyme aspartate aminotransferase (AST) levels in serum from C57Bl/6 mice (n=7/group) immunized at a weekly interval with $10^{10}$ VP of Ad5 [E1-]-CEA(6D), Ad5 [E1-, E2b-]-CEA(6D) or injection buffer alone. Three days after one immunization (Day 3) or three immunizations (Day 17), AST levels were determined. The error bars depict the SEM.

Figure 64B:
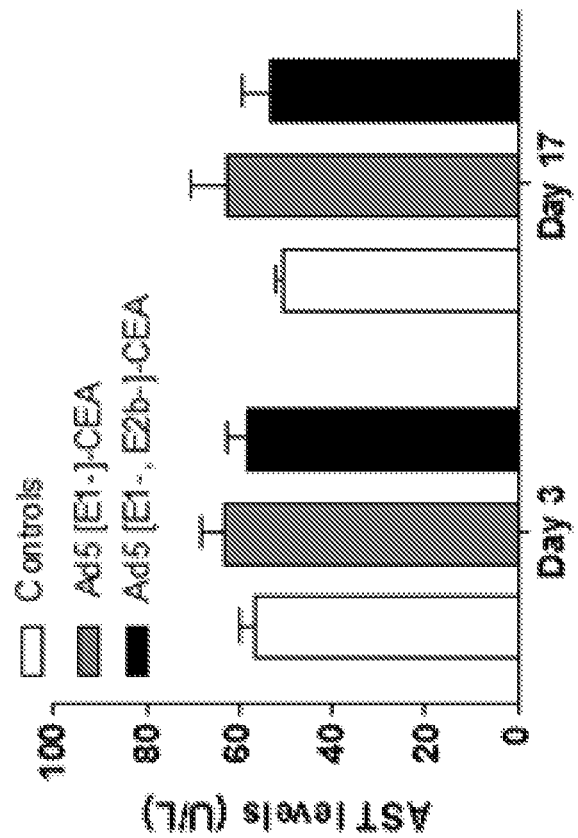

FIGS. 64A-64B exemplifies adverse effects in Ad5 naïve mice following immunization with Ad5 [E1-]-CEA(6D) or Ad5 [E1-, E2b-]-CEA(6D). Adverse effects were determined by evaluation of the liver enzyme alanine aminotransferase (ALT) levels in serum from C57Bl/6 mice (n=7/group) immunized at a weekly interval with $10^{10}$ VP of Ad5 [E1-]-CEA(6D), Ad5 [E1-, E2b-]-CEA(6D) or injection buffer alone. Three days after one immunization (Day 3) or three immunizations (Day 17), ALT levels were determined. The error bars depict the SEM.

Figure 65B:
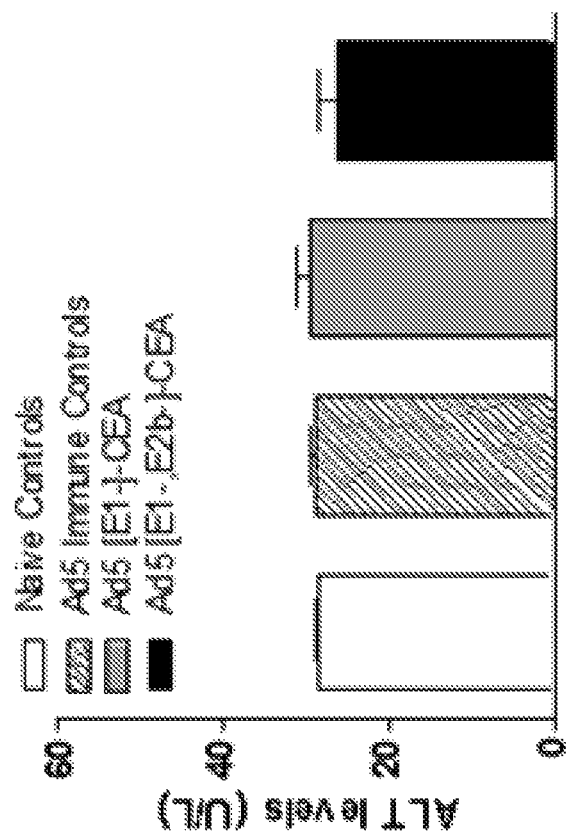
Figure 65A:
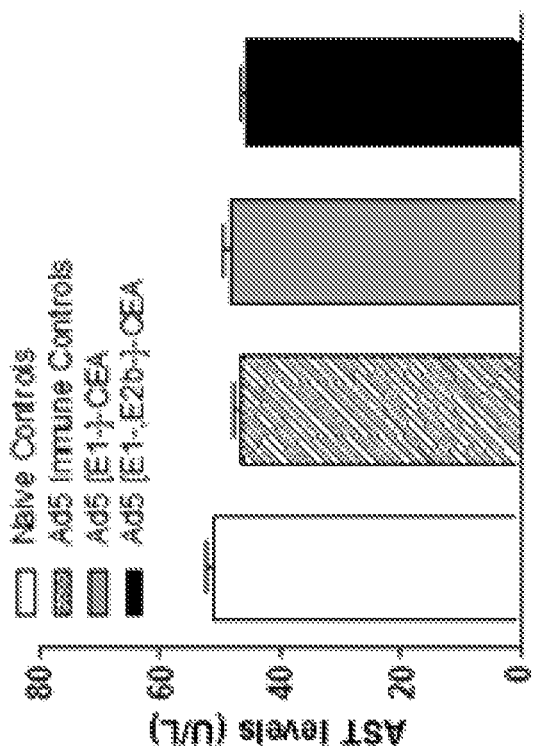

FIGS. 65A-65B exemplifies adverse effects in Ad5 immune mice following immunization with Ad5 [E1-]-CEA (6D) or Ad5 [E1-, E2b-]-CEA(6D). Adverse effects were determined by evaluation of the liver enzyme aspartate aminotransferase (AST) levels in serum from Ad5 immune C57Bl/6 mice immunized three times at a weekly interval with $10^{10}$ VP of Ad5 [E1-]-CEA(6D), Ad5 [E1-, E2b-]-CEA (6D) or injection buffer alone. Three days after three immunizations (Day 17), AST levels were determined. The error bars depict the SEM.

Figure 66:
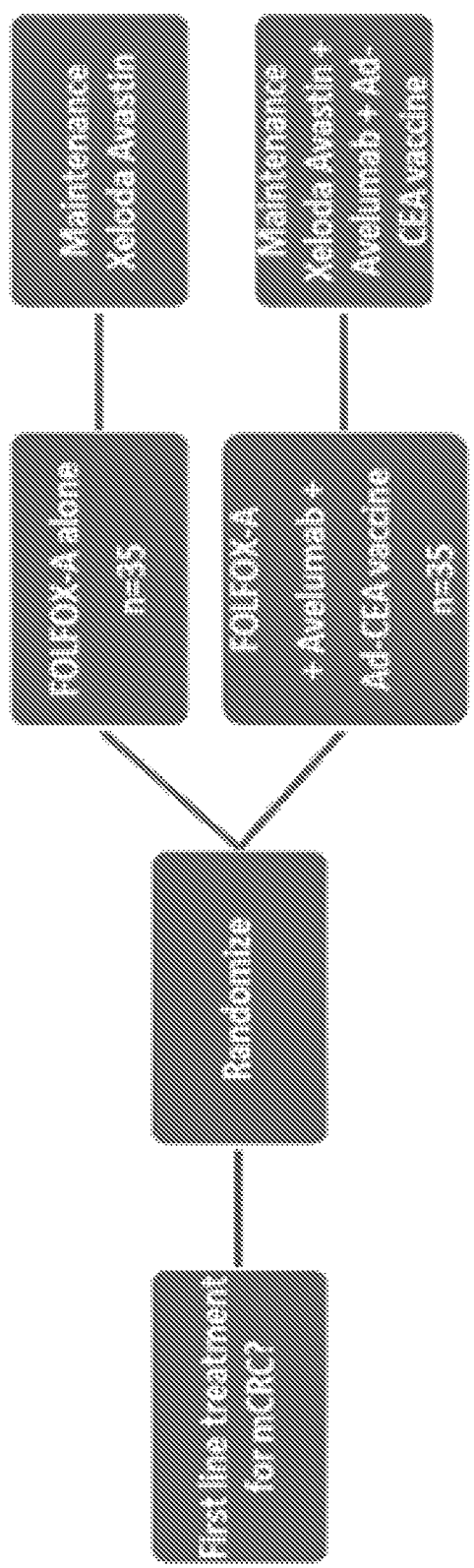

FIG. 66 exemplifies a randomization schema of the clinical trial (the star indicates that patients on standard of care are allowed to cross-over to Avelumab+Ad-CEA vaccine+ standard of care at progression of disease).

Figure 67:
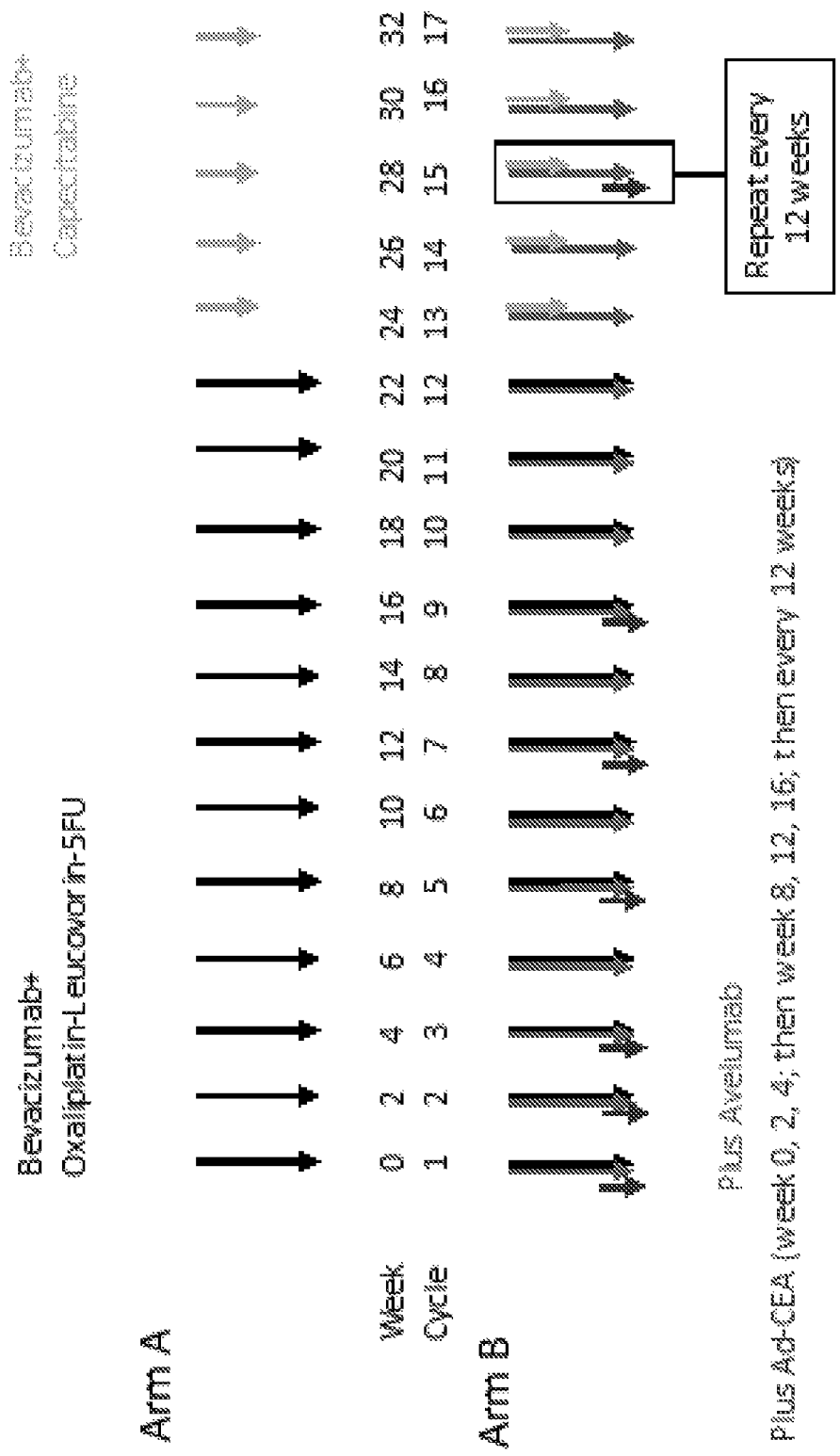

FIG. 67 exemplifies a dosing regimen of the clinical trial.

Figure 68:
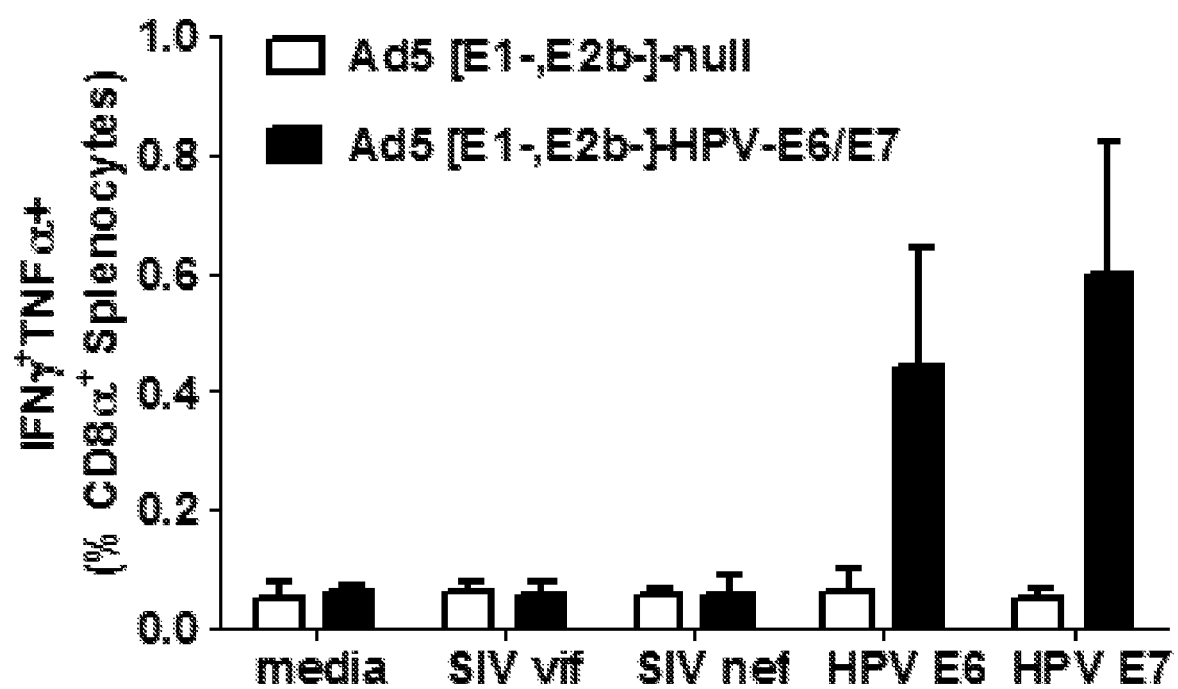

FIG. 68 exemplifies CMI response as assessed by flow cytometry. C57BL/6 mice were immunized three times with $10^{10}$ VP Ad5[E1-, E2b-]-null or $10^{10}$ VP Ad5[E1-,E2b-]-E6/E7 at two week intervals. Two weeks after the final immunization CD8α+ splenocytes were assayed for intracellular expression of IFNγ after 6 hour stimulation with antigen specific peptide pools. Mean+/−standard deviation is plotted.

Figure 69:
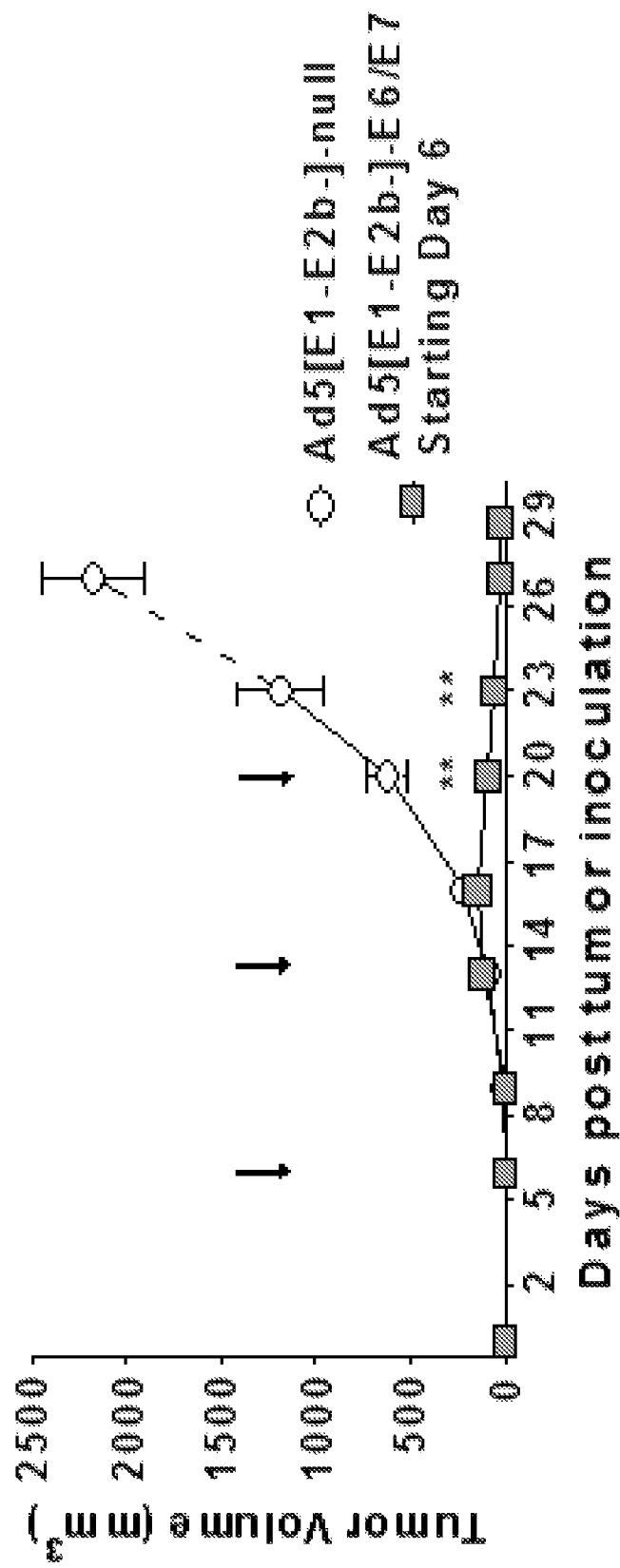

FIG. 69 exemplifies a result of immunotherapy of small established HPV-E6/E7 expressing tumors with Ad5 [E1-, E2b-]-E6/E7. C57BL/6 mice were implanted on day 0 with $2 \times 10^5$ TC-1 tumor cells and administered $10^{10}$ VP Ad5 [E1-, E2b-]-null (vector control) or $10^{10}$ VP Ad5 [E1-, E2b-]-E6/E7 on days 6, 13 and 20 as indicated by arrows. (A) Tumor size was determined and volumes calculated according to the formula $V=(a^2 \times b)/2$. On day 23, mice were euthanized from the vector control group. No analyses of significance could be performed after this 23 day time point and this is denoted by a dashed line. Analysis of significance was performed between experimental and vector control groups using unpaired t-tests and significance is denoted by ** (p<0.01). Error bars represent the standard error of the means.

DETAILED DESCRIPTION

The following passages describe different aspects of certain embodiments in greater detail. Each aspect may be combined with any other aspect or aspects unless clearly indicated to the contrary. In particular, any feature indicated as being preferred or advantageous may be combined with any other feature of features indicated as being preferred or advantageous.

Unless otherwise indicated, any embodiment can be combined with any other embodiment. A variety of aspects can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range as if explicitly written out. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When ranges are present, the ranges include the range endpoints.

Compared to first generation adenovirus vectors, certain embodiments of the Second Generation E2b deleted adenovirus vectors contain additional deletions in the DNA polymerase gene (pol) and deletions of the pre-terminal protein (pTP). E2b deleted vectors have up to a 13 kb gene-carrying capacity as compared to the 5 to 6 kb capacity of First Generation adenovirus vectors, easily providing space for nucleic acid sequences encoding any of a variety of target antigens. The E2b deleted adenovirus vectors also have reduced adverse reactions as compared to first generation adenovirus vectors.

The innate immune response to wild type Ad can be complex, and it appears that Ad proteins expressed from adenovirus vectors play an important role. Specifically, the deletions of pre-terminal protein and DNA polymerase in the E2b deleted vectors appear to reduce inflammation during the first 24 to 72 h following injection, whereas First Generation adenovirus vectors stimulate inflammation during this period. In addition, it has been reported that the additional replication block created by E2b deletion also leads to a 10,000 fold reduction in expression of Ad late genes, well beyond that afforded by E1, E3 deletions alone. The decreased levels of Ad proteins produced by E2b deleted adenovirus vectors effectively reduce the potential for competitive, undesired, immune responses to Ad antigens, responses that prevent repeated use of the platform in Ad immunized or exposed individuals. The reduced induction of inflammatory response by second generation E2b deleted vectors results in increased potential for the vectors to express desired vaccine antigens during the infection of antigen presenting cells (i.e., dendritic cells), decreasing the potential for antigenic competition, resulting in greater immunization of the vaccine to the desired antigen relative to identical attempts with First Generation adenovirus vectors. E2b deleted adenovirus vectors provide an improved Ad-based vaccine candidate that is safer, more effective, and more versatile than previously described vaccine candidates using First Generation adenovirus vectors. Thus, first generation, E1-deleted Adenovirus subtype 5 (Ad5)-based vectors, although promising platforms for use as cancer vaccines, are impeded in activity by naturally occurring or induced Ad-specific neutralizing antibodies. Without being bound by theory, Ad5-based vectors with deletions of the E1 and the E2b regions (Ad5 [E1-, E2b-]), the latter encoding the DNA polymerase and the pre-terminal protein, for example by virtue of diminished late phase viral protein expression, may avoid immunological clearance and induce more potent immune responses against the encoded tumor antigen transgene in Ad-immune hosts.

Some embodiments relate to methods and compositions (e.g., viral vectors) for generating immune responses against target antigens, in particular, those associated or related to infectious disease or proliferative cell disease such as cancer. Some embodiments relate to methods and compositions for generating immune responses in an individual against target antigens, in particular, those related to cell proliferation diseases such as cancer. In some embodiments, compositions and methods described herein relate to generating an immune response in an individual against cells expressing and/or presenting a target antigen or a target antigen signature comprising at least one target antigen. Some embodiments provide compositions and methods for immunotherapy against human papilloma virus (HPV) using a viral gene delivery platform to immunize against HPV genes E6 and E7 combined with PD1 checkpoint blockade. These compositions and methods utilize an Ad5 [E1-, E2b-]-E6/E7 vaccine combined with an immune pathway checkpoint modulator.

The compositions and methods can be used to generate an immune response against a target antigen expressed and/or presented by a cell. For example, the compositions and methods can be used to generate immune responses against a carcinoembryonic antigen (CEA), such as CEA expressed or presented by a cell. For example, the compositions and methods can be used to generate an immune response against CEA(6D) expressed or presented by a cell. For example, the compositions and methods can be used to generate an immune response against Mucin 1 (MUC1) expressed and/or presented by a cell. For example, the compositions and methods can be used to generate an immune response against MUC1c expressed and/or presented by a cell. For example, the compositions and methods can be used to generate an immune response against Brachyury (T protein (T)) expressed and/or presented by a cell.

The compositions and methods can be used to generate an immune response against multiple target antigens expressed and/or presented by a cell. For example, the compositions and methods can be used to generate an immune response against MUC1c, T, or any combination thereof. For example, the compositions and methods can be used to generate an immune response against T and CEA. For example, the compositions and methods can be used to generate an immune response against MUC1c and CEA. For example, the compositions and methods can be used to generate an immune response against MUC1 and T. For example, the compositions and methods can be used to generate an immune response against MUC1c, T, and CEA.

A modified form of CEA, MUC1c, or T can be used in a vaccine directed to raising an immune response against CEA, MUC1c, or T, or cells expressing and/or presenting CEA, MUC1c, or T. In particular, some embodiments provide an improved Ad-based vaccine such that multiple vaccinations against one or more antigenic target entity can be achieved. In some embodiments, the improved Ad-based vaccine comprises a replication defective adenovirus carrying a target antigen, a fragment, a variant or a variant fragment thereof, such as Ad5 [E1-, E2b-]-CEA(6D). Variants or fragments of target antigens, such as CEA, MUC1c, or T, can be selected based on a variety of factors, including immunogenic potential. A mutant CEA, CEA(6D) can utilized for its increased capability to raise an immune response relative to the CEA(WT). Importantly, vaccination can be performed in the presence of preexisting immunity to the Ad or administered to subjects previously immunized multiple times with the Ad vector as described herein or other Ad vectors. The Ad vectors can be administered to subjects multiple times to induce an immune response against an antigen of interest, such as CEA, MUC1c, or T, including but not limited to, the production of antibodies and CMI responses against one or more target antigens.

As used herein, unless otherwise indicated, the article "a" means one or more unless explicitly otherwise provided for. As used herein, unless otherwise indicated, terms such as "contain," "containing," "include," "including," and the like mean "comprising." As used herein, unless otherwise indicated, the term "or" can be conjunctive or disjunctive. As used herein, unless otherwise indicated, any embodiment can be combined with any other embodiment.

An "adenovirus" (Ad) refers to non-enveloped DNA viruses from the family Adenoviridae. These viruses can be found in, but are not limited to, human, avian, bovine, porcine and canine species. Some embodiments contemplate the use of any Ad from any of the four genera of the family Adenoviridae (e.g., Aviadenovirus, Mastadenovirus, Atadenovirus and Siadenovirus) as the basis of an E2b deleted virus vector, or vector containing other deletions as described herein. In addition, several serotypes are found in each species. Ad also pertains to genetic derivatives of any of these viral serotypes, including but not limited to, genetic mutations, deletions or transpositions.

A "helper adenovirus" or "helper virus" refers to an Ad that can supply viral functions that a particular host cell cannot (the host may provide Ad gene products such as E1 proteins). This virus is used to supply, in trans, functions (e.g., proteins) that are lacking in a second virus, or helper dependent virus (e.g., a gutted or gutless virus, or a virus deleted for a particular region such as E2b or other region as described herein); the first replication-incompetent virus is said to "help" the second, helper dependent virus thereby permitting the production of the second viral genome in a cell.

An "adenovirus 5 null (Ad5-null)" refers to a non-replicating Ad that does not contain any heterologous nucleic acid sequences for expression.

A "first generation adenovirus" refers to an Ad that has the early region 1 (E1) deleted. In additional cases, the early region 3 (E3) may also be deleted.

"Gutted" or "gutless" refers to an Ad vector that has been deleted of all viral coding regions.

"Transfection" refers to the introduction of foreign nucleic acid into eukaryotic cells. Exemplary means of transfection include calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

"Stable transfection" or "stably transfected" refers to the introduction and integration of foreign nucleic acid, DNA or RNA, into the genome of the transfected cell. The term "stable transfectant" refers to a cell which has stably integrated foreign DNA into the genomic DNA.

A "reporter gene" indicates a nucleotide sequence that encodes a reporter molecule (e.g., an enzyme). A "reporter molecule" is detectable in any of a variety of detection systems, including, but not limited to, enzyme-based detection assays (e.g., ELISA, histochemical assays), fluorescent, radioactive, and luminescent systems. The *E. coli* β-galactosidase gene, green fluorescent protein (GFP), the human placental alkaline phosphatase gene, the chloramphenicol acetyltransferase (CAT) gene; and other reporter genes may be employed.

A "heterologous sequence" refers to a nucleotide sequence that is ligated to, or is manipulated to become ligated to, a nucleic acid sequence to which it is not ligated in nature, or to which it is ligated at a different location in nature. Heterologous nucleic acid may include a naturally occurring nucleotide sequence or some modification relative to the naturally occurring sequence.

A "transgene" refers to any gene coding region, either natural or heterologous nucleic acid sequences or fused homologous or heterologous nucleic acid sequences, introduced into cells or a genome of subject. Transgenes may be carried on any viral vector used to introduce transgenes to the cells of the subject.

A "second generation adenovirus" refers to an Ad that has all or parts of the E1, E2, E3, and, in certain embodiments, E4 DNA gene sequences deleted (removed) from the virus.

A "subject" refers to any animal, including, but not limited to, humans, non-human primates (e.g., rhesus or other types of macaques), mice, pigs, horses, donkeys, cows, sheep, rats and fowls.

An "immunogenic fragment" refers to a fragment of a polypeptide that is specifically recognized (i.e., specifically bound) by a B-cell and/or T-cell surface antigen receptor resulting in a generation of an immune response specifically against a fragment.

A "target antigen" or "target protein" refers to a molecule, such as a protein, against which an immune response is to be directed.

"E2b deleted" refers to a DNA sequence mutated in such a way so as to prevent expression and/or function of at least one E2b gene product. Thus, in certain embodiments, "E2b deleted" is used in relation to a specific DNA sequence that is deleted (removed) from an Ad genome. E2b deleted or "containing a deletion within an E2b region" refers to a deletion of at least one base pair within an E2b region of an Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, a deletion is of more than 150, 160, 170, 180, 190, 200, 250, or 300 base pairs within an E2b region of an Ad genome. An E2b deletion may be a deletion that prevents expression and/or function of at least one E2b gene product and therefore, encompasses deletions within exons of encoding portions of E2b-specific proteins as well as deletions within promoter and leader sequences. In certain embodiments, an E2b deletion is a deletion that prevents expression and/or function of one or both a DNA polymerase and a preterminal protein of an E2b region. In a further embodiment, "E2b deleted" refers to one or more point mutations in a DNA sequence of this region of an Ad genome such that one or more encoded proteins is non-functional. Such mutations include residues that are replaced with a different residue leading to a change in an amino acid sequence that result in a nonfunctional protein.

"E1-deleted" refers to a DNA sequence that is mutated in such a way so as to prevent expression and/or function of at least one E1 gene product. Thus, in certain embodiments, "E1 deleted" is used in relation to a specific DNA sequence that is deleted (removed) from the Ad genome. E1 deleted or "containing a deletion within the E1 region" refers to a deletion of at least one base pair within the E1 region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, the deletion is of more than 150, 160, 170, 180, 190, 200, 250, or 300 base pairs within the E1 region of the Ad genome. An E1 deletion may be a deletion that prevents expression and/or function of at least one E1 gene product and therefore, encompasses deletions within exons of encoding portions of E1-specific proteins as well as deletions within promoter and leader sequences. In certain embodiments, an E1 deletion is a deletion that prevents expression and/or function of one or both of a trans-acting transcriptional regulatory factor of the E1 region. In a further embodiment, "E1 deleted" refers to one or more point mutations in the DNA sequence of this region of an Ad genome such that one or more encoded proteins is non-functional. Such mutations include residues that are replaced with a different residue leading to a change in the amino acid sequence that result in a nonfunctional protein.

"Generating an immune response" or "inducing an immune response" refers to a statistically significant change, e.g., increase or decrease, in the number of one or more immune cells (T-cells, B-cells, antigen-presenting cells, dendritic cells, neutrophils, and the like) or in the activity of one or more of these immune cells (CTL activity, HTL activity, cytokine secretion, change in profile of cytokine secretion, etc.).

The terms "nucleic acid" and "polynucleotide" are used essentially interchangeably herein. Polynucleotides may be single-stranded (coding or antisense) or double-stranded, and may be DNA (e.g. genomic, cDNA, or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide as described herein, and a polynucleotide may, but need not, be linked to other molecules and/or support materials. An isolated polynucleotide, as used herein, means that a polynucleotide is substantially away from other coding sequences. For example, an isolated DNA molecule as used herein does not contain large portions of unrelated coding DNA, such as large chromosomal fragments or other functional genes or polypeptide coding regions. This refers to the DNA molecule as originally isolated, and does not exclude genes or coding regions later added to the segment recombinantly in the laboratory.

As will be understood by those skilled in the art, the polynucleotides can include genomic sequences, extra-genomic and plasmid-encoded sequences and smaller engineered gene segments that express, or may be adapted to express target antigens as described herein, fragments of antigens, peptides and the like. Such segments may be naturally isolated, or modified synthetically by the hand of man.

Typically, polynucleotide variants will contain one or more substitutions, additions, deletions and/or insertions, preferably such that the immunogenicity of the epitope of the polypeptide encoded by the variant polynucleotide or such that the immunogenicity of the heterologous target protein is not substantially diminished relative to a polypeptide encoded by the native polynucleotide sequence. In some cases, the one or more substitutions, additions, deletions and/or insertions may result in an increased immunogenicity of the epitope of the polypeptide encoded by the variant polynucleotide. As described elsewhere herein, the polynucleotide variants can encode a variant of the target antigen, or a fragment (e.g., an epitope) thereof wherein the propensity of the variant polypeptide or fragment (e.g., epitope) thereof to react with antigen-specific antisera and/or T-cell lines or clones is not substantially diminished relative to the native polypeptide. The polynucleotide variants can encode a variant of the target antigen, or a fragment thereof wherein the propensity of the variant polypeptide or fragment thereof to react with antigen-specific antisera and/or T-cell lines or clones is substantially increased relative to the native polypeptide.

The term "variants" should also be understood to encompass homologous genes of xenogenic origin. In particular embodiments, variants or fragments of target antigens are modified such that they have one or more reduced biological activities. For example, an oncogenic protein target antigen may be modified to reduce or eliminate the oncogenic activity of the protein, or a viral protein may be modified to reduce or eliminate one or more activities or the viral protein. An example of a modified CEA protein is a CEA having a N610D mutation, resulting in a variant protein with increased immunogenicity.

When comparing polynucleotide sequences, two sequences are "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned. Optimal alignment of sequences for comparison may be conducted using the Megalign program in the Lasergene suite of bioinformatics software using default parameters. Alternatively, optimal alignment of sequences for comparison may be conducted by the local identity algorithm of Smith and Waterman, Add. APL. Math 2:482 (1981), by the identity alignment algorithm of Needleman and Wunsch, J. Mol. Biol. 48:443 (1970), by the search for similarity methods of Pearson and Lipman, Proc. Natl. Acad. Sci. USA 85: 2444 (1988), by computerized implementations of these algorithms (GAP, BESTFIT, BLAST, FASTA, and TFASTA), or by inspection. One example of algorithms that are suitable for determining percent sequence identity and sequence similarity are the BLAST and BLAST 2.0 algorithms. BLAST and BLAST 2.0 can be used, for example with the parameters described herein, to determine percent sequence identity for the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program uses as defaults a word length (W) of 11, and expectation (E) of 10, and the BLOSUM62 scoring matrix alignments, (B) of 50, expectation (E) of 10, M=5, N=−4 and a comparison of both strands.

The "percentage of sequence identity" can be determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence and multiplying the results by 100 to yield the percentage of sequence identity.

It will be appreciated by those of ordinary skill in the art that, as a result of the degeneracy of the genetic code, there are many nucleotide sequences that encode a particular antigen of interest, or fragment thereof, as described herein. Some of these polynucleotides bear minimal homology to the nucleotide sequence of any native gene. Nonetheless, polynucleotides that vary due to differences in codon usage are specifically contemplated. Further, alleles of the genes comprising the polynucleotide sequences provided herein are within the scope of some embodiments. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Viral Vectors for Immunotherapies and Vaccines

Recombinant viral vectors can be used to express protein coding genes or antigens (e.g., TAAs (tumor-associated antigens) and/or IDAAs (infectious-disease associated antigens)). The advantages of recombinant viral vector based vaccines and immunotherapy include high efficiency gene transduction, highly specific delivery of genes to target cells, induction of robust immune responses, and increased cellular immunity. Certain embodiments provide for recombinant adenovirus vectors comprising deletions or insertions of crucial regions of the viral genome. The viral vectors of provided herein can comprise heterologous nucleic acid sequences that encode one or more target antigens of interest, or variants, fragments or fusions thereof, against which it is desired to generate an immune response.

Suitable viral vectors that can be used with the methods and compositions as provided herein, include but are not limited to retroviruses, lentiviruses, provirus, Vaccinia virus, adenoviruses, adeno-associated viruses, self-complementary adeno-associated virus, Cytomegalovirus, or Sendai virus. In some embodiments, the viral vector can be replication-competent. In some embodiments, the viral vector can be replication-defective. For replication-defective viral vectors, the viruses' genome can have the coding regions necessary for additional rounds of replication and packaging replaced with other genes, or deleted. These viruses are capable of infecting their target cells and delivering their viral payload, but then fail to continue the typical lytic pathway that leads to cell lysis and death. Depending on the viral vector, the typical maximum length of an allowable DNA or cDNA insert in a replication-defective viral vector is can be about 8-10 kilobases (kB).

Retroviruses have been used to express antigens, such as an enveloped, single-stranded RNA virus that contains reverse transcriptase. Retrovirus vectors can be replication-defective. Retrovirus vectors can be of murine or avian origin. Retrovirus vectors can be from Moloney murine leukemia virus (MoMLV). Retrovirus vectors can be used that require genome integration for gene expression. Retrovirus vectors can be used to provide long-term gene expression. For example, retrovirus vectors can have a genome size of approximately 7-11 kb and the vector can harbor 7-8 kb long foreign DNA inserts. Retrovirus vectors can be used to display low immunogenicity and most patients do not show pre-existing immunity to retroviral vectors. Retrovirus vectors can be used to infect dividing cells. Retrovirus vectors can be used to not infect non-dividing cells.

Lentivirus vectors have been used to express antigens. Lentiviruses constitute a subclass of retroviruses. Lentivirus vectors can be used to infect non-dividing cells. Lentivirus vectors can be used to infect dividing cells. Lentivirus vectors can be used to infect both non-dividing and dividing cells. Lentiviruses generally exhibit broader tropism than retroviruses. Several proteins such as tat and rev regulate the replication of lentiviruses. These regulatory proteins are typically absent in retroviruses. HIV is an exemplary lentivirus that can been engineered into a transgene delivery vector. The advantages of lentivirus vectors are similar to those of retroviral vectors. Although lentiviruses can potentially trigger tumorigenesis, the risk is lower than that of retroviral vectors, as the integration sites of lentiviruses are away from the sites harboring cellular promoters. HIV-based vectors can be generated, for example, by deleting the HIV viral envelope and some of the regulatory genes not required during vector production. Instead of parental envelope, several chimeric or modified envelope vectors are generated because it determines the cell and tissue specificity.

Cytomegalovirus (CMV) vectors have been used to express antigens and is a member of the herpesviruses. Species-specific CMVs can be used (e.g., human CMV (HCMV), e.g., human herpesvirus type 5. HCMV contains a 235-kb double-stranded linear DNA genome surrounded by a capsid. The envelope contains glycoproteins gB and gH, which bind to cellular receptors.

Sendai virus (SeV) vectors have been used to express antigens. SeV is an enveloped, single-stranded RNA virus of the family Paramyxovirus. The SeV genome encodes six protein and two envelope glycoproteins, HN and F proteins, that mediate cell entry and determine its tropism. SeV vectors that lack F protein can be used as a replication-defective virus to improve the safety of the vector. SeV vector produced in a packaging cell can be used to expresses the F protein. An F gene-deleted and transgene-inserted genome can be transfected into a packaging cell. SeV contains RNA dependent RNA polymerase and viral genome localizes to the cytoplasm. This ensures that fast gene expression occurs soon after infection and the genotoxic advantage of SeV. SeV vectors can be used to exhibit highly efficient gene transfer. SeV vectors can be used to transduce both dividing and non-dividing cells. SeV vectors can be used to transduce non-dividing cells. SeV vectors can be used to transduce dividing cells. SeV vectors can be used, for example, to efficiently transduce human airway epithelial cells. SeV vectors can be, for example, administered by a mucosal (e.g., oral and nasal) route. Intranasal administration can be used to potentially reduce the influence of a pre-existing immunity to SeV, as compared to intramuscular administration. Compared to other viral vectors, its transgene capacity (3.4 kb) is low. SeV is highly homologous to the human parainfluenza type 1 (hPIV-1) virus; thus, a pre-existing immunity against hPIV-1 can work against the use of SeV.

Human papillomavirus (HPV) vectors can be used to express antigens. For example, by modifying oncogenes in the genome, such as by deletion or insertion of crucial regions of the HPV viral genome, a recombinant vector can be engineered to increase predictability of infection and reduce unwanted side effects. An exemplary HPV vector is a fusion vector with an adenovirus vector. An exemplary HPV vector is Ad5 [E1-, E2b-]-HPV-E6/E7 viral vector comprising a modified non-oncogenic and fused HPV-E6/E7.

Adenovirus Vectors

In general, adenoviruses are attractive for clinical because they can have a broad tropism, they can infect a variety of dividing and non-dividing cell types and hey can be used systemically as well as through more selective mucosal surfaces in a mammalian body. In addition, their relative thermostability further facilitates their clinical use. Adenoviruses are a family of DNA viruses characterized by an icosahedral, non-enveloped capsid containing a linear double-stranded genome. Generally, adenoviruses are found as non-enveloped viruses comprising double-stranded DNA genome approximated ~30-35 kilobases in size. Of the human Ads, none are associated with any neoplastic disease, and only cause relatively mild, self-limiting illness in immunocompetent individuals. The first genes expressed by the virus are the E1 genes, which act to initiate high-level gene expression from the other Ad5 gene promoters present in the wild type genome. Viral DNA replication and assembly of progeny virions occur within the nucleus of infected cells, and the entire life cycle takes about 36 hr with an output of approximately $10^4$ virions per cell. The wild type Ad5 genome is approximately 36 kb, and encodes genes that are divided into early and late viral functions, depending on whether they are expressed before or after DNA replication. The early/late delineation is nearly absolute, since it has been demonstrated that super-infection of cells previously infected with an Ad5 results in lack of late gene expression from the super-infecting virus until after it has replicated its own genome. Without bound by theory, this is likely due to a replication dependent cis-activation of the Ad5 major late promoter (MLP), preventing late gene expression (primarily the Ad5 capsid proteins) until replicated genomes are present to be encapsulated. The composition and methods as described herein, in some embodiments, take advantage of feature in the development of advanced generation Ad vectors/vaccines. The linear genome of the adenovirus is generally flanked by two origins for DNA replication (ITRs) and has eight units for RNA polymerase II-mediated transcription. The genome carries five early units E1A, E1B, E2, E3, E4, and E5, two units that are expressed with a delay after initiation of viral replication (IX and IVa2), and one late unit (L) that is subdivided into L1-L5. Some adenoviruses can further encode one or two species of RNA called virus-associated (VA) RNA.

Adenoviruses that induce innate and adaptive immune responses in human patient are provided. By deletion or insertion of crucial regions of the viral genome, recombinant vectors are provided that have been engineered to increase their predictability and reduce unwanted side effects. In some aspects, there is provided an adenovirus vector comprising the genome deletion or insertion selected from the group consisting of: E1A, E1B, E2, E3, E4, E5, IX, IVa2, L1, L2, L3, L4, and L5, and any combination thereof.

Certain embodiments provide recombinant adenovirus vectors comprising an altered capsid. Generally, the capsid of an adenovirus is primarily comprises 20 triangular facets of an icosahedron each icosahedron contains 12 copies of hexon trimers. In addition there are also other several additional minor capsid proteins, IIIa, VI, VIII, and IX.

Certain embodiments provide recombinant adenovirus vectors comprising one or more altered fiber proteins. In general the fiber proteins, which also form trimers, are inserted at the 12 vertices into the pentameric penton bases. The fiber can comprise of a thin N-terminal tail, a shaft, and a knob domain. The shaft can comprise a variable numbers of β-strand repeats. The knob can comprise one or more loops A, B, C, D, E, F, G, H, I, J. The fiber knob loops can bind to cellular receptors. Certain embodiments provide adenovirus vectors to be used in vaccine systems for the treatment of cancers and infectious diseases.

Suitable adenoviruses that can be used with the present methods and compositions of the disclosure include but are not limited to species-specific adenovirus including human subgroups A, B1, B2, C, D, E and F or their crucial genomic regions as provided herein, which subgroups can further classified into immunologically distinct serotypes. Further, suitable adenoviruses that can be used with the present methods and compositions of the disclosure include, but are not limited to, species-specific adenovirus or their crucial genomic regions identified from primates, bovines, fowls, reptiles, or frogs.

Some adenoviruses serotypes preferentially target distinct organs. Serotypes such as AdHu1, AdHu2, and AdHu5 (subgenus C), generally effect the infect upper respiratory, while subgenera A and F effect gastrointestinal organs. Certain embodiments provide recombinant adenovirus vectors to be used in preferentially target distinct organs for the treatment of organ-specific cancers or organ-specific infectious diseases. In some applications the recombinant adenovirus vector is altered to reduce tropism to a specific organ in a mammal. In some applications the recombinant adenovirus vector is altered to increase tropism to a specific organ in a mammal.

The tropism of an adenovirus can be determined by their ability to attach to host cell receptors. In some instances the process of host cell attachment can involve the initial binding of the distal knob domain of the fiber to a host cell surface molecule followed by binding of the RGD motif within the penton base with αV integrins. Certain embodiments provide recombinant adenovirus vectors with altered tropism such that they can be genetic engineered to infect specific cell types of a host. Certain embodiments provide recombinant adenovirus vectors with altered tropism for the treatment of cell-specific cancers or cell-specific infectious diseases. Certain embodiments provide recombinant adenovirus vectors with altered fiber knob from one or more adenoviruses of subgroups A, B, C, D, or F, or a combination thereof or the insertion of RGD sequences. In some applications the recombinant adenovirus vectors comprising an altered fiber knob results in a vector with reduced tropism for one or more particular cell types. In some applications the recombinant adenovirus vectors comprising an altered fiber knob results in a vector with enhanced tropism for one or more particular cell types. In some applications the recombinant adenovirus vectors comprising an altered fiber knob results in a vector with reduced product-specific B or T-cell responses. In some applications the recombinant adenovirus vectors comprising an altered fiber knob results in a vector with enhanced product-specific B or T-cell responses.

Certain embodiments provide recombinant adenovirus vectors that are coated with other molecules to circumvent the effects of virus-neutralizing antibodies or improve transduction in to a host cell. Certain embodiments provide recombinant adenovirus vectors that are coated with an adaptor molecule that aids in the attachment of the vector to a host cell receptor. By way of example an adenovirus vector can be coated with adaptor molecule that connects coxsackie Ad receptor (CAR) with CD40L resulting in increased transduction of dendritic cells, thereby enhancing immune responses in a subject. Other adenovirus vectors similarly engineered for enhancing the attachment to other target cell types are also contemplated.

Ad5 Vectors

Studies in humans and animals have demonstrated that pre-existing immunity against Ad5 can be an inhibitory factor to commercial use of Ad-based vaccines. The preponderance of humans have antibody against Ad5, the most widely used subtype for human vaccines, with two-thirds of humans studied having lympho-proliferative responses against Ad5. This pre-existing immunity can inhibit immunization or re-immunization using typical Ad5 vaccines and may preclude the immunization of a vaccine against a second antigen, using an Ad5 vector, at a later time. Overcoming the problem of pre-existing anti-vector immunity has been a subject of intense investigation. Investigations using alternative human (non-Ad5 based) Ad5 subtypes or even non-human forms of Ad5 have been examined. Even if these approaches succeed in an initial immunization, subsequent vaccinations may be problematic due to immune responses to the novel Ad5 subtype. To avoid the Ad5 immunization barrier, and improve upon the limited efficacy of first generation Ad5 [E1-] vectors to induce optimal immune responses, some embodiments relate to a next generation Ad5 vector based vaccine platform.

First generation, or E1-deleted adenovirus vectors Ad5 [E1-] are constructed such that a transgene replaces only the E1 region of genes. Typically, about 90% of the wild-type Ad5 genome is retained in the vector. Ad5 [E1-] vectors have a decreased ability to replicate and cannot produce infectious virus after infection of cells that do not express the Ad5 E1 genes. The recombinant Ad5 [E1-] vectors are propagated in human cells (e.g., 293 cells) allowing for Ad5 [E1-] vector replication and packaging. Ad5 [E1-] vectors have a number of positive attributes; one of the most important is their relative ease for scale up and cGMP production. Currently, well over 220 human clinical trials utilize Ad5 [E1-] vectors, with more than two thousand subjects given the virus sc, im, or iv. Additionally, Ad5 vectors do not integrate; their genomes remain episomal. Generally, for vectors that do not integrate into the host genome, the risk for insertional mutagenesis and/or germline transmission is extremely low if at all. Conventional Ad5 [E1-] vectors have a carrying capacity that approaches 7 kb.

Ad5-based vectors with deletions of the E1 and the E2b regions (Ad5 [E1-, E2b-]), the latter encoding the DNA polymerase and the pre-terminal protein, by virtue of diminished late phase viral protein expression, provide an opportunity to avoid immunological clearance and induce more potent immune responses against the encoded tumor antigen transgene in Ad-immune hosts. The new Ad5 platform has additional deletions in the E2b region, removing the DNA polymerase and the preterminal protein genes. The Ad5 [E1-, E2b-] platform has an expanded cloning capacity that is sufficient to allow inclusion of many possible genes. Ad5 [E1-, E2b-] vectors have up to about 12 kb gene-carrying capacity as compared to the 7 kb capacity of Ad5 [E1-] vectors, providing space for multiple genes if needed. In some embodiments, an insert of more than 1, 2, 3, 4, 5, 6, 7, 8, 9, 10, or 11 kb is introduced into an Ad5 vector, such as the Ad5 [E1-, E2b-] vector. Deletion of the E2b region confers advantageous immune properties on the Ad5 vectors, often eliciting potent immune responses to target transgene antigens while minimizing the immune responses to Ad viral proteins.

In various embodiments, Ad5 [E1-, E2b-] vectors induce a potent CMI, as well as antibodies against the vector expressed vaccine antigens even in the presence of Ad immunity. Ad5 [E1-, E2b-] vectors also have reduced adverse reactions as compared to Ad5 [E1-] vectors, in particular the appearance of hepatotoxicity and tissue damage. A key aspect of these Ad5 vectors is that expression of Ad late genes is greatly reduced. For example, production of the capsid fiber proteins could be detected in vivo for Ad5 [E1-] vectors, while fiber expression was ablated from Ad5 [E1-, E2b-] vector vaccines. The innate immune response to wild type Ad is complex. Proteins deleted from the Ad5 [E1-, E2b-] vectors generally play an important role. Specifically, Ad5 [E1-, E2b-] vectors with deletions of preterminal protein or DNA polymerase display reduced inflammation during the first 24 to 72 h following injection compared to Ad5 [E1-] vectors. In various embodiments, the lack of Ad5 gene expression renders infected cells invisible to anti-Ad activity and permits infected cells to express the transgene for extended periods of time, which develops immunity to the target.

Some embodiments contemplate increasing the capability for the Ad5 [E1-, E2b-] vectors to transduce dendritic cells, improving antigen specific immune responses in the vaccine by taking advantage of the reduced inflammatory response against Ad5 [E1-, E2b-] vector viral proteins and the resulting evasion of pre-existing Ad immunity.

Replication Defective Ad5 Vector

Attempts to overcome anti-Ad immunity have included use of alternative Ad serotypes and/or alternations in the Ad5 viral capsid protein each with limited success and the potential for significantly altering biodistribution of the resultant vaccines. Therefore, a completely novel approach was attempted by further reducing the expression of viral proteins from the E1 deleted Ad5 vectors, proteins known to be targets of pre-existing Ad immunity. Specifically, a novel recombinant Ad5 platform has been described with deletions in the early 1 (E1) gene region and additional deletions in the early 2b (E2b) gene region (Ad5 [E1-, E2b-]). Deletion of the E2b region (that encodes DNA polymerase and the pre-terminal protein) results in decreased viral DNA replication and late phase viral protein expression. This vector platform can be used to induce CMI responses in animal models of cancer and infectious disease and more importantly, this recombinant Ad5 gene delivery platform overcomes the barrier of Ad5 immunity and can be used in the setting of pre-existing and/or vector-induced Ad immunity thus enabling multiple homologous administrations of the vaccine. In particular embodiments, some embodiments relate to a replication defective adenovirus vector of serotype 5 comprising a sequence encoding an immunogenic polypeptide. The immunogenic polypeptide may be a mutant, natural variant, or a fragment thereof.

In some embodiments, the replication defective adenovirus vector comprises a modified sequence encoding a polypeptide with at least 50%, 60%, 65%, 70%, 75%, 80%, 85%, 90%, 95%, 98%, 99%, 99.5%, 99.9%, 100% identity to a wild-type immunogenic polypeptide or a fragment thereof. In some embodiments, the replication defective adenovirus vector comprises a modified sequence encoding a subunit of a wild-type polypeptide. The compositions and methods, in some embodiments, relate to an adenovirus-derived vector comprising at least 60% sequence identity to SEQ. ID. NO:3.

In some embodiments, an adenovirus-derived vector, optionally relating to a replication defective adenovirus, comprises a sequence with at least 75%, 80%, 85%, 90%, 95%, 98%, 99%, 99.5%, 99.8%, 99.9% identity to SEQ. ID. NO:3 or a sequence generated from SEQ. ID. NO:3 by alternative codon replacements. In various embodiments, the adenovirus-derived vectors described herein have a deletion in the E2b region, and optionally, in the E1 region, the deletion conferring a variety of advantages to the use of the vectors in immunotherapy as described herein.

Certain regions within the adenovirus genome serve essential functions and may need to be substantially conserved when constructing the replication defective adenovirus vectors. These regions are further described in Lauer et al., J. Gen. Virol., 85, 2615-25 (2004), Leza et al., J. Virol., p. 3003-13 (1988), and Miralles et al., J. Bio Chem., Vol. 264, No. 18, p. 10763-72 (1983), which are incorporated by reference in their entirety. Recombinant nucleic acid vectors comprising a sequence with identity values of at least 50%, 60%, 65%, 70%, 75%, 80%, 85%, 90%, 95%, 98%, 99%, 99.5%, 99.8%, 99.9%, 100% to a portion of SEQ. ID. NO:3, such as a portion comprising at least about 100, 250, 500, 1000 or more bases of SEQ. ID. NO:3 are used in some embodiments.

Certain embodiments contemplate the use of E2b deleted adenovirus vectors, such as those described in U.S. Pat. Nos. 6,063,622; 6,451,596; 6,057,158; 6,083,750; and 8,298,549, which are each incorporated herein by reference in their entirety. The vectors with deletions in the E2b regions in many cases cripple viral protein expression and/or decrease the frequency of generating replication competent Ad (RCA). Propagation of these E2b deleted adenovirus vectors can be done utilizing cell lines that express the deleted E2b gene products. Such packaging cell lines are provided herein; e.g., E.C7 (formally called C-7), derived from the HEK-2p3 cell line.

Further, the E2b gene products, DNA polymerase and preterminal protein, can be constitutively expressed in E.C7, or similar cells along with the E1 gene products. Transfer of gene segments from the Ad genome to the production cell line has immediate benefits: (1) increased carrying capacity; and, (2) a decreased potential of RCA generation, typically requiring two or more independent recombination events to generate RCA. The E1, Ad DNA polymerase and/or preterminal protein expressing cell lines used in some embodiments can enable the propagation of adenovirus vectors with a carrying capacity approaching 13 kb, without the need for a contaminating helper virus. In addition, when genes critical to the viral life cycle are deleted (e.g., the E2b genes), a further crippling of Ad to replicate or express other viral gene proteins occurs. This can decrease immune recognition of infected cells, and extend durations of foreign transgene expression.

E1, DNA polymerase, and preterminal protein deleted vectors are typically unable to express the respective proteins from the E1 and E2b regions. Further, they may show a lack of expression of most of the viral structural proteins. For example, the major late promoter (MLP) of Ad is responsible for transcription of the late structural proteins L1 through L5. Though the MLP is minimally active prior to Ad genome replication, the highly toxic Ad late genes are primarily transcribed and translated from the mLP only after viral genome replication has occurred. This cis-dependent activation of late gene transcription is a feature of DNA viruses in general, such as in the growth of polyoma and SV-40. The DNA polymerase and preterminal proteins are important for Ad replication (unlike the E4 or protein IX proteins). Their deletion can be extremely detrimental to adenovirus vector late gene expression, and the toxic effects of that expression in cells such as APCs.

The adenovirus vectors can include a deletion in the E2b region of the Ad genome and, optionally, the E1 region. In some cases, such vectors do not have any other regions of the Ad genome deleted. The adenovirus vectors can include a deletion in the E2b region of the Ad genome and deletions in the E1 and E3 regions. In some cases, such vectors have no other regions deleted. The adenovirus vectors can include a deletion in the E2b region of the Ad genome and deletions in the E1, E3 and partial or complete removal of the E4 regions. In some cases, such vectors have no other deletions. The adenovirus vectors can include a deletion in the E2b region of the Ad genome and deletions in the E1 and/or E4 regions. In some cases, such vectors contain no other deletions. The adenovirus vectors can include a deletion in the E2a, E2b and/or E4 regions of the Ad genome. In some cases, such vectors have no other deletions. The adenovirus vectors can have the E1 and/or DNA polymerase functions of the E2b region deleted. In some cases, such vectors have no other deletions. The adenovirus vectors can have the E1 and/or the preterminal protein functions of the E2b region deleted. In some cases, such vectors have no other deletions. The adenovirus vectors can have the E1, DNA polymerase and/or the preterminal protein functions deleted. In some cases, such vectors have no other deletions. The adenovirus vectors can have at least a portion of the E2b region and/or the E1 region. In some cases, such vectors are not gutted adenovirus vectors. In this regard, the vectors may be deleted for both the DNA polymerase and the preterminal protein functions of the E2b region. The adenovirus vectors can have a deletion in the E1, E2b and/or 100K regions of the adenovirus genome. The adenovirus vectors can comprise vectors having the E1, E2b and/or protease functions deleted. In some cases, such vectors have no other deletions. The adenovirus vectors can have the E1 and/or the E2b regions deleted, while the fiber genes have been modified by mutation or other alterations (for example to alter Ad tropism). Removal of genes from the E3 or E4 regions may be added to any of the adenovirus vectors mentioned. In certain embodiments, the adenovirus vector may be a gutted adenovirus vector.

Other regions of the Ad genome can be deleted. A "deletion" in a particular region of the Ad genome refers to a specific DNA sequence that is mutated or removed in such a way so as to prevent expression and/or function of at least one gene product encoded by that region (e.g., E2b functions of DNA polymerase or preterminal protein function). Deletions encompass deletions within exons encoding portions of proteins as well as deletions within promoter and leader sequences. A deletion within a particular region refers to a deletion of at least one base pair within that region of the Ad genome. More than one base pair can be deleted. For example, at least 20, 30, 40, 50, 60, 70, 80, 90, 100, 110, 120, 130, 140, or 150 base pairs can be deleted from a particular region. The deletion can be more than 150, 160, 170, 180, 190, 200, 250, or 300 base pairs within a particular region of the Ad genome. These deletions can prevent expression and/or function of the gene product encoded by the region. For example, a particular region of the Ad genome can include one or more point mutations such that one or more encoded proteins is non-functional. Such mutations include residues that are replaced with a different residue leading to a change in the amino acid sequence that result in a nonfunctional protein. Exemplary deletions or mutations in the Ad genome include one or more of E1a, E1b, E2a, E2b, E3, E4, L1, L2, L3, L4, L5, TP, POL, IV, and VA regions. Deleted adenovirus vectors can be made, for example, using recombinant techniques.

Ad vectors in certain embodiments can be successfully grown to high titers using an appropriate packaging cell line that constitutively expresses E2b gene products and products of any of the necessary genes that may have been deleted. HEK-293-derived cells that not only constitutively express the E1 and DNA polymerase proteins, but also the Ad-preterminal protein, can be used. E.C7 cells can be used, for example, to grow high titer stocks of the adenovirus vectors.

To delete critical genes from self-propagating adenovirus vectors, proteins encoded by the targeted genes can first be coexpressed in HEK-293 cells, or similar, along with E1 proteins. For example, those proteins which are non-toxic when coexpressed constitutively (or toxic proteins inducibly-expressed) can be selectively utilized. Coexpression in HEK-293 cells of the E1 and E4 genes is possible (for example utilizing inducible, not constitutive, promoters). The E1 and protein IX genes, a virion structural protein, can be coexpressed. Further coexpression of the E1, E4, and protein IX genes is also possible. E1 and 100K genes can be expressed in trans-complementing cell lines, as can E1 and protease genes.

Cell lines coexpressing E1 and E2b gene products for use in growing high titers of E2b deleted Ad particles can be used. Useful cell lines constitutively express the approximately 140 kDa Ad-DNA polymerase and/or the approximately 90 kDa preterminal protein. Cell lines that have high-level, constitutive coexpression of the E1, DNA polymerase, and preterminal proteins, without toxicity (e.g. E.C7), are desirable for use in propagating Ad for use in multiple vaccinations. These cell lines permit the propagation of adenovirus vectors deleted for the E1, DNA polymerase, and preterminal proteins.

The recombinant Ad can be propagated using, for example, tissue culture plates containing E.C7 cells infected with Ad vector virus stocks at an appropriate MOI (e.g., 5) and incubated at 37° C. for 40-96 h. The infected cells can be harvested, resuspended in 10 mM Tris-Cl (pH 8.0), and sonicated, and the virus can be purified by two rounds of cesium chloride density centrifugation. The virus containing band can be desalted over a column, sucrose or glycerol can be added, and aliquots can be stored at −80° C. Virus can be placed in a solution designed to enhance its stability, such as A195. The titer of the stock can be measured (e.g., by measurement of the optical density at 260 nm of an aliquot of the virus after lysis). Plasmid DNA, either linear or circular, encompassing the entire recombinant E2b deleted adenovirus vector can be transfected into E.C7, or similar cells, and incubated at 37° C. until evidence of viral production is present (e.g. cytopathic effect). Conditioned media from cells can be used to infect more cells to expand the amount of virus produced before purification. Purification can be accomplished, for example, by two rounds of cesium chloride density centrifugation or selective filtration. Virus may be purified by chromatography using commercially available products or custom chromatographic columns.

The compositions as described herein can comprise enough virus to ensure that cells to be infected are confronted with a certain number of viruses. Thus, some embodiments provide a stock of recombinant Ad, such as an RCA-free stock of recombinant Ad. Viral stocks can vary considerably in titer, depending largely on viral genotype and the protocol and cell lines used to prepare them. Viral stocks can have a titer of at least about $10^6$, $10^7$, or $10^8$ pfu/mL, or higher, such as at least about $10^9$, $10^{10}$, $10^{11}$, or $10^{12}$ pfu/mL. Depending on the nature of the recombinant virus and the packaging cell line, a viral stock can have a titer of even about $10^{13}$ particles/ml or higher.

A replication defective adenovirus vector (e.g., SEQ. ID. NO.:3) can comprise a sequence encoding a target antigen, a fragment thereof, or a variant thereof, at a suitable position. In some embodiments, a replication defective adenovirus vector (e.g., SEQ. ID. NO.:3) can comprise a sequence encoding a target antigen described herein, or a fragment, a variant, or a variant fragment thereof, at a position replacing the nucleic acid sequence encoding a CEA or a variant CEA (e.g., SEQ. ID. NO.:1). In some embodiments, a replication defective adenovirus vector (e.g., SEQ. ID. NO.:3) can comprise a sequence encoding a target antigen described herein, or a fragment, a variant, or a variant fragment thereof, at a position replacing the nucleic acid sequence encoding a CEA or a variant CEA (e.g., SEQ. ID. NO.:2). In some embodiments, a replication defective adenovirus vector (e.g., SEQ. ID. NO.:3) can comprise a sequence encoding a target antigen described herein, or a fragment, a variant, or a variant fragment thereof, at a position replacing the nucleic acid sequence encoding a MUC1 or a variant MUC1 (e.g., SEQ. ID. NO.:5, SEQ. ID. NO.:6 or SEQ. ID. NO.:9). In some embodiments, a replication defective adenovirus vector (e.g., SEQ. ID. NO.:3) can comprise a sequence encoding a target antigen described herein, or a fragment, a variant, or a variant fragment thereof, at a position replacing the nucleic acid sequence encoding a T or a variant T (e.g., SEQ. ID. NO.:7 or SEQ. ID. NO.:8).

Polynucleotides and Variants Encoding Antigen Targets

Certain embodiments provide nucleic acid sequences, also referred to herein as polynucleotides that encode one or more target antigens of interest, or fragments or variants thereof. As such, some embodiments provide polynucleotides that encode target antigens from any source as described further herein, vectors comprising such polynucleotides and host cells transformed or transfected with such expression vectors. In order to express a desired target antigen polypeptide, nucleotide sequences encoding the polypeptide, or functional equivalents, can be inserted into an appropriate Ad vector (e.g., using recombinant techniques). The appropriate adenovirus vector may contain the necessary elements for the transcription and translation of the inserted coding sequence and any desired linkers. Methods which are well known to those skilled in the art may be used to construct these adenovirus vectors containing sequences encoding a polypeptide of interest and appropriate transcriptional and translational control elements. These methods include in vitro recombinant DNA techniques, synthetic techniques, and in vivo genetic recombination.

Polynucleotides may comprise a native sequence (i.e., an endogenous sequence that encodes a target antigen polypeptide/protein/epitope or a portion thereof) or may comprise a sequence that encodes a variant, fragment, or derivative of such a sequence. Polynucleotide sequences can encode target antigen proteins. In some embodiments, polynucleotides represent a novel gene sequence optimized for expression in specific cell types that may substantially vary from the native nucleotide sequence or variant but encode a similar protein antigen.

In other related embodiments, polynucleotide variants have substantial identity to native sequences encoding proteins (e.g., target antigens of interest), for example those comprising at least 70% sequence identity, preferably at least 75%, 80%, 85%, 90%, 95%, 96%, 97%, 98%, or 99% or higher, sequence identity compared to a native polynucleotide sequence encoding the polypeptides (e.g., BLAST analysis using standard parameters). These values can be appropriately adjusted to determine corresponding identity of proteins encoded by two nucleotide sequences by taking into account codon degeneracy, amino acid similarity, reading frame positioning and the like. Polynucleotides can encode a protein comprising for example at least 70% sequence identity, preferably at least 75%, 80%, 85%, 90%, 95%, 96%, 97%, 98%, or 99% or higher, sequence identity compared to a protein sequence encoded by a native polynucleotide sequence.

Polynucleotides can comprise at least about 5, 10, 15, 20, 25, 30, 35, 40, 45, 50, 55, 60, 65, 70, 75, 80, 85, 90, 95, 100, 11, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, or 1000 or more contiguous nucleotides encoding a polypeptide (e.g., target protein antigens), and all intermediate lengths there between. "Intermediate lengths", in this context, refers to any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. A polynucleotide sequence may be extended at one or both ends by additional nucleotides not found in the native sequence encoding a polypeptide, such as an epitope or heterologous target protein. This additional sequence may consist of 1, 2, 3, 4, 5, 6, 7, 8, 9, 10, 11, 12, 13, 14, 15, 16, 17, 18, 19, or 20 nucleotides or more, at either end of the disclosed sequence or at both ends of the disclosed sequence.

The polynucleotides, regardless of the length of the coding sequence itself, may be combined with other DNA sequences, such as promoters, expression control sequences, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. Illustrative polynucleotide segments with total lengths of about 1000, 2000, 3000, 4000, 5000, 6000, 7000, 8000, 9000, 10,000, about 500, about 200, about 100, about 50 base pairs in length, and the like, (including all intermediate lengths) are contemplated to be useful in many embodiments.

A mutagenesis approach, such as site-specific mutagenesis, can be employed to prepare target antigen sequences. Specific modifications in a polypeptide sequence can be made through mutagenesis of the underlying polynucleotides that encode them. Site-specific mutagenesis can be used to make mutants through the use of oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. For example, a primer comprising about 14 to about 25 nucleotides or so in length can be employed, with about 5 to about 10 residues on both sides of the junction of the sequence being altered. Mutations may be made in a selected polynucleotide sequence to improve, alter, decrease, modify, or otherwise change the properties of the polynucleotide, and/or alter the properties, activity, composition, stability, or primary sequence of the encoded polypeptide.

Mutagenesis of polynucleotide sequences can be used to alter one or more properties of the encoded polypeptide, such as the immunogenicity of an epitope comprised in a polypeptide or the oncogenicity of a target antigen. Assays to test the immunogenicity of a polypeptide include, but are not limited to, T-cell cytotoxicity assays (CTL/chromium release assays), T-cell proliferation assays, intracellular cytokine staining, ELISA, ELISpot, etc. Other ways to obtain sequence variants of peptides and the DNA sequences encoding them can be employed. For example, recombinant vectors encoding the desired peptide sequence may be treated with mutagenic agents, such as hydroxylamine, to obtain sequence variants.

Polynucleotide segments or fragments encoding the polypeptides as described herein may be readily prepared by, for example, directly synthesizing the fragment by chemical means. Fragments may be obtained by application of nucleic acid reproduction technology, such as PCR, by introducing selected sequences into recombinant vectors for recombinant production.

A variety of vector/host systems may be utilized to contain and produce polynucleotide sequences. Exemplary systems include microorganisms such as bacteria transformed with recombinant bacteriophage, plasmid, or cosmid DNA vectors; yeast transformed with yeast vectors; insect cell systems infected with virus vectors (e.g., baculovirus); plant cell systems transformed with virus vectors (e.g., cauliflower mosaic virus, CaMV; tobacco mosaic virus, TMV) or with bacterial vectors (e.g., Ti or pBR322 plasmids); or animal cell systems.

Control elements or regulatory sequences present in an Ad vector may include those non-translated regions of the vector-enhancers, promoters, and 5' and 3' untranslated regions. Such elements may vary in their strength and specificity. Depending on the vector system and host utilized, any number of suitable transcription and translation elements, including constitutive and inducible promoters, may be used. For example, sequences encoding a polypeptide of interest may be ligated into an Ad transcription/translation complex consisting of the late promoter and tripartite leader sequence. Insertion in a non-essential E1 or E3 region of the viral genome may be used to obtain a viable virus which is capable of expressing the polypeptide in infected host cells. In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest (e.g., ATG initiation codon and adjacent sequences). Exogenous translational elements and initiation codons may be of various origins, both natural and synthetic. The efficiency of expression may be enhanced by the inclusion of enhancers which are appropriate for the particular cell system which is used. Specific termination sequences, either for transcription or translation, may also be incorporated in order to achieve efficient translation of the sequence encoding the polypeptide of choice.

A variety of protocols for detecting and measuring the expression of polynucleotide-encoded products (e.g., target antigens), can be used (e.g., using polyclonal or monoclonal antibodies specific for the product). Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed.

The Ad vectors can comprise a product that can be detected or selected for, such as a reporter gene whose product can be detected, such as by fluorescence, enzyme activity on a chromogenic or fluorescent substrate, and the like, or selected for by growth conditions. Exemplary reporter genes include green fluorescent protein (GFP), β-galactosidase, chloramphenicol acetyltransferase (CAT), luciferase, neomycin phosphotransferase, secreted alkaline phosphatase (SEAP), and human growth hormone (HGH). Exemplary selectable markers include drug resistances, such as neomycin (G418), hygromycin, and the like.

The Ad vectors can also comprise a promoter or expression control sequence. The choice of the promoter will depend in part upon the targeted cell type and the degree or type of control desired. Promoters that are suitable include, without limitation, constitutive, inducible, tissue specific, cell type specific, temporal specific, or event-specific. Examples of constitutive or nonspecific promoters include the SV40 early promoter, the SV40 late promoter, CMV early gene promoter, bovine papilloma virus promoter, and adenovirus promoter. In addition to viral promoters, cellular promoters are also amenable and useful in some embodiments. In particular, cellular promoters for the so-called housekeeping genes are useful (e.g., β-actin). Viral promoters are generally stronger promoters than cellular promoters. Inducible promoters may also be used. These promoters include MMTV LTR, inducible by dexamethasone, metallothionein, inducible by heavy metals, and promoters with cAMP response elements, inducible by cAMP, heat shock promoter. By using an inducible promoter, the nucleic acid may be delivered to a cell and will remain quiescent until the addition of the inducer. This allows further control on the timing of production of the protein of interest. Event-type specific promoters (e.g., HIV LTR) can be used, which are active or upregulated only upon the occurrence of an event, such as tumorigenicity or viral infection, for example. The HIV LTR promoter is inactive unless the tat gene product is present, which occurs upon viral infection. Some event-type promoters are also tissue-specific. Preferred event-type specific promoters include promoters activated upon viral infection.

Examples of promoters include promoters for α-fetoprotein, α-actin, myo D, carcinoembryonic antigen, VEGF-receptor; FGF receptor; TEK or tie 2; tie; urokinase receptor; E- and P-selectins; VCAM-1; endoglin; endosialin; αV-β3 integrin; endothelin-1; ICAM-3; E9 antigen; von Willebrand factor; CD44; CD40; vascular-endothelial cadherin; notch 4, high molecular weight melanoma-associated antigen; prostate specific antigen-1, probasin, FGF receptor, VEGF receptor, erb B2; erb B3; erb B4; MUC-1; HSP-27; int-1; int-2, CEA, HBEGF receptor; EGF receptor; tyrosinase, MAGE, IL-2 receptor; prostatic acid phosphatase, probasin, prostate specific membrane antigen, α-crystallin, PDGF receptor, integrin receptor, α-actin, SM1 and SM2 myosin heavy chains, calponin-hl, SM22 α-angiotensin receptor, IL-1, IL-2, IL-3, IL-4, IL-5, IL-6, IL-7, IL-8, IL-9, IL-10, IL-11, IL-12, IL-13, IL-14, immunoglobulin heavy chain, immunoglobulin light chain, and CD4.

Repressor sequences, negative regulators, or tissue-specific silencers may be inserted to reduce non-specific expression of the polynucleotide. Multiple repressor elements may be inserted in the promoter region. Repression of transcription is independent of the orientation of repressor elements or distance from the promoter. One type of repressor sequence is an insulator sequence. Such sequences inhibit transcription and can silence background transcription. Negative regulatory elements can be located in the promoter regions of a number of different genes. The repressor element can function as a repressor of transcription in the absence of factors, such as steroids, as does the NSE in the promoter region of the ovalbumin gene. These negative regulatory elements can bind specific protein complexes from oviduct, none of which are sensitive to steroids. Three different elements are located in the promoter of the ovalbumin gene. Oligonucleotides corresponding to portions of these elements can repress viral transcription of the TK reporter. One of the silencer elements shares sequence identity with silencers in other genes (TCTCTCCNA (SEQ ID NO:11)).

Elements that increase the expression of the desired target antigen can be incorporated into the nucleic acid sequence of the Ad vectors described herein. Exemplary elements include internal ribosome binding sites (IRESs). IRESS can increase translation efficiency. As well, other sequences may enhance expression. For some genes, sequences especially at the 5' end may inhibit transcription and/or translation. These sequences are usually palindromes that can form hairpin structures. In some cases, such sequences in the nucleic acid to be delivered are deleted. Expression levels of the transcript or translated product can be assayed to confirm or ascertain which sequences affect expression. Transcript levels may be assayed by any known method, including Northern blot hybridization, RNase probe protection and the like. Protein levels may be assayed by any known method, including ELISA.

Antigen-Specific Immunotherapies and Vaccines

Certain embodiments provide single antigen or combination antigen immunization against MUC1, MUC1c, MUC1n, T, or CEA utilizing such vectors and other vectors as provided herein Certain embodiments provide therapeutic vaccines against MUC1, MUC1c, MUC1n, T, or CEA. Certain embodiments provide prophylactic vaccines against MUC1, MUC1c, MUC1n, T, or CEA. Further, in various embodiments, the composition and methods provide herein can lead to clinical responses, such as altered disease progression or life expectancy.

Ad5 [E1-] vectors encoding a variety of antigens can be used to efficiently transduce 95% of ex vivo exposed DC's to high titers of the vector. In certain embodiments, increasing levels of foreign gene expression in the DC was found to correlate with increasing multiplicities of infection (MOI) with the vector. DCs infected with Ad5 [E1-] vectors can encode a variety of antigens (including the tumor antigens MART-1, MAGE-A4, DF3/MUC1, p53, hugp100 melanoma antigen, polyoma virus middle-T antigen) that have the propensity to induce antigen specific CTL responses, have an enhanced antigen presentation capacity, and/or have an improved ability to initiate T-cell proliferation in mixed lymphocyte reactions. Immunization of animals with dendritic cells (DCs) previously transduced by Ad5 vectors encoding tumor specific antigens can be used to induce significant levels of protection for the animals when challenged with tumor cells expressing the respective antigen. Interestingly, intra-tumoral injection of Ads encoding IL-7 is less effective than injection of DCs transduced with IL-7 encoding Ad5 vectors at inducing antitumor immunity. Ex vivo transduction of DCs by Ad5 vectors is contemplated in certain embodiments. Ex vivo DC transduction strategies can been used to induce recipient host tolerance. For example, Ad5 mediated delivery of the CTLA4Ig into DCs can block interactions of the DCs CD80 with CD28 molecules present on T-cells.

Ad5 vector capsid interactions with DCs may trigger several beneficial responses, which may be enhancing the propensity of DCs to present antigens encoded by Ad5 vectors. For example, immature DCs, though specialized in antigen uptake, are relatively inefficient effectors of T-cell activation. DC maturation coincides with the enhanced ability of DCs to drive T-cell immunity. In some instances, the compositions and methods take advantage of an Ad5 infection resulting in direct induction of DC maturation Ad vector infection of immature bone marrow derived DCs from mice may upregulate cell surface markers normally associated with DC maturation (MHC I and II, CD40, CD80, CD86, and ICAM-1) as well as down-regulation of CD11c, an integrin down regulated upon myeloid DC maturation. In some instances, Ad vector infection triggers IL-12 production by DCs, a marker of DC maturation. Without being bound by theory, these events may possibly be due to Ad5 triggered activation of NF-κB pathways. Mature DCs can be efficiently transduced by Ad vectors, and do not lose their functional potential to stimulate the proliferation of naive T-cells at lower MOI, as demonstrated by mature CD83+ human DC (derived from peripheral blood monocytes). However, mature DCs may also be less infectable than immature ones. Modification of capsid proteins can be used as a strategy to optimize infection of DC by Ad vectors, as well as enhancing functional maturation, for example using the CD40L receptor as a viral vector receptor, rather than using the normal CAR receptor infection mechanisms.

In some embodiments the compositions and methods comprising an Ad5 [E1-, E2b-] vector(s) MUC1, T and CEA vaccine have effects of increased overall survival (OS) within the bounds of technical safety. In some embodiments the compositions and methods comprising an Ad5 [E1-, E2b-] vector(s) MUC1c, T and CEA vaccine have effects of increased overall survival (OS) within the bounds of technical safety. In certain embodiments the compositions and methods comprising an Ad5 [E1-, E2b-] vector(s) MUC1n, T and CEA vaccine have effects of increased overall survival (OS) within the bounds of technical safety.

In some embodiments, the antigen targets are associated with benign tumors. In some embodiments, the antigens targeted are associated with pre-cancerous tumors.

In some embodiments, the antigens targeted are associated with carcinomas, in situ carcinomas, metastatic tumors, neuroblastoma, sarcomas, myosarcoma, leiomyosarcoma, retinoblastoma, hepatoma, rhabdomyosarcoma, plasmocytomas, adenomas, gliomas, thymomas, or osteosarcoma. In some embodiments, the antigens targeted are associated with a specific type of cancer such as neurologic cancers, brain cancer, thyroid cancer, head and neck cancer, melanoma, leukemia, acute lymphoblastic leukemia (ALL), acute myelogenous leukemia (AML), chronic myelogenous leukemia (CML), and chronic lymphocytic leukemia (CLL), non-Hodgkin's lymphoma, multiple myeloma, Hodgkin's disease, breast cancer, bladder cancer, prostate cancer, colorectal cancer, colon cancer, kidney cancer, renal cell carcinoma, pancreatic cancer, esophageal cancer, lung cancer, mesothelioma, ovarian cancer, cervical cancer, endometrial cancer, uterine cancer, germ cell tumors, testicular cancer, gastric cancer, or other cancers, or any clinical (e.g. TNM, Histopathological, Staging or Grading systems or a combination thereof) or molecular subtype thereof. In some embodiments, the antigens targeted are associated with a specific clinical or molecular subtype of cancer. By way of example, breast cancer can be divided into at least four molecular subtypes including Luminal A, Luminal B, Triple negative/basal-like, and HER2 type. By way of example, Prostate cancer can be subdivided TNM, Gleason score, or molecular expression of the PSA protein.

As noted above, the adenovirus vectors comprise nucleic acid sequences that encode one or more target proteins or antigens of interest. In this regard, the vectors may contain nucleic acid encoding 1, 2, 3, 4, 5, 6, 7, 8, 9, 10, 11, 12, 13, 14, 15, 16, 17, 18, 19, 20 or more different target antigens of interest. The target antigens may be a full length protein or may be a fragment (e.g., an epitope) thereof. The adenovirus vectors may contain nucleic acid sequences encoding multiple fragments or epitopes from one target protein of interest or may contain one or more fragments or epitopes from numerous different target proteins of interest. A target antigen may comprise any substance against which it is desirable to generate an immune response but generally, the target antigen is a protein. A target antigen may comprise a full length protein, a subunit of a protein, an isoform of a protein, or a fragment thereof that induces an immune response (i.e., an immunogenic fragment). A target antigen or fragment thereof may be modified, e.g., to reduce one or more biological activities of the target antigen or to enhance its immunogenicity. The target antigen or target protein can be MUC1, MUC1c, MUC1n, T, CEA, or any combination thereof.

In certain embodiments, immunogenic fragments bind to an MHC class I or class II molecule. An immunogenic fragment may "bind to" an MHC class I or class II molecule if such binding is detectable using any assay known in the art. For example, the ability of a polypeptide to bind to MHC class I may be evaluated indirectly by monitoring the ability to promote incorporation of $^{125}$I labeled β-2-microglobulin (β-2m) into MHC class I/β2m/peptide heterotrimeric complexes. Alternatively, functional peptide competition assays that are known in the art may be employed. Immunogenic fragments of polypeptides may generally be identified using well known techniques. Representative techniques for identifying immunogenic fragments include screening polypeptides for the ability to react with antigen-specific antisera and/or T-cell lines or clones. An immunogenic fragment of a particular target polypeptide is a fragment that reacts with such antisera and/or T-cells at a level that is not substantially less than the reactivity of the full length target polypeptide (e.g., in an ELISA and/or T-cell reactivity assay). In other words, an immunogenic fragment may react within such assays at a level that is similar to or greater than the reactivity of the full length polypeptide. Such screens may be performed using methods known in the art.

In some embodiments, the viral vectors comprise heterologous nucleic acid sequences that encode one or more proteins, variants thereof, fusions thereof, or fragments thereof, that can modulate the immune response. In some embodiments, the viral vector encodes one or more antibodies against specific antigens, such as anthrax protective antigen, permitting passive immunotherapy. In some embodiments, the viral vectors comprise heterologous nucleic acid sequences encoding one or more proteins having therapeutic effect (e.g., anti-viral, anti-bacterial, anti-parasitic, or anti-tumor function). In some embodiments the Second Generation E2b deleted adenovirus vectors comprise a heterologous nucleic acid sequence. In some embodiments, the heterologous nucleic acid sequence is CEA, MUC1, MUC1c, MUC1n, T, a variant, a portion, or any combination thereof.

Target antigens include, but are not limited to, antigens derived from a variety of tumor proteins. In some embodiments, parts or variants of tumor proteins are employed as target antigens. In some embodiments, parts or variants of tumor proteins being employed as target antigens have a modified, for example, increased ability to effect and immune response against the tumor protein or cells containing the same. A vaccine can vaccinate against an antigen. A vaccine can also target an epitope. An antigen can be a tumor cell antigen. An epitope can be a tumor cell epitope. Such a tumor cell epitope may be derived from a wide variety of tumor antigens, such as antigens from tumors resulting from mutations, shared tumor specific antigens, differentiation antigens, and antigens overexpressed in tumors. Tumor-associated antigens (TAAs) may be antigens not normally expressed by the host; they can be mutated, truncated, misfolded, or otherwise abnormal manifestations of molecules normally expressed by the host; they can be identical to molecules normally expressed but expressed at abnormally high levels; or they can be expressed in a context or environment that is abnormal. Tumor-associated antigens may be, for example, proteins or protein fragments, complex carbohydrates, gangliosides, haptens, nucleic acids, other biological molecules or any combinations thereof.

Illustrative useful tumor proteins include, but are not limited to any one or more of, CEA, human epidermal growth factor receptor 2 (HER2/neu), human epidermal growth factor receptor 3 (HER3), Human papillomavirus (HPV) E6, HPV E7, MUC1, Prostate-specific antigen (PSA), PSMA, WT1, p53, MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-8, GAGE-3, GAGE-4, GAGE-5, GAGE-6, GAGE-7B, NA88-A, NY-ESO-1, MART-1, MC1R, Gp100, PSA, PSM, Tyrosinase, TRP-1, TRP-2, ART-4, CAMEL, CEA, Cyp-B, Her2/neu, BRCA1, Brachyury, Brachyury (TIVS7-2, polymorphism), Brachyury (IVS7 T/C polymorphism), T Brachyury, T, hTERT, hTRT, iCE, MUC1, MUC1 (VNTR polymorphism), MUC1c, MUC1n, MUC2, PRAME, P15, RU1, RU2, SART-1, SART-3, AFP, β-catenin/m, Caspase-8/m, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, ETV6/AML, LDLR/FUT, Pml/RARa, and TEL/AML1.

In some embodiments, the viral vector comprises a target antigen sequence encoding a modified polypeptide selected from CEA, human epidermal growth factor receptor 2 (HER2/neu), human epidermal growth factor receptor 3 (HER3), Human papillomavirus (HPV) E6, HPV E7, MUC1, Prostate-specific antigen (PSA), PSMA (i.e., PSM), WT1, p53, MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-8, GAGE-3, GAGE-4, GAGE-5, GAGE-6, GAGE-7B, NA88-A, NY-ESO-1, MART-1, MC1R, Gp100, Tyrosinase, TRP-1, TRP-2, ART-4, CAMEL, Cyp-B, BRCA1, Brachyury, Brachyury (TIVS7-2, polymorphism), Brachyury (IVS7 T/C polymorphism), T Brachyury, T, hTERT, hTRT, iCE, MUC1 (VNTR polymorphism), MUC1c, MUC1n, MUC2, PRAME, P15, RU1, RU2, SART-1, SART-3, AFP, β-catenin/m, Caspase-8/m, CDK-4/m, ELF2M, GnT-V, G250, HSP70-2M, HST-2, KIAA0205, MUM-1, MUM-2, MUM-3, Myosin/m, SART-2, TRP-2/INT2, 707-AP, Annexin II, CDC27/m, TPI/mbcr-abl, ETV6/AML, LDLR/FUT, Pml/RARα, and TEL/AML1, wherein the polypeptide or a fragment thereof has at least 60%, 65%, 70%, 75%, 80%, 85%, 90%, 95%, 98%, 99%, 99.5%, 99.9% identity to the corresponding native sequence.

Additional illustrative useful tumor proteins useful include, but are not limited to any one or more of alpha-actinin-4, ARTC1, CAR-ABL fusion protein (b3a2), B-RAF, CASP-5, CASP-8, beta-catenin, Cdc27, CDK4, CDKN2A, COA-1, dek-can fusion protein, EFTUD2, Elongation factor 2, ETV6-AML1 fusion protein, FLT3-ITD, FN1, GPNMB, LDLR-fucosyltransferase fusion protein, HLA-A2d, HLA-A1 1d, hsp70-2, KIAAO205, MART2, ME1, MUM-1f, MUM-2, MUM-3, neo-PAP, Myosin class I, NFYC, OGT, OS-9, p53, pml-RARalpha fusion protein, PRDX5, PTPRK, K-ras, N-ras, RBAF600, SIRT2, SNRPD1, SYT-SSX1- or -SSX2 fusion protein, TGF-betaRII, triosephosphate isomerase, BAGE-1, GnTVf, HERV-K-MEL, KK-LC-1, LAGE-1, MAGE-A9, MAGE-C2, mucink, NA-88, NY-ESO-1/LAGE-2, SAGE, Sp17, SSX-2, SSX-4, TAG-1, TAG-2, TRAG-3, TRP2-INT2g, XAGE-1b, gp100/Pme117, Kallikrein 4, mammaglobin-A, Melan-A/MART-1, NY-BR-1, OA1, PSA, RAB38/NY-MEL-1, TRP-1/gp75, TRP-2, tyrosinase, adipophilin, AIM-2, ALDH1A1, BCLX (L), BCMA, BING-4, CPSF, cyclin D1, DKK1, ENAH (hMena), EP-CAM, EphA3, EZH2, FGF5, G250/MN/CAIX, IL13Ralpha2, intestinal carboxyl esterase, alpha fetoprotein, M-CSFT, MCSP, mdm-2, MMP-2, PBF, PRAME, RAGE-1, RGS5, RNF43, RU2AS, secernin 1, SOX10, STEAP1, survivin, Telomerase, and/or VEGF.

Tumor-associated antigens may be antigens from infectious agents associated with human malignancies. Examples of infectious agents associated with human malignancies include Epstein-Barr virus, *Helicobacter pylori*, Hepatitis B virus, Hepatitis C virus, Human heresvirus-8, Human immunodeficiency virus, Human papillomavirus, Human T-cell leukemia virus, liver flukes, and *Schistosoma haematobium*.

CEA Antigen Targets

CEA represents an attractive target antigen for immunotherapy since it is over-expressed in nearly all colorectal cancers and pancreatic cancers, and is also expressed by some lung and breast cancers, and uncommon tumors such as medullary thyroid cancer, but is not expressed in other cells of the body except for low-level expression in gastrointestinal epithelium. CEA contains epitopes that may be recognized in an MHC restricted fashion by T-cells.

It was discovered that multiple homologous immunizations with Ad5 [E1-, E2b-]-CEA(6D), encoding the tumor antigen CEA, induced CEA-specific cell-mediated immune (CMI) responses with antitumor activity in mice despite the presence of pre-existing or induced Ad5-neutralizing antibody. In the present phase VII study, cohorts of patients with advanced colorectal cancer were immunized with escalating doses of Ad5 [E1-, E2b-]-CEA(6D). CEA-specific CMI responses were observed despite the presence of pre-existing Ad5 immunity in a majority (61.3%) of patients. Importantly, there was minimal toxicity, and overall patient survival (48% at 12 months) was similar regardless of pre-existing Ad5 neutralizing antibody titers. The results demonstrate that, in cancer patients, the novel Ad5 [E1-, E2b-] gene delivery platform generates significant CMI responses to the tumor antigen CEA in the setting of both naturally acquired and immunization-induced Ad5specific immunity.

CEA antigen specific CMI can be, for example, greater than 10, 20, 30, 40, 50, 100, 200, 300, 400, 500, 600, 700, 800, 900, 1000, 5000, 10000, or more IFN-γ spot forming cells (SFC) per $10^6$ peripheral blood mononuclear cells (PBMC). In some embodiments, the immune response is raised in a human subject with a preexisting inverse Ad5 neutralizing antibody titer of greater than 50, 100, 150, 200, 300, 400, 500, 600, 700, 800, 900, 1000, 1500, 2000, 2500, 3000, 3500, 4000, 4500, 5000, 6000, 7000, 8000, 9000, 1000, 12000, 15000 or higher. The immune response may comprise a cell-mediated immunity and/or a humoral immunity as described herein. The immune response may be measured by one or more of intracellular cytokine staining (ICS), ELISpot, proliferation assays, cytotoxic T-cell assays including chromium release or equivalent assays, and gene expression analysis using any number of polymerase chain reaction (PCR) or RT-PCR based assays, as described herein and to the extent they are available to a person skilled in the art, as well as any other suitable assays known in the art for measuring immune response.

In some embodiments, the replication defective adenovirus vector comprises a modified sequence encoding a subunit with at least 75%, 80%, 85%, 90%, 95%, 98%, 99%, 99.5%, 99.9% identity to a wild-type subunit of the polypeptide.

The immunogenic polypeptide may be a mutant CEA or a fragment thereof. In some embodiments, the immunogenic polypeptide comprises a mutant CEA with an Asn→Asp substitution at position 610. In some embodiments, the replication defective adenovirus vector comprises a sequence encoding a polypeptide with at least 75%, 80%, 85%, 90%, 95%, 98%, 99%, 99.5%, 99.9% identity to the immunogenic polypeptide. In some embodiments, the sequence encoding the immunogenic polypeptide comprises the sequence of SEQ ID NO: SEQ ID NO:1 encodes SEQ ID NO:23.

In some embodiments, the sequence encoding the immunogenic polypeptide comprises a sequence with at least 70% 75%, 80%, 85%, 90%, 95%, 98%, 99%, 99.5%, 99.9% identity to SEQ. ID. NO:1 or a sequence generated from SEQ ID NO:1 by alternative codon replacements. In some embodiments, the immunogenic polypeptide encoded by the adenovirus vectors comprise up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type human CEA sequence.

In some embodiments, the immunogenic polypeptide comprises a sequence from SEQ ID NO.:2 or a modified version, e.g., comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, of SEQ ID NO.:2.

Members of the CEA gene family are subdivided into three subgroups based on sequence similarity, developmental expression patterns and their biological functions: the CEA-related Cell Adhesion Molecule (CEACAM) subgroup containing twelve genes (CEACAM1, CEACAM3-CEACAM8, CEACAM16 and CEACAM18-CEACAM21), the Pregnancy Specific Glycoprotein (PSG) subgroup containing eleven closely related genes (PSG1-PSG11) and a subgroup of eleven pseudogenes (CEACAMP1-CEACAMP11). Most members of the CEACAM subgroup have similar structures consist of an extracellular Ig-like domains composed of a single N-terminal V-set domain, with structural homology to the immunoglobulin variable domains, followed by varying numbers of C2-set domains of A or B subtypes, a transmembrane domain and a cytoplasmic domain. There are two members of CEACAM subgroup (CEACAM-16 and CEACAM20) that show a few exceptions in the organization of their structures. CEACAM16 contains two Ig-like V-type domains at its N and C termini and CEACAM20 contains a truncated Ig-like V-type 1 domain. The CEACAM molecules can be anchored to the cell surface via their transmembrane domains (CEACAM5 thought CEACAM8) or directly linked to glycophosphatidylinositol (GPI) lipid moiety (CEACAM5, CEACAM18 thought CEACAM21).

CEA family members are expressed in different cell types and have a wide range of biological functions. CEACAMs are found prominently on most epithelial cells and are present on different leucocytes. In humans, CEACAM1, the ancestor member of CEA family, is expressed on the apical side of epithelial and endothelial cells as well as on lymphoid and myeloid cells. CEACAM1 mediates cell-cell adhesion through hemophilic (CEACAM1 to CEACAM1) as well as heterothallic (e.g., CEACAM1 to CEACAM5) interactions. In addition, CEACAM1 is involved in many other biological processes, such as angiogenesis, cell migration, and immune functions. CEACAM3 and CEACAM4 expression is largely restricted to granulocytes, and they are able to convey uptake and destruction of several bacterial pathogens including *Neisseria, Moraxella*, and *Haemophilus* species.

Thus, in various embodiments, compositions and methods relate to raising an immune response against a CEA, selected from the group consisting of CEACAM1, CEACAM3, CEACAM4, CEACAM5, CEACAM6, CEACAM7, CEACAM8, CEACAM16, CEACAM18, CEACAM19, CEACAM20, CEACAM21, PSG1, PSG2, PSG3, PSG4, PSG5, PSG6, PSG7, PSG8, PSG9, and PSG11. An immune response may be raised against cells, e.g. cancer cells, expressing or overexpressing one or more of the CEAs, using the methods and compositions. In some embodiments, the overexpression of the one or more CEAs in such cancer cells is over 5, 10, 20, 30, 40, 50, 60, 70, 80, 90, 100 fold or more compared to non-cancer cells.

In certain embodiments, the CEA antigen used herein is a wild-type CEA antigen or a modified CEA antigen having a least a mutation in YLSGANLNL (SEQ ID NO:4), a CAP1 epitope of CEA. The mutation can be conservative or non-conservative, substitution, addition, or deletion. In certain embodiments, the CEA antigen used herein has an amino acid sequence set forth in YLSGADLNL (SEQ ID NO:10), a mutated CAP1 epitope. In further embodiments, the first replication-defective vector or a replication-defective vector that express CEA has a nucleotide sequence at least 50%, 60%, 65%, 70%, 75%, 80%, 85%, 90%, 95%, 98%, 99%, 99.5%, 99.9%, 100% identical to any portion of SEQ ID NO:3 (the predicted sequence of an adenovirus vector express a modified CEA antigen), such as positions 1057 to 3165 of SEQ ID NO:3 or full-length SEQ ID NO:3.

Mucin Family Antigen Targets

The human mucin family (MUC1 to MUC21) includes secreted and transmembrane mucins that play a role in forming protective mucous barriers on epithelial surfaces in the body. These proteins function in to protecting the epithelia lining the respiratory, gastrointestinal tracts, and lining ducts in important organs such as, for example the mammary gland, liver, stomach, pancreas, and kidneys.

MUC1 (CD227) is a TAA that is over-expressed on a majority of human carcinomas and several hematologic malignancies. MUC1 (GenBank: X80761.1, NCBI: NM_001204285.1) and activates many important cellular pathways known to be involved in human disease. MUC1 is a heterodimeric protein formed by two subunits that is commonly overexpressed in several human cancers. MUC1 undergoes autoproteolysis to generate two subunits MUC1n and MUC1c that, in turn, form a stable noncovalent heterodimer.

The MUC1 C-terminal subunit (MUC1c) can comprise a 58 aa extracellular domain (ED), a 28 aa transmembrane domain (TM) and a 72 aa cytoplasmic domain (CD). The MUC1c also can contains a "CQC" motif that can allow for dimerization of MUC1 and it can also impart oncogenic function to a cell. In some cases MUC1 can in part oncogenic function through inducing cellular signaling via MUC1c. MUC1c can interact with EGFR, ErbB2 and other receptor tyrosine kinases and contributing to the activation of the PI3K→AKT and MEK→ERK cellular pathways. In the nucleus, MUC1c activates the Wnt/β-catenin, STAT and NF-κB RelA cellular pathways. In some cases MUC1 can impart oncogenic function through inducing cellular signaling via MUC1n. The MUC1 N-terminal subunit (MUC1n) can comprise variable numbers of 20 amino acid tandem repeats that can be glycosylated. MUC1 is normally expressed at the surface of glandular epithelial cells and is over-expressed and aberrantly glycosylated in carcinomas. MUC1 is a TAA that can be utilized as a target for tumor immunotherapy. Several clinical trials have been and are being performed to evaluate the use of MUC1 in immunotherapeutic vaccines. Importantly, these trials indicate that immunotherapy with MUC1 targeting is safe and may provide survival benefit.

However, clinical trials have also shown that MUC1 is a relatively poor immunogen. To overcome this, the inventors have identified a T lymphocyte immune enhancer peptide sequence in the C terminus region of the MUC1 oncoprotein (MUC1-C or MUC1c). Compared with the native peptide sequence, the agonist in their modified MUC1-C (a) bound HLA-A2 at lower peptide concentrations, (b) demonstrated a higher avidity for HLA-A2, (c) when used with antigen-presenting cells, induced the production of more IFN-γ by T-cells than with the use of the native peptide, and (d) was capable of more efficiently generating MUC1-specific human T-cell lines from cancer patients. Importantly, T-cell lines generated using the agonist epitope were more efficient than those generated with the native epitope for the lysis of targets pulsed with the native epitope and in the lysis of HLA-A2 human tumor cells expressing MUC1. Additionally, the inventors have identified additional CD8+ cytotoxic T lymphocyte immune enhancer agonist sequence epitopes of MUC1-C.

Certain embodiments provide a potent MUC1-C modified for immune enhancer capability (mMUC1-C or MUC1-C or MUC1c). Certain embodiments provide a potent MUC1-C modified for immune enhancer capability incorporated it into a recombinant Ad5 [E1-, E2b-] platform to produce a new and more potent immunotherapeutic vaccine. For example, the immunotherapeutic vaccine can be Ad5 [E1-, E2b-]-mMUC1-C for treating MUC1 expressing cancers or infectious diseases.

Post-translational modifications play an important role in controlling protein function in the body and in human disease. For example, in addition to proteolytic cleavage discussed above, MUC1 can have several post-translational modifications such as glycosylation, sialylation, palmitoylation, or a combination thereof at specific amino acid residues. Provided herein are immunotherapies targeting glycosylation, sialylation, phosphorylation, or palmitoylation modifications of MUC1.

MUC1 can be highly glycosylated (N- and O-linked carbohydrates and sialic acid at varying degrees on serine and threonine residues within each tandem repeat, ranging from mono- to penta-glycosylation). Differentially O-glycosylated in breast carcinomas with 3,4-linked GlcNAc. N-glycosylation consists of high-mannose, acidic complex-type and hybrid glycans in the secreted form MUC1/SEC, and neutral complex-type in the transmembrane form, MUC1/TM.4. Certain embodiments provide immunotherapies targeting differentially O-glycosylated forms of MUC1.

Further, MUC1 can be sialylated. Membrane-shed glycoproteins from kidney and breast cancer cells have preferentially sialylated core 1 structures, while secreted forms from the same tissues display mainly core 2 structures. The O-glycosylated content is overlapping in both these tissues with terminal fucose and galactose, 2- and 3-linked galactose, 3- and 3,6-linked GalNAc-ol and 4-linked GlcNAc predominating. Certain embodiments provide immunotherapies targeting various sialylation forms of MUC1. Dual palmitoylation on cysteine residues in the CQC motif is required for recycling from endosomes back to the plasma membrane. Certain embodiments provide for immunotherapies targeting various palmitoylation forms of MUC1.

Phosphorylation can affect MUC1's ability to induces specific cell signaling responses that are important for human health. Certain embodiments provide for immunotherapies targeting various phosphorylated forms of MUC1. For example, MUC1 can be phosphorylated on tyrosine and serine residues in the C-terminal domain. Phosphorylation on tyrosines in the C-terminal domain can increase nuclear location of MUC1 and β-catenin. Phosphorylation by PKC delta can induce binding of MUC1 to β-catenin/CTNNB1 and decrease formation of β-catenin/E-cadherin complexes. Src-mediated phosphorylation of MUC1 can inhibits interaction with GSK3B. Src- and EGFR-mediated phosphorylation of MUC1 on Tyr-1229 can increase binding to β-catenin/CTNNB1. GSK3B-mediated phosphorylation of MUC1 on Ser-1227 can decrease this interaction but restores the formation of the β-cadherin/E-cadherin complex. PDGFR-mediated phosphorylation of MUC1 can increase nuclear colocalization of MUC1CT and CTNNB1. Certain embodiments provide immunotherapies targeting different phosphorylated forms of MUC1, MUC1c and MUC1n known to regulate its cell signaling abilities.

The disclosure provides for immunotherapies that modulate MUC1c cytoplasmic domain and its functions in the cell. The disclosure provides for immunotherapies that comprise modulating a CQC motif in MUC1c. The disclosure provides for immunotherapies that comprise modulating the extracellular domain (ED), the transmembrane domain (TM), the cytoplasmic domain (CD) of MUC1c, or a combination thereof. The disclosure provides for immunotherapies that comprise modulating MUC1c's ability to induce cellular signaling through EGFR, ErbB2 or other receptor tyrosine kinases. The disclosure provides for immunotherapies that comprise modulating MUC1c's ability to induce PI3K→AKT, MEK→ERK, Wnt/β-catenin, STAT, NF-κB RelA cellular pathways, or combination thereof. In some embodiments, the MUC1c immunotherapy can further comprise CEA.

The disclosure also provides for immunotherapies that modulate MUC1n and its cellular functions. The disclosure also provides for immunotherapies comprising tandem repeats of MUC1n, the glycosylation sites on the tandem repeats of MUC1n, or a combination thereof. In some embodiments, the MUC1n immunotherapy further comprises CEA.

The disclosure also provides vaccines comprising MUC1n, MUC1c, CEA, or a combination thereof. The disclosure provides vaccines comprising MUC1c and CEA. The disclosure also provides vaccines targeting MUC1n and CEA. In some embodiments, the antigen combination is contained in one vector as provided herein. In some embodiments, the antigen combination is contained in a separate vector as provided herein.

Some embodiments relate to a replication defective adenovirus vector of serotype 5 comprising a sequence encoding an immunogenic polypeptide. The immunogenic polypeptide may be an isoform of MUC1 or a subunit or a fragment thereof. In some embodiments, the replication defective adenovirus vector comprises a sequence encoding a polypeptide with at least 75%, 80%, 85%, 90%, 95%, 98%, 99%, 99.5%, 99.9% identity to the immunogenic polypeptide. In some embodiments, the sequence encoding the immunogenic polypeptide comprises the sequence of SEQ. ID. NO.:5. In some embodiments, the sequence encoding the immunogenic polypeptide comprises the following sequence identified by SEQ. ID. NO.:6. In some embodiments, the sequence encoding the immunogenic polypeptide comprises the following sequence identified by SEQ. ID. NO.:9. In some embodiments, the sequence encoding the immunogenic polypeptide comprises a sequence with at least 70%, 75%, 80%, 85%, 90%, 95%, 98%, 99%, 99.5%, 99.9% identity to SEQ. ID. NO:5, SEQ. ID. NO:6, SEQ. ID. NO.:9 or a sequence generated from SEQ. ID. NO.:5, SEQ. ID. NO:6, SEQ. ID. NO.:9 by alternative codon replacements. In some embodiments, the immunogenic polypeptide encoded by the adenovirus vectors described herein comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type human MUC1 sequence.

In certain embodiments, the MUC1 antigen used herein is a wild-type MUC1 antigen or a modified MUC1 antigen. In certain embodiments, the modified MUC1 antigen has at least 50%, 60%, 65%, 70%, 75%, 80%, 85%, 90%, 95%, 98%, 99%, 99.5%, 99.9%, 100% identity to SEQ ID NO:9 (a mutated MUC1 protein sequence). In certain embodiments, the MUC-1 antigen is a modified antigen having one or more mutations at positions 93, 141-142, 149-151, 392, 404, 406, 422, 430-431, 444-445, or 460 of SEQ ID NO:9. The mutation can be conservative or non-conservative, substitution, addition, or deletion. In further embodiments, the MUC-1 antigen binds to HLA-A2, HLA-A3, HLA-A24, or a combination thereof. In certain embodiments, the third replication-defective vector or a replication-defective vector that express MUC1 has a nucleotide sequence at least 50%, 60%, 65%, 70%, 75%, 80%, 85%, 90%, 95%, 98%, 99%, 99.5%, 99.9%, 100% identical to SEQ ID NO:5 (MUC_1 wild-type nucleotide sequence). In further embodiments, the third replication-defective vector or a replication-defective vector that express MUC1 has a nucleotide sequence at least 50%, 60%, 65%, 70%, 75%, 80%, 85%, 90%, 95%, 98%, 99%, 99.5%, 99.9%, 100% identical to SEQ ID NO:6 (a mutated MUC1 nucleotide sequence). In certain embodiments, the third replication-defective vector or a replication-defective vector that express MUC1 has a nucleotide sequence at least 50%, 60%, 65%, 70%, 75%, 80%, 85%, 90%, 95%, 98%, 99%, 99.5%, 99.9%, 100% identical to any portion of or full-length SEQ ID NO:14 (the predicted sequence of an adenovirus vector express a modified CEA antigen), such as positions 1033-2858 of SEQ ID NO:14.

Brachyury Antigen Targets

Certain embodiment provide immunotherapies that comprise one or more antigens to Brachyury. Brachyury (also known as the "T" protein in humans) is a member of the T-box family of transcription factors that play key roles during early development, mostly in the formation and differentiation of normal mesoderm and is characterized by a highly conserved DNA-binding domain designated as T-domain. The epithelial to mesenchymal transition (EMT) is a key step during the progression of primary tumors into a metastatic state in which Brachyury plays a crucial role. The expression of Brachyury in human carcinoma cells induces changes characteristic of EMT, including up-regulation of mesenchymal markers, down-regulation of epithelial markers, and an increase in cell migration and invasion. Conversely, inhibition of Brachyury resulted in down-regulation of mesenchymal markers and loss of cell migration and invasion and diminished the ability of human tumor cells to form metastases. Brachyury can function to mediate epithelial-mesenchymal transition and promotes invasion.

The disclosure also provides for immunotherapies that modulate Brachyury effect on epithelial-mesenchymal transition function in cell proliferation diseases, such as cancer. The disclosure also provides for immunotherapies that modulate Brachyury's ability to promote invasion in cell proliferation diseases, such as cancer. The disclosure also provides for immunotherapies that modulate the DNA binding function of T-box domain of Brachyury. In some embodiments, the Brachyury immunotherapy can further comprise one or more antigens to CEA or MUC1, MUC1c or MUC1n.

Brachyury expression is nearly undetectable in most normal human tissues and is highly restricted to human tumors and often overexpressed making it an attractive target antigen for immunotherapy. In human, Brachyury is encoded by the T gene (GenBank: AJ001699.1, NCBI: NM_003181.3). There are at least two different isoforms produced by alternative splicing found in humans. Each isoform has a number of natural variants.

Brachyury is immunogenic and Brachyury-specific CD8+ T-cells expanded in vitro can lyse Brachyury expressing tumor cells. These features of Brachyury make it an attractive TAA for immunotherapy. The Brachyury protein is a T-box transcription factor. It can bind to a specific DNA element, a near palindromic sequence "TCACACCT" through a region in its N-terminus, called the T-box to activate gene transcription when bound to such a site.

The disclosure also provides vaccines comprising Brachyury, CEA, or a combination thereof. In some embodiments, the antigen combination is contained in one vector as provided herein. In some embodiments, the antigen combination is contained in a separate vector as provided herein.

In particular embodiments, there is provided a replication defective adenovirus vector of serotype 5 comprising a sequence encoding an immunogenic polypeptide. The immunogenic polypeptide may be an isoform of Brachyury or a subunit or a fragment thereof. In some embodiments, the replication defective adenovirus vector comprises a sequence encoding a polypeptide with at least 70%, 75%, 80%, 85%, 90%, 95%, 98%, 99%, 99.5%, 99.9% identity to the immunogenic polypeptide. In some embodiments, the sequence encoding the immunogenic polypeptide comprises the following sequence identified by SEQ. ID. NO.:7. In some embodiments, the replication defective adenovirus vector comprises a sequence encoding a polypeptide with at least 70%, 75%, 80%, 85%, 90%, 95%, 98%, 99%, 99.5%, 99.9% identity to the immunogenic polypeptide. In some embodiments, the sequence encoding the immunogenic polypeptide comprises the sequence of SEQ. ID. NO.:8. In some embodiments, the sequence encoding the immunogenic polypeptide comprises a sequence with at least 70%, 75%, 80%, 85%, 90%, 95%, 98%, 99%, 99.5%, 99.9% identity to SEQ. ID. NO:7, SEQ. ID. NO:8 or a sequence generated from SEQ. ID. NO:7, SEQ. ID. NO:8 by alternative codon replacements. In some embodiments, the immunogenic polypeptide encoded by the adenovirus vectors described herein comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type human Brachyury sequence.

In certain embodiments, the Brachyury antigen used herein is a wild-type antigen or a modified antigen. In certain embodiments, the Brachyury antigen binds to HLA-A2. In further embodiments, the Brachyury antigen is a modified Brachyury antigen having an amino acid sequence set forth in WLLPGTSTV (SEQ ID NO:22), a HLA-A2 epitope of Brachyury. In further embodiments, the Brachyury antigen is a modified Brachyury antigen having an amino acid sequence at least 50%, 60%, 65%, 70%, 75%, 80%, 85%, 90%, 95%, 98%, 99%, 99.5%, 99.9%, 100% identity to SEQ ID NO:21, a modified Brachyury protein sequence. In certain embodiments, the replication-defective vector has a nucleotide sequence at least 80% identical SEQ ID NO:8 or positions 1033 to 2283 of SEQ ID NO:16. In further embodiments, the second replication-defective vector has a nucleotide sequence at least 50%, 60%, 65%, 70%, 75%, 80%, 85%, 90%, 95%, 98%, 99%, 99.5%, 99.9%, 100% identical to any portion or full-length of SEQ ID NO:16 (the predicted sequence of an adenovirus vector express a modified Brachyury antigen), such as positions 1033 to 2283 of SEQ ID NO:16. In some embodiments, the Brachyury antigen is a modified Brachyury antigen having an amino acid sequence at least 80% identical to SEQ ID NO:15 (another mutated Brachyury protein sequence). In certain embodiments, the second replication-defective vector or a replication-defective vector that express Brachyury has a nucleotide sequence at least 50%, 60%, 65%, 70%, 75%, 80%, 85%, 90%, 95%, 98%, 99%, 99.5%, 99.9%, 100% identical to positions 520-1824 of SEQ ID NO:7 (wild-type Brachyury), SEQ ID NO:7, or SEQ ID NO:8.

Infectious Disease Associated Antigen Targets

Target antigens include, but are not limited to, antigens derived from any of a variety of infectious agents such as parasites, bacteria, virus, prions, and the like. An infectious agent may refer to any living organism capable of infecting a host. Infectious agents include, for example, bacteria, any variety of viruses, such as, single stranded RNA viruses, single stranded DNA viruses, fungi, parasites, and protozoa.

Examples of infectious disease associated target antigens that can be used with the compositions and the methods can be derived from the following: *Actinobacillus* spp., *Actinomyces* spp., Adenovirus (types 1, 2, 3, 4, 5 et 7), Adenovirus (types 40 and 41), *Aerococcus* spp., *Aeromonas hydrophila*, *Ancylostoma duodenale*, *Angiostrongylus cantonensis*, *Ascaris lumbricoides*, *Ascaris* spp., *Aspergillus* spp., *Babesia* spp, *B. microti*, *Bacillus anthracis*, *Bacillus cereus*, *Bacteroides* spp., *Balantidium coli*, *Bartonella bacilliformis*, *Blastomyces dermatitidis*, Bluetongue virus, *Bordetella bronchiseptica*, *Bordetella pertussis*, *Borrelia afzelii*, *Borrelia burgdorferi*, *Borrelia garinii*, *Branhamella catarrhalis*, *Brucella* spp. (*B. abortus*, *B. canis*, *B. melitensis*, *B. suis*), *Brugia* spp., *Burkholderia*, (*Pseudomonas*) *mallei*, *Burkholderia* (*Pseudomonas*) *pseudomallei*, California serogroup, *Campylobacter fetus* subsp. *Fetus*, *Campylobacter jejuni*, *C. coli*, *C. fetus* subsp. *Jejuni*, *Candida albicans*, *Capnocytophaga* spp., *Chikungunya* virus, *Chlamydia psittaci*, *Chlamydia trachomatis*, *Citrobacter* spp., *Clonorchis sinensis*, *Clostridium botulinum*, *Clostridium difficile*, *Clostridium perfringens*, *Clostridium tetani*, *Clostridium* spp. (with the exception of those species listed above),

*Coccidioides immitis*, Colorado tick fever virus, *Corynebacterium diphtheriae*, *Coxiella burnetii*, Coxsackievirus, Creutzfeldt-Jakob agent, Kuru agent, Crimean-Congo hemorrhagic fever virus, *Cryptococcus neoformans*, *Cryptosporidium parvum*, Cytomegalovirus, *Cyclospora cayatanesis*, Dengue virus (1, 2, 3, 4), Diphtheroids, Eastern (Western) equine encephalitis virus, Ebola virus, *Echinococcus granulosus*, *Echinococcus multilocularis*, Echovirus, *Edwardsiella tarda*, *Entamoeba histolytica*, *Enterobacter* spp., Enterovirus 70, *Epidermophyton floccosum*, *Ehrlichia* spp, *Ehrlichia sennetsu*, *Microsporum* spp. *Trichophyton* spp., Epstein-Barr virus, *Escherichia coli*, enterohemorrhagic, *Escherichia coli*, enteroinvasive, *Escherichia coli*, enteropathogenic, *Escherichia coli*, enterotoxigenic, *Fasciola hepatica*, *Francisella tularensis*, *Fusobacterium* spp., *Gemella haemolysans*, *Giardia lamblia*, *Guanarito virus*, *Haemophilus ducreyi*, *Haemophilus influenzae* (group b), Hantavirus, Hepatitis A virus, Hepatitis B virus, Hepatitis C virus, Hepatitis D virus, Hepatitis E virus, Herpes simplex virus, Herpesvirus simiae, *Histoplasma capsulatum*, Human coronavirus, Human immunodeficiency virus, Human papillomavirus, Human rotavirus, Human T-lymphotrophic virus, Influenza virus including H5N1, Junin virus/Machupo virus, *Klebsiella* spp., Kyasanur Forest disease virus, *Lactobacillus* spp., Lassa virus, *Legionella pneumophila*, *Leishmania major*, *Leishmania infantum*, *Leishmania* spp., *Leptospira interrogans*, *Listeria monocytogenes*, Lymphocytic choriomeningitis virus, Machupo virus, Marburg virus, Measles virus, *Micrococcus* spp., *Moraxella* spp., *Mycobacterium* spp. (other than *M. bovis*, *M. tuberculosis*, *M. avium*, *M. leprae*), *Mycobacterium tuberculosis*, *M. bovis*, *Mycoplasma hominis*, *M. orale*, *M. salivarium*, *M. fermentans*, *Mycoplasma pneumoniae*, *Naegleria fowleri*, *Necator americanus*, *Neisseria gonorrhoeae*, *Neisseria meningitides*, *Neisseria* spp. (other than *N. gonorrhoeae* and *N. meningitidis*), *Nocardia* spp., Norwalk virus, Omsk hemorrhagic fever virus, *Onchocerca volvulus*, *Opisthorchis* spp., Parvovirus B19, *Pasteurella* spp., *Peptococcus* spp., *Peptostreptococcus* spp., *Plasmodium falciparum*, *Plasmodium vivax*, *Plasmodium* spp., *Plesiomonas shigelloides*, Powassan encephalitis virus, *Proteus* spp., *Pseudomonas* spp. (other than *P. mallei*, *P. pseudomallei*), Rabies virus, Respiratory syncytial virus, Rhinovirus, *Rickettsia akari*, *Rickettsia prowazekii*, *R. Canada*, *Rickettsia rickettsii*, Rift Valley virus, Ross river virus/O'Nyong-Nyong virus, Rubella virus, *Salmonella choleraesuis*, *Salmonella paratyphi*, *Salmonella typhi*, *Salmonella* spp. (with the exception of those species listed above), *Schistosoma* spp., Scrapie agent, *Serratia* spp., *Shigella* spp., Sindbis virus, *Sporothrix schenckii*, St. Louis encephalitis virus, Murray Valley encephalitis virus, *Staphylococcus aureus*, *Streptobacillus moniliformis*, *Streptococcus agalactiae*, *Streptococcus faecalis*, *Streptococcus pneumoniae*, *Streptococcus pyogenes*, *Streptococcus salivarius*, *Taenia saginata*, *Taenia solium*, *Toxocara canis*, *T. cati*, *T. cruzi*, *Toxoplasma gondii*, *Treponema pallidum*, *Trichinella* spp., *Trichomonas vaginalis*, *Trichuris trichiura*, *Trypanosoma brucei*, *Trypanosoma cruzi*, *Ureaplasma urealyticum*, Vaccinia virus, Varicella-zoster virus, eastern equine encephalitis virus (EEEV), severe acute respiratory virus (SARS), Venezuelan equine encephalitis virus (VEEV), Vesicular stomatitis virus, *Vibrio cholerae*, serovar 01, *Vibrio parahaemolyticus*, West Nile virus, *Wuchereria bancrofti*, Yellow fever virus, *Yersinia enterocolitica*, *Yersinia pseudotuberculosis*, and *Yersinia pestis*. Target antigens may include proteins, or variants or fragments thereof, produced by any of the infectious organisms.

A number of viruses are associated with viral hemorrhagic fever, including filoviruses (e.g., Ebola, Marburg, and Reston), arenaviruses (e.g. Lassa, Junin, and Machupo), and bunyaviruses. In addition, phleboviruses, including, for example, Rift Valley fever virus, have been identified as etiologic agents of viral hemorrhagic fever. Etiological agents of hemorrhagic fever and associated inflammation may also include paramyxoviruses, particularly respiratory syncytial virus. In addition, other viruses causing hemorrhagic fevers in man have been identified as belonging to the following virus groups: togavirus (*Chikungunya*), flavivirus (dengue, yellow fever, Kyasanur Forest disease, Omsk hemorrhagic fever), nairovirus (Crimian-Congo hemorrhagic fever) and hantavirus (hemorrhagic fever with renal syndrome, nephropathic epidemia). Furthermore, Sin Nombre virus was identified as the etiologic agent of the 1993 outbreak of hantavirus pulmonary syndrome in the American Southwest.

Target antigens may include viral coat proteins, i.e., influenza neuraminidase and hemagglutinin, HIV gp160 or derivatives thereof, HIV Gag, HIV Nef, HIV Pol, SARS coat proteins, herpes virion proteins, WNV proteins, etc. Target antigens may also include bacterial surface proteins including pneumococcal PsaA, PspA, LytA, surface or virulence associated proteins of bacterial pathogens such as *Nisseria gonnorhea*, outer membrane proteins or surface proteases.

HPV Antigen Targets

Target antigens may also include proteins, or variants or fragments thereof, associated with human papillomavirus (HPV), such as oncoproteins E6 and E7. In certain embodiments, the oncoprotein is modified to produce a non-oncogenic variant or a variant having reduced oncogenicity relative to the wild type protein. For example, the portion of the peptide that is responsible for binding a tumor suppressor protein (e.g., p53 and pRb) may be deleted or modified so that it no longer interacts with the tumor suppressor protein. As another example, an oncoprotein that is a kinase, such as Her2/neu, may be kinase-inactivated, e.g., by point mutation. In some instances, two or more target antigens may be used during immunization. For example, the E6 and E7 antigens can be combined in a fusion protein, or separate vectors containing heterologous nucleotides encoding the modified or unmodified E6 and E7 target antigens are used in combination. For example, an Ad5-E6 vector can be administered with an Ad5-E7 vector. In this example, the Ad5-E6 vector and Ad5-E7 vector may be administered simultaneously or they may be administered sequentially.

High-risk human papillomavirus (HPV) such as HPV type-16 is associated with the etiology of cervical and more than 90% of HPV-related head and neck squamous cell carcinomas. Preventive vaccines such as human papillomavirus bivalent [Types 16 and 18] vaccine and recombinant and human papillomavirus quadrivalent [Types 6, 11, 16, and 18] vaccine can be a primary defense against HPV associated cancers by preventing infection with the virus but reports indicate that they are not effective for active immunotherapy of established disease. The HPV early 6 (E6) and early 7 (E7) genes are expressed at high levels in HPV-induced cancers and are involved in the immortalization of primary human epidermal cells. Thus, these are ideal targets for tumor-specific immunotherapy because unlike many other tumor-associated antigens these viral antigens are "non-self" and thus do not have the potential to induce autoimmunity.

Disclosed herein is an immunotherapy against human papilloma virus (HPV) using a viral gene delivery platform to immunize against HPV 16 genes E6 and E7 (Ad5 [E1-, E2b-]-E6/E7) combined with programmed death-ligand 1 (PD1) blockade. Also disclosed herein is an immunotherapeutic comprised of a gene delivery vehicle (Ad5 [E1-, E2b-]) carrying modified genes for HPV type-16 E6 and E7. The HPV E6 and E7 genes can be modified to render them non-oncogenic while retaining the antigenicity necessary to produce an immune response against HPV induced tumors. The modified genes can lack the capacity to degrade p53, pRb, and PTPN13. The modified genes can be incorporated into a vaccine (Ad5 [E1-, E2b-]-E6/E7). The Ad5 [E1-, E2b-]-E6/E7 vaccine can retain the ability to induce an HPV-specific cell-mediated immune (CMI) response and can synergize with standard clinical therapy, enhancing immune-mediated clearance of an HPV-E6/E7 expressing tumor.

A balance between activation and inhibitory signals regulates the interaction between T lymphocytes and tumor cells, wherein T cell responses are initiated through antigen recognition by T-cell receptors (TCRs). In some cases, when combined with chemotherapy/radiation treatment in HPV-E6/E7 expressing tumor bearing mice, immunotherapy treatment with Ad5 [E1-, E2b-]-E6/E7 can result in significant improvement in overall survival as compared to subjects that receive chemotherapy/radiation alone.

In particular embodiments, the HPV antigen used herein is a wild-type HPV antigen or a modified HPV antigen. For example, the modified HPV antigen a non-oncogenic HPV antigen or a modified HPV antigen that has reduced oncogenicity as compared with a wild-type HPV. For example, the antigen used herein is a modified HPV E6 antigen having an amino acid sequence set forth in SEQ ID NO:17, a modified HPV E7 antigen having an amino acid sequence set forth in SEQ ID NO:18, or a combination thereof. In further embodiments, the antigen used herein is a modified HPV E6 antigen that has one or more mutations at positions 26, 98, or 106 of SEQ ID NO:17, a modified HPV E7 antigen that a mutation at position 86 of SEQ ID NO:18, or a combination thereof. In particular embodiments, the nucleotide sequence of the antigen has a region at least 50%, 60%, 65%, 70%, 75%, 80%, 85%, 90%, 95%, 98%, 99%, 99.5%, 99.9%, 100% identical to positions 123-545 of SEQ ID NO:19, positions 602-895 of SEQ ID NO:9, or a combination thereof. For example, the nucleic acid sequence has at least 80% identity to SEQ ID NO:19 (the nucleotide sequence of a HPV E6 and E7 fusion protein). In further embodiments, the nucleic acid sequence has at least 50%, 60%, 65%, 70%, 75%, 80%, 85%, 90%, 95%, 98%, 99%, 99.5%, 99.9%, 100% identity to any portion of or full-length to SEQ ID NO:20 (the predicted sequence of an adenovirus vector expressing HPV E6 and E7), such as positions 1033 to 2179 of SEQ ID NO:20.

Personalized Tumor Associated Antigens

In certain embodiments tumor associated antigens used with the compositions and methods as described herein may be identified directly from an individual with a proliferative disease or cancer. In certain embodiments, cancers may include benign tumors, metastatic tumors, carcinomas, or sarcomas and the like. In some embodiments, a personalized tumor antigen comprises MUC1, MUC1c, MUC1n, T, or CEA characterized from a patient and further utilized as the target antigen as a whole, in part or as a variant.

In this regard, screens can be carried out using a variety of known technologies to identify tumor target antigens from an individual. For example, in one embodiment, a tumor biopsy is taken from a patient, RNA is isolated from the tumor cells and screened using a gene chip (for example, from Affymetrix, Santa Clara, Calif.) and a tumor antigen is identified. Once the tumor target antigen is identified, it may then be cloned, expressed and purified using techniques known in the art.

This target antigen can then linked to one or more epitopes or incorporated or linked to cassettes or viral vectors described herein and administered to the patient in order to alter the immune response to the target molecule isolated from the tumor. In this manner, "personalized" immunotherapy and vaccines are contemplated in certain embodiments. Where cancer is genetic, that is inherited, for example the patient has been identified to have a BRAC1 or BRAC2 mutation, the vaccine can be used prophylactically. When the cancer is sporadic the immunotherapy can be used to reduce the size of the tumor, enhance overall and reduce reoccurrence of the cancer in a subject.

Combination Immunotherapies and Vaccines

Certain embodiments provide a combination immunotherapy and vaccine compositions for the treatment of cancer and infectious diseases. In some aspects, combination immunotherapies and vaccines provided herein can comprise a multi-targeted immunotherapeutic approach against antigens associated with the development of cancer such as tumor associated antigen, (TAA) or antigens know to be involved in a particular infectious disease, such as infectious disease associated antigen (IDAA). In some aspects, combination immunotherapies and vaccines provided herein can comprise a multi-targeted antigen signature immunotherapeutic approach against antigens associated with the development of cancer or infectious disease. The compositions and methods, in various embodiments, provide viral based vectors expressing a variant of MUC1, MUC1c, MUC1n, T, and/or CEA for immunization of a disease, as provided herein. These vectors can raise an immune response against MUC1, MUC1c, MUC1n, T, and/or CEA.

In some aspects, the vector comprises at least one antigen. In some aspects, the vector comprises at least two antigens. In some aspects, the vector comprises at least three antigens. In some aspects, the vector comprises more than three antigens. In some aspects, the vaccine formulation comprises 1:1 ratio of vector to antigen. In some aspects, the vaccine comprises 1:2 ratio of vector to antigen. In some aspects, the vaccine comprises 1:3 ratio of vector to antigen. In some aspects, the vaccine comprises 1:4 ratio of vector to antigen. In some aspects, the vaccine comprises 1:5 ratio of vector to antigen. In some aspects, the vaccine comprises 1:6 ratio of vector to antigen. In some aspects, the vaccine comprises 1:7 ratio of vector to antigen. In some aspects, the vaccine comprises 1:8 ratio of vector to antigen. In some aspects, the vaccine comprises 1:9 ratio of vector to antigen. In some aspects, the vaccine comprises 1:10 ratio of vector to antigen.

In some aspects, the vaccine is a combination vaccine, wherein the vaccine comprises at least two vectors each containing at least a single antigen. In some aspects the vaccine is a combination vaccine, wherein the vaccine comprises at least three vectors each containing at least a single antigen target. In some aspects the vaccine is a combination vaccine, wherein the vaccine comprises more than three vectors each containing at least a single antigen.

In some aspects, the vaccine is a combination vaccine, wherein the vaccine comprises at least two vectors, wherein a first vector of the at least two vectors comprises at least a single antigen and wherein a second vector of the at least two vectors comprises at least two antigens. In some aspects, the vaccine is a combination vaccine, wherein the vaccine comprises at least three vectors, wherein a first vector of the at least three vectors comprises at least a single antigen and wherein a second vector of the at least three vectors comprises at least two antigens. In some aspects, the vaccine is a combination vaccine, wherein the vaccine comprises three or more vectors, wherein a first vector of the three or more vectors comprises at least a single antigen and wherein a second vector of the three or more vectors comprises at least two antigens. In some aspects the vaccine is a combination vaccine, wherein the vaccine comprises more than three vectors each containing at least two antigens.

When a mixture of different antigens are simultaneously administered or expressed from a same or different vector in an individual, they may compete with one another. As a result the formulations comprising different concentration and ratios of expressed antigens in a combination immunotherapy or vaccine must be evaluated and tailored to the individual or group of individuals to ensure that effective and sustained immune responses occur after administration.

Composition that comprises multiple antigens can be present at various ratios. For example, formulations with more than vector can have various ratios. For example, immunotherapies or vaccines can have two different vectors in a stoichiometry of 1:1, 1:2, 1:3, 1:4, 1:5, 1:6, 1:7, 1:8, 1:9, 1:10, 1:15, 1:20, 1:30, 2:1, 2:3, 2:4, 2:5, 2:6, 2:7, 2:8, 3:1, 3:3, 3:4, 3:5, 3:6, 3:7, 3:8, 3:1, 3:3, 3:4, 3:5, 3:6, 3:7, 3:8, 4:1, 4:3, 4:5, 4:6, 4:7, 4:8, 5:1, 5:3, 5:4, 5:6, 5:7, 5:8, 6:1, 6:3, 6:4, 6:5, 6:7, 6:8, 7:1, 7:3, 7:4, 7:5, 7:6, 7:8, 8:1, 8:3, 8:4, 8:5, 8:6, or 8:7. For example, immunotherapies or vaccines can have three different vectors in a stoichiometry of: 1:1:1, 1:2:1, 1:3:1, 1:4:1, 1:5:1, 1:6:1, 1:7:1, 1:8:1, 2:1:1, 2:3:1, 2:4:1, 2:5:1, 2:6:1, 2:7:1, 2:8:1, 3:1, 3:3:1, 3:4:1, 3:5:1, 3:6:1, 3:7:1, 3:8:1, 3:1:1, 3:3:1, 3:4:1, 3:5:1, 3:6:1, 3:7:1, 3:8:1, 4:1:1, 4:3:1, 4:4:1, 4:5:1, 4:6:1, 4:7:1, 4:8:1, 5:1:1, 5:3:1, 5:4:1, 5:5:1, 5:6:1, 5:7:1, 5:8:1, 6:1:1, 6:3:1, 6:4:1, 6:5:1, 6:6:1, 6:7:1, 6:8:1, 7:1:1, 7:3:1, 7:4:1, 7:5:1, 7:6:1, 7:7:1, 7:8:1, 8:1:1, 8:3:1, 8:4:1, 8:5:1, 8:6:1, 8:7:1, 8:8:1, 1:1:2, 1:2:2, 1:3:2, 1:4:2, 1:5:2, 1:6:2, 1:7:2, 1:8:2, 2:1:2, 2:3:2, 2:4:2, 2:5:2, 2:6:2, 2:7:2, 2:8:2, 3:1:2, 3:3:2, 3:4:2, 3:5:2, 3:6:2, 3:7:2, 3:8:2, 3:1:2, 3:3:2, 3:4:2, 3:5:2, 3:6:2, 3:7:2, 3:8:2, 4:1:2, 4:3:2, 4:4:2, 4:5:2, 4:6:2, 4:7:2, 4:8:2, 5:1:2, 5:3:2, 5:4:2, 5:5:2, 5:6:2, 5:7:2, 5:8:2, 6:1:2, 6:3:2, 6:4:2, 6:5:2, 6:6:2, 6:7:2, 6:8:2, 7:1:2, 7:3:2, 7:4:2, 7:5:2, 7:6:2, 7:7:2, 7:8:2, 8:1:2, 8:3:2, 8:4:2, 8:5:2, 8:6:2, 8:7:2, 8:8:2, 1:1:3, 1:2:3, 1:3:3, 1:4:3, 1:5:3, 1:6:3, 1:7:3, 1:8:3, 2:1:3, 2:3:3, 2:4:3, 2:5:3, 2:6:3, 2:7:3, 2:8:3, 3:1:3, 3:3:3, 3:4:3, 3:5:3, 3:6:3, 3:7:3, 3:8:3, 4:1:3, 4:3:3, 4:4:3, 4:5:3, 4:6:3, 4:7:3, 4:8:3, 5:1:3, 5:3:3, 5:4:3, 5:5:3, 5:6:3, 5:7:3, 5:8:3, 6:1:3, 6:3:3, 6:4:3, 6:5:3, 6:6:3, 6:7:3, 6:8:3, 7:1:3, 7:3:3, 7:4:3, 7:5:3, 7:6:3, 7:7:3, 7:8:3, 8:1:3, 8:3:3, 8:4:3, 8:5:3, 8:6:3, 8:7:3, 8:8:3, 1:1:4, 1:2:4, 1:3:4, 1:4:4, 1:5:4, 1:6:4, 1:7:4, 1:8:4, 2:1:4, 2:3:4, 2:4:4, 2:5:4, 2:6:4, 2:7:4, 2:8:4, 3:1:4, 3:3:4, 3:4:4, 3:5:4, 3:6:4, 3:7:4, 3:8:4, 3:1:4, 3:3:4, 3:4:4, 3:5:4, 3:6:4, 3:7:4, 3:8:4, 4:1:4, 4:3:4, 4:4:4, 4:5:4, 4:6:4, 4:7:4, 4:8:4, 5:1:4, 5:3:4, 5:4:4, 5:5:4, 5:6:4, 5:7:4, 5:8:4, 6:1:4, 6:3:4, 6:4:4, 6:5:4, 6:6:4, 6:7:4, 6:8:4, 7:1:4, 7:3:4, 7:4:4, 7:5:4, 7:6:4, 7:7:4, 7:8:4, 8:1:4, 8:3:4, 8:4:4, 8:5:4, 8:6:4, 8:7:4, 8:8:4, 1:1:5, 1:2:5, 1:3:5, 1:4:5, 1:5:5, 1:6:5, 1:7:5, 1:8:5, 2:1:5, 2:3:5, 2:4:5, 2:5:5, 2:6:5, 2:7:5, 2:8:5, 3:1:5, 3:3:5, 3:4:5, 3:5:5, 3:6:5, 3:7:5, 3:8:5, 3:1:5, 3:3:5, 3:4:5, 3:5:5, 3:6:5, 3:7:5, 3:8:5, 4:1:5, 4:3:5, 4:4:5, 4:5:5, 4:6:5, 4:7:5, 4:8:5, 5:1:5, 5:3:5, 5:4:5, 5:5:5, 5:6:5, 5:7:5, 5:8:5, 6:1:5, 6:3:5, 6:4:5, 6:5:5, 6:6:5, 6:7:5, 6:8:5, 7:1:5, 7:3:5, 7:4:5, 7:5:5, 7:6:5, 7:7:5, 7:8:5, 8:1:5, 8:3:5, 8:4:5, 8:5:5, 8:6:5, 8:7:5, 8:8:5, 1:1:6, 1:2:6, 1:3:6, 1:4:6, 1:5:6, 1:6:6, 1:7:6, 1:8:6, 2:1:6, 2:3:6, 2:4:6, 2:5:6, 2:6:6, 2:7:6, 2:8:6, 3:1:6, 3:3:6, 3:4:6, 3:5:6, 3:6:6, 3:7:6, 3:8:6, 3:1:6, 3:3:6, 3:4:6, 3:5:6, 3:6:6, 3:7:6, 3:8:6, 4:1:6, 4:3:6, 4:4:6, 4:5:6, 4:6:6, 4:7:6, 4:8:6, 5:1:6, 5:3:6, 5:4:6, 5:5:6, 5:6:6, 5:7:6, 5:8:6, 6:1:6, 6:3:6, 6:4:6, 6:5:6, 6:6:6, 6:7:6, 6:8:6, 7:1:6, 7:3:6, 7:4:6, 7:5:6, 7:6:6, 7:7:6, 7:8:6, 8:1:6, 8:3:6, 8:4:6, 8:5:6, 8:6:5, 8:7:6, 8:8:6, 1:1:7, 1:2:7, 1:3:7, 1:4:7, 1:5:7, 1:6:7, 1:7:7, 1:8:7, 2:1:7, 2:3:7, 2:4:7, 2:5:7, 2:6:7, 2:7:7, 2:8:7, 3:1:7, 3:3:7, 3:4:7, 3:5:7, 3:6:7, 3:7:7, 3:8:7, 3:1:7, 3:3:7, 3:4:7, 3:5:7, 3:6:7, 3:7:7, 3:8:7, 4:1:7, 4:3:7, 4:4:7, 4:5:7, 4:6:7, 4:7:7, 4:8:7, 5:1:7, 5:3:7, 5:4:7, 5:5:7, 5:6:7, 5:7:7, 5:8:7, 6:1:7, 6:3:7, 6:4:7, 6:5:7, 6:6:7, 6:7:7, 6:8:7, 7:1:7, 7:3:7, 7:4:7, 7:5:7, 7:6:7, 7:7:7, 7:8:7, 8:1:7, 8:3:7, 8:4:7, 8:5:7, 8:6:7, 8:7:7, or 8:8:7.

Certain embodiments provide combination immunotherapies comprising multi-targeted immunotherapeutic directed TAAs. Certain embodiments provide combination immunotherapies comprising multi-targeted immunotherapeutic directed to IDAAs.

Certain embodiments provide a combination immunotherapies or vaccines comprising: at least two, at least three, or more than three different target antigens comprising a sequence encoding a modified CEA, MUC1c, and/or Brachyury. For example, a combination immunotherapy or vaccine can comprise at least two, at least three, or more than three different target antigens comprising a sequence encoding a modified CEA, MUC1c, and/or Brachyury, wherein the modified CEA comprises a sequence with an identity value of at least 70%, 75%, 80%, 85%, 90%, 95%, 98%, 99%, 99.5%, or 99.9% to SEQ ID NO:1 or SEQ ID NO:2; wherein the modified MUC1c comprises a sequence with an identity value of at least 70%, 75%, 80%, 85%, 90%, 95%, 98%, 99%, 99.5%, or 99.9% to SEQ ID NO:5 or SEQ ID NO:6; and wherein the modified Brachyury comprises a sequence with an identity value of at least 70%, 75%, 80%, 85%, 90%, 95%, 98%, or 99%, 99.5%, 99.9% to SEQ ID NO:7 or SEQ ID NO:8. In some embodiments, the modified CEA comprises a sequence with an identity value of at least 70%, 75%, 80%, 85%, 90%, 95%, 98%, 99%, 99.5%, 99.9% or 100% SEQ ID NO:1 or SEQ ID NO:2 and has a Asn→Asp substitution at position 610.

Certain embodiments provide combination immunotherapies comprising multi-targeted immunotherapeutic directed to TAAs and molecular compositions comprising an immune pathway checkpoint modulator that targets at least one immune checkpoint protein of the immune inhibitory pathway. Certain embodiments provide combination immunotherapies comprising multi-targeted immunotherapeutic directed to IDAAs and molecular compositions comprising an immune pathway checkpoint modulator that targets at least one immune checkpoint protein of the immune inhibitory pathway. Certain embodiments provide a combination immunotherapies or vaccines comprising: at least two, at least three, or more than three different target antigens comprising a sequence encoding a modified CEA, MUC1c, and/or Brachyury, and at least one molecular composition comprising an immune pathway checkpoint modulator. For example, a combination immunotherapy or vaccine can comprise at least two, at least three, or more than three different target antigens comprising a sequence encoding a modified CEA, MUC1c, and/or Brachyury, wherein the modified CEA comprises a sequence with an identity value of at least 70%, 75%, 80%, 85%, 90%, 95%, 98%, 99%, 99.5%, or 99.9% to SEQ ID NO:1 or SEQ ID NO:2; wherein the modified MUC1c comprises a sequence with an identity value of at least 70%, 75%, 80%, 85%, 90%, 95%, 98%, 99%, 99.5%, or 99.9% to SEQ ID NO:5 or SEQ ID NO:6; wherein the modified Brachyury comprises a sequence with an identity value of at least 70%, 75%, 80%, 85%, 90%, 95%, 98%, or 99%, 99.5%, 99.9% to SEQ ID NO:7 or SEQ ID NO:8, and at least one molecular composition comprising an immune pathway checkpoint modulator. In some embodiments, the modified CEA comprises a sequence with an identity value of at least 70%, 75%, 80%, 85%, 90%, 95%, 98%, 99%, 99.5%, 99.9% or 100% SEQ ID NO:1 or SEQ ID NO:2 and has a Asn→Asp substitution at position 610.

In some embodiments, the immune pathway checkpoint modulator targets CTLA4. In some embodiments, the immune pathway checkpoint modulator targets PD1. In some embodiments, the immune pathway checkpoint modulator targets PDL1. In some embodiments, the immune pathway checkpoint modulator targets LAG3. In some embodiments, the immune pathway checkpoint modulator targets B7-H3. In some embodiments, the immune pathway checkpoint modulator targets B7-H4. In some embodiments, the immune pathway checkpoint modulator targets TIM3. In some embodiment, the immune pathway checkpoint modulator is a monoclonal or polyclonal antibody directed to PD1, PDL1, PDL2, CD28, CD80, CD86, CTLA4, B7RPI, ICOS, B7RPI, B7-H3, B7-H4, BTLA, HVEM, KIR, TCR, LAG3, CD137, CD137L, OX40, OX40L, CD27, CD70, CD40, CD40L, TIM3 (i.e., HAVcr2), GALS, and A2aR.

In some embodiments, at least one of the recombinant nucleic acid vectors is a replication defective adenovirus vector that comprises a replication defective adenovirus 5 vector comprising a first identity value. In some embodiments, the replication defective adenovirus vector comprises a deletion in the E2b region. In some embodiments, the replication defective adenovirus vector further comprises a deletion in the E1 region. In some embodiments, the first identity value is at least 90%. In some embodiments, the first identity value is at least 95%. In some embodiments, the first identity value is at least 99%. In some embodiments, the first identity value is 100%. In some embodiments, the first identity value is at least 90%. In some embodiments, the first identity value is at least 95%. In some embodiments, the first identity value is at least 99%. In some embodiments, the first identity value is 100%. In some embodiments, the first identity value is at least 90%. In some embodiments, the first identity value is at least 95%. In some embodiments, the first identity value is at least 99%. In some embodiments, the first identity value is 100%.

In some embodiments, at least one of the recombinant nucleic acid vector comprises a sequence with at least 80%, 85%, 90%, 95%, 99%, or 100% sequence identity to SEQ ID NO:3. In some embodiments, the recombinant nucleic acid vector comprises a region with at least 80%, 85%, 90%, 95%, 99%, or 100% sequence identity to a region in SEQ ID NO:3, wherein the region is selected from 26048-26177, 26063-26141, 1-103, 54-103, 32214-32315, and 32214-32262. In some embodiments, the recombinant nucleic acid vector further comprises a region encoding a peptide with at least 80%, 85%, 90%, 95%, 99%, or 100% sequence identity to a peptide encoded by a region in SEQ ID NO:3 between positions 1057 and 3165.

Combination Therapy

In certain embodiments, there is provided a method of treating a CEA-expression cancer in an individual in need thereof, the method comprising: administering to the individual a first pharmaceutical composition comprising a replication-defective vector comprising a nucleic acid sequence encoding a CEA antigen or any suitable antigen; and administering to the individual an immune checkpoint inhibitor. The method may further comprise administering to the individual a VEGF inhibitor, a chemotherapy, or a combination thereof.

In certain embodiments, the chemotherapy used herein is capecitabine, leucovorin, fluorouracil, oxaliplatin, fluoropyrimidine, irinotecan, mitomycin, regorafenib, cetuxinab, panitumumab, acetinophen, or a combination thereof. In particular embodiments, the chemotherapy used herein is FOLFOX (leucovorin, fluorouracil and oxaliplatin) or capecitabine. In certain embodiments, the immune checkpoint inhibitor is an anti-PD-1 or anti-PD-L1 antibody, such as avelumab. In certain embodiments, the VEGF inhibitor is an anti-VEGF antibody, such as bevacizumab.

FOLFOX (5-Fluorouracil, Leucovorin, Oxaliplatin)

A randomized trial comparing irinotecan and bolus fluorouracil plus leucovorin (IFL, control combination), oxaliplatin and infused fluorouracil plus leucovorin (FOLFOX), or irinotecan and oxaliplatin (IROX) established the FOLFOX combination, given for a total of 6 months, as the standard of care for first line treatment in patients with metastatic colorectal cancer (mCRC). Though multiple infusion schedules of FOLFOX have been validated, typically denominated as 'modified FOLFOX, there are no essential changes in the constituent cytotoxic agents of the regimen. Of these, mFOLFOX6 is one of the most widely used.

Oxaliplatin, however, is very difficult for patients to receive for greater than 6 months (12 cycles) due to progressive neurotoxicity. Though 6 months of combination therapy remains the standard of care in mCRC, clinical judgment may influence the decision to limit the number of oxaliplatin-containing cycles towards the end of treatment Other trials, including the CAIRO3 study, have demonstrated the feasibility and benefit of discontinuation of oxaliplatin after a 3 month "induction" period with continuation of 5-FU and leucovorin as "maintenance" therapy.

Bevacizumab (Avastin®)

Addition of bevacizumab to first-line 5-FU and Oxaliplatin containing regimens was demonstrated to increase time to progression in mCRC patients with a manageable side effect profile and non-overlapping toxicities. Later trials indicated that continuing bevacizumab beyond first progression (in combination with subsequent chemotherapy) improved overall survival in an unselected group of patients by KRAS mutational status, which has led to its approved use in the maintenance setting.

Capecitabine

This agent is a prodrug that is enzymatically converted to 5-fluorouracil by 3 enzymatic steps following oral ingestion. As an orally active fluoropyrimidine, capecitabine has been approved for use in the adjuvant setting. In the advanced colon cancer setting, it has been shown to be equally efficacious as 5-fluorouracil, though with more reported rates of hand-foot syndrome. This agent offers the convenience of the oral route with its benefits of reducing infusion commitments for patients in the maintenance setting, while achieving high concentrations intratumorally, given the higher concentrations of thymidine phosphorylase in tumor as compared to normal tissues.

Immunological Fusion Partner Antigen Targets

The viral vectors may also include nucleic acid sequences that encode proteins that increase the immunogenicity of the target antigen. In this regard, the protein produced following immunization with the viral vector containing such a protein may be a fusion protein comprising the target antigen of interest fused to a protein that increases the immunogenicity of the target antigen of interest.

In one embodiment, such an immunological fusion partner is derived from a *Mycobacterium* sp., such as a *Mycobacterium tuberculosis*-derived Ra12 fragment. Ra12 compositions and methods for their use in enhancing the expression and/or immunogenicity of heterologous polynucleotide/polypeptide sequences are described in U.S. Patent Application 60/158,585 and U.S. Pat. No. 7,009,042, which are herein incorporated by reference in their entirety. Briefly, Ra12 refers to a polynucleotide region that is a subsequence of a *Mycobacterium tuberculosis* MTB32A nucleic acid. MTB32A is a serine protease of 32 kDa encoded by a gene in virulent and avirulent strains of *M. tuberculosis*. The nucleotide sequence and amino acid sequence of MTB32A have been described (see, e.g., U.S. Patent Application 60/158,585; Skeiky et al., Infection and Immun. 67:3998-4007 (1999), incorporated herein by reference in their entirety). C-terminal fragments of the MTB32A coding sequence express at high levels and remain as soluble polypeptides throughout the purification process. Moreover, Ra12 may enhance the immunogenicity of heterologous immunogenic polypeptides with which it is fused. One Ra12 fusion polypeptide comprises a 14 kDa C-terminal fragment corresponding to amino acid residues 192 to 323 of MTB32A. Other Ra12 polynucleotides generally comprise at least about 15, 30, 60, 100, 200, 300, or more nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants can have at least about 70%, 80%, or 90% identity, or more, to a polynucleotide sequence that encodes a native Ra12 polypeptide or a portion thereof.

An immunological fusion partner can be derived from protein D, a surface protein of the gram-negative bacterium *Haemophilus* influenza B. In some cases, a protein D derivative comprises approximately the first third of the protein (e.g., the first N-terminal 100-110 amino acids). A protein D derivative may be lipidated. Within certain embodiments, the first 109 residues of a Lipoprotein D fusion partner is included on the N-terminus to provide the polypeptide with additional exogenous T-cell epitopes, which may increase the expression level in *E. coli* and may function as an expression enhancer. The lipid tail may ensure optimal presentation of the antigen to antigen presenting cells. Other fusion partners include the non-structural protein from influenza virus, NS1 (hemagglutinin). Typically, the N-terminal 81 amino acids are used, although different fragments that include T-helper epitopes may be used.

The immunological fusion partner can be the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus can be employed. Within another embodiment, a repeat portion of LYTA may be incorporated into a fusion polypeptide. A repeat portion can, for example, be found in the C-terminal region starting at residue 178. One particular repeat portion incorporates residues 188-305.

In some embodiments, the antigen target comprises an immunogenic component comprising a cytokine selected from the group of IFN-γ, TNFα IL-2, IL-8, IL-12, IL-18, IL-7, IL-3, IL-4, IL-5, IL-6, IL-9, IL-10, and IL-13. In some embodiments, the antigen target further comprises one or more immunogenic component comprises a cytokine selected from the group of IFN-γ, TNFα IL-2, IL-8, IL-12, IL-18, IL-7, IL-3, IL-4, IL-5, IL-6, IL-9, IL-10, and IL-13. In some embodiments, the antigen target comprises an immunogenic component comprising a nucleic acid encoding of IFN-γ, TNFα IL-2, IL-8, IL-12, IL-18, IL-7, IL-3, IL-4, IL-5, IL-6, IL-9, IL-10, and IL-13, a protein with substantial identity to one or more of IFN-γ, TNFα IL-2, IL-8, IL-12, IL-18, IL-7, IL-3, IL-4, IL-5, IL-6, IL-9, IL-10, and IL-13, and a nucleic acid encoding a protein with substantial identity to one or more of IFN-γ, TNFα IL-2, IL-8, IL-12, IL-18, IL-7, IL-3, IL-4, IL-5, IL-6, IL-9, IL-10, and IL-13.

In some embodiments, the antigen target is fused or linked to an immunogenic component comprising a cytokine selected from the group of IFN-γ, TNFα IL-2, IL-8, IL-12, IL-18, IL-7, IL-3, IL-4, IL-5, IL-6, IL-9, IL-10, and IL-13. In some embodiments, the antigen target is co-expressed in a cell with an immunogenic component comprising a cytokine selected from the group of IFN-γ, TNFα IL-2, IL-8, IL-12, IL-18, IL-7, IL-3, IL-4, IL-5, IL-6, IL-9, IL-10, and IL-13.

Immune Pathway Checkpoint Modulators

In some embodiments, compositions are administered with one or more immune checkpoint modulator, such as immune checkpoint inhibitors. In some embodiments, the composition comprises a replication-defective vector comprising a nucleotide sequence encoding a target antigen, such as CEA, MUC1, Brachyury, HPV E6, HPV E7, or a combination thereof, or any suitable antigens.

A balance between activation and inhibitory signals regulates the interaction between T lymphocytes and disease cells, wherein T-cell responses are initiated through antigen recognition by the T-cell receptor (TCR). The inhibitory pathways and signals are referred to as immune checkpoints. In normal circumstances, immune checkpoints play a critical role in control and prevention of autoimmunity and also protect from tissue damage in response to pathogenic infection.

In certain aspect, there are provided combination immunotherapies comprising viral vector based vaccines and compositions for modulating immune checkpoint inhibitory pathways for the treatment of cancer and infectious diseases. In some embodiments, modulating is increasing expression or activity of a gene or protein. In some embodiments, modulating is decreasing expression or activity of a gene or protein. In some embodiments, modulating affects a family of genes or proteins.

In general, the immune inhibitory pathways are initiated by ligand-receptor interactions. It is now clear that in diseases, the disease can co-opt immune-checkpoint pathways as mechanism for inducing immune resistance in a subject.

The induction of immune resistance or immune inhibitory pathways in a subject by a given disease can be blocked by molecular compositions such as siRNAs, antisense, small molecules, mimic, a recombinant form of ligand, receptor or protein, or antibodies (which can be an Ig fusion protein) that are known to modulate one or more of the Immune Inhibitory Pathways. For example, preliminary clinical findings with blockers of immune-checkpoint proteins, such as Cytotoxic T-lymphocyte-associated antigen 4 (CTLA4) and programmed cell death protein 1 (PD1) have shown promise for enhancing antitumor immunity.

Because diseased cells can express multiple inhibitory ligands, and disease-infiltrating lymphocytes express multiple inhibitory receptors, dual or triple blockade of immune checkpoints proteins may enhance anti-disease immunity. Combination immunotherapies as provide herein can comprise one or more molecular compositions of the following immune-checkpoint proteins: PD1, PDL1, PDL2, CD28, CD80, CD86, CTLA4, B7RPI, ICOS, B7RPI, B7-H3 (also known as CD276), B7-H4 (also known as B7-S1, B7x and VCTN1), BTLA (also known as CD272), HVEM, KIR, TCR, LAG3 (also known as CD223), CD137, CD137L, OX40, OX40L, CD27, CD70, CD40, CD40L, TIM3 (also known as HAVcr2), GALS, and A2aR. In some embodiments, the molecular composition comprises siRNAs. In some embodiments, the molecular composition comprises a small molecule. In some embodiments, the molecular composition comprises a recombinant form of a ligand. In some embodiments, the molecular composition comprises a recombinant form of a receptor. In some embodiments, the molecular composition comprises an antibody. In some embodiments, the combination therapy comprises more than one molecular composition and/or more than one type of molecular composition. As it will be appreciated by those in the art, future discovered proteins of the immune checkpoint inhibitory pathways are also envisioned to be encompassed in certain aspects.

In some embodiments, combination immunotherapies comprise molecular compositions for the modulation of CTLA4. In some embodiments, combination immunotherapies comprise molecular compositions for the modulation PD1. In some embodiments, combination immunotherapies comprise molecular compositions for the modulation PDL1. In some embodiments, combination immunotherapies comprise molecular compositions for the modulation LAG3. In some embodiments, combination immunotherapies comprise molecular compositions for the modulation B7-H3. In some embodiments, combination immunotherapies comprise molecular compositions for the modulation B7-H4. In some embodiments, combination immunotherapies comprise molecular compositions for the modulation TIM3. In some embodiments, modulation is an increase or enhancement of expression. In other embodiments, modulation is the decrease of absence of expression.

Two exemplary immune checkpoint inhibitors include the cytotoxic T lymphocyte associated antigen-4 (CTLA-4) and the programmed cell death protein-1 (PD1). CTLA-4 can be expressed exclusively on T-cells where it regulates early stages of T-cell activation. CTLA-4 interacts with the co-stimulatory T-cell receptor CD28 which can result in signaling that inhibits T-cell activity. Once TCR antigen recognition occurs, CD28 signaling may enhances TCR signaling, in some cases leading to activated T-cells and CTLA-4 inhibits the signaling activity of CD28. Certain embodiments provide immunotherapies as provided herein in combination with anti-CTLA-4 monoclonal antibody for the treatment of proliferative disease and cancer. Certain embodiments provide immunotherapies as provided herein in combination with CTLA-4 molecular compositions for the treatment of proliferative disease and cancer.

Programmed death cell protein ligand-1 (PDL1) is a member of the B7 family and is distributed in various tissues and cell types. PDL1 can interact with PD1 inhibiting T-cell activation and CTL mediated lysis. Significant expression of PDL1 has been demonstrated on various human tumors and PDL1 expression is one of the key mechanisms in which tumors evade host antitumor immune responses. Programmed death-ligand 1 (PDL1) and programmed cell death protein-1 (PD1) interact as immune checkpoints. This interaction can be a major tolerance mechanism which results in the blunting of anti-tumor immune responses and subsequent tumor progression. PD1 is present on activated T cells and PDL1, the primary ligand of PD1, is often expressed on tumor cells and antigen-presenting cells (APC) as well as other cells, including B cells. Significant expression of PDL1 has been demonstrated on various human tumors including HPV-associated head and neck cancers. PDL1 interacts with PD1 on T cells inhibiting T cell activation and cytotoxic T lymphocyte (CTL) mediated lysis. Certain embodiments provide immunotherapies as provided herein in combination with anti-PD1 or anti-PDL1 monoclonal antibody for the treatment of proliferative disease and cancer. Certain embodiments provide immunotherapies as provided herein in combination with PD1 or anti-PDL1 molecular compositions for the treatment of proliferative disease and cancer. Certain embodiments provide immunotherapies as provided herein in combination with anti-CTLA-4 and anti-PD1 monoclonal antibodies for the treatment of proliferative disease and cancer. Certain embodiments provide immunotherapies as provided herein in combination with anti-CTLA-4 and PDL1 monoclonal antibodies for the treatment of proliferative disease and cancer. Certain embodiments provide immunotherapies as provided herein in combination with anti-CTLA-4, anti-PD1, PDL1, monoclonal antibodies, or a combination thereof, for the treatment of proliferative disease and cancer.

Certain embodiments provide immunotherapies as provided herein in combination with several antibodies directed against the PD-L1/PD-1 pathway that are in clinical development for cancer treatment. In certain embodiments, anti-PD-L1 antibodies may be used. Compared with anti-PD-1 antibodies that target T-cells, anti-PDL1 antibodies that target tumor cells are expected to have less side effects, including a lower risk of autoimmune-related safety issues, as blockade of PD-L1 leaves the PD-L2/PD-1 pathway intact to promote peripheral self-tolerance.

To this end, avelumab, a fully human IgG1 anti-PDL1 antibody (drug code MSB0010718C) has been produced. Avelumab selectively binds to PD-L1 and competitively blocks its interaction with PD-1.

Avelumab is also cross-reactive with murine PD-L1, thus allowing in vivo pharmacology studies to be conducted in normal laboratory mice. However, due to immunogenicity directed against the fully human avelumab molecule, the dosing regimen was limited to three doses given within a week.

The key preclinical pharmacology findings for avelumab are summarized below. Avelumab showed functional enhancement of primary T cell activation in vitro in response to antigen-specific and antigen non-specific stimuli; and significant inhibition of in vivo tumor growth (PD-L1 expressing MC38 colon carcinoma) as a monotherapy. Its in vivo efficacy is driven by CD8+ T cells, as evidenced by complete abrogation of anti-tumor activity when this cell type was systemically depleted. Its combination with localized, fractionated radiotherapy resulted in complete regression of established tumors with generation of anti-tumor immune memory. Its use in chemotherapy combinations also showed promising activity: additive combination effect when partnered with oxaliplatin and 5-fluorouracil (5-FU) (core components of FOLFOX [oxaliplatin, 5-FU, and folinic acid]) against MC38 colon tumors; significant increase in survival when partnered with gemcitabine against PANC02 pancreatic tumors. Its antibody-dependent cell-mediated cytotoxicity (ADCC) was demonstrated against human tumor cells in vitro; furthermore, studies in ADCC deficient settings in vivo support a contribution of ADCC to anti-tumor efficacy. Additional findings of Avelumab include: no complement-dependent cytotoxicity was observed in vitro. Immunomonitoring assays with translational relevance for the clinic further support an immunological mechanism of action: consistent increases in CD8+ PD-1+ T cells and CD8+ effector memory T cells as measured by fluorescence-activated cell sorter (FACS); enhanced tumor-antigen specific CD8+ T cell responses as measured by pentamer staining and enzyme-linked immunosorbent spot (ELISPOT) assays.

Despite reports indicating that anti-tumor radiographic responses were unlikely using agents that interfere with PD-1 PD-L1 binding in colorectal cancer, there have been reports of radiographic responses. Additionally, a correlation has been demonstrated in multiple clinical trials indicating that PD-L1 expression levels on tumor tissue predict the likelihood of radiographic response. However, it has become clear that PD-L1 expression, as it is currently measured, is not a definitive requirement for anti-tumor efficacy. It has been noted that colorectal tumors rarely express PD-L1 compared with other tumors that are more likely to respond to PD-1-PD-L1 blockade. However, it is known that a strong anti-tumor T cell response, producing IFN-gamma, will induce PD-L1 expression.

In some embodiments, without being bound by theory, it was contemplated that an underlying immune response is necessary for PD-1-PD-L1 blockade to have an anti-tumor effect. Without being bound by theory, it was further contemplated that this combination of an immune checkpoint inhibitor with the standard therapy and an adenoviral vector composition such as Ad-CEA immunizations, Ad-E6/E7 immunizations, or Ad-CEA/MUC1/Brachyury immunizations may be capable of induction of PD-L1 expression and thereby increase the anti-tumor activity of PD-1-PD-L1 blockade.

Some embodiments provide Ad5 [E1-, E2b-]-E6/E7 immunizations combined with PD1 blockade that can increase an anti-tumor effect. A CMI response induced by the Ad5 [E1-, E2b-]-E6/E7 vaccine was characterized to show kinetics of an anti-tumor response to evaluate the therapeutic potential of treating small versus large established tumors.

Immune checkpoint molecules can be expressed by T cells. Immune checkpoint molecules can effectively serve as "brakes" to down-modulate or inhibit an immune response. Immune checkpoint molecules include, but are not limited to Programmed Death 1 (PD1, also known as PDCD1 or CD279, accession number: NM_005018), Cytotoxic T-Lymphocyte Antigen 4 (CTLA-4, also known as CD152, GenBank accession number AF414120.1), LAG3 (also known as CD223, accession number: NM_002286.5), Tim3 (also known as HAVCR2, GenBank accession number: JX049979.1), BTLA (also known as CD272, accession number: NM_181780.3), BY55 (also known as CD160, GenBank accession number: CR541888.1), TIGIT (also known as IVSTM3, accession number: NM_173799), LAIR1 (also known as CD305, GenBank accession number: CR542051.1), SIGLEC10 (GeneBank accession number: AY358337.1), 2B4 (also known as CD244, accession number: NM_001166664.1), PPP2CA, PPP2CB, PTPN6, PTPN22, CD96, CRTAM, SIGLEC7, SIGLEC9, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, ILIORA, IL10RB, HMOX2, IL6R, IL6ST, EIF2AK4, CSK, PAG1, SIT1, FOXP3, PRDM1, BATF, GUCY1A2, GUCY1A3, GUCY1B2, GUCY1B3 which directly inhibit immune cells. For example, PD1 can be combined with an adenoviral vaccine to treat a patient in need thereof. Table 1, without being exhaustive, shows exemplary immune checkpoint genes that can be inactivated to improve the efficiency of the adenoviral vaccine. Immune checkpoints gene can be selected from such genes listed in Table 1 and others involved in co-inhibitory receptor function, cell death, cytokine signaling, arginine tryptophan starvation, TCR signaling, Induced T-reg repression, transcription factors controlling exhaustion or anergy, and hypoxia mediated tolerance.

TABLE 1

| Gene Symbol | NCBI # (GRCh38.p2) | Start | Stop | Genome location |
|---|---|---|---|---|
| ADORA2A | 135 | 24423597 | 24442360 | 22q11.23 |
| CD276 | 80381 | 73684281 | 73714518 | 15q23-q24 |
| VTCN1 | 79679 | 117143587 | 117270368 | 1p13.1 |
| BTLA | 151888 | 112463966 | 112499702 | 3q13.2 |
| CTLA4 | 1493 | 203867788 | 203873960 | 2q33 |
| IDO1 | 3620 | 39913809 | 39928790 | 8p12-p11 |
| KIR3DL1 | 3811 | 54816438 | 54830778 | 19q13.4 |
| LAG3 | 3902 | 6772483 | 6778455 | 12p13.32 |
| PDCD1 | 5133 | 241849881 | 241858908 | 2q37.3 |
| HAVCR2 | 84868 | 157085832 | 157109237 | 5q33.3 |
| VISTA | 64115 | 71747556 | 71773580 | 10q22.1 |
| CD244 | 51744 | 160830158 | 160862902 | 1q23.3 |
| CISH | 1154 | 50606454 | 50611831 | 3p21.3 |

The combination of an adenoviral-based vaccine and an immune pathway checkpoint modulator may result in reduction in cancer recurrences in treated patients, as compared to either agent alone. In yet another embodiment the combination of an adenoviral-based vaccine and an immune pathway checkpoint modulator may result in reduction in the presence or appearance of metastases or micro metastases in treated patients, as compared to either agent alone. In another embodiment, the combination of a adenoviral-based vaccine and an immune pathway checkpoint modulator may result improved overall survival of treated patients, as compared to either agent alone. In some cases, the combination of an adenoviral vaccine and an immune pathway checkpoint modulator may increase the frequency or intensity of tumor-specific T cell responses in patients compared to either agent alone.

Some embodiments also disclose the use of immune checkpoint inhibition to improve performance of an adenoviral vector-based vaccine. The immune checkpoint inhibition may be administered at the time of the vaccine. The immune checkpoint inhibition may also be administered after a vaccine. Immune checkpoint inhibition may occur simultaneously to an adenoviral vaccine administration. Immune checkpoint inhibition may occur 1, 2, 3, 4, 5, 6, 7, 8, 9, 10, 15, 20, 30, 40, 50, or 60 minutes after vaccination. Immune checkpoint inhibition may also occur 1, 2, 3, 4, 5, 6, 7, 8, 9, 10, 11, 12, 13, 14, 15, 16, 17, 18, 19, 20, 21, 22, 23, or 24 hours post vaccination. In some cases, immune inhibition may occur 1, 2, 3, 4, 5, 6, or 7 days after vaccination. Immune checkpoint inhibition may occur at any time before or after vaccination.

In another aspect, there is provided a vaccine comprising an antigen and an immune pathway checkpoint modulator. Some embodiments pertain to a method for treating a subject having a condition that would benefit from downregulation of an immune checkpoint, PD1 for example, and its natural binding partner(s) on cells of the subject.

An immune pathway checkpoint modulator may be combined with an adenoviral vaccine comprising nucleotide sequences encoding any antigen. For example, an antigen can be MUC1c, HER3, Brachyury, HER2NEU, CEA, or PSA. An immune pathway checkpoint modulator may produce a synergistic effect when combined with a vaccine. An immune pathway checkpoint modulator may also produce an additive effect when combined with a vaccine.

In particular embodiments, a checkpoint immune inhibitor may be combined with a vector comprising nucleotide sequences encoding any antigen, optionally with a chemotherapy or any other cancer care or therapy, such as VEGF inhibitors, angiogenesis inhibitors, radiation, other immune therapy, or any suitable cancer care or therapy.

Formulations

Some embodiments provide pharmaceutical compositions comprising a vaccination regime that can be administered either alone or together with a pharmaceutically acceptable carrier or excipient, by any routes, and such administration can be carried out in both single and multiple dosages. More particularly, the pharmaceutical composition can be combined with various pharmaceutically acceptable inert carriers in the form of tablets, capsules, lozenges, troches, hand candies, powders, sprays, aqueous suspensions, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. The compositions described throughout can be formulated into a pharmaceutical medicament and be used to treat a human or mammal, in need thereof, diagnosed with a disease, e.g., cancer.

For administration, viral vector stock can be combined with an appropriate buffer, physiologically acceptable carrier, excipient or the like. In certain embodiments, an appropriate number of virus vector particles (VP) are administered in an appropriate buffer, such as, sterile PBS or saline. In certain embodiment, vector compositions disclosed herein are provided in specific formulations for subcutaneously, parenterally, intravenously, intramuscularly, or even intraperitoneally administration. In certain embodiments, formulations in a solution of the active compounds as free base or pharmacologically acceptable salts may be prepared in water suitably mixed with a surfactant, such as hydroxypropylcellulose. Dispersions may also be prepared in glycerol, liquid polyethylene glycols, squalene-based emulsion, Squalene-based oil-in-water emulsions, water-in-oil emulsions, oil-in-water emulsions, nonaqueous emulsions, water-in-paraffin oil emulsion, and mixtures thereof and in oils. In other embodiments, viral vectors may be provided in specific formulations for pill form administration by swallowing or by suppository.

Illustrative pharmaceutical forms suitable for injectable use include sterile aqueous solutions or dispersions and sterile powders for the extemporaneous preparation of sterile injectable solutions or dispersions (see, e.g., U.S. Pat. No. 5,466,468). Fluid forms to the extent that easy syringability exists may be preferred. Forms that are stable under the conditions of manufacture and storage are provided in some embodiments. In various embodiments, forms are preserved against the contaminating action of microorganisms, such as bacteria, molds and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, and thimerosal. It may be suitable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution can be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see, e.g., "Remington's Pharmaceutical Sciences" 15th Edition, pages 1035-1038 and 1570-1580). Some variation in dosage may occur depending on the condition of the subject being treated.

Carriers of formulation can comprise any and all solvents, dispersion media, vehicles, coatings, diluents, antibacterial and antifungal agents, isotonic and absorption delaying agents, buffers, carrier solutions, suspensions, colloids, and the like. Except insofar as any conventional media or agent is incompatible with the active ingredient, its use in the therapeutic compositions is contemplated. Supplementary active ingredients can also be incorporated into the compositions.

In certain embodiments, the viral vectors may be administered in conjunction with one or more immunostimulants, such as an adjuvant. An immunostimulant refers to essentially any substance that enhances or potentiates an immune response (antibody and/or cell-mediated) to an antigen. One type of immunostimulant comprises an adjuvant. Many adjuvants contain a substance designed to protect the antigen from rapid catabolism, such as aluminum hydroxide or mineral oil, and a stimulator of immune responses, such as lipid A, *Bordetella pertussis* or *Mycobacterium tuberculosis* derived proteins. Certain adjuvants are commercially available as, for example, Freund's Incomplete Adjuvant and Complete Adjuvant (Difco Laboratories); Merck Adjuvant 65 (Merck and Company, Inc.) AS-2 (SmithKline Beecham); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, IFN-γ, TNFα, IL-2, IL-8, IL-12, IL-18, IL-7, IL-3, IL-4, IL-5, IL-6, IL-9, IL-10, and/or IL-13, and others, like growth factors, may also be used as adjuvants.

Within certain embodiments, the adjuvant composition can be one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient may support an immune response that includes Th1- and/or Th2-type responses. Within certain embodiments, in which a response is predominantly Th1-type, the level of Th1-type cytokines will increase to a greater extent than the level of Th2-type cytokines. The levels of these cytokines may be readily assessed using standard assays. Thus, various embodiments relate to therapies raising an immune response against a target antigen, for example MUC1, MUC1c, MUC1n, T, or CEA, using cytokines, e.g. IFN-γ, TNFα, IL-2, IL-8, IL-12, IL-18, IL-7, IL-3, IL-4, IL-5, IL-6, IL-9, IL-10, and/or IL-13 supplied concurrently with a replication defective viral vector treatment. In some embodiments, a cytokine or a nucleic acid encoding a cytokine, is administered together with a replication defective viral described herein. In some embodiments, cytokine administration is performed prior or subsequent to viral vector administration. In some embodiments, a replication defective viral vector capable of raising an immune response against a target antigen, for example MUC1, MUC1c, MUC1n, T, and/or CEA, further comprises a sequence encoding a cytokine.

Certain illustrative adjuvants for eliciting a predominantly Th1-type response include, for example, a combination of monophosphoryl lipid A, such as 3-de-O-acylated monophosphoryl lipid A, together with an aluminum salt. MPL® adjuvants are commercially available (see, e.g., U.S. Pat. Nos. 4,436,727; 4,877,611; 4,866,034 and 4,912,094). CpG-containing oligonucleotides (in which the CpG dinucleotide is unmethylated) also induce a predominantly Th1 response. (see, e.g., WO 96/02555, WO 99/33488 and U.S. Pat. Nos. 6,008,200 and 5,856,462). Immunostimulatory DNA sequences can also be used. Another adjuvant for use comprises a saponin, such as Quil A, or derivatives thereof, including QS21 and QS7 (Aquila Biopharmaceuticals Inc.), Escin; Digitonin; or *Gypsophila* or *Chenopodium quinoa* saponins. Other formulations may include more than one saponin in the adjuvant combinations, e.g., combinations of at least two of the following group comprising QS21, QS7, Quil A, β-escin, or digitonin.

In some embodiments, the compositions may be delivered by intranasal sprays, inhalation, and/or other aerosol delivery vehicles. The delivery of drugs using intranasal microparticle resins and lysophosphatidyl-glycerol compounds can be employed (see, e.g., U.S. Pat. No. 5,725,871). Likewise, illustrative transmucosal drug delivery in the form of a polytetrafluoroethylene support matrix can be employed (see, e.g., U.S. Pat. No. 5,780,045).

Liposomes, nanocapsules, microparticles, lipid particles, vesicles, and the like, can be used for the introduction of the compositions into suitable hot cells/organisms. Compositions as described herein may be formulated for delivery either encapsulated in a lipid particle, a liposome, a vesicle, a nanosphere, or a nanoparticle or the like. Alternatively, compositions as described herein can be bound, either covalently or non-covalently, to the surface of such carrier vehicles. Liposomes can be used effectively to introduce genes, various drugs, radiotherapeutic agents, enzymes, viruses, transcription factors, allosteric effectors and the like, into a variety of cultured cell lines and animals. Furthermore, the use of liposomes does not appear to be associated with autoimmune responses or unacceptable toxicity after systemic delivery. In some embodiments, liposomes are formed from phospholipids dispersed in an aqueous medium and spontaneously form multilamellar concentric bilayer vesicles (i.e. multilamellar vesicles (MLVs).

In some embodiments, pharmaceutically-acceptable nanocapsule formulations of the compositions are provided. Nanocapsules can generally entrap compounds in a stable and reproducible way. To avoid side effects due to intracellular polymeric overloading, such ultrafine particles (sized around 0.1 μm) may be designed using polymers able to be degraded in vivo.

The compositions in some embodiments comprise or are administered with a chemotherapeutic agent (e.g., a chemical compound useful in the treatment of cancer). Chemotherapeutic cancer agents that can be used in combination with the disclosed T cell include, but are not limited to, mitotic inhibitors (vinca alkaloids), such as vincristine, vinblastine, vindesine and Navelbine™ (vinorelbine, 5'-noranhydroblastine); topoisomerase I inhibitors, such as camptothecin compounds (e.g., Camptosar™ (irinotecan HCL), Hycamtin™ (topotecan HCL) and other compounds derived from camptothecin and its analogues); podophyllotoxin derivatives, such as etoposide, teniposide and mitopodozide; alkylating agents such as cisplatin, cyclophosphamide, nitrogen mustard, trimethylene thiophosphoramide, carmustine, busulfan, chlorambucil, belustine, uracil mustard, chlomaphazin, and dacarbazine; antimetabolites such as cytosine arabinoside, fluorouracil, methotrexate, mercaptopurine, azathioprime, and procarbazine; antibiotics, such as doxorubicin, bleomycin, dactinomycin, daunorubicin, mithramycin, mitomycin, mytomycin C, and daunomycin; anti-tumor antibodies; dacarbazine; azacytidine; amsacrine; melphalan; ifosfamide; and mitoxantrone.

Compositions disclosed herein can be administered in combination with other anti-tumor agents, including cytotoxic/antineoplastic agents and anti-angiogenic agents. Cytotoxic/anti-neoplastic agents can be defined as agents who attack and kill cancer cells. Some cytotoxic/anti-neoplastic agents can be alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents can be antimetabolites for tumor cells, e.g., cytosine arabinoside, fluorouracil, methotrexate, mercaptopuirine, azathioprime, and procarbazine. Other cytotoxic/anti-neoplastic agents can be antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents can be mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents can also be used. Suitable anti-angiogenic agents for use in the disclosed methods and compositions include anti-VEGF antibodies, including humanized and chimeric antibodies, anti-VEGF aptamers and antisense oligonucleotides. Other inhibitors of angiogenesis include angiostatin, endostatin, interferons, interleukin 1 (including α and β) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Methods of Preparation

In some embodiments, compositions and methods make use of human cytolytic T-cells (CTLs), such as those that recognize MUC1, T, or CEAs epitopes which bind to selected MHC molecules, e.g. HLA-A2, A3, and A24. Individuals expressing MHC molecules of certain serotypes, e.g. HLA-A2, A3, and A24 may be selected for therapy using the methods and compositions as described herein. For example, individuals expressing MHC molecules of certain serotypes, e.g. HLA-A2, A3, and A24, may be selected for a therapy including raising an immune response against MUC1, T, or CEAs, using the methods and compositions described herein.

In various embodiments, these T-cells can be generated by in vitro cultures using antigen-presenting cells pulsed with the epitope of interest to stimulate peripheral blood mononuclear cells. In addition, T-cell lines can also be generated after stimulation with MUC1, T, or CEAs latex beads, MUC1, T, or CEAs protein-pulsed plastic adherent peripheral blood mononuclear cells, or DCs sensitized with MUC1, T, or CEAs RNA. T-cells can also be generated from patients immunized with a vaccine vector encoding MUC1, T, or CEAs immunogen. HLA A2-presented peptides from MUC1, T, or CEAs can further be found in primary gastrointestinal tumors.

Some embodiments relate to an HLA A2 restricted epitope of MUC1, T, or CEAs, CAP-1, a nine amino acid sequence (YLSGANLNL; SEQ. ID. NO.:4), with ability to stimulate CTLs from cancer patients immunized with vaccine-MUC1, T, or CEAs. Cap-1(6D) (YLSGADLNL; SEQ. ID. NO.:10) is a peptide analog of CAP-1. Its sequence includes a heteroclitic (nonanchor position) mutation, resulting in an amino acid change from Asn to Asp, enhancing recognition by the T-cell receptor. The Asn to Asp mutation appears to not cause any change in the binding of the peptide to HLA A2. Compared with the non-mutated CAP-1 epitope, Cap-1(6D) can enhance the sensitization of CTLs by 100 to 1,000 times. CTL lines can be elicited from peripheral blood mononuclear cells of healthy volunteers by in vitro sensitization to the Cap-1(6D) peptide, but not significantly to the CAP-1 peptide. These cell lines can lyse human tumor cells expressing endogenous CEA. Thus, polypeptide sequences comprising CAP-1 or CAP-1(6D), nucleic acid sequences encoding such sequences, an adenovirus vectors; for example replication defective adenovirus vectors, comprising such nucleic acid sequences are provided in some embodiments.

Methods of Treatment

The adenovirus vectors can be used in a number of vaccine settings for generating an immune response against one or more target antigens as described herein. Some embodiments provide methods of generating an immune response against any target antigen, such as those described elsewhere herein. The adenovirus vectors are of particular importance because of the unexpected finding that they can be used to generate immune responses in subjects who have preexisting immunity to Ad and can be used in vaccination regimens that include multiple rounds of immunization using the adenovirus vectors, regimens not possible using previous generation adenovirus vectors.

Generally, generating an immune response comprises an induction of a humoral response and/or a cell-mediated response. It may desirable to increase an immune response against a target antigen of interest. Generating an immune response may involve a decrease in the activity and/or number of certain cells of the immune system or a decrease in the level and/or activity of certain cytokines or other effector molecules. Any suitable methods for detecting alterations in an immune response (e.g., cell numbers, cytokine expression, cell activity) can be used in some embodiments. Illustrative methods useful in this context include intracellular cytokine staining (ICS), ELISpot, proliferation assays, cytotoxic T-cell assays including chromium release or equivalent assays, and gene expression analysis using any number of polymerase chain reaction (PCR) or RT-PCR based assays.

Generating an immune response can comprise an increase in target antigen-specific CTL activity of between 1.5 and 5 fold in a subject administered the adenovirus vectors as described herein as compared to a control. In another embodiment, generating an immune response comprises an increase in target-specific CTL activity of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold in a subject administered the adenovirus vectors as compared to a control.

Generating an immune response can comprise an increase in target antigen-specific HTL activity, such as proliferation of helper T-cells, of between 1.5 and 5 fold in a subject administered the adenovirus vectors that comprise nucleic acid encoding the target antigen as compared to an appropriate control. In another embodiment, generating an immune response comprises an increase in target-specific HTL activity of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold as compared to a control. In this context, HTL activity may comprise an increase as described above, or decrease, in production of a particular cytokine, such as interferon-γ (IFN-γ), interleukin-1 (IL-1), IL-2, IL-3, IL-6, IL-7, IL-12, IL-15, tumor necrosis factor-α (TNF-α), granulocyte macrophage colony-stimulating factor (GM-CSF), granulocyte-colony stimulating factor (G-CSF), or other cytokine. In this regard, generating an immune response may comprise a shift from a Th2 type response to a Th1 type response or in certain embodiments a shift from a Th1 type response to a Th2 type response. In other embodiments, generating an immune response may comprise the stimulation of a predominantly Th1 or a Th2 type response.

Generating an immune response can comprise an increase in target-specific antibody production of between 1.5 and 5 fold in a subject administered the adenovirus vectors as compared to an appropriate control. In another embodiment, generating an immune response comprises an increase in target-specific antibody production of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold in a subject administered the adenovirus vector as compared to a control.

Thus, some embodiments provide methods for generating an immune response against a target antigen of interest comprising administering to the individual an adenovirus vector comprising: a) a replication defective adenovirus vector, wherein the adenovirus vector has a deletion in the E2b region, and b) a nucleic acid encoding the target antigen; and readministering the adenovirus vector at least once to the individual; thereby generating an immune response against the target antigen. In certain embodiments, the vector administered to the individual is not a gutted vector. In particular embodiments, the target antigen may be a wild-type protein, a fragment, a variant, or a variant fragment thereof. In some embodiments, the target antigen comprises MUC1, MUC1c, MUC1n, T, or CEA, a fragment, a variant, or a variant fragment thereof.

In a further embodiment, there is provided methods for generating an immune response against a target antigen in an individual, wherein the individual has preexisting immunity to Ad, by administering to the individual an adenovirus vector comprising: a) a replication defective adenovirus vector, wherein the adenovirus vector has a deletion in the E2b region, and b) a nucleic acid encoding the target antigen; and readministering the adenovirus vector at least once to the individual; thereby generating an immune response against the target antigen. In particular embodiments, the target antigen may be a wild-type protein, a fragment, a variant, or a variant fragment thereof. In some embodiments, the target antigen comprises MUC1, MUC1c, MUC1n, T, or CEA, a fragment, a variant, or a variant fragment thereof.

With regard to preexisting immunity to Ad, this can be determined using any suitable methods, such as antibody-based assays to test for the presence of Ad antibodies. Further, in certain embodiments, the methods include first determining that an individual has preexisting immunity to Ad then administering the E2b deleted adenovirus vectors as described herein.

One embodiment provides a method of generating an immune response against one or more target antigens in an individual comprising administering to the individual a first adenovirus vector comprising a replication defective adenovirus vector, wherein the adenovirus vector has a deletion in the E2b region, and a nucleic acid encoding at least one target antigen; administering to the individual a second adenovirus vector comprising a replication defective adenovirus vector, wherein the adenovirus vector has a deletion in the E2b region, and a nucleic acid encoding at least one target antigen, wherein the at least one target antigen of the second adenovirus vector is the same or different from the at least one target antigen of the first adenovirus vector. In particular embodiments, the target antigen may be a wild-type protein, a fragment, a variant, or a variant fragment thereof. In some embodiments, the target antigen comprises MUC1, MUC1c, MUC1n, T, or CEA, a fragment, a variant, or a variant fragment thereof.

Thus, multiple immunizations with the same E2b deleted adenovirus vector or multiple immunizations with different E2b deleted adenovirus vectors are contemplated in some embodiments. In each case, the adenovirus vectors may comprise nucleic acid sequences that encode one or more target antigens as described elsewhere herein. In certain embodiments, the methods comprise multiple immunizations with an E2b deleted adenovirus encoding one target antigen, and re-administration of the same adenovirus vector multiple times, thereby inducing an immune response against the target antigen. In some embodiments, the target antigen comprises MUC1, MUC1c, MUC1n, T, or CEA, a fragment, a variant, or a variant fragment thereof.

In a further embodiment, the methods comprise immunization with a first adenovirus vector that encodes one or more target antigens, and then administration with a second adenovirus vector that encodes one or more target antigens that may be the same or different from those antigens encoded by the first adenovirus vector. In this regard, one of the encoded target antigens may be different or all of the encoded antigens may be different, or some may be the same and some may be different. Further, in certain embodiments, the methods include administering the first adenovirus vector multiple times and administering the second adenovirus multiple times. In this regard, the methods comprise administering the first adenovirus vector 1, 2, 3, 4, 5, 6, 7, 8, 9, 10, 11, 12, 13, 14, 15, or more times and administering the second adenovirus vector 1, 2, 3, 4, 5, 6, 7, 8, 9, 10, 11, 12, 13, 14, 15, or more times. The order of administration may comprise administering the first adenovirus one or multiple times in a row followed by administering the second adenovirus vector one or multiple times in a row. In certain embodiments, the methods include alternating administration of the first and the second adenovirus vectors as one administration each, two administrations each, three administrations each, and so on. In certain embodiments, the first and the second adenovirus vectors are administered simultaneously. In other embodiments, the first and the second adenovirus vectors are administered sequentially. In some embodiments, the target antigen comprises MUC1, MUC1c, MUC1n, T, or CEA, a fragment, a variant, or a variant fragment thereof.

As would be readily understood by the skilled artisan, more than two adenovirus vectors may be used in the methods. Three, 4, 5, 6, 7, 8, 9, 10 or more different adenovirus vectors may be used in the methods as described herein. In certain embodiments, the methods comprise administering more than one E2b deleted adenovirus vector at a time. In this regard, immune responses against multiple target antigens of interest can be generated by administering multiple different adenovirus vectors simultaneously, each comprising nucleic acid sequences encoding one or more target antigens.

The adenovirus vectors can be used to generate an immune response against a cancer, such as carcinomas or sarcomas (e.g., solid tumors, lymphomas and leukemia). The adenovirus vectors can be used to generate an immune response against an infectious disease, such as an HPV infection, or a cancer, such as any CEA-expressing cancer, Brachyury-expressing cancer, MUC1-expressing cancer, HPV-associated cancer, an epithelial cancer, a neurologic cancer, melanoma, non-Hodgkin's lymphoma, Hodgkin's disease, leukemia, plasmocytomas, adenomas, gliomas, thymomas, breast cancer, prostate cancer, colorectal cancer, kidney cancer, renal cell carcinoma, uterine cancer, pancreatic cancer, esophageal cancer, lung cancer, ovarian cancer, cervical cancer, testicular cancer, gastric cancer, multiple myeloma, hepatoma, acute lymphoblastic leukemia (ALL), acute myelogenous leukemia (AML), chronic myelogenous leukemia (CML), and chronic lymphocytic leukemia (CLL), gastrointestinal cancer, or other cancers.

Methods are also provided for treating or ameliorating the symptoms of any of the infectious diseases or cancers as described herein. The methods of treatment comprise administering the adenovirus vectors one or more times to individuals suffering from or at risk from suffering from an infectious disease or cancer as described herein. As such, some embodiments provide methods for vaccinating against infectious diseases or cancers in individuals who are at risk of developing such a disease. Individuals at risk may be individuals who may be exposed to an infectious agent at some time or have been previously exposed but do not yet have symptoms of infection or individuals having a genetic predisposition to developing a cancer or being particularly susceptible to an infectious agent. Individuals suffering from an infectious disease or cancer described herein may be determined to express and/or present a target antigen, which may be use to guide the therapies herein. For example, an example can be found to express and/or present a target antigen and an adenovirus vector encoding the target antigen, a variant, a fragment or a variant fragment thereof may be administered subsequently.

Some embodiments contemplate the use of adenovirus vectors for the in vivo delivery of nucleic acids encoding a target antigen, or a fragment, a variant, or a variant fragment thereof. Once injected into a subject, the nucleic acid sequence is expressed resulting in an immune response against the antigen encoded by the sequence. The adenovirus vector vaccine can be administered in an "effective amount", that is, an amount of adenovirus vector that is effective in a selected route or routes of administration to elicit an immune response as described elsewhere herein. An effective amount can induce an immune response effective to facilitate protection or treatment of the host against the target infectious agent or cancer. The amount of vector in each vaccine dose is selected as an amount which induces an immune, immunoprotective or other immunotherapeutic response without significant adverse effects generally associated with typical vaccines. Once vaccinated, subjects may be monitored to determine the efficacy of the vaccine treatment. Monitoring the efficacy of vaccination may be performed by any method known to a person of ordinary skill in the art. In some embodiments, blood or fluid samples may be assayed to detect levels of antibodies. In other embodiments, ELISpot assays may be performed to detect a cell-mediated immune response from circulating blood cells or from lymphoid tissue cells.

Routes and frequency of administration of the therapeutic compositions described herein, as well as dosage, may vary from individual to individual, and from disease to disease, and may be readily established using standard techniques. In general, the pharmaceutical compositions and vaccines may be administered by injection (e.g., intracutaneous, intramuscular, intravenous or subcutaneous), intranasally (e.g., by aspiration), in pill form (e.g., swallowing, suppository for vaginal or rectal delivery). In certain embodiments, between 1 and 10 doses may be administered over a 52 week period. In certain embodiments, 6 doses are administered, at intervals of 1 month, and further booster vaccinations may be given periodically thereafter. Alternate protocols may be appropriate for individual patients. As such, 1, 2, 3, 4, 5, 6, 7, 8, 9, 10, 11, 12, 13, 14, 15, 16, 17, 18, 19, 20, or more doses may be administered over a 1 year period or over shorter or longer periods, such as over 35, 40, 45, 50, 55, 60, 65, 70, 75, 80, 85, 90, 95 or 100 week periods. Doses may be administered at 1, 2, 3, 4, 5, or 6 week intervals or longer intervals.

A vaccine can be infused over a period of less than about 4 hours, and more preferably, over a period of less than about 3 hours. For example, the first 25-50 mg could be infused within 30 minutes, preferably even 15 min, and the remainder infused over the next 2-3 hrs. More generally, the dosage of an administered vaccine construct may be administered as one dosage every 2 or 3 weeks, repeated for a total of at least 3 dosages. Or, the construct may be administered twice per week for 4-6 weeks. The dosing schedule can optionally be repeated at other intervals and dosage may be given through various parenteral routes, with appropriate adjustment of the dose and schedule. Compositions can be administered to a patient in conjunction with (e.g., before, simultaneously, or following) any number of relevant treatment modalities.

A suitable dose is an amount of an adenovirus vector that, when administered as described above, is capable of promoting a target antigen immune response as described elsewhere herein. In certain embodiments, the immune response is at least 10-50% above the basal (i.e., untreated) level. In certain embodiments, the immune response is at least 2, 3, 4, 5, 6, 7, 8, 9, 10, 12, 15, 20, 25, 30, 35, 40, 45, 50, 55, 60, 65, 70, 75, 80, 85, 90, 100, 110, 125, 150, 200, 250, 300, 400, 500 or more over the basal level. Such response can be monitored by measuring the target antigen(s) antibodies in a patient or by vaccine-dependent generation of cytolytic effector cells capable of killing patient tumor or infected cells in vitro, or other methods known in the art for monitoring immune responses. Such vaccines should also be capable of causing an immune response that leads to an improved clinical outcome of the disease in question in vaccinated patients as compared to non-vaccinated patients. In some embodiments, the improved clinical outcome comprises treating disease, reducing the symptoms of a disease, changing the progression of a disease, or extending life.

In general, an appropriate dosage and treatment regimen provides the adenovirus vectors in an amount sufficient to provide therapeutic and/or prophylactic benefit. Such a response can be monitored by establishing an improved clinical outcome for the particular disease being treated in treated patients as compared to non-treated patients. The monitoring data can be evaluated over time. The progression of a disease over time can be altered. Such improvements in clinical outcome would be readily recognized by a treating physician. Increases in preexisting immune responses to a target protein can generally correlate with an improved clinical outcome. Such immune responses may generally be evaluated using standard proliferation, cytotoxicity or cytokine assays, which may be performed using samples obtained from a patient before and after treatment.

While one advantage is the capability to administer multiple vaccinations with the same or different adenovirus vectors, particularly in individuals with preexisting immunity to Ad, the adenoviral vaccines may also be administered as part of a prime and boost regimen. A mixed modality priming and booster inoculation scheme may result in an enhanced immune response. Thus, one aspect is a method of priming a subject with a plasmid vaccine, such as a plasmid vector comprising a target antigen of interest, by administering the plasmid vaccine at least one time, allowing a predetermined length of time to pass, and then boosting by administering the adenovirus vector. Multiple primings, e.g., 1-4, may be employed, although more may be used. The length of time between priming and boost may typically vary from about four months to a year, but other time frames may be used. In certain embodiments, subjects may be primed 1, 2, 3, 4, 5, 6, 7, 8, 9, 10, or more times with plasmid vaccines, and then boosted 4 months later with the adenovirus vector.

Any of the compositions provided herein may be administered to an individual. "Individual" may be used interchangeably with "subject" or "patient." An individual may be a mammal, for example a human or animal such as a non-human primate, a rodent, a rabbit, a rat, a mouse, a horse, a donkey, a goat, a cat, a dog, a cow, a pig, or a sheep. In embodiments, the individual is a human. In embodiments, the individual is a fetus, an embryo, or a child. In some cases, the compositions provided herein are administered to a cell ex vivo. In some cases, the compositions provided herein are administered to an individual as a method of treating a disease or disorder. In some embodiments, the individual has a genetic disease. In some cases, the individual is at risk of having the disease, such as any of the diseases described herein. In some embodiments, the individual is at increased risk of having a disease or disorder caused by insufficient amount of a protein or insufficient activity of a protein. If an individual is "at an increased risk" of having a disease or disorder, the method involves preventative or prophylactic treatment. For example, an individual can be at an increased risk of having such a disease or disorder because of family history of the disease. Typically, individuals at an increased risk of having such a disease or disorder benefit from prophylactic treatment (e.g., by preventing or delaying the onset or progression of the disease or disorder).

In some cases, a subject does not have a disease. In some cases, the treatment is administered before onset of a disease. A subject may have undetected disease. A subject may have a low disease burden. A subject may also have a high disease burden. In certain cases, a subject may be administered a treatment as described herein according to a grading scale. A grading scale can be a Gleason classification. A Gleason classification reflects how different tumor tissue is from normal prostate tissue. It uses a scale from 1 to 5. A physician gives a cancer a number based on the patterns and growth of the cancer cells. The lower the number, the more normal the cancer cells look and the lower the grade. The higher the number, the less normal the cancer cells look and the higher the grade. In certain cases, a treatment may be administered to a patient with a low Gleason score. Particularly, a patient with a Gleason score of 3 or below may be administered a treatment as described herein.

Various embodiments relate to compositions and methods for raising an immune response against one or more MUC1, MUC1c, MUC1n, T, or CEA antigens in selected patient populations. Accordingly, methods and compositions may target patients with a cancer including but not limited to carcinomas or sarcomas such as neurologic cancers, melanoma, non-Hodgkin's lymphoma, Hodgkin's disease, leukemia, plasmocytomas, adenomas, gliomas, thymomas, breast cancer, gastrointestinal cancer, prostate cancer, colorectal cancer, kidney cancer, renal cell carcinoma, uterine cancer, pancreatic cancer, esophageal cancer, lung cancer, ovarian cancer, cervical cancer, testicular cancer, gastric cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers can be targeted for therapy. In some cases, the targeted patient population may be limited to individuals having colorectal adenocarcinoma, metastatic colorectal cancer, advanced MUC1, MUC1c, MUC1n, T, or CEA expressing colorectal cancer, head and neck cancer, liver cancer, breast cancer, lung cancer, bladder cancer, or pancreas cancer. A histologically confirmed diagnosis of a selected cancer, for example colorectal adenocarcinoma, may be used. A particular disease stage or progression may be selected, for example, patients with one or more of a metastatic, recurrent, stage III, or stage IV cancer may be selected for therapy with the methods and compositions. In some embodiments, patients may be required to have received and, optionally, progressed through other therapies including but not limited to fluoropyrimidine, irinotecan, oxaliplatin, bevacizumab, cetuximab, or panitumumab containing therapies. In some cases, individual's refusal to accept such therapies may allow the patient to be included in a therapy eligible pool with methods and compositions. In some embodiments, individuals to receive therapy using the methods and compositions may be required to have an estimated life expectancy of at least, 1, 2, 3, 4, 5, 6, 7, 8, 9, 10, 11, 12, 14, 15, 18, 21, or 24 months. The patient pool to receive a therapy using the methods and compositions may be limited by age. For example, individuals who are older than 2, 3, 4, 5, 6, 7, 8, 9, 10, 11, 12, 13, 14, 15, 16, 17, 18, 19, 20, 21, 25, 30, 35, 40, 50, 60, or more years old can be eligible for therapy with methods and compositions. For another example, individuals who are younger than 75, 70, 65, 60, 55, 50, 40, 35, 30, 25, 20, or fewer years old can be eligible for therapy with methods and compositions.

In some embodiments, patients receiving therapy using the methods and compositions are limited to individuals with adequate hematologic function, for example with one or more of a WBC count of at least 1000, 1500, 2000, 2500, 3000, 3500, 4000, 4500, 5000 or more per microliter, a hemoglobin level of at least 5, 6, 7, 8, 9, 10, 11, 12, 13, 14 or higher g/dL, a platelet count of at least 50,000; 60,000; 70,000; 75,000; 90,000; 100,000; 110,000; 120,000; 130,000; 140,000; 150,000 or more per microliter; with a PT-INR value of less than or equal to 0.8, 1.0, 1.2, 1.3, 1.4, 1.5, 1.6, 1.8, 2.0, 2.5, 3.0, or higher, a PTT value of less than or equal to 1.2, 1.4, 1.5, 1.6, 1.8, 2.0×ULN or more. In various embodiments, hematologic function indicator limits are chosen differently for individuals in different gender and age groups, for example 0-5, 5-10, 10-15, 15-18, 18-21, 21-30, 30-40, 40-50, 50-60, 60-70, 70-80 or older than 80.

In some embodiments, patients receiving therapy using the methods and compositions are limited to individuals with adequate renal and/or hepatic function, for example with one or more of a serum creatinine level of less than or equal to 0.8, 0.9, 1.0, 1.1, 1.2, 1.3, 1.4, 1.5, 1.6, 1.7, 1.8, 1.9, 2.0, 2.1, 2.2 mg/dL or more, a bilirubin level of 0.8, 0.9, 1.0, 1.1, 1.2, 1.3, 1.4, 1.5, 1.6, 1.7, 1.8, 1.9, 2.0, 2.1, 2.2 mg/dL or more, while allowing a higher limit for Gilbert's syndrome, for example, less than or equal to 1.5, 1.6, 1.8, 1.9, 2.0, 2.1, 2.2, 2.3, or 2.4 mg/dL, an ALT and AST value of less than or equal to less than or equal to 1.5, 2.0, 2.5, 3.0× upper limit of normal (ULN) or more. In various embodiments, renal or hepatic function indicator limits are chosen differently for individuals in different gender and age groups, for example 0-5, 5-10, 10-15, 15-18, 18-21, 21-30, 30-40, 40-50, 50-60, 60-70, 70-80 or older than 80.

In some embodiments, the K-ras mutation status of individuals who are candidates for a therapy using the methods and compositions as described herein can be determined. Individuals with a preselected K-ras mutational status can be included in an eligible patient pool for therapies using the methods and compositions as described herein.

In various embodiments, patients receiving therapy using the methods and compositions as described herein are limited to individuals without concurrent cytotoxic chemotherapy or radiation therapy, a history of, or current, brain metastases, a history of autoimmune disease, such as but not restricted to, inflammatory bowel disease, systemic lupus erythematosus, ankylosing spondylitis, scleroderma, multiple sclerosis, thyroid disease and vitiligo, serious intercurrent chronic or acute illness, such as cardiac disease (NYHA class III or IV), or hepatic disease, a medical or psychological impediment to probable compliance with the protocol, concurrent (or within the last 5 years) second malignancy other than non-melanoma skin cancer, cervical carcinoma in situ, controlled superficial bladder cancer, or other carcinoma in situ that has been treated, an active acute or chronic infection including: a urinary tract infection, HIV (e.g. as determined by ELISA and confirmed by Western Blot), and chronic hepatitis, or concurrent steroid therapy (or other immuno-suppressives, such as azathioprine or cyclosporin A). In some cases, patients with at least 3, 4, 5, 6, 7, 8, 9, or 10 weeks of discontinuation of any steroid therapy (except that used as pre-medication for chemotherapy or contrast-enhanced studies) may be included in a pool of eligible individuals for therapy using the methods and compositions as described herein.

In some embodiments, patients receiving therapy using the methods and compositions as described herein include individuals with thyroid disease and vitiligo.

In various embodiments, samples, for example serum or urine samples, from the individuals or candidate individuals for a therapy using the methods and compositions as described herein may be collected. Samples may be collected before, during, and/or after the therapy for example, within 2, 4, 6, 8, 10 weeks prior to the start of the therapy, within 1 week, 10 day, 2 weeks, 3 weeks, 4 weeks, 6 weeks, 8 weeks, or 12 weeks from the start of the therapy, within 2, 4, 6, 8, 10 weeks prior to the start of the therapy, within 1 week, 10 day, 2 weeks, 3 weeks, 4 weeks, 6 weeks, 8 weeks, 9 weeks, or 12 weeks from the start of the therapy, in 1 week, 10 day, 2 weeks, 3 weeks, 4 weeks, 6 weeks, 8 weeks, 9 weeks, or 12 weeks intervals during the therapy, in 1 month, 3 month, 6 month, 1 year, 2 year intervals after the therapy, within 1 month, 3 months, 6 months, 1 year, 2 years, or longer after the therapy, for a duration of 6 months, 1, 2, 3, 4, 5, 6, 7, 8, 9, 10 years or longer. The samples may be tested for any of the hematologic, renal, or hepatic function indicators described herein as well as suitable others known in the art, for example a ß-HCG for women with childbearing potential. In that regard, hematologic and biochemical tests, including cell blood counts with differential, PT, INR and PTT, tests measuring Na, K, Cl, $CO_2$, BUN, creatinine, Ca, total protein, albumin, total bilirubin, alkaline phosphatase, AST, ALT and glucose may be used in some embodiments. In some embodiments, the presence or the amount of HIV antibody, Hepatitis BsAg, or Hepatitis C antibody are determined in a sample from individuals or candidate individuals for a therapy using the methods and compositions as described herein. Biological markers, such as antibodies to MUC1, MUC1c, MUC1n, T, or CEA or the neutralizing antibodies to Ad5 vector can be tested in a sample, such as serum, from individuals or candidate individuals for a therapy using the methods and compositions as described herein. In some cases, one or more samples, such as a blood sample can be collected and archived from an individuals or candidate individuals for a therapy using the methods and compositions as described herein. Collected samples can be assayed for immunologic evaluation. Individuals or candidate individuals for a therapy using the methods and compositions as described herein can be evaluated in imaging studies, for example using CT scans or MRI of the chest, abdomen, or pelvis. Imaging studies can be performed before, during, or after therapy using the methods and compositions as described herein, during, and/or after the therapy, for example, within 2, 4, 6, 8, 10 weeks prior to the start of the therapy, within 1 week, 10 day, 2 weeks, 3 weeks, 4 weeks, 6 weeks, 8 weeks, or 12 weeks from the start of the therapy, within 2, 4, 6, 8, 10 weeks prior to the start of the therapy, within 1 week, 10 day, 2 weeks, 3 weeks, 4 weeks, 6 weeks, 8 weeks, 9 weeks, or 12 weeks from the start of the therapy, in 1 week, 10 day, 2 week, 3 week, 4 week, 6 week, 8 week, 9 week, or 12 week intervals during the therapy, in 1 month, 3 month, 6 month, 1 year, 2 year intervals after the therapy, within 1 month, 3 months, 6 months, 1 year, 2 years, or longer after the therapy, for a duration of 6 months, 1, 2, 3, 4, 5, 6, 7, 8, 9, 10 years or longer.

Methods of Treating HPV-Associated Diseases

In certain embodiments, there is provided a method of enhancing an immune response in an individual in need thereof, the method comprising: administering to the individual a first pharmaceutical composition comprising a replication-defective adenovirus vector comprising a nucleic acid sequence encoding an HPV antigen; and administering to the individual an immune checkpoint inhibitor. In certain embodiments, the method may be further defined as treating an HPV infection or an HPV-associated disease, such as an HPV-associated cancer, including, but not limited to, head and neck squamous cell carcinoma (HNSCC), oropharyngeal and tonsillar cancer, cervical cancer, or anal cancer.

Human Papilloma Virus (HPV)-Associated HNSCC

Evidence has demonstrated that infection with high-risk HPV16 is associated with the development and progression of HPV-associated HNSCC and, more specifically, the HPV early 6 (E6) and early 7 (E7) genes contribute to cancer development. The prevalence of head and neck cancers in the United States is estimated to be about 370,000 and between 25% to 38% of these are HPV-associated HNSCC. Thus, the prevalence of HPV-associated HNSCC is estimated to range from 92,750 to 140,000 cases. A recent study on HPV-associated HNSCC estimated an incidence of about 35,000 new cases in the United States, with an expected 7,600 cancer related deaths annually despite current therapy. Thus, there remains an unmet medical need to investigate new treatment methods for this patient population. Based upon the estimated prevalence of HPV-associated HNSCC, this population qualifies for orphan product drug development by the FDA and Etubics has received orphan product designation for the development of a new immunotherapeutic vaccine (Ad5 [E1-, E2b-]-HPV-E6/E7) to treat HPV-associated HNSCC.

HIV and HPV-Associated Oropharyngeal and Tonsillar Cancer

Human papilloma virus (HPV) is responsible for as many as 100,000 cases of head and neck squamous cell carcinoma (HNSSC) worldwide per year. The majority of these are oropharyngeal and tonsillar cancers. In the United States, prevalence estimates of oropharynx HPV infection range from 9.2 to 18.6 percent. HPV type16 (HPV16) is the most prevalent HPV found in oral carcinomas and is involved in the etiology of these cancers. The incidence of tonsillar cancer in the United States has increased by 2-3% per year from 1973 to 1995. HIV-infected individuals have a 2 to 6-fold increase in risk of developing oropharyngeal and tonsillar cancers. Despite significant advances in the therapy of AIDS, this pandemic continues to be responsible for devastating morbidity and mortality throughout the world, especially in regions with limited access to antiretroviral medications. HPV infection and disease has not dramatically declined since the introduction of potent combination therapy to control HIV and highly active antiretroviral therapy appears to have little beneficial effect on HPV-associated oral disease. Thus, it remains imperative to investigate new vaccines that can be applied to HIV and HIV-associated malignancies.

Certain aspects provide a therapeutic strategy for HIV-associated malignancy based on the pathogenic role of HPV. The vaccine to be used is based upon a new recombinant adenovirus serotype 5 (Ad5) vector platform (Ad5 [E1-, E2b-]) described below. This recombinant vector allows for the insertion of specific disease associated antigen genes that will be expressed after direct transfection of antigen presenting cells. Importantly, this new vaccine can be utilized in multiple homologous immunization regimens designed to stimulate potent cell mediated immune (CMI) responses against specific target antigens and has the potential to become an important immunotherapeutic agent in the battle against HIV/HPV-associated oropharyngeal and tonsillar malignancies.

Patients with HPV associated HNSCC will be administered a multi-facetted treatment, and immunotherapy with the Etubics Ad5 [E1-, E2b-]-HPV-E6/E7 vaccine will play an important role in the armamentarium of treatments against this disease.

HPV Associated Cervical Cancer

Cervical cancer is the second leading cause of cancer-related death in women. It is known that oncogenic human papillomavirus (HPV) plays a critical etiological role in anogenital cancers and at least 70% of cervical cancers are associated with type 16 (HPV-16) or 18 (HPV-18). HPV-16 and 18 are also the virus types with which the majority of vulval and vaginal pre-cancer are associated. Vulvar intra-epithelial neoplasia is a chronic premalignant disorder of the vulvar skin that is caused by high-risk types of human papillomavirus (HPV); HPV type 16 (HPV-16) is involved in more than 75% of cases. The lifetime risk of a woman acquiring any HPV infection is more than 80%. Half of women acquire cervical infection within 3 years of initiating sexual activity. About 90% of HPV infections are cleared by the immune system within 6-24 months. The prevalence of HPV infection in sexually active women is 10-20% and even higher in young women. HPV-16/18 bivalent (Cervarix) and HPV-6/11/16/18 quadrivalent (Gardasil) vaccines are highly effective in preventing vaccine-type HPV-related genital pre-cancer in women who are HPV-negative at the time of vaccination. Although these vaccines are highly effective at preventing HPV infection, there is still a population of women who are not vaccinated and become HPV infected and thus are at high risk of developing neoplasia. In a recent meta-analysis study, there was no indication that the above HPV vaccines given to women with evidence of prior vaccine-type HPV exposure can prevent premalignant lesions related to these HPV types over a 3 to 4-year time frame. It is this population of women that are believed to benefit from vaccination with this new adenoviral vaccine (Ad5 [E1-, E2b-]-HPV-E6/E7 vaccine) designed to prevent development of HPV associated cancer.

Dosages and Administration

Compositions and methods as described herein contemplate various dosage and administration regimens during therapy. Patients may receive one or more replication defective adenovirus or adenovirus vector, for example Ad5 [E1-, E2B-]-CEA(6D), Ad5 [E1-, E2b-]-MUC1, Ad5 [E1-, E2b-]-MUC1c, Ad5 [E1-, E2b-]-MUC1n, Ad5 [E1-, E2b-]-T (i.e., Ad5 [E1-, E2b-]-Brachyury) that is capable of raising an immune response in an individual against a target antigen described herein. In various embodiments, the replication defective adenovirus is administered at a dose that suitable for effecting such immune response. In some cases, the replication defective adenovirus is administered at a dose that is greater than or equal to $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $1.5\times10^{12}$, $2\times10^{12}$, $3\times10^{12}$, or more virus particles (VP) per immunization. In some cases, the replication defective adenovirus is administered at a dose that is less than or equal to $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10$, $9\times10^{11}$, $1\times10^{12}$, $1.5\times10^{12}$, $2\times10^{12}$, $3\times10^{12}$, or more virus particles per immunization. In various embodiments, a desired dose described herein is administered in a suitable volume of formulation buffer, for example a volume of about 0.1-10 mL, 0.2-8 mL, 0.3-7 mL, 0.4-6 mL, 0.5-5 mL, 0.6-4 mL, 0.7-3 mL, 0.8-2 mL, 0.9-1.5 mL, 0.95-1.2 mL, or 1.0-1.1 mL. Those of skill in the art appreciate that the volume may fall within any range bounded by any of these values (e.g., about 0.5 mL to about 1.1 mL). Administration of virus particles can be through a variety of suitable paths for delivery, for example it can be by injection (e.g., intradermally, intracutaneously, intramuscularly, intravenously or subcutaneously), intranasally (e.g., by aspiration), in pill form (e.g. swallowing, suppository for vaginal or rectal delivery. In some embodiments, a subcutaneous delivery may be preferred and can offer greater access to dendritic cells.

Administration of virus particles to an individual may be repeated. Repeated deliveries of virus particles may follow a schedule or alternatively, may be performed on an as needed basis. For example, an individual's immunity against a target antigen, for example MUC1, T and/or CEA, may be tested and replenished as necessary with additional deliveries. In some embodiments, schedules for delivery include administrations of virus particles at regular intervals. Joint delivery regimens may be designed comprising one or more of a period with a schedule and/or a period of need based administration assessed prior to administration. For example, a therapy regimen may include an administration, such as subcutaneous administration once every three weeks then another immunotherapy treatment every three months until removed from therapy for any reason including death. Another example regimen comprises three administrations every three weeks then another set of three immunotherapy treatments every three months. Another example regimen comprises a first period with a first number of administrations at a first frequency, a second period with a second number of administrations at a second frequency, a third period with a third number of administrations at a third frequency, etc., and optionally one or more periods with undetermined number of administrations on an as needed basis. The number of administrations in each period can be independently selected and can for example be 1, 2, 3, 4, 5, 6, 7, 8, 9, 10, 11, 12, 13, 14, 15, 16, 17, 18, 19, 20 or more. The frequency of the administration in each period can also be independently selected, can for example be about every day, every other day, every third day, twice a week, once a week, once every other week, every three weeks, every month, every six weeks, every other month, every third month, every fourth month, every fifth month, every sixth month, once a year etc. The therapy can take a total period of up to 1, 2, 3, 4, 5, 6, 7, 8, 9, 10, 11, 12, 13, 14, 15, 16, 17, 18, 19, 20, 21, 22, 23, 24, 30, 36 months or more. The scheduled interval between immunizations may be modified so that the interval between immunizations is revised by up to a fifth, a fourth, a third, or half of the interval. For example, for a 3-week interval schedule, an immunization may be repeated between 20 and 28 days (3 weeks–1 day to 3 weeks+7 days). For the first 3 immunizations, if the second and/or third immunization is delayed, the subsequent immunizations may be shifted allowing a minimum amount of buffer between immunizations. For example, for a three week interval schedule, if an immunization is delayed, the subsequent immunization may be scheduled to occur no earlier than 17, 18, 19, or 20 days after the previous immunization.

Compositions, such as Ad Ad5 [E1-, E2B-]-CEA(6D), Ad5 [E1-, E2B-]-MUC1, Ad5 [E1-, E2B-]-MUC1c, Ad5 [E1-, E2B-]-MUC1n, Ad5 [E1-, E2B-]-T virus particles, can be provided in various states, for example, at room temperature, on ice, or frozen. Compositions may be provided in a container of a suitable size, for example a vial of 2 mL vial. In one embodiment, a 2-ml vial with 1.0 mL of extractable vaccine contains $5\times10^{11}$ total virus particles/mL. Storage conditions including temperature and humidity may vary. For example, compositions for use in therapy may be stored at room temperature, 4° C., −20° C., or lower.

In various embodiments, general evaluations are performed on the individuals receiving treatment according to the methods and compositions as described herein. One or more of any tests may be performed as needed or in a scheduled basis, such as on weeks 0, 3, 6 etc. A different set of tests may be performed concurrent with immunization vs. at time points without immunization.

General evaluations may include one or more of medical history, ECOG Performance Score, Karnofsky performance status, and complete physical examination with weight by the attending physician. Any other treatments, medications, biologics, or blood products that the patient is receiving or has received since the last visit may be recorded. Patients may be followed at the clinic for a suitable period, for example approximately 30 minutes, following receipt of vaccine to monitor for any adverse reactions. Local and systemic reactogenicity after each dose of vaccine will may be assessed daily for a selected time, for example for 3 days (on the day of immunization and 2 days thereafter). Diary cards may be used to report symptoms and a ruler may be used to measure local reactogenicity. Immunization injection sites may be assessed. CT scans or MRI of the chest, abdomen, and pelvis may be performed.

In various embodiments, hematological and biochemical evaluations are performed on the individuals receiving treatment according to the methods and compositions as described herein. One or more of any tests may be performed as needed or in a scheduled basis, such as on weeks 0, 3, 6 etc. A different set of tests may be performed concurrent with immunization vs. at time points without immunization. Hematological and biochemical evaluations may include one or more of blood test for chemistry and hematology, CBC with differential, Na, K, Cl, $CO_2$, BUN, creatinine, Ca, total protein, albumin, total bilirubin, alkaline phosphatase, AST, ALT, glucose, and ANA In various embodiments, biological markers are evaluated on individuals receiving treatment according to the methods and compositions as described herein. One or more of any tests may be performed as needed or in a scheduled basis, such as on weeks 0, 3, 6 etc. A different set of tests may be performed concurrent with immunization vs. at time points without immunization.

Biological marker evaluations may include one or more of measuring antibodies to MUC1, MUC1c, MUC1n, CEA or the Ad5 vector, from a serum sample of adequate volume, for example about 5 ml Biomarkers (e.g., CEA or CA15-3) may be reviewed if determined and available.

In various embodiments, an immunological assessment is performed on individuals receiving treatment according to the methods and compositions as described herein. One or more of any tests may be performed as needed or in a scheduled basis, such as on weeks 0, 3, 6 etc. A different set of tests may be performed concurrent with immunization vs. at time points without immunization.

Peripheral blood, for example about 90 mL may be drawn prior to each immunization and at a time after at least some of the immunizations, to determine whether there is an effect on the immune response at specific time points during the study and/or after a specific number of immunizations. Immunological assessment may include one or more of assaying peripheral blood mononuclear cells (PBMC) for T-cell responses to MUC1, MUC1c, MUC1n, T or CEA using ELISpot, proliferation assays, multi-parameter flow cytometric analysis, and cytoxicity assays. Serum from each blood draw may be archived and sent and determined.

In various embodiments, a tumor assessment is performed on individuals receiving treatment according to the methods and compositions as described herein. One or more of any tests may be performed as needed or in a scheduled basis, such as prior to treatment, on weeks 0, 3, 6 etc. A different set of tests may be performed concurrent with immunization vs. at time points without immunization. Tumor assessment may include one or more of CT or MRI scans of chest, abdomen, or pelvis performed prior to treatment, at a time after at least some of the immunizations and at approximately every three months following the completion of a selected number, for example 2, 3, or 4, of first treatments and for example until removal from treatment.

Immune responses against a target antigen described herein, such as CEA, may be evaluated from a sample, such as a peripheral blood sample of an individual using one or more suitable tests for immune response, such as ELISpot, cytokine flow cytometry, or antibody response. A positive immune response can be determined by measuring a T-cell response. A T-cell response can be considered positive if the mean number of spots adjusted for background in six wells with antigen exceeds the number of spots in six control wells by 10 and the difference between single values of the six wells containing antigen and the six control wells is statistically significant at a level of $p \leq 0.05$ using the Student's t-test. Immunogenicity assays may occur prior to each immunization and at scheduled time points during the period of the treatment. For example, a time point for an immunogenicity assay at around week 1, 2, 3, 4, 5, 6, 7, 8, 9, 10, 11, 12, 13, 14, 15, 18, 20, 24, 30, 36, or 48 of a treatment may be scheduled even without a scheduled immunization at this time. In some cases, an individual may be considered evaluable for immune response if they receive at least a minimum number of immunizations, for example 1, 2, 3, 4, 5, 6, 7, 8, 9, or more immunizations.

In some embodiments, disease progression or clinical response determination is made according to the RECIST 1.1 criteria among patients with measurable/evaluable disease. In some embodiments, therapies using the methods and compositions as described herein affect a Complete Response (CR; disappearance of all target lesions for target lesions or disappearance of all non-target lesions and normalization of tumor marker level for non-target lesions) in an individual receiving the therapy. In some embodiments, therapies using the methods and compositions affect a Partial Response (PR; at least a 30% decrease in the sum of the LD of target lesions, taking as reference the baseline sum LD for target lesions) in an individual receiving the therapy.

In some embodiments, therapies using the methods and compositions affect a Stable Disease (SD; neither sufficient shrinkage to qualify for PR nor sufficient increase to qualify for PD, taking as reference the smallest sum LD since the treatment started for target lesions) in an individual receiving the therapy. In some embodiments, therapies using the methods and compositions as described herein affect an Incomplete Response/Stable Disease (SD; persistence of one or more non-target lesion(s) or/and maintenance of tumor marker level above the normal limits for non-target lesions) in an individual receiving the therapy. In some embodiments, therapies using the methods and compositions as described herein affect a Progressive Disease (PD; at least a 20% increase in the sum of the LD of target lesions, taking as reference the smallest sum LD recorded since the treatment started or the appearance of one or more new lesions for target lesions or persistence of one or more non-target lesion(s) or/and maintenance of tumor marker level above the normal limits for non-target lesions) in an individual receiving the therapy.

Additional Compositions and Methods

Some embodiments provide combination multi-targeted vaccines, immunotherapies and methods for enhanced therapeutic response to complex diseases such as infectious diseases and cancers. Certain embodiments provide compositions, methods and kits for generating an immune response in an individual to fight infectious diseases and cancer. Certain embodiments provide compositions, methods and kits for generating an immune response against a target antigen or cells expressing or presenting a target antigen or a target antigen signature comprising at least one target antigen.

It has been discovered that Ad5 [E1-, E2b-] vectors are not only are safer than, but appear to be superior to Ad5 [E1-] vectors in regard to induction of antigen specific immune responses, making them much better suitable as a platform to deliver MUC1, T and/or CEA vaccines that can result in a clinical response. In other cases, immune induction may take months. Ad5 [E1-, E2b-] vectors not only are safer than, but appear to be superior to Ad5 [E1-] vectors in regard to induction of antigen specific immune responses, making them much better suitable as a platform to deliver MUC1c, T and/or CEA vaccines that can result in a clinical response.

Certain embodiments use the new Ad5 [E1-, E2b-] vector system to deliver a long sought-after need for a develop a therapeutic vaccine against MUC1, T and/or CEA, overcome barriers found with other Ad5 systems and permit the immunization of people who have previously been exposed to Ad5.

To address the low immunogenicity of self-tumor antigens, a variety of advanced, multi-component vaccination strategies including co-administration of adjuvants and immune stimulating cytokines are provided. Some embodiments relate to recombinant viral vectors that provide innate pro-inflammatory signals, while simultaneously engineered to express the antigen of interest. Of particular interest are adenovirus serotype-5 (Ad5)-based immunotherapeutics that have been repeatedly used in humans to induce robust T-cell-mediated immune (CMI) responses, all while maintaining an extensive safety profile.

In one aspect, a composition is provided comprising a recombinant replication defective viral vector comprising a sequence encoding a MUC1-C antigen, wherein the sequence encoding the MUC1-C antigen has at least 80% sequence identity to SEQ ID NO:5 or SEQ ID NO:6. In some embodiments, the MUC1-C antigen comprises a sequence with at least 80% sequence identity to SEQ ID NO:9.

In one aspect, a composition is provided comprising a recombinant replication defective viral vector comprising a sequence encoding a Brachyury antigen, wherein sequence encoding the Brachyury antigen has at least 80% sequence identity to SEQ ID NO:7 or SEQ ID NO:8. In some embodiments, an immune response against the antigen or cells expressing the antigen is induced in a human administered the viral vector.

In one aspect, a composition is provided comprising a recombinant replication defective viral vector comprising a sequence encoding at least two antigens selected from the group consisting of a MUC1-C antigen, a Brachyury antigen, and a CEA antigen. In some embodiments, an immune response against the at least two antigens or cells expressing the at least two antigens is induced in a human administered the viral vector.

In some embodiments, the immune response comprises generation of an antibody to the antigen. In some embodiments, the immune response comprises cell mediated immunity (CMI). In some embodiments, the sequence encoding the MUC1-C antigen has at least 80% sequence identity to SEQ ID NO:5 or SEQ ID NO:6. In some embodiments, the sequence encoding the Brachyury antigen has at least 80% sequence identity to SEQ ID NO:7 or SEQ ID NO:8. In some embodiments, the sequence encoding the CEA antigen has at least 80% sequence identity to SEQ ID NO:1, SEQ ID NO:2, or SEQ ID NO:3. In some embodiments, the antigen comprises a modification of 25, 15, 10, 5, or less amino acids. In some embodiments, the antigen comprises a modification in 1 amino acid. In some embodiments, the recombinant viral vector is selected from the group consisting of: retrovirus, lentivirus, cytomegalovirus, Sendai virus, HPV virus, and adenovirus. In some embodiments, the recombinant viral vector comprises a replication defective adenovirus vector. In some embodiments, the recombinant viral vector comprises a replication defective adenovirus 5 vector. In some embodiments, the replication defective adenovirus vector comprises a deletion in an E2b gene region. In some embodiments, the replication defective adenovirus vector comprises a deletion in an E1 gene region. In some embodiments, the replication defective adenovirus vector comprises a deletion in an E3 gene region. In some embodiments, the replication defective adenovirus vector comprises a deletion in an E4 gene region. In some embodiments, the recombinant viral vector effects overexpression of the antigen in transfected cells. In some embodiments, the recombinant viral induces a specific immune response against cells expressing the antigen in a human that is at least 2, 3, 4, 5, 6, 7, 8, 9, 10, 15, 20, or 25 fold over basal. In some embodiments, the human has an inverse Ad5 neutralizing antibody titer of greater than 50, 75, 100, 125, 150, 160, 175, or 200. In some embodiments, the human has an inverse Ad5 neutralizing antibody titer of greater than 250, 500, 750, 1000, 1500, 2000, 2500, 3000, 3500, 4000, 4500, or 4767. In some embodiments, the immune response is measured as antigen specific antibody response.

In some embodiments, the immune response is measured as antigen specific cell-mediated immunity (CMI). In some embodiments, the immune response is measured as antigen specific IFN-γ secretion. In some embodiments, the immune response is measured as antigen specific IL-2 secretion. In some embodiments, the immune response against the antigen is measured by ELISpot assay. In some embodiments, the antigen specific CMI is greater than 25, 50, 75, 100, 150, 200, 250, or 300 IFN-γ spot forming cells (SFC) per $10^6$ peripheral blood mononuclear cells (PBMC). In some embodiments, the immune response is measured by T-cell lysis of CAP-1 pulsed antigen-presenting cells, allogeneic antigen expressing cells from a tumor cell line or from an autologous tumor. In some embodiments, the composition further comprises an immunogenic component. In some embodiments, the immunogenic component comprises a cytokine selected from the group of IFN-γ, TNFα IL-2, IL-8, IL-12, IL-18, IL-7, IL-3, IL-4, IL-5, IL-6, IL-9, IL-10, and IL-13. In some embodiments, the immunogenic component is selected from the group consisting of IL-7, a nucleic acid encoding IL-7, a protein with substantial identity to IL-7, and a nucleic acid encoding a protein with substantial identity to IL-7. In some embodiments, the CEA antigen comprises a modification that comprises a substitution of aspartate at a position corresponding to position 610 in SEQ ID NO:3. In some embodiments, the composition further comprises a molecular composition comprising an immune pathway checkpoint modulator. In some embodiments, the immune pathway checkpoint modulator activates or potentiates an immune response. In some embodiments, the immune pathway checkpoint modulator inhibits an immune response inhibitor. In some embodiments, the immune pathway checkpoint inhibits an immune response. In some embodiments, the immune pathway checkpoint modulator targets an endogenous immune pathway checkpoint protein or fragment thereof selected from the group consisting of: PD1, PDL1, PDL2, CD28, CD80, CD86, CTLA4, B7RPI, ICOS, B7RPI, B7-H3, B7-H4, BTLA, HVEM, KIR, TCR, LAG3, CD137, CD137L, OX40, OX40L, CD27, CD70, CD40, CD40L, TIM3, GALS, ADORA, CD276, VTCN1, IDO1, KIR3DL1, HAVCR2, VISTA, and CD244. In some embodiments, the immune pathway checkpoint modulator targets a PD1 protein. In some embodiments, the molecular composition comprises siRNAs, antisense, small molecules, mimic, a recombinant form of a ligand, a recombinant form of a receptor, antibodies, or a combination thereof.

In one aspect, a method of selecting a human for administration of the compositions is provided comprising: determining a HLA subtype of the human; and administering the composition to the human, if the HLA subtype is determined to be one of a preselected subgroup of HLA subtypes. In some embodiments, the preselected subgroup of HLA subtypes comprises one or more of HLA-A2, HLA-A3, and HLA-A24.

In one aspect, a method of treating a human for cancer or an infectious disease is provided comprising administering the recombinant viral vector to the human.

In one aspect, a method of generating an immune response in a human to MUC1-C, Brachyury, CEA, or any combination thereof is provided comprising administering to the human the composition. In some embodiments, the administering step is repeated at least once. In some embodiments, the administering step is repeated after about 2, 3, 4, 5, or 6 weeks following a previous administering step. In some embodiments, the administering step is repeated after about 2, 3, 4, 5, or 6 months following a previous administering step. In some embodiments, the administering step is repeated twice.

In one aspect, a method of treatment is provided comprising: selecting a first phase of treatment and a second phase of treatment; during the first phase, administering to a human a total of 3 times, in about 3 week intervals, a first composition comprising a first replication defective adenovirus vector encoding a MUC1-C antigen; and during the second phase, administering to the human a total of 3 times, in about 3 month intervals, a second composition comprising a second replication defective adenovirus vector encoding an antigen that induces an immune response in a human against cells expressing the MUC1-C antigen.

In one aspect, a method of treatment is provided comprising: selecting a first phase and a second phase of treatment; during the first phase, administering to a human a total of 3 times, in about 3 week intervals, a first composition comprising a first replication defective adenovirus vector encoding a Brachyury antigen; and during the second phase, administering to the human a total of 3 times, in about 3 month intervals, a second composition comprising a second replication defective adenovirus vector encoding an antigen that induces an immune response in a human against cells expressing the Brachyury antigen.

In one aspect, a method of treatment is provided comprising: selecting a first phase of treatment and a second phase of treatment; during the first phase, administering to a human a total of 3 times, in about 3 week intervals, a first composition comprising a first replication defective adenovirus vector encoding at least two antigens selected from the group consisting of a MUC1-C antigen, a Brachyury antigen, and a CEA antigen; and during the second phase, administering to the human a total of 3 times, in about 3 month intervals, a second composition comprising a second replication defective adenovirus vector encoding an antigen that induces an immune response in a human against cells expressing the at least two antigens. In some embodiments, the second phase starts about 3 months after the end of the first phase.

In one aspect, a method of treatment is provided comprising: selecting a first phase of treatment and a second phase of treatment; during the first phase, administering to a human, a total of n times, a first composition comprising a first replication defective adenovirus vector encoding a Brachyury antigen; during the second phase, administering the human, a total of m times, a second composition comprising a second replication defective adenovirus vector encoding an antigen that induces an immune response in a human against cells expressing the Brachyury antigen.

In one aspect, a method of treatment is provided comprising: selecting a first phase of treatment and a second phase of treatment; during the first phase, administering to a human, a total of n times, a first composition comprising a first replication defective adenovirus vector encoding a MUC1-C antigen; during the second phase, administering the human, a total of m times, a second composition comprising a second replication defective adenovirus vector encoding an antigen that induces an immune response in a human against cells expressing the MUC1-C antigen.

In one aspect, a method of treatment is provided comprising: selecting a first phase of treatment and a second phase of treatment; during the first phase, administering to a human, a total of n times, a first composition comprising a first replication defective adenovirus vector encoding at least two antigens selected from the group consisting of a MUC1-C antigen, a Brachyury antigen, and a CEA antigen; during the second phase, administering the human, a total of m times, a second composition comprising a second replication defective adenovirus vector encoding the at least two antigens that induces an immune response in a human against cells expressing the at least two antigens. In some embodiments, n is greater than 1. In some embodiments, n is 3. In some embodiments, m is greater than 1. In some embodiments, m is 3. In some embodiments, the first phase is at least 2, 3, 4, 5, 6, 7, or 8 weeks. In some embodiments, the second phase is at least 2, 3, 4, 5, 6, 7, or 8 months. In some embodiments, the second phase starts 3-16 weeks after first phase ends. In some embodiments, in the first phase two administrations of the replication defective adenovirus are at least 18 days apart. In some embodiments, in the first phase two administrations of the replication defective adenovirus are about 21 days apart. In some embodiments, in the first phase two administrations of the replication defective adenovirus are at most 24 days apart. In some embodiments, in the second phase two administrations of the replication defective adenovirus are at least 10 weeks apart. In some embodiments, in the second phase two administrations of the replication defective adenovirus are about 13 weeks apart. In some embodiments, in the second phase two administrations of the replication defective adenovirus are at most 16 weeks apart. In some embodiments, the method further comprises administering a molecular composition comprising an immune pathway checkpoint modulator.

In one aspect, a method of treatment is provided comprising: selecting a first phase of treatment and a second phase of treatment; during the first phase, administering to a human, a total of n times, a first composition comprising a first replication defective adenovirus vector encoding an antigen that induces an immune response in a human against cells expressing a MUC1-C, Brachyury, or CEA antigen; and during the second phase, administering the human, a total of m times, a second composition comprising a second replication defective adenovirus vector encoding an antigen that is capable of inducing an immune response directed towards cells expressing MUC1-C, Brachyury, or CEA antigen in a human; wherein a molecular composition comprising and an immune pathway checkpoint modulator is administered during the first phase, the second phase, or both.

In one aspect, a method of treating a subject in need thereof is provided, comprising administering to the subject: (a) a recombinant replication deficient adenovirus vector encoding (i) a MUC1-C antigen, (ii) a Brachyury antigen, or (iii) at least two antigens selected from the group consisting of a MUC1-C antigen, a Brachyury antigen, and a CEA antigen; and (b) a molecular composition comprising an immune pathway checkpoint modulator; thereby generating an immune response in the subject. In some embodiments, (a) and (b) are administered in series. In some embodiments, (a) and (b) are administered at the same time. In some embodiments, (a) and (b) are administered a month apart.

In some embodiments, the immune pathway checkpoint modulator activates or potentiates an immune response. In some embodiments, the immune pathway checkpoint modulator inhibits an immune response inhibitor. In some embodiments, the immune pathway checkpoint inhibits an immune response. In some embodiments, the immune pathway checkpoint modulator targets an endogenous immune pathway checkpoint protein or fragment thereof selected from the group consisting of: PD1, PDL1, PDL2, CD28, CD80, CD86, CTLA4, B7RPI, ICOS, B7RPI, B7-H3, B7-H4, BTLA, HVEM, KIR, TCR, LAG3, CD137, CD137L, OX40, OX40L, CD27, CD70, CD40, CD40L, TIM3, GALS, ADORA, CD276, VTCN1, IDO1, KIR3DL1, HAVCR2, VISTA, and CD244. In some embodiments, the immune pathway checkpoint modulator targets a PD1 protein. In some embodiments, the molecular composition comprises siRNAs, antisense, small molecules, mimic, a recombinant form of a ligand, a recombinant form of a receptor, antibodies, or a combination thereof.

In some embodiments, the immune response is increased at least 2, 3, 4, 5, 6, 7, 8, 9, 10, 15, 20, or 25 fold. In some embodiments, the first replication defective adenovirus vector and the second replication defective adenovirus vector are the same. In some embodiments, the first replication defective adenovirus vector comprises a replication defective adenovirus 5 vector. In some embodiments, the second replication defective adenovirus vector comprises a replication defective adenovirus 5 vector. In some embodiments, the human expresses a human leukocyte antigen of serotype HLA-A2, HLA-A3, or HLA-A24. In some embodiments, the first replication defective adenovirus vector comprises a deletion in an E2b gene region. In some embodiments, the first replication defective adenovirus vector further comprises a deletion in an E1 gene region. In some embodiments, the first replication defective adenovirus vector further comprises a deletion in an E3 gene region. In some embodiments, the first replication defective adenovirus vector further comprises a deletion in an E4 gene region. In some embodiments, the second replication defective adenovirus vector comprises a deletion in an E2b gene region. In some embodiments, the second replication defective adenovirus vector further comprises a deletion in an E1 gene region. In some embodiments, the second replication defective adenovirus vector further comprises a deletion in an E3 gene region. In some embodiments, the second replication defective adenovirus vector further comprises a deletion in an E4 gene region. In some embodiments, the first composition, the second composition, or both, comprises at least $1.0 \times 10^{11}$, $2.0 \times 10^{11}$, $3.0 \times 10^{11}$, $3.5 \times 10^{11}$, $4.0 \times 10^{11}$, $4.5 \times 10^{11}$, $4.8 \times 10^{11}$, $4.9 \times 10^{11}$, $4.95 \times 10^{11}$, or $4.99 \times 10^{11}$ virus particles comprising the recombinant nucleic acid vector. In some embodiments, the first composition, the second composition, or both, comprises at most $7.0 \times 10^{11}$, $6.5 \times 10^{11}$, $6.0 \times 10^{11}$, $5.5 \times 10^{11}$, $5.2 \times 10^{11}$, $5.1 \times 10^{11}$, $5.05 \times 10^{11}$, or $5.01 \times 10^{11}$ virus particles. In some embodiments, the first composition, the second composition, or both, comprises $1.0$-$7.0 \times 10^{11}$ or $1.0$-$5.5 \times 10^{11}$ virus particles. In some embodiments, the first composition, the second composition, or both, comprises $4.5$-$5.5 \times 10^{11}$ virus particles. In some embodiments, the first composition, the second composition, or both, comprises $4.8$-$5.2 \times 10^{11}$ virus particles. In some embodiments, the first composition, the second composition, or both, comprises $4.9$-$5.1 \times 10^{11}$ virus particles. In some embodiments, the first composition, the second composition, or both, comprises $4.95$-$5.05 \times 10^{11}$ virus particles. In some embodiments, the first composition, the second composition, or both, comprises $4.99$-$5.01 \times 10^{11}$ virus particles. In some embodiments, the first phase is at least 2, 3, 4, 5, 6, 7, or 8 weeks. In some embodiments, the second phase is at least 2, 3, 4, 5, 6, 7, or 8 months. In some embodiments, the immune response is measured as antigen specific antibody response. In some embodiments, the immune response is measured as antigen specific cell-mediated immunity (CMI). In some embodiments, the immune response is measured as antigen specific IFN-γ secretion. In some embodiments, the immune response is measured as antigen specific IL-2 secretion. In some embodiments, the immune response against the antigen is measured by ELISpot assay. In some embodiments, the antigen specific CMI is greater than 25, 50, 75, 100, 150, 200, 250, or 300 IFN-γ spot forming cells (SFC) per $10^6$ peripheral blood mononuclear cells (PBMC). In some embodiments, the immune response is measured by T-cell lysis of CAP-1 pulsed antigen-presenting cells, allogeneic antigen expressing cells from a tumor cell line or from an autologous tumor. In some embodiments, a first or a second replication defective adenovirus infects dendritic cells in the human and wherein the infected dendritic cells present the antigen, thereby inducing the immune response. In some embodiments, the administering steps comprise subcutaneous (sc) administration. In some embodiments, the human carries an inverse Ad5 neutralizing antibody titer that is of greater than 50, 75, 100, 125, 150, 160, 175, 200, 225, 250, 275, or 300 prior to the administering step. In some embodiments, the human has an inverse Ad5 neutralizing antibody titer of greater than 250, 500, 750, 1000, 1500, 2000, 2500, 3000, 3500, 4000, 4500, or 4767. In some embodiments, the human is not concurrently being treated by any one of steroids, corticosteroids, and immunosuppressive agents. In some embodiments, the human does not have an autoimmune disease. In some embodiments, the human does not have inflammatory bowel disease, systemic lupus erythematosus, ankylosing spondylitis, scleroderma, multiple sclerosis, viral hepatitis, or HIV. In some embodiments, the human has or may have in the future an infectious disease. In some embodiments, the human has autoimmune related thyroid disease or vitiligo. In some embodiments, the human has or may have in the future a proliferative disease cancer. In some embodiments, the human has colorectal adenocarcinoma, metastatic colorectal cancer, advanced MUC1-C, Brachyury, or CEA expressing colorectal cancer, breast cancer, lung cancer, bladder cancer, or pancreas cancer. In some embodiments, the human has at least 1, 2, or 3 sites of metastatic disease. In some embodiments, the human comprises cells overexpressing MUC1-C, Brachyury, or CEA. In some embodiments, the cells overexpressing MUC1-C, Brachyury, or CEA, overexpress the MUC1-C, Brachyury, or CEA by at least 2, 3, 4, 5, 6, 7, 8, 9, or 10 times over a baseline MUC1-C, Brachyury, or CEA expression in a non-cancer cell. In some embodiments, the cells overexpressing MUC1-C, Brachyury, or CEA comprise cancer cells. In some embodiments, the subject has a diagnosed disease predisposition. In some embodiments, the subject has a stable disease. In some embodiments, the subject has a genetic predisposition for a disease. In some embodiments, the disease is a cancer. In some embodiments, the cancer is selected from the group consisting of prostate cancer, colon cancer, breast cancer, or gastric cancer. In some embodiments, the cancer is prostate cancer. In some embodiments, the subject has a Gleason score of 6 or less. In some embodiments, the subject has a Gleason score greater than 6. In some embodiments, the first or the second replication defective adenovirus vector comprises a sequence with at least 80% sequence identity to SEQ ID NO:3. In some embodiments, the first or the second replication defective adenovirus vector comprises a region with at least 80% sequence identity to a region in SEQ ID NO:3 selected from 26048-26177, 26063-26141, 1-103, 54-103, 32214-32315, and 32214-32262. In some embodiments, the first or the second replication defective adenovirus vector comprises a region with at least 80% sequence identity to a region in SEQ ID NO:3 between positions 1057 and 3165. In some embodiments, the first or second replication defective adenovirus vector comprises a sequence encoding a MUC1-C, Brachyury, or CEA antigen; wherein the MUC1-C antigen is encoded by a sequence with at least 80% sequence identity to SEQ ID NO:5 or SEQ ID NO:6; wherein the Brachyury antigen is encoded by a sequence with at least 80% sequence identity to SEQ ID NO:7 or SEQ ID NO:8; wherein the CEA antigen is encoded by a sequence with at least 80% sequence identity to SEQ ID NO:1, SEQ ID NO:2, or SEQ ID NO:3.

In one aspect a kit for inducing an immune response in a human is provided comprising: a composition comprising a therapeutic solution of a volume in the range of 0.8-1.2 mL, the therapeutic solution comprising at least $1.0 \times 10^{11}$ virus particles; wherein the virus particles comprise a recombinant replication defective adenovirus vector; a composition comprising of a therapeutic solution of a molecular composition comprising an immune pathway checkpoint modulator and; instructions.

In some embodiments, the therapeutic solution comprises $1.0\text{-}5.5 \times 10^{11}$ virus particles. In some embodiments, adenovirus vector is capable of effecting overexpression of the modified MUC1-C, Brachyury, or CEA in transfected cells. In some embodiments, therapeutic solution comprises a first, second and third replication defective adenovirus vector each comprising an antigen selected from the group consisting of a MUC1-C antigen, a Brachyury antigen, a CEA antigen, and combinations thereof. In some embodiments, the adenovirus vector comprises a nucleic acid sequence encoding an antigen that induces a specific immune response against MUC1-C, Brachyury, or CEA expressing cells in a human. In some embodiments, the immune pathway checkpoint modulator targets an endogenous immune pathway checkpoint protein or fragment thereof selected from the group consisting of: PD1, PDL1, PDL2, CD28, CD80, CD86, CTLA4, B7RPI, ICOS, B7RPI, B7-H3, B7-H4, BTLA, HVEM, KIR, TCR, LAG3, CD137, CD137L, OX40, OX40L, CD27, CD70, CD40, CD40L, TIM3, GALS, ADORA, CD276, VTCN1, IDO1, KIR3DL1, HAVCR2, VISTA, and CD244. In some embodiments, the molecular composition comprises siRNAs, antisense, small molecules, mimic, a recombinant form of a ligand, a recombinant form of a receptor, antibodies, or a combination thereof. In some embodiments, the instructions are for the treatment of a proliferative disease or cancer. In some embodiments, the instructions are for the treatment of an infectious disease. In some embodiments, the adenovirus vector comprises a replication defective adenovirus 5 vector. In some embodiments, the therapeutic solution comprises at least $1.0 \times 10^{11}$, $2.0 \times 10^{11}$, $3.0 \times 10^{11}$, $3.5 \times 10^{11}$, $4.0 \times 10^{11}$, $4.5 \times 10^{11}$, $4.8 \times 10^{11}$, $4.9 \times 10^{11}$, $4.95 \times 10^{11}$, or $4.99 \times 10^{11}$ virus particles comprising the recombinant nucleic acid vector. In some embodiments, the therapeutic solution comprises at most $7.0 \times 10^{11}$, $6.5 \times 10^{11}$, $6.0 \times 10^{11}$, $5.5 \times 10^{11}$, $5.2 \times 10^{11}$, $5.1 \times 10^{11}$, $5.05 \times 10^{11}$, or $5.01 \times 10^{11}$ virus particles. In some embodiments, the therapeutic solution comprises $1.0\text{-}7.0 \times 10^{11}$ or $1.0\text{-}5.5 \times 10^{11}$ virus particles. In some embodiments, the therapeutic solution comprises $4.5\text{-}5.5 \times 10^{11}$ virus particles. In some embodiments, the therapeutic solution comprises $4.8\text{-}5.2 \times 10^{11}$ virus particles. In some embodiments, the therapeutic solution comprises $4.9\text{-}5.1 \times 10^{11}$ virus particles. In some embodiments, the therapeutic solution comprises $4.95\text{-}5.05 \times 10^{11}$ virus particles. In some embodiments, the therapeutic solution comprises $4.99\text{-}5.01 \times 10^{11}$ virus particles In some embodiments, the kit further comprises an immunogenic component. In some embodiments, the immunogenic component comprises a cytokine selected from the group of IFN-γ, TNFα IL-2, IL-8, IL-12, IL-18, IL-7, IL-3, IL-4, IL-5, IL-6, IL-9, IL-10, and IL-13. In some embodiments, the immunogenic component is selected from the group consisting of IL-7, a nucleic acid encoding IL-7, a protein with substantial identity to IL-7, and a nucleic acid encoding a protein with substantial identity to IL-7.

Kits

The compositions, immunotherapy or vaccines may be supplied in the form of a kit. The kits may further comprise instructions regarding the dosage and or administration including treatment regimen information.

In some embodiments, kits comprise the compositions and methods for providing combination multi-targeted cancer immunotherapy. In some embodiments, kits comprise the compositions and methods for the combination multi-targeted treatment of an infectious disease. In some embodiment's kits may further comprise components useful in administering the kit components and instructions on how to prepare the components. In some embodiments, the kit can further comprise software for conducting monitoring patient before and after treatment with appropriate laboratory tests, or communicating results and patient data with medical staff.

The components comprising the kit may be in dry or liquid form. If they are in dry form, the kit may include a solution to solubilize the dried material. The kit may also include transfer factor in liquid or dry form. If the transfer factor is in dry form, the kit will include a solution to solubilize the transfer factor. The kit may also include containers for mixing and preparing the components. The kit may also include instrument for assisting with the administration such for example needles, tubing, applicator, inhalant, syringe, pipette, forceps, measured spoon, eye dropper or any such medically approved delivery vehicle. In some embodiments, the kits or drug delivery systems as described herein also include a means for containing compositions disclosed herein in close confinement for commercial sale and distribution.

EXAMPLES

Example 1: Peptides and Vectors

The following HLA-A2 and HLA-A24 binding peptides were used in this and other examples: (a) the HLA-A2 binding CEA agonist peptide CAP1-6D (YLSGADLNL), (b) the HLA-A2 MUC1 agonist peptide P93L (ALWGQDVTSV), (c) the HLA-A24 binding MUC1 agonist peptide C6A (KYHPMSEYAL), and (d) the HLA-A2 binding brachyury agonist peptide (WLLPGTSTV). All peptides were greater than 96% pure.

Ad5 [E1-, E2b-]-brachyury, Ad5 [E1-, E2b-]-CEA and Ad5 [E1-, E2b-]-MUC1 were constructed and produced. Briefly, the transgenes were sub-cloned into the E1 region of the Ad5 [E1-, E2b-] vector using a homologous recombination-based approach. The replication deficient virus was propagated in the E.C7 packaging cell line, $CsCl_2$ purified, and titered. Viral infectious titer was determined as plaque-forming units (PFUs) on an E.C7 cell monolayer. The VP concentration was determined by sodium dodecyl sulfate (SDS) disruption and spectrophotometry at 260 nm and 280 nm. The CEA transgene also contained a modified CEA containing the highly immunogenic epitope CAP1-6D.

The sequence encoding for the human Brachyury protein (T, NM_003181.3) was modified by introducing the enhancer T-cell HLA-A2 epitope (WLLPGTSTV; SEQ ID NO:22) and removal of a 25 amino acid fragment involved in DNA binding. The resulting construct was subsequently subcloned into the Ad5 vector to generate the Ad5 [E1-, E2b-]-Brachyury construct.

The MUC1 molecule consisted of two regions: the N-terminus (MUC1-n), which is the large extracellular domain of MUC1, and the C-terminus (MUC1-c), which has three regions: a small extracellular domain, a single transmembrane domain, and a cytoplasmic tail. The cytoplasmic tail contained sites for interaction with signaling proteins and acts as an oncogene and a driver of cancer motility, invasiveness and metastasis. For construction of the Ad5 [E1-, E2b-]-MUC1, the entire MUC1 transgene, including eight agonist epitopes, was subcloned into the Ad5 vector. The agonist epitopes included in the Ad5 [E1-, E2b-]-MUC1 vector bind to HLA-A2 (epitope P93L in the N-terminus, V1A and V2A in the VNTR region, and C1A, C2A and C3A in the C-terminus), HLA-A3 (epitope C5A), and HLA-A24 (epitope C6A in the C-terminus). The Tri-Ad5 vaccine was produced by combining of $10^{10}$ VP of Ad5 [E1-, E2b-]-Brachyury, Ad5 [E1-, E2b-]-CEA and Ad5 [E1-, E2b-]-MUC1 at a ratio of 1:1:1 ($3\times10^{10}$ VP total).

Example 2: Multiple Injections of Ad5Null Adenovirus Vector Produces Anti-Adenovirus Antibodies This example shows that multiple injections of Ad5-null results in the production of anti-adenovirus antibodies in the injected subjects.

It was demonstrated that the Ad5-null adenovirus vector that does not contain any heterologous nucleic acid sequences, generated a neutralizing immune response in mice. In one experiment, female Balb/c mice aged 5-7 weeks were immunized with Ad5Null viral particles at 14 day intervals. To determine the presence of anti-adenovirus antibodies, an enzyme linked immunosorbent assay (ELISA) was used. For this ELISA, $10^9$ viral particles were coated onto microtiter wells in 100 µL of 0.05M carbonate/bicarbonate buffer, pH 9.6, and incubated overnight at room temperature. For a standard immunoglobulin G (IgG) reference curve, 200 ng, 100 ng, 50 ng, 25 ng, and 0 ng of purified mouse IgG were coated onto microtiter wells as described above. After incubation, all wells were washed 3 times with 250 µL of 1% bovine serum albumin (BSA) in phosphate buffered saline (PBS), pH 7.4. After washing, 250 µL of BSA/PBS was added to all and incubated for 30 minutes at room temperature to block unbound sites. After incubation, all wells were washed 3 times with 250 µL of BSA/PBS. After washing, 200 µL of a 1/100 serum dilution in BSA/PBS was added to wells and incubated for 1 hour at room temperature. For a positive control, 200 µL of a 1/10000 dilution of anti-adenovirus antiserum in BSA/PBS was added to wells. Control wells contained BSA/PBS only. After incubation, all wells were washed 3 times with 250 µL of BSA/PBS. After washing, 200 µL of a 1/10000 dilution of peroxidase conjugated γ-chain specific goat anti-mouse IgG (Sigma Chemicals) in BSA/PBS were added to each well and incubated for 1 hour at room temperature. After incubation, all wells were washed 3 times with 250 µL of BSA/PBS. After washing, 200 µL of developing reagent (0.5 mg/mL 1,2-phenylene-diamine in 0.2M potassium phosphate buffer, pH 5.0, containing 0.06% hydrogen peroxide) was added to each well and incubated for 30-40 minutes at room temperature. After incubation, the color reaction was stopped by addition of 50 µL 5N HCl to each well. All wells were then read in a microwell plate reader at 492 nm. After readings were obtained, the optical density readings of unknown samples were correlated with the standard IgG curve to obtain the ngs of IgG bound per well. This was performed using the INSTAT statistical package.

ELISA to Detect Antibodies Against CEA

ELISA plates were coated with 100 ng of human CEA (Sigma-Aldrich) in 0.05 M carbonate-bicarbonate buffer pH 9.6 and incubated overnight at room temperature. Plates were washed three times with phosphate buffered saline containing 1% Tween-20 (PBS-T) and then blocked with PBS containing 1% BSA for 60 min at room temperature. After an additional three washes, serum diluted 1/50 in PBS-T was added to the wells and the plates were incubated for 1 hour at room temperature. Peroxidase labeled goat anti-mouse immunoglobulin (Ig) G (γ-chain specific) (Sigma-Aldrich) antibody at a 1:5000 dilution was added to the wells after washings and plates were incubated for 1 hour. Plates were washed three times and 1,2-phenylene-diamine substrate solution was added to each well. The reaction was stopped by adding 10% phosphoric acid. Absorbance was measured at 492 nm on a SpectraMax 190 ELISA reader. The nanogram equivalents of IgG bound to CEA per well was obtained by reference to a standard curve generated using purified mouse IgG and developed at the same time as the CEA ELISA. The results were analyzed and quantitated using SoftMax Pro 6.3 software.

Figure 1:
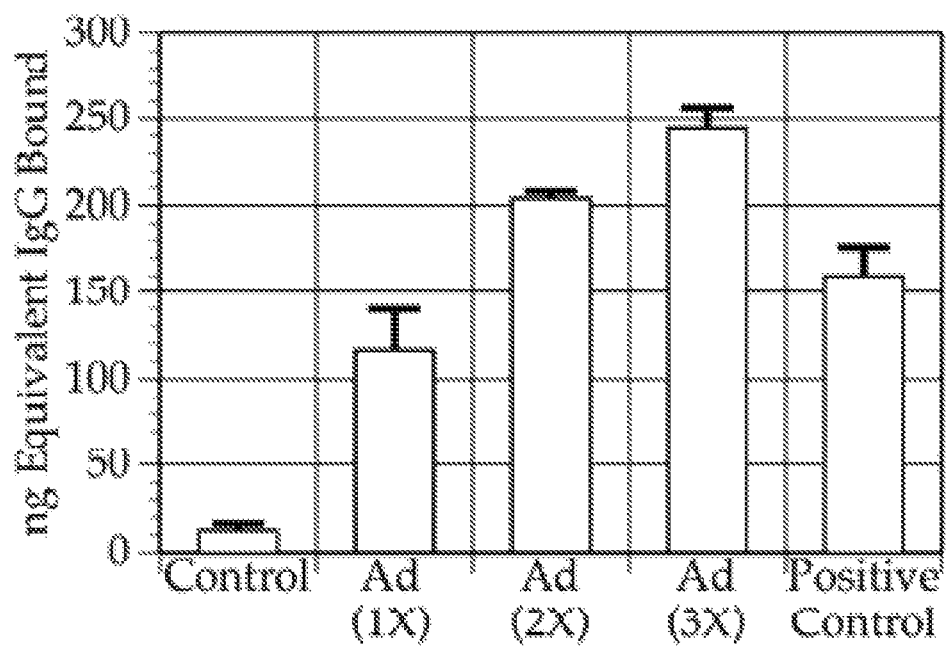
FIG. 1 exemplifies a bar graph showing antibody levels from mice immunized with Ad5-null (empty vector). Mice were immunized three times with Ad5-null viral particles (VPs) at 14 day intervals. Anti-Ad antibody (neutralizing antibody) levels increased after each immunization.

Significant levels (P<0.001) of anti-adenovirus IgG antibody were detected in mice 2 weeks after a first injection with $10^{10}$ Ad-5-null (FIG. 1). A significantly higher level (P<0.001) was observed 2 weeks after a second injection with $10^{10}$ adenovirus. Significantly higher (P<0.001) levels of antibody were continued to be observed 2 weeks after a third injection with $10^{10}$ Ad5-null. Each value represents the average of triplicate determinations from pooled sera of 5 mice in each group. Multiple injections of Ad5-null resulted in production of anti-adenovirus antibodies in the subjects.

To determine the presence of neutralizing antibody to Ad, the following assay was utilized. A HEK-293T-cell line was cultured in 200 µL of culture medium consisting of DMEM containing 10% fetal calf serum (DMEM/FCS) in microwell tissue culture plates at a cell concentration of $2\times10^3$ cells per well for 24 hours at 37° C. in 5% $CO_2$. After incubation, 100 µL of culture medium was removed from triplicate wells and mixed with 20 µL of DMEM/FCS containing viral particles (VP). After mixing, the 120 µL mixture was added back to the respective microwells. In another set of triplicate wells, 100 μL of culture medium was removed and mixed with 20 μL of heat inactivated (56° C. for 1 h) Ad immune mouse serum previously incubated with VP for one hour at room temperature. After mixing, the 120 μL mixture was added back to the respective wells. In triplicate cell control wells, 20 μL of DMEM/FCS was added to control for total culture medium volume. Triplicate medium-only control wells contained 220 μL of DMEM/FCS. The tissue culture plate was incubated for an additional 3 days at 37° C. in 5% $CO_2$. After incubation, 40 μL of PROMEGA cell viability reagent (Owen's reagent) was added to all wells and incubated for 75 minutes at 37 C in 5% $CO_2$. In this assay, the Owen's reagent (MTS tetrazolium compound) is bioreduced by viable cells into a colored formazan product that is soluble in tissue culture medium. The quantity of formazan product as measured by absorbance at 490 nm is directly proportional to the number of living cells in culture. After incubation, 150 μL was removed from each well and transferred to another microwell plate for optical density readings. Optical density readings at 492 nm were subsequently obtained using a microwell plate reader.

Figure 2:
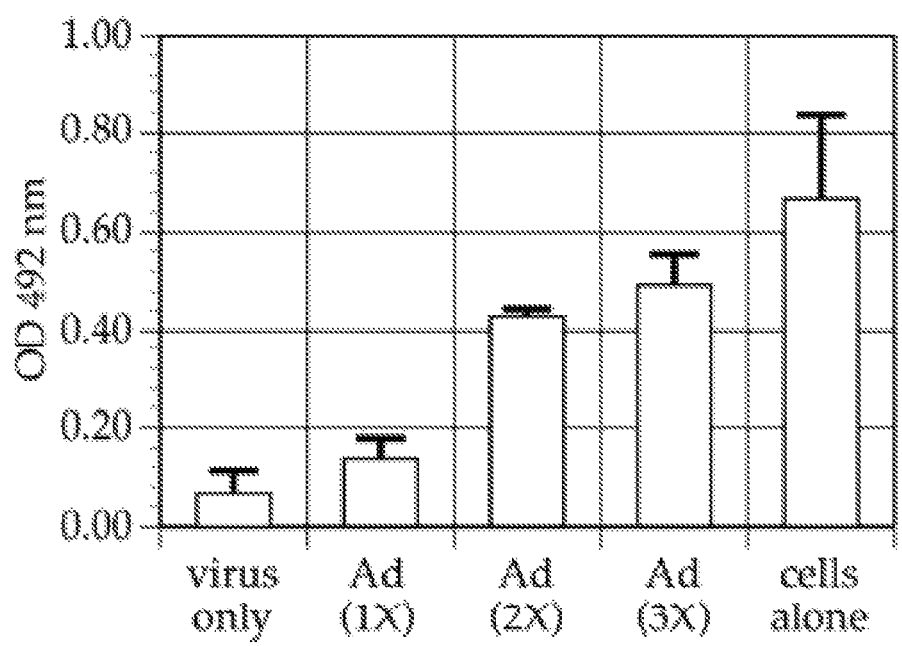
FIG. 2 exemplifies a bar graph showing neutralizing antibody (NAb) levels from mice immunized with Ad5-null. Mice were immunized three times with Ad5-null VPs at 14 day intervals. Neutralizing antibody levels increased after each immunization. Optical density readings indicate the presence of viable target cells.

To detect the presence of neutralizing antibodies to Ad, groups of 5 mice each were injected once, twice, or three times with $10^{10}$ Ad5-null at two week intervals. Two weeks after the final injection of virus, mice were bled, pooled, and assessed for neutralizing antibody as described above using $4\times10^7$ VP incubated with or without heat inactivated sera. Cells cultured alone served as a control group. Normal mice and mice injected one time with Ad5null did not exhibit significant levels of neutralizing antibody (FIG. 2). Mice injected two times with Ad exhibited significant (P<0.05) levels of neutralizing antibody as compared with cells incubated with virus only. Mice injected three times with Ad5-null also exhibited significant (P<0.01) levels of neutralizing antibody as compared with cells incubated with virus only.

Figure 3:
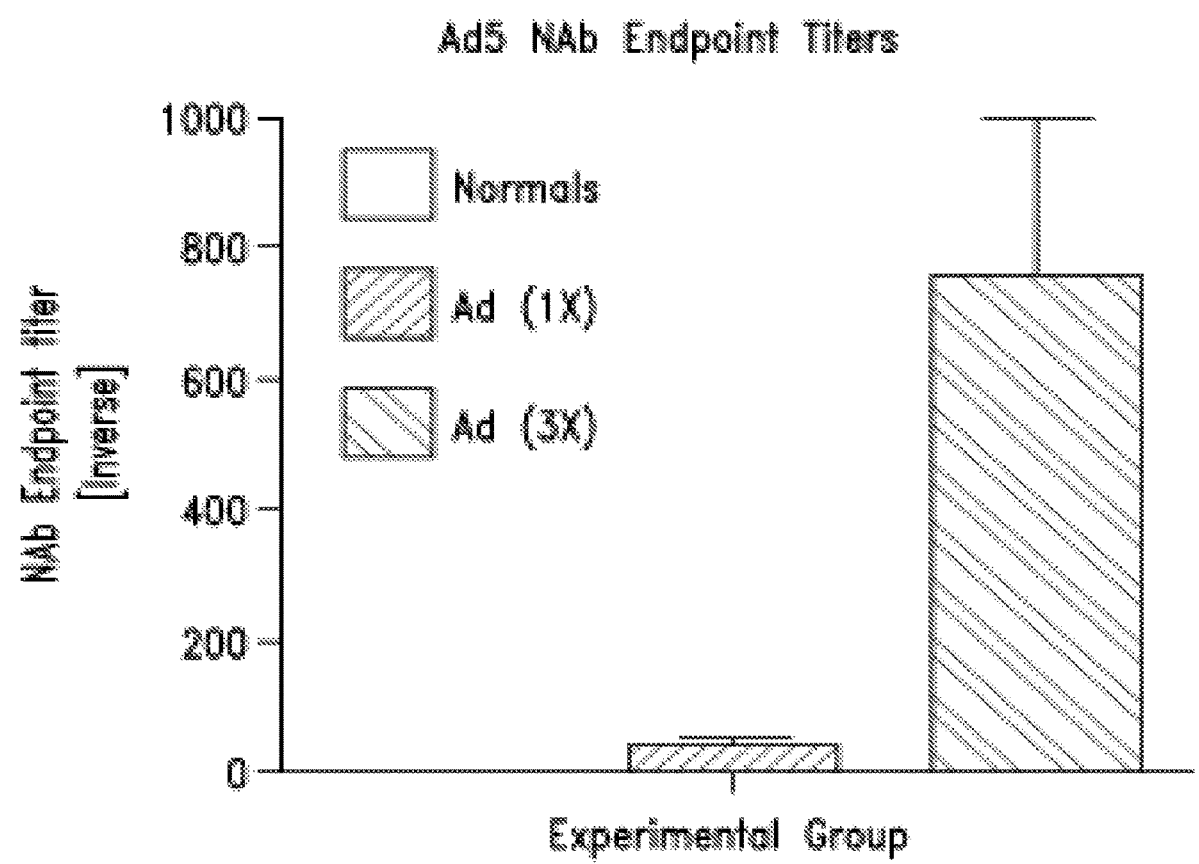
FIG. 3 exemplifies a bar graph showing the induction of NAbs in C57Bl/6 mice after injections with Ad5-null vector platform. Increasing levels of NAbs were induced in mice after repeated injections with Ad particles.

Example 3: The Ad5 [E1-]-CEA Vector Vaccine Induces CEA Specific Immune Response Upon Re-Immunization in Ad5 Immune Mice This example shows that the Ad5 [E1-, E2b-] vector platform induces CMI responses against the tumor associated antigen (TAA) carcinoembryonic antigen (CEA) in the presence of pre-existing Ad5 immunity in mice.
Characterization of Ad5 CEA Vectors
Initial studies were performed to confirm CEA gene expression of two Ad5-CEA vector platforms. It was first determined that the CEA antigen could be expressed on cells transfected with the vaccine vector platforms. A549 cells were obtained from ATCC and transfected with Ad5 [E1-]-CEA or Ad5 [E1-, E2b-]-CEA. Western blot analysis revealed that cells transfected with the vector platforms expressed CEA antigen. (FIG. 35)
Methods
A549 cells were inoculated at a MOI of 555 VPs/cell with Ad5 [E1-, E2b-]-CEA. Cells were incubated for 48 hours at 37° C. in 5% $CO_2$. After 48 hours cells were harvested and washed with PBS and freeze/thawed three times. The whole cell lysate was heated for 70° C. for 10 min prior to loading on the gel. Recombinant CEA control was loaded at 30 ng/Lane and the prepared lysate at 20 μL/lane. Sample loading buffer was included as an additional negative control and the positive controls were Magic Mark CP Western markers and the recombinant CEA. The gel was transferred to a nitrocellulose membrane and blocked with SuperBlock Blocking solution for 60 min. The membrane was probed with mouse monoclonal anti-CEA primary antibody (1:1000) and a secondary anti-mouse HRP (1:2500) conjugated antibody. The membrane was washed three times then incubated with SuperSignal chemiluminescent reagent and banding was visualized by exposing X-ray film to the membrane followed by development.
Induction of Ad5 Immunity in Mice
To assess the levels of Ad5 immunity that could be induced, groups of Ad5 naive C57Bl/6 mice were injected subcutaneously with the Ad5 vector platform (VP). Twenty eight to forty two days later, serum samples were collected and assessed for endpoint Ad5 NAb titers. As shown in FIG. 3, undetectable Ad5 NAb titers (endpoint Ad5 NAb titer <1/25) were observed in normal control mice. Ad5 NAb (endpoint titers of 1/25 to 1/50) was detectable after one injection but dramatically increased after three injections of $10^{10}$ Ad5. Therefore, in additional Ad5 immune studies, mice were injected twice with $10^{10}$ Ad5 VP to render the animals Ad5 immune.
Immunization of Ad5 Immune Mice with Ad5 [E1-]-CEA or Ad5 [E1-, E2b-]-CEA.
These experiments were designed to determine and compare the immunization induction potential of Ad5 [E1-]-CEA and Ad5 [E1-, E2b-]-CEA vaccines in Ad5 immune mice. Groups of female C57Bl/6 mice, 4 to 8 weeks old, were immunized 2 times at 2 week intervals with $10^{10}$ Ad5-null VP. Two weeks following the last Ad5-null immunization, the mice were immunized 3 times at weekly intervals with $10^{10}$ VP of Ad5 [E1-]-CEA or Ad5 [E1-, E2b-]-CEA. Two weeks following the last immunization, mice were euthanized and their spleens and sera harvested for analyses.

Figure 4A:
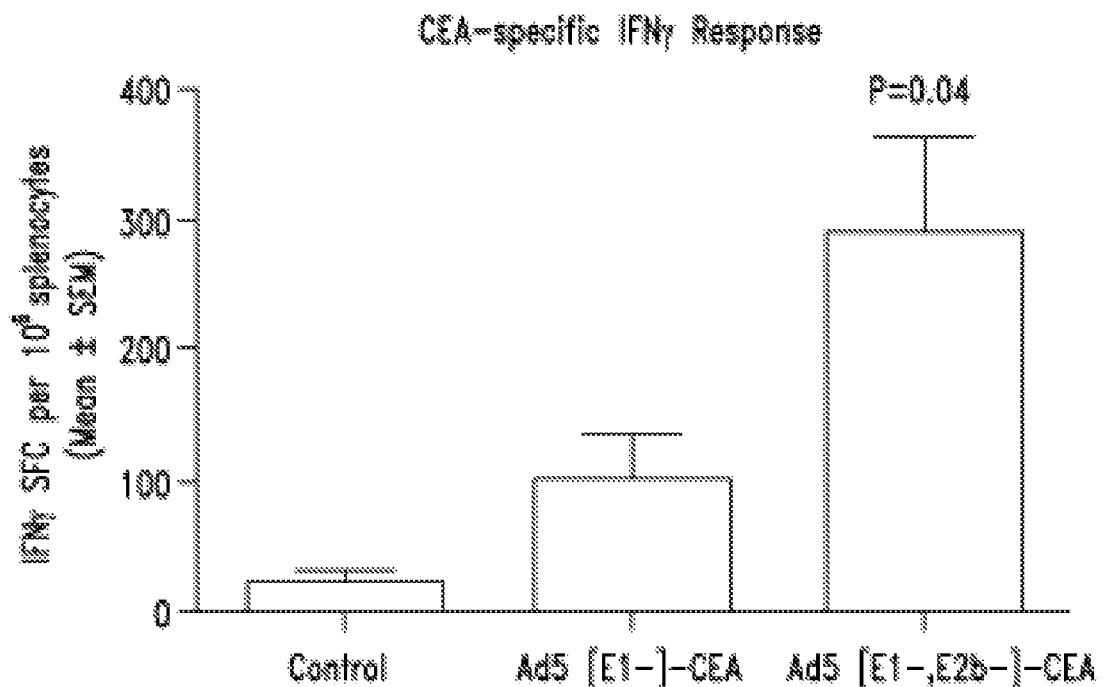
FIG. 4A exemplifies a bar graph showing INF-γ levels secreted from splenocytes from Ad5-immune mice immunized with Ad5 [E1-]-CEA or Ad5 [E1-, E2b-]-CEA. A significantly elevated response is shown in the Ad5 [E1-, E2b-]-CEA immunized group.
Figure 4B:
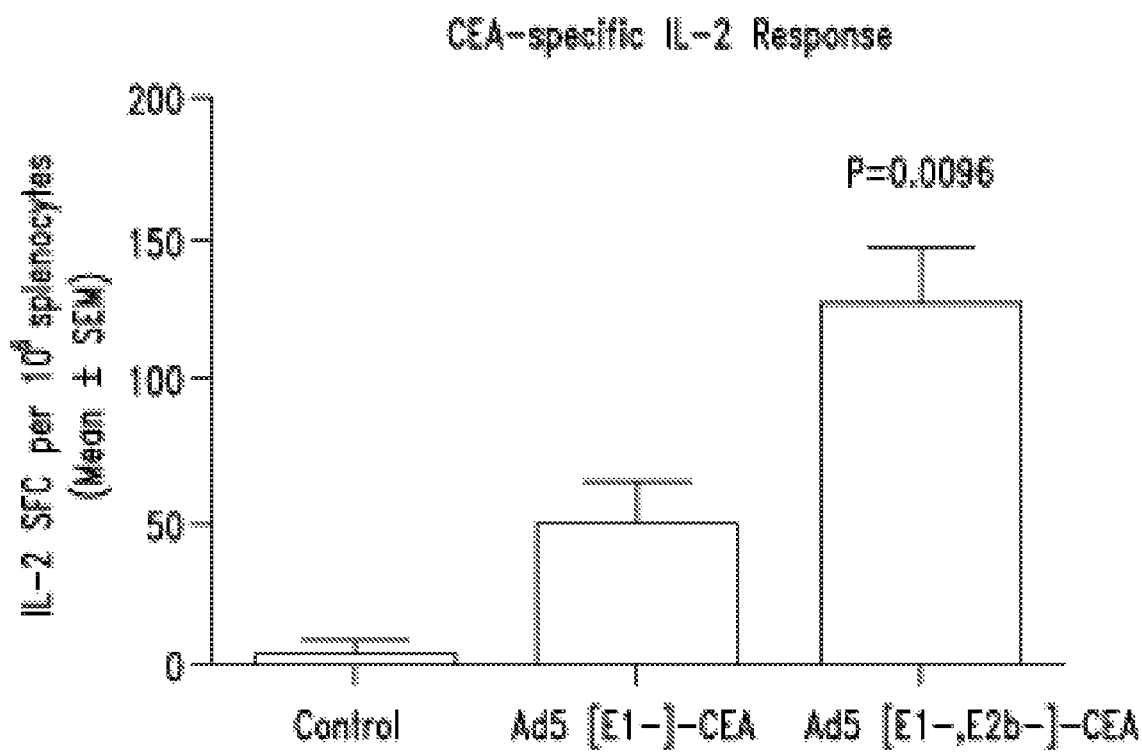
FIG. 4B exemplifies a bar graph showing IL-2 secreted from splenocytes from Ad5-immune mice immunized with Ad5 [E1-]-CEA or Ad5 [E1-, E2b-]-CEA. A significantly elevated response is shown in the Ad5 [E1-, E2b-]-CEA immunized group.
Figure 5:
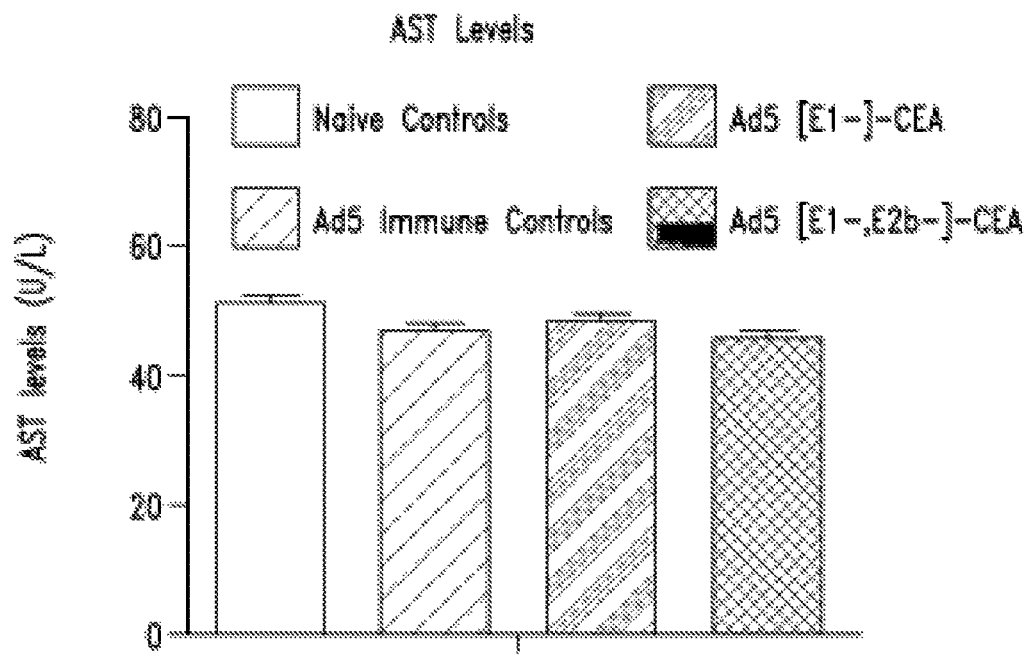
FIG. 5 exemplifies a bar graph showing serum aspartate aminotransferase (AST) levels in control mice and mice vaccinated with $1 \times 10^{10}$ Ad5 [E1-]-CEA VPs or Ad5 [E1-, E2b-]-CEA VPs.

CMI responses were assessed by ELISpot assays performed on splenocytes exposed to intact CEA antigen. Splenocytes from Ad5 immune C57Bl/6 mice that were immunized subcutaneously with Ad5 E1-]-CEA or Ad5 [E1-, E2b-]-CEA were harvested and assessed for the number of IFN-γ and IL-2 secreting cells as described above. Significantly elevated numbers of both IFN-γ and IL-2 secreting cells were observed in spleens assayed from mice immunized with Ad5 [E1-, E2b-]-CEA as compared to immunized Ad5 [E1-]-CEA mice (FIG. 4A and FIG. 4B). Specificity studies revealed that immunizations with Ad5 CEA vectors induced specific CEA associated CMI responses and not responses against other irrelevant antigens such as the HIV-gag protein or β-galactosidase. These results demonstrate that immunization of Ad5 immune mice with Ad5 [E1-, E2b-]-CEA induce significantly higher CMI responses.
Lack of Adverse Liver Effects in Immunized Mice
Toxicity studies were performed on serum from Ad5 immune female C57Bl/6 mice immunized with Ad5 [E1-]-CEA, Ad5 [E1-, E2b-]-CEA as described above. Ad5 naive or Ad5 immune mice injected with buffer alone served as controls. Three days after the third immunization, aspartate aminotransferase (AST) levels were assessed on the blood samples to determine liver toxicity due to the treatment. AST levels were not elevated over controls following immunization with either vector (FIG. 5). Alanine aminotransferase (ALT) levels were also assessed and similar results were observed.
Ad5 [E1-, E2b-]-CEA Immunotherapy in Ad5 Immune Tumor Bearing Mice
Based upon the successful immunological results observed above, studies in which MC38 tumors were established in mice and then treated were performed as described below. For these studies a CEA expressing MC38 murine cell line was used. This cell line has been genetically modified to express human CEA and can be implanted into C57Bl/6 mice. After tumor establishment, the mice were treated with the novel Ad5 [E1-, E2b-]-CEA vector platform. To determine if Ad5 immune tumor bearing mice could be treated with the Ad5 [E1-, E2b-]-CEA vector, C57Bl/6 mice were injected two times subcutaneously with $10^{10}$ Ad5 [E1-]-null VP at 14 day intervals to render the mice Ad5 immune. Two weeks after the last injection, two groups of 7 C57Bl/6 mice were injected subcutaneously with $10^6$ CEA expressing MC38 tumor cells. Seven days later, when tumors were palpable, one group of mice was treated by distal subcutaneous injection with $10^{10}$ VP of Ad5 [E1-, E2b-]-CEA on days 7, 13 and 19. A group of 7 injection buffer only treated C57Bl/6 mice served as untreated controls. All mice were monitored for tumor size over a 21 day period and tumor volumes were determined as previously described.

Figure 6:
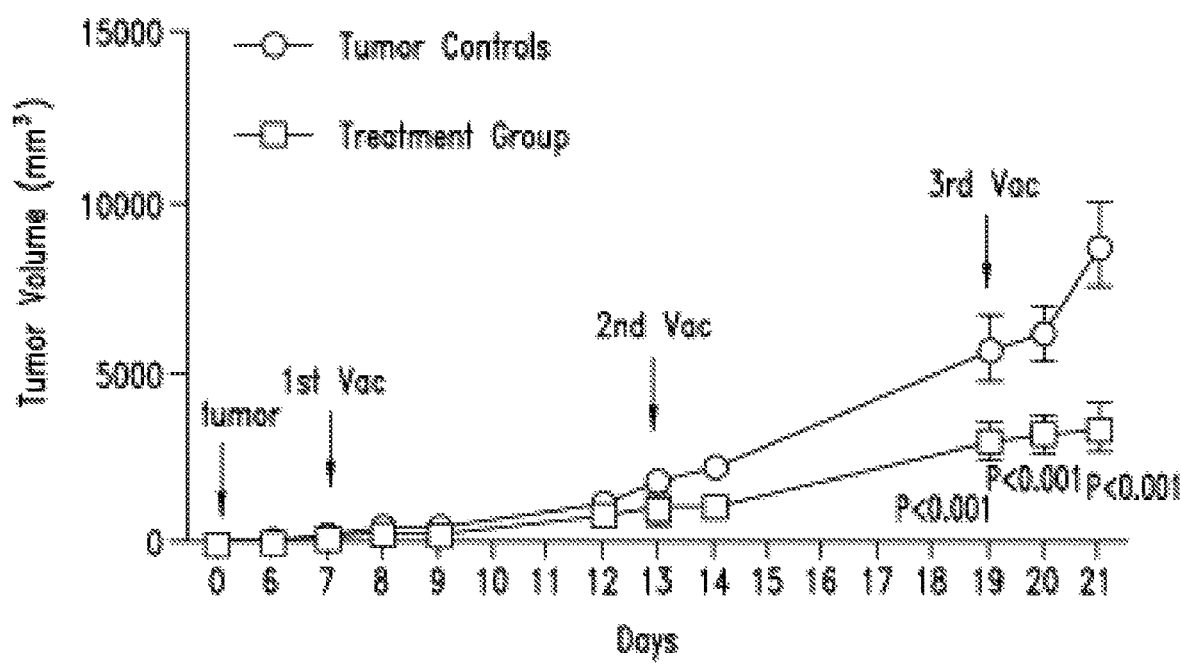
FIG. 6 exemplifies a line graph showing tumor volume over time in Ad5-immune C57Bl/6 mice injected with MC38 CEA-expressing tumor cells and subsequently treated (Vac) with Ad5 [E1-, E2b-]-CEA vaccine. Tumor size is shown to be significantly reduced by days 19-21 compared to untreated tumor-bearing mice.
Figure 7:
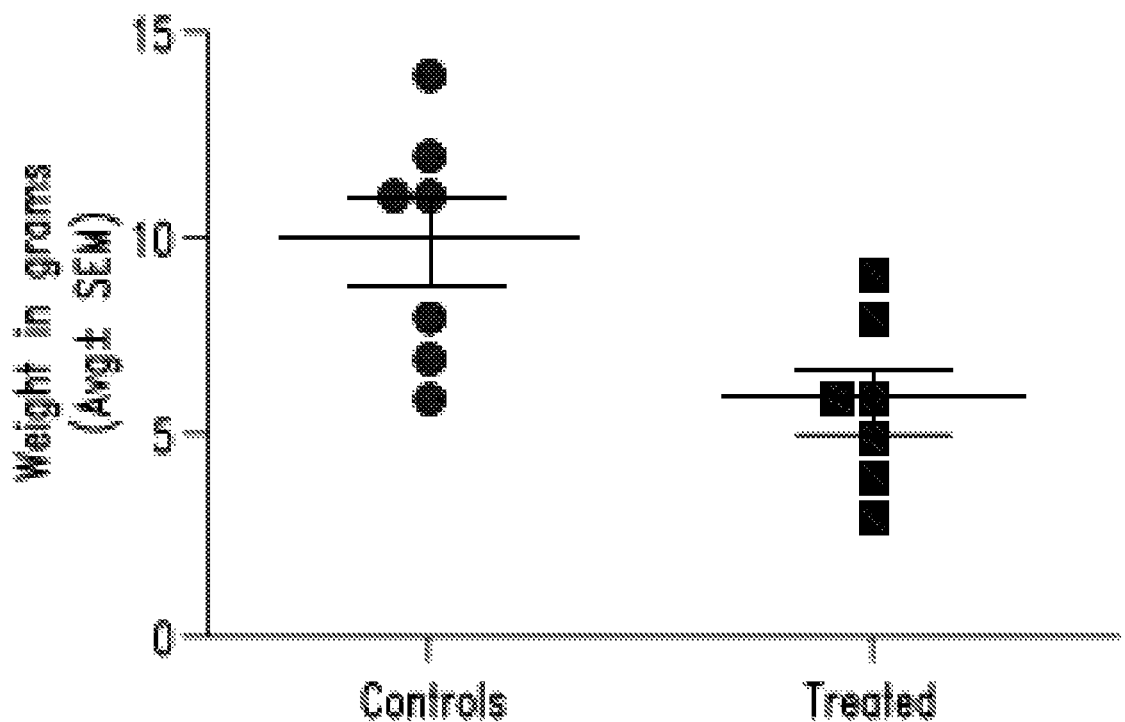
FIG. 7 exemplifies a graph showing tumor weight from 7 treated and 7 untreated Ad5-immune MC38 tumor-bearing mice. A significant (p=0.0124) reduction in tumor weight in mice treated with Ad5 [E1-, E2b-]-CEA is shown.

The tumor growth by day 19 was significantly reduced in the Ad5 [E1-, E2b-]-CEA treated mice and remained so (FIG. 6). At the end of the study (Day 22), the mice were sacrificed and the tumors were excised and weighed. Tumor measurements were taken and volumes were determined. Statistical analysis was performed using the Bonferroni post-tests analysis with PRISM software. The tumors in the mice treated with Ad5 [E1-, E2b-]-CEA were significantly ($P<0.05$) smaller in weight than the untreated controls (FIG. 7).

At the termination of the study, spleens were collected from mice and the CEA specific CMI response was determined by ELISpot assay. CEA specific IFN-γ secretion response was significantly higher in mice immunized with Ad5 [E1-, E2b-]-CEA than in mice who received MC-38 tumor cells alone. These results indicate that treatment of CEA expressing tumors in Ad5 immunized mice using the Ad5 [E1-, E2b-]-CEA vaccine can significantly decrease tumor growth progression.

Example 4: Quantitative ELISA for CEA Expression on A549 Cells after Infection This example shows a dose response evaluation using the Ad5 [E1-, E2b-] CEA vector to transduce the human cancerous lung cell line, A-549. The results show that the CEA antigen can be expressed in a dose dependent manner.

Experimental Design

On day one, of the assay a BD Falcon Tissue Culture 96-well plate was seeded with A549 cells passaged three days prior (lot #30Jul02, passage p+23), ($7.7 \times 10^3$ cells/well) and placed into a 37±2° C. incubator with a 5±2% $CO_2$ atmosphere overnight.

The next day, a dilution series of the test article were prepared and replicate wells were inoculated at levels ranging from $1.56 \times 10^3$ to $2.5 \times 10^4$ viral particles/well. Untreated A549 cells were used to serve as the mock sample. On day four of the assay wells were treated with a 10% Triton X-100 solution for analysis by ELISA to measure CEA concentration. For the ELISA, a microtiter plate was coated overnight with an anti-CEA capture antibody (abcam Carcino embryonic antigen CEA antibody [(NCRC16(AKA161))]). The wells were washed to remove unbound reactants, and the plate was blocked with a Phosphate Buffered Saline (PBS) solution containing 1% Tween 20 to fall within the range of the standard curve. After the blocking period, the wells were washed, and samples, controls, and standards were incubated in assigned triplicate wells. Unbound reactants were removed by washing, and a rabbit polyclonal antibody to a CEA detection antibody was added. After incubation, the wells were washed and incubated with 3,3',5,5'-tetramethylbenzidine (TMB), the peroxidase substrate. The substrate formed a colored product in the presence of the enzyme, reaction was stopped with 1 M phosphoric acid solution, and the absorbance was determined on a calibrated microplate reader. A calibration curve was generated from standards containing known concentrations of CEA, and the curve was used to determine the concentration of CEA in the samples. The quantity of CEA produced per virus particle was calculated from the concentration of CEA measured by ELISA, after adjusting for dilution and multiplicity of infection (MOI). The value determined in a similar manner for culture media alone was subtracted to compensate for background levels present in the media. The sample analysis is shown in Table 2.

TABLE 2

| Sample ID | $A_{450}$-$A_{540}$ Rep 1 | Rep 2 | Mean | SD | RSD | Blank Subtr | ELISA Dil'n Fact | CEA (ng/ml) | AVG CEA (ng/mL) | Total CEA (ng/mL) | CEA (ng/vp) |
|---|---|---|---|---|---|---|---|---|---|---|---|
| 10-002917 Well 1 at 2.5E+04 vp | 1.3387 0.7121 | 1.2977 0.6789 | 1.318 0.693 | 0.029 0.023 | 2.2% 3.4% | 1.244 0.622 | 1000 2000 | 7,731 7,797 | 7,691 | 7,621 | 0.30 |
| 10-002917 Well 2 at 2.5E+04 vp | 1.1717 0.6222 | 1.1329 0.6151 | 1.152 0.619 | 0.027 0.005 | 2.4% 0.8% | 1.078 0.545 | 1000 2000 | 6,563 6,975 | | | |
| 10-002917 Well 3 at 2.5E+04 vp | 1.1659 0.6131 | 2.0492 0.5946 | 1.608 0.604 | 0.625 0.013 | 38.9% 2.2% | 1.534 0.530 | 1000 2000 | 10,264 6,815 | | | |
| 10-002917 Well 1 at 1.25E+04 vp | 1.1051 0.5970 | 1.0759 0.5716 | 1.091 0.584 | 0.021 0.018 | 1.9% 3.1% | 1.017 0.510 | 1000 2000 | 6,169 6,602 | 6,049 | 5,979 | 0.48 |
| 10-002917 Well 2 at 1.25E+04 vp | 1.0652 0.5726 | 1.0376 0.5770 | 1.051 0.575 | 0.020 0.003 | 1.9% 0.5% | 0.977 0.501 | 1000 2000 | 5,919 6,506 | | | |
| 10-002917 Well 3 at 1.25E+04 vp | 0.9731 0.5049 | 0.9514 0.4970 | 0.962 0.501 | 0.015 0.006 | 1.6% 1.1% | 0.888 0.427 | 1000 2000 | 5,383 5,716 | | | |
| 10-002917 Well 1 at 6.25E+03 vp | 0.7601 0.4041 | 0.7210 0.3881 | 0.741 0.396 | 0.028 0.011 | 3.7% 2.9% | 0.667 0.322 | 1000 2000 | 4,141 4,566 | 4,286 | 4,216 | 0.67 |

TABLE 2-continued

| Sample ID | $A_{450}$-$A_{540}$ Rep 1 | Rep 2 | Mean | SD | RSD | Blank Subtr | ELISA Dil'n Fact | CEA (ng/ml) | AVG CEA (ng/mL) | Total CEA (ng/mL) | CEA (ng/vp) |
|---|---|---|---|---|---|---|---|---|---|---|---|
| 10-002917 Well 1 at 6.25E+03 vp | 0.7157 | 0.7068 | 0.711 | 0.006 | 0.9% | 0.637 | 1000 | 3,979 | | | |
| | 0.3893 | 0.3843 | 0.387 | 0.004 | 0.9% | 0.313 | 2000 | 4,465 | | | |
| 10-002917 Well 2 at 6.25E+03 vp | 0.7360 | 0.7188 | 0.727 | 0.012 | 1.7% | 0.653 | 1000 | 4,065 | | | |
| | 0.3995 | 0.3807 | 0.390 | 0.013 | 3.4% | 0.316 | 2000 | 4,499 | | | |
| 10-002917 Well 3 at 6.25E+03 vp | 0.8920 | 0.8878 | 0.890 | 0.003 | 0.3% | 0.816 | 500 | 2,483 | 2,690 | 2,620 | 0.84 |
| | 0.4573 | 0.4613 | 0.459 | 0.003 | 0.6% | 0.385 | 1000 | 2,631 | | | |
| 10-002917 Well 1 at 3.13E+03 vp | 0.8615 | 0.8544 | 0.858 | 0.005 | 0.6% | 0.784 | 500 | 2,393 | | | |
| | 0.4425 | 0.4406 | 0.442 | 0.001 | 0.3% | 0.368 | 1000 | 2,538 | | | |
| 10-002917 Well 2 at 3.13E+03 vp | 1.0518 | 1.0464 | 1.049 | 0.004 | 0.4% | 0.975 | 500 | 2,953 | | | |
| | 0.5519 | 0.5565 | 0.554 | 0.003 | 0.6% | 0.480 | 1000 | 3,141 | | | |
| 10-002917 Well 3 at 3.13E+03 vp | 1.8771 | 1.8616 | 1.869 | 0.011 | 0.6% | 1.795 | 100 | 1,351 | 1,271 | 1,201 | 0.77 |
| | 1.1963 | 1.1695 | 1.183 | 0.019 | 1.6% | 1.109 | 200 | 1,354 | | | |
| 10-002917 Well 1 at 1.56E+03 vp | 1.7435 | 1.7436 | 1.744 | 0.000 | 0.0% | 1.670 | 100 | 1,179 | | | |
| | 1.0960 | 1.0788 | 1.087 | 0.012 | 1.1% | 1.013 | 200 | 1,229 | | | |
| 10-002917 Well 2 at 1.56E+03 vp | 1.7801 | 1.8098 | 1.795 | 0.021 | 1.2% | 1.721 | 100 | 1,245 | | | |
| | 1.1041 | 1.1263 | 1.115 | 0.016 | 1.4% | 1.041 | 200 | 1,264 | | | |
| 10-002917 Well 3 at 1.56E+03 vp | 1.2509 | 1.2278 | 1.239 | 0.016 | 1.3% | 1.165 | 10 | 72 | 70 | 0 | — |
| | 0.7146 | 0.6952 | 0.705 | 0.014 | 1.9% | 0.631 | 20 | 79 | | | |
| 10-002917 Well 1 Mock | 1.2290 | 1.2382 | 1.234 | 0.007 | 0.5% | 1.160 | 10 | 71 | | | |
| | 0.7246 | 0.7133 | 0.719 | 0.008 | 1.1% | 0.645 | 20 | 80 | | | |
| 10-002917 Well 2 Mock | 0.9769 | 0.9750 | 0.976 | 0.001 | 0.1% | 0.902 | 10 | 55 | | | |
| | 0.5579 | 0.5454 | 0.552 | 0.009 | 1.6% | 0.478 | 20 | 63 | | | |
| 10-002917 Well 3 Mock | | | | | | | | | | | |

Example 5: Schedule, Dose, Route of Immunization Safety Data

Figure 8:
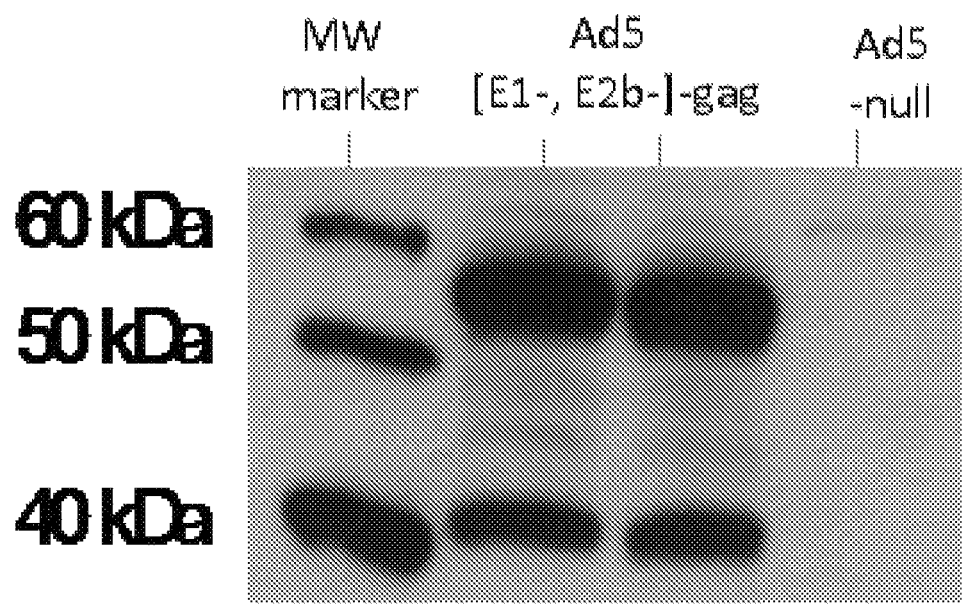
FIG. 8 is an immunoblot using a mouse monoclonal antibody against Gag and exemplifies Gag production by A549 cells infected with Ad5 [E1-, E2b-]-Gag. A549 whole cell lysate was infected with Ad5 [E1-, E2b-]-gag or Ad5-null at a multiplicity of infection (MOI) of 200 for 44 h. The upper band (55 kDa) comprises the gag precursor. The lower band (41 kDa) comprises the p17/p24 gag complex.

Initial pre-clinical studies were performed to evaluate and confirm that an Ad5 [E1-, E2b-] vector platform could express the antigen proteins on transfected cells. A-549 cells were transfected with vaccine platforms and analyzed by Western Blot Analysis (FIG. 8). Antigen proteins such as HIV-gag, HIV-pol, or HIV-nef were observed to be expressed on cells once they were transfected with the Ad5 [E1-, E2b-] vector platforms.

Figure 9:
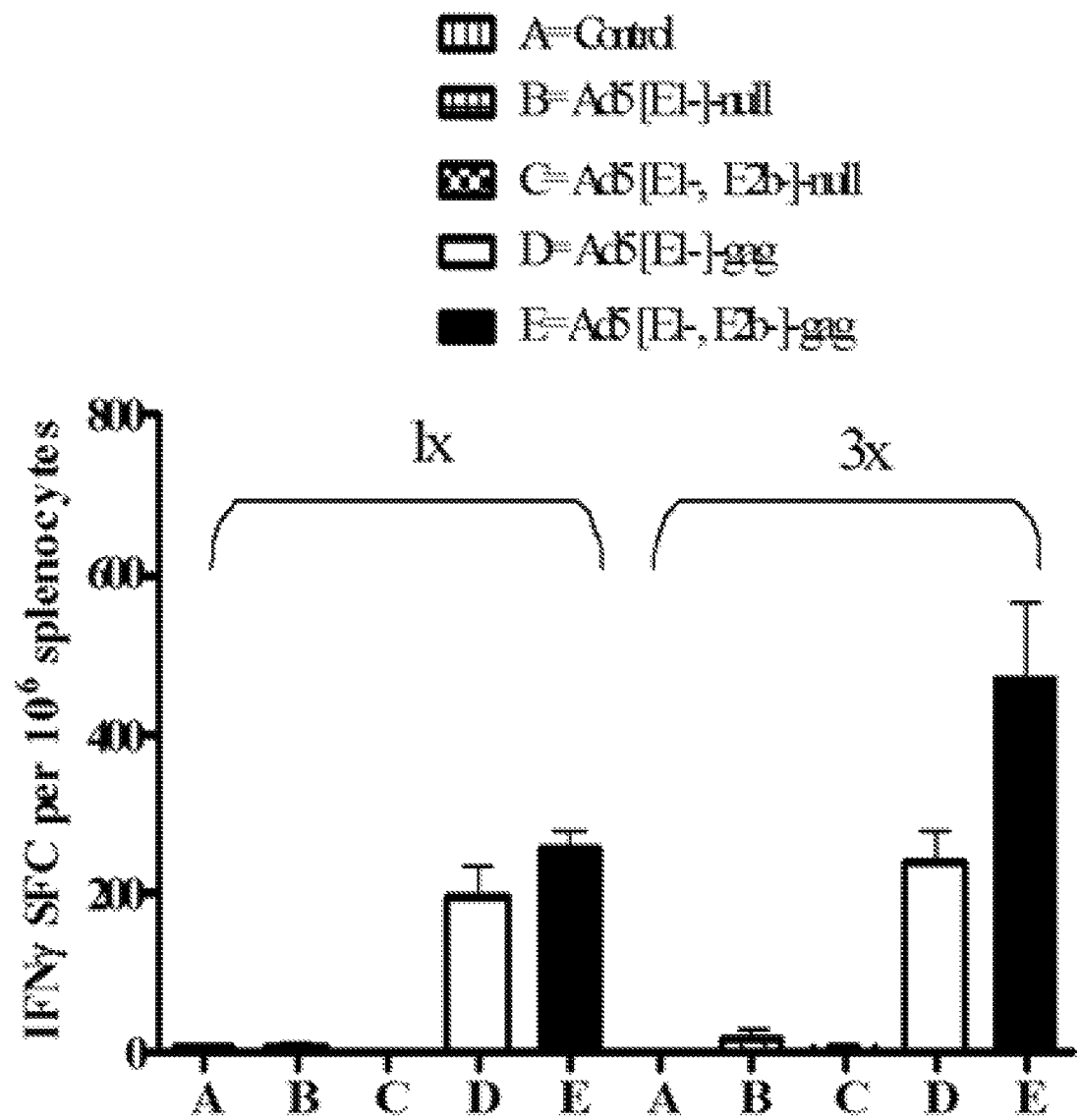
FIG. 9 is a graph exemplifying the effect of multiple immunizations on inducing a greater cell-mediated immunity (CMI) response. Ad5-Naïve BALB/C mice (n=5/group) were immunized once or three times at 14 day intervals with $1 \times 10^{10}$ Ad5 [E1-]-null VPs, Ad5 [E1-, E2b-]-null VPs, Ad5 [E1-]-Gag VPs, Ad5 [E1-, E2b-]-Gag VPs, or buffer alone. IFN-γ secretion from splenocytes was assessed by ELISpot analysis 14 days after the final immunization. Positive control splenocytes were exposed to Concanavalin A (Con A).

A dose response evaluation was performed using the Ad5 [E1-, E2b-] vector platform and demonstrated that $10^{10}$ virus particles (VP) is a dose that results in a desired CMI response against a transgene product in a murine model. CMI responses were assessed by utilizing an ELISpot assay to detect interferon-γ (IFN-γ) and IL-2 secreting cells (splenocytes) from spleens of mice. Furthermore, in murine and non-human primate (NHP) models, three immunizations using $10^{10}$ VP separated by two weeks to four weeks, respectively, resulted in the desired CMI responses. In mice, a greater degree of CMI responses were observed after multiple immunizations as compared with one immunization only (FIG. 9).

Figure 10A:
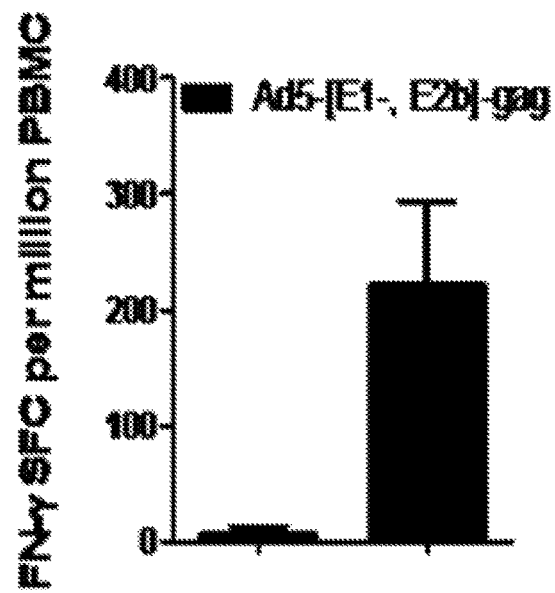
FIG. 10A exemplifies results of an ELISpot INF-γ analysis of peripheral blood mononuclear cells (PBMCs) from Cynomolgus Macaques (n=3) pre-immunized against wild type Ad5. Elevated levels of INF-γ induction (P<0.05) are shown. Positive control splenocytes were exposed to Con A.
Figure 10B:
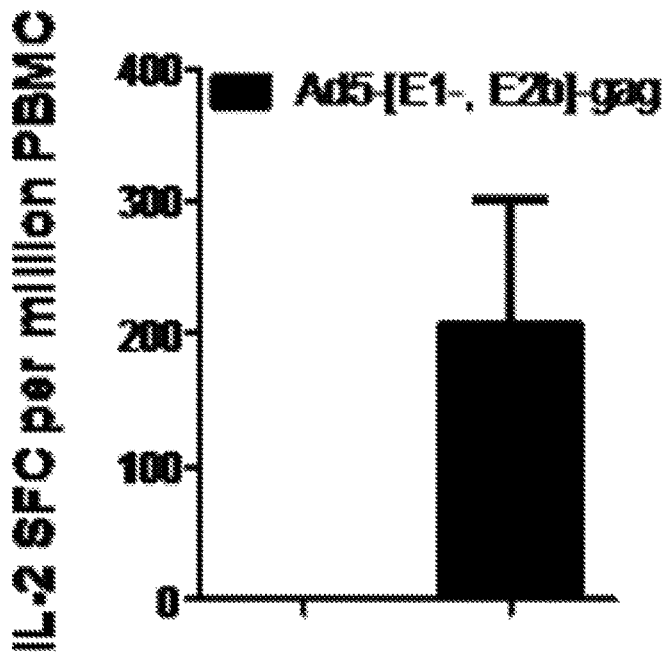
FIG. 10B exemplifies the results of an ELISpot IL-2 analysis from FIG. 10A.

In a NHP model, the animals were rendered Ad5 immune by injection with wild type Ad5 virus. When Ad5 neutralizing antibody titers reached 1:50 or greater, which confirmed that the animals were immune to Ad5, they were immunized intradermally three times at 30 day intervals with Ad5-[E1-, E2b-]-gag at a dose of $1 \times 10^{10}$ VP. 32 days after last vaccination and 124 days after the first immunization (wild type Ad5), the NAb titers were equal to or greater than 1:1000. After immunizations, the presence of robust CMI responses was detected, when peripheral blood mononuclear cells (PBMCs) of animals were assessed for IFN-γ and IL-2 secreting cells (FIG. 10).

In addition to the preliminary immunology studies performed in the initial vaccine trial in 3 NHP shown above, toxicity studies were also performed on the same NHP vaccinated with Ad5 [E1-, E2b-]-HIV gag. Animal temperatures and weights were assessed during the study period. The animals gained weight as they grew during the study period. No temperature differences were observed during the study period. Hematology studies were also performed on the vaccinated NHP. There appeared to be a small increase in the white blood cell count 2 weeks after the second vaccination that normalized thereafter.

Other than fluctuation in values, there appeared to be no other differences in hematology values during the course of the study. Chemistry values were also determined in the NHP during the course of the study. Alkaline phosphatase levels declined slightly during the course of the study but remained in the normal range. Albumin levels declined slightly during the course of the study but remained in the normal. There were no other differences observed in the blood chemistries during the course of the study. The route of immunization in this clinical study is chosen since the preponderance of DCs reside in the dermis.

Figure 11:
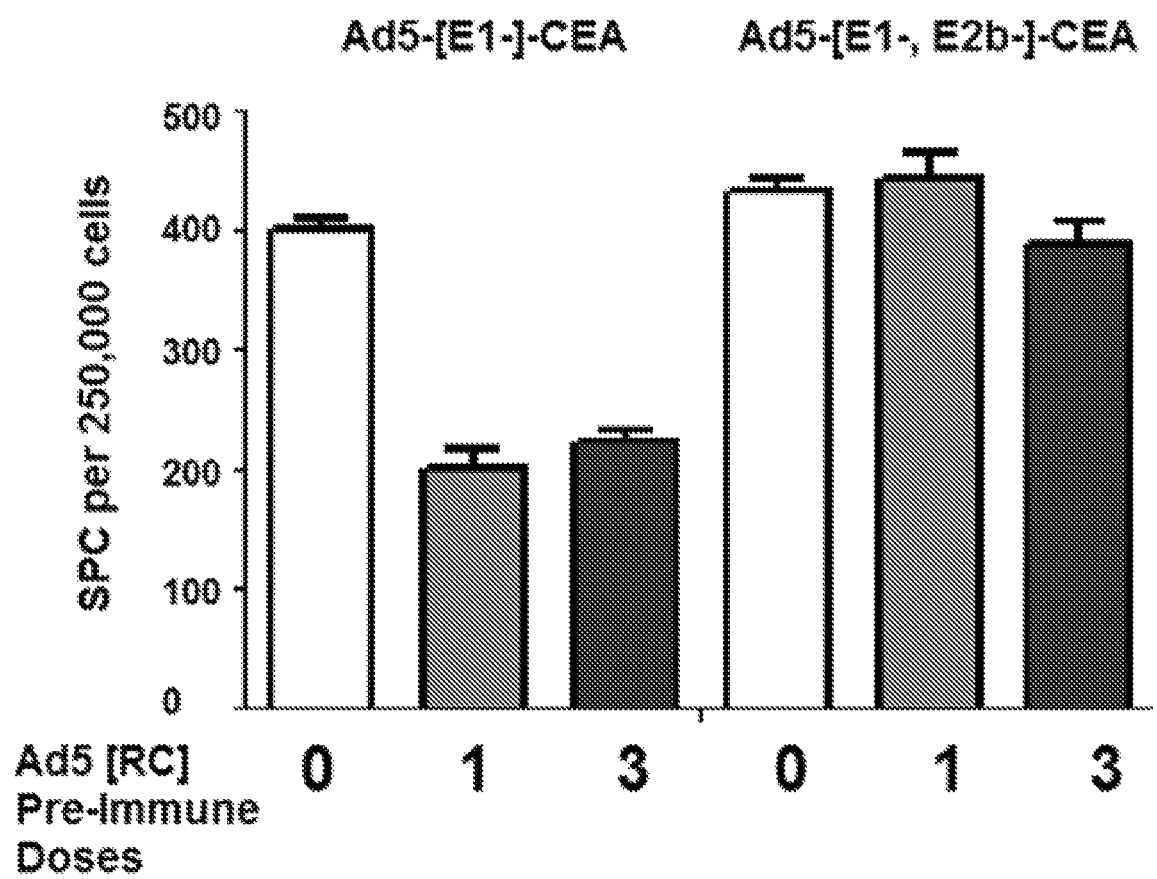
FIG. 11 exemplifies a graph depicting the number of spot-forming cells (SFCs) from mice vaccinated with recombinant Ad5 CEA expression vectors secreting IFN-γ. The reduction in SFCs from mice vaccinated with Ad5 [E1-, E2b-]-CEA compared to the reduction in SFCs from Ad5 [E1-]-CEA vaccinated mice is shown.

A desired level of CMI response was induced using the Ad5 [E1-, E2b-] platform employing CEA and other transgenes. Using an Ad5 [E1-, E2b-]-CEA vector platform, both non-Ad5 immune and Ad5 pre-immunized mice were injected three times with the vaccine. After immunizations, the splenocytes from mice were assessed by ELISpot for IFN-γ secreting cells. Elevated CMI responses were observed after immunizations and the levels of CMI responses were similar in both non-Ad5 immune and Ad5 pre-immunized mice (FIG. 11). These results indicate that robust CMI responses can be induced despite the presence of pre-existing Ad5 immunity. A III clinical study was designed using three immunizations separated by three weeks via a needle subcutaneous delivery method.

Rationale for Schedule, Dose, Route of Administration

A clinical study design flowed from pre-clinical and clinical studies in animals and humans using the Ad5 [E1-, E2b-] vector platform. A dose response evaluation using the Ad5 [E1-, E2b-] vector platform was performed demonstrating that $10^{10}$ VPs is a dose which results in a desired CMI response against a transgene product in a murine model. Furthermore, in murine and non-human primate (NHP) models three immunizations using $10^{10}$ VP separated by two to four weeks respectively resulted in the desired CMI. The route of immunization is chosen since a preponderance of dendritic cells (DCs) reside in the dermis. Using this premise, multiple murine and NHP studies were performed using a subcutaneous injection protocol. A desired level of circulating CMI was induced using the Ad5 [E1-, E2b-] platform employing CEA and other transgenes. A phase III clinical study followed using three immunizations separated by three weeks via a needle subcutaneous (SQ) delivery method continuing immunotherapy treatment every three months until removed from study for any reason including death.

Summary

The cDNA sequence containing the modified CEA with the CAP1(6D) mutation was produced. Clinical grade Ad5 [E1-, E2b-]-CEA(6D) was constructed and manufactured using the E.C7 cell line. A total of 34 patients (32 colorectal cancer patients, one bladder cancer patient, and one lung cancer patient) were entered into the Phase I/II clinical study under IND14325. The majority received all three scheduled immunotherapy treatments with Ad5 [E1-, E2b-]-CEA(6D). Five patients who stopped immunotherapy early did so due to significant disease progression. RECIST 1.0 criteria using CT or MRI scans obtained at baseline and after treatments were completed. Toxicity was assessed according to the National Cancer Institute Common Terminology Criteria for Adverse Events (CTCAE) version 4.0. Peripheral blood CEA levels, hematology, serum chemistries, and antinuclear antibody titers were compared between baseline and 9 weeks following the initiation of immunotherapy. Survival was measured from the day of the first immunization until death from any cause.

A total of 94 treatments were administered to patients. No dose limiting toxicity or serious adverse events (SAE) that resulted in treatment discontinuation at any treatment dose level. There was only one significant change in a blood hematology value. As a group, the basophil count was significantly lower at week 9, three weeks after treatment ended. However, this value remained in the normal range for basophil counts and, overall, there appeared to be no significant biological effect. With a median follow-up of 7.4 months, all 34 patients as a group (cohorts 1, 2, 3/phase II, and cohort 5) experienced a 12-month survival proportion of 41.4%. Of the 34 patients entered into the study, 28 patients received the three immunotherapy treatments and experienced a 12-month survival proportion of 55%. For the colorectal adenocarcinoma patients, 27 patients received the three immunotherapy treatments and experienced a 12-month survival proportion of 53%. A dose response to increasing levels of Ad5 [E1-, E2b-]-CEA(6D) was observed with the highest cell-mediated immune (CMI) responses occurring in patients that received the highest dose of $5 \times 10^{11}$ VP of Ad5 [E1-, E2b-]-CEA(6D). When the highest CEA specific CMI responses were compared with pre-existing or vector induced Ad5 NAb activity, there was no correlation between levels of CEA specific CMI and Ad5 neutralizing antibody (NAb) level. These clinical trial data lead us to believe that there is sufficient data to advance to a randomized Phase III trial for the treatment of metastatic colorectal adenocarcinoma with overall survival as the clinical endpoint.

Protocol Schema and Patient Treatment.

The clinical study was performed under an FDA-approved Investigational New Drug Exemption and registered at ClinicalTrials.gov. Participants were recruited from medical oncology clinics at Duke University Medical Center (NC) and Medical Oncology Associates (WA). Patients provided informed consent approved by the respective Institutional Review Boards (IRB). Eligibility requirements included metastatic cancer expressing CEA and adequate hematologic, renal, and hepatic function. Trial participants were required to have received treatment with standard therapy known to have a possible overall survival benefit or refused such therapy. Exclusion criteria included chemotherapy or radiation within the prior 4 weeks, history of autoimmune disease, viral hepatitis, HIV, or use of immunosuppressive agents. Patients who had been receiving bevacizumab or cetuximab for at least 3 months prior to enrollment were permitted to continue receiving these antibodies. Prior CEA immunotherapy was permitted. The study employed a standard 3+3 dose escalation strategy with dose limiting toxicities (DLT) defined as grade 3 or 4 major organ toxicity. The Ad5 [E1-, E2b-]-CEA(6D) doses were delivered to patients as follows: cohort 1: dose of $1 \times 10^9$ VP in 0.5 mL subcutaneously (SQ) in the same thigh every 3 weeks for 3 immunizations; cohort 2: dose of $1 \times 10^{10}$ VP in 0.5 mL SQ every 3 weeks for 3 treatments; cohort 3: dose of $1 \times 10^{11}$ in 0.5 mL SQ every 3 weeks for 3 treatments. Following establishment of the dose of $1 \times 10^{11}$ VP as safe, an additional 12 patients received Ad5 [E1-, E2b-]-CEA(6D) at this dose and schedule (phase II cohort). After completing the phase II cohort, an additional cohort (cohort 5) of six (6) patients received a dose of $5 \times 10^{11}$ VP in 2.5 mL SQ every 3 weeks for 3 treatments to determine safety of the highest achievable dose. PMBC were collected from patients just prior to the immunizations at weeks 0, 3, 6, and three weeks following the last treatment. The PBMC were frozen in liquid nitrogen until ELISpot assays were performed. In cohort 5, fresh PBMC were analyzed in preliminary flow cytometry assays for polyfunctional CD8+T lymphocytes.

Assessment of Clinical Activity.

Clinical activity was assessed according to Response Evaluation Criteria in Solid Tumors (RECIST 1.0 criteria) using computed tomography (CT) or magnetic resonance imaging (MRI) scans obtained at baseline and after treatments were completed. Toxicity was assessed according to the National Cancer Institute Common Terminology Criteria for Adverse Events (CTCAE) version 4. Peripheral blood CEA levels, hematology, serum chemistries, and antinuclear antibody titers were compared at baseline and 3 weeks following the final treatment. Survival was measured from the day of the first immunization until death from any cause Analysis of CMI Responses by ELISpot Assay.

An ELISpot assay for IFN-γ secreting lymphocytes was performed. Briefly, isolated PBMCs ($2 \times 10^5$ cells/well) from individual patient samples were incubated 36-40 h with a CEA peptide pool (15mers with 11aa overlap covering full length CEA with the 6D modification; 0.1 µg/well) to stimulate IFN-γ producing T-cells. CMI responses to Ad5 were determined after exposure of patient PBMC to Ad5-null (empty vector). Cells stimulated with concanavalin A (Con A) at a concentration of 0.25 μg/well served as positive controls. Colored spot-forming cells (SFC) were counted using an Immunospot ELISpot plate reader and responses were considered to be positive if 50 SFC were detected/$10^6$ cells after subtraction of the negative control and SFC were ≥2-fold higher than those in the negative control wells Determination of Ad5 Neutralizing Antibody (NAb) Titers.

Endpoint Ad5 NAb titers were determined. Briefly, dilutions of heat inactivated test sera in 100 μL of DMEM containing 10% fetal calf serum were mixed with $4\times10^7$ VP of Ad5 [E1-]-null and incubated for 60 minutes at room temperature. The samples were added to microwells containing HEK293 cells cultured in DMEM containing 10% heat inactivated calf serum at $2\times10^3$ cells/well for 24 hours at 37° C. in 5% $CO_2$. The mixture was incubated for an additional 72 hours at 37° C. in 5% $CO_2$. An MTS tetrazolium bioreduction assay was used to measure cell killing and endpoint Ad5 NAb titers. Endpoint titers with a value less than 1:25 were assigned a value of 0.

Statistics

Statistical analyses comparing immune responses were performed employing the Mann-Whitney test (PRISM, Graph Pad). Survival comparisons were performed employing Kaplan-Meier plots (PRISM, Graph Pad). Ad5 NAb titer and CEA-specific CMI were analyzed as continuous variables. The association of Ad5 NAb titer with change in CEA-specific CMI was tested with the Spearman correlation coefficient. The association of Ad5 NAb titer with survival was tested with the Wald test of the proportional hazards model. All tests used a 2-sided a of 0.05.

Demographics: All Patients.

Thirty two patients with metastatic colorectal cancer, one with lung cancer and one with bladder cancer, median age 58 (range 38-77), who had failed a median of three prior chemotherapeutic regimens (range: 2→5), had a median performance status of 90% (range 70%-100%), and had a median of three sites of metastatic disease (range 1-5), were enrolled (Table 3). The majority of patients were able to receive all three immunizations. Five patients who stopped immunizations prior to completion of all three treatments did so due to significant disease progression. Patient demographics are shown in Table 3.

TABLE 3

| Patient ID/ Cohort | Dose (VP) | Dx | Age | Sex | KPS | # prior CTx | Mets (# sites) | # doses | ++Status after tx | Survival (Mos) | base-line | CEA Week 9 |
|---|---|---|---|---|---|---|---|---|---|---|---|---|
| 002/1 | $10^9$ | C | 67 | M | 70 | >3 | 4 | 3 | PD | 3 (−) | 98.8 | 867.4 |
| 003/1 | $10^9$ | R | 63 | M | 100 | 5 | 2 | 3 | PD | 9 (−) | 195.1 | 472.2 |
| 004/1 | $10^9$ | C | 53 | F | 100 | 2 | 3 | 3 | PD | 11 (−) | 65.4 | 196.8 |
| 005/2 | $10^{10}$ | C | 60 | M | 100 | 3 | 3 | 3 | SD | 12 (+) | 2.5 | 3.7 (7 month follow-up) |
| 007/2 | $10^{10}$ | C | 52 | M | 80 | 2 | 5 | 1 | PD | 1 (−) | 120.7 | Not Done |
| 008/2 | $10^{10}$ | C | 42 | F | 100 | 3 | 3 | 3 | PD | 12 (+) | 3.0 | 3.1 |
| 010/2 | $10^{10}$ | C | 58 | M | 90 | 3 | 3 | 3 | PD | 12 (−) | 7.1 | 5.8 |
| 011/3 | $10^{11}$ | R | 50 | M | 100 | 5 | 1 | 3 | PD | 12 (+) | 21.0 | 25.9 |
| 012/3 | $10^{11}$ | C | 48 | M | 100 | 1 | 2 | 3 | PD | 12 (+) | 5.8 | 18.4 |
| 013/3 | $10^{11}$ | R | 62 | M | 100 | 3 | 2 | 2 | PD | 4 (−) | 172.9 | Not Done |
| 500/3 | $10^{11}$ | C | 55 | M | 80 | 4 | 3 | 3 | PD | 12 (+) | 3.2 | 11.5 |
| 015/3 | $10^{11}$ | C | 58 | F | 80 | 3 | 4 | 3 | PD | 10 (−) | 2.0 | 2.4 |
| 016/3 | $10^{11}$ | C | 53 | F | 100 | 3 | 4 | 3 | PD | 6 (−) | 6.1 | 12.7 |
| 017/3* | $10^{11}$ | R | 52 | F | 90 | 3 | 2 | 3 | PD | 3 (−) | 204.8 | Not Done |
| 501/II | $10^{11}$ | R | 54 | M | 90 | 1 | 1 | 3 | PD | 12 (+) | 17.1 | 96.4 |
| 502/II | $10^{11}$ | C | 66 | F | 80 | 1 | 2 | 2 | PD | 3 (−) | 2549.5 | Not Done |
| 503/II | $10^{11}$ | Bl | 73 | M | 70 | 4 | 5 | 1 | PD | 0.25 (−) | Not Done | Not Done |
| 019/II | $10^{11}$ | C | 69 | M | 90 | 1 | 3 | 3 | PD | 12 (+) | 264.3 | 638.0 |
| 020/II^ | $10^{11}$ | C | 59 | M | 100 | 5 | 4 | 3 | SD | 12 (+) | 2.2 | 2.2 |
| 021/II^ | $10^{11}$ | C | 51 | F | 100 | 4 | 3 | 3 | PD | 12 (+) | 2.0 | 2.7 |
| 506/II | $10^{11}$ | C | 77 | F | 80 | 2 | 2 | 3 | PD | 3 (−) | 16.5 | 38.2 |
| 023/II | $10^{11}$ | C | 51 | F | 100 | 3 | 4 | 3 | PD | 4 (−) | 32.4 | 211.4 |
| 504/II | $10^{11}$ | C | 57 | M | 90 | 3 | 3 | 3 | PD | 12 (+) | 424.7 | 2073.6 |
| 507/II | $10^{11}$ | R | 58 | M | 90 | 2 | 2 | 3 | PD | 12 (+) | <0.5 | 0.6 |
| 508/II | $10^{11}$ | L | 67 | M | 100 | 2 | 0 | 3 | Unknown | 12 (+) | 109.2 | Not Done |
| 024/II | $10^{11}$ | C | 67 | M | 90 | 2 | 3 | 3 | PD | 12 (+) | 7.8 | 6.4 |
| 025/II | $10^{11}$ | C | 62 | F | 100 | 2 | 4 | 3 | PD | 7 (−) | 391.2 | Not Done |
| 026/II | $10^{11}$ | C | 53 | M | 100 | 3 | 2 | 2 | PD | 4 (−) | 4057.5 | 7859.1 (treatment # 2) |
| 030/5 | $5\times10^{11}$ | C | 38 | M | 90 | 4 | 3 | 3 | PD | 8 (+) | 9.2 | 18.7 |
| 031/5 | $5\times10^{11}$ | R | 72 | F | 90 | 4 | 2 | 3 | SD | 7 (+) | 3.9 | 5.6 |
| 032/5@ | $5\times10^{11}$ | R | 53 | M | 90 | 4 | 3 | 3 | PD | 6 (−) | 31.9 | 75.4 |

TABLE 3-continued

| Patient ID/Cohort | Dose (VP) | Dx | Age | Sex | KPS | # prior CTx | Mets (# sites) | # doses | ++Status after tx | Survival (Mos) | baseline | CEA Week 9 |
|---|---|---|---|---|---|---|---|---|---|---|---|---|
| 033/5@ | $5 \times 10^{11}$ | R | 48 | F | 90 | >3 | 2 | 3 | PD | 5 (−) | 21.3 | 21.1 |
| 034/5 | $5 \times 10^{11}$ | C | 62 | M | 100 | 5 | 4 | 3 | PD | 6 (+) | 1.9 | 2.4 |
| 035/5 | $5 \times 10^{11}$ | C | 60 | F | 90 | 3 | 5 | 2 | PD | 2 (−) | 9.5 | Not Done |

Dx = diagnosis
(Bl = bladder cancer; C = colon cancer; L = lung cancer; R = rectal cancer)
KPS = Karnofsky Performance Status
*concurrent cetuximab;
^concurrent bevacizumab;
@concurrent panitumumab
++Represents disease status at 9 weeks post-initiation of immunizations
PD = Progressive Disease;
SD = Stable Disease
(+) Alive;
(−) Dead at last follow-up; survival rounded off to nearest month Demographics: Colorectal Adenocarcinoma Patients Thirty two patients, median age 57.5 (range 38-77) with metastatic colorectal cancer, who had failed a median of three prior chemotherapeutic regimens (range: 2→5), had a median performance status of 90% (range 70%-100%), and had a median of three sites of metastatic disease (range 1-5), were enrolled (Table 2). The majority was able to receive all three immunizations. Four patients who stopped immunizations early did so due to significant disease progression. The colorectal adenocarcinoma patient demographic compares favorably with previously published studies of patients with chemotherapy-refractory colorectal cancer.

Adverse Effects

A total of 94 immunization treatments were administered to all patients. There was no dose limiting toxicity and no serious adverse events that resulted in treatment discontinuation at any vaccine dose level. The most common toxicity (Table 3) was a self-limited, injection site reaction. Other reactions that occurred at a low frequency include fever, flu-like symptoms, anorexia, chills, nausea, and headache. These symptoms were also self-limiting and did not require intervention other than symptomatic measures such as acetaminophen.

Summary of Hematology, Chemistry, and ANA Values Pre and Post Treatment

Biological effects of Ad5 [E1-, E2b-]-CEA(6D) injections were monitored by recording blood hematology, chemistry, and anti-nuclear antibody (ANA) values of individual patients in case record forms (CRFs). Of 34 total patients entered into the trial, 28 received all three treatments with Ad5 [E1-, E2b-]-CEA(6D). For the 28 patients which received all three treatments, the blood hematology, chemistry, and ANA values at week 0 (prior to first treatment) were compared with those obtained at week 9 (three weeks after the third treatment). As shown in Table 4 below, there were no significant changes in chemistry or ANA values after treatments with Ad5 [E1-, E2b-]-CEA(6D). There was only one significant change in the blood hematology values. The basophil count was significantly (P=0.0403) lower at week 9 after treatments. However, this value remained in the normal range for basophil counts and overall there were no significant biological effects.

Clinical Outcomes

CEA levels at baseline and week 9 were assessed in patients. Among those with CEA levels available at baseline and follow-up, three (patients 010, 020, and 024) had no increase in CEA levels at the end of the immunization period while the remaining patients showed increased CEA levels.

There were three patients with stable disease who remained so during the 9 week study period. All other patients experienced some level of progressive disease (Table 2). Of the seven patients in cohorts 1 and 2, there were five deaths and two patients remained alive at 12 months following the initiation of immunization. Of the 21 patients in cohort 3 and phase II, there were 10 deaths and all the remaining 11 patients were alive at 12 months, respectively. Of the six patients in cohort 5, there were three deaths and three patients were alive at 6, 7, and 8 months, respectively.

Of the 34 patients enrolled into the study, two patients received one treatment, four patients received two immunization treatments, and the remaining 28 patients received all three immunization treatments. All patients were followed for survival and Kaplan-Meier plots and survival proportions performed (PRISM software). Patient deaths were determined by information gathered from the social security death index (SSDI) database and clinical charts.

Figure 12A:
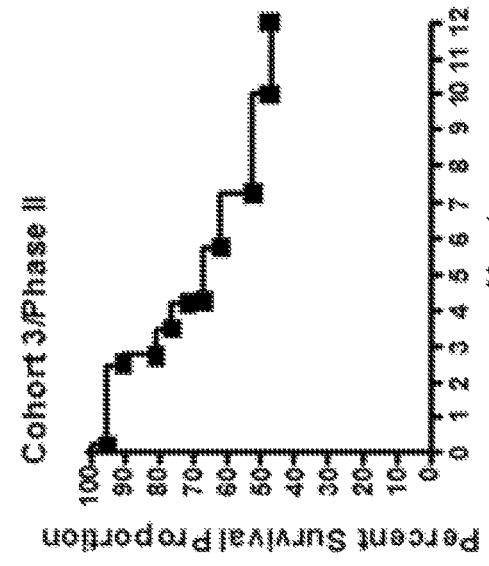
FIG. 12A exemplifies a Kaplan-Meier survival plot of 7 patients in cohorts 1 and 2 treated with Ad5 [E1-, E2b-]-CEA(6D).

The seven patients in cohorts 1 and 2 experienced a 12-month survival proportion of 29% (FIG. 12A). Of the patients in cohorts 1 and 2, patient 004 survived 11 months and received additional post-immunization treatments with bevacizumab, folfox, and xeloda. Patient 003 survived nine months and received irradiation treatment after Ad5 [E1-, E2b-]-CEA(6D) immunizations. Patient 005, alive at 12+ months, received irradiation treatment and entered another clinical trial after immunizations. Patient 010 survived up to 12 months and entered two clinical trials after immunizations. Patients 002, 007, and 008 received no further treatments after immunizations and survived 3, 1, and 12+ months, respectively.

Figure 12B:
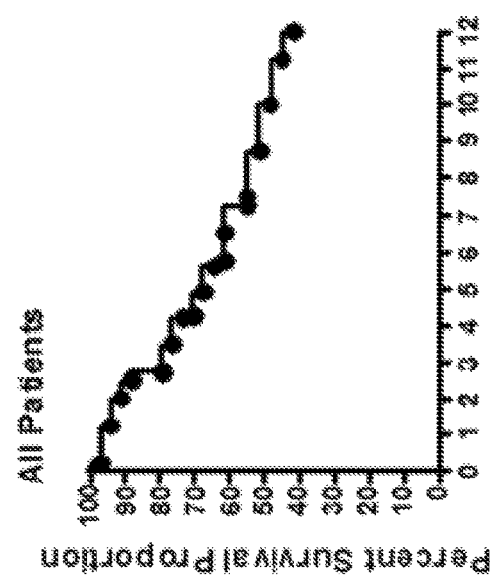
FIG. 12B exemplifies a Kaplan-Meier survival plot of 21 patients in cohort 3 and Ph II treated with Ad5 [E1-, E2b-]-CEA(6D).

The 21 patients in cohort 3 and phase II experienced a 12-month survival proportion of 48% (FIG. 12B). Of the patients in cohort 3 and phase II, one patient (017) received concurrent cetuximab during immunizations. Patients 020 and 021 received concurrent bevacizumab during immunizations. Patient 011 surviving over 12 months received radiation treatment after Ad5 [E1-, E2b-]-CEA(6D) immunizations. Patients 012 and 016 survived over 12 months and 6 months, respectively, and received additional chemotherapy treatment after immunizations. Patient 013 survived 4 months and received treatment with nexavar after immunizations. Patient 015 survived 10 months and received follow-on treatment with cetuximab. Patient 019 survived over 12 months and received treatment with bevacizumab and xeliri after protocol immunizations. Patient 020 survived over 12 months and received treatment with bevacizumab after immunizations. Patient 021 survived over 12 months and received follow-on treatment with bevacizumab and xeloda. Patient 500 survived over 12 months and received treatment with cetuximab and xeloda and entered a clinical trial after immunizations. Patient 501 survived over 12 months and received treatment with cetuximab and irinotecan after Ad5 [E1-, E2b-]-CEA(6D) immunizations. Patient 508 has survived over 12 months; however, further data on the characteristics of this patient was unable to be obtained. Patients 017, 023, 024, 025, 026, 502, 504, 506, and 507 received no further treatment after immunizations and survived 3, 4, 12+, 7, 4, 3, 12+, 3, and 12+ months, respectively (+means still alive at the time of writing).

Figure 12C:
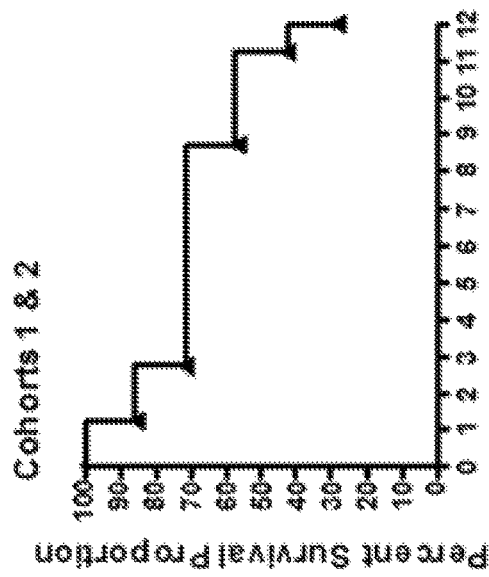
FIG. 12C exemplifies a Kaplan-Meier survival plot of 6 patients in cohort 5 treated with Ad5 [E1-, E2b-]-CEA(6D).

The six patients in cohort 5 experienced a 12-month survival proportion of 50% (FIG. 12C). Of the patients in this cohort, one patient (030) is currently alive at 8 months and received treatment with pazopanib and threshold 302 chemotherapy after Ad5 [E1-, E2b-]-CEA(6D) immunizations. Patient 031 is currently alive at 7 months and has not received further treatment after immunizations. Patient 032 received concurrent panitumumab, survived 6 months, and received treatment with folfox after immunizations. Patient 033 received concurrent panitumumab, survived 5 months with no additional therapy after immunizations. Patient 034 is currently alive at 6+ months and received radiation and treatment with xeloda after immunizations. Patient 035 received two treatments and survived 2 months.

Figure 12D:
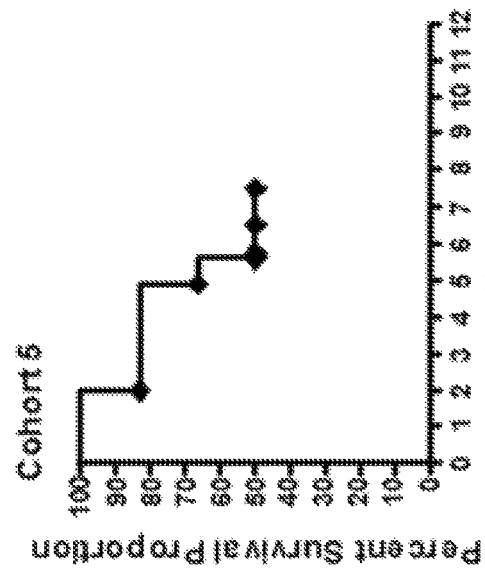
FIG. 12D exemplifies a Kaplan-Meier survival plot of all 34 patients treated with Ad5 [E1-, E2b-]-CEA(6D).
Figure 13B:
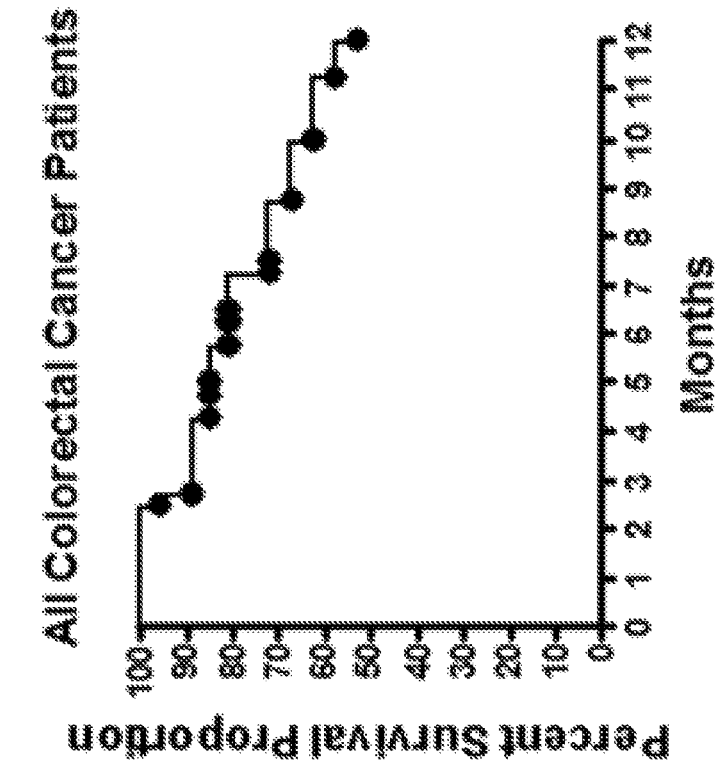
FIG. 13B exemplifies a Kaplan-Meier survival plot of 27 colorectal cancer patients treated with Ad5 [E1-, E2b-]-CEA (6D).
Figure 13A:
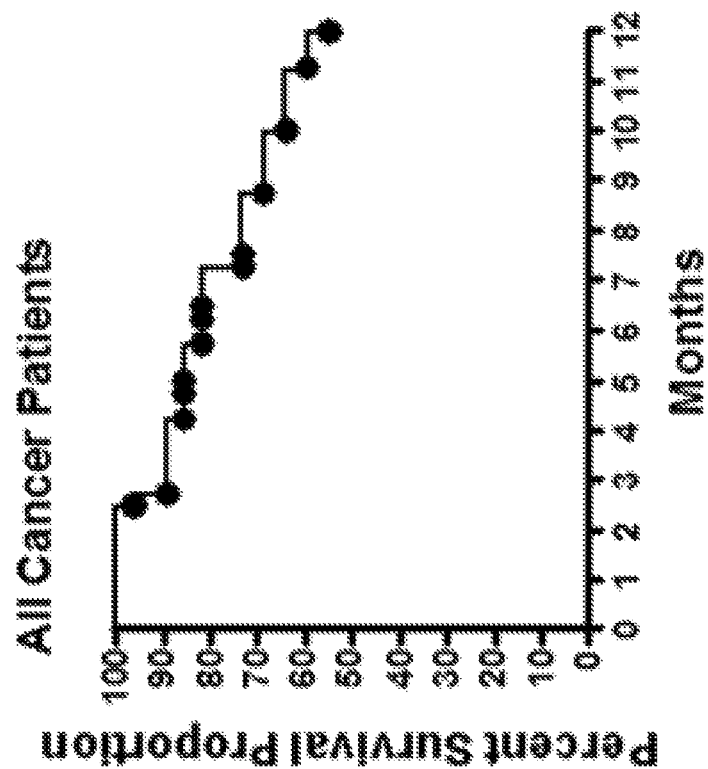
FIG. 13A exemplifies a Kaplan-Meier survival plot of 28 cancer patients treated three times with Ad5 [E1-, E2b-]-CEA(6D).

With a median survival of 7.4 months, all 34 patients as a group (cohorts 1, 2, 3/phase II, and cohort 5) experienced a 12-month survival proportion of 41% (FIG. 12D). Of the 34 patients entered in to the study, 28 patients received the three immunization treatments and experienced a 12-month survival proportion of 55% (FIG. 13A) with a median survival of 10.625 months. For the colorectal adenocarcinoma patients, 27 patients received the three immunization treatments and experienced a 12-month survival proportion of 53% (FIG. 13B) with a median survival of 10.00 months.

Evaluation of Immune Parameters in Treated Metastatic Colorectal Cancer Patients A secondary objective was to evaluate CEA specific immune responses following immunization treatments with the product.

Dendritic cells were generated from the peripheral blood mononuclear cells (PBMCs) of a prostate cancer patient (HLA-A2$^+$ and -A24$^+$) enrolled in a clinical trial employing a PSA-TRICOM vaccine in combination with ipilimumab; using PBMCs from this patient post-vaccination, individual T-cell lines specific for CEA, MUC1, and Brachyury were unable to be established. Briefly, PBMCs were isolated using lymphocyte separation medium gradient, resuspended in AIM-V medium ($2\times10^7$ cells) and allowed to adhere in a 6-well plate for 2 hours. Adherent cells were cultured for 5 days in AIM-V medium containing 100 ng/ml of recombinant human (rh) GM-CSF and 20 ng/ml of rhIL-4. The culture medium was replenished every 3 days.

Figure 14:
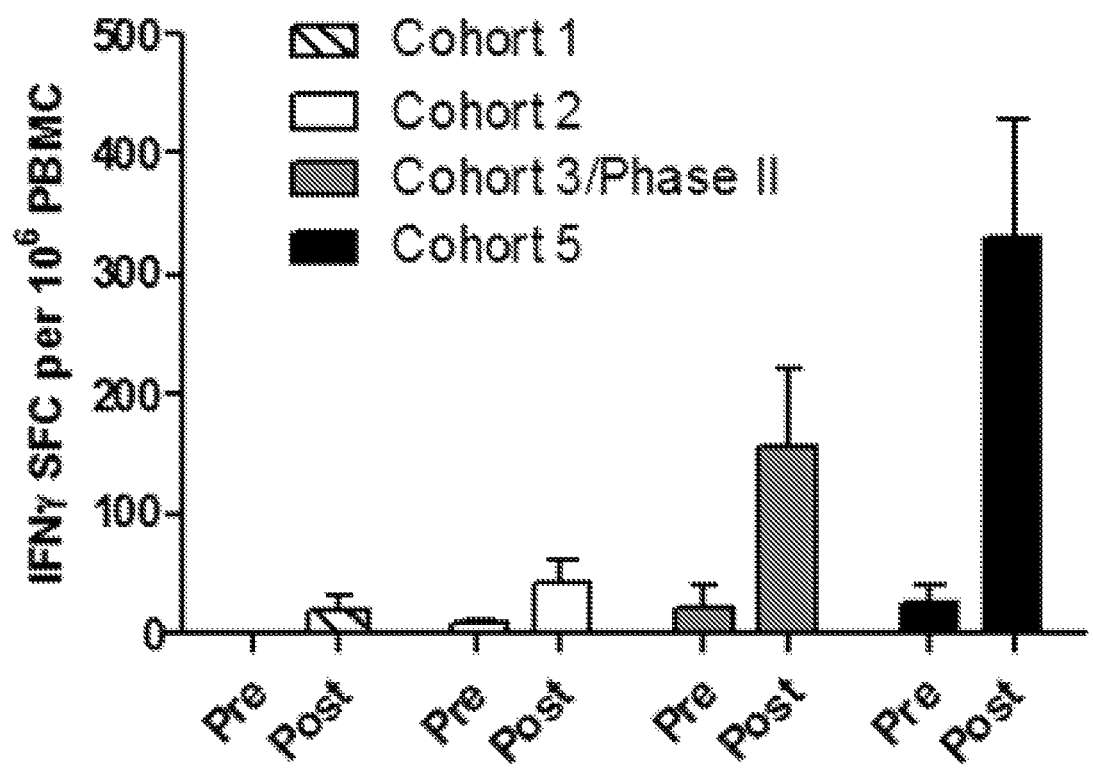
FIG. 14 exemplifies CEA-directed CMI responses in treated patients. CMI (IFN-γ secretion) was assessed at baseline (Pre) and after administrations of Ad5 [E1-, E2b-]-CEA(6D) (Post). The highest CMI responses (regardless of time point) observed in the patients after treatment revealed a dose response. The highest CMI levels occurred in patients that received the highest dose of $5 \times 10^{11}$ VP (Cohort 5). The CMI responses for Cohort 3/Phase II and Cohort 5 were significantly elevated (P=0.0002 and P=0.0317, respectively; Mann-Whitney test) as compared to their baseline (Pre) values. Specificity of the responses was demonstrated by the lack of reactivity with the irrelevant antigens β-galactosidase and HIV-gag. For positive controls, PBMCs were exposed to concanavalin A. Values=Mean±SEM for each Cohort.

As determined by ELISA, no antibody activity directed against CEA was observed. CMI responses in colorectal cancer patients treated in cohort 1, cohort 2, cohort 3/Phase II, and cohort 5 were assessed. PBMCs were isolated prior to Ad5 [E1-, E2b-]-CEA(6D) treatment and after all treatments as well as three weeks following the last treatment from patients. CEA specific ELISpot assays were performed on PBMCs to determine the numbers of interferon γ (IFN-γ) secreting lymphocytes after exposure to CEA peptides in vitro. The highest CMI responses during immunizations were determined, regardless of time point (weeks 3, 6, or 9) in the patients treated in cohort 1, cohort 2, cohort 3/Phase II, and cohort 5. This analysis revealed a dose response to increasing levels of product. The highest CMI levels occurred in patients that received the highest dose of $5\times10^{11}$VP (Cohort 5) (FIG. 14).

Determination of Induced CMI Responses to CEA.

Figure 15:
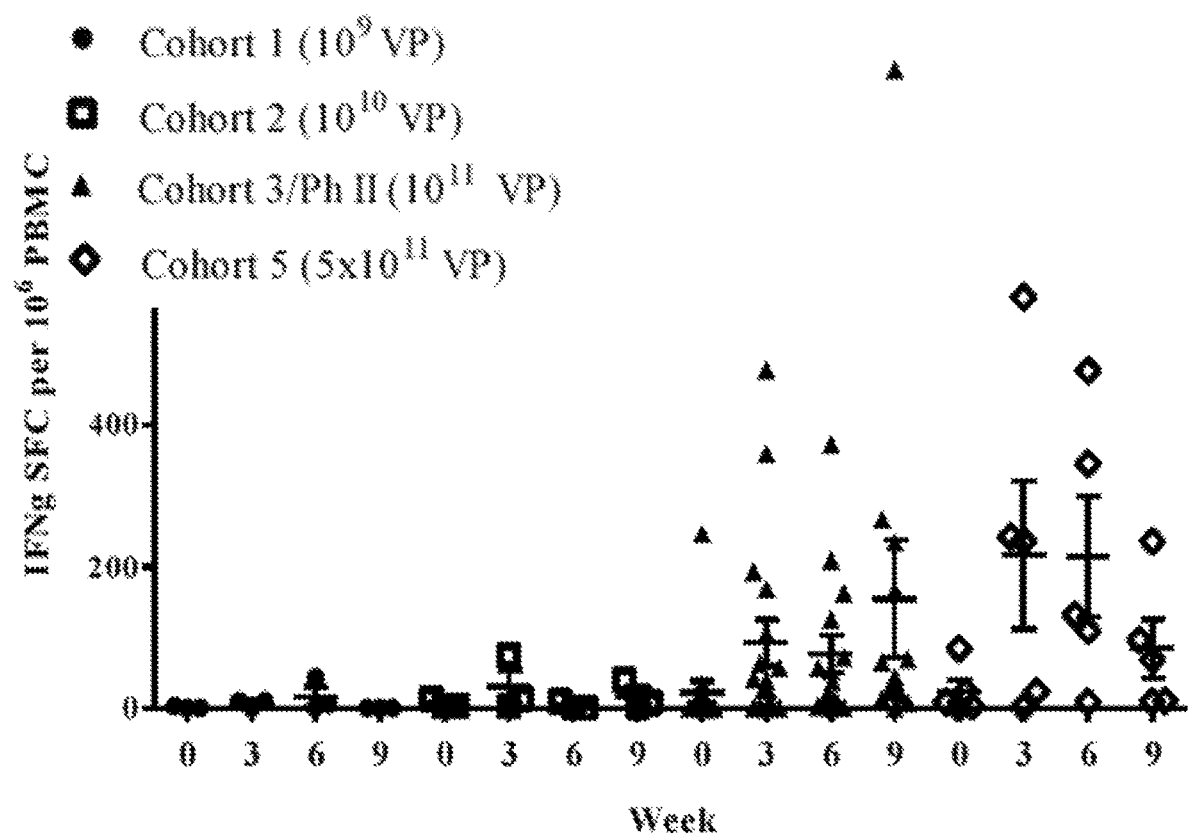
FIG. 15 exemplifies CEA directed CMI responses in treated patients. CMI (IFN-γ secretion) was assessed at baseline (week 0) and 3 weeks after the last immunotherapy (week 9) for patients in all 4-dose cohorts. A dose response is shown and the highest CMI level occurred in patients that received the highest dose. The CMI response with the highest dose was significantly elevated (P<0.02; Mann-Whitney test). Response specificity was shown by the lack of reactivity with the irrelevant antigens β-galactosidase and HIV-gag. Positive control PBMCs were exposed to Con A.

ELISpot analysis was performed on cryopreserved PBMC samples drawn before each immunization and after completion of the final immunization to assess CEA-specific CMI responses. A dose response effect with the highest magnitude CEA-specific CMI responses occurring in patients who received the highest dose of Ad5 [E1-, E2b-]-CEA(6D) was observed (FIG. 14). Of the doses received, 0/3 (0%) patients in cohort 1 exhibited positive CEA-directed CMI responses, 1/4 (25%) patients in cohort 2 exhibited positive CEA-directed CMI responses, 10/19 (53%) patients in cohort 3/phase II exhibited positive CEA-directed CMI responses, and 4/6 (67%) patients in cohort 5 exhibited positive CEA-directed CMI responses. The time course of induction of CEA-specific CMI (FIG. 15) demonstrated that there may be plateau in the magnitude of CEA CMI prior to the last dose. In the largest group of patients who received the same dose (cohort 3 plus phase II), a significant increase over baseline in the average CEA-directed CMI responses at the 6 week evaluation ($P<0.05$, Mann-Whitney test) was observed, averaging 94 SFC/106 PBMC, which increased further by the 9 week evaluation (FIG. 15). One patient (patient ID 13) had a highly elevated baseline CEA-specific immune response (1100 SFC) and had elevated CMI at week six (2305 SFC) but did not return for 9-week evaluation and was not included in CEA CMI analysis.

Figure 16B:
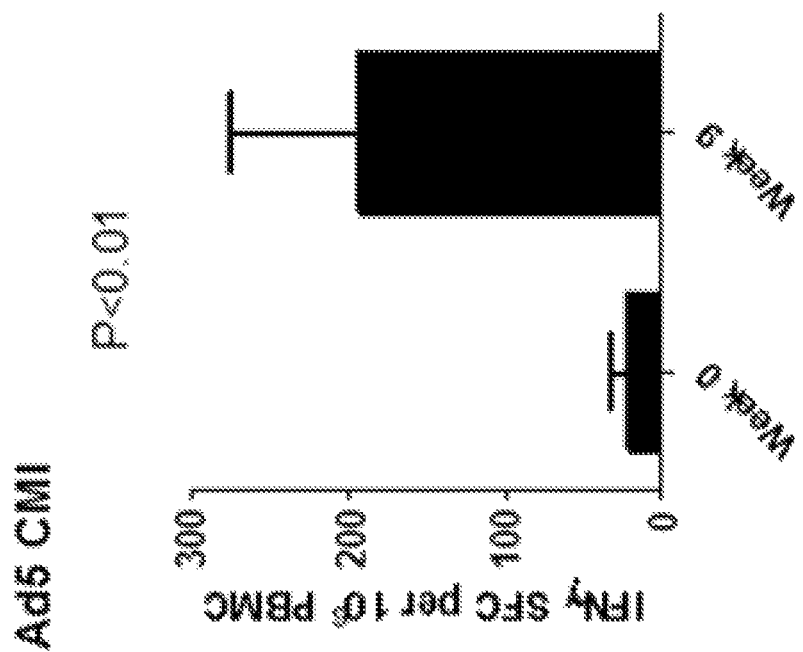
FIG. 16B exemplifies Ad5 immune responses in patients receiving immunizations with Ad5 [E1-, E2b-]-CEA(6D) vaccine. CMI responses were determined in patients at baseline (week 0) and 3 weeks (week 9) after the third immunization. The number of IFN-γ secreting PBMCs from patients specific for Ad5 was determined by ELISpot. The Ad5 CMI responses were significantly elevated at week 9 (P<0.01; Mann-Whitney test).
Figure 16A:
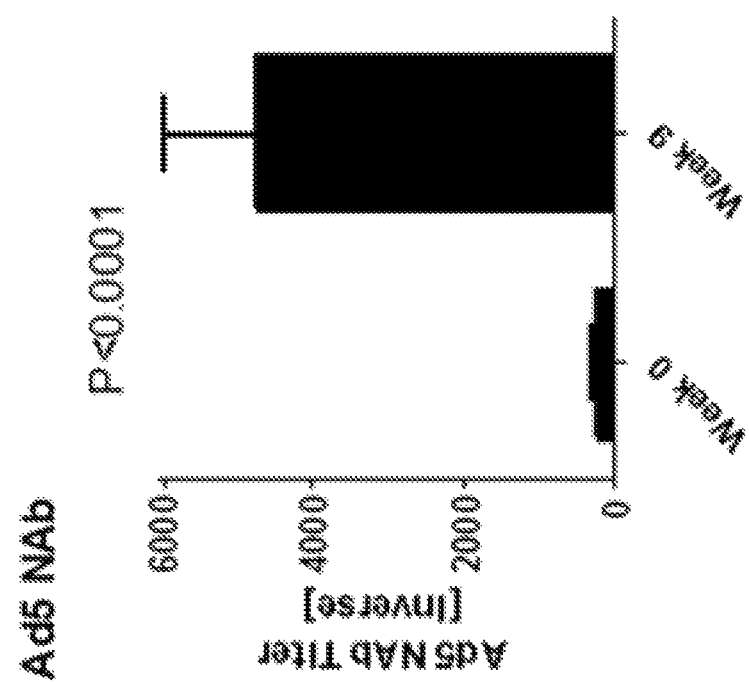
FIG. 16A exemplifies Ad5 immune responses in patients receiving immunizations with Ad5 [E1-, E2b-]-CEA(6D) vaccine. Ad5 NAb titers to Ad5 were determined in patients at baseline (week 0) and 3 weeks (week 9) after the third immunization. The number of IFN-γ secreting PBMCs from patients specific for Ad5 was determined by ELISpot. The Ad5 NAb titers were significantly elevated at week 9 (p<0.0001; Mann-Whitney test).

Ad5 NAb and CMI against Ad5 was also measured and correlated with CEA-specific CMI. Each patient had their serum and PBMC sample tested at baseline (prior to treatment) and at 9 weeks after completion of 3 treatments. Nineteen of 31 colorectal cancer patients (61%) tested in this study had Ad5 neutralizing activity in serum samples prior to the onset of treatment with Ad5 [E1-, E2b-]-CEA(6D). The mean pre-treatment Ad5 NAb titer value obtained among all patients was 1:189±1:71 SEM (geometric mean 1:21) and the mean pre-treatment Ad5 NAb titer among seropositive patients was 1:308±1:108 (geometric mean 1:146). Analysis of serum samples from patients who received 3 immunizations revealed Ad5 NAb titers that were significantly increased ($P<0.0001$, Mann-Whitney test) by week 9 (mean 1:4767±1:1225 SEM (geometric mean 1:1541) when compared with their respective baseline values (FIG. 16). Analysis of PBMC for CMI responses to Ad5 also revealed a significant increase ($P<0.01$, Mann-Whitney test) in Ad5 directed CMI responses after immunizations with Ad5 [E1-, E2b-]-CEA(6D) (FIG. 16).

Comparison of week 9 CEA-directed CMI responses from patients with low baseline pre-existing Ad5 immunity (Ad5 NAb ≥200) verses those with high baseline Ad5 immunity (Ad5 NAb>200) revealed no significant difference in immune responses ($P>0.4$, Mann Whitney test) (FIG. 17). Further, when the highest CEA specific CMI responses were compared with pre-existing or vector induced Ad5 NAb activity, there was no correlation between levels of CEA CMI and Ad5 NAb activity (FIG. 17). These data indicate that immunizations with Ad5 [E1-, E2b-]-CEA(6D) were not only able to overcome self-tolerance, but were also able to induce CEA-specific immune responses in colorectal cancer patients despite the presence of pre-existing and/or immunization induced Ad5 immunity. Together these clinical trial data support the advancement to a Phase III clinical trial with overall survival as the primary endpoint.

Adverse Effects, Hematology, Chemistry, and ANA Values

In this Phase trial, the Ad5 [E1-, E2b-]-CEA(6D) was demonstrated to be suitable to be manufactured to scale, as well be easily and repeatedly administered by conventional subcutaneous injection techniques. The most common adverse effects were site of injection reactions and flu-like symptoms consisting of fever, chills, headache, and nausea. There was no impact on blood hematology or serum chemistries and, overall, the treatments were well tolerated. Specifically, no SAE were noted, and no treatments were stopped due to adverse events, indicating that a dose limitation to use of Ad5 [E1-, E2b-]-CEA(6D) in this clinical application had not been met.

These data suggest that patients with advanced colorectal cancer which are treated with Ad5 [E1-, E2b-]-CEA(6D) do not have serious adverse effects and may experience extension of life even if they have pre-existing immunity to Ad5. The results of this trial were encouraging enough to advance to a large, randomized, single agent trial. The observation that some of the patients experienced an increase of CMI which is dose dependent, indicates that this may play a role in their clinical outcome.

TABLE 4

Adverse Events

| Adverse Events | # Events | Unrelated/ Unlikely | Possible | Probably Definite | *Grade | **% Incidence |
|---|---|---|---|---|---|---|
| Injection Site Reaction | 21 | | | 21 | G1 (19): G2 (2) | 22.3 |
| Pain (all types) | 17 | 17 | | | G1 (8); G2 (7); G3 (2) | 18.1 |
| Fever | 10 | 4 | 2 | 4 | G1 (7); G2 (3) | 10.6 |
| Flu-like symptoms | 10 | 3 | 5 | 2 | G1 (9); G2 (1) | 10.6 |
| Fatigue | 8 | 6 | 2 | | G1 (5); G2 (2); G3 (1) | 8.5 |
| Shortness of Breath | 6 | 6 | | | G1 (3); G2 (3) | 6.4 |
| Anorexia | 5 | 4 | 1 | | G1 (3); G2 (2) | 5.3 |
| Chills | 5 | 1 | 1 | 3 | G1 (5) | 5.3 |
| Nausea | 5 | 4 | 1 | | G1 (5) | 5.3 |
| Constipation | 5 | 5 | | | G1 (3); G2 (2) | 5.3 |
| Edema | 5 | 5 | | | G1 (3); G2 (2) | 5.3 |
| Vomiting | 4 | 4 | | | G1 (4) | 4.3 |
| Hypertension | 3 | 3 | | | G1 (2); G2 (1) | 3.2 |
| Anemia | 3 | 3 | | | G1 (1); G2 (1); G3 (1) | 3.2 |
| Cough | 2 | 2 | | | G1 (2) | 2.1 |
| Depression | 2 | 2 | | | G1 (2) | 2.1 |
| Diarrhea | 2 | 2 | | | G1 (2) | 2.1 |
| Headache | 2 | 1 | 1 | | G1 (2) | 2.1 |
| Hypoalbuminemia | 2 | 2 | | | G1 (1); G2 (1) | 2.1 |
| Hypokalemia | 2 | 2 | | | G1 (1); G2 (1) | 2.1 |
| Pleural Effusion | 2 | 2 | | | G2 (1); G3 (1) | 2.1 |
| Alkaline Phosphatase Increase | 2 | 2 | | | G1 (1); G3 (1) | 2.1 |
| Myalgia | 2 | | 2 | | G1 (2) | 2.1 |
| Night Sweats | 2 | 2 | | | G1 (1); G2 (1) | 2.1 |
| Sleep | 2 | 2 | | | G1 (2) | 2.1 |
| Low Magnesium | 2 | 2 | | | G1 (2) | 2.1 |
| Abdominal Bloating | 1 | 1 | | | G1 (1) | 1.1 |
| Abdominal Distention | 1 | 1 | | | G3 (1) | 1.1 |
| Abdominal Swelling | 1 | 1 | | | G2 (1) | 1.1 |
| Abdominal Wound | 1 | 1 | | | G2 (1) | 1.1 |
| ALT Increase | 1 | 1 | | | G1 (1) | 1.1 |
| AST Increase | 1 | 1 | | | G2 (1) | 1.1 |
| Biliary Obstruction | 1 | 1 | | | G3 (1) | 1.1 |
| Bowel Obstruction | 1 | 1 | | | G3 (1) | 1.1 |
| Cold | 1 | 1 | | | G1 (1) | 1.1 |
| Dyspnea | 1 | 1 | | | G3 (1) | 1.1 |
| Dysuria | 1 | 1 | | | G1 (1) | 1.1 |
| Frequent Urination | 1 | 1 | | | G1 (1) | 1.1 |
| GI Disorder | 1 | 1 | | | G3 (1) | 1.1 |
| Extra Pyramidial Movements | 1 | 1 | | | G1 (1) | 1.1 |
| Insomnia | 1 | 1 | | | G1 (1) | 1.1 |
| Herpes Simplex | 1 | 1 | | | G1 (1) | 1.1 |
| Hypotension | 1 | 1 | | | G1 (1) | 1.1 |
| Loss of Appetite | 1 | 1 | | | G1 (1) | 1.1 |
| Low White Blood Cells | 1 | 1 | | | G1 (1) | 1.1 |
| Numbness/Sensation in Fingertips | 1 | 1 | | | G1 (1) | 1.1 |

TABLE 4-continued

Adverse Events

| Adverse Events | # Events | Unrelated/ Unlikely | Possible | Probably Definite | *Grade | **% Incidence |
|---|---|---|---|---|---|---|
| Onset of Menses | 1 | 1 | | | G1 (1) | 1.1 |
| Poor Quality Sleep | 1 | 1 | | | G1 (1) | 1.1 |
| Presyncope | 1 | 1 | | | G2 (1) | 1.1 |
| Pruritis | 1 | 1 | | | G1 (1) | 1.1 |
| Rash-Right Lower Eye Lid | 1 | 1 | | | G1 (1) | 1.1 |
| Red/Swelling Right Upper Eyelid | 1 | 1 | | | G1 (1) | 1.1 |
| Renal Calculi | 1 | 1 | | | G2 (1) | 1.1 |
| Runny Nose | 1 | | 1 | | G1 (1) | 1.1 |
| Shallow Breathing | 1 | 1 | | | G1 (1) | 1.1 |
| Skin Rash | 1 | 1 | | | G1 (1) | 1.1 |
| Vaginal Discharge | 1 | 1 | | | G1 (1) | 1.1 |
| Concentration | 1 | | | | G1 (1) | 1.1 |
| Weight Loss | 1 | 1 | | | G2 (1) | 1.1 |
| Arthritis Joint Inflammation | 1 | 1 | | | G1 (1) | 1.1 |
| Flushing | 1 | | | 1 | G1 (1) | 1.1 |
| Acute Renal Failure | Disease progression | | | | G3 (1) | 1.1 |

*Parenthesis ( ) indicates numbers of events.
**Based on 94treatments

TABLE 5

Hematology, Chemistry, and ANA values

| | Week 0 value (Mean ± SEM) | Week 9 value (Mean ± SEM) |
|---|---|---|
| Hematology Test | | |
| Hgb (g/dL) | 13.09 ± 0.313 | 12.48 ± 0.413 |
| Hct (%) | 39.63 ± 0.875 | 37.92 ± 1.140 |
| Plts (×109/L) | 225.1 ± 20.76 | 247.3 ± 23.57 |
| WBC (×103/mm3) | 6.81 ± 0.532 | 8.21 ± 0.741 |
| Neutrophils (%) | 64.46 ± 2.068 | 67.28 ± 3.268 |
| Lymphocytes (%) | 23.23 ± 1.874 | 18.34 ± 2.071 |
| Monocytes (%) | 8.86 ± 0.462 | 7.68 ± 0.569 |
| Eosinophils (%) | 3.97 ± 0.677 | 3.16 ± 0.685 |
| Basophils (%) | 0.52 ± 0.056 | 0.38 ± 0.048 |
| Chemistry Test | | |
| Na (mEq/L) | 139.2 ± 0.424 | 137.9 ± 0.718 |
| K (mEq/L) | 3.90 ± 0.085 | 3.80 ± 0.073 |
| Cl (mEq/L) | 105.0 ± 0.561 | 103.3 ± 1.061 |
| CO2 (mEq/L) | 27.8 ± 0.374 | 27.63 ± 0.458 |
| BUN (mg/dL) | 17.0 ± 1.136 | 17.1 ± 1.611 |
| Creatinine (mg/dL) | 0.81 ± 0.046 | 0.86 ± 0.054 |
| Glucose (mg/dL) | 121.8 ± 7.458 | 123.5 ± 7.885 |
| Ca (mg/dL) | 8.84 ± 0.075 | 8.87 ± 0.073 |
| Total protein (g/dL) | 6.95 ± 0.078 | 6.67 ± 0.100 |
| Albumin (g/dL) | 3.78 ± 0.085 | 3.62 ± 0.113 |
| AST (U/L) | 31.71 ± 3.846 | 31.88 ± 3.506 |
| ALT (U/L) | 27.83 ± 4.228 | 25.67 ± 3.414 |
| Alkaline phosphatase (U/L) | 107.0 ± 13.30 | 124.0 ± 17.40 |
| Bilirubin (mg/dL) | 0.78 ± 0.071 | 0.75 ± 0.079 |
| *ANA Test | | |
| Titer | 103.3 ± 51.04 | 123.3 ± 50.56 |

*Values represent inverse of the titer and are from patients with positive values.

Discussion

Adenoviral vectors have significant potential for use as cancer therapeutic vaccines because of their propensity to induce robust adaptive immune responses specifically against transgene products in general. However, recombinant first generation Ad5 [E1-] vectors used in homologous prime/boost regimens have been greatly limited in their potential efficacy due to the presence of pre-existing Ad5 immunity as well as vector induced immunity. Specifically, Ad5-directed immunity mitigates immune responses to TAA that have been incorporated into earlier generation Ad5 [E1-] based platforms. The Ad5 [E1-, E2b-] platform utilized in the present study was intended to accommodate a homologous prime-boost regimen, by avoiding presentation of antigens that are the targets of pre-existing Ad5 immunity.

CEA was investigated as a transgene to be incorporated into the new Ad5 [E1-, E2b-] vector platform for use as a cancer therapeutic vaccine. CEA expression in adults is normally limited to low levels in the gastrointestinal epithelium, whereas, CEA is over-expressed in adenocarcinomas of the colon and rectum and in many breast, lung, and pancreas cancers. The HLA A2 restricted CAP1(6D) modification of CEA was chosen because compared with the wild type CAP1 epitope, CAP1(6D) can enhance the sensitization of CTLs and has been included in recent CEA-based vaccine constructs. Although HLA type was not tested for because a full length CEA was used that is not HLA-restricted, A*0201 is the allele observed most frequently in Caucasians (allele frequency 0.2717) and is common in other populations. However, it is possible to test patients for HLA type and utilize the relationship between HLA type and clinical and/or CMI responses.

Multiple subcutaneous immunizations employing three administrations of a single dose level ($1 \times 10^{10}$ VP) of this class of Ad5 vaccine expressing the TAA CEA, (Ad5 [E1-, E2b-]-CEA(6D)) were tested in a pre-clinical murine model of CEA expressing cancer. In mice with pre-existing Ad5 immunity, the induction of potent CEA directed CMI responses were demonstrated that resulted in anti-tumor activity and noted that these CMI and anti-tumor responses were significantly greater than those responses induced by a current generation Ad5 [E1-] based vector vaccine. In additional animal models (both cancer and infectious disease targeted) it was demonstrated that multiple subcutaneous immunizations with vaccines based on the new Ad5 [E1-, E2b-] platform induce CMI responses that were superior to those of current generation Ad5 [E1-] based vaccines, can overcome the barrier of Ad5 immunity, and can be utilized in multiple immunization regimens requiring a generation of robust CMI responses. The greatest magnitude of CEA-directed CMI responses occurred in patients receiving the highest dose of the vector. A CEA-directed CMI response was induced in a dose-responsive manner despite the presence of pre-existing and/or vector induced Ad5 immunity. No CEA directed antibody responses were observed either pre- or post-vaccination employing an ELISA technique. A population of polyfunctional CD8+ T-cells (those that secrete more than one cytokine when activated) after immunizations were also observed, a sign of greater functionality of T-cells induced by the vaccine. These data support the use of the Ad5 [E1, E2b-]-CEA(6D) vector in homologous prime-boost regimens designed to induce and increase CEA-directed CMI responses in patients with advanced colorectal adenocarcinoma, as well as any number of other vaccine amenable diseases or applications.

As compared to earlier generation Ad5 [E1-] vectors containing deletion in the early 1 (E1) gene region, the Ad5 [E1-, E2b-] vector platform with additional deletions in the early 2b (E2b) gene region exhibits significantly reduced inflammatory responses directed at the vector. This can result in longer transgene expression and a reduction in elimination of transgene expressing cells (e.g., antigen presenting cells) that would otherwise occur due to induced inflammatory responses. Since Ad5 late gene antigen expression is significantly reduced as compared to earlier generation Ad5 platforms, this could enable the Ad5 [E1-, E2b-] platform to evade Ad5 immune mediated neutralizing activity for significantly longer periods of time resulting in greater longevity and amplification of TAA expression. In addition, an E2b gene product, a polymerase, is a target of human cellular memory immune responses to Ad5 infection and its elimination from the vaccine could be furthering its capability in the setting of pre-existing Ad5 immunity. Without being bound by theory, the extended and/or greater expression of TAA by the vector in this milieu could result in a more effective immune response against the target antigen. However, it is also possible that this vector configuration produces better transgene expression, different biodistribution, or different innate/adaptive immune effects that impact the effectiveness of this vector, rather than escape from pre-existing immunity.

Of interest is the observation that treated patients in this study exhibited favorable survival probability. Overall, all 25 patients treated at least 2 times with Ad5 [E1-, E2b-]-CEA(6D) exhibited a 12-month survival probability of 48% and this was achieved despite the presence of significant levels of pre-existing Ad5 neutralizing antibody titers. Without being bound by theory, by engaging the patient's immune system, active immunotherapeutics, such as Ad5 [E1-, E2b-]-CEA(6D), could induce continuous immunologic anti-tumor responses over a long period of time that could result in a "deceleration" or alteration in specific aspects of the rapid growth rate or spread of the tumor not measured by standard response assessments. Indeed, slower tumor progression in Ad5 immune mice harboring established CEA-expressing tumors following treatment with Ad5 [E1-, E2b-]-CEA(6D) were observed. Moreover, it has been noted that overall survival might be the only true parameter for determination of clinical efficacy of any potential cancer (immune) therapy.

Example 6: Clinical Study of CEA (6D) Immunotherapeutic in Metastatic Colorectal Cancer Phase I/II clinical trial in mCRC using Ad5 [E1-, E2b-]-CEA(6D): The objectives of this first in man phase I/II dosing trial were to assess safety, evaluate CEA-specific immune responses in mCRC patients, and obtain data on overall survival. The trial was performed under FDA-approved IND14325 and registered at ClinicalTrials.gov (NCT01147965). The Ad5 [E1-, E2b-]-CEA(6D) doses were administered subcutaneous (sc) every 3 weeks for 3 treatments as follows: Cohort 1 (3 patients) received $10^9$ VP each treatment; Cohort 2 (3 patients) received $10^{10}$ VP; Cohorts 3/4 (21 patients) received $10^{11}$ VP; and Cohort 5 (5 patients) received $5 \times 10^{11}$ VP.

Patient Demographics:

Thirty-two mCRC patients with CEA expressing cancers were enrolled into the study. The 32 mCRC patients enrolled had a median age 57.5 (range 38-77), had failed a median of three prior chemotherapeutic regimens (range: 2-5), had a median performance status of 90% (range 70%-100%), and had a median of three sites of metastatic disease (range 1-5). The majority of patients received all three immunizations. Patients who stopped immunizations early did so due to significant disease progression. The mCRC demographics compared favorably with previously published studies with chemotherapy-refractory mCRC.

Adverse Effects:

There were no dose-limiting toxicities and no serious adverse events that resulted in treatment discontinuation at any dose level. The most common toxicity was a self-limited, injection site reaction. The blood hematology, chemistry, and anti-nuclear antibody (ANA) values at week 0 (before the first treatment) were compared with those obtained at week 9. There were no biologically relevant changes in chemistry, hematology, or ANA values.

Clinical Outcomes:

Patients were washed out from anti-cancer treatments for 30 days prior to immunotherapy. Both Kras wild type and mutated patients were enrolled.

The mCRC patients were followed for long-term survival and Kaplan-Meier survival plots performed (PRISM software). Events were determined from the social security death index database and clinical charts. Median overall survival was 11 months and overall survival was 30% at 18 months and 20% at 29 months (FIG. 18).

Immune Responses:

A secondary objective was to evaluate CEA-specific immune responses during immunotherapy. Again, since the mCRC patients represented the highest number of patients treated, immunogenicity studies were performed on them. As determined by ELISA there was no detectable antibody activity directed against CEA in serum samples.

CMI responses of mCRC patients treated in all cohorts were assessed. Peripheral blood mononuclear cells (PBMC) were isolated from patients before and after each immunotherapy treatment, as well as three weeks after the last treatment. CEA-specific ELISpot assays were performed on PBMC as previously described to determine the number of IFN-γ-secreting cells (SFC) after exposure to CEA peptides. The highest CMI responses during immunizations, regardless of time point (weeks 3, 6, or 9) were determined. This analysis revealed a dose-response relationship with increasing levels of vaccine (FIG. 19); the highest CMI levels occurred in patients who received the highest dose of $5 \times 10^{11}$ VP (Cohort 5) and the responses were observed despite the presence of pre-existing Ad5 immunity in a majority (61%) of patients. Analysis of serial PBMC samples over time indicated that CEA directed CMI responses were induced and increased over the course of 3 immunizations (FIG. 20).

Briefly, CMI (IFN-γ secretion) was assessed at baseline (Pre) and after administrations of Ad5 [E1-, E2b-]-CEA(6D)

(Post). The highest CMI responses (regardless of time point) observed in the patients after treatment revealed a dose response. The highest CMI levels occurred in patients receiving the highest dose (Cohort 5) and was significantly elevated (P<0.02; Mann-Whitney test). Specificity of the responses was demonstrated by lack of reactivity with irrelevant antigens β-galactosidase and HIV-gag. For positive controls, PBMCs were exposed to concanavalin A. Values=Mean±SEM (FIG. 19).

Briefly, CMI (ELISpot IFN-γ SFC) responses in immunized mCRC patients were assessed at weeks 0, 3, 6, and 9. Note the increase in CMI responses during immunizations. Values=Mean SEM (FIG. 20).

Additional Immune Analyses on Treated mCRC Patients Using Flow Cytometry.

Flow cytometry testing on PBMC from a patient with high CMI activity (>1000 ELISpot IFN-γ SFC) after exposure to CEA peptides revealed CD8+/IFN-γ+ cells (3.5%), CD8+/IFN-γ+/TNF-α+ cells (1.0%), CD4+/IFN-γ+ cells (0.4%), and CD4+/IFN-γ+/TNF-α+ cells (0.2%) demonstrating that polyfunctional cells were present.

Patient PBMC samples were also tested for HLA-A2 positivity by flow cytometry and 63% of the samples tested were HLA-A2 positive. When the highest CMI response level achieved per patient was assessed in association with the presence of HLA-A2, there was no significant difference observed between HLA-A2+ and HLA-A2-patients (264.6±119.0 IFN-γ SFC versus 165.6±108.1 IFN-γ SFC).

To assess the induction of cytolytic T lymphocyte (CTL) responses, ELISpot assays for granzyme B activity were performed. Granzyme B is a key mediator of target cell death via the granule-mediated pathway and the release of granzyme B by cytolytic lymphocytes upon effector-target interaction is an indicator of CTLs. The granzyme B ELISpot assay is a superior alternative to the 51Cr-release assay since it is significantly more sensitive and provides an estimation of cytotoxic effector cell frequency.

Increased granzyme B activity in PBMCs were observed after immunization (FIG. 16). Importantly, in an extended follow-up on PBMC samples from 5 mCRC patients, CMI responses were observed to decrease after immunizations (FIG. 22) were stopped indicating that further "booster" immunizations may be required to maintain induced CEA directed CMI activity.

Briefly, CTL responses (ELISpot granzyme B secreting SFC) were assessed pre (week 0) and post (week 6-9) treatment. Responses increased after immunizations (P<0.05 i). Values=Mean±SEM (FIG. 21).

Briefly, PBMC samples from 5 patients as assessed by ELISpot IFN-γ SFC. CMI responses peaked at week 9 and decreased by week 26 after treatment was stopped (FIG. 22).

These data indicate that multiple homologous immunizations with Ad5 [E1-, E2b-]-CEA(6D) induce CEA-specific CMI immune responses in patients despite pre-existing Ad5-neutralizing activity. These data further indicate that importantly, there was minimal toxicity and a favorable overall survival profile was observed. Finally, the results indicate that the novel Ad5 [E1-, E2b-]-CEA(6D) gene delivery/expression platform can overcome tolerance to TAA and generate significant CMI responses to CEA in the setting of naturally acquired Ad5-specific immunity.

Example 7: GLP Production of Clinical Grade Multi-Targeted Vaccine

This example shows the production of clinical-grade multi-target vaccine using good laboratory practice (GLP) standards. Previously, the Ad5 [E1-, E2b-]-CEA(6D) product was produced using a 5 L Cell Bioreactor under GLP conditions in accordance with good manufacturing practice standards. This example shows that the Ad5 [E1-, E2b-]-mMUC1-C and the Ad5 [E1-, E2b-]-Brachyury products can be produced in a 5 L Cell Bioreactor using a similar approaches.

Briefly, vials of the E.C7 manufacturing cell line will be thawed, transferred into a T225 flasks, and initially cultured at 37° C. in 5% $CO_2$ in DMEM containing 10% FBS/4 mM L-glutamine. After expansion, the E.C7 cells will be expanded using 10-layered CellSTACKS (CS-10) and transitioned to FreeStyle serum-free medium (SFM). The E.C7 cells will be cultured in SFM for 24 hours at 37° C. in 5% $CO_2$ to a target density of $5 \times 10^5$ cells/mL in the Cell Bioreactor. The E.C7 cells will then be infected with Ad5 [E1-, E2b-]-mMUC1-C or Ad5 [E1-, E2b-]-Brachyury, respectively, and cultured for 48 hours.

Mid-stream processing will be performed in an identical manner as that used to prepare clinical grade Ad5 [E1-, E2b-]-CEA(6D) product under IND14325. 30 minutes before harvest, Benzonase nuclease will be added to the culture to promote better cell pelleting for concentration. After pelleting by centrifugation, the supernatant will be discarded and the pellets re-suspended in Lysis Buffer containing 1% Polysorbate-20 for 90 minutes at room temperature. The lysate will then be treated with Benzonase and the reaction quenched by addition of 5M NaCl. The slurry will be centrifuged and the pellet discarded. The lysate will be clarified by filtration and subjected to a two-column ion exchange procedure.

To purify the vaccine products, a two-column anion exchange procedure will be performed. A first column will be packed with Q Sepharose XL resin, sanitized, and equilibrated with loading buffer. The clarified lysate will be loaded onto the column and washed with loading buffer. The vaccine product will be eluted and the main elution peak (eluate) containing Ad5 [E1-, E2b-]-mMUC1-C or Ad5 [E1-, E2b-]-Brachyury carried forward to the next step. A second column will be packed with Source 15Q resin, sanitized, and equilibrated with loading buffer. The eluate from the first anion exchange column will be loaded onto the second column and the vaccine product eluted with a gradient starting at 100% Buffer A (20 mM Tris, 1 mM $MgCl_2$, pH 8.0) running to 50% Buffer B (20 mM Tris, 1 mM $MgCl_2$, 2M NaCl, pH 8.0). The elution peak containing Ad5 [E1-, E2b-]-mMUC1-C or Ad5 [E1-, E2b-]-Brachyury will be collected and stored overnight at 2-8° C. The peak elution fraction will be processed through a tangential flow filtration (TFF) system for concentration and diafiltration against formulation buffer (20 mM Tris, 25 mM NaCl, 2.5% (v/v) glycerol, pH 8.0). After processing, the final vaccine product will be sterile filtered, dispensed into aliquots, and stored at ≤−60° C. A highly purified product approaching 100% purity is typically produced and similar results for these products are predicted.

The concentration and total number of VP product produced will be determined spectrophotometrically. Product purity is assessed by HPLC. Infectious activity is determined by performing an Ad5 hexon-staining assay for infectious particles using kits.

Western blots will be performed using lysates from vector transfected A549 cells to verify mMUC1-C or Brachyury expression. Quality control tests will be performed to determine that the final vaccine products are mycoplasma-free, have no microbial bioburden, and exhibit endotoxin levels less than 2.5 endotoxin units (EU) per mL. To confirm immunogenicity, the individual vectors will tested in mice as described below (Example 8).

Example 8: Immunogenicity of Multi-Targeted CEA, MUC1, T Viral Vector

This example shows immunogenicity results using the multi-targeted vaccine directed to CEA, MUC1 and T (Brachyury). Each viral vector product was tested for purity, infectivity, and antigen expression, as described herein and each passed these criteria.

Vaccination and Splenocyte Preparation

Female C57BL/6 mice (n=5) were injected s.c. with $10^{10}$ VP of Ad5 [E1-, E2b-]-Brachyury or Ad5 [E1-, E2b-]-CEA or Ad5 [E1-, E2b-]-MUC1 or a combination of $10^{10}$ VP of all three viruses at a ratio of 1:1:1 (Tri-Ad5). Control mice were injected with $3 \times 10^{10}$ VP of Ad-null (no transgene insert). Doses were administered in 25 µl of injection buffer (20 mM HEPES with 3% sucrose) and mice were vaccinated three times at 14-day intervals. Fourteen days after the final injection spleens and sera were collected. Sera were frozen at −20° C. Splenocyte suspensions were generated by gently crushing the spleens through a 70 µM nylon cell strainer (BD Falcon, San Jose, Calif.). Red cells were removed by the addition of red cell lysis buffer (Sigma-Aldrich, St. Louis, Mo.) and the splenocytes were washed twice and resuspended in R10 (RPMI 1640 supplemented with L-glutamine (2 mM), HEPES (20 mM), penicillin 100 U/ml and streptomycin 100 µg/ml, and 10% fetal bovine serum. Splenocytes were assayed for cytokine production by ELISPOT and flow cytometry.

Immunogenicity Studies:

Previous studies assess induced immunity generated by the multi-targeted vaccine mixture. Immunization with Ad5 [E1-, E2b-] vectors is dose-dependent and $1 \times 10^{10}$ VP per dose was routinely used. Groups (N=5) of C57Bl/6 mice were used.

This is study C57Bl/6 mice were injected subcutaneously 3 times at 2-week intervals with tri-immunization comprising $3 \times 10^{10}$ viral particles (VP) Ad5 [E1-, E2b-]-null (empty vector controls) or with $3 \times 10^{10}$ VP containing a 1:1:1 mixture of Ad5 [E1-, E2b-]-CEA(6D), Ad5 [E1-, E2b-]-mMUC1-C, and Ad5 [E1-, E2b-]-Brachyury.

Two weeks after the last immunization CMI activity was determined employing ELISpot assays for IFN-γ secreting cells (SFC) after exposure of splenocytes to CEA, MUC1, or Brachyury peptide pools, respectively.

Significant CMI responses to were detected in immunized mice (FIG. 23). Flow cytometry utilizing intracellular cytokine staining was performed on spleen cells after exposure to CEA peptides to assess the quantity of activated CD4+ and CD8+ T-cells.

Briefly, CMI responses against CEA, MUC1, and Brachyury as assessed by ELISpot assays for IFN-γ secreting splenocytes (SFC) were detected in multi-targeted immunized mice but not control mice (injected with Ad5-Null empty vector). Specificity of the ELISpot assay responses was confirmed by lack of reactivity to irrelevant SIV-nef or SIV-vif peptide antigens. A positive control included cells exposed to concanavalin A (Con A, data not shown). Values=Mean±SEM (FIG. 23).

ELISpot Assay

Brachyury-, CEA- and MUC1-specific IFN-γ- or IL-2-secreting T cells were determined by ELISpot assay from freshly isolated mouse splenocytes, as described above. Briefly, $2 \times 10^5$ splenocytes were stimulated with 0.2 µg/well of overlapping 15-mer peptides in a single pool derived from Brachyury or CEA, or MUC1. Cells were stimulated with Con A at a concentration of 0.0625 µg/per well as a positive control and overlapping 15-mer complete peptides pools derived from SIV-Nef and SIV-Vif were used as irrelevant peptide controls. The numbers of SFCs were determined using an Immunospot ELISpot plate reader and results were reported as the number of SFCs per $10^6$ splenocytes.

TNF-α and IFN-γ expressing polyfunctional CD4+ and CD8+ cells were detected in immunized but not control splenocytes (FIG. 24). Testing was also performed on sera to detect induced CEA antibody using a previously described quantitative ELISA assay with purified CEA protein. Polyfunctional CD8+(top) and CD4+(bottom) cells expressing IFN-γ and TNF-α in mice immunized with the multi-targeted vaccine (right) but not in controls injected with Ad5-null (left). Specificity of the responses was confirmed by lack of reactivity to media alone or irrelevant SIV-nef or SIV-vif peptides. Values=Mean±SEM (FIG. 24).

Significant antibody responses to CEA were detected in immunized but not control mice (FIG. 8). To determine the level of complement dependent cellular cytotoxicity (CDCC), a CDCC test was performed using murine MC38-CEA target cells. Significant CDCC activity was detected in sera of immune, but not control mice (injected with Ad5-null) (FIG. 25). Significant (P<0.0001) CEA antibody (left) and CDCC (right) responses were induced in mice immunized with the multi-targeted vaccine but not in control mice. Values=Mean±SEM (FIG. 25).

Intracellular Cytokine Stimulation

Splenocytes were prepared as indicated for above. Stimulation assays were performed using $1 \times 10^6$ live splenocytes per well in 96-well U-bottom plates. Pools of overlapping peptides spanning the entire coding sequences of Brachyury, CEA and MUC1 were synthesized as 15-mers with 11-amino acid overlaps and lyophilized peptide pools were dissolved in DMSO. Similarly constructed peptide pools corresponding to SIV-Vif and SIV-Nef served as off-target controls. Splenocytes in R10 media (RPMI 1640, 10% fetal bovine serum, and antibiotics) were stimulated by the addition of peptide pools at 2 µg/mL/peptide for 6 h at 37° C. and 5% $CO_2$, with protein transport inhibitor (GolgiStop, BD) added 2 h into the incubation. Stimulated splenocytes were then stained for lymphocyte surface markers CD8a and CD4, fixed, permeabilized, and then stained for the intracellular accumulation of IFN-γ and TNFα. Antibodies against mouse CD8α, CD4, IFN-γ, and TNFα were used and staining was performed in the presence of anti-CD16/CD32. Flow cytometry was performed and analyzed in BD Accuri C6 Software.

Complement-Dependent Cytotoxicity Assay (CDC)

MC38-CEA2 tumor cells were cultured overnight at a density of $2 \times 10^4$ cells per well in 96-well tissue culture microplates. Pooled heat inactivated mouse sera were added at a 1:50 dilution and incubated at 37° C. for 1 hour. Rabbit serum was then added at a 1:50 dilution as a source of complement and cells were incubated an additional 2.5 hours at 37° C. Cell culture supernatants were assayed using Promega Cytotox 96 non-radioactive cytotoxicity assay, according to the manufacturer's instructions. Percent lysis of MC38-CEA2 cells was calculated by the formula % lysis= (experimental−target spontaneous)/(target maximum−target spontaneous)×100%.

Anti-Tumor Immunotherapy Studies:

Studies were conducted to test the anti-tumor capability of Ad5 [E1-, E2b-]-based tri-vaccines in immunotherapy studies in mice with established CEA, MUC1, or Brachyury expressing tumors, respectively. In this study the anti-tumor activity of the individual components of the Ad5 [E1-, E2b-]-based tri-vaccine was assessed.

Groups (n=7) of C57Bl/6 mice were injected subcutaneously in the right flank with 5×10⁵ CEA, MUC1, and/or Brachyury expressing murine tumor cells. After palpable tumors were detected, mice were treated by 3 subcutaneous injections with 1×10¹⁰ VP each of Ad5 [E1-, E2b-]-null (no transgene, e.g., empty vector), Ad5 [E1-, E2b-]-CEA(6D), Ad5 [E1-, E2b-]-mMUC1-C, and/or Ad5 [E1-, E2b-]-Brachyury, respectively. Tumor volumes were calculated and tumor growth curves were plotted. 7-10 mice/group are sufficient for statistical evaluation of treatment.

For in vivo tumor treatment studies, female C57BL/6 mice, 8-10 weeks old, were implanted with $10^6$ MC38-MUC1 cells s.c. in the left flank. Mice were treated three times at a 7-day interval with $10^{10}$ VP Adeno-MUC1 or Tri-Ad5. Control mice were injected with 3×10¹⁰ VP of Adeno-null. Tumor growth was assessed by measuring two opposing dimensions (a, b) and the volume calculated according to the formula $V=(a\times b)^2/2$ where the shorter dimension was "a". Tumor studies were terminated when tumors reached 1500 m³ or became severely ulcerated.

Significant anti-tumor activity and increased survival in MUC1 expressing tumor-bearing mice treated by immunotherapy (FIG. 26). Importantly, flow cytometry was used to determine that the MC38-MUC1 cell line expressed PDL1 and anti-tumor activity was achieved despite its presence. C57Bl/6 mice (n=7/group) were inoculated with MC38-MUC1 expressing tumor cells subcutaneously in the left flank and administered $10^{10}$ VP of Ad5-Null (empty vector) or $10^{10}$ VP of Ad5 [E1-, E2b-]-mMUC1-C in the right flank on days 0, 7, 14.

Mice treated with Ad5 [E1-, E2b-]-mMUC1-C had significantly ($P<0.05$) smaller tumors on days 15 and 18 as compared to controls (top) and significantly longer survival (bottom). Values=Mean±SEM. Experiment was terminated on day 36 (FIG. 26).

Immunotherapy of mice with Ad5 [E1-, E2b-]-Brachyury resulted in smaller tumors (FIG. 27). Briefly, C57Bl/6 mice were inoculated with MC38-Brachyury expressing tumor cells subcutaneously in the left flank and administered $10^{10}$ VP of Ad5-Null (empty vector) (N=4) or $10^{10}$ VP of Ad5 [E1-, E2b-]-Brachyury (N=5) in the right flank on days 5, 11, and 17. Tumors were smaller in treated mice on days 15, 19, and 22. Values=Mean±SEM (FIG. 27)

Larger numbers of mice will be treated to show significant anti-tumor activity and to combine immunotherapy with immune pathway checkpoint modulators, such as anti-checkpoint inhibitor antibodies, to determine if anti-tumor activity is enhanced.

Example 9: In Vitro Validation of Human T-Cell Activation by Recombinant Viral Vectors Tumor Cell Culture Human colon carcinoma SW620 (HLA-A2⁺, HLA-A24⁺, Brachyury⁺, MUC1⁺, CEA⁺) and pancreatic carcinoma ASPC-1 (HLA-A1⁺, HLA-A26⁺, MUC1⁺) cell lines were used. Cell cultures were free of mycoplasma and maintained in complete medium (RPMI-1640 supplemented with 10% FBS, 100 U/ml penicillin, 100 μg/ml streptomycin and 2 mM L-glutamine).

Detection of Cytokines

Supernatants of T cells stimulated for 24 h with DCs infected with adenovirus vectors or peptide-pulsed DCs in IL-2-free medium were evaluated for secretion of IFN-γ using an ELISA kit. The antigen-specific T-cell lines used in this analysis have been reported previously: (a) an HLA-A2 CEA-specific CTL, (b) an HLA-A2 MUC1-specific CTL, (c) an HLA-A24 MUC1-specific CTL, and (d) an HLA-A2 Brachyury-specific CTL.

Cytotoxic Assay

In brief, target cells were labeled with 50 μCi of ¹¹¹In oxide at 37° C. for 20 min and used at 3,000 cells/well in 96-well round-bottom culture plates. T cells were added at different ratios and incubated at 37° C. for 16 h. Supernatants were harvested for gamma counting. Determinations were carried out in triplicate and SDs were calculated. Spontaneous release was determined by incubating target cells with medium alone and complete lysis was determined by incubating with 0.25% Triton X-100. Specific lysis was calculated with the use of the following formula: Lysis (%)=[observed release (CPM)−spontaneous release (CPM)]/[Complete release (CPM)−spontaneous release (CPM)]×100.

An in vitro study was performed to assess dendritic cells (DC) function and antigen-specific T-cell activation using the Ad5 [E1-, E2b-]-CEA(6D), and Ad5 [E1-, E2b-]-Brachyury vectors. Briefly, human DC were cultured 6-7 days in media with IL-2 and GM-CSF. DC cultured in AIM-V medium were infected with Ad5 [E1-, E2b-]-CEA (6D), or Ad5 [E1-, E2b-]-Brachyury, or Ad5 [E1-, E2b-]-null (empty vector) and incubated for 2 days. Uninfected DCs were used as controls.

Human DC cells were then analyzed by flow cytometry for expression of CD80 (a marker for DC maturation), CD83 (a marker for DC maturation), CD86 (a DC marker) and DR (a DC marker) as measured by mean fluorescence intensity. As shown in Table 6, infection of DC with Ad5 [E1-, E2b-]-based vectors induced activation and maturation of human DCs.

TABLE 6

| Treatment | MOI | % CD80+ cells | % CD83+ cells | % CD86+ cells | % DR+ cells |
|---|---|---|---|---|---|
| Non-infected controls | 0 | 20.2% | 33.6% | 99.5% | 94.4% |
| Ad5 [E1-, E2b-]-null infected | 10,000 | 40.7% | 40.9% | 99.2% | 98.0% |
| Ad5 [E1-, E2b-]-CEA(6D) infected | 10,000 | 56.8% | 48.7% | 99.2% | 98.3% |

Dendritic cells (2×10⁵) in 1 mL of AIM-V medium were infected with adenovirus vectors (Ad5 [E1-, E2b-]-CEA, Ad5 [E1-, E2b-]-MUC1, Ad5 [E1-, E2b-]-Brachyury, and Ad5 [E1-, E2b-]-null at indicated multiplicity of infection (MOI of 10,000 or 20,000) for 1 hour in 6-well plates. AIM-V medium (4 mL) was then added to each well and incubated for an additional 2 days. To analyze the efficacy of transgene expression, DCs were harvested and analyzed using flow cytometry and Western blot. For phenotypic analysis, DCs were stained for the expression of CD80, CD83, CD86, CEA, and HLA-DR using BV421-conjugated anti-CD80, PerCP Cy5.5-conjugated anti-CD83, APC-Cy7-conjugated anti-HLA-DR, PE-conjugated anti-CD86, and FITC-conjugated anti-CEA. As shown in Table 7, Ad5 vectors induced maturation and activation of human DCs. Indicated adenovirus vectors were used at a concentration of 10,000 or 20,000 multiplicity of infection (MOI) for infection of human dendritic cells (DCs). Expression of CD80, CD83, CD86 and HLA-DR were analyzed by flow cytometry. Results are expressed in % of positive cells (mean fluorescence intensity).

TABLE 7

| Treatment | MOI | CD80 | CD83 | CD86 | HLA-DR |
|---|---|---|---|---|---|
| Control | 0 | 20.2 (146) | 33.6 (259) | 99.5 (4586) | 94.4 (1355) |
| Ad5 [E1-, E2b-]-null | 10,000 | 40.7 (162) | 40.9 (253) | 99.2 (3794) | 98.0 (4489) |
| Ad5 [E1-, E2b-]-null | 20,000 | 47.4 (169) | 46.8 (266) | 98.6 (3012) | 95.7 (3203) |
| Ad5 [E1-, E2b-]-CEA | 10,000 | 56.8 (189) | 48.7 (262) | 99.2 (3877) | 98.3 (6553) |
| Ad5 [E1-, E2b-]-CEA | 20,000 | 54.5 (185) | 46.6 (271) | 99.1 (3628) | 98.0 (6015) |
| Ad5 [E1-, E2b-]-MUC1 | 10,000 | 41.4 (167) | 42.4 (251) | 98.5 (3178) | 96.9 (5227) |
| Ad5 [E1-, E2b-]-MUC1 | 20,000 | 46.7 (172) | 44.3 (260) | 98.9 (3591) | 97.2 (5779) |

To determine if infected human DCs could stimulate human antigen-specific T-cell lines to secrete IFN-γ, infected DCs were incubated with antigen-specific T-cell lines and tested for IFN-γ secreting activity. As shown in Table 8, only the CEA or Brachyury antigen-specific HLA-A2+ T-cell lines incubated with respective HLA-A2+DC infected with Ad5 [E1-, E2b-]-CEA(6D) or Ad5 [E1-, E2b-]-Brachyury were stimulated to secrete IFN-γ. No IFN-γ secretion was detected in the controls. Infection of HLA-A2+DC with Ad5 [E1-, E2b-]-based vectors can activate antigen-specific T-cells to produce IFN-γ.

TABLE 8

| | | Antigen-specific T-cell line | |
|---|---|---|---|
| Treatment | MOI | CEA (HLA-A2+) (pgIFN-γ/ $10^5$ cells/mL) | Brachyury (HLA-A2+) (pg IFN-γ/ $10^5$ cells/mL) |
| Non-infected controls | 0 | <15.6 | <15.6 |
| No DC | 0 | <15.6 | <15.6 |
| Ad5 [E1-, E2b-]-null infected | 10,000 | <15.6 | <15.6 |
| Ad5 [E1-, E2b-]-CEA(6D) infected | 10,000 | 122.7 | Not Done |
| Ad5 [E1-, E2b-]-Brachyury infected | 10,000 | Not Done | 145.6 |

HLA-A2+DC were infected with a mixture of Ad5 [E1-, E2b-]-CEA(6D) and Ad5 [E1-, E2b-]-Brachyury. Infected DCs were used to generate specific cytotoxic HLA-A2+T-lymphocytes (CTL) using autologous PBMC. The autologous DCs were used as APC for three in vitro stimulations (IVSs). Autologous B cells pulsed with CEA or Bracyhyury were used to re-stimulate antigen-specific CTLs after the 3 IVSs. The effector T-cell to target tumor cell ratio was 30:1 and the percent cytolytic activity was determined. As shown in Table 9, infection of HLA-A2+DC with a mixture of Ad5 [E1-, E2b-]-CEA(6D) and Ad5 [E1-, E2b-]-Brachyury can generate antigen-specific cytolytic T-cells. Cytolytic activity was detected in an HLA-A2 dependent manner.

TABLE 9

| Antigen-specific T-cell line | % lysis of SW620 cells (HLA-A2+, CEA, and Brachyury expressing) | % lysis of ASPC-1 cells (HLA-A1+ and CEA expressing) |
|---|---|---|
| CEA-specific HLA-A2+ T-cells | 42.4% | 4.3% |
| Brachyury-specific HLA-A2+ T-cells | 64.4% | 8.3% |

To determine if infected human DCs could stimulate human antigen-specific T-cell lines to lyse target tumor cells. Human DCs (6-day culture in IL-4 and granulocyte-macrophage colony-stimulating factor (GM-CSF) $2\times10^4$ cells/well in 0.5 mL of AIM-V) were infected with indicated adenovirus vectors at 20,000 multiplicity of infection (MOI). After 48 hours, DCs were washed and used for stimulation of human antigen-specific T cells. Results are expressed in pg/ml of IFN-γ per $1\times10^5$ T cells/ml. Table 10 demonstrates that infection of human DCs with recombinant adenovirus vectors encoding CEA, MUC1, or Brachyury, can activate antigen specific T-cell lines. Numbers in bold indicate a significant enhancement of IFN-γ secretion compared to corresponding wells with uninfected DCs. [-- indicates that the assay was not performed.]

TABLE 10

| | Antigen-specific T-cell lines | | | |
|---|---|---|---|---|
| DCs infected with | CEA | MUC1 (HLA-A2) | MUC1 (HLA-A24) | Brachyury |
| Ad5 [E1-, E2b-]-null | <15.6 | <15.6 | <15.6 | <15.6 |
| Ad5 [E1-, E2b-]-Brachyury | <15.6 | — | — | 351.9 |
| Ad5 [E1-, E2b-]-MUC1 | <15.6 | 335.2 | 806.4 | — |
| Ad5 [E1-, E2b-]-CEA | 350.0 | <15.6 | <15.6 | — |
| Uninfected DCs | <15.6 | <15.6 | <15.6 | <15.6 |
| T cells only | <15.6 | <15.6 | <15.6 | <15.6 |

Human DCs (6-day culture in IL-4 and GM-CSF) from an HLA-A2 and -A24 donor were infected with Tri-Ad5 vector at $2\times10^4$/well (24-well plate) in 0.5 mL of AIM-V. Tri-Ad5 vectors were used at 20,000 MOI for 1 hour and then 1.5 mL of AIM-V were added to each well. Infected DCs were incubated for 48 hours and then washed and used for stimulation of human antigen-specific T cells. Results are expressed in pg of IFN-γ per $1\times10^5$ T cells/ml. Numbers in bold indicate a significant enhancement of IFN-γ secretion compared to corresponding wells with uninfected DCs.

CEA-, MUC1- and Brachyury-specific cytotoxic T lymphocytes (CTLs) were generated. Dendritic cells ($1-2\times10^5$/well in 1 mL of AIM-V) were infected with 20,000 MOI of Tri-Ad5, as described above. Infected DCs were used as APCs for stimulation of autologous nonadherent cells at an effector-APC ratio of 10:1. Cultures were incubated for 3 days at 37° C. in a humidified atmosphere containing 5% $CO_2$. The cultures were then supplemented with rhIL-2 for 7 days; IL-2 containing medium was replenished every 3 days. The 10-day stimulation constituted one in vitro stimulation (IVS) cycle. Autologous vector-infected DCs were used as APCs for three IVS. Autologous peptide-pulsed B cells were used to re-stimulate antigen-specific CTLs after three IVS. T-cell lines were maintained in medium containing IL-7 and IL-15 (10 ng/ml).

Human DCs from a prostate cancer patient (6-day culture in IL-4 and GM-CSF; $2\times10^4$ cells/well in 0.5 mL of AIM-V) were infected with Tri-Ad5 at 20,000 MOI. After 48 h, infected DCs were washed and used to generate specific cytotoxic T lymphocytes (CTLs) using autologous peripheral blood mononuclear cells (PBMCs) as effectors. Following 3 cycles of in vitro stimulations, autologous peptides-pulsed B cells were used as antigen-presenting cells. Results are expressed in pg/ml of IFN-γ. [-- indicates that the assay was not performed.] As shown in Table 11, infection of human dendritic cells can generate antigen-specific T cells to Brachyury, MUC1 and CEA and produce IFN-γ when stimulated with autologous B cells pulsed with the peptides.

TABLE 11

| Antigen-specific | Peptides (10 μg/ml) | | | |
|---|---|---|---|---|
| T-cell lines | CEA | MUC1 (A2) | MUC1 (A24) | Brachyury |
| T-Brachyury | <15.6 | — | — | 243 |
| T-MUC1 (A2) | <15.6 | 174 | — | — |
| T-MUC1 (A24) | <15.6 | — | 206 | — |
| T-CEA | 211 | <15.6 | — | — |

CEA-, MUC1- and Brachyury-specific cytotoxic T lymphocytes (CTLs) were generated. Dendritic cells ($1-2\times10^5$/well in 1 mL of AIM-V) were infected with 20,000 MOI of Tri-Ad5, as described above. Infected DCs were used as APCs for stimulation of autologous nonadherent cells at an effector-APC ratio of 10:1. Cultures were incubated for 3 days at 37° C. in a humidified atmosphere containing 5% $CO_2$. The cultures were then supplemented with rhIL-2 for 7 days; IL-2 containing medium was replenished every 3 days. The 10-day stimulation constituted one in vitro stimulation (IVS) cycle. Autologous vector-infected DCs were used as APCs for three IVS. Autologous peptide-pulsed B cells were used to re-stimulate antigen-specific CTLs after three IVS. T-cell lines were maintained in medium containing IL-7 and IL-15 (10 ng/ml).

Human DCs (6-day culture in IL-4 and GM-CSF) from an HLA-A2 and -A24 donor were infected with Tri-Ad5 vector at $2\times10^4$/well (24-well plate) in 0.5 mL of AIM-V. Tri-Ad5 vectors were used at 20,000 MOI for 1 hour and then 1.5 mL of AIM-V were added to each well. Infected DCs were incubated for 48 hours and then washed and used for stimulation of human antigen-specific T cells. Results are expressed in pg of IFN-γ per $1\times10^5$ T cells/ml. Infection of human dendritic cells with Tri-Ad5 vectors encoding transgenes can activate antigen-specific T cell lines to produce IFN-γ. As shown in Table 12, infection of human dendritic cells with Tri-Ad5 can generate antigen-specific T cells to Brachyury, MUC1 and CEA and produce IFN-γ when stimulated with autologous B cells pulsed with the corresponding peptides. Numbers in bold indicate a significant enhancement of IFN-γ secretion compared to corresponding wells with uninfected DCs.

TABLE 12

| | Antigen-specific T-cell lines | | | |
|---|---|---|---|---|
| DCs infected with | CEA (HLA-A2) | MUC1 (HLA-A2) | MUC1 (HLA-A24) | Brachyury (HLA-A2) |
| Tri-Ad5 | 480 | 236 | 763 | 496 |
| Ad5 [E1, E2b]-null | <15.6 | <15.6 | <15.6 | <15.6 |
| Uninfected DCs | <15.6 | <15.6 | <15.6 | <15.6 |
| T cells only | <15.6 | <15.6 | <15.6 | <15.6 |

These studies show that Ad5 [E1-, E2b-]-based vectors can induce maturation of human DCs in vitro, infected DCs can stimulate antigen-specific human T-cells, and infected DCs can generate antigen-specific human CTLs. In the studies reported here, multi-TAA targeted immunotherapy (Tri-Ad5), which consisted of a mixture of three Ad5 vectors expressing different TAAs, is as efficient in the activation of human T cells as the use of each of the adenovirus vectors alone, with only minor differences. Nine different in vivo parameters were measured via vaccinating mice with each of the Ad5 [E1-, E2b-]-CEA, Ad5 [E1-, E2b-]-MUC1, and Ad5 [E1-, E2b-]-Brachyury vectors individually versus vaccination with Tri-Ad5. Of the 21 assays performed, statistical differences observed were (a) an enhanced number of MUC1-specific splenocytes and CD8$^+$ IFN-producing and multifunctional CD8$^+$ T cells, and (b) more CEA-specific CD8$^+$ IFN-producing T cells, in the mice vaccinated with one vector than in the Tri-Ad5 vaccinated mice. On the other hand, the Tri-Ad5 vaccinated mice produced more CEA-specific IL-2-producing cells than the Ad5 [E1-, E2b-]-CEA vaccinated mice. In the other 16/21 assays, however, there were no statistical differences in the results between the use of the individual vector versus the use of the Tri-Ad5 in terms of antigen-specific activation of (a) splenocytes for IFN-γ and IL-2 production, (b) CD8$^+$ T cells for IFN-γ production, (c) CD4$^+$ T cells for IFN-γ production, (d) multifunctional CD8$^+$ T cells for IFN-γ and TNF-α production, (e) multifunctional CD4$^+$ T cells for IFN-γ and TNF-α production, and (f) production of antigen-specific antibodies. There was also no difference in anti-tumor activity using a single vector (Ad5 [E1-, E2b-]-MUC1) versus the Tri-Ad5 vaccine; while both vaccines did not eliminate the tumor, both vaccines reduced the tumor growth rate in a similar manner. While Tri-Ad5 was not as efficient in T-cell activation in some assays, the potential ability of the Tri-Ad5 platform to overcome the TAA heterogeneity that exists in human solid tumors far outweighs the relatively minor differences in potency of T-cell activation of Tri-Ad5 vs. individual vectors in some assays.

CEA, MUC1 and Brachyury are all human TAAs and are not expressed in murine solid tumors. Moreover, human solid tumors are very heterogeneous with respect to expression of different TAAs. It would be extremely difficult to transfect a murine tumor cell line with all three transgenes to define the effect of vaccination of Tri-Ad5 vs. each vector alone. The targeting of a murine tumor expressing MUC1 was chosen because the single Ad5 [E1-, E2b-]-MUC1 vector was more potent in some of the murine T-cell assays compared to the Tri-Ad5 than the CEA and Brachyury vectors compared to Tri-Ad5. Thus this appeared to be the most stringent model to compare the Tri-Ad5 platform to a single vector platform. The studies reported herein were designed to provide the rationale for potential clinical studies as a vaccine immunotherapy, or use in combination with other therapeutics, using this novel adenovirus vaccine delivery platform (Ad5 [E1-, E2b-] targeting a diverse range of TAA transgenes in the Tri-Ad5 regimen.

While the checkpoint inhibitor antibodies have shown evidence of clinical activity in melanoma and squamous non-small cell lung cancer, clinical benefit in other cancer types has been observed in a minority of patients. For some tumor types, such as colorectal cancer and prostate cancer, the anti-PDL1/PD1 checkpoint inhibitors have shown little clinical activity. One hypothesis that has been put forth for the lack of PDL1/PD1 therapeutic activity in some patients is the lack of T-cell infiltrates in tumors. Consequently, if a vaccine targeting TAAs in the tumor would result in the presence of antigen-specific T cells in the tumor microenvironment, then an immune pathway checkpoint modulator employed in combination or following vaccination would be able to "release the brakes" of the tumor-infiltrating anergized T cells leading to clinical effect.

Example 10: Immunotherapy for HPV and ETBX-041 (Ad5 [E1-, E2b-]-HPV-E6/E7) Vaccine This example shows that the combination therapy as provided herein reduces tumors and a murine model of HPV-associated cancers which express HPV early 6 (E6) and early 7 (E7) oncogenes. Briefly, tumor bearing HPV murine model mice were treated with the Ad5 [E1-, E2b-]-HPV-E6/E7 vaccine comprising a modified non-oncogenic and fused HPV-E6/E7 gene and treated tumor bearing mice. The TC-1 murine tumor cell line used to induce tumors in the mice expressed HPV-E6/E7 as well as PDL1.

Flow cytometry was used to examine the tumors in HPV tumor bearing mice and calculated the abundance of various tumor infiltrating lymphocytes (TILs). The TILs in the tumors were observed to have the following cell types and abundance levels: myeloid derived suppressor cells (MDSC) (7.5%±2.4 SD), FoxP3 expressing T regulatory (Treg) lymphocytes (7.1%±2.5), PD1 expressing CD8α+ lymphocytes (25.5%±16.4), and LAG-3 expressing CD8α+ lymphocytes (4.1%±2.3). This profile of TILs indicates that a suppressive immune pathway in present in the tumors.

The addition of immune checkpoint inhibitor antibodies, such as anti-PD1 antibody, to the Ad5 [E1-, E2b-]-HPV-E6/E7 immunotherapy resulted in greater anti-tumor responses (FIG. 28). Additionally two mice in this group were observed to have essentially complete tumor regression (FIG. 29). Briefly, C57Bl/6 mice (n=7/group) were implanted with HPV-E6/E7 expressing TC-1 tumor cells (day 0) and treated by immunotherapy on days 10, 17, 24 with $10^{10}$ VP of Ad5-null (empty vector) plus 100 µg control IgG (intraperitoneal), $10^{10}$ VP of Ad5-Null (empty vector) plus 100 µg anti-PD1, $10^{10}$ VP of Ad5 [E1-, E2b-]-HPV-E6/E7 plus 100 µg mouse IgG, or $10^{10}$ VP of Ad5 [E1-, E2b-]-HPV-E6/E7 plus 100 µg anti-PD1. Immunotherapy with or without anti-PD1 resulted in significant inhibition of tumor growth by day 23 (P<0.05). All control mice were terminated by day 23 due to tumor mass. Values=Mean±SEM (FIG. 28).

Tumor growth and regression in 2 mice treated by immunotherapy with anti-PD1 injections were analyzed (FIG. 29). Tumor growth peaked on days 20 & 27, respectively, and then regressed thereafter. This study demonstrates that the combination of immune checkpoint inhibitor drugs in combination with use of multi-targeted vaccines can enhance anti-tumor effects.

Immunotherapy against human papilloma virus (HPV) using a viral gene delivery platform to immunize against HPV 16 genes E6 and E7 (Ad5 [E1-, E2b-]-E6/E7) combined with programmed death-ligand 1 (PD1) blockade was investigated to determine whether it could increase therapeutic effect as compared to the vaccine alone. Ad5 [E1-, E2b-]-E6/E7 as a single agent induced HPV-E6/E7 cell-mediated immunity. Immunotherapy using Ad5 [E1-, E2b-]-E6/E7 resulted in clearance of small tumors and an overall survival benefit in mice with larger established tumors. When immunotherapy was combined with immune checkpoint blockade, an increased level of anti-tumor activity against large tumors was observed. Analysis of the tumor microenvironment in Ad5 [E1-, E2b-]-E6/E7 treated mice revealed elevated CD8+ tumor infiltrating lymphocytes (TILs); however, induction of suppressive mechanisms such as programmed death-ligand 1 (PDL1) expression on tumor cells and an increase in PD1+ TILs was seen. When Ad5 [E1-, E2b-]-E6/E7 immunotherapy was combined with anti-PD1 antibody, CD8+ TILs were observed at the same level but a reduction in tumor PDL1 expression on tumor cells and reduced PD1+ TILs providing a mechanism by which combination therapy favors a tumor clearance state and a rationale for pairing antigen-specific vaccines with immune pathway checkpoint modulators in future clinical trials.

Herein, Ad5 [E1-, E2b-]-E6/E7 immunizations combined with PD1 blockade were examined for an increase an anti-tumor effect. Also, the CMI response induced by the Ad5 [E1-, E2b-]-E6/E7 vaccine was characterized and the kinetics of an anti-tumor response was determined to evaluate the therapeutic potential of treating small versus large established tumors. To investigate a possible mechanism of action, the relationship between the levels of effector T cells and suppressor T cells within the parenchyma of the tumor was evaluated and lymphocyte populations and expression of co-inhibitory molecules that may play a role in the observed anti-tumor responses were characterized.

Viral Construction

Ad5 [E1-, E2b-]-E6/E7 was constructed and produced. Briefly, the transgenes were sub-cloned into the Ad5 [E1-, E2b-] vector using a homologous recombination-based approach and the replication deficient virus was propagated in the E.C7 packaging cell line, $CsCl_2$ purified, and titered Viral infectious titer was determined as plaque forming units (PFU) on an E.C7 cell monolayer. The viral particle (VP) concentration was determined by sodium dodecyl sulfate (SDS) disruption and spectrophotometry at 260 nm and 280 nm. As a vector control, Ad5 [E1-, E2b-]-null was employed, which is the Ad5 platform backbone with no transgene insert.

Immunization and Splenocyte Preparation

Female C57BL/6 mice (n=5/group) were injected subcutaneously (SQ) with varying doses of Ad5 [E1-, E2b-]-E6/E7 or Ad5 [E1-, E2b-]-null. Doses were administered in 254 injection buffer (20 mM HEPES with 3% sucrose) and mice were immunized three times at 14-day intervals. Fourteen days after the final injection, spleens and sera were collected. Serum from mice was frozen at −20° C. until evaluation. Suspensions of splenocytes were generated by disrupting the spleen capsule and gently pressing the contents through a 70 µm nylon cell strainer. Red blood cells were lysed by the addition of red cell lysis buffer and after lysis, the splenocytes were washed twice in R10 (RPMI 1640 supplemented with L-glutamine (2 mM), HEPES (20 mM) (Corning, Corning, N.Y.), penicillin (100 U/ml) and streptomycin (100 µg/mL), and 10% fetal bovine serum. Splenocytes were assayed for cytokine production by ELISpot and flow cytometry.

Enzyme-Linked Immunosorbent Spot (ELISpot) Assay

HPV E6 and E7 specific interferon-γ (IFN-γ) secreting T cells were determined by ELISpot assays using freshly isolated mouse splenocytes prepared as described above. The ELISpot assay was performed. Pools of overlapping peptides spanning the entire coding sequences of HPV E6 and E7 were synthesized as 15-mers with 11-amino acid overlaps (and lyophilized peptide pools were dissolved in DMSO. Splenocytes ($2\times10^5$ cells) were stimulated with 2 µg/mL/peptide of overlapping 15-mer peptides in pools derived from E6 or E7. Cells were stimulated with Concanavalin A (Con A) at a concentration of 0.06 µg/per well as a positive control. Overlapping 15-mer complete peptide pools derived from SIV-Nef (AIDS Research and Reference Reagent Program, Division of AIDS, MAID, NIH) were used as irrelevant peptide controls. The numbers of Spot Forming Cells (SFC) were determined using an Immunospot ELISpot plate reader (and results reported as the number of SFC per $10^6$ splenocytes.

Intracellular Cytokine Stimulation

Splenocytes were prepared as described for the ELISpot assay above. Stimulation assays were performed using $10^6$ live splenocytes per well in 96-well U-bottom plates. Splenocytes in R10 media were stimulated by the addition of HPV E6, HPV E7, or SIV-Nef peptide pools at 2 µg/mL/peptide for 6 h at 37° C. in 5% $CO_2$, with protein transport inhibitor (GolgiStop, BD) added two hours after initiation of incubation. Stimulated splenocytes were then stained for lymphocyte surface markers CD8a and CD4, fixed with paraformaldehyde, permeabilized, and stained for intracellular accumulation of IFN-γ and TNF-α. Fluorescent-conjugated antibodies against mouse CD8a (clone 53-6.7), CD4 (clone RM4-5), IFN-γ (clone XMG1.2), and TNF-α (clone MP6-XT22) were purchased from BD and staining was performed in the presence of anti-CD16/CD32 (clone 2.4G2). Flow cytometry was performed using an Accuri C6 Flow Cytometer (BD) and analyzed using BD Accuri C6 Software.

Tumor Immunotherapy

For in vivo tumor immunotherapy studies, female C57BL/6 mice, 8-10 weeks old, were implanted with $2 \times 10^5$ TC-1 HPV-E6/E7 expressing tumor cells SQ in the left flank. Mice were treated three times at 7-day intervals with SQ injections of $10^{10}$ VP Ad5 [E1-, E2b-]-E6/E7. Control mice were injected with $10^{10}$ VP Ad5 [E1-, E2b-]-null under the same protocol. In combinational studies, mice were given 100 µg of rat anti-PD1 (clone RMP1-14) or an isotype rat control antibody (clone 2A3) IP at the same time as immunization. Rat anti-PD1 antibody and rat $IgG_{2a}$ isotype control antibodies were purchased from BioXcell. Tumor size was measured by two opposing dimensions (a, b) and volume was calculated according to the formula $V=(a^2 \times b)/2$ where a was the shorter dimension. Animals were euthanized when tumors reached 1500 $mm^3$ or when tumors became ulcerated.

Analysis of Tumor Infiltrating Cells (TILs) by Flow Cytometry

Four groups of 8-10 week old female C57BL/6 mice (n=5/group) were implanted with $2 \times 10^5$ TC-1 tumor cells SQ in the left flank at day 0. Two of these groups were immunized SQ with $10^{10}$ VP Ad5 [E1-, E2b-]-null vector control and the other two groups SQ with $10^{10}$ VP Ad5 [E1-, E2b-]-E6/E7 vaccine. These immunizations were administered twice at 7-day intervals starting on day 12. In addition to immunizations, mice in one Ad5 [E1-, E2b-]-E6/E7 group and one Ad5 [E1-, E2b-]-null group were administered 100 µg rat anti-PD1 (clone RMP1-14) SQ at days 12 and 16 and 100 µg hamster anti-PD1 (clone J43) at days 19 and 23 to increase the effective dose of anti-PD1. To control for treatment with these immune pathway checkpoint modulators, mice in the remaining Ad5 [E1-, E2b-]-E6/E7 and Ad5 [E1-, E2b-]-null groups were administered the relevant rat and hamster control IgG antibodies on the same days. Hamster anti-PD1 antibody and isotype control were purchased from BioXcell. At day 27, tumors were measured, excised, and weighed. Tumors were minced and digested with a mixture of collagenase IV (1 mg/ml), hyaluronidase (100 µg/ml), and DNase IV (200 U/ml) in Hank's Balanced Salt Solution (HBSS) at room temperature for 30 min and rotating at 80 rpm. Enzymes were purchased from Sigma-Aldrich. After digestion, the tumor suspension was placed through a 70 µm nylon cell strainer and centrifuged. Red cells were removed by the addition of red cell lysis buffer (Sigma-Aldrich) and after lysis, the tumor suspensions were washed twice in phosphate buffered saline (PBS) containing 1% (w/v) bovine serum albumin and resuspended in fluorescent activated cell sorting (FACS) buffer (PBS pH 7.2, 1% fetal bovine serum, and 2 mM EDTA) for staining. Fluorescent-conjugated antibodies against CD45 (30-F11), CD4 (RM4-5), and PDL1 (MIH5) were purchased from BD. Fluorescent-conjugated antibodies against CD8β (H35-17.2), CD25 (PC61.5), FoxP3 (FJK-16s), PD1 (RMP1-30), LAG-3 (C9B7W), and CTLA4 (UC10-4B9) were all purchased from eBioscience. Surface staining was performed for 30 minutes at 4° C. in 1004 FACS buffer containing anti-CD16/CD32 (clone 2.4G2). Stained cells were washed in FACS buffer, fixed with paraformaldehyde, and (if needed) permeabilized in permeabilization buffer (eBioscience) before staining with fluorescent-conjugated anti-FoxP3 or anti-CTLA4 for 60 minutes at 4° C. in 1004 permeabilization buffer containing anti-CD16/CD32 (clone 2.4G2). Cells were washed with permeabilization buffer, washed back into FACS buffer, and a fixed volume of each sample was analyzed by flow cytometry using a BD Accuri C6 flow cytometer. Tumor cells were defined as $CD45^{--}$ events in a scatter gate that includes small and large cells. $CD4^+$ TILs were defined as $CD45^+/CD4^+$ events in a lymphocyte scatter gate. $CD8^+$ TILs were defined as $CD45^+/CD8\beta^+$ events in a lymphocyte scatter gate. Regulatory T cells (Tregs) were defined as $CD45^+/CD4^+/CD25^+/FoxP3^+$ events in a lymphocyte scatter gate. Effector $CD4^+$ T cells were defined as $CD45^+/CD4^+/CD25^{--}/FoxP3^{--}$ events in a lymphocyte scatter gate. Isotype-matched control antibodies were used to determine positive expression of FoxP3, PDL1, PD1, LAG-3, and CTLA4. Flow cytometry was performed using an Accuri C6 Flow Cytometer (BD) and analyzed in BD Accuri C6 Software.

HPV-E6/E7 Specific Cell Mediated Immune Responses Induced by Ad5 [E1-, E2b-]-E6/E7

A study was performed to determine the effect of increasing doses of Ad5 [E1-, E2b-]-E6/E7 immunizations on the induction of CMI responses in mice. Groups of C57BL/6 mice (n=5/group) were immunized SQ three times at 14-day intervals with $10^8$, $10^9$, or $10^{10}$ VP Ad5 [E1-, E2b-]-E6/E7. Control mice received $10^8$ VP, $10^9$ VP, or $10^{10}$ VP Ad5 [E1-, E2b-]-null (empty vector controls). Two weeks after the last immunization, splenocyte CMI responses were assessed by ELISpot analysis for IFN-γ secreting cells. A dose effect was observed and the highest CMI response level was obtained by immunizations with $10^{10}$ VP Ad5 [E1-, E2b-]-E6/E7 (FIG. 36). No responses were detected in control mice injected with Ad5 [E1-, E2b-]-null.

Intracellular accumulation of IFN-γ and TNF-α in both $CD8\alpha^+$ and $CD4^+$ splenocytes populations was also determined in mice immunized with $10^{10}$ VP Ad5 [E1-, E2b-]-E6/E7. Intracellular cytokine staining (ICS) after stimulation with overlapping peptide pools revealed E6 and E7 antigen-specific IFN-γ accumulation in $CD8\alpha^+$ lymphocytes isolated from all mice immunized with Ad5 [E1-, E2b-]-E6/E7 (FIG. 37A). Peptide-stimulated splenocytes were also stained for the intracellular accumulation of TNF-α, and a significant population of multifunctional (IFN-$\gamma^+$/TNF-$\alpha^+$) $CD8\alpha^+$ splenocytes specific for both E6 and E7 were able to be detected (FIG. 37B).

Treatment of HPV-E6/E7 Expressing Tumors

The anti-tumor effect of immunotherapy treatment in mice bearing HPV-E6/E7 TC-1 tumors was investigated. These tumor cells expressed PDL1 as assessed by flow cytometry analysis. When labeled with PE-conjugated anti-PDL1, the TC-1 cells had a median fluorescent intensity (MFI) of 537 whereas cells labeled with a PE-conjugated isotype control antibody had an MFI of 184, demonstrating the presence of the immune suppressive PDL1 on the surface of the TC-1 cells. Two groups of C57BL/6 mice (n=5/group) were inoculated with $2\times10^5$ TC-1 tumor cells SQ into the right subcostal area on day 0. On days 1, 8, and 14 mice were treated by SQ injections of $10^{10}$ VP Ad5 [E1-, E2b-]-null (vector control) or $10^{10}$ VP Ad5 [E1-, E2b-]-E6/E7. All mice were monitored for tumor size and tumor volumes were calculated. Mice immunized with Ad5 [E1-, E2b-]-E6/E7 had significantly smaller tumors than control mice beginning on day 12 (p<0.01) and remained significantly smaller for the remainder of the experiment (p<0.02), including 3 of 5 mice showing complete tumor regression (FIG. 38A). Tumors in mice from the vector control treated group began reaching the threshold for euthanasia starting on day 26 and all mice in this group were euthanized by day 33, whereas mice in the Ad5 [E1-, E2b-]-E6/E7 treated group were all alive with complete tumor regression of small tumors (<150 mm$^3$) at the end of experiment on day 36 (FIG. 38B).

To determine if immunotherapy with Ad5 [E1-, E2b-]-E6/E7 was effective against larger tumors, TC-1 tumor cells tumors were implanted in two groups of C57BL/6 mice (n=4/group) and then delayed weekly treatment with Ad5 [E1-, E2b-]-E6/E7 for 6 days post tumor implantation, at a time when tumors were small but palpable. Mice beginning treatment on day 6 initially demonstrated tumor growth similar to the control group; however, beginning on day 16, tumor regression was observed (FIG. 39A). The tumors in mice that began treatment on day 6 were significantly smaller (p<0.05) than the control group beginning on day 20 and 3 of 4 mice had complete regression by day 27. Ad5 [E1-, E2b-]-E6/E7 administration beginning on day 6 also conferred a significant survival benefit (p<0.01) (FIG. 39B).

Finally, to determine if immunotherapy with Ad5 [E1-, E2b-]-E6/E7 was effective against large established tumors, TC-1 tumor cells were implanted in two groups of C57BL/6 mice (n=4/group) then delayed weekly treatment with Ad5 [E1-, E2b-]-E6/E7 until 13 days post tumor implantation, when tumors were ~100 mm$^3$. In this treatment group, initial tumor growth was observed to be similar to the control group but some mice in the control group reached euthanasia criteria on day 23, preventing analysis of significance at further time points (FIG. 40A). However, tumor volumes in the Ad5 [E1-, E2b-]-E6/E7 treated group were below the euthanasia threshold through day 29, at which point tumors from all mice in the vector control group had exceeded 1500 mm$^3$ and were euthanized (FIG. 40B). These results indicate that in the TC-1 tumor model the Ad5 [E1-, E2b-]-E6/E7 immunotherapeutic was a potent inhibitor of tumor growth and lead to significant overall survival benefit, however complete clearance of tumors was only observed when treatment was initiated in smaller tumors. Furthermore, these results demonstrate that, despite the presence of immune suppressing PDL1 on tumor cells, immunotherapeutic treatment with Ad5 [E1-, E2b-]-E6/E7 resulted in significant inhibition of tumor growth.

Combination Immunotherapy with Immune Checkpoint Inhibition

To determine if the therapeutic effect of Ad5 [E1-, E2b-]-E6/E7 could be improved in the setting of large tumors, anti-PD1 antibody was co-administered. Four groups of mice (n=7/group) were implanted with $2\times10^5$ TC-1 tumor cells on day 0 and beginning on day 10 the mice received weekly administrations of SQ $10^{10}$ VP Ad5 [E1-, E2b-]-E6/E7 plus IP 100 µg anti-PD1, $10^{10}$ VP Ad5 [E1-, E2b-]-null plus 100 µg anti-PD1, $10^{10}$ VP Ad5 [E1-, E2b-]-E6/E7 plus 100 µg rat IgG$_{2a}$ isotype control, or $10^{10}$ VP Ad5 [E1-, E2b-]-null plus 100 µg rat IgG$_{2a}$ isotype control. Tumor size was monitored over time and mice were euthanized when tumor size exceeded 1500 mm$^3$ or when tumor ulceration was present. Control mice that received Ad5 [E1-, E2b-]-null plus 100 µg rat IgG$_{2a}$ isotype control (FIG. 41A) and mice treated with Ad5 [E1-, E2b-]-null plus 100 µg anti-PD1 (FIG. 41B) exhibited a similar tumor growth pattern. No significant survival benefit was observed between these two groups. Mice that received Ad5 [E1-, E2b-]-E6/E7 plus rat IgG$_{2a}$ isotype control had a delayed tumor growth pattern as compared to the controls and 2 of the mice had tumor regressions to near baseline level at day 52 post tumor implantation (FIG. 41C). Four of the 7 mice that received Ad5 [E1-, E2b-]-E6/E7 and anti-PD1 had tumor regression starting at day 25, and two of these resulted in tumor clearance through the end of experiment at day 53 (FIG. 41D).

Mice treated with Ad5 [E1-, E2b-]-E6/E7 plus rat IgG$_{2a}$ isotype control (FIG. 42) also experienced a survival benefit with 28.6% of the animals surviving at termination of the study whereas 100% of the control mice (Ad5 [E1-, E2b-]-null plus rat IgG$_{2a}$ isotype control) and the Ad5 [E1-, E2b-]-null plus anti-PD1 treated mice had to be terminated by day 28 and 32, respectively (FIG. 42). Mice treated with both Ad5 [E1-, E2b-]-E6/E7 and anti-PD1 antibody had the greatest treatment benefit (FIG. 42), demonstrating delayed tumor growth and a significant improvement (P 0.0006) in survival as compared to the controls.

Mouse anti-rat IgG antibody responses were induced by the second injection (endpoint antibody titer 1:200 by ELISA, data not shown) with rat anti-PD1 antibody and these responses were dramatically increased by the third injection (endpoint antibody titer 1:4000 to 1:8000 by ELISA, data not shown). This anti-rat antibody response may explain why no anti-tumor activity was observed after injections with anti-PD1 antibody alone. Also, it is likely that the first and possibly the second injections of anti-PD1 antibody combined with Ad5 [E1-, E2b-]-E6/E7 immunotherapy were effective but the third injection with anti-PD1 was effectively neutralized by the induced mouse anti-rat IgG response.

Tumor Microenvironment Following Combination Immunotherapy

To analyze cell populations that contributed to delayed tumor growth and survival in Ad5 [E1-, E2b-]-E6/E7 treated mice, tumor infiltrating lymphocytes (TILs) were by flow cytometry. Four groups of mice were implanted with $2\times10^5$ TC-1 cells and began treatment 10 days later with two weekly immunizations of Ad5 [E1-, E2b-]-E6/E7 plus PD1 antibody. On day 27 whole tumors were collected and processed as described in the materials and methods. The number of infiltrating CD8$^+$ T cells per mg of tumor was significantly increased in the Ad5 [E1-, E2b-]-E6/E7 treated groups as compared to the groups that received Ad5 [E1-, E2b-]-null (FIG. 43C). Anti-PD1 antibody treatment had little or no effect on the number of infiltrating CD8$^+$ T cells (FIG. 43C). There was no difference between any of the four groups, in terms of the number of infiltrating Tregs (CD4$^+$CD25$^+$Foxp3$^+$) per mg of tumor (FIG. 43B). However, the increase in CD8$^+$ T cells led to a decrease in the Treg:CD8$^+$ T cell ratio in the tumor microenvironment when the mice were treated with the Ad5 [E1-, E2b-]-E6/E7 vaccine or Ad5 [E1-, E2b-]-E6/E7 vaccine plus anti-PD1 antibody treatment (FIG. 43A).

To further study the synergistic/additive effect of anti-PD1 antibody to Ad5 [E1-, E2b-]-E6/E7 immunotherapy, the expression of PD1, LAG-3, and CTLA-4 was examined on TILs. The expression of these co-inhibitory molecules on T cells within the tumor microenvironment has been shown to down regulate activation of antigen-specific T cells. Immunizations with Ad5 [E1-, E2b-]-E6/E7 plus control antibody treatment significantly increased the fraction of PD1$^+$ and LAG-3$^+$ CD8$^+$ TILs, whereas, expression of these co-inhibitory molecules on CD4$^+$ TILs was unaffected by this treatment. The percentage of CD4$^+$ and CD8$^+$ TILs expressing CTLA-4 was not significantly affected by vaccine treatment (data not shown). Combining anti-PD1 antibody injections with Ad5 [E1-, E2b-]-E6/E7 vaccine treatment resulted in a significant reduction in the fraction of PD1$^+$ CD8$^+$ and CD4$^+$ TILs, as compared with those found in tumors from mice treated with Ad5 [E1-, E2b-]-E6/E7 plus control antibody (p=0.0083 for CD8$^+$ TILs and p=0.0016 for CD4$^+$ TILs). Furthermore the fraction of PD1$^+$ CD8$^+$ TILs was decreased to the level of expression observed in the Ad5 [E1-, E2b-]-null treated control groups, and the fraction of PD1$^+$ CD4$^+$ TILs was significantly reduced to below that observed in the control groups (p=0.0016, FIG. 44A). In addition, the percentage of LAG-3$^+$ CD8$^+$ TILs was also observed to decrease when the Ad5 [E1-, E2b-]-E6/E7 immunization was combined with the anti-PD1 checkpoint inhibitor (p=0.0363, FIG. 44B). Since it has previously been shown that vaccine treatment can enhance PDL1 expression on tumor cells ex vivo, the expression of PDL1 was examined on tumor cells. There was an augmentation in the median fluorescence intensity of PDL1 on tumor cells after vaccine treatment. However, PDL1 expression was reduced in mice treated with the combination of Ad5 [E1-, E2b-]-E6/E7 and anti-PD1 antibody, although this level was still significantly expressed above that observed in Ad5 [E1-, E2b-]-null treated control mice.

In summary, the data demonstrate that Ad5 [E1-, E2b-]-E6/E7 can induce HPV-E6/E7 directed CMI responses in a dose dependent manner, which results in upregulation of PDL1 on tumor cells. Multiple homologous immunizations in tumor bearing mice with the highest dose of vaccine resulted in significant anti-tumor activity and increased survival, particularly in mice bearing small tumors. Importantly, a greater degree of anti-tumor activity was achieved when immunotherapy with Ad5 [E1-, E2b-]-E6/E7 was combined with anti-PD1 in mice with large tumors. Overall, immunizations with the Ad5 [E1-, E2b-]-E6/E7 vaccine combined with anti-PD1 antibody results in an increase in CD8$^+$ and CD4$^+$ effector populations that have a less exhaustive/anergic phenotype and therefore favor the balance to a more pro-inflammatory state in the tumor microenvironment. The observation that the combined treatment was associated with reductions in large tumor mass indicates that immunotherapy with Ad5 [E1-, E2b-]-E6/E7 combined with anti-PD1 antibody might increase clinical effectiveness during the immunotherapy of patients with HPV-associated head and neck or cervical cancers. Furthermore, the data suggests that clinical trials with the Ad5 [E1-, E2b-]-E6/E7 vaccine should be combined with an immune pathway checkpoint modulator and remains a high priority.

Example 11: Clinical Trial of ETBX-041 (Ad5 [E1-, E2b-]-HPV-E6/E7 Vaccine

The objective of the study is to evaluate the safety and immunogenicity of immunizations with the ETBX-041 (Ad5 [E1-, E2b-]-HPV-E6/E7) vaccine in patients that are human papilloma virus type 16 (HPV-16) positive, in patients with HPV associated head and neck squamous cell carcinoma (HNSCC), and in patients with HPV associated cervical cancer. Current interventions in HNSCC patients include therapy with cisplatin and radiation. However, many HNSCC patients that initially respond or do not respond ultimately relapse. The ETBX-041 vaccine is designed to induce anti-tumor T cell-mediated immune responses directed against the early 6 (E6) and early 7 (E7) genes of HPV. One of the important features of the ETBX-011 vaccine is that it can be combined with chemotherapy/radiation treatment.

ETBX-041 is an adenovirus serotype 5 (Ad5) vector that has been modified by removal of the E1, E2b and E3 genes and insertion of a modified fused non-oncogenic HPV-E6/E7 gene. The resulting recombinant replication-defective vector can only be propagated in the newly engineered, proprietary human 293 based cell line (E.C7) that supplies the E1 and E2b gene functions in trans required for vector production.

A Phase VII clinical trial of ETBX-011 (Ad5 [E1-, E2b-]-CEA) was performed, which employs the same Ad5 vector backbone that expresses a modified tumor associated antigen carcinoembryonic antigen (CEA(6D)). The maximum dose level of $5 \times 10^{11}$ viral particles (VP) was reached without any reported toxicity including dose-limiting toxicity. CEA-specific T cell responses by ELISpot have been observed in treated patients. The safety profile from the treatment of over expressing CEA cancer patients using the same Ad5 vector backbone gives us a rationale to use the same Ad5 backbone expressing HPV-E6/E7 for the treatment of patients with HNSCC cancers expressing HPV-E6/E7 to evaluate the safety and immunogenicity. No gene transfer insertion is proposed for this protocol; the product functions and remains episomal.

The ETBX-041 vaccine product is used to induce HPV-E6/E7 specific cell mediated immune responses in a safe and effective manner in patients. An open-label, dose-escalation clinical study will be conducted to evaluate the safety and immunogenicity of ETBX-041 injections. The dosage levels to be evaluated are $5 \times 10^{10}$, $1 \times 10^{11}$ and $5 \times 10^{11}$ virus particles (VP) of ETBX-041. Patients will be enrolled into successive increasing dosage levels involving three (3) cohorts of patients that will be monitored for dose-limiting toxicity (DLT). Each patient will be given ETBX-041 by SQ injection every 3 weeks for 3 immunizations. Assessment of DLT for dose escalation will be made after all patients in a cohort have had a study visit at least 3 weeks after receiving their last dose of vaccine.

A total of 94 immunization treatments were administered to all patients. There was no dose-limiting toxicity and no serious adverse effects (SAE) that resulted in treatment discontinuation at any vaccine dose level. The most common toxicity was a self-limited, injection site reaction. Other reactions occurred with less than a 10% incidence and included fever, flu-like symptoms, anorexia, chills, nausea, and headache. These symptoms were also self-limiting and did not require intervention other than symptomatic measures such as acetaminophen.

The safety profile from the treatment of over expressing CEA cancer patients using the same Ad5 vector backbone gives us a rationale to use the same Ad5 backbone expressing HPV-E6/E7 for the immunization (vaccination) of patients that are HPV-16+ and at high risk for developing HPV+ cancers or who have HPV+ cancers.

Preclinical Studies

Studies were performed to assess the use of Ad5 [E1-, E2b-]-HPV-E6/E7 as a cancer vaccine in a C57Bl/6 mouse model. Ad5 [E1-, E2b-]-HPV-E6/E7 induced potent CMI against HPV-E6/E7 in mice. The Ad5 [E1-, E2b-]-HPV-E6/E7 significantly inhibited progression of established HPV-E6/E7 tumors in a murine model of HPV E6/E7 expressing cancer. These data indicate that in vivo delivery of Ad5 [E1-, E2b-]-HPV-E6/E7 can induce anti-HPV E6/E7 immunity and inhibit progression of HPV E6/E7 expressing cancers.

Dose Response of Ad5 [E1-, E2b-]-HPV-E6/E7

A study was performed to determine the effect of immunizations with increasing doses of Ad5 [E1-, E2b-]-HPV-E6/E7 on the induction of cell-mediated immune (CMI) responses in Ad5 naive mice. Groups of Ad5 naïve BALB/c mice (n=5/group) were immunized subcutaneously (SQ) three times at 2-week intervals with $10^8$, $10^9$, or $10^{10}$ VP of Ad5 [E1-, E2b-]-HPV-E6/E7, respectively. Control mice were injected with buffer solution only. Two weeks after the last immunization, T cell CMI responses were assessed by IFNγ ELISpot analysis. As shown in FIG. 36, a dose response effect was observed on the CMI response with the highest CMI response level being obtained after immunizations with $10^{10}$ VP using Ad5 [E1-, E2b-]-HPV-E6/E7 immunization. Specificity studies revealed that CMI responses were specific to HPV E6 and E7 and there were no responses against the irrelevant antigen SIV-1 nef.

Induction of CMI Responses after Ad5 [E1-, E2b-]-HPV-E6/E7 Vaccination as Assessed by Flow Cytometry.

To assess CMI induction by flow cytometry following multiple homologous immunizations with Ad5 [E1-, E2b-]-HPV-E6/E7, groups of C57Bl/6 mice (n=5/group) were immunized three times SQ at 2-week intervals with $10^{10}$ VP of Ad5 [E1-, E2b-]-HPV-E6/E7. Two weeks following the last immunization, splenocytes were exposed to HPV-E6/E7 peptides or irrelevant antigens and analyzed by flow cytometry for the number of IFN-γ and/or TNFα expressing T cells. As shown in FIG. 68, both IFN-γ and/or TNFα expressing T cells were induced as a result of multiple homologous immunizations with the highest dose of Ad5 [E1-, E2b-]-HPV-E6/E7. Specificity studies revealed that CMI responses were specific to HPV E6 and E7 and there were no responses against irrelevant antigens such as SIV-vif or SIV-nef.

Toxicology.

An extensive pre-clinical toxicology study will be conducted to assess the toxicity of Ad5 [E1-, E2b-]-HPV-E6/E7 following SQ injections on in C57/Bl/6 mice. Toxicity endpoints will be assessed at various time points post-injection. The animals will be administered up to 3 SQ injections on Days 1, 22 and 43, with either vehicle control or Ad5 [E1-, E2b-]-HPV-E6/E7 at a dose consistent with that to be used in clinical trials accounting for difference in body mass. Evaluations will consist of effects on body weights, body weight gain, food consumption pathology, blood hematology analyses, blood chemistry analyses, and test on coagulation time.

Treatment of Established HPV E6/E7 Expressing Tumors with Vaccine Alone

The effectiveness of treating established HPV E6/E7 expressing tumors in vivo with Ad5 [E1-, E2b-]-HPV-E6/E7 was evaluated. C57Bl/6 mice were implanted SQ into the right subcostal with $10^6$ HPV E6/E7 expressing tumor cells on day 0. Tumors were palpable by days 4-6. On days 6, 13, and 20, mice were treated by SQ injections of $10^{10}$ VP of Ad5 [E1-, E2b-]-null (empty vector controls) or $10^{10}$ VP of Ad5 [E1-, E2b-]-HPV-E6/E7. All mice were monitored for tumor growth and tumor volumes were calculated. As shown in FIG. 69, mice immunized with Ad5 [E1-, E2b-]-HPV-E6/E7 had significantly smaller tumors than control mice (p<0.01). These results demonstrate that the Ad5 [E1-, E2b-]-HPV-E6/E7 vector platform has the potential to be utilized as an immunotherapeutic agent to treat HPV-E6/E7 expressing tumors.

Treatment of Established HPV E6/E7 Expressing Tumors with Vaccine and Chemotherapy/Radiation Treatment.

The effectiveness of treating HPV E6/E7 expressing tumors in vivo with Ad5 [E1-, E2b-]-HPV-E6/E7 combined with chemotherapy/radiation treatment was evaluated. C57Bl/6 mice were implanted SQ with $10^6$ HPV E6/E7 expressing tumor cells on day 0. Established HPV-E6/E7 expressing tumors were treated by immunotherapy on days 7, 14, and 21 combined with cisplatin/radiation treatment on days 13, 20, and 27. Control tumor bearing mice were treated by injections with Ad-null combined with cisplatin/radiation treatment. As shown in FIG. 52, combination treatment using Ad5 [E1-, E2b-]-HPV-E6/E7 and chemotherapy/radiation resulted in significant extension of survival time as compared with control mice receiving treatment Ad5 [E1-, E2b-]-null (Empty vector control) and chemotherapy/radiation. These results show that vaccine immunotherapy can be combined with chemotherapy/radiation treatment and that this combination results in a significantly greater extension of survival in a mouse model of HPV E6/E7 expressing cancer.

In summary, ETBX-041 (Ad5 [E1-, E2b-]-HPV-E6/E7) is a non-oncogenic vaccine targeting HPV-E6 and E7 that induces robust immune responses. Ad5 [E1-, E2b-]-HPV-E6/E7 induced potent CMI against HPV-E6/E7 in mice assessed in ELISpot and flow cytometry studies. Ad5 [E1-, E2b-]-HPV-E6/E7 significantly inhibited progression of established tumors in a murine model of HPV E6/E7 expressing cancer. Immunotherapy with Ad5 [E1-, E2b-]-HPV-E6/E7 could be combined with chemotherapy/radiation treatment to significantly increase survival in tumor bearing mice. The goal is to further develop this novel Ad5 vector system that overcomes barriers found with other Ad5 systems and clinically tests this vaccine to determine that significant HPV-E6/E7 directed immune responses are induced in immunized (vaccinated) individuals. The results of this clinical study will establish the safety and immunogenicity of using this new Ad5 [E1-, E2b-]-HPV-E6/E7 vaccine.

Example 12: Preclinical Data of Ad-CEA Vaccine

Ad5 Vaccine Expressing CEA (ETBX-011): The Ad5 [E1-, E2b-]-CEA(6D) vaccine (ETBX-011) is an adenovirus vector vaccine in which the E1, E2b and E3 gene regions have been removed and replaced with a gene encoding CEA with the CAP1-6D mutation.

ETBX-011 vaccine is supplied as a sterile, clear solution in a single-dose vial. Vials will contain a single dose of 5×1011 VP. Dose will be administered according to the clinical protocol. The maximum tolerated dose will be determined in a dose escalation study as outlined in the clinical protocol.

Instructions for Storage, Handling and Administration

ETBX-011 vaccine should be stored at −20° C.

Prior to injection, the appropriate vial should be removed from the freezer and allowed to thaw at controlled room temperature (20-25° C., 68-77° F.) for at least 20 minutes and not more than 30 minutes, after which it should be kept at 28° C. (35 46° F.). The vaccine is stable for at least 8 hours after removal from the freezer when kept refrigerated at 28° C. (35-46° F.).

The thawed vial should be swirled and then, using aseptic technique, the pharmacist should withdraw the appropriate volume (1.0 mL) from the vial using a 1 mL syringe. The vaccine should be injected as soon as possible using a 1 to ½ inch, 20 to 25 gauge needle. If the vaccine cannot be injected immediately, the syringe should be stored at 28° C. (35-46° F.).

All injections of vaccine should be given as a volume of 1.0 mL by subcutaneous injection in the upper arm after preparation of the site with alcohol. Either arm may be used for each injection.

When preparing a dose in a syringe and administering the dose, consideration should be given to the volume of solution that may remain in the needle after the dose is administered, to ensure that the full dose specified in the protocol is administered.

Immunization with Ad5-CEA(6D) Platforms:

In pre-clinical studies, the immunogenicity of Ad5 [E1-, E2b-]-CEA(6D) vaccine was tested in an Ad5 naïve and an Ad5 immune murine model. To assess the induction of cellular meditated immunity following immunization, Ad5 naïve C57Bl/6 mice (n=7/group) were immunized three times subcutaneously (SQ) with $10^{10}$ VP of Ad5 [E1-]-CEA (6D), Ad5 [E1-, E2b-]-CEA(6D), or injection buffer alone (control) at weekly intervals. Three immunizations were used because prior studies in an HIV-1 model demonstrated that the Ad5 [E1-, E2b-] vector induced a maximum immune boost after three immunizations. Fourteen days after the final immunization, CEA-specific CMI responses were determined by IFN-γ and IL-2 ELISpot assays. Mice immunized with Ad5 [E1-, E2b-]-CEA(6D) induced a significantly greater number of IFN-γ ($p<0.01$) and IL-2 ($p<0.01$) secreting splenocytes than mice immunized with Ad5 [E1-]-CEA(6D) (FIG. 45A and FIG. 45B). Splenocytes from vaccinated mice and controls were assessed for non-specific cytokine secretion following stimulation with HIV-1 Gag and β-galactosidase. Non-specific IFN-γ or IL-2 secretion was not detected in T-cells from the spleens of mice vaccinated with either CEA expressing vector (FIG. 45A and FIG. 45B). Splenocytes were also stimulated with Ad5-null to confirm positive vaccination against Ad5 and splenocytes derived from all such immunized mice harbored Ad5 specific T-cells (FIG. 45A and FIG. 45B). Elevated levels of CEA specific IgG antibody were detected after immunizations and these levels were comparable for both Ad5-CEA vectors.

CMI Against Ad5 [E1]-CEA(6D) and Ad5 [E1-, E2b]-CEA(6D) in Ad5 Immune Mice:

To assess whether Ad5 [E1-, E2b-]-CEA(6D) is more effective than Ad5 [E1-]-CEA(6D) in the presence of Ad5 immunity, Ad5 naive C57Bl/6 mice (n=7/group) were immunized twice with $10^{10}$ VP of Ad5 [E1-]-null to induce Ad5 immunity. The presence of anti-Ad5 IgG antibody was confirmed by ELISA as 0.028±0.028 ng Equivalents of IgG antibody for baseline samples versus 39.50±3.78 ng Equivalents of IgG antibody in samples after Ad5-null immunizations ($p<0.0001$). Ad5 immune mice were then immunized three times at weekly intervals with $10^{10}$ VP of Ad5 [E1-]-CEA(6D) or Ad5 [E1-, E2b-]-CEA(6D). Controls received injection buffer alone. Splenocytes were collected 14 days after the final immunization and assessed by IFN-γ and IL-2 ELISpot. Ad5-immune mice immunized with Ad5 [E1-, E2b-]-CEA(6D) exhibited significantly higher levels of IFN-γ ($p=0.04$) and IL-2 ($p<0.01$) secreting splenocytes as compared to Ad5 immune mice immunized with Ad5 [E1-]-CEA(6D) (FIG. 46A and FIG. 46B). Splenocytes were also assessed for non-specific secreting T-cells of IFN-γ (FIG. 46A) or IL-2 (FIG. 46B) by stimulation with the non-immunizing antigens Beta-galactosidase (β-gal) and HIV-1 Gag. When compared to the results for naïve mice above, levels of CEA specific IgG antibody generated after immunizations were greatly reduced.

Ability of the Ad5 [E1-, E2b-]-CEA(6D) Vector to Break Tolerance:

Having immunologically compared the two Ad5-CEA (6D) vectors, a study was then performed to assess if the Ad5 [E1-, E2b-]-CEA(6D) vector could break tolerance in the more stringent CEA transgenic mouse model in which CEA is a self-antigen. Mice were immunized once with $2.6\times10^{10}$ VP of Ad5 [E1-, E2b-]-CEA(6D) and 14 days later, their splenocytes were assessed for CMI responses by IFN-γ ELISpot assays. Elevated numbers of IFN-γ secreting splenocytes were observed after only one injection with the vector platform (FIG. 47). ELISpot studies employing Cytomegalovirus (CMVpp65) and HIV-gag antigens showed that the response was specific to CEA.

Treatment of CEA Expressing Tumors in Ad5 Naïve Mice:

The efficacy of immunizations with Ad5 [E1-, E2b-]-CEA (6D) was evaluated by the treatment of CEA expressing MC-38 tumors that were growing in Ad5 naïve and Ad5 immune mice. A group of C57Bl/6 mice (n=7) were implanted SQ in the flank with $10^6$ CEA expressing MC-38 tumor cells (MC38-CEA). Six days later, when tumors were palpable (3-5 mm), the mice were treated with three SQ injections of $10^{10}$ VP of Ad5 [E1-, E2b-]-CEA(6D) on days 7, 13 and 19. Untreated C57Bl/6 mice (n=7) implanted with $10^6$ MC38-CEA cells and injected at the same time points with injection buffer alone served as controls. Tumor volumes were measured and reported as previously described. Briefly, tumors were measured by two opposing diameters and reported as a multiple of those numbers to determine tumor volumes. Statistical differences were determined using the Bonferroni posttests analysis with PRISM software. The sizes of treated and control tumors are shown in FIG. 48A as a function of time. At Day 20 post implant the tumors in mice treated with Ad5 [E1-, E2b-]-CEA(6D) were significantly ($p<0.05$) smaller as compared to controls (FIG. 48A). Tumors were excised and weighed at the termination of the study. Tumors from mice treated with Ad5 [E1-, E2b-]-CEA(6D) weighed significantly ($p<0.05$) less than tumors from control mice (FIG. 48B). Splenocytes from both groups of mice were assessed for the number of CEA stimulated IFN-γ secreting T cells by ELISpot. Mice immunized with Ad5 [E1-, E2b-]-CEA(6D) had a significantly ($p<0.05$) greater number of INF-γ secreting T-cells in their spleens as compared to control mice (FIG. 48C).

Treatment of CEA Expressing Tumors in Ad5 Immune Mice:

To determine if Ad5 immune MC38-CEA tumor bearing mice could be treated with Ad5 [E1-, E2b-]-CEA(6D), C57Bl/6 mice (n=7) were immunized two times at a two-week interval with $10^{10}$ VP of Ad5 [E1-]-null. Two weeks after the second Ad5 [E1-]-null immunization, mice were implanted SQ with $10^6$ CEA expressing MC-38 tumor cells. Six days later tumors were measurable (3-5 mm) and the mice were treated with three SQ injections of $10^{10}$ VP of Ad5 [E1-, E2b-]-CEA(6D) at weekly intervals. C57Bl/6 mice (n=7) which were immunized twice with Ad5 [E1-]-null, inoculated with $10^6$ MC38-CEA cells and injected three times SQ with injection buffer alone served as controls. All mice were monitored for tumor growth and tumor volumes are reported using previously described methods. Briefly, tumors were measured by two opposing diameters and reported as a multiple of those numbers to determine tumor volumes. Statistical differences were determined using the Bonferroni posttests analysis with PRISM software. Evaluation was over a 21-day period and the size of MC38-CEA tumors was determined as a function of time. At day 19 the tumors in mice treated with Ad5 [E1-, E2b-]-CEA(6D) were significantly smaller as compared to the controls (FIG. 49A). At the end of the study all mice were sacrificed and the tumors were excised and weighed. Tumors from the mice treated with Ad5 [E1-, E2b-]-CEA(6D) weighed significantly less than the tumors from controls (FIG. 49B). The number of CEA stimulated T-cells in the spleen which secreted IFN-γ was determined by ELISpot assay. Mice immunized with Ad5 [E1-, E2b-]-CEA(6D) had a significantly greater number of IFN-γ secreting T-cells than did control mice that received injection buffer alone (FIG. 49C).

In summary, Ad5 [E1-, E2b-]-CEA(6D) is a therapeutic vaccine targeting CEA that induces robust immune responses, even in the presence of pre-existing Ad5 immunity. When compared directly with a conventional Ad5 [E1-]-CEA(6D) vector, the Ad5 [E1-, E2b-]-CEA(6D) platform induced superior cellular mediated immune responses in both Ad5 naïve and Ad5 immune animals. In therapeutic efficacy studies, treatment with Ad5 [E1-, E2b-]-CEA(6D) resulted in significantly decreased established MC38-CEA tumor growth even in mice which had been pre-immunized against Ad5. Treatment with Ad5 [E1-, E2b-]-CEA(6D) did not result in any adverse effects in pre-clinical studies. The results of these pre-clinical studies exemplify the technical and immunological merit of using the Ad5 [E1-, E2b-]-CEA (6D) vaccine as a therapeutic agent.

Example 13: Clinical Study of Ad-CEA(6D) Vaccine

Clinical safety: Phase I/II clinical trial of Ad-CEA (Ad5 [E1-, E2b-]-CEA(6D)) (IND #14325) have been performed. The Phase I/II study consisted of a dose-escalation study of four dosage levels ($1\times10^9$, $1\times10^{10}$, $1\times10^{11}$, $5\times10^{11}$ VP/dose) of ETBX-011 (Phase I component), and the maximally tolerated dose of ETBX-011 (Phase II and $5\times10^{11}$ VP/dose components). Ad-CEA was administered by SQ injection every 3 weeks. Thirty-two patients with metastatic colorectal cancer, median age 57.5 (range 38-77) who had failed a median of three prior chemotherapeutic regimens (range 2-5), had a performance status of 90% (range 70-100%), and had three sites of metastatic disease (range 1-4), were enrolled. The majority of patients were able to receive all three immunizations. Four patients who stopped immunizations early did so due to significant disease progression.

A total of 94 immunization treatments were administered to all patients. There was no dose-limiting toxicity and no serious adverse effects (SAE) that resulted in treatment discontinuation at any vaccine dose level. The most common toxicity was a self-limited, injection site reaction. Other reactions occurred with less than a 10% incidence of all adverse effects (AE) reported and included fever, flu-like symptoms, anorexia, chills, nausea, and headache. These symptoms were also self-limiting and did not require intervention other than symptomatic measures such as acetaminophen.

CMI Response in Treated Patients:

CEA specific immune responses following immunization treatments with the product candidate were evaluated. As determined by an ELISA technique, no antibody activity directed against CEA was observed. CMI responses in colorectal cancer patients treated in cohort 1, cohort 2, cohort 3/Phase II, and cohort 5 was assessed. PBMCs were isolated prior to immunotherapy treatment and after all treatments as well as three weeks following the last treatment from patients. CEA specific ELISpot assays were performed on PBMC to determine the numbers of interferon gamma (IFN-γ) secreting lymphocytes (SFC) after exposure to CEA peptides in vitro. The highest CMI responses during immunizations, regardless of time point (weeks 3, 6, or 9) in the patients treated in cohort 1, cohort 2, cohort 3/Phase II, and cohort 5 was determined. This analysis revealed a dose response to increasing levels of product (FIG. 14). The highest CMI levels occurred in patients that received the highest dose of $5\times10^{11}$ VP (Cohort 5). In a preliminary study, it was observed that a population of polyfunctional CD8+ T cells (those that secrete more than 1 cytokine when activated) after immunizations secreted multiple cytokines, a sign of greater functionality of T cells induced by the vaccine. In further follow-up analysis of a few patient blood samples, a decrease in CEA directed after immunotherapy was stopped was noted (FIG. 50). This observation supports a rationale for booster immunizations.

Ad5 NAb (neutralizing antibodies) and CMI against Ad5 were also measured and correlated with CEA-specific CMI. Each patient had their serum and PBMC sample tested at baseline (prior to treatment) and at 9 weeks after completion of 3 treatments. Nineteen of 31 colorectal cancer patients (61%) tested in this study had Ad5 neutralizing activity in serum samples prior to the onset of treatment with Ad5 [E1-, E2b-]-CEA(6D). The mean pre-treatment Ad5 NAb titer value obtained among all patients was 1:189±1:71 SEM and the mean pre-treatment Ad5 NAb titer among seropositive patients was 1:308±1:108. Analysis of serum samples from patients who received 3 immunizations revealed Ad5 NAb titers that were significantly increased (P<0.0001, Mann-Whitney test) by week 9 (mean 1:4767±1:1225 SEM) when compared with their respective baseline values. Analysis of PBMC for CMI responses to Ad5 also revealed a significant increase (P<0.01, Mann-Whitney test) in Ad5 directed CMI responses after immunizations with Ad5 [E1-, E2b-]-CEA (6D) (22.6±9.3 SEM IFN-γ secreting SFC at week 0 versus 191.1±83.7 IFN-γ SFC at week 9).

Clinical Evidence of Activity:

The Ad-CEA treated colorectal cancer patients (total=32) were followed for survival and Kaplan-Meier plots and survival proportions performed (PRISM software). Events were determined by information from the social security death index (SSDI) database, clinical charts and telephone calls (FIG. 51A-FIG. 51C).

The seven patients in cohorts 1 and 2 experienced a 12-month survival proportion of 29%. The 21 patients in cohort 3 and Phase II experienced a 12-month survival proportion of 48%. The six patients in cohort 5 experienced a 12-month survival proportion of 50%. Twenty-nine month overall survival of the intent-to-treat population (32 patients) was 20% (FIG. 51A) with a median survival time of 11 months from informed consent/first injection. For the subset of 28 patients that received all 3 immunizations, the 29-month survival was 23% (FIG. 51B) with a median survival time of 13 months. For the 22 patients optimally dosed with the two highest doses of vaccine (1 and $5\times10^{11}$) and receiving all 3 immunizations, the 28-month overall survival was 19% (FIG. 51C). Median overall survival was 13 months in the optimally treated patients. There were 3 stable disease events observed immediately after completion of treatment.

Evidence of an Ad5 [E1-, E2b-]-Based Vaccine Driving T Cell Infiltration and PD-L1 Upregulation:

High-risk human papillomavirus (HPV) such as HPV type-16 is associated with the etiology of cervical and more than 90% of HPV-related head and neck squamous cell carcinomas (HNSCC). The HPV early 6 (E6) and early 7 (E7) genes are expressed at high levels in HPV-induced cancers and are involved in the immortalization of primary human epidermal cells. The Ad5 [E1-, E2b-]-based vector platform was investigated in a murine model of HPV-associated E6/E7 expressing cancer. The immunotherapy against human papilloma virus (HPV) using a viral gene delivery platform to immunize against HPV 16 genes E6 and E7 (Ad5 [E1-, E2b-]-E6/E7) combined with programmed death-ligand 1 (PD-1) blockade increased therapeutic effect as compared to the vaccine alone. Ad5 [E1-, E2b-]-E6/E7 as a single agent induced HPV-E6/E7 cell-mediated immunity. Immunotherapy using Ad5 [E1-, E2b-]-E6/E7 resulted in clearance of small tumors and an overall survival benefit in mice with larger established tumors. When immunotherapy was combined with immune checkpoint blockade, an increased level of anti-tumor activity against large tumors was observed (FIG. 44A-FIG. 44C). Analysis of the tumor microenvironment in Ad5 [E1-, E2b-]-E6/E7 treated mice revealed elevated $CD8^+$ tumor infiltrating lymphocytes (TILs); however, induction of suppressive mechanisms such as programmed death-ligand 1 (PD-L1) expression was observed on tumor cells and an increase in $PD-1^+$ TILs was also shown. When Ad5 [E1-, E2b-]-E6/E7 immunotherapy was combined with anti-PD-1 antibody, it was observed that $CD8^+$ TILs at the same level but a reduction in tumor PD-L1 expression on tumor cells and reduced $PD-1^+$ TILs providing a mechanism by which combination therapy favors a tumor clearance state and a rationale for pairing antigen-specific vaccines with checkpoint inhibitors in future clinical trials.

Combining Chemotherapy Treatment with Ad5 [E1-, E2b-]-Based Vaccine Immunotherapy:

Using the same murine model of HPV-associated E6/E7 expressing cancer described above, immunotherapy using Ad5 [E1-, E2b-]-E6/E7 combined with cisplatin/radiation treatment that is utilized to treat HNSCC was investigated. When immunotherapy was combined with cisplatin/radiation treatment, a significant increase in survival time demonstrated in tumor bearing mice treated with the combination of immunotherapy and cisplatin/radiation treatment as compared to control mice receiving cisplatin/radiation treatment alone was seen (FIG. 52).

The effects of combining immunizations with Ad5 [E1-, E2b-]-E6/E7 with cisplatin/radiation treatment versus cisplatin/radiation treatment alone in a murine model was assessed. The combination of Ad5 [E1-, E2b-]-E6/E7 immunizations plus cisplatin/radiation treatment resulted in the induction greater CMI responses as compared to immunizations with Ad5 [E1-, E2b-]-E6/E7 alone (FIG. 53). These results provide a rationale for combining immunotherapy with chemotherapy treatment in order to achieve greater anti-tumor CMI responses.

Toxicology

Because of the possibility that the lower host reactivity against the Ad5 [E1-, E2b-]-CEA(6D) could result in an altered hepatic toxicity profile, hepatic adverse effects were determined following immunization with the CEA expressing vectors or injection buffer alone in Ad5-naïve and Ad5-immune mice. Studies to evaluate adverse hepatic effects of vaccination were performed first using Ad5-naive mice immunized at weekly intervals with 1010 VP of Ad5 [E1-]-CEA(6D), Ad5 [E1-, E2b-]-CEA(6D) or controls injected with injection buffer alone. Three days after one immunization (Day 3) or three immunizations (Day 17), alanine aminotransferase (ALT) and aspartate aminotransferase (AST) levels were assessed in blood samples to determine liver adverse effects due to treatment. All liver enzyme levels were within normal range after immunization with either vector platform (FIGS. 64A-64B). Liver necrosis is determined by a change in the AST/ALT ratio from greater than one to less than one. There was no indication of liver necrosis following vector immunization or in control animals.

Studies of hepatic adverse effects were also performed using Ad5 immune mice. C57Bl/6 mice (n=7) were injected twice at a two week interval with 1010 VP of Ad5 [E1-]-null and then immunized three times with Ad5 [E1-]-CEA(6D) or Ad5 [E1-, E2b-]-CEA(6D) as described above. A group (n=7) of Ad5 naïve and Ad5 immune mice immunized with injection buffer alone served as controls. Three days after the last immunization, ALT and AST levels were assessed on the blood samples to determine hepatic adverse effects due to treatment (FIGS. 65A-65B). AST and ALT levels remained within the normal control range after immunizations with either vector. There was no change in the AST/ALT ratios, indicating lack of liver necrosis following vector immunization in Ad5 immune animals. No hepatic adverse effects were detected following immunization by either platform as determined by little change in serum ALT and AST levels.

Clinical Trial for ETBX-011 (Ad5 [E1-, E2b-]-CEA(6D)) Vaccine

A Phase I/II clinical trial of ETBX-011 (Ad5 [E1-, E2b-]-CEA(6D)) (IND #14325) that expresses the tumor-associated antigen carcinoembryonic antigen (CEA) was performed. The Phase I/II study consisted of a dose-escalation study of four dosage levels ($1\times10^9$, $1\times10^{10}$, $1\times10^{11}$, $5\times10^{11}$ VP/dose) of ETBX-011 (Phase I component), and the maximally tolerated dose of ETBX-011 (Phase II and $5\times10^{11}$ VP/dose components). ETBX-011 was administered by subcutaneous injection every 3 weeks for three treatments. Thirty-two patients with metastatic colorectal cancer, median age 57.5 (range 38-77) who had failed a median of three prior chemotherapeutic regimens (range 2-5), had a performance status of 90% (range 70-100%), and had three sites of metastatic disease (range 1-4), were enrolled. The majority of patients were able to receive all three immunizations. Four patients who stopped immunizations early did so due to significant disease progression. A total of 94 immunization treatments were administered to all patients. There was no dose-limiting toxicity and no serious adverse effects (SAE) that resulted in treatment discontinuation at any vaccine dose level. The most common toxicity was a self-limited, injection site reaction. Other reactions occurred with less than a 10% incidence and included fever, flu-like symptoms, anorexia, chills, nausea, and headache. These symptoms were also self-limiting and did not require intervention other than symptomatic measures such as acetaminophen.

The safety profile from the treatment of over expressing CEA cancer patients using the Ad5 [E1-, E2b-]-CEA(6D) vector gives us a rationale to use the vaccine for the treatment of additional patients with carcinomas expressing CEA to evaluate the safety and immunogenicity. ETBX-011 is a clear colorless liquid filled in a 2-mL amber vial containing 1.0 mL of extractable vaccine. There are total of 5×10¹¹ total virus particles in 1.0 ml of the product. Each vial is sealed with a rubber stopper and has a white flip off seal. End user of the product will need to flip the white plastic portion of the cap up/off with their thumb to expose the rubber stopper, and then puncture the stopper with an injection needle to withdraw the liquid. The rubber stopper is secured to the vial with an aluminum crimped seal.

Example 14: Clinical Trial for Combination of FOLFOX-A, Ad-CEA Vaccine, and Avelumab Objectives:

To determine if there is an improvement in time to progression among patients with metastatic colorectal cancer who are treated with standard of care+anti-PDL1 monoclonal antibody+Ad-CEA therapeutic cancer vaccine compared with standard of care alone Primary Objective:

To determine if there is an improvement in time to progression among patients with metastatic colorectal cancer who are treated with standard of care+Ad-CEA vaccine+Avelumab compared with standard of care alone Secondary Objective(s):

Safety of the combination versus standard of care alone

Immunologic effects of the combination compared with standard of care

Peripheral

Quantitate T cell responses against CEA, and other tumor associated antigens using methods such as intracellular cytokine staining, ELIspot, and/or others Flow-based assay for analysis of PBMC subsets T-cell clonal expansion assay Serum cytokine and soluble factor analysis ELISA for antibody generation against CEA Tumoral Immunohistochemistry analysis of T cell infiltrate (may include CD3, CD4, CD8, FoxP3 and others), immune regulatory markers (may include IDO, LAG3, TIM3, PD-1, PD-L1 and others)

RNA and proteomic analysis for immune signature changes

Whole genome sequencing for identification of mutation correlate with clinical outcome Correlative analysis of immune endpoints with clinical outcomes Overall response rate (CR+PR by RECIST 1.1)

Overall survival

Eligibility:

Subjects age 18 and older with previously untreated pathologically confirmed metastatic colorectal cancer; prior adjuvant therapy is acceptable ECOG performance status ≤1

Normal organ and bone marrow function

Subjects with active autoimmune diseases requiring treatment and subjects requiring system steroids (except for physiologic doses for steroid replacement) are not allowed Design:

This is a randomized, multicenter phase 2.5 clinical trial designed to evaluate the potential improvement in Progression Free Survival (PFS) when Avelumab and Ad-CEA vaccine are used in combination with standard of care therapy in metastatic colorectal cancer when compared with standard of care alone (FOLFOX-B).

A lead in cohort, comprising the first 6 evaluable subjects enrolled, will be treated with avelumab+Ad-CEA vaccine+standard of care in order to assess the safety of the combination.

If no more than 1 subject in the lead in cohort experiences a dose limiting toxicity attributable to the IND agents, 70 evaluable subjects will be randomized on a 1:1 basis to receive either Avelumab+Ad-CEA vaccine+standard of care (Arm B) or standard of care alone (Arm A)

Standard of care therapy consists of 6-12 two week cycles of bevacizumab+FOLFOX (5-FU, leucovorin, oxaliplatin) followed by two week cycles of bevacizumab+capecitabine until disease progression Subjects assigned Arm A that have progressive disease will be offered Avelumab+Ad-CEA vaccine in combination with a standard chemotherapy regimen Kaplan-Meier curves and a two-tailed log-rank test will be the primary analysis methods.

The accrual ceiling for the study is set at 81

Preclinical Data Support:

Preclinical model evaluation of the combination of FOLFOX with anti-PD-L1 was performed by EMD-Serono. The study was conducted in compliance with GLP and the global policy "Quality management system (QMS) for Merck Serono research (MSR)" of Merck KGaA.

The study investigated the potential of combining avelumab with the core components of FOLFOX (5-fluorouracil and oxaliplatin) in two separate studies (TI10-079 & TI11-001) conducted in mice bearing subcutaneous MC38 tumors.

The therapeutic combination of oxaliplatin/5-FU and anti-PD-L1 blockade using avelumab in MC38 tumor-bearing mice yielded superior tumor growth inhibition relative to control mice and either form of monotherapy (FIG. 56). Additionally, the avelumab and oxaliplatin/5-FU combination significantly extended survival compared to mice receiving either vehicle control or monotherapy (FIG. 57).

In both in vivo studies (TI10-079 and TI11-001), a subset of mice in each treatment group was sacrificed to evaluate trends in immune phenotype in the spleen and tumor tissues. Using a pentamer analysis of splenic tissue, the avelumab and oxaliplatin/5-FU combination was shown to significantly elevate the precursor frequency of tumor-reactive P15E-specific CD8+ T cells (P15E is a known tumor antigen expressed in MC38 colorectal cancer tumor lines (FIG. 58). Additionally, avelumab therapy was shown to consistently and significantly increase the percentage of splenic CD8+ T cells expressing the PD-1 receptor (FIG. 59).

Consistent with the findings in the spleen, intratumoral CD8+ T cells and NK1.1+ cells were elevated in mice receiving combination therapy with avelumab and oxaliplatin/5-FU (FIG. 60 and FIG. 61, respectively). Taken together, the phenotypic data from mice treated with the avelumab and oxaliplatin/5-FU combination suggest that this immunotherapeutic regimen is successfully activating immune effector cell populations with known tumoricidal potential (NK1.1+ and CD8+ T cells).

The frequency of IFN-γ producing CD8+T effector cells directed against the p15E tumor antigen was also measured using an ELISPOT assay that detects IFN-γ secretion as a marker of T cell activation. Using the ELISPOT assay, a strong p15E-specific response was detected in all treated groups in study TI10-079 (FIG. 62). In study TI11-001, the highest p15E-specific response was measured in the combination treatment group (FIG. 61).

One interpretation of this data is that chemotherapy initiates a cascading sequence in which tumor cell destruction and the shedding of tumor antigen in the tumor microenvironment activates innate and adaptive immune responses to the tumor. In this scenario, PD-L1 blockade is thought to potentiate the adaptive immune response, which may indirectly activate innate effector cells such as NK cells.

By blocking negative costimulation of tumor-reactive T cells mediated by the PD-1/PD-L1 interaction, avelumab may be employed in a variety of settings and indications to maximize the potential efficacy of standard of care cytotoxic therapies as well as immunotherapy combinations.

The use of standard chemotherapy in patients with previously untreated metastatic colorectal cancer was studied, and no difference was found in the number of 40+ different immune cell subsets pre-versus post-treatment with standard therapy (5-FU based chemotherapy). Thus, chemotherapy should not diminish the potential immune benefits of anti-PD-L1 therapy.

In summary, Avelumab is a monoclonal antibody with excellent binding capability against PD-L1. A recently completed dose escalation of study of avelumab demonstrated safety and binding capability against PD-L1 in humans. FOLFOX+Bevacizumab is the standard of care for $1^{st}$ line metastatic colorectal cancer treatment. A preclinical model has demonstrated increased immune reactivity, decreased tumor growth rate, and improved survival in mice bearing MC38 tumors. Clinical data from patients pre- and post-treatment with FOLFOX+Bevacizumab demonstrates no significant difference in 40 immune cell subsets indicating standard agents will not negatively affect peripheral immune subsets. 5-FU and Oxaliplatin are involved in improving immune response to tumors through immunogenic cell death and immunogenic modulation. Standard of care with or without a novel immunotherapy may allow identification of longer term benefit where radiographic tumor responses are less common.

Randomization Procedures

Randomization begins after the first 6 evaluable subjects are enrolled (lead in). These subjects are assigned to the Arm B regimen. Thereafter, subjects are randomized on a 1:1 basis to the following arms (as exemplified in FIG. 66):

Arm A: Subjects receive FOLFOX6+bevacizumab for up to 12 2-week cycles followed by maintenance therapy with bevacizumab+capecitabine until disease progression.

Arm B: Subjects receive FOLFOX6+bevacizumab+avelumab for up to 12 2-week cycles followed by maintenance therapy with bevacizumab+capecitabine+avelumab until disease progression.

Study Implementation

Study design: This is an open-label, randomized, multi-center phase 2.5 clinical trial designed to evaluate the potential improvement in time to progression (TTP) when avelumab is used on combination with standard of care therapy in metastatic colorectal cancer when compared with standard of care alone. Patients in the standard of care alone arm are offered the opportunity to cross-over and receive avelumab in combination with any combination of the Arm A standard of care deemed appropriate by the investigator at the time of disease progression (as defined by RECIST 1.1.). Cross-over is not offered in the case of rapid or symptomatic progression due to the need for implementation of a standard option with known efficacy. Other clinical and immunologic endpoints are captured with the goal of establishing correlative data that can later be prospectively tested in a larger phase 3 study.

A dosing regimen is exemplified in FIG. 67.

Initially, 6 patients assigned to receive the combination of chemotherapy and avelumab are enrolled to evaluate safety and feasibility of this treatment schedule.

Dose Limiting Toxicity (Lead-In Period Only):

The DLT evaluation period is the period from the first dose of avelumab until 4 weeks (28 days) have passed. DLT is assessed in the first 6 patients enrolled. If >1/6 patients experience a DLT, with the combination. Subjects who do not complete the DLT observation period for reasons other than a DLT are replaced.

The goal of the safety evaluation for the combination is to determine if there are any increased or unexpected toxicities due to the combination of therapies that would not be expected with either regimen alone (FOLFOX-A or avelumab). As such, a DLT for the combination is any adverse event that is unexpected relative to the known safety profile of the standard and investigational agents in the opinion of the investigator. The phase 2.5 portion of the study will proceed when DLT evaluation period for 6 patients is completed.

Drug Administration

All subjects: During the course of the study subjects in study Arm A receive intravenous (IV) bevacizumab plus FOLFOX (first line therapy) on Days 1 and 2 of a 2 week cycle as tolerated per investigator discretion for up to a total of 12 cycles in keeping with standard of care treatment guidelines. Subjects in study Arm B receive bevacizumab plus FOLFOX (first line therapy) on Days 2 and 3. After completion of first-line induction therapy, both study arm subjects continue treatment with capecitabine plus bevacizumab on a 2-week cycle in the maintenance period. Body surface area (BSA) and dosing are calculated based on the weight recorded within 2 days prior to avelumab dosing.

Administration of Bevacizumab Plus mFOLFOX6 (Induction Therapy):

Bevacizumab 5 mg/kg IV over 30-90 min on day 1 (infusion rate will be dependent on rate escalation tolerance) (Arm A) or 2 (Arm B), Oxaliplatin 85 mg/m$^2$ IV over 2 hours on day 1 (Arm A) or 2 (Arm B), Leucovorin* 400 mg/m$^2$ IV over 2 hours on day 1 (Arm A) or 2 (Arm B), 5-FU* 400 mg/m$^2$ IV bolus on day 1 (Arm A) or 2 (Arm B), 5-FU* 2400 mg/m$^2$ IV over 46 hours to start on day 1 (Arm A) or 2 (Arm B).

5-Fluorouracil and leucovorin should be administered separately to avoid the formation of a precipitate. Per package insert, leucovorin is administered first.

Administration of Capecitabine Plus Bevacizumab (Maintenance Therapy):

Capecitabine 625 mg/m$^2$ twice a day every day by mouth. Patients are instructed to take capecitabine with water within 30 minutes after a meal. Doses are rounded to the nearest dose achievable without splitting pills.

Bevacizumab 5 mg/kg IV over 30-90 min on day 1 (Arm A) or 2 (Arm B), repeat every 14 days (infusion rate dependent on rate escalation tolerance)

Bevacizumab Rate Escalation

The first dose of bevacizumab is given over 90 minutes. If the dose is well tolerated with no infusion reactions, the rate is increased for the second dose, which is given over 60 minutes. If the second dose is well tolerated, the third dose and all subsequent doses are given over 30 minutes. If there is an initial infusion reaction at 90 or 60 minute infusion times, but subsequent doses are well-tolerated, the rate is escalated at the investigator's discretion.

Lead-In, Arm A Crossovers and Arm B Subjects:

Subjects in the lead in portion of the study and subjects in Arm B additionally receive the study drugs, Avelumab and Ad-CEA vaccine, during the induction treatment period as well as during the maintenance phase of therapy. Avelumab and Ad-CEA vaccine are given on day 1 and FOLFOX+ bevacizumab are given on day 2. Subjects in arm A that progress are offered the opportunity to receive Ad-CEA vaccine and avelumab in combination with a standard chemotherapy regimen Avelumab Administration:

As a routine precaution, subjects enrolled in this trial are observed for 1 hour post infusion, in an area with resuscitation equipment and emergency agents. At all times during avelumab treatment, immediate emergency treatment of an infusion-related reaction or a severe hypersensitivity reaction according to institutional standards must be assured. In order to treat possible anaphylactic reactions, for instance, dexamethasone 10 mg and epinephrine in a 1:1000 dilution or equivalents are available along with equipment for assisted ventilation.

Subjects receive intravenous infusion of avelumab over 1 hour (−10 minutes/+20 minutes, i.e., 50 to 80 minutes) as applicable at a dose of 10 mg/kg.

Premedication with an antihistamine and with acetaminophen approximately 30 to 60 minutes prior to each dose of avelumab is mandatory (for example, 25-50 mg diphenhydramine and 500-650 mg acetaminophen i.v. or oral equivalent). This regimen is modified based on local treatment standards and guidelines, as appropriate.

The dose of avelumab is calculated based on the weight of the subject obtained within 2 days prior to avelumab administration. Subjects receive avelumab at the appropriate schedule until confirmed progression, unacceptable toxicity, or any criterion for withdrawal from the therapy.

Avelumab is given prior to IV chemotherapy during each cycle, when possible.

Ad-CEA Vaccine Administration:

Ad-CEA vaccine is administered as subcutaneous injection on Day 1 of specific cycles, prior to avelumab. Ad-CEA is administered on cycles 1, 2, and 3; 5, 7, and 9; and every 6 cycles thereafter.

Ad-CEA is provided in a frozen state in a 2 ml vial with a fill volume of 1 ml of extractable vaccine which contains $5 \times 10^{11}$ total virus particles. The product is stored at −20° C. until used and immediately thawed before use.

To Administer $5 \times 10^{11}$ Virus Particles by Subcutaneous Injection:

1.0 mL of contents from the previously thawed, supplied Ad-CEA is withdrawn from the vial and administered subcutaneously to the patient without any further manipulation.

Lead-In and Arm B Induction and Maintenance:

During the induction and maintenance phases (FOLFOX plus bevacizumab, and capecitabine plus bevacizumab, respectively), avelumab are given on day 1 of each cycle (+/−2 days for logistical reasons).

Crossovers from Arm A:

Subjects that have progressed during the induction phase on Arm A are given the option to cross over to avelumab in combination FOLFOX in order to exploit the synergistic effects of the combination therapy. Subjects on Arm A who have progressed during the maintenance phase are given the option to cross over to avelumab in combination with either capecitabine+bevacizumab or capecitabine+bevacizumab+oxaliplatin based on investigator choice. Subjects that cross over are treated on a 2 week cycle. Avelumab is given on day 1 of each cycle (+/−2 days for logistical reasons are allowed) and prior to the other agents to avoid giving steroids prior to avelumab.

Cross-over is not offered in the case of rapid or symptomatic progression due to the need for implementation of a standard option with known efficacy.

Clinical Outcomes in Patients with Colorectal Cancer: Progression Free Survival (PFS):

18 patients were enrolled on the single-agent phase I study of avelumab with mCRC at the 10 mg/kg dose level. Of these 18, 14 had reached the first restaging for evaluation. Of the 14 evaluable patients, 3 remain on study without evidence of progression for >100 days. Two of these patients have had stable disease for >200 days. Of the remaining evaluable patients (n=11), 9 have had disease progression within 85 days of initial treatment. The remaining 2 patients came off study for adverse events (transaminase elevation and infusion reaction, respectively). FIG. 54 illustrates the outcomes to date for patients with CRC treated with avelumab (MSB0010718C) by Response Evaluation Criteria for Solid Tumors (RECIST) criteria.

CEA Response:

One patient with mCRC on the phase I study had a remarkable decrease in serum CEA. At baseline his CEA was 267. After starting avelumab, he had a rapid and consistent fall in CEA over the following 5 months with stable disease on scans. He has now been on study for over 11 months with stable disease on scans. Notably, a biopsy of one of his retroperitoneal lymph nodes, being followed as measurable disease on CT scan, revealed "fibroadipose tissue with focal chronic inflammation. No tumor seen." This patient still has elevated CEA in the range of 22-41 that has been holding in this range for 5 months. FIG. 55 demonstrates the change in this patient's CEA.

Immune Data:

An analysis of immune cell subset changes from baseline to day 15 and day 43 was performed on PBMC samples from the first 23 patients enrolled on the phase I study of avelumab on clinical trial 13-C-0063 (NCT01772004), which included patients at 4 dose levels (1, 3, 10, and 20 mg/kg). There was no clear pattern of change (defined as 20% increase or decrease) pre-versus post-treatment in absolute lymphocyte count. A panel of markers was used to define >50 immune cell subsets by flow-cytometry at the same intervals. There were no significant changes in any of the immune cell subsets. Notably, there was no decrease in the number of circulating immune cells expressing PD-L1 (including B lymphocytes and dendritic cells).

Avelumab Phase I Safety

The dose escalation portion of clinical trial 13-C-0063 (NCT01772004) was completed. 4, 14 (1 withdrew before treatment), 12 and 21 patients, respectively, were enrolled into 4 escalating dose levels: 1 mg/kg, 3 mg/kg, 10 mg/kg, and 20 mg/kg. The maximum tolerated dose was not exceeded. At the 20 mg/kg dose level, 1 dose limiting toxicity was experienced out of 6 patients treated. This DLT was associated with a significant anti-tumor response and was attributed to drug because of the possibility that it was an immune-related adverse event (with transient elevated creatine kinase, muscle weakness, myalgia, transaminitis, myocarditis with elevated troponin and inferiolateral ST-elevation on ECG). To date, 80 patients have been enrolled. 55 pts (71.2%) have come off-study: 43 (53.7%) for progression and 6 (7.5%) for toxicity. Grade 3 AEs attributable to drug comprised of 7 laboratory abnormalities (4 increased liver transaminases, 1 decreased lymphocytes, 1 elevated creatine kinase and 1 elevated lipase) in 5 patients and symptomatic myositis requiring intervention in 2 other patients.

Pharmacokinetics and Receptor Occupancy Data:

Data from 25 patients was evaluable for PK and RO analysis. Median time to maximum concentration was approximately 1.5 to 2 hours after infusion (for all doses with a linear PK). Half-life was 63.4, 80.7, 93.9 and 115.1 hours for dose levels 1, 2, 3 and 4 respectively, measured by ELISA. Target RO data was available for 13 patients, measured by PD-L1 binding on peripheral leucocytes via flow cytometry. Mean RO was 75.7, 93.8 and 93.2% for dose levels 1, 2 and 3 respectively. Avelumab: Adverse Drug Reactions (ADRs) Requiring Treatment Discontinuation or Modifications (Note: standard of care therapy will be continued during any AE related delay or discontinuation of avelumab)

Any Grade 4 ADRs require treatment discontinuation except for single laboratory values out of normal range that are unlikely related to trial treatment as assessed by the investigator, do not have any clinical correlate, and resolve within 7 days with adequate medical management.

Any Grade 3 ADRs require treatment discontinuation except for any of the following:

Transient (≤6 hours) Grade 3 flu-like symptoms or fever, which is controlled with medical management.

Transient (≤24 hours) Grade 3 fatigue, local reactions, headache, nausea, emesis that resolves to ≤Grade 1.

Single laboratory values out of normal range (excluding ≥Grade 3 liver function test increase) that are unlikely related to trial treatment according to the investigator, do not have any clinical correlate, and resolve to ≤Grade 1 within 7 days with adequate medical management.

Tumor flare phenomenon defined as local pain, irritation, or rash localized at sites of known or suspected tumor.

Any Grade ≥3 drug-related amylase or lipase abnormality that is not associated with symptoms or clinical manifestations of pancreatitis does not require dose delay. The Study Medical Monitor should be consulted for such Grade ≥3 amylase or lipase abnormalities.

Increases in ECOG performance status ≥3, which do not resolve to ≤2 by cycle Day 14 of the following cycle (infusions should not be given on the following cycle, if the ECOG performance status is ≥3 on the day of study drug administration).

Any Grade 2 ADR should be Managed as Follows:

If a Grade 2 ADR resolves to Grade ≤1 by the last day of the current cycle, treatment may continue.

If a Grade 2 ADR does not resolve to Grade ≤1 by the last day of the current cycle, infusions should not be given on the following cycle. If at the end of the following cycle, the event has not resolved to Grade 1, the subject should permanently discontinue treatment with avelumab ADR (except for hormone insufficiencies, that can be managed by replacement therapy; for these hormone insufficiencies, up to 2 subsequent doses may be omitted).

Upon the second occurrence of the same Grade 2 ADR (except for hormone insufficiencies that can be managed by replacement therapy) in the same subject, treatment with avelumab is permanently discontinued.

Infusion-related reactions, hypersensitivity reactions (Grades 1 to 4), and tumor lysis syndrome should be handled.

Recommendations for the Management of Avelumab Infusion Related Reactions:

Infusion of avelumab is stopped in case of ≥Grade 2 hypersensitivity, inflammatory response, or anaphylactic reaction. The treatment recommendations for infusion-related reactions, severe hypersensitivity reactions, and tumor lysis syndrome according to the NCI are outlined in the Table 13 below. All infusion-related reactions, occurring during study drug infusion or after completion of the study drug administration, are reported as AESIs or SAEs in case any serious criterion is met.

TABLE 13

| NCI-CTCAE Grade | Treatment Modification for Avelumab |
| --- | --- |
| Grade 1 - mild<br>Mild transient reaction; infusion interruption not indicated; intervention not indicated. | Decrease the avelumab infusion rate by 50% and monitor closely for any worsening.<br>The total infusion time for avelumab should not exceed 120 minutes. |
| Grade 2 - moderate<br>Therapy or infusion interruption indicated but responds promptly to symptomatic treatment (e.g., antihistamines, NSAIDs, narcotics, i.v. fluids); prophylactic medications indicated for ≤24 hours. | Stop avelumab infusion.<br>Resume infusion at 50% of previous rate once infusion related reaction has resolved or decreased to at least Grade 1 in severity, and monitor closely for any worsening. |
| Grade 3 or Grade 4 - severe or life-threatening<br>Grade 3: Prolonged (e.g., not rapidly responsive to symptomatic medication and/or brief interruption of infusion); recurrence of symptoms following initial improvement; hospitalization indicated for clinical sequelae.<br>Grade 4: Life-threatening consequences; urgent intervention indicated. | Stop the avelumab infusion immediately and disconnect infusion tubing from the subject. Subjects have to be withdrawn immediately from avelumab treatment and must not receive any further avelumab treatment. |

Once the avelumab infusion rate has been decreased by 50% or interrupted due to an infusion related reaction, it must remain decreased for all subsequent infusions. If the subject has a second infusion-related reaction Grade ≥2 on the slower infusion rate, the infusion is stopped and the subject is removed from avelumab treatment. If a subject experiences a Grade 3 or 4 infusion-related reaction at any time, the subject must discontinue avelumab. If an infusion reaction occurs, all details about drug preparation and infusion must be recorded.

Management of Immune Related Adverse Events (irAEs):

Since inhibition of PD-L1 stimulates the immune system, irAEs may occur. Treatment of irAEs is mainly dependent upon severity (NCI-CTCAE grade):

Grade 1 to 2: treat symptomatically or with moderate dose steroids, more frequent monitoring Grade 1 to 2 (persistent): manage similar to high grade AE (Grade 3 to 4)

Grade 3 to 4: treat with high dose corticosteroids

Treatment of irAEs should follow guidelines set forth in the tables below.

TABLE 14

Management of Gastrointestinal irAEs

| Severity of Diarrhea/Colitis (NCI-CTCAE v4) | Management | Follow-up |
|---|---|---|
| Grade 1<br>Diarrhea: <4 stools/day over Baseline<br>Colitis: asymptomatic | Continue avelumab therapy<br>Symptomatic treatment (e.g., loperamide) | Close monitoring for worsening symptoms<br>Educate subject to report worsening immediately<br>If worsens: Treat as Grade 2 or 3/4 |
| Grade 2<br>Diarrhea: 4 to 6 stools per day over baseline; i.v. fluids indicated <24 hours; not interfering with ADL<br>Colitis: abdominal pain; blood in stool | Delay avelumab therapy<br>Symptomatic treatment | If improves to Grade 1:<br>Resume avelumab therapy<br>If persists >5 to 7 days or recur: 0.5 to 1.0 mg/kg/day methylprednisolone or equivalent<br>When symptoms improve to Grade 1, taper steroids over at least 1 month, consider prophylactic antibiotics for opportunistic infections, and resume avelumab therapy per section "Avelumab: Adverse Drug Reactions (ADRs) Requiring Treatment Discontinuation or Modifications"<br>If worsens or persists >3 to 5 days with oral steroids:<br>Treat as Grade 3 to 4 |
| Grade 3 to 4<br>Diarrhea (Grade 3): ≥7 stools per day over Baseline; incontinence; i.v. fluids ≥24 hrs; interfering with ADL<br>Colitis (Grade 3): severe abdominal pain, medical intervention indicated, peritoneal signs<br>Grade 4: life-threatening, perforation | Discontinue avelumab therapy per section "Avelumab: Adverse Drug Reactions (ADRs) Requiring Treatment Discontinuation or Modifications"<br>1.0 to 2.0 mg/kg/day methylprednisolone i.v. or equivalent<br>Add prophylactic antibiotics for opportunistic infections<br>Consider lower endoscopy | If improves:<br>Continue steroids until Grade 1, then taper over at least 1 month<br>If persists >3 to 5 days, or recurs after improvement:<br>Add infliximab 5 mg/kg (if no contraindication), Note: Infliximab should not be used in cases of perforation or sepsis |

ADL = activities of daily living

TABLE 15

Management of Dermatological irAEs

| Grade of Rash (NCI-CTCAE v4) | Management | Follow-up |
|---|---|---|
| Grade 1 to 2<br>Covering ≤30% body surface area | Symptomatic therapy (for example, antihistamines, topical steroids)<br>Continue avelumab therapy | If persists >1 to 2 weeks or recurs:<br>Consider skin biopsy<br>Delay avelumab therapy<br>Consider 0.5 to 1.0 mg/kg/day methylprednisolone i.v. or oral equivalent. Once improving, taper steroids over at least 1 month, consider prophylactic antibiotics for opportunistic infections, and resume avelumab therapy<br>If worsens:<br>Treat as Grade 3 to 4 |
| Grade 3 to 4<br>Covering >30% body surface area; life threatening consequences | Delay or discontinue avelumab therapy<br>Consider skin biopsy<br>Dermatology consult<br>1.0 to 2.0 mg/kg/day methylprednisolone i.v. or i.v. equivalent | If improves to Grade 1:<br>Taper steroids over at least 1 month and add prophylactic antibiotics for opportunistic infections<br>Resume avelumab therapy |

TABLE 16

Management of Pulmonary irAEs

| Grade of Pneumonitis (NCI-CTCAE v4) | Management | Follow-up |
|---|---|---|
| Grade 1<br>Radiographic changes only | Consider delay of avelumab therapy<br>Monitor for symptoms every 2 to 3 days<br>Consider Pulmonary and Infectious Disease consults | Re-image at least every 3 weeks<br>If worsens:<br>Treat as Grade 2 or Grade 3 to 4 |
| Grade 2<br>Mild to moderate new symptoms | Delay avelumab therapy<br>Pulmonary and Infectious Disease consults<br>Monitor symptoms daily, consider hospitalization<br>1.0 mg/kg/day methylprednisolone i.v. or oral equivalent<br>Consider bronchoscopy, lung biopsy | Re-image every 1 to 3 days<br>If improves:<br>When symptoms return to near baseline, taper steroids over at least 1 month and then resume avelumab therapy and consider prophylactic antibiotics<br>If not improving after 2 weeks or worsening:<br>Treat as Grade 3 to 4 |
| Grade 3 to 4<br>Severe new symptoms; New/worsening hypoxia; life-threatening | Discontinue avelumab therapy<br>Hospitalize<br>Pulmonary and Infectious Disease consults<br>2 to 4 mg/kg/day methylprednisolone i.v. or i.v. equivalent<br>Add prophylactic antibiotics for opportunistic infections<br>Consider bronchoscopy, lung biopsy | If improves to baseline:<br>Taper steroids over at least 6 weeks<br>If not improving after 48 hours or worsening:<br>Add additional immunosuppression (for example, infliximab, cyclophosphamide, i.v. immunoglobulin, or mycophenolate mofetil) |

TABLE 17

Management of Hepatic irAEs

| Grade of Liver Test Elevation (NCI-CTCAE v4) | Management | Follow-up |
|---|---|---|
| Grade 1<br>Grade 1 AST or ALT > ULN to 3.0 × ULN and/or total bilirubin > ULN to 1.5 × ULN | Consider delay of avelumab therapy<br>Monitor for symptoms every 2 to 3 days<br>Consider Pulmonary and Infectious Disease consults | Re-image at least every 3 weeks<br>If worsens:<br>Treat as Grade 2 or Grade 3 to 4 |
| Grade 2<br>AST or ALT >3.0 to ≤5 × ULN and/or total bilirubin >1.5 to ≤3 × ULN | Delay avelumab therapy<br>Increase frequency of monitoring to every 3 days | If returns to baseline:<br>Resume routine monitoring, resume avelumab therapy<br>If elevations persist >5 to 7 days or worsen:<br>0.5 to 1 mg/kg/day methylprednisolone or oral equivalent and when LFT returns to Grade 1 or Baseline, taper steroids over at least 1 month, consider prophylactic antibiotics for opportunistic infections, and resume avelumab therapy |
| Grade 3 to 4<br>AST or ALT >5 × ULN and/or total bilirubin >3 × ULN | Discontinue avelumab therapy<br>Increase frequency of monitoring to every 1 to 2 days<br>1.0 to 2.0 mg/kg/day methylprednisolone i.v. or i.v. equivalent<br>Add prophylactic antibiotics for opportunistic infections<br>Consult gastroenterologist<br>Consider obtaining MRI/CT scan of liver and liver biopsy if clinically warranted | If returns to Grade 2:<br>Taper steroids over at least 1 month<br>If does not improve in >3 to 5 days, worsens or rebounds:<br>Add mycophenolate mofetil 1 gram (g) twice daily<br>If no response within an additional 3 to 5 days:<br>consider other immunosuppressants per local guidelines |

TABLE 18

Management of Endocrine irAEs

| Endocrine Disorder | Management | Follow-up |
|---|---|---|
| Asymptomatic TSH abnormality | Continue avelumab therapy If TSH <0.5 × LLN, or TSH >2 × ULN, or consistently out of range in 2 subsequent measurements: include T4 at subsequent cycles as clinically indicated; consider endocrinology consult; may administer replacement treatment if clinically indicated. | |
| Symptomatic endocrinopathy | Evaluate endocrine function Consider pituitary scan Symptomatic with abnormal lab/ pituitary scan: Delay avelumab therapy 1 to 2 mg/kg/day methylprednisolone i.v. or by mouth equivalent Initiate appropriate hormone therapy No abnormal lab/pituitary MRI scan but symptoms persist: Repeat labs in 1 to 3 weeks/MRI in 1 month | If returns to baseline: Resume routine monitoring, resume avelumab therapy If elevations persist >5 to 7 days or worsen: 0.5 to 1 mg/kg/day methylprednisolone or oral equivalent and when LFT returns to Grade 1 or Baseline, taper steroids over at least 1 month, consider prophylactic antibiotics for opportunistic infections, and resume avelumab therapy |
| Grade 3 to 4 Suspicion of adrenal crisis (for example, severe dehydration, hypotension, shock out of proportion to current illness) | Delay or discontinue avelumab therapy per section "Avelumab: Adverse Drug Reactions (ADRs) Requiring Treatment Discontinuation or Modifications" Rule out sepsis Stress dose of i.v. steroids with mineralocorticoid activity i.v. fluids Consult endocrinologist If adrenal crisis ruled out, then treat as above for symptomatic endocrinopathy | |

Active Immunotherapy with Ad-CEA Vaccine Will be Discontinued for:

Life-threatening anaphylactic reactions related to active immunotherapy

DLT related to active immunotherapy with Ad-CEA as follows: a) If one or more patients develop a Grade 4 allergic reaction without a clear attributable cause, other than study vaccine, b) Death not attributed to disease Disease progression (by RECIST criteria). Patients are offered referral to a medical oncologist for discussion of other treatment options, and for continued medical care.

Disease progression prior to completing the study immunizations: In the event that a patient undergoes reimaging studies prior to the completion of their 6 study immunizations and is found to have disease progression, they are permitted to continue on the study as long as the progression has been 50% or less by RECIST criteria.

Dose Delays/Modifications—Bevacizumab

Hypertension

Bevacizumab is administered unless SBP <150 and DBP <90. Management of hypertension is outlined below.

Mild/Moderate Hypertension: For SBP >140 and <210 mm Hg or DBP >90 and <120 mm Hg that is sustained over at least a two week period, initiate or adjust anti-hypertensive therapy. Bevacizumab must be delayed until the blood SBP <150 and DBP <90.

Severe Hypertension: For SBP ≥210 mm Hg or DBP ≥120 mm Hg but without end organ damage, begin anti-hypertensive therapy. Bevacizumab must be delayed until blood SBP <150 and DBP <90.

Hypertensive Urgency or Emergency: Bevacizumab therapy will be permanently discontinued in the presence of hypertensive urgency (DBP >120 with evidence of optic disc edema or progressive end-organ complications) or hypertensive emergency (SBP >210 and DBP >120 presenting with headaches, blurred vision, or focal neurological symptoms, or papilledema). Only grade 4 hypertension will require expedited reporting to the NCI-IRB.

Thrombotic Events

Deep Vein Thrombosis: Bevacizumab will not be administered in the presence of deep vein thrombosis. Anticoagulation may be used and bevacizumab may be restated when thrombosis is resolved.

Arterial Thromboembolic Events: Bevacizumab will be permanently discontinued in the presence of new arterial thrombotic disease, including but not limited to, myocardial infarct due to coronary thrombosis and ischemic stroke.

Neutropenia: Bevacizumab will be held if the absolute neutrophil count (ANC) is less than 750 cells/µL until ANC is again above 750 cells/4. Filgrastim or pegfilgrastim may be scheduled to individual patient requirement in order to maintain a neutrophil count targeted to meet or exceed 750 cells/µL.

Hemorrhage

Life Threatening: In the case of hemoptysis, hematemesis, hematochezia, intracranial hemorrhage or any significant blood loss, bevacizumab will not be administered.

Proteinuria: If urine dipstick indicates ≥2+proteinuria, bevacizumab administration will be delayed pending the results of a 24-hour urine collection for protein. If the 24-hour urine protein is ≥2 grams, bevacizumab will be delayed for up to 6 weeks, until the proteinuria is <2+ or the 24-hour urine protein is <1 grams/24 hr.

Liver Function Abnormalities: Bevacizumab should be withheld in the event of ≥Grade 3 LFT elevations and should not resume until the abnormalities have recovered to ≤Grade 1 (with the exception of hyperbilirubinemia attributable to protease inhibitor therapy, in which case the total bilirubin must recover to ≤7.5 mg/dL and the direct fraction ≤0.7 mg/dl.) If LFT elevations recur with re-treatment, bevacizumab should be permanently discontinued. Liver function tests included are the transaminases alanine aminotransferase (ALT, SGPT), aspartate aminotransferase (AST, SGOT), alkaline phosphatase, and bilirubin. Elevated bilirubin due to protease inhibitor therapy will not require treatment modification.

Allergic Reaction: In case of flushing, shortness of breath, facial edema, headache, chills, back pain, tightness of the chest and throat, and/or hypotension, fever or rash, the infusion should be suspended until the patient is assessed until the events have subsided. For grade 3 or 4 allergic reactions, bevacizumab will be permanently discontinued.

Surgical or periodontal procedures: If there is need for an elective major surgical or periodontal procedure, bevacizumab should be held beginning at least 6 weeks prior to the procedure and must not be resumed before 4 weeks after the surgical procedure. For urgent or emergent surgery or endoscopic procedures, bevacizumab will be held for 4 weeks after the procedure. Longer delays may be necessary, if clinically indicated, in order to insure that adequate healing has taken place prior to bevacizumab resumption. For minor procedures (i.e. interventional radiology diagnostic procedures), bevacizumab will be held only if there is evidence that healing is compromised.

Reversible Posterior Leukoencephalopathy Syndrome (RPLS): Bevacizumab should not be administered to patients with signs or symptoms of RPLS. Evaluation should include neurologic evaluation, ocular examination, head MRI, and blood pressure assessment. If these clinical criteria are consistent with the diagnosis of RPLS, bevacizumab will be permanently discontinued.

Gastrointestinal Perforations and Fistula Formation: Bevacizumab will be discontinued in the event of a gastrointestinal perforation or the formation of a fistula.

Other Grade 3 or 4 Toxicities: Bevacizumab will be held for any other Grade 3 or 4 toxicity thought to be at least possibly related to bevacizumab. Lymphopenia and other toxicities clearly related to HIV or its therapy or to the Kaposi's sarcoma itself will not require dose modification. Grade 3 or higher asymptomatic hyperuricemia, hypophosphatemia, elevated creatinine phosphokinase levels will not result in dose delay.

Dose Delays/Modifications—Capecitabine

Dose adjustments for toxicities per CTCAE as per table.

TABLE 19

Summary of management of common Capecitabine toxicities

| Toxicity | Capecitabine dose modification |
| --- | --- |
| Grade 2 hand foot syndrome | Interrupt until ≤ grade 1. May then restart capecitabine at full dose. For second occurrence, hold capecitabine until ≤ grade 1, then restart capecitabine one dose level lower (75% of starting dose first occurrence, 50% of the starting dose the second occurrence, discontinue the third occurrence). |
| Grade 3 hand foot syndrome | Interrupt until ≤ grade 1. Then restart capecitabine one dose level lower (75% of starting dose first occurrence, 50% of the starting dose the second occurrence, discontinue the third occurrence). |
| Grade 2 Nausea/Vomiting | Continue at current dose, modify anti-emetic regimen |
| Grade 3 Nausea/Vomiting | Hold until recovery to grade 1 (or grade 2 if present at baseline) then resume one dose level lower* |
| Grade 2 Diarrhea | Continue current dose, add optimal anti-diarrheal therapy |
| Grade 3 (or greater) Diarrhea | Hold until recovery to grade 1 (or grade 2 if present at baseline) then resume one dose level lower* |
| Grade 3 (or greater) fatigue | Hold until recovery to grade 1 (or grade 2 if present at baseline) then resume one dose level lower* |
| Grade 3 (or greater) mucositis | Hold until recovery to grade 1 (or grade 2 if present at baseline) then resume one dose level lower* |
| Grade 2 thrombocytopenia | Continue at current dose |
| Grade 3 thrombocytopenia | Hold until recovery until ≤ grade 1 then resume one dose level lower* |
| Grade 4 thrombocytopenia | Hold until recovery until ≤ grade 1 then resume one dose level lower* |
| Grade 3 neutropenia | Hold until recovery until ≤ grade 1 then resume one dose level lower* |
| Grade 4 neutropenia | Hold until recovery until ≤ grade 1 then resume one dose level lower* |
| ≥ Grade 3 febrile neutropenia | Hold until resolution of fever and neutropenia to ≤ grade 1. Then resume on dose level lower* |

*Dose reductions for capecitabine

1. Starting dose: 625 mg/m$^2$ BID continuously
2. DL-1: 470 mg/m$^2$ BID continuously
3. DL-2: 310 mg/m$^2$ BID continuously
4. Discontinuation of capecitabine.

TABLE 20

FOLFOX dose adjustment

| | Adverse Event | First Occurrence | Second Occurrence |
|---|---|---|---|
| Hematologic Toxicity | ANC <1000/mL OR Platelets <75000/mL OR Any Febrile Neutropenia | 1. Hold all therapy and check CBC weekly until recovery to: ANC ≥1000/mL and Platelets ≥75000/mL AND 2. Discontinue 5-FU bolus on Day 1 at the next cycle | 1. Hold all therapy and check CBC weekly until recovery to: ANC ≥1000/mL and Platelets ≥75000/mL AND 2. Decrease Oxaliplatin to 65 mg/m2 on Day 1 at the next cycle |
| | ANC ≥1000/ml but <1500/mL OR Platelets ≥75000/ml but <100000/mL | 1. Discontinue 5-FU bolus on Day 1 at the next cycle | 1. Decrease Oxaliplatin to 65 mg/m2 on Day 1 at the next cycle |
| | Any other CTC ≥ Grade 3 hematologic toxicity, (e.g. HgB <8.0 g/dL) | 1. Hold all therapy until recovery to Grade 1 (or Grade 2 level, if present at baseline) AND 2. Discontinue 5-FU bolus on Day 1 at the next cycle | 1. Hold all therapy until recovery to Grade 1 (or Grade 2 level, if present at baseline) AND 2. Decrease Oxaliplatin to 65 mg/m2 on Day 1 at the next cycle |
| Non-Hematologic Toxicity | Nausea/Vomiting CTC ≥ Grade 3 | 1. Hold all therapy until recovery to Grade 1 (or Grade 2 level, if present at baseline) AND 2. Add Fosaprepitant 150 mg IV Day 1, and Dexamethasone 4 mg PO days 2-5 at the next cycle | 1. Hold all therapy until recovery to Grade 1 (or Grade 2 level, if present at baseline) AND 2. Discontinue 5-FU bolus and reduce oxaliplatin to 65 mg/m2 on Day 1 at the next cycle |
| | Diarrhea CTC ≥ Grade 3, despite optimal antidiarrheal therapy | 1. Hold all therapy until recovery to Grade 1 (or Grade 2 level, if present at baseline) AND 2. Discontinue 5-FU bolus at the next cycle | 1. Hold all therapy until recovery to Grade 1 (or Grade 2 level, if present at baseline) AND 2. Decrease 5-FU continuous infusion to 1800 mg/m2 on Day 1 at the next cycle |
| | Fatigue CTC ≥ Grade 3 OR Mucositis CTC ≥ Grade 3 OR Other Toxicity Not Defined Herein CTC ≥ Grade 3 despite optimal supportive care | 1. Hold all therapy until recovery to Grade 1 (or Grade 2 level, if present at baseline) AND 2. Discontinue 5-FU bolus on Day 1 at the next cycle | 1. Hold all therapy until recovery to Grade 1 (or Grade 2 level, if present at baseline) AND 2. Decrease Oxaliplatin to 65 mg/m2 on Day 1 at the next cycle |
| FOLFOX-Specific Toxicities | Peripheral Neuropathy CTC ≥ Grade 2 | 1. Hold all therapy until recovery to Grade ≤2 AND 2. Decrease Oxaliplatin to 65 mg/m2 on Day 1 at the next cycle | 1. Hold all therapy until recovery to Grade ≤2 AND 2. Decrease Oxaliplatin to 50 mg/m2 on Day 1 at the next cycle |
| | Hand-Foot Syndrome CTC ≥ Grade 3 | 1. Hold all therapy until recovery to Grade 1 (or Grade 2 level, if present at baseline) AND 2. Decrease 5-FU continuous infusion to 1800 mg/m2 on Day 1 at the next cycle | 1. Hold all therapy until recovery to Grade 1 (or Grade 2 Level, if present at baseline) AND 2. Discontinue 5-FU bolus on Day 1 at the next cycle |

| | Adverse Event | Third Occurrence | Fourth Occurrence |
|---|---|---|---|
| Hematologic Toxicity | ANC <1000/mL OR Platelets <75000/mL OR Any Febrile Neutropenia | 1. Hold all therapy and check CBC weekly until recovery to: ANC ≥1000/mL and Platelets ≥75000/mL AND 2. Decrease 5-FU continuous infusion to 1800 mg/m2 and decrease Oxaliplatin to 50 mg/m2 on Day 1 at the next cycle | 1. Hold all therapy and check CBC weekly until recovery to: ANC ≥1000/mL and Platelets ≥75000/mL AND 2. Decrease 5-FU continuous infusion to 1200 mg/m2 and discontinue Oxaliplatin on Day 1 at the next cycle |
| | ANC ≥1000/ml but <1500/mL OR Platelets ≥75000/ml but <100000/mL | 1. Decrease Oxaliplatin to 50 mg/m2 on Day 1 at the next cycle | 1. Decrease 5-FU continuous infusion to 1800 mg/m2 on Day 1 at the next cycle |
| | Any other CTC ≥ Grade 3 hematologic toxicity, (e.g. HgB <8.0 g/dL) | 1. Hold all therapy until recovery to Grade 1 (or Grade 2 level, if present at baseline) AND 2. Decrease Oxaliplatin to 50 mg/m2 on Day 1 at the next cycle | 1. Hold all therapy until recovery to Grade 1 (or Grade 2 level, if present at baseline) AND 2. Decrease 5-FU continuous infusion to 1800 mg/m2 on Day 1 at the next cycle |
| Non-Hematologic Toxicity | Nausea/Vomiting CTC ≥ Grade 3 | 1. Hold all therapy until recovery to Grade 1 (or Grade 2 level, if present at baseline) AND 2. Decrease 5-FU continuous infusion to 1200 mg/m2 and decrease Oxaliplatin to 50 mg/m2 on Day 1 at the next cycle | Off Study |
| | Diarrhea CTC ≥ Grade 3, despite optimal antidiarrheal therapy | 1. Hold all therapy until recovery to Grade 1 (or Grade 2 level, if present at baseline) AND 2. Decrease 5-FU continuous infusion to 1200 mg/m2 at the next cycle | 1. Hold all therapy until recovery to Grade 1 (or Grade 2 level, if present at baseline) AND 2. Decrease Oxaliplatin to 65 mg/m2 on Day 1 at the next cycle |

TABLE 20-continued

FOLFOX dose adjustment

| | Adverse Event | First Occurrence | Second Occurrence |
|---|---|---|---|
| FOLFOX-Specific Toxicities | Fatigue CTC ≥ Grade 3 OR Mucositis CTC ≥ Grade 3 OR Other Toxicity Not Defined Herein CTC ≥ Grade 3 despite optimal supportive care | 1. Hold all therapy until recovery to Grade 1 (or Grade 2 Level, if present at baseline) AND 2. Decrease 5-FU continuous infusion to 1800 mg/m2 on Day 1 at the next cycle | 1. Hold all therapy until recovery to Grade 1 (or Grade 2 Level, if present at baseline) AND 2. Decrease 5-FU continuous infusion to 1200 mg/m2 and decrease Oxaliplatin to 50 mg/m2 on Day 1 at the next cycle |
| | Peripheral Neuropathy CTC ≥ Grade 2 | 1. Hold all therapy until recovery to Grade ≤2 AND 2. Discontinue Oxaliplatin on Day 1 at the next cycle | Off Study |
| | Hand-Foot Syndrome CTC ≥ Grade 3 | 1. Hold all therapy until recovery to Grade 1 (or Grade 2 level, if present at baseline) AND 2. Decrease 5-FU continuous infusion to 1200 mg/m2 at the next cycle | 1. Hold all therapy until recovery to Grade 1 (or Grade 2 level, if present at baseline) AND 2. Decrease Oxaliplatin to 65 mg/m2 on Day 1 at the next cycle |

Study Calendar

Weight may be assessed within 2 days prior to avelumab dosing for all cycles

Cycle 1 day 1 assessments may be performed within 16 days prior to what is indicated Other day 1 assessments in cycles 2 and beyond may be performed within 1 week prior to indicated time

TABLE 21

| Procedure | Screening | Baseline | C1D1 | C2D1 | C3D1 | C4D1 | C5D1 | C6D1 | C7D1 | C8D1 | C9D1 | C10D1 | C11D1 | C12D1 | Maintenance Therapy CXD1 | Post Therapy Follow-up 30 day safety visit[1] | Long term follow up |
|---|---|---|---|---|---|---|---|---|---|---|---|---|---|---|---|---|---|
| History and PE | X | | X | X | X | X | X | X | X | X | X | X | X | X | Every 4 cycles | X | |
| Height | | X | | | | | | | | | | | | | | | |
| Weight | | X | X | X | X | X | X | X | X | X | X | X | X | X | X | X | |
| Vital signs | X | | X | X | X | X | X | X | X | X | X | X | X | X | X | X | |
| Performance Score | X | | X | X | X | X | X | X | X | X | X | X | X | X | X | X | |
| CBC with differential | X | | X[2] | X | X | X | X | X | X | X | X | X | X | X | X | X | |
| Hepatic + Acute Care Panels[3] | X | | X | X | X | X | X | X | X | X | X | X | X | X | X | X | |
| Mineral Panel[3] | | X | X | X | X | X | X | X | X | X | X | X | X | X | X | | |
| ACTH, ANA, RF, TSH, T4[4] | | X | X | | | | | | | | | | | | Every 4 cycles | | |
| PT/INR, PTT | X | | X | X | | | | | | | | | | | X | | |
| Urinalysis[5] | X | | X | X | | | | | | | | | | | X | | |
| 12 lead EKG | X | | X | | | | | | | | | | | | Every 4 cycles | | |
| HBV, HCV and HIV testing | X | | | | | | | | | | | | | | | | |
| Serum or urine HCG in women of childbearing potential | X | | X | | | | | | | | | | | | X | X | |
| Pathology confirmation of dx | X | | | | | | | | | | | | | | | | |
| Archival tumor tissue (if not available biopsy required) | X | | | | | | | | | | | | | | | | |
| Optional Biopsy[6] | | | | | | | | | | | | | | | X | | |
| Correlative research blood[7] | | | X | | X | | X | | X | | X | | X | | Every 4 cycles (with restaging) | | |
| PK/PD | | | | | | | | | | | | | | | | | |
| CT CAP or CT chest + MRI abdomen/pelvis | X | | | | | X | | | | | X | | | | Every 4 cycles | | |
| Adverse Events | | | X | | | | | | | | | | | | | | |
| Concomitant Medications | | | X | | | | | | | | | | | | | | |
| Annual phone call for survival and other cancer rx | | | | | | | | | | | | | | | | | X |

[1] 30 day safety visit occurs 4-5 weeks after the last administration of study drug regardless of reason for discontinuation. Information may be obtained by telephone if patient refuses visit.
[2] May be performed within 16 days prior to initiation of study therapy.
[3] Acute Care Panel: Sodium (NA), Potassium (K), Chloride (CL) Total CO2 (Bicarbonate), Creatinine, Glucose, Urea nitrogen, eGFR; Heptic Panel: Alkaline Phosphatase, ALT/GPT, AST/GOT, Total Bilirubin, Direct Bilirubin; Mineral Panel: Albumin, Calcium, Magnesium (Mg), Phosphorus
[4] ACTH: adrenocorticotropic hormone; ANA: anti-nuclear antibody; RF: rheumatoid factor, TSH: Thyroid-stimulating hormone; T4: Free thyroxine.
[5] Only urine dipstick required initially. If positive for protein content, a 24 hour urine collection for protein will be performed.
[6] Optional biopsy can be performed at any time on study, after first restaging with patient consent. Initial on-study biopsy should be after at least 4 cycles of SOC. A biopsy at the time of disease progression and/or response should be considered as well.
[7] Correlative blood samples: blood collected pre-dose: 6 (10 mL) green top sodium heparin tubes for PBMC; 2 (8 mL) SST tubes for serum samples.

Supportive Care

Recommended Management for Severe Hypersensitivity Reaction and Flu-Like Symptoms:

Management: 1) Epinephrine injection and dexamethasone infusion, 2) Patient should be placed on monitor immediately, 3) Alert intensive care unit (ICU) for possible transfer if required. For prophylaxis of flu-like symptoms, 25 mg indomethacin or comparable NSAID dose (e.g., ibuprofen 600 mg, naproxen sodium 500 mg) may be administered 2 hours before and 8 hours after the start of each dose of avelumab i.v. infusion. Alternative treatments for fever (e.g., acetaminophen) may be given to subjects at the discretion of the investigator.

Recommendations for the Management of Tumor Lysis Syndrome:

Since avelumab can induce ADCC, there is a potential risk of tumor lysis syndrome. Should this occur, subjects should be treated as per local guidelines and the management algorithm (FIG. 63).

General Supportive Care:

Because there is a potential for interaction of capecitabine with other concomitantly administered drugs through the CYP2C9 system, the case report form (CRF) must capture the concurrent use of all other drugs, over-the-counter medications, or alternative therapies. The Principal Investigator should be alerted if the patient is taking any agent known to affect or with the potential to interact with capecitabine. Patients will be transitioned to an acceptable alternative if available. Common examples include aluminum and magnesium hydroxide containing antacids, coumadin, and phenytoin.

Diarrhea will be managed with the following regimen: loperamide (4 mg PO) at onset of symptoms, followed by 2 mg loperamide every 2 hours while awake (or 4 mg PO every 4 hours while sleeping) up to a maximum of 16 mg loperamide per day. Additional agents may be used concurrently if loperamide is not adequate to control diarrhea as a single agent.

Nausea and vomiting will be managed through the use of appropriate simple supportive measures. Recommended premedication for oxalaplatin includes 10-20 mg IV dexamethasone and 16 mg ondansetron intravenously 30-60 minutes prior to infusion.

Patients will receive full supportive care per NIH CC guidelines as needed while on this study including blood product support, intravenous hydration, antibiotic treatment and treatment of other newly diagnosed or concurrent medical conditions.

Patients should be advised to drink plenty of water or take rehydration fluids to avoid dehydration if diarrhea occurs.

Correlative Studies for Research/Pharmacokinetic Studies

Immunological Studies: Samples from patients enrolled at Georgetown and the Clinical Center will be available for immunologic correlative studies as described below.

Peripheral blood: Six (10 mL) green top sodium heparin tubes for PBMC; 2 (8 mL) SST tubes for serum samples will be drawn on day 1 of Cycle 1, 3, 5, 9 and every 4 cycles thereafter as described in the Table 21. The following assessments are planned in the Laboratory of Tumor Immunology and Biology (LTIB), CCR, NCI for the samples collected.

Leukocyte subpopulations and immune activation status: Leukocyte subpopulations and immune activation status will be assessed by flow cytometry (FACS) on PBMC. Multiparameter FACS analysis using combination of markers will be performed to characterize leukocyte subpopulations and their functional state such as:

T-cells subsets and activation state
T-cells functionality
PD-1 signaling pathway
Regulatory T-cells
Other leukocytes subsets including B-cells, monocytes
NK cells and related cytotoxicity
Differentiation stage of T-cells subsets
Myeloid derived suppressor cells and APCs Comparison presence of TAA-specific T lymphocytes using TAA-specific peptides will be performed on pre- and post-treatment samples if enough PBMCs are available Further exploratory markers related to the mechanism of action of the drug such as soluble PD-L1 sera level, cytokine profile, and auto-antigen proteomic arrays may be explored.

T Cell Clonal Expansion Assay: cDNA from PBMC will be amplified using locus specific primers for TCR-$\beta$. Previously described methods will be used to map the V region and identify the J region (Klinger) and identify clonal sequences of interest. Analytics tools will be used to sort and identify clonal populations of interest in the post-versus pre-treatment samples. Correlation of expansion of a clonal TCR population post treatment will be correlated with clinical outcomes.

Serum soluble factors and ADCC-related side effects (such as in vitro ADCC activity assays, sCD40L and/or sCD27) may be explored.

Tissue analysis (Optional): Specimens will be collected after 4 cycles of standard of care therapy, and at disease progression and/or response. Remaining tissue from the mandatory samples collected at baseline (archived or fresh) may also be used in this study. Biopsies will be collected using standard techniques which may include which may include CT, cone beam CT, ultrasound, or fusion guided biopsy. Biopsies will be obtained from primary tumor sites and metastatic sites (if applicable). No more than 4 cores may be obtained per site. When possible, the same site of disease should be biopsied on repeat evaluation as was biopsied at baseline.

Specimens are used for the following studies conducted in the LTIB, CCR, NCI:

Level of PD-L1 expression will be assessed by immunohistochemistry staining (IHC). Of note, further techniques to evaluate the expression of PD-L1 and/or marker candidates impacting the targeting or contributing to improve its expression may be also investigated if needed.

Frequency and localization of tumor-infiltrated leukocytes (e.g., CD8, CD4 T-cells, Treg, NK cells, macrophage (M1/2 profile) by IHC Gene Expression-Based Subtyping Analysis to be performed in an outside lab, to be determined, using the methods described in Guinney, et al. (The consensus molecular subtypes of colorectal cancer, Nature Medicine, 2015). The clinical and immunologic effects of treatment in the standard and combination arms by subtype will be evaluated. Additional analysis may be performed to evaluate the expression of immune-related genes in tumor tissue pre- and post-treatment in each arm.

Whole Genome/RNA Expression/Proteomic Analysis

FFPE and/or fresh frozen tissue will be sent to NantOmics (Rockville, Md.) for analysis of genetic mutations, RNA expression profiling, and proteomic profiling of patient tumor samples from baseline and on treatment. Number of mutations, mutation patterns, RNA expression, and protein expression will be correlated with clinical outcomes in both arms. These analyses will be exploratory and retrospective and used for future hypothesis generation.

Data Collection and Evaluation

Data will be entered in C3D at all study sites. All data will be kept secure. The PI will be responsible for overseeing entry of data into an in-house password protected electronic system and ensuring data accuracy, consistency and timeliness. The principal investigator, associate investigators/research nurses and/or a contracted data manager will assist with the data management efforts. All human subjects personally identifiable information (PH) as defined in accordance to the Health Insurance Portability and Accountability Act, eligibility and consent verification will be recorded. Primary data obtained during the conduct of the protocol will be kept in secure network drives or in approved alternative sites that comply with NIH security standards. Primary and final analyzed data will have identifiers so that research data can be attributed to an individual human subject participant.

Response Criteria:

For the purposes of this study, patients should be re-evaluated for response every 8 weeks. In addition to a baseline scan, confirmatory scans should also be obtained up to 6 (not less than 4) weeks following initial documentation of objective response.

Response and progression will be evaluated in this study using the new international criteria proposed by the revised Response Evaluation Criteria in Solid Tumors (RECIST) guideline (version 1.1)[73]. Changes in the largest diameter (unidimensional measurement) of the tumor lesions and the shortest diameter in the case of malignant lymph nodes are used in the RECIST criteria.

DEFINITIONS

Evaluable for toxicity: All patients will be evaluable for toxicity from the time of their first treatment with avelumab.

Evaluable for DLT: The first 6 subjects enrolled enrolled will be evaluable for DLT from the time of their first treatment with avelumab until 28 days have passed. Subjects who do not complete the DLT observation period for reasons other than a DLT will be replaced.

Evaluable for objective response: Only those patients who have measurable disease present at baseline, have received at least one cycle of therapy, and have had their disease re-evaluated will be considered evaluable for response. These patients will have their response classified according to the definitions stated below.

Evaluable Non-Target Disease Response: Patients who have lesions present at baseline that are evaluable but do not meet the definitions of measurable disease, have received at least one cycle of therapy, and have had their disease re-evaluated will be considered evaluable for non-target disease. The response assessment is based on the presence, absence, or unequivocal progression of the lesions.

Disease Parameters:

Measurable disease: Measurable lesions are defined as those that can be accurately measured in at least one dimension (longest diameter to be recorded) as >20 mm by chest x-ray, as >10 mm with CT scan, or >10 mm with calipers by clinical exam. All tumor measurements must be recorded in millimeters (or decimal fractions of centimeters).

Malignant lymph nodes. To be considered pathologically enlarged and measurable, a lymph node must be >15 mm in short axis when assessed by CT scan (CT scan slice thickness recommended to be no greater than 5 mm). At baseline and in follow-up, only the short axis will be measured and followed.

Non-measurable disease. All other lesions (or sites of disease), including small lesions (longest diameter <10 mm or pathological lymph nodes with ≥10 to <15 mm short axis), are considered non-measurable disease. Bone lesions, leptomeningeal disease, ascites, pleural/pericardial effusions, lymphangitis cutis/pulmonitis, inflammatory breast disease, and abdominal masses (not followed by CT or MRI), are considered as non-measurable.

Note: Cystic lesions that meet the criteria for radiographically defined simple cysts should not be considered as malignant lesions (neither measurable nor non-measurable) since they are, by definition, simple cysts.

'Cystic lesions' thought to represent cystic metastases can be considered as measurable lesions, if they meet the definition of measurability described above. However, if non-cystic lesions are present in the same patient, these are preferred for selection as target lesions.

Target lesions. All measurable lesions up to a maximum of 2 lesions per organ and 5 lesions in total, representative of all involved organs, should be identified as target lesions and recorded and measured at baseline. Target lesions should be selected on the basis of their size (lesions with the longest diameter), be representative of all involved organs, but in addition should be those that lend themselves to reproducible repeated measurements. It may be the case that, on occasion, the largest lesion does not lend itself to reproducible measurement in which circumstance the next largest lesion which can be measured reproducibly should be selected. A sum of the diameters (longest for non-nodal lesions, short axis for nodal lesions) for all target lesions will be calculated and reported as the baseline sum diameters. If lymph nodes are to be included in the sum, then only the short axis is added into the sum. The baseline sum diameters will be used as reference to further characterize any objective tumor regression in the measurable dimension of the disease.

Non-target lesions. All other lesions (or sites of disease) including any measurable lesions over and above the 5 target lesions should be identified as non-target lesions and should also be recorded at baseline. Measurements of these lesions are not required, but the presence, absence, or in rare cases unequivocal progression of each should be noted throughout follow-up.

Methods for Evaluation of Measurable Disease:

All measurements should be taken and recorded in metric notation using a ruler or calipers. All baseline evaluations should be performed as closely as possible to the beginning of treatment and never more than 4 weeks before the beginning of the treatment.

The same method of assessment and the same technique should be used to characterize each identified and reported lesion at baseline and during follow-up. Imaging-based evaluation is preferred to evaluation by clinical examination unless the lesion(s) being followed cannot be imaged but are assessable by clinical exam.

Clinical lesions: Clinical lesions will only be considered measurable when they are superficial (e.g., skin nodules and palpable lymph nodes) and ● 10 mm diameter as assessed using calipers (e.g., skin nodules). In the case of skin lesions, documentation by color photography, including a ruler to estimate the size of the lesion, is recommended.

Chest x-ray: Lesions on chest x-ray are acceptable as measurable lesions when they are clearly defined and surrounded by aerated lung. However, CT is preferable.

Conventional CT and MRI: This guideline has defined measurability of lesions on CT scan based on the assumption that CT slice thickness is 5 mm or less. If CT scans have slice thickness greater than 5 mm, the minimum size for a measurable lesion should be twice the slice thickness. MRI is also acceptable in certain situations (e.g. for body scans).

Use of MRI remains a complex issue. MRI has excellent contrast, spatial, and temporal resolution; however, there are many image acquisition variables involved in MRI, which greatly impact image quality, lesion conspicuity, and measurement. Furthermore, the availability of MRI is variable globally. As with CT, if an MRI is performed, the technical specifications of the scanning sequences used should be optimized for the evaluation of the type and site of disease. Furthermore, as with CT, the modality used at follow-up should be the same as was used at baseline and the lesions should be measured/assessed on the same pulse sequence. It is beyond the scope of the RECIST guidelines to prescribe specific MRI pulse sequence parameters for all scanners, body parts, and diseases. Ideally, the same type of scanner should be used and the image acquisition protocol should be followed as closely as possible to prior scans. Body scans should be performed with breath-hold scanning techniques, if possible.

PET-CT: At present, the low dose or attenuation correction CT portion of a combined PET-CT is not always of optimal diagnostic CT quality for use with RECIST measurements. However, if the site can document that the CT performed as part of a PET-CT is of identical diagnostic quality to a diagnostic CT (with IV and oral contrast), then the CT portion of the PET-CT can be used for RECIST measurements and can be used interchangeably with conventional CT in accurately measuring cancer lesions over time. Note, however, that the PET portion of the CT introduces additional data which may bias an investigator if it is not routinely or serially performed.

Ultrasound: Ultrasound is not useful in assessment of lesion size and should not be used as a method of measurement. Ultrasound examinations cannot be reproduced in their entirety for independent review at a later date and, because they are operator dependent, it cannot be guaranteed that the same technique and measurements will be taken from one assessment to the next. If new lesions are identified by ultrasound in the course of the study, confirmation by CT or MRI is advised. If there is concern about radiation exposure at CT, MRI may be used instead of CT in selected instances.

Endoscopy, Laparoscopy: The utilization of these techniques for objective tumor evaluation is not advised. However, such techniques may be useful to confirm complete pathological response when biopsies are obtained or to determine relapse in trials where recurrence following complete response (CR) or surgical resection is an endpoint.

Tumor markers: Tumor markers alone cannot be used to assess response. If markers are initially above the upper normal limit, they must normalize for a patient to be considered in complete clinical response. Specific guidelines for both CA-125 response (in recurrent ovarian cancer) and PSA response (in recurrent prostate cancer) have been published [JNCI 96:487-488, 2004; J Clin Oncol 17, 3461-3467, 1999; J Clin Oncol 26:1148-1159, 2008]. In addition, the Gynecologic Cancer Intergroup has developed CA-125 progression criteria which are to be integrated with objective tumor assessment for use in first-line trials in ovarian cancer [JNCI 92:1534-1535, 2000].

Cytology, Histology: These techniques can be used to differentiate between partial responses (PR) and complete responses (CR) in rare cases (e.g., residual lesions in tumor types, such as germ cell tumors, where known residual benign tumors can remain).

The cytological confirmation of the neoplastic origin of any effusion that appears or worsens during treatment when the measurable tumor has met criteria for response or stable disease is mandatory to differentiate between response or stable disease (an effusion may be a side effect of the treatment) and progressive disease.

FDG-PET: While FDG-PET response assessments need additional study, it is sometimes reasonable to incorporate the use of FDG-PET scanning to complement CT scanning in assessment of progression (particularly possible 'new' disease). New lesions on the basis of FDG-PET imaging can be identified according to the following algorithm: a) Negative FDG-PET at baseline, with a positive FDG-PET at follow-up is a sign of PD based on a new lesion, b) No FDG-PET at baseline and a positive FDG-PET at follow-up: If the positive FDG-PET at follow-up corresponds to a new site of disease confirmed by CT, this is PD. If the positive FDG-PET at follow-up is not confirmed as a new site of disease on CT, additional follow-up CT scans are needed to determine if there is truly progression occurring at that site (if so, the date of PD will be the date of the initial abnormal FDG-PET scan). If the positive FDG-PET at follow-up corresponds to a pre-existing site of disease on CT that is not progressing on the basis of the anatomic images, this is not PD, c) FDG-PET may be used to upgrade a response to a CR in a manner similar to a biopsy in cases where a residual radiographic abnormality is thought to represent fibrosis or scarring. The use of FDG-PET in this circumstance should be prospectively described in the protocol and supported by disease-specific medical literature for the indication. However, it must be acknowledged that both approaches may lead to false positive CR due to limitations of FDG-PET and biopsy resolution/sensitivity.

Note: A 'positive' FDG-PET scan lesion means one which is FDG avid with an uptake greater than twice that of the surrounding tissue on the attenuation corrected image.

Response Criteria:

Evaluation of Target Lesions:

Complete Response (CR): Disappearance of all target lesions. Any pathological lymph nodes (whether target or non-target) must have reduction in short axis to <10 mm.

Partial Response (PR): At least a 30% decrease in the sum of the diameters of target lesions, taking as reference the baseline sum of diameters.

Progressive Disease (PD): At least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progressions).

Stable Disease (SD): Neither sufficient shrinkage to qualify for PR nor sufficient increase to qualify for PD, taking as reference the smallest sum of diameters while on study.

Evaluation of Non-Target Lesions:

Complete Response (CR): Disappearance of all non-target lesions and normalization of tumor marker level. All lymph nodes must be non-pathological in size (<10 mm short axis).

Note: If tumor markers are initially above the upper normal limit, they must normalize for a patient to be considered in complete clinical response.

Non-CR/Non-PD: Persistence of one or more non-target lesion(s) and/or maintenance of tumor marker level above the normal limits.

Progressive Disease (PD): Appearance of one or more new lesions and/or unequivocal progression of existing non-target lesions. Unequivocal progression should not normally trump target lesion status. It must be representative of overall disease status change, not a single lesion increase.

Although a clear progression of "non-target" lesions only is exceptional, the opinion of the treating physician should prevail in such circumstances, and the progression status should be confirmed at a later time by the review panel (or Principal Investigator).

Evaluation of Best Overall Response:

The best overall response is the best response recorded from the start of the treatment until disease progression/recurrence (taking as reference for progressive disease the smallest measurements recorded since the treatment started). The patient's best response assignment will depend on the achievement of both measurement and confirmation criteria.

TABLE 22

For Patients with Measurable Disease (i.e., Target Disease)

| Target Lesions | Non-Target Lesions | New Lesions | Overall Response | Best Overall Response when Confirmation is Required* |
|---|---|---|---|---|
| CR | CR | No | CR | ≥4 wks. Confirmation** |
| CR | Non-CR/Non-PD | No | PR | >4 wks. Confirmation** |
| CR | Not evaluated | No | PR | |
| PR | Non-CR/Non-PD/not evaluated | No | PR | |
| SD | Non-CR/Non-PD/not evaluated | No | SD | Documented at least once ≥4 wks. from baseline** |
| PD | Any | Yes or No | PD | no prior SD, PR or CR |
| Any | PD*** | Yes or No | PD | |
| Any | Any | Yes | PD | |

See RECIST 1.1 manuscript for further details on what is evidence of a new lesion. Only for non-randomized trials with response as primary endpoint. In exceptional circumstances, unequivocal progression in non-target lesions may be accepted as disease progression.
Patients with a global deterioration of health status requiring discontinuation of treatment without objective evidence of disease progression at that time should be reported as "symptomatic deterioration." Every effort should be made to document the objective progression even after discontinuation of treatment.

TABLE 23

For Patients with Non-Measurable Disease (i.e., Non-Target Disease)

| Non-Target Lesions | New Lesions | Overall Response |
|---|---|---|
| CR | No | CR |
| Non-CR/non-PD | No | Non-CR/non-PD* |
| Not all evaluated | No | not evaluated |
| Unequivocal PD | Yes or No | PD |
| Any | Yes | PD |

*'Non-CR/non-PD' is preferred over 'stable disease' for non-target disease since SD is increasingly used as an endpoint for assessment of efficacy in some trials so to assign this category when no lesions can be measured is not advised Duration of Response Duration of overall response: The duration of overall response is measured from the time measurement criteria are met for CR or PR (whichever is first recorded) until the first date that recurrent or progressive disease is objectively documented (taking as reference for progressive disease the smallest measurements recorded since the treatment started).

The duration of overall CR is measured from the time measurement criteria are first met for CR until the first date that progressive disease is objectively documented.

Duration of stable disease: Stable disease is measured from the start of the treatment until the criteria for progression are met, taking as reference the smallest measurements recorded since the treatment started, including the baseline measurements.

Progression-Free Survival (PFS) or Time to Progression (TTP): PFS or TTP is defined as the duration of time from start of treatment to time of progression or death, whichever occurs first.

Response Review

An independent review of CT scans and MRIs used in determining response will be undertaken at the end of the study by a collaborator in the Radiology and Imaging Sciences. Images will be reviewed using RECIST 1.1. Initial evaluation of progression should be confirmed with a follow up scan in 4-6 weeks, if clinically reasonable. Date of progression should be the initial date of progression when confirmation is obtained. If no confirmation scan is performed, the initial scan demonstrating progression will determine progression.

Statistical Consideration

The primary objective of the trial is to determine if there is a difference in time to progression among patients with metastatic colorectal cancer who are treated with standard of care vs. standard of care+anti-PD-L1 monoclonal antibody.

Based upon results in the literature, patients who would be eligible to be randomized on this trial would be expected to have an estimated 10 month median time to progression with standard of care alone. The goal of this study will be to determine if the use of the anti-PD-L1 monoclonal antibody along with standard of care will result in patients having an increased median time to progression of 18 months. Kaplan-Meier curves and a two-tailed log-rank test will be the primary analysis methods. Assuming exponential time to progression curves, the hazard rate for standard of care alone is 0.0693 or approximately a 7% probability of progressing each month when the median time to progression is 10 months. If it is contemplated that the combination arm will be associated with a median time to progression of 18 months, this corresponds to a hazard rate of 0.0385 and the resulting hazard ratio for the comparison of the two overall actuarial curves would be 1.80. Following the principals of a phase 2.5 design, to compare these curves and detect a difference with a 0.10 one-tailed log-rank test, a total of 35 evaluable subjects per arm (70 total) will need to be randomized over a one year period and a maximum follow-up of three years, with occurrence of 52 total progressions, in order to have 80% power to compare the curves.

It is expected that all 76 patients (6 for safety lead-in plus 70 for phase 2.5) can be accrued onto this trial in one year. In order to allow for a very small number of inevaluable patients, the accrual ceiling will be set at 81 patients.

Pharmaceutical Information—AD-CEA Vaccine

Source-Ad-CEA will be supplied by the manufacturer, Etubics Corporation, through a Cooperative Research and Development Agreement (CRADA). The manufacturing department of Etubics will supply the vaccine, which will be distributed to the sites by Etubics Corporation.

Toxicity

A Phase I/II clinical trial of ETBX-011 (Ad5 [E1-, E2b-]-CEA(6D)) (IND #14325) that expresses the tumor-associated antigen carcinoembryonic antigen (CEA) has been performed. A summary of the study results on the clinical trial is presented below.

Schedule, Dosing, and Safety: The primary objective of the Phase I/II dosing trial was to assess safety and a secondary objective was to evaluate CEA-specific immune responses to CEA and to obtain preliminary data on response rate. The study was performed under an FDA-approved IND (IND14325) and registered at ClinicalTrials.gov (NCT01147965). Participants were recruited from oncology clinics at Duke University Medical Center and Medical Oncology Associates, Spokane, Wash. and provided informed consent that was approved by IRB's. Patients with a histological confirmed diagnosis of metastatic malignancy who were previously treated with standard therapy known to have a possible survival benefit were enrolled into the study. For this study, the carcinoma must have had over expression of CEA as defined by immunohistochemical staining (at least 50% of the tumor with at least moderate intensity of staining) or a carcinoma known to be universally CEA positive i.e. colorectal adenocarcinoma). Patients were not treated until 4 or more weeks after any prior chemotherapy or radiation therapy. They could not have a history of autoimmune disease, serious intercurrent chronic or acute illness, active hepatitis, serologic evidence for HIV infection, or be receiving steroid or immunosuppressive therapy. All patients were >21 years old and had a Karnofsky Performance Score of 70% or higher and a life expectancy of at least 3 months. Pregnant women and nursing mothers were excluded. Dose Limiting Toxicities (DLTs) were defined as any Grade 3 or 4 immediate hypersensitivity reactions, Grade 3 or 4 fever that may possibly be associated with the immunization, Grade ≥2 autoimmune events except for vitiligo or fever for less than 2 days and less than 101.5° F., Grade ≥2 allergic reactions (Grade 2 is defined as generalized urticaria as defined by NCI Common Terminology Criteria for Adverse Events (CTCAE version 4.0), or Grade ≥3 non-hematologic toxicity. The Ad5 [E1-, E2b-]-CEA(6D) injections were given subcutaneously in the same thigh. The doses were administered every 3 weeks for 3 treatments as follows: Cohort 1 (3 patients) 109 VP in 0.5 ml; Cohort 2 (3 patients): 1010 VP; Cohort 3 (6 patients) 1011 VP. Following establishment of safety in Phase I, 12 additional patients were entered into a Phase II using the 1011 VP/dose. To evaluate a higher dose, 6 additional patients (cohort 5) received 5×1011 VP/dose.

Patient Demographics: One patient with CEA expressing bladder and one patient with lung carcinoma was enrolled. Thirty two patients, median age 57.5 (range 38-77) with metastatic colorectal cancer, who had failed a median of three prior chemotherapeutic regimens (range: 2-5), had a median performance status of 90% (range 70-100%), and had a median of three sites of metastatic disease (range 1-5), were enrolled. The majority was able to receive all three immunizations. Five patients who stopped immunizations early did so due to significant disease progression. The colorectal adenocarcinoma patient demographics compares favorably with previously published studies of patients with chemotherapy-refractory colorectal cancer.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety to the same extent as if each individual publication, patent, or patent application was specifically and individually indicated to be incorporated by reference.

Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for treating cancer, the method comprising administering to a subject in need thereof:
   a) from $1\times10^9$ to $5\times10^{11}$ recombinant, replication-defective adenoviral vectors, each comprising a nucleotide sequence encoding a CEA antigen having at least 90% sequence identity to SEQ ID NO:23, wherein the CEA antigen comprises SEQ ID NO:10 at positions 605-613 of SEQ ID NO:23;
   b) avelumab; and
   c) a chemotherapy.

2. The method of claim 1, wherein the avelumab is administered every two weeks.

3. The method of claim 1, wherein the nucleotide sequence is SEQ ID NO:12.

4. The method of claim 1, wherein the recombinant replication-defective adenoviral vector comprises a deletion in an E1 gene region and a deletion in an E2b gene region.

5. The method of claim 4, wherein the replication defective vector is a replication defective adenovirus 5 vector.

6. The method of claim 1, wherein the recombinant viral vector comprises a deletion in an E2b gene region, an E1 gene region, an E3 gene region, an E4 gene region, or any combination thereof.

7. The method of claim 2, wherein the chemotherapy comprises cisplatin, leucovorin, fluorouracil, oxaliplatin, or any combination thereof.

8. The method of claim 7, wherein the chemotherapy comprises leucovorin, fluorouracil, and oxaliplatin.

9. The method of claim 1, further comprising administering an anti-VEGF antibody.

10. The method of claim 9, wherein the anti-VEGF antibody is bevacizumab.

11. The method of claim 1, further comprising administering a vector comprising a nucleic acid sequence encoding a costimulatory molecule.

12. The method of claim 11, wherein the costimulatory molecule comprises B7, ICAM-1, LFA-3, or any combination thereof.

13. The method of claim 1, wherein the administering comprises administering $5\times10^{11}$ virus particles (VPs) of the recombinant viral vector comprising the nucleotide sequence encoding the CEA antigen.

14. The method of claim 1, wherein the administering comprises administering the recombinant viral vector comprising the nucleotide sequence encoding the CEA antigen every two weeks, every three weeks, every four weeks, or every 12 weeks.

15. The method of claim 1, wherein the administering comprises intravenously, subcutaneously, intramuscularly, or intradermally administering the recombinant viral vector comprising the nucleotide sequence encoding the CEA antigen.

16. The method of claim 1, wherein the subject has cancer of the colon, rectum, breast, lung, pancreas, prostate, gastrointestinal tract, ovary, cervix, head and neck, or any combination thereof.

17. The method of claim 1, wherein the subject is a human.

18. The method of claim 1, wherein the subject has a neutralizing antibody against adenovirus.

19. The method of claim 1, wherein the recombinant viral vector comprising the nucleotide sequence encoding the CEA antigen is administered on week 1, 2, 3, 5, 7, and 9.

20. The method of claim 19, further comprising administering the recombinant viral vector comprising the nucleotide sequence encoding the CEA antigen every 6 weeks after the 9th week.

21. The method of claim 1, wherein the avelumab and the chemotherapy are administered once per week.

22. The method of claim 1, wherein the recombinant viral vector comprising the nucleotide sequence encoding the CEA antigen is administered prior to administration of the avelumab.

23. The method of claim 1, wherein the recombinant viral vector comprising the nucleotide sequence encoding the CEA antigen and the avelumab are administered prior to administration of the chemotherapy and bevacizumab.

24. The method of claim 10, wherein the recombinant viral vector comprising the nucleotide sequence encoding the CEA antigen and the avelumab are administered concurrently with the administering of the chemotherapy and the bevacizumab.

25. The method of claim 1, wherein the chemotherapy comprises taxol or a taxol-derivative.

* * * * *

SEQUENCE LISTING

<160> NUMBER OF SEQ ID NOS: 23

<210> SEQ ID NO 1
<211> LENGTH: 2109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atggagtctc cctcggcccc tccccacaga tggtgcatcc cctggcagag gctcctgctc      60
acagcctcac ttctaacctt ctggaacccg cccaccactg ccaagctcac tattgaatcc     120
acgccgttca atgtcgcaga ggggaaggag gtgcttctac ttgtccacaa tctgccccag     180 catcttttg gctacagctg gtacaaaggt gaaagagtgg atggcaaccg tcaaattata     240
ggatatgtaa taggaactca acaagctacc ccagggcccg catacagtgg tcgagagata     300 atataccccca atgcatccct gctgatccag aacatcatcc agaatgacac aggattctac     360
accctacacg tcataaagtc agatcttgtg aatgaagaag caactggcca gttccgggta     420
tacccggagc tgcccaagcc ctccatctcc agcaacaact ccaaacccgt ggaggacaag     480
gatgctgtgg ccttcacctg tgaacctgag actcaggacg caacctacct gtggtgggta     540
```

```
aacaatcaga gcctcccggt cagtcccagg ctgcagctgt ccaatggcaa caggaccctc    600
actctattca atgtcacaag aaatgacaca gcaagctaca aatgtgaaac ccagaaccca    660
gtgagtgcca ggcgcagtga ttcagtcatc ctgaatgtcc tctatggccc ggatgccccc    720
accatttccc ctctaaacac atcttacaga tcaggggaaa atctgaacct ctcctgccac    780
gcagcctcta acccacctgc acagtactct tggtttgtca atgggacttt ccagcaatcc    840
acccaagagc tctttatccc caacatcact gtgaataata gtggatccta tacgtgccaa    900
gcccataact cagacactgg cctcaatagg accacagtca cgacgatcac agtctatgca    960
gagccaccca aaccttcat caccagcaac aactccaacc ccgtggagga tgaggatgct   1020
gtagccttaa cctgtgaacc tgagattcag aacacaacct acctgtggtg ggtaaataat   1080
cagagcctcc cggtcagtcc caggctgcag ctgtccaatg acaacaggac cctcactcta   1140
ctcagtgtca caaggaatga tgtaggaccc tatgagtgtg aatccagaa cgaattaagt   1200 gttgaccaca cgacccagt catcctgaat gtcctctatg cccagacga ccccaccatt   1260 tccccctcat acacctatta ccgtccaggg gtgaacctca gcctctcctg ccatgcagcc   1320
tctaacccac ctgcacagta ttcttggctg attgatggga acatccagca acacacacaa   1380
gagctcttta tctccaacat cactgagaag aacagcggac tctatacctg ccaggccaat   1440
aactcagcca gtggccacag caggactaca gtcaagacaa tcacagtctc tgcggagctg   1500
cccaagccct ccatctccag caacaactcc aaacccgtgg aggacaagga tgctgtggcc   1560
ttcacctgtg aacctgaggc tcagaacaca acctacctgt ggtgggtaaa tggtcagagc   1620
ctcccagtca gtcccaggct gcagctgtcc aatggcaaca ggaccctcac tctattcaat   1680
gtcacaagaa atgacgcaag agcctatgta tgtggaatcc agaactcagt gagtgcaaac   1740
cgcagtgacc cagtcacccct ggatgtcctc tatgggccgg acacccccat catttccccc   1800
ccagactcgt cttaccttc gggagcgaac ctcaacctct cctgccactc ggcctctaac   1860
ccatccccgc agtattcttg gcgtatcaat gggataccgc agcaacacac acaagttctc   1920
tttatcgcca aaatcacgcc aaataataac gggacctatg cctgttttgt ctctaacttg   1980
gctactggcc gcaataattc catagtcaag agcatcacag tctctgcatc tggaacttct   2040
cctggtctct cagctggggc cactgtcggc atcatgattg gagtgctggt tggggttgct   2100
ctgatatag                                                         2109
```

<210> SEQ ID NO 2
<211> LENGTH: 2109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
atggagtctc cctcggcccc tccccacaga tggtgcatcc cctggcagag gctcctgctc     60
acagcctcac ttctaacctt ctggaacccg cccaccactg ccaagctcac tattgaatcc    120
acgccgttca atgtcgcaga ggggaaggag gtgcttctac ttgtccacaa tctgccccag    180 catcttttg gctacagctg gtacaaaggt gaaagagtgg atggcaaccg tcaaattata    240
ggatatgtaa taggaactca acaagctacc ccagggcccg catacagtgg tcgagagata    300
atatacccca atgcatccct gctgatccag aacatcatcc agaatgacac aggattctac    360
accctacacg tcataaagtc agatcttgtg aatgaagaag caactggcca gttccgggta    420
```

```
tacccggagc tgcccaagcc ctccatctcc agcaacaact ccaaacccgt ggaggacaag      480
gatgctgtgg ccttcacctg tgaacctgag actcaggacg caacctacct gtggtgggta      540
aacaatcaga gcctcccggt cagtcccagg ctgcagctgt ccaatggcaa caggaccctc      600
actctattca atgtcacaag aaatgacaca gcaagctaca aatgtgaaac ccagaaccca      660
gtgagtgcca ggcgcagtga ttcagtcatc ctgaatgtcc tctatggccc ggatgccccc      720
accatttccc ctctaaacac atcttacaga tcaggggaaa atctgaacct ctcctgccac      780
gcagcctcta acccacctgc acagtactct tggtttgtca atgggacttt ccagcaatcc      840
acccaagagc tctttatccc caacatcact gtgaataata gtggatccta tcgtgccaa       900 gcccataact cagacactgg cctcaatagg accacagtca cgacgatcac agtctatgca      960
gagccaccca aacccttcat caccagcaac aactccaacc ccgtggagga tgaggatgct     1020
gtagccttaa cctgtgaacc tgagattcag aacacaacct acctgtggtg ggtaaataat     1080
cagagcctcc cggtcagtcc caggctgcag ctgtccaatg acaacaggac cctcactcta     1140
ctcagtgtca caaggaatga tgtaggaccc tatgagtgtg aatccagaa cgaattaagt      1200 gttgaccaca cgcacccagt catcctgaat gtcctctatg gcccagacga ccccaccatt     1260
tccccctcat acacctatta ccgtccaggg gtgaacctca gcctctcctg ccatgcagcc     1320
tctaacccac ctgcacagta ttcttggctg attgatggga acatccagca acacacacaa     1380
gagctcttta tctccaacat cactgagaag aacagcggac tctatacctg ccaggccaat     1440
aactcagcca gtggccacag caggactaca gtcaagacaa tcacagtctc tgcggagctg     1500
cccaagccct ccatctccag caacaactcc aaacccgtgg aggacaagga tgctgtggcc     1560
ttcacctgtg aacctgaggc tcagaacaca acctacctgt ggtgggtaaa tggtcagagc     1620
ctcccagtca gtcccaggct gcagctgtcc aatggcaaca ggaccctcac tctattcaat     1680
gtcacaagaa atgacgcaag agcctatgta tgtggaatcc agaactcagt gagtgcaaac     1740
cgcagtgacc cagtcaccct ggatgtcctc tatgggccgg acacccccat catttccccc     1800
ccagactcgt cttacctttc gggagcgaac ctcaacctct cctgccactc ggcctctaac     1860
ccatccccgc agtattcttg gcgtatcaat gggataccgc agcaacacac acaagttctc     1920
tttatcgcca aaatcacgcc aaataataac gggacctatg cctgttttgt ctctaacttg     1980
gctactggcc gcaataattc catagtcaag agcatcacag tctctgcatc tggaacttct     2040
cctggtctct cagctggggc cactgtcggc atcatgattg agtgctggt tggggttgct     2100 ctgatatag                                                           2109
```

<210> SEQ ID NO 3  
<211> LENGTH: 32315  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 3

```
catcatcaat aatatacctt attttggatt gaagccaata tgataatgag ggggtggagt       60
ttgtgacgtg gcgcggggcg tgggaacggg gcgggtgacg tagtagtgtg gcggaagtgt      120
gatgttgcaa gtgtggcgga acacatgtaa gcgacggatg tggcaaaagt gacgttttg       180 gtgtgcgccg gtgtacacag gaagtgacaa ttttcgcgcg gttttaggcg gatgttgtag      240
taaatttggg cgtaaccgag taagatttgg ccattttcgc gggaaaactg aataagagga      300
```

```
agtgaaatct gaataatttt gtgttactca tagcgcgtaa tactgtaata gtaatcaatt    360
acggggtcat tagttcatag cccatatatg gagttccgcg ttacataact tacggtaaat    420
ggcccgcctg gctgaccgcc caacgacccc cgcccattga cgtcaataat gacgtatgtt    480
cccatagtaa cgccaatagg gactttccat tgacgtcaat gggtggagta tttacggtaa    540
actgcccact tggcagtaca tcaagtgtat catatgccaa gtacgccccc tattgacgtc    600
aatgacggta aatggcccgc ctggcattat gcccagtaca tgaccttatg ggactttcct    660
acttggcagt acatctacgt attagtcatc gctattacca tggtgatgcg gttttggcag    720
tacatcaatg ggcgtggata gcggtttgac tcacggggat ttccaagtct ccaccccatt    780
gacgtcaatg ggagtttgtt ttggcaccaa atcaacggg actttccaaa atgtcgtaac    840
aactccgccc cattgacgca aatgggcggt aggcgtgtac ggtgggaggt ctatataagc    900
agagctggtt tagtgaaccg tcagatccgc tagagatctg gtaccgtcga cgcggccgct    960
cgagcctaag cttggtaccg agctcggatc cactagtaac ggccgccagt gtgctggaat   1020
tcggcttaaa ggtacccaga gcagacagcc gccaccatgg agtctccctc ggcccctccc   1080
cacagatggt gcatcccctg gcagaggctc ctgctcacag cctcacttct aaccttctgg   1140
aacccgccca ccactgccaa gctcactatt gaatccacgc cgttcaatgt cgcagagggg   1200
aaggaggtgc ttctacttgt ccacaatctg ccccagcatc ttttggcta cagctggtac   1260
aaaggtgaaa gagtggatgg caaccgtcaa attataggat atgtaatagg aactcaacaa   1320
gctaccccag ggcccgcata cagtggtcga gagataatat accccaatgc atccctgctg   1380
atccagaaca tcatccagaa tgacacagga ttctacaccc tacacgtcat aaagtcagat   1440
cttgtgaatg aagaagcaac tggccagttc cgggtatacc cggagctgcc caagcccctcc   1500
atctccagca acaactccaa acccgtggag gacaaggatg ctgtggcctt cacctgtgaa   1560
cctgagactc aggacgcaac ctacctgtgg tgggtaaaca atcagagcct cccggtcagt   1620
cccaggctgc agctgtccaa tggcaacagg accctcactc tattcaatgt cacaagaaat   1680
gacacagcaa gctacaaatg tgaaacccag aacccagtga gtgccaggcg cagtgattca   1740
gtcatcctga atgtcctcta tggcccggat gcccccacca tttcccctct aaacacatct   1800
tacagatcag gggaaaatct gaacctctcc tgccacgcag cctctaaccc acctgcacag   1860
tactcttggt ttgtcaatgg gacttttcag caatccaccc aagagctctt tatccccaac   1920
atcactgtga ataatagtgg atcctatacg tgccaagccc ataactcaga cactggcctc   1980
aataggacca cagtcacgac gatcacagtc tatgcagagc cacccaaacc cttcatcacc   2040
agcaacaact ccaacccggt ggaggatgag gatgctgtag ccttaacctg tgaacctgag   2100
attcagaaca caacctacct gtggtgggta aataatcaga gcctcccggt cagtcccagg   2160
ctgcagctgt ccaatgacaa caggacccte actctactca gtgtcacaag gaatgatgta   2220
ggaccctatg agtgtggaat ccagaacgaa ttaagtgttg accacagcga cccagtcatc   2280
ctgaatgtcc tctatggccc agacgacccc accatttccc cctcatacac ctattaccgt   2340
ccaggggtga acctcagcct ctcctgccat gcagcctcta cccacctgc acagtattct   2400
tggctgattg atgggaacat ccagcaacac acacaagagc tctttatctc caacatcact   2460
gagaagaaca gcggactcta tacctgccag gccaataact cagccagtgg ccacagcagg   2520
actacagtca agacaatcac agtctctgcg gagctgccca gccctccat ctccagcaac   2580
aactccaaac ccgtggagga caaggatgct gtggccttca cctgtgaacc tgaggctcag   2640
```

| | |
|---|---|
| aacacaacct acctgtggtg ggtaaatggt cagagcctcc cagtcagtcc caggctgcag | 2700 |
| ctgtccaatg gcaacaggac cctcactcta ttcaatgtca caagaaatga cgcaagagcc | 2760 |
| tatgtatgtg gaatccagaa ctcagtgagt gcaaaccgca gtgacccagt caccctggat | 2820 |
| gtcctctatg ggccggacac ccccatcatt tccccccag actcgtctta cctttcggga | 2880 |
| gcggacctca acctctcctg ccactcggcc tctaacccat ccccgcagta ttcttggcgt | 2940 |
| atcaatggga taccgcagca acacacacaa gttctcttta tcgccaaaat cacgccaaat | 3000 |
| aataacggga cctatgcctg ttttgtctct aacttggcta ctggccgcaa taattccata | 3060 |
| gtcaagagca tcacagtctc tgcatctgga acttctcctg gtctctcagc tggggccact | 3120 |
| gtcggcatca tgattggagt gctggttggg gttgctctga tatagcagcc ctggtgtagt | 3180 |
| ttcttcattt caggaagact gacagttgtt ttgcttcttc cttaaagcat ttgcaacagc | 3240 |
| tacagtctaa aattgcttct ttaccaagga tatttacaga aaagactctg accagagatc | 3300 |
| gagaccatcc tctagataag atatccgatc caccggatct agataactga tcataatcag | 3360 |
| ccataccaca tttgtagagg ttttacttgc tttaaaaaac ctcccacacc tcccccctgaa | 3420 |
| cctgaaacat aaaatgaatg caattgttgt tgttaacttg tttattgcag cttataatgg | 3480 |
| ttacaaataa agcaatagca tcacaaattt cacaaataaa gcattttttt cactgcattc | 3540 |
| tagttgtggt ttgtccaaac tcatcaatgt atcttaacgc ggatctgggc gtggttaagg | 3600 |
| gtgggaaaga atatataagg tgggggtctt atgtagtttt gtatctgttt tgcagcagcc | 3660 |
| gccgccgcca tgagcaccaa ctcgtttgat ggaagcattg tgagctcata tttgacaacg | 3720 |
| cgcatgcccc catgggccgg ggtgcgtcag aatgtgatgg gctccagcat tgatggtcgc | 3780 |
| cccgtcctgc ccgcaaactc tactaccttg acctacgaga ccgtgtctgg aacgccgttg | 3840 |
| gagactgcag cctccgccgc cgcttcagcc gctgcagcca ccgcccgcgg gattgtgact | 3900 |
| gactttgctt tcctgagccc gcttgcaagc agtgcagctt cccgttcatc cgcccgcgat | 3960 |
| gacaagttga cggctctttt ggcacaattg gattctttga cccgggaact taatgtcgtt | 4020 |
| tctcagcagc tgttggatct cgccagcag gtttctgccc tgaaggcttc ctccccctccc | 4080 |
| aatgcggttt aaaacataaa taaaaaacca gactctgttt ggatttggat caagcaagtg | 4140 |
| tcttgctgtc tttatttagg ggttttgcgc gcgcggtagg cccgggacca gcggtctcgg | 4200 |
| tcgttgaggg tcctgtgtat tttttccagg acgtggtaaa ggtgactctg gatgttcaga | 4260 |
| tacatgggca taagcccgtc tctggggtgg aggtagcacc actgcagagc ttcatgctgc | 4320 |
| ggggtggtgt tgtagatgat ccagtcgtag caggagcgct gggcgtggtg cctaaaaatg | 4380 |
| tctttcagta gcaagctgat tgccaggggc aggcccttgg tgtaagtgtt tacaaagcgg | 4440 |
| ttaagctggg atgggtgcat acgtggggat atgagatgca tcttggactg tattttttagg | 4500 |
| ttggctatgt tcccagccat atccctccgg ggattcatgt tgtgcagaac caccagcaca | 4560 |
| gtgtatccgg tgcacttggg aaatttgtca tgtagcttag aaggaaatgc gtggaagaac | 4620 |
| ttggagacgc ccttgtgacc tccaagattt tccatgcatt cgtccataat gatggcaatg | 4680 |
| ggcccacggg cggcggcctg ggcgaagata tttctgggat cactaacgtc atagttgtgt | 4740 |
| tccaggatga gatcgtcata ggccattttt acaaagcgcg ggcggagggt gccagactgc | 4800 |
| ggtataatgg ttccatccgg cccaggggcg tagttaccct cacagatttg catttcccac | 4860 |
| gctttgagtt cagatggggg gatcatgtct acctgcgggg cgatgaagaa aacggtttcc | 4920 |
| ggggtagggg agatcagctg gaagaaagc aggttcctga gcagctgcga cttaccgcag | 4980 |
| ccggtgggcc cgtaaatcac acctattacc ggctgcaact ggtagttaag agagctgcag | 5040 |

```
ctgccgtcat ccctgagcag gggggccact tcgttaagca tgtccctgac tcgcatgttt     5100
tccctgacca aatccgccag aaggcgctcg ccgcccagcg atagcagttc ttgcaaggaa     5160
gcaaagtttt tcaacggttt gagaccgtcc gccgtaggca tgcttttgag cgtttgacca     5220
agcagttcca ggcggtccca cagctcggtc acctgctcta cggcatctcg atccagcata     5280
tctcctcgtt tcgcggggttg gggcggcttt cgctgtacgg cagtagtcgg tgctcgtcca     5340
gacgggccag ggtcatgtct ttccacgggc gcagggtcct cgtcagcgta gtctgggtca     5400
cggtgaaggg gtgcgctccg ggctgcgcgc tggccagggt gcgcttgagg ctggtcctgc     5460
tggtgctgaa gcgctgccgg tcttcgccct gcgcgtcggc caggtagcat ttgaccatgg     5520
tgtcatagtc cagcccctcc gcggcgtggc ccttggcgcg cagcttgccc ttggaggagg     5580
cgccgcacga ggggcagtgc agacttttga gggcgtagag cttgggcgcg agaaataccg     5640
attccgggga gtaggcatcc gcgccgcagg ccccgcagac ggtctcgcat ccacgagcc      5700 aggtgagctc tggccgttcg gggtcaaaaa ccaggtttcc cccatgcttt ttgatgcgtt     5760
tcttacctct ggtttccatg agccggtgtc cacgctcggt gacgaaaagg ctgtccgtgt     5820
ccccgtatac agacttgaga ggcctgtcct cgagcggtgt tccgcggtcc tcctcgtata     5880
gaaactcgga ccactctgag acaaaggctc gcgtccaggc cagcacgaag gaggctaagt     5940 gggagggggta gcggtcgttg tccactaggg ggtccactcg ctccagggtg tgaagacaca     6000
tgtcgccctc ttcggcatca aggaaggtga ttggtttgta ggtgtaggcc acgtgaccgg     6060
gtgttcctga aggggggcta taaaggggg tgggggcgcg ttcgtcctca ctctcttccg     6120
catcgctgtc tgcgagggcc agctgttggg gtgagtactc cctctgaaaa gcgggcatga     6180
cttctgcgct aagattgtca gtttccaaaa acgaggagga tttgatattc acctggcccg     6240
cggtgatgcc tttgagggtg gccgcatcca tctggtcaga aaagacaatc ttttttgttgt     6300 caagcttggt ggcaaacgac ccgtagaggg cgttggacag caacttggcg atggagcgca     6360
gggtttggtt tttgtcgcga tcggcgcgct ccttggccgc gatgtttagc tgcacgtatt     6420
cgcgcgcaac gcaccgccat tcgggaaaga cggtggtgcg ctcgtcgggc accaggtgca     6480
cgcgccaacc gcggttgtgc agggtgacaa ggtcaacgct ggtggctacc tctccgcgta     6540
ggcgctcgtt ggtccagcag aggcggccgc ccttgcgcga gcagaatggc ggtaggggt      6600 ctagctgcgt ctcgtccggg gggtctgcgt ccacggtaaa gaccccggc agcaggcgcg      6660 cgtcgaagta gtctatcttg catccttgca agtctagcgc ctgctgccat gcgcgggcgg     6720
caagcgcgcg ctcgtatggg ttgagtgggg gaccccatgg catggggtgg gtgagcgcgg     6780
aggcgtacat gccgcaaatg tcgtaaacgt agagggctc tctgagtatt ccaagatatg      6840
tagggtagca tcttccaccg cggatgctgg cgcgcacgta atcgtatagt tcgtgcgagg     6900
gagcgaggag gtcgggaccg aggttgctac gggcgggctg ctctgctcgg aagactatct     6960
gcctgaagat ggcatgtgag ttggatgata tggttggacg ctggaagacg ttgaagctgg     7020
cgtctgtgag acctaccgcg tcacgcacga aggaggcgta ggagtcgcgc agcttgttga     7080
ccagctcggc ggtgacctgc acgtctaggg cgcagtagtc cagggtttcc ttgatgatgt     7140
catacttatc ctgtcccttt ttttttccaca gctcgcggtt gaggacaaac tcttcgcggt     7200
ctttccagta tcttggatc ggaaacccgt cggcctccga acggtaagag cctagcatgt      7260
agaactggtt gacggcctgg taggcgcagc atcccttttc tacgggtagc gcgtatgcct     7320
gcgcggcctt ccggcatgac cagcatgaag ggcacgagct gcttcccaaa ggcccccatc     7380
```

```
caagtatagg tctctacatc gtaggtgaca aagagacgct cggtgcgagg atgcgagccg    7440
atcgggaaga actggatctc ccgccaccaa ttggaggagt ggctattgat gtggtgaaag    7500
tagaagtccc tgcgacgggc cgaacactcg tgctggcttt tgtaaaaacg tgcgcagtac    7560
tggcagcggt gcacgggctg tacatcctgc acgaggttga cctgacgacc gcgcacaagg    7620
aagcagagtg ggaatttgag cccctcgcct ggcgggtttg gctggtggtc ttctacttcg    7680
gctgcttgtc cttgaccgtc tggctgctcg aggggagtta cggtggatcg gaccaccacg    7740
ccgcgcgagc ccaaagtcca gatgtccgcg cgcggcggtc ggagcttgat gacaacatcg    7800
cgcagatggg agctgtccat ggtctggagc tcccgcggcg tcaggtcagg cgggagctcc    7860
tgcaggttta cctcgcatag acgggtcagg gcgcgggcta gatccaggtg atacctaatt    7920
tccaggggct ggttggtggc ggcgtcgatg gcttgcaaga ggccgcatcc ccgcggcgcg    7980
actacggtac cgcgcggcgg gcggtgggcc gcggggtgt ccttggatga tgcatctaaa     8040
agcggtgacg cgggcgagcc cccggaggta gggggggctc cggacccgcc gggagagggg    8100
gcaggggcac gtcggcgccg cgcgcgggca ggagctggtg ctgcgcgcgt aggttgctgg    8160
cgaacgcgac gacgcggcgg ttgatctcct gaatctggcg cctctgcgtg aagacgacgg    8220
gcccggtgag cttgaacctg aaagagagtt cgacagaatc aatttcggtg tcgttgacgg    8280
cggcctggcg caaaatctcc tgcacgtctc ctgagttgtc ttgataggcg atctcggcca    8340
tgaactgctc gatctcttcc tcctggagat ctccgcgtcc ggctcgctcc acggtggcgg    8400
cgaggtcgtt ggaaatgcgg gccatgagct gcgagaaggc gttgaggcct ccctcgttcc    8460
agacgcggct gtagaccacg ccccccttcgg catcgcgggc gcgcatgacc acctgcgcga   8520
gattgagctc cacgtgccgg gcgaagacgg cgtagtttcg caggcgctga aagaggtagt    8580
tgagggtggt ggcggtgtgt tctgccacga agaagtacat aacccagcgt cgcaacgtgg    8640
attcgttgat aattgttgtg taggtactcc gccgccgagg gacctgagcg agtccgcatc    8700
gaccggatcg gaaaacctct cgagaaaggc gtctaaccag tcacagtcgc aaggtaggct    8760
gagcaccgtg gcgggcggca gcgggcggcg gtcggggttg tttctggcgg aggtgctgct    8820
gatgatgtaa ttaaagtagg cggtcttgag acggcggatg gtcgacagaa gcaccatgtc    8880
cttgggtccg gcctgctgaa tgcgcaggcg gtcggccatg ccccaggctt cgttttgaca    8940
tcggcgcagg tctttgtagt agtcttgcat gagcctttct accggcactt cttcttctcc    9000
ttcctcttgt cctgcatctc ttgcatctat cgctgcggcg gcggcggagt ttggccgtag    9060
gtggcgccct cttcctccca tgcgtgtgac cccgaagccc ctcatcggct gaagcagggc    9120
taggtcggcg acaacgcgct cggctaatat ggcctgctgc acctgcgtga gggtagactg    9180
gaagtcatcc atgtccacaa agcggtggta tgcgcccgtg ttgatggtgt aagtgcagtt    9240
ggccataacg gaccagttaa cggtctggtg accggctgc gagagctcgg tgtacctgag     9300
acgcgagtaa gccctcgagt caaatacgta gtcgttgcaa gtccgcacca ggtactggta    9360
tcccaccaaa aagtgcggcg gcggctgcg gtagaggggc cagcgtaggg tggccggggc     9420 tccggggcg agatcttcca acataaggcg atgatatccg tagatgtacc tggacatcca     9480
ggtgatgccg gcggcggtgg tggaggcgcg cggaaagtcg cggacgcggt tccagatgtt    9540
gcgcagcggc aaaaagtgct ccatggtcgg gacgctctgg ccggtcaggc gcgcgcaatc    9600
gttgacgctc tagcgtgcaa aaggagagcc tgtaagcggg cactcttccg tggtctggtg    9660
gataaattcg caagggtatc atggcggacg accggggttc gagcccgta tccggccgtc     9720 cgccgtgatc catgcggtta ccgcccgcgt gtcgaaccca ggtgtgcgac gtcagacaac    9780
```

-continued

```
gggggagtgc tccttttggc ttccttccag gcgcggcggc tgctgcgcta gcttttttgg      9840
ccactggccg cgcgcagcgt aagcggttag gctggaaagc gaaagcatta agtggctcgc      9900
tccctgtagc cggagggtta ttttccaagg gttgagtcgc gggaccccg gttcgagtct      9960 cggaccggcc ggactgcggc gaacgggggt ttgcctcccc gtcatgcaag accccgcttg     10020
caaattcctc cggaaacagg gacgagcccc ttttttgctt ttcccagatg catccggtgc     10080
tgcggcagat gcgcccccct cctcagcagc ggcaagagca agagcagcgg cagacatgca     10140
gggcaccctc ccctcctcct accgcgtcag gaggggcgac atccgcggtt gacgcggcag     10200
cagatggtga ttacgaaccc ccgcggcgcc gggcccggca ctacctggac ttggaggagg     10260
gcgagggcct ggcgcggcta ggagcgccct ctcctgagcg gcacccaagg gtgcagctga     10320
agcgtgatac gcgtgaggcg tacgtgccgc ggcagaacct gtttcgcgac cgcgagggag     10380
aggagcccga ggagatgcgg gatcgaaagt ccacgcagg gcgcgagctg cggcatggcc      10440
tgaatcgcga gcggttgctg cgcgaggagg actttgagcc cgacgcgcga accgggatta     10500
gtcccgcgcg cgcacacgtg gcggccgccg acctggtaac cgcatacgag cagacggtga     10560
accaggagat taactttcaa aaaagcttta acaaccacgt gcgtacgctt gtggcgcgcg     10620
aggaggtggc tataggactg atgcatctgt gggactttgt aagcgcgctg gagcaaaacc     10680
caaatagcaa gccgctcatg gcgcagctgt tccttatagt gcagcacagc agggacaacg     10740
aggcattcag ggatgcgctg ctaaacatag tagagcccga gggccgctgg ctgctcgatt     10800
tgataaacat cctgcagagc atagtggtgc aggagcgcag cttgagcctg gctgacaagg     10860
tggccgccat caactattcc atgcttagcc tgggcaagtt ttacgcccgc aagatatacc     10920 ataccccctta cgttcccata gacaaggagg taaagatcga ggggttctac atgcgcatgg     10980
cgctgaaggt gcttaccttg agcgacgacc tgggcgttta tcgcaacgag cgcatccaca     11040
aggccgtgag cgtgagccgg cggcgcgagc tcagcgaccg cgagctgatg cacagcctgc     11100
aaagggccct ggctggcacg ggcagcggcg atagagaggc cgagtcctac tttgacgcgg     11160
gcgctgacct gcgctgggcc ccaagccgac gcgccctgga ggcagctggg gccggacctg     11220
ggctggcggt ggcacccgcg cgcgctggca acgtcggcgg cgtggaggaa tatgacgagg     11280
acgatgagta cgagccagag gacggcgagt actaagcggt gatgtttctg atcagatgat     11340
gcaagacgca acgacccgg cggtgcgggc ggcgctgcag agccagccgt ccggccttaa      11400
ctccacggac gactggcgcc aggtcatgga ccgcatcatg tcgctgactg cgcgcaatcc     11460
tgacgcgttc cggcagcagc cgcaggccaa ccggctctcc gcaattctgg aagcggtggt     11520
cccggcgcgc gcaaacccca cgcacgagaa ggtgctggcg atcgtaaacg cgctggccga     11580
aaacagggcc atccggcccg acgaggcgg cctggtctac gacgcgctgc ttcagcgcgt     11640
ggctcgttac aacagcggca acgtgcagac caacctggac cggctggtgg gggatgtgcg     11700
cgaggccgtg gcgcagcgtg agcgcgcgca gcagcagggc aacctgggct ccatggttgc     11760
actaaacgcc ttcctgagta cacagcccgc caacgtgccg cggggacagg aggactacac     11820
caactttgtg agcgcactgc ggctaatggt gactgagaca ccgcaaagtg aggtgtacca     11880
gtctgggcca gactatttt tccagaccag tagacaaggc ctgcagaccg taaacctgag     11940
ccaggctttc aaaaacttgc aggggctgtg ggggtgcgg gctcccacag gcgaccgcgc      12000
gaccgtgtct agcttgctga cgcccaactc gcgcctgttg ctgctgctaa tagcgccctt     12060
cacggacagt ggcagcgtgt cccgggacac atacctaggt cacttgctga cactgtaccg     12120
```

```
cgaggccata ggtcaggcgc atgtggacga gcatactttc caggagatta caagtgtcag    12180
ccgcgcgctg gggcaggagg acacgggcag cctggaggca accctaaact acctgctgac    12240
caaccggcgg cagaagatcc cctcgttgca cagtttaaac agcgaggagg agcgcatttt    12300
gcgctacgtg cagcagagcg tgagccttaa cctgatgcgc gacggggtaa cgcccagcgt    12360
ggcgctggac atgaccgcgc gcaacatgga accgggcatg tatgcctcaa accggccgtt    12420
tatcaaccgc ctaatggact acttgcatcg cgcggccgcc gtgaacccg agtatttcac      12480 caatgccatc ttgaacccgc actggctacc gccccctggt ttctacaccg ggggattcga    12540
ggtgcccgag gtaacgatg gattcctctg ggacgacata gacgcagcg tgttttcccc       12600 gcaaccgcag accctgctag agttgcaaca gcgcgagcag gcagaggcgg cgctgcgaaa    12660
ggaaagcttc cgcaggccaa gcagcttgtc cgatctaggc gctgcggccc gcggtcaga    12720 tgctagtagc ccatttccaa gcttgatagg gtctcttacc agcactcgca ccacccgccc    12780
gcgcctgctg ggcgaggagg agtacctaaa caactcgctg ctgcagccgc agcgcgaaaa    12840
aaacctgcct ccggcatttc ccaacaacgg gatagagagc ctagtggaca agatgagtag    12900
atggaagacg tacgcgcagg agcacaggga cgtgccaggc ccgcgcccgc ccacccgtcg    12960
tcaaaggcac gaccgtcagc ggggtctggt gtgggaggac gatgactcgg cagacgacag    13020
cagcgtcctg gatttgggag ggagtggcaa cccgtttgcg caccttcgcc ccaggctggg    13080
gagaatgttt taaaaaaaaa aaagcatgat gcaaaataaa aaactcacca aggccatggc    13140
accgagcgtt ggttttcttg tattcccctt agtatgcggc gcgcggcgat gtatgaggaa    13200
ggtcctcctc cctcctacga gagtgtggtg agcgcggcgc cagtggcggc ggcgctgggt    13260
tctcccttcg atgctcccct ggacccgccg tttgtgcctc cgcggtacct gcggcctacc    13320 gggggggagaa acagcatccg ttactctgag ttggcacccc tattcgacac cacccgtgtg    13380
tacctggtgg acaacaagtc aacggatgtg gcatccctga actaccagaa cgaccacagc    13440
aactttctga ccacggtcat tcaaaacaat gactacagcc gggggaggc aagcacacag      13500 accatcaatc ttgacgaccg gtcgcactgg ggcggcgacc tgaaaaccat cctgcatacc    13560
aacatgccaa atgtgaacga gttcatgttt accaataagt ttaaggcgcg ggtgatggtg    13620
tcgcgcttgc ctactaagga caatcaggtg gagctgaaat acgagtgggt ggagttcacg    13680
ctgcccgagg gcaactactc cgagaccatg accatagacc ttatgaacaa cgcgatcgtg    13740
gagcactact tgaaagtggg cagacagaac ggggttctgg aaagcgacat cggggtaaag    13800
tttgacaccc gcaacttcag actggggttt gaccccgtca ctggtcttgt catgcctggg    13860
gtatatacaa acgaagcctt ccatccagac atcatttttgc tgccaggatg cggggtggac    13920
ttcacccaca gccgcctgag caacttgttg ggcatccgca agcggcaacc cttccaggag    13980
ggctttagga tcacctacga tgatctggag ggtggtaaca ttcccgcact gttggatgtg    14040
gacgcctacc aggcgagctt gaaagatgac accgaacagg gcgggggtgg cgcaggcggc    14100
agcaacagca gtggcagcgg cgcggaagag aactccaacg cggcagccgc ggcaatgcag    14160
ccggtggagg acatgaacga tcatgccatt cgcggcgaca cctttgccac acgggctgag    14220
gagaagcgcg ctgaggccga agcagcggcc gaagctgccg ccccgctgc gcaacccgag    14280 gtcgagaagc ctcagaagaa accggtgatc aaacccctga cagaggacag caagaaacgc    14340
agttacaacc taataagcaa tgacagcacc ttcacccagt accgcagctg gtaccttgca    14400
tacaactacg gcgacccttca gaccggaatc cgctcatgga ccctgctttg cactcctgac    14460
gtaacctgcg gctcggagca ggtctactgg tcgttgccag acatgatgca agacccgtg    14520
```

```
accttccgct ccacgcgcca gatcagcaac tttccggtgg tgggcgccga gctgttgccc   14580
gtgcactcca agagcttcta caacgaccag gccgtctact cccaactcat ccgccagttt   14640
acctctctga cccacgtgtt caatcgcttt cccgagaacc agattttggc gcgcccgcca   14700
gcccccacca tcaccaccgt cagtgaaaac gttcctgctc tcacagatca cgggacgcta   14760
ccgctgcgca acagcatcgg aggagtccag cgagtgacca ttactgacgc cagacgccgc   14820 acctgccccct acgtttacaa ggccctgggc atagtctcgc cgcgcgtcct atcgagccgc   14880 acttttttgag caagcatgtc catccttata tcgcccagca ataacacagg ctggggcctg   14940
cgcttcccaa gcaagatgtt tggcgggggcc aagaagcgct ccgaccaaca cccagtgcgc   15000
gtgcgcgggc actaccgcgc gccctggggc gcgcacaaac gcggccgcac tgggcgcacc   15060
accgtcgatg acgccatcga cgcggtggtg gaggaggcgc gcaactacac gcccacgccg   15120
ccaccagtgt ccacagtgga cgcggccatt cagaccgtgg tgcgcggagc ccggcgctat   15180
gctaaaatga agagacgcg gaggcgcgta gcacgtcgcc accgccgccg acccggcact   15240
gccgcccaac gcgcggcggc ggccctgctt aaccgcgcac gtcgcaccgg ccgacgggcg   15300
gccatgcggg ccgctcgaag gctggccgcg ggtattgtca ctgtgccccc caggtccagg   15360
cgacgagcgg ccgccgcagc agccgcggcc attagtgcta tgactcaggg tcgcaggggc   15420
aacgtgtatt gggtgcgcga ctcggttagc ggcctgcgcg tgcccgtgcg cacccgcccc   15480
ccgcgcaact agattgcaag aaaaaactac ttagactcgt actgttgtat gtatccagcg   15540
gcggcggcgc gcaacgaagc tatgtccaag cgcaaaatca agaagagat gctccaggtc   15600 atcgcgccgg agatctatgg ccccccgaag aaggaagagc aggattacaa gccccgaaag   15660
ctaaagcggg tcaaaaagaa aaagaaagat gatgatgatg aacttgacga cgaggtggaa   15720
ctgctgcacg ctaccgcgcc caggcgacgg gtacagtgga aggtcgacg cgtaaaacgt   15780 gttttgcgac ccggcaccac cgtagtcttt acgcccggtg agcgctccac ccgcacctac   15840
aagcgcgtgt atgatgaggt gtacggcgac gaggacctgc ttgagcaggc caacgagcgc   15900 ctcgggggagt ttgcctacgg aaagcggcat aaggacatgc tggcgttgcc gctgacgag   15960 ggcaacccaa cacctagcct aaagcccgta acactgcagc aggtgctgcc cgcgcttgca   16020
ccgtccgaag aaaagcgcgg cctaaagcgc gagtctggtg acttggcacc caccgtgcag   16080
ctgatggtac ccaagcgcca gcgactggaa gatgtcttgg aaaaaatgac cgtggaacct   16140
gggctggagc ccgaggtccg cgtgcggcca atcaagcagg tggcgccggg actgggcgtg   16200
cagaccgtga acgttcagat acccactacc agtagcacca gtattgccac cgccacagag   16260
ggcatggaga cacaaacgtc cccggttgcc tcagcggtgg cggatgccgc ggtgcaggcg   16320
gtcgctgcgg ccgcgtccaa gacctctacg gaggtgcaaa cggacccgtg gatgtttcgc   16380
gtttcagccc ccggcgccc gcgccgttcg aggaagtacg gcgccgccag cgcgctactg   16440
cccgaatatg ccctacatcc ttccattgcg cctaccccg gctatcgtgg ctacacctac   16500
cgccccagaa gacgagcaac tacccgacgc gaaccacca ctggaacccg ccgccgccgt   16560
cgccgtcgcc agcccgtgct ggccccgatt ccgtgcgca gggtggctcg cgaaggaggc   16620
aggaccctgg tgctgccaac agcgcgctac caccccagca tcgtttaaaa gccggtcttt   16680
gtggttcttg cagatatggc cctcacctgc cgcctccgtt tcccggtgcc gggattccga   16740
ggaagaatgc accgtaggag gggcatggcc ggccacggcc tgacgggcgg catgcgtcgt   16800
gcgcaccacc ggcggcggcg cgcgtcgcac cgtcgcatgc gcggcggtat cctgcccctc   16860
```

```
cttattccac tgatcgccgc ggcgattggc gccgtgcccg gaattgcatc cgtggccttg    16920
caggcgcaga gacactgatt aaaaacaagt tgcatgtgga aaaatcaaaa taaaaagtct    16980
ggactctcac gctcgcttgg tcctgtaact attttgtaga atggaagaca tcaactttgc    17040
gtctctggcc ccgcgacacg gctcgcgccc gttcatggga aactggcaag atatcggcac    17100
cagcaatatg agcggtggcg ccttcagctg gggctcgctg tggagcggca ttaaaaattt    17160
cggttccacc gttaagaact atggcagcaa ggcctggaac agcagcacag gccagatgct    17220
gagggataag ttgaaagagc aaaatttcca acaaaggtg gtagatggcc tggcctctgg    17280
cattagcggg gtggtggacc tggccaacca ggcagtgcaa aataagatta acagtaagct    17340
tgatccccgc cctcccgtag aggagcctcc accggccgtg gagacagtgt ctccagaggg    17400
gcgtggcgaa aagcgtccgc gccccgacag gaagaaaact ctggtgacgc aaatagacga    17460
gcctccctcg tacgaggagg cactaaagca aggcctgccc accacccgtc ccatcgcgcc    17520
catggctacc ggagtgctgg gccagcacac cccgtaacg ctggacctgc ctcccccgc     17580 cgacacccag cagaaacctg tgctgccagg cccgaccgcc gttgttgtaa cccgtcctag    17640
ccgcgcgtcc ctgcgccgcg ccgccagcgg tccgcgatcg ttgcggcccg tagccagtgg    17700
caactggcaa agcacactga acagcatcgt gggtctgggg gtgcaatccc tgaagcgccg    17760
acgatgcttc tgatagctaa cgtgtcgtat gtgtgtcatg tatgcgtcca tgtcgccgcc    17820
agaggagctg ctgagccgcc gcgcgcccgc tttccaagat ggctacccct cgatgatgc    17880 cgcagtggtc ttacatgcac atctcgggcc aggacgcctc ggagtacctg agccccgggc    17940
tggtgcagtt tgcccgcgcc accgagacgt acttcagcct gaataacaag tttagaaacc    18000
ccacggtggc gcctacgcac gacgtgacca cagaccggtc ccagcgtttg acgctgcggt    18060
tcatccctgt ggaccgtgag gatactgcgt actcgtacaa ggcgcggttc accctagctg    18120
tgggtgataa ccgtgtgctg gacatggctt ccacgtactt tgacatccgc ggcgtgctgg    18180
acaggggccc tactttaag ccctactctg gcactgccta caacgccctg gctcccaagg    18240
gtgccccaaa tccttgcgaa tgggatgaag ctgctactgc tcttgaaata aacctagaag    18300
aagaggacga tgacaacgaa gacgaagtag acgagcaagc tgagcagcaa aaaactcacg    18360
tatttgggca ggcgccttat tctggtataa atattacaaa ggagggtatt caaataggtg    18420
tcgaaggtca aacacctaaa tatgccgata aacatttca acctgaacct caaataggag    18480
aatctcagtg gtacgaaaca gaaattaatc atgcagctgg gagagtccta aaaaagacta    18540
ccccaatgaa accatgttac ggttcatatg caaaacccac aaatgaaaat ggagggcaag    18600
gcattcttgt aaagcaacaa aatggaaagc tagaaagtca agtggaaatg caattttct     18660 caactactga ggcagccgca ggcaatggtg taacttgac tcctaaagtg gtattgtaca    18720
gtgaagatgt agatatagaa accccagaca ctcatatttc ttacatgccc actattaagg    18780
aaggtaactc acgagaacta atgggccaac aatctatgcc caacaggcct aattacattg    18840
cttttaggga caattttatt ggtctaatgt attacaacag cacgggtaat atgggtgttc    18900
tggcgggcca agcatcgcag ttgaatgctg ttgtagattt gcaagacaga aacacagagc    18960
tttcatacca gcttttgctt gattccattg gtgatagaac caggtacttt tctatgtgga    19020
atcaggctgt tgacagctat gatccagatg ttagaattat tgaaaatcat ggaactgaag    19080
atgaacttcc aaaattactgc tttccactgg gaggtgtgat taatacagag actcttacca    19140
aggtaaaacc taaacaggt caggaaaatg gatgggaaaa agatgctaca gaattttcag    19200
ataaaaatga aataagagtt ggaaataatt ttgccatgga aatcaatcta aatgccaacc    19260
```

```
tgtggagaaa tttcctgtac tccaacatag cgctgtattt gcccgacaag ctaaagtaca   19320
gtccttccaa cgtaaaaatt tctgataacc caaacaccta cgactacatg aacaagcgag   19380
tggtggctcc cgggctagtg gactgctaca ttaaccttgg agcacgctgg tcccttgact   19440
atatggacaa cgtcaaccca tttaaccacc accgcaatgc tggcctgcgc taccgctcaa   19500
tgttgctggg caatggtcgc tatgtgccct tccacatcca ggtgcctcag aagttctttg   19560
ccattaaaaa cctccttctc ctgccgggct catacaccta cgagtggaac ttcaggaagg   19620
atgttaacat ggttctgcag agctccctag gaaatgacct aagggttgac ggagccagca   19680
ttaagtttga tagcatttgc ctttacgcca ccttcttccc catggcccac aacaccgcct   19740
ccacgcttga ggccatgctt agaaacgaca ccaacgacca gtcctttaac gactatctct   19800
ccgccgccaa catgctctac cctataccg ccaacgctac caacgtgccc atatccatcc   19860
cctcccgcaa ctgggcggct ttccgcggct gggccttcac gcgccttaag actaaggaaa   19920
ccccatcact gggctcgggc tacgacccttt attacaccta ctctggctct atacccacc   19980 tagatggaac cttttacctc aaccacacct ttaagaaggt ggccattacc tttgactctt   20040
ctgtcagctg gcctggcaat gaccgcctgc ttacccccaa cgagtttgaa attaagcgct   20100
cagttgacgg ggagggttac aacgttgccc agtgtaacat gaccaaagac tggttcctgg   20160
tacaaatgct agctaactat aacattggct accagggctt ctatatccca gagagctaca   20220
aggaccgcat gtactccttc tttagaaact tccagcccat gagccgtcag gtggtggatg   20280
atactaaata caaggactac caacaggtgg gcatcctaca ccaacacaac aactctggat   20340
ttgttggcta ccttgccccc accatgcgcg aaggacaggc ctaccctgct aacttcccct   20400
atccgcttat aggcaagacc gcagttgaca gcattaccca gaaaaagttt ctttgcgatc   20460 gcacccttg gcgcatccca ttctccagta actttatgtc catgggcgca ctcacagacc   20520
tgggccaaaa ccttctctac gccaactccg cccacgcgct agacatgact tttgaggtgg   20580
atcccatgga cgagcccacc cttctttatg ttttgtttga agtctttgac gtggtccgtg   20640
tgcaccagcc gcaccgcggc gtcatcgaaa ccgtgtacct gcgcacgccc ttctcggccg   20700
gcaacgccac aacataaaga agcaagcaac atcaacaaca gctgccgcca tgggctccag   20760
tgagcaggaa ctgaaagcca ttgtcaaaga tcttggttgt gggccatatt ttttgggcac   20820
ctatgacaag cgcttttccag gctttgtttc tccacacaag ctcgcctgcg ccatagtcaa   20880
tacggccggt cgcgagactg ggggcgtaca ctggatggcc tttgcctgga cccgcactc   20940 aaaaacatgc tacctctttg agccctttgg cttttctgac cagcgactca gcaggttta   21000 ccagtttgag tacgagtcac tcctgcgccg tagcgccatt gcttcttccc ccgaccgctg   21060
tataacgctg gaaaagtcca cccaaagcgt acagggcccc aactcggccg cctgtggact   21120
attctgctgc atgtttctcc acgcctttgc caactggccc caaactccca tggatcacaa   21180
ccccaccatg aaccttatta ccggggtacc caactccatg ctcaacagtc cccaggtaca   21240 gcccacctg cgtcgcaacc aggaacagct ctacagcttc ctggagcgcc actcgcccta   21300
cttccgcagc cacagtgcgc agattaggag cgccacttct ttttgtcact tgaaaaacat   21360
gtaaaaataa tgtactagag acactttcaa taaaggcaaa tgcttttatt tgtacactct   21420
cgggtgatta tttacccca cccttgccgt ctgcgccgtt taaaaatcaa aggggttctg   21480
ccgcgcatcg ctatgcgcca ctggcaggga cacgttgcga tactggtgtt tagtgctcca   21540
cttaaactca ggcacaacca tccgcggcag ctcggtgaag ttttcactcc acaggctgcg   21600
```

```
caccatcacc aacgcgttta gcaggtcggg cgccgatatc ttgaagtcgc agttggggcc    21660
tccgccctgc gcgcgcgagt tgcgatacac agggttgcag cactggaaca ctatcagcgc    21720
cgggtggtgc acgctggcca gcacgctctt gtcggagatc agatccgcgt ccaggtcctc    21780
cgcgttgctc agggcgaacg gagtcaactt tggtagctgc cttcccaaaa agggcgcgtg    21840
cccaggcttt gagttgcact cgcaccgtag tggcatcaaa aggtgaccgt gcccggtctg    21900
ggcgttagga tacagcgcct gcataaaagc cttgatctgc ttaaaagcca cctgagcctt    21960
tgcgccttca gagaagaaca tgccgcaaga cttgccggaa aactgattgg ccggacaggc    22020
cgcgtcgtgc acgcagcacc ttgcgtcggt gttggagatc tgcaccacat tcggccccca    22080
ccggttcttc acgatcttgg ccttgctaga ctgctccttc agcgcgcgct gcccgttttc    22140
gctcgtcaca tccatttcaa tcacgtgctc cttatttatc ataatgcttc cgtgtagaca    22200
cttaagctcg ccttcgatct cagcgcagcg gtgcagccac aacgcgcagc ccgtgggctc    22260
gtgatgcttg taggtcacct ctgcaaacga ctgcaggtac gcctgcagga atcgccccat    22320
catcgtcaca aaggtcttgt tgctggtgaa ggtcagctgc aacccgcggt gctcctcgtt    22380
cagccaggtc ttgcatacgg ccgccagagc ttccacttgg tcaggcagta gtttgaagtt    22440
cgcctttaga tcgttatcca cgtggtactt gtccatcagc gcgcgcgcag cctccatgcc    22500
cttctcccac gcagacacga tcggcacact cagcgggttc atcaccgtaa tttcactttc    22560
cgcttcgctg ggctcttcct cttcctcttg cgtccgcata ccacgcgcca ctgggtcgtc    22620
ttcattcagc cgccgcactg tgcgcttacc tcctttgcca tgcttgatta gcaccggtgg    22680
gttgctgaaa cccaccattt gtagcgccac atcttctctt tcttcctcgc tgtccacgat    22740
tacctctggt gatggcgggc gctcgggctt gggagaaggg cgcttctttt tcttcttggg    22800
cgcaatggcc aaatccgccg ccgaggtcga tggccgcggg ctgggtgtgc gcggcaccag    22860
cgcgtcttgt gatgagtctt cctcgtcctc ggactcgata cgccgcctca tccgcttttt    22920
tgggggcgcc cggggaggcg gcggcgacgg ggacggggac gacacgtcct ccatggttgg    22980
gggacgtcgc gccgcaccgc gtccgcgctc ggggtggtt tcgcgctgct cctcttcccg    23040
actggccatt tccttctcct ataggcagaa aaagatcatg gagtcagtcg agaagaagga    23100
cagcctaacc gccccctctg agttcgccac caccgcctcc accgatgccg ccaacgcgcc    23160
taccaccttc cccgtcgagg cacccccgct tgaggaggag gaagtgatta tcgagcagga    23220
cccaggtttt gtaagcgaag acgacgagga ccgctcagta ccaacagagg ataaaaagca    23280
agaccaggac aacgcagagg caaacgagga acaagtcggg cgggggacg aaaggcatgg    23340
cgactaccta gatgtgggag acgacgtgct gttgaagcat ctgcagcgcc agtgcgccat    23400
tatctgcgac gcgttgcaag agcgcagcga tgtgccccctc gccatagcgg atgtcagcct    23460
tgcctacgaa cgccacctat tctcaccgcg cgtaccccc aaacgccaag aaaacggcac    23520
atgcgagccc aacccgcgcc tcaacttcta ccccgtattt gccgtgccag aggtgcttgc    23580
cacctatcac atcttttttcc aaaactgcaa gatacccta cctgccgtg ccaaccgcag    23640
ccgagcggac aagcagctgg ccttgcggca gggcgctgtc atacctgata tcgcctcgct    23700
caacgaagtg ccaaaaatct ttgagggtct tggacgcgac gagaagcgcg cggcaaacgc    23760
tctgcaacag gaaaacagcg aaaatgaaag tcactctgga gtgttggtgg aactcgaggg    23820
tgacaacgcg cgcctagccg tactaaaacg cagcatcgag gtcacccact ttgcctaccc    23880
ggcacttaac ctacccccca aggtcatgag cacagtcatg agtgagctga tcgtgcgccg    23940
tgcgcagccc ctggagaggg atgcaaattt gcaagaacaa acagaggagg gcctacccgc    24000
```

```
agttggcgac gagcagctag cgcgctggct tcaaacgcgc gagcctgccg acttggagga  24060
gcgacgcaaa ctaatgatgg ccgcagtgct cgttaccgtg gagcttgagt gcatgcagcg  24120
gttctttgct gacccggaga tgcagcgcaa gctagaggaa acattgcact acacctttcg  24180
acagggctac gtacgccagg cctgcaagat ctccaacgtg gagctctgca acctggtctc  24240
ctaccttgga attttgcacg aaaaccgcct tgggcaaaac gtgcttcatt ccacgctcaa  24300
gggcgaggcg cgccgcgact acgtccgcga ctgcgtttac ttatttctat gctacacctg  24360
gcagacggcc atgggcgttt ggcagcagtg cttggaggag tgcaacctca aggagctgca  24420
gaaactgcta aagcaaaact tgaaggacct atggacggcc ttcaacgagc gctccgtggc  24480
cgcgcacctg gcggacatca ttttccccga acgcctgctt aaaaccctgc aacagggtct  24540
gccagacttc accagtcaaa gcatgttgca aactttagg aactttatcc tagagcgctc  24600
aggaatcttg cccgccacct gctgtgcact tcctagcgac tttgtgccca ttaagtaccg  24660
cgaatgccct ccgccgcttt ggggccactg ctaccttctg cagctagcca actaccttgc  24720
ctaccactct gacataatgg aagacgtgag cggtgacggt ctactggagt gtcactgtcg  24780
ctgcaaccta tgcaccccgc accgctccct ggtttgcaat tcgcagctgc ttaacgaaag  24840
tcaaattatc ggtacctttg agctgcaggg tccctcgcct gacgaaaagt ccgcggctcc  24900
ggggttgaaa ctcactccgg ggctgtggac gtcggcttac cttcgcaaat ttgtacctga  24960
ggactaccac gcccacgaga ttaggttcta cgaagaccaa tcccgcccgc ctaatgcgga  25020
gcttaccgcc tgcgtcatta cccagggcca cattcttggc caattgcaag ccatcaacaa  25080
agcccgccaa gagtttctgc tacgaaaggg acggggggtt tacttggacc cccagtccgg  25140
cgaggagctc aacccaatcc cccgccgcc gcagccctat cagcagcagc cgcgggccct  25200
tgcttcccag gatggcaccc aaaaagaagc tgcagctgcc gccgccaccc acggacgagg  25260
aggaatactg ggacagtcag gcagaggagg ttttggacga ggaggaggag gacatgatgg  25320
aagactggga gagcctagac gaggaagctt ccgaggtcga agaggtgtca gacgaaacac  25380
cgtcaccctc ggtcgcattc ccctcgccgg cgccccagaa atcggcaacc ggttccagca  25440
tggctacaac ctccgctcct caggcgccgc cggcactgcc cgttcgccga cccaaccgta  25500
gatgggacac cactggaacc agggccggta agtccaagca gccgccgccg ttagcccaag  25560
agcaacaaca gcgccaaggc taccgctcat ggcgcgggca caagaacgcc atagttgctt  25620
gcttgcaaga ctgtgggggc aacatctcct tcgcccgccg cttcttctc taccatcacg  25680
gcgtggcctt cccccgtaac atcctgcatt actaccgtca tctctacagc ccatactgca  25740
ccggcggcag cggcagcaac agcagcggcc acacagaagc aaaggcgacc ggatagcaag  25800
actctgacaa agcccaagaa atccacagcg cggcagcag caggaggagg agcgctgcgt  25860
ctggcgccca acgaacccgt atcgacccgc gagcttagaa acaggatttt tcccactctg  25920
tatgctatat ttcaacagag caggggccaa gaacaagagc tgaaaataaa aaacaggtct  25980
ctgcgatccc tcacccgcag ctgcctgtat cacaaaagcg aagatcagct tcggcgcacg  26040
ctggaagacg cggaggctct cttcagtaaa tactgcgcgc tgactcttaa ggactagttt  26100
cgcgcccttt ctcaaattta agcgcgaaaa ctacgtcatc tccagcggcc acaccggcg  26160
ccagcacctg ttgtcagcgc cattatgagc aaggaaattc ccacgcccta catgtggagt  26220
taccagccaa aaatgggact tgcggctgga gctgccaag actactcaac ccgaataaac  26280
tacatgagcg cggaccccca catgatatcc cgggtcaacg gaatacgcgc ccaccgaaac  26340
```

| | |
|---|---|
| cgaattctcc tggaacaggc ggctattacc accacacctc gtaataacct taatccccgt | 26400 |
| agttggcccg ctgccctggt gtaccaggaa agtcccgctc ccaccactgt ggtacttccc | 26460 |
| agagacgccc aggccgaagt tcagatgact aactcagggg cgcagcttgc gggcggcttt | 26520 |
| cgtcacaggt gcggtcgcc cgggcagggt ataactcacc tgacaatcag agggcgaggt | 26580 |
| attcagctca acgacgagtc ggtgagctcc tcgcttggtc tccgtccgga cgggacattt | 26640 |
| cagatcggcg cgccggccg ctcttcattc acgcctcgtc aggcaatcct aactctgcag | 26700 |
| acctcgtcct ctgagccgcg ctctggaggc attggaactc tgcaatttat tgaggagttt | 26760 |
| gtgccatcgg tctactttaa ccccttctcg ggacctcccg gccactatcc ggatcaattt | 26820 |
| attcctaact ttgacgcggt aaaggactcg gcggacggct acgactgaat gttaagtgga | 26880 |
| gaggcagagc aactgcgcct gaaacacctg gtccactgtc gccgccacaa gtgctttgcc | 26940 |
| cgcgactccg gtgagttttg ctactttgaa ttgcccgagg atcatatcga gggcccggcg | 27000 |
| cacggcgtcc ggcttaccgc ccagggagag cttgcccgta gcctgattcg ggagtttacc | 27060 |
| cagcgccccc tgctagttga gcgggacagg ggaccctgtg ttctcactgt gatttgcaac | 27120 |
| tgtcctaacc ctggattaca tcaagatcct ctagttaatg tcaggtcgcc taagtcgatt | 27180 |
| aactagagta cccggggatc ttattccctt aactaataa aaaaaaataa taaagcatca | 27240 |
| cttacttaaa atcagttagc aaatttctgt ccagtttatt cagcagcacc tccttgccct | 27300 |
| cctcccagct ctggtattgc agcttcctcc tggctgcaaa cttctccac aatctaaatg | 27360 |
| gaatgtcagt ttcctcctgt tcctgtccat ccgcacccac tatcttcatg ttgttgcaga | 27420 |
| tgaagcgcgc aagaccgtct gaagatacct tcaaccccgt gtatccatat gacacggaaa | 27480 |
| ccggtcctcc aactgtgcct tttcttactc ctcccttttgt atccccaat gggtttcaag | 27540 |
| agagtccccc tggggtactc tctttgcgcc tatccgaacc tctagttacc tccaatggca | 27600 |
| tgcttgcgct caaaatgggc aacggcctct ctctggacga ggccggcaac cttacctccc | 27660 |
| aaaatgtaac cactgtgagc ccacctctca aaaaaaccaa gtcaaacata aacctggaaa | 27720 |
| tatctgcacc cctcacagtt acctcagaag ccctaactgt ggctgccgcc gcacctctaa | 27780 |
| tggtcgcggg caacacactc accatgcaat cacaggcccc gctaaccgtg cacgactcca | 27840 |
| aacttagcat tgccacccaa ggacccctca cagtgtcaga aggaaagcta gccctgcaaa | 27900 |
| catcaggccc cctcaccacc accgatagca gtacccttac tatccactgcc tcacccctc | 27960 |
| taactactgc cactggtagc ttgggcattg acttgaaaga gcccatttat acacaaaatg | 28020 |
| gaaaactagg actaaagtac ggggctcctt tgcatgtaac agacgaccta aacactttga | 28080 |
| ccgtagcaac tggtccaggt gtgactatta ataatacttc cttgcaaact aaagttactg | 28140 |
| gagccttggg ttttgattca caaggcaata tgcaacttaa tgtagcagga ggactaagga | 28200 |
| ttgattctca aaacagacgc cttatacttg atgttagtta tccgtttgat gctcaaaacc | 28260 |
| aactaaatct aagactagga cagggccctc tttttataaa ctcagcccac aacttggata | 28320 |
| ttaactacaa caaaggcctt tacttgttta cagcttcaaa caattccaaa aagcttgagg | 28380 |
| ttaacctaag cactgccaag gggttgatgt ttgacgctac agccatagcc attaatgcag | 28440 |
| gagatgggct tgaatttggt tcacctaatg caccaaacac aaatcccctc aaaacaaaaa | 28500 |
| ttggccatgg cctagaattt gattcaaaca aggctatggt tcctaaacta ggaactggcc | 28560 |
| ttagttttga cagcacaggt gccattacag taggaaacaa aaataatgat aagctaactt | 28620 |
| tgtggaccac accagctcca tctcctaact gtagactaaa tgcagagaaa gatgctaaac | 28680 |
| tcactttggt cttaacaaaa tgtggcagtc aaatacttgc tacagtttca gttttggctg | 28740 |

```
ttaaaggcag tttggctcca atatctggaa cagttcaaag tgctcatctt attataagat   28800
ttgacgaaaa tggagtgcta ctaaacaatt ccttcctgga cccagaatat tggaacttta   28860
gaaatggaga tcttactgaa ggcacagcct atacaaacgc tgttggattt atgcctaacc   28920
tatcagctta tccaaaatct cacggtaaaa ctgccaaaag taacattgtc agtcaagttt   28980
acttaaacgg agacaaaact aaacctgtaa cactaaccat tacactaaac ggtacacagg   29040
aaacaggaga cacaactcca agtgcatact ctatgtcatt ttcatgggac tggtctggcc   29100
acaactacat taatgaaata tttgccacat cctcttacac ttttttcatac attgcccaag   29160 aataaagaat cgtttgtgtt atgtttcaac gtgtttattt ttcaattgca gaaaatttca   29220
agtcattttt cattcagtag tatagcccca ccaccacata gcttatacag atcaccgtac   29280
cttaatcaaa ctcacagaac cctagtattc aacctgccac ctccctccca acacacagag   29340
tacacagtcc tttctccccg gctggcctta aaaagcatca tatcatgggt aacagacata   29400
ttcttaggtg ttatattcca cacggtttcc tgtcgagcca aacgctcatc agtgatatta   29460
ataaactccc cggcagctc acttaagttc atgtcgctgt ccagctgctg agccacaggc   29520
tgctgtccaa cttgcggttg cttaacgggc ggcgaaggag aagtccacgc ctacatgggg   29580
gtagagtcat aatcgtgcat caggatagg cggtggtgct gcagcagcgc gcgaataaac   29640
tgctgccgcc gccgctccgt cctgcaggaa tacaacatgg cagtggtctc ctcagcgatg   29700
attcgcaccg cccgcagcat aaggcgcctt gtcctccggg cacagcagcg caccctgatc   29760
tcacttaaat cagcacagta actgcagcac agcaccacaa tattgttcaa aatcccacag   29820
tgcaaggcgc tgtatccaaa gctcatggcg gggaccacag aacccacgtg gccatcatac   29880
cacaagcgca ggtagattaa gtggcgaccc ctcataaaca cgctggacat aaacattacc   29940
tcttttggca tgttgtaatt caccacctcc cggtaccata taaacctctg attaaacatg   30000
gcgccatcca ccaccatcct aaaccagctg gccaaaacct gcccgccggc tatacactgc   30060
agggaaccgg gactggaaca atgacagtgg agagcccagg actcgtaacc atggatcatc   30120
atgctcgtca tgatatcaat gttggcacaa cacaggcaca cgtgcataca cttcctcagg   30180
attacaagct cctcccgcgt tagaaccata tcccagggaa caacccattc ctgaatcagc   30240
gtaaatccca cactgcaggg aagacctcgc acgtaactca cgttgtgcat tgtcaaagtg   30300
ttacattcgg gcagcagcgg atgatcctcc agtatggtag cgcgggtttc tgtctcaaaa   30360
ggaggtagac gatccctact gtacggagtg cgccgagaca accgagatcg tgttggtcgt   30420
agtgtcatgc caaatggaac gccggacgta gtcatatttc ctgaagcaaa accaggtgcg   30480
ggcgtgacaa acagatctgc gtctccggtc tcgccgctta gatcgctctg tgtagtagtt   30540
gtagtatatc cactctctca aagcatccag gcgcccctg gcttcgggtt ctatgtaaac   30600
tccttcatgc gccgctgccc tgataacatc caccaccgca gaataagcca cacccagcca   30660
acctacacat tcgttctgcg agtcacacac gggaggagcg ggaagagctg gaagaaccat   30720 gtttttttttt ttattccaaa agattatcca aaacctcaaa atgaagatct attaagtgaa   30780
cgcgctcccc tccggtggcg tggtcaaact ctacagccaa agaacagata atggcatttg   30840
taagatgttg cacaatggct tccaaaaggc aaacggccct cacgtccaag tggacgtaaa   30900
ggctaaaccc ttcagggtga atctcctcta taaacattcc agcaccttca accatgccca   30960
aataattctc atctcgccac cttctcaata tatctctaag caaatcccga atattaagtc   31020
cggccattgt aaaaatctgc tccagagcgc cctccacctt cagcctcaag cagcgaatca   31080
```

-continued

```
tgattgcaaa aattcaggtt cctcacagac ctgtataaga ttcaaaagcg gaacattaac    31140
aaaaataccg cgatcccgta ggtcccttcg cagggccagc tgaacataat cgtgcaggtc    31200
tgcacggacc agcgcggcca cttccccgcc aggaaccatg acaaaagaac ccacactgat    31260
tatgacacgc atactcggag ctatgctaac cagcgtagcc ccgatgtaag cttgttgcat    31320
gggcggcgat ataaaatgca aggtgctgct caaaaaatca ggcaaagcct cgcgcaaaaa    31380
agaaagcaca tcgtagtcat gctcatgcag ataaaggcag gtaagctccg gaaccaccac    31440
agaaaaagac accattttc tctcaaacat gtctgcgggt ttctgcataa acacaaaata    31500
aaataacaaa aaacattta aacattagaa gcctgtctta caacaggaaa acaacccctt    31560
ataagcataa gacggactac ggccatgccg gcgtgaccgt aaaaaaactg gtcaccgtga    31620
ttaaaaagca ccaccgacag ctcctcggtc atgtccggag tcataatgta agactcggta    31680
aacacatcag gttgattcac atcggtcagt gctaaaaagc gaccgaaata gcccggggga    31740
atacataccc gcaggcgtag agacaacatt acagccccca taggaggtat aacaaaatta    31800
ataggagaga aaaacacata aacacctgaa aaaccctcct gcctaggcaa aatagcaccc    31860
tcccgctcca gaacaacata cagcgcttcc acagcggcag ccataacagt cagccttacc    31920
agtaaaaaag aaaacctatt aaaaaaacac cactcgacac ggcaccagct caatcagtca    31980
cagtgtaaaa aagggccaag tgcagagcga gtatatatag gactaaaaaa tgacgtaacg    32040
gttaaagtcc acaaaaaaca cccagaaaac cgcacgcgaa cctacgccca gaaacgaaag    32100
ccaaaaaacc cacaacttcc tcaaatcgtc acttccgttt tcccacgtta cgtcacttcc    32160
cattttaaga aaactacaat tcccaacaca tacaagttac tccgccctaa aacctacgtc    32220
acccgccccg ttcccacgcc ccgcgccacg tcacaaactc cacccccctca ttatcatatt    32280
ggcttcaatc caaaataagg tatattattg atgat                              32315
```

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Leu Ser Gly Ala Asn Leu Asn Leu
1               5

<210> SEQ ID NO 5
<211> LENGTH: 1826
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
cgctccacct ctcaagcagc cagcgcctgc ctgaatctgt tctgccccct ccccacccat     60
ttcaccacca ccatgacacc gggcacccag tctcctttct tcctgctgct gctcctcaca    120
gtgcttacag ttgttacggg ttctggtcat gcaagctcta ccccaggtgg agaaaaggag    180
acttcggcta cccagagaag ttcagtgccc agctctactg agaagaatgc tgtgagtatg    240
accagcagcg tactctccag ccacagcccc ggttcaggct cctccaccac tcagggacag    300
gatgtcactc tggccccggc cacggaacca gcttcaggtt cagctgccac ctggggacag    360
```

```
gatgtcacct cggtcccagt caccaggcca gccctgggct ccaccacccc gccagcccac    420
gatgtcacct cagccccgga caacaagcca gccccgggct ccaccgcccc ccagcccac     480 ggtgtcacct cggccccgga caccaggccg gccccgggct ccaccgcccc ccagcccat     540 ggtgtcacct cggccccgga caacaggccc gccttgggct ccaccgcccc tccagtccac    600
aatgtcacct cggcctcagg ctctgcatca ggctcagctt ctactctggt gcacaacggc    660
acctctgcca gggctaccac aaccccagcc agcaagagca ctccattctc aattcccagc    720
caccactctg atactcctac cacccttgcc agccatagca ccaagactga tgccagtagc    780
actcaccata gcacggtacc tcctctcacc tcctccaatc acagcacttc tccccagttg    840
tctactgggg tctcttctt tttcctgtct tttcacattt caaacctcca gtttaattcc     900
tctctggaag atcccagcac cgactactac caagagctgc agagagacat ttctgaaatg    960
tttttgcaga tttataaaca aggggg tttt ctgggcctct ccaatattaa gttcaggcca   1020
ggatctgtgg tggtacaatt gactctggcc ttccgagaag gtaccatcaa tgtccacgac    1080
gtggagacac agttcaatca gtataaaacg aagcagcct c tcgatataa cctgacgatc    1140 tcagacgtca gcgtgagtga tgtgccattt cctttctctg cccagtctgg ggctggggtg    1200
ccaggctggg catcgcgct gctggtgctg gtctgtgttc tggttgcgct ggccattgtc     1260
tatctcattg ccttggctgt ctgtcagtgc cgccgaaaga actacgggca gctggacatc    1320
tttccagccc gggatcccta ccatcctatg agcgagtacc ccacctacca cacccatggg    1380
cgctatgtgc cccctagcag taccgatcgt agccctatg agaaggtttc tgcaggtaat     1440
ggtggcagca gcctctctta cacaaaccca gcagtggcag ccacttctgc caacttgtag    1500
gggcacgtcg cccgctgagc tgagtggcca gccagtgcca ttccactcca ctcaggttct    1560
tcagggccag agccctgca ccctgtttgg gctggtgagc tgggagttca ggtgggctgc     1620
tcacagcctc cttcagaggc cccaccaatt tctcggacac ttctcagtgt gtggaagctc    1680
atgtgggccc ctgagggctc atgcctggga agtgttgtgg tgggggctcc caggaggact    1740
ggcccagaga gccctgagat agcggggatc ctgaactgga ctgaataaaa cgtggtctcc    1800
cactgcgcca aaaaaaaaaa aaaaaa                                         1826
```

<210> SEQ ID NO 6
<211> LENGTH: 1826
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
cgctccacct ctcaagcagc cagcgcctgc ctgaatctgt tctgccccct ccccacccat     60
ttcaccacca ccatgacacc gggcacccag tctcctttct tcctgctgct gctcctcaca    120
gtgcttacag ttgttacggg ttctggtcat gcaagctcta ccccaggtgg agaaaaggag    180
acttcggcta cccagagaag ttcagtgccc agctctactg agaagaatgc tgtgagtatg    240
accagcagcg tactctccag ccacagcccc ggttcaggct cctccaccac tcagggacag    300
gatgtcactc tggccccggc cacggaacca gcttcaggtt cagctgccct tggggacag    360 gatgtcacct cggtcccagt caccaggcca gccctgggct ccaccacccc gccagcccac    420
gatgtcacct cagccccgga caacaagcca gccccgggct ccaccgcccc ccagcccac     480 ggtgtcacct cgtatcttga caccaggccg gccccggttt atcttgcccc cccagcccat    540
```

```
ggtgtcacct cggccccgga caacaggccc gccttgggct ccaccgcccc tccagtccac    600
aatgtcacct cggcctcagg ctctgcatca ggctcagctt ctactctggt gcacaacggc    660
acctctgcca gggctaccac aaccccagcc agcaagagca ctccattctc aattcccagc    720
caccactctg atactcctac cacccttgcc agccatagca ccaagactga tgccagtagc    780
actcaccata gcacggtacc tcctctcacc tcctccaatc acagcacttc tccccagttg    840
tctactgggg tctctttctt tttcctgtct tttcacattt caaacctcca gtttaattcc    900
tctctggaag atcccagcac cgactactac caagagctgc agagagacat ttctgaaatg    960
tttttgcaga tttataaaca aggggggtttt ctgggcctct ccaatattaa gttcaggcca   1020
ggatctgtgg tggtacaatt gactctggcc ttccgagaag gtaccatcaa tgtccacgac   1080
gtggagacac agttcaatca gtataaaacg aagcagcct ctcgatataa cctgacgatc    1140
tcagacgtca gcgtgagtga tgtgccattt cctttctctg cccagtctgg ggctggggtg    1200
ccaggctggg gcatcgcgct gctggtgctg gtctgtgttc tggtttatct ggccattgtc    1260
tatctcattg ccttggctgt cgctcaggtt cgccgaaaga actacgggca gctggacatc    1320
tttccagccc gggataaata ccatcctatg agcgagtacg ctctttacca cacccatggg    1380
cgctatgtgc cccctagcag tctttttccgt agcccctatg agaaggtttc tgcaggtaat   1440
ggtggcagct atctctctta cacaaaccca gcagtggcag ccgcttctgc caacttgtag   1500
gggcacgtcg cccgctgagc tgagtggcca gccagtgcca ttccactcca ctcaggttct   1560
tcagggccag agccctgca ccctgtttgg gctggtgagc tgggagttca ggtgggctgc    1620
tcacagcctc cttcagaggc cccaccaatt tctcggacac ttctcagtgt gtggaagctc   1680
atgtgggccc ctgagggctc atgcctggga agtgttgtgg tgggggctcc caggaggact   1740
ggcccagaga gccctgagat agcggggatc ctgaactgga ctgaataaaa cgtggtctcc   1800
cactgcgcca aaaaaaaaaa aaaaaa                                        1826

<210> SEQ ID NO 7
<211> LENGTH: 2500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
ggaggacact tctcagaagg ggttgttttg cttttgctta tttccgtcca tttccctctc     60
tgcgcgcgga ccttcctttt ccagatggtg agagccgcgg ggacacccga cgccggggca    120
ggctgatcca cgatcctggg tgtgcgtaac gccgcctggg gctccgtggg cgagggacgt    180
gtggggacag gtgcaccgga aactgccaga ctggagagtt gaggcatcgg aggcgcgaga    240
acagcactac tactgcggcg agacgagcgc ggcgcatccc aaagcccggc caaatgcgct    300
cgtccctggg aggggaggga ggcgcgcctg gagcggggac agtcttggtc cgcgccctcc    360
tcccgggtct gtgccgggac ccgggacccg ggagccgtcg caggtctcgg tccaaggggc    420
cccttttctc ggaagggcgg cggccaagag cagggaaggt ggatctcagg tagcgagtct    480
gggcttcggg gacggcgggg aggggagccg gacgggagga tgagctcccc tggcaccgag    540
agcgcgggaa agagcctgca gtaccgagtg gaccacctgc tgagcgccgt ggagaatgag    600
ctgcaggcgg gcagcgagaa gggcgacccc acagagcgcg aactgcgcgt gggcctggag    660
gagagcgagc tgtggctgcg cttcaaggag ctcaccaatg agatgatcgt gaccaagaac    720
```

```
ggcaggagga tgtttccggt gctgaaggtg aacgtgtctg gcctggaccc caacgccatg    780
tactccttcc tgctggactt cgtggcggcg gacaaccacc gctggaagta cgtgaacggg    840
gaatgggtgc cgggggggcaa gccggagccg caggcgccca gctgcgtcta catccacccc    900
gactcgccca acttcggggc ccactggatg aaggctcccg tctccttcag caaagtcaag    960
ctcaccaaca agctcaacgg agggggccag atcatgctga actccttgca taagtatgag   1020
cctcgaatcc acatagtgag agttgggggt ccacagcgca tgatcaccag ccactgcttc   1080
cctgagaccc agttcatagc ggtgactgct tatcagaacg aggagatcac agctcttaaa   1140
attaagtaca atccatttgc aaaagctttc cttgatgcaa aggaaagaag tgatcacaaa   1200
gagatgatgg aggaacccgg agacagccag caacctgggt actcccaatg ggggtggctt   1260
cttcctggaa ccagcaccct gtgtccacct gcaaatcctc atcctcagtt tggaggtgcc   1320
ctctccctcc cctccacgca cagctgtgac aggtacccaa ccctgaggag ccaccggtcc   1380 tcacctacc ccagccccta tgctcatcgg aacaattctc caacctattc tgacaactca   1440
cctgcatgtt tatccatgct gcaatcccat gacaattggt ccagccttgg aatgcctgcc   1500
catcccagca tgctccccgt gagccacaat gccagcccac ctaccagctc cagtcagtac   1560
cccagcctgt ggtctgtgag caacggcgcc gtcaccccgg ctcccaggc agcagccgtg    1620 tccaacgggc tgggggccca gttcttccgg ggctcccccg cgcactacac acccctcacc   1680
catccggtct cggcgccctc ttcctcggga tccccactgt acgaagggggc ggccgcggcc   1740 acagacatcg tggacagcca gtacgacgcc gcagcccaag gccgcctcat agcctcatgg   1800
acacctgtgt cgccaccttc catgtgaagc agcaaggccc aggtcccgaa agatgcagtg   1860 acttttttgtc gtggcagcca gtggtgactg gattgaccta ctaggtaccc agtggcagtc   1920
tcaggttaag aaggaaatgc agcctcagta acttcctttt caaagcagtg gaggagcaca   1980 cggcacctttt ccccagagcc ccagcatccc ttgctcacac ctgcagtagc ggtgctgtcc   2040
caggtggctt acagatgaac ccaactgtgg agatgatgca gttggcccaa cctcactgac   2100
ggtgaaaaaa tgtttgccag ggtccagaaa ctttttttgg tttatttctc atacagtgta   2160
ttggcaactt tggcacacca gaatttgtaa actccaccag tcctactta gtgagataaa    2220 aagcacactc ttaatcttct tccttgttgc tttcaagtag ttagagttga gctgttaagg   2280
acagaataaa atcatagttg aggacagcag gttttagttg aattgaaaat ttgactgctc   2340 tgcccctag aatgtgtgta ttttaagcat atgtagctaa tctcttgtgt tgttaaacta    2400
taactgtttc atattttct tttgacaaag tagccaaaga caatcagcag aaagcatttt    2460
ctgcaaaata aacgcaatat gcaaaaaaaa aaaaaaaaa                         2500
```

<210> SEQ ID NO 8
<211> LENGTH: 1251
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
tctagagcca ccatgagctc ccctggcacc gagagcgcgg gaaagagcct gcagtaccga    60
gtggaccacc tgctgagcgc cgtggagaat gagctgcagg cgggcagcga aagggcgac    120 cccacagagc gcgaactgcg cgtgggcctg gaggagagcg agctgtggct gcgcttcaag   180
gagctcacca atgagatgat cgtgaccaag aacggcagga ggatgtttcc ggtgctgaag    240
```

```
gtgaacgtgt ctggcctgga ccccaacgcc atgtactcct tcctgctgga cttcgtggcg    300
gcggacaacc accgctggaa gtacgtgaac ggggaatggg tgccggggggg caagccggag    360 ccgcaggcgc ccagctgcgt ctacatccac cccgactcgc ccaacttcgg ggcccactgg    420
atgaaggctc ccgtctcctt cagcaaagtc aagctcacca acaagctcaa cggagggggc    480
cagatcatgc tgaactcctt gcataagtat gagcctcgaa tccacatagt gagagttggg    540
ggtccacagc gcatgatcac cagccactgc ttccctgaga cccagttcat agcggtgact    600
gctagaagtg atcacaaaga gatgatggag gaacccggag acagccagca acctgggtac    660
tcccaatggg ggtggcttct tcctggaacc agcaccgtgt gtccacctgc aaatcctcat    720
cctcagtttg gaggtgccct ctccctcccc tccacgcaca gctgtgacag gtacccaacc    780
ctgaggagcc accggtcctc accctacccc agccccatatg ctcatcggaa caattctcca    840
acctattctg acaactcacc tgcatgttta tccatgctgc aatcccatga caattggtcc    900
agccttggaa tgcctgccca tcccagcatg ctccccgtga ccacaatgc cagcccacct    960 accagctcca gtcagtaccc cagcctgtgg tctgtgagca acggcgccgt caccccgggc   1020
tcccaggcag cagccgtgtc caacgggctg ggggcccagt tcttccgggg ctcccccgcg   1080
cactacacac ccctcaccca tccggtctcg gcgccctctt cctcgggatc cccactgtac   1140 gaagggggcgg ccgcggccac agacatcgtg gacagccagt acgacgccgc agcccaaggc   1200
cgcctcatag cctcatggac acctgtgtcg ccaccttcca tgtgagatat c           1251
```

<210> SEQ ID NO 9
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Leu Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Tyr Leu Asp Thr
    130                 135                 140

Arg Pro Ala Pro Val Tyr Leu Ala Pro Ala His Gly Val Thr Ser
145                 150                 155                 160

Ala Pro Asp Asn Arg Pro Ala Leu Gly Ser Thr Ala Pro Pro Val His
                165                 170                 175

Asn Val Thr Ser Ala Ser Gly Ser Ala Ser Gly Ser Ala Ser Thr Leu

```
            180                 185                 190
Val His Asn Gly Thr Ser Ala Arg Ala Thr Thr Pro Ala Ser Lys
            195                 200                 205
Ser Thr Pro Phe Ser Ile Pro Ser His His Ser Asp Thr Pro Thr
            210                 215                 220
Leu Ala Ser His Ser Thr Lys Thr Asp Ala Ser Ser Thr His His Ser
225                 230                 235                 240
Thr Val Pro Pro Leu Thr Ser Ser Asn His Ser Thr Ser Pro Gln Leu
                    245                 250                 255
Ser Thr Gly Val Ser Phe Phe Leu Ser Phe His Ile Ser Asn Leu
                260                 265                 270
Gln Phe Asn Ser Ser Leu Glu Asp Pro Ser Thr Asp Tyr Tyr Gln Glu
                275                 280                 285
Leu Gln Arg Asp Ile Ser Glu Met Phe Leu Gln Ile Tyr Lys Gln Gly
                290                 295                 300
Gly Phe Leu Gly Leu Ser Asn Ile Lys Phe Arg Pro Gly Ser Val Val
305                 310                 315                 320
Val Gln Leu Thr Leu Ala Phe Arg Glu Gly Thr Ile Asn Val His Asp
                325                 330                 335
Val Glu Thr Gln Phe Asn Gln Tyr Lys Thr Glu Ala Ala Ser Arg Tyr
                340                 345                 350
Asn Leu Thr Ile Ser Asp Val Ser Val Ser Asp Val Pro Phe Pro Phe
                355                 360                 365
Ser Ala Gln Ser Gly Ala Gly Val Pro Gly Trp Gly Ile Ala Leu Leu
                370                 375                 380
Val Leu Val Cys Val Leu Val Tyr Leu Ala Ile Val Tyr Leu Ile Ala
385                 390                 395                 400
Leu Ala Val Ala Gln Val Arg Arg Lys Asn Tyr Gly Gln Leu Asp Ile
                405                 410                 415
Phe Pro Ala Arg Asp Lys Tyr His Pro Met Ser Glu Tyr Ala Leu Tyr
                420                 425                 430
His Thr His Gly Arg Tyr Val Pro Pro Ser Ser Leu Phe Arg Ser Pro
                435                 440                 445
Tyr Glu Lys Val Ser Ala Gly Asn Gly Gly Ser Tyr Leu Ser Tyr Thr
                450                 455                 460
Asn Pro Ala Val Ala Ala Ala Ser Ala Asn Leu
465                 470                 475

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Leu Ser Gly Ala Asp Leu Asn Leu
1               5

<210> SEQ ID NO 11
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (8)..(8)
<223> OTHER INFORMATION: a, c, t, g, unknown or other
<220> FEATURE:
<221> NAME/KEY: misc_feature
<222> LOCATION: (8)..(8)
<223> OTHER INFORMATION: n is a, c, g, or t

<400> SEQUENCE: 11 tctctccna                                                                 9

<210> SEQ ID NO 12
<211> LENGTH: 2109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
```

| | | | | | |
|---|---|---|---|---|---|
| atggagtctc | cctcggcccc | tccccacaga | tggtgcatcc | cctggcagag | gctcctgctc | 60 |
| acagcctcac | ttctaacctt | ctggaacccg | cccaccactg | ccaagctcac | tattgaatcc | 120 |
| acgccgttca | atgtcgcaga | ggggaaggag | gtgcttctac | ttgtccacaa | tctgccccag | 180 |
| catcttttg | gctacagctg | gtacaaaggt | gaaagagtgg | atggcaaccg | tcaaattata | 240 |
| ggatatgtaa | taggaactca | acaagctacc | ccagggcccg | catacagtgg | tcgagagata | 300 |
| atataccccca | atgcatccct | gctgatccag | aacatcatcc | agaatgacac | aggattctac | 360 |
| accctacacg | tcataaagtc | agatcttgtg | aatgaagaag | caactggcca | gttccgggta | 420 |
| tacccggagc | tgcccaagcc | ctccatctcc | agcaacaact | ccaaacccgt | ggaggacaag | 480 |
| gatgctgtgg | ccttcacctg | tgaacctgag | actcaggacg | caacctacct | gtggtgggta | 540 |
| aacaatcaga | gcctcccggt | cagtcccagg | ctgcagctgt | ccaatggcaa | caggaccctc | 600 |
| actctattca | atgtcacaag | aaatgacaca | gcaagctaca | aatgtgaaac | ccagaaccca | 660 |
| gtgagtgcca | ggcgcagtga | ttcagtcatc | ctgaatgtcc | tctatggccc | ggatgccccc | 720 |
| accatttccc | ctctaaacac | atcttacaga | tcaggggaaa | atctgaacct | ctcctgccac | 780 |
| gcagcctcta | acccacctgc | acagtactct | tggtttgtca | atgggacttt | ccagcaatcc | 840 |
| acccaagagc | tctttatccc | caacatcact | gtgaataata | gtggatccta | tacgtgccaa | 900 |
| gcccataact | cagacactgg | cctcaatagg | accacagtca | cgacgatcac | agtctatgca | 960 |
| gagccaccca | aacccttcat | caccagcaac | aactccaacc | ccgtggagga | tgaggatgct | 1020 |
| gtagccttaa | cctgtgaacc | tgagattcag | aacacaacct | acctgtggtg | ggtaaataat | 1080 |
| cagagcctcc | cggtcagtcc | caggctgcag | ctgtccaatg | acaacaggac | cctcactcta | 1140 |
| ctcagtgtca | caaggaatga | tgtaggaccc | tatgagtgtg | gaatccagaa | cgaattaagt | 1200 |
| gttgaccaca | gcgacccagt | catcctgaat | gtcctctatg | gcccagacga | ccccaccatt | 1260 |
| tcccccctcat | acacctatta | ccgtccaggg | gtgaacctca | gcctctcctg | ccatgcagcc | 1320 |
| tctaacccac | ctgcacagta | ttcttggctg | attgatggga | acatccagca | acacacacaa | 1380 |
| gagctctttta | tctccaacat | cactgagaag | aacagcggac | tctataccctg | ccaggccaat | 1440 |
| aactcagcca | gtggccacag | caggactaca | gtcaagacaa | tcacagtctc | tgcggagctg | 1500 |
| cccaagccct | ccatctccag | caacaactcc | aaacccgtgg | aggacaagga | tgctgtggcc | 1560 |
| ttcacctgtg | aacctgaggc | tcagaacaca | acctacctgt | ggtgggtaaa | tggtcagagc | 1620 |
| ctcccagtca | gtcccaggct | gcagctgtcc | aatggcaaca | ggaccctcac | tctattcaat | 1680 |

-continued

```
gtcacaagaa atgacgcaag agcctatgta tgtggaatcc agaactcagt gagtgcaaac    1740
cgcagtgacc cagtcaccct ggatgtcctc tatgggccgg acacccccat catttccccc    1800
ccagactcgt cttacctttc gggagcggac ctcaacctct cctgccactc ggcctctaac    1860
ccatccccgc agtattcttg gcgtatcaat gggataccgc agcaacacac acaagttctc    1920
tttatcgcca aaatcacgcc aaataataac gggacctatg cctgttttgt ctctaacttg    1980
gctactggcc gcaataattc catagtcaag agcatcacag tctctgcatc tggaacttct    2040
cctggtctct cagctggggc cactgtcggc atcatgattg gagtgctggt tggggttgct    2100
ctgatatag                                                            2109
```

<210> SEQ ID NO 13
<211> LENGTH: 702
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
```

```
            275                 280                 285
Ile Thr Val Asn Asn Ser Gly Ser Tyr Thr Cys Gln Ala His Asn Ser
290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
                340                 345                 350

Thr Tyr Leu Trp Trp Val Asn Asn Gln Ser Leu Pro Val Ser Pro Arg
                355                 360                 365

Leu Gln Leu Ser Asn Asp Asn Arg Thr Leu Thr Leu Leu Ser Val Thr
370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
                420                 425                 430

Leu Ser Leu Ser Cys His Ala Ala Ser Asn Pro Pro Ala Gln Tyr Ser
                435                 440                 445

Trp Leu Ile Asp Gly Asn Ile Gln Gln His Thr Gln Glu Leu Phe Ile
450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
                500                 505                 510

Val Glu Asp Lys Asp Ala Val Ala Phe Thr Cys Glu Pro Glu Ala Gln
                515                 520                 525

Asn Thr Thr Tyr Leu Trp Trp Val Asn Gly Gln Ser Leu Pro Val Ser
                530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
                580                 585                 590

Pro Asp Thr Pro Ile Ile Ser Pro Pro Asp Ser Ser Tyr Leu Ser Gly
                595                 600                 605

Ala Asp Leu Asn Leu Ser Cys His Ser Ala Ser Asn Pro Ser Pro Gln
                610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Gly Thr Tyr Ala Cys Phe
                645                 650                 655

Val Ser Asn Leu Ala Thr Gly Arg Asn Asn Ser Ile Val Lys Ser Ile
                660                 665                 670

Thr Val Ser Ala Ser Gly Thr Ser Pro Gly Leu Ser Ala Gly Ala Thr
                675                 680                 685

Val Gly Ile Met Ile Gly Val Leu Val Gly Val Ala Leu Ile
                690                 695                 700
```

<210> SEQ ID NO 14
<211> LENGTH: 32040
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

| | | | | | |
|---|---|---|---|---|---|
| catcatcaat | aatatacctt | attttggatt | gaagccaata | tgataatgag | ggggtggagt | 60 |
| ttgtgacgtg | gcgcggggcg | tgggaacggg | gcgggtgacg | tagtagtgtg | gcggaagtgt | 120 |
| gatgttgcaa | gtgtggcgga | acacatgtaa | gcgacggatg | tggcaaaagt | gacgttttg | 180 |
| gtgtgcgccg | gtgtacacag | gaagtgacaa | ttttcgcgcg | gttttaggcg | gatgttgtag | 240 |
| taaatttggg | cgtaaccgag | taagatttgg | ccattttcgc | gggaaaactg | aataagagga | 300 |
| agtgaaatct | gaataatttt | gtgttactca | tagcgcgtaa | tactgtaata | gtaatcaatt | 360 |
| acggggtcat | tagttcatag | cccatatatg | gagttccgcg | ttacataact | tacggtaaat | 420 |
| ggcccgcctg | gctgaccgcc | caacgacccc | cgcccattga | cgtcaataat | gacgtatgtt | 480 |
| cccatagtaa | cgccaatagg | gactttccat | tgacgtcaat | gggtggagta | tttacggtaa | 540 |
| actgcccact | tggcagtaca | tcaagtgtat | catatgccaa | gtacgccccc | tattgacgtc | 600 |
| aatgacggta | aatggcccgc | ctggcattat | gcccagtaca | tgaccttatg | ggactttcct | 660 |
| acttggcagt | acatctacgt | attagtcatc | gctattacca | tggtgatgcg | gttttggcag | 720 |
| tacatcaatg | ggcgtggata | gcggtttgac | tcacggggat | ttccaagtct | ccaccccatt | 780 |
| gacgtcaatg | ggagtttgtt | ttggcaccaa | aatcaacggg | actttccaaa | atgtcgtaac | 840 |
| aactccgccc | cattgacgca | aatgggcggt | aggcgtgtac | ggtgggaggt | ctatataagc | 900 |
| agagctggtt | tagtgaaccg | tcagatccgc | tagagatctg | gtaccgtcga | cgcggccgct | 960 |
| cgagcctaag | cttctagatg | catgctcgag | cggccgccag | tgtgatggat | atctgcagaa | 1020 |
| ttcgcccttg | ctcgctccac | ctctcaagca | gccagcgcct | gcctgaatct | gttctgcccc | 1080 |
| ctccccaccc | atttcaccac | caccatgaca | ccgggcaccc | agtctccttt | cttcctgctg | 1140 |
| ctgctcctca | cagtgcttac | agttgttacg | ggttctggtc | atgcaagctc | taccccaggt | 1200 |
| ggagaaaagg | agacttcggc | tacccagaga | agttcagtgc | ccagctctac | tgagaagaat | 1260 |
| gctgtgagta | tgaccagcag | cgtactctcc | agccacagcc | ccggttcagg | ctcctccacc | 1320 |
| actcagggac | aggatgtcac | tctggcccg | gccacggaac | cagcttcagg | ttcagctgcc | 1380 |
| cttttgggac | aggatgtcac | ctcggtccca | gtcaccaggc | cagccctggg | ctccaccacc | 1440 |
| ccgccagccc | acgatgtcac | ctcagcccg | gacaacaagc | cagccccggg | ctccaccgcc | 1500 |
| cccccagccc | acggtgtcac | ctcgtatctt | gacaccaggc | cggcccggt | ttatcttgcc | 1560 |
| cccccagccc | atggtgtcac | ctcggccccg | gacaacaggc | ccgccttggg | ctccaccgcc | 1620 |
| cctccagtcc | acaatgtcac | ctcggcctca | ggctctgcat | caggctcagc | ttctactctg | 1680 |
| gtgcacaacg | gcacctctgc | cagggctacc | acaaccccag | ccagcaagag | cactccattc | 1740 |
| tcaattccca | gccaccactc | tgatactcct | accacccttg | ccagccatag | caccaagact | 1800 |
| gatgccagta | gcactcacca | tagcacggta | cctcctctca | cctcctccaa | tcacagcact | 1860 |
| tctccccagt | tgtctactgg | ggtctctttc | tttttcctgt | cttttcacat | ttcaaacctc | 1920 |
| cagtttaatt | cctctctgga | agatcccagc | accgactact | accaagagct | gcagagagac | 1980 |
| atttctgaaa | tgttttttgca | gatttataaa | caagggggtt | ttctgggcct | ctccaatatt | 2040 |

```
aagttcaggc caggatctgt ggtggtacaa ttgactctgg ccttccgaga aggtaccatc    2100
aatgtccacg acgtggagac acagttcaat cagtataaaa cggaagcagc ctctcgatat    2160
aacctgacga tctcagacgt cagcgtgagt gatgtgccat ttcctttctc tgcccagtct    2220
ggggctgggg tgccaggctg gggcatcgcg ctgctggtgc tggtctgtgt tctggtttat    2280
ctggccattg tctatctcat tgccttggct gtcgctcagg ttcgccgaaa gaactacggg    2340
cagctggaca tcttttccagc ccgggataaa taccatccta tgagcgagta cgctcttttac   2400 cacacccatg ggcgctatgt gcccctagc agtcttttcc gtagccccta tgagaaggtt    2460
tctgcaggta atggtggcag ctatctctct tacacaaacc cagcagtggc agccgcttct    2520
gccaacttgt aggggcacgt cgcccgctga gctgagtggc cagccagtgc cattccactc    2580
cactcaggtt cttcagggcc agagcccctg caccctgttt gggctggtga gctgggagtt    2640
caggtgggct gctcacagcc tccttcagag gccccaccaa tttctcggac acttctcagt    2700
gtgtggaagc tcatgtgggc ccctgagggc tcatgcctgg gaagtgttgt ggtgggggct    2760
cccaggagga ctgcccaga gagccctgag atagcgggga tcctgaactg gactgaataa    2820
aacgtggtct cccactgcgc caaaaaaaaa aaaaaaacg atccaccgga tctagataac    2880
tgatcataat cagccatacc acatttgtag aggttttact tgctttaaaa aacctcccac    2940
acctccccct gaacctgaaa cataaaatga atgcaattgt tgttgttaac ttgtttattg    3000
cagcttataa tggttacaaa taaagcaata gcatcacaaa tttcacaaat aaagcatttt    3060
tttcactgca ttctagttgt ggtttgtcca aactcatcaa tgtatcttaa cgcggatctg    3120
gaaggtgctg aggtacgatg agacccgcac caggtgcaga ccctgcgagt gtggcggtaa    3180
acatattagg aaccagcctg tgatgctgga tgtgaccgag gagctgaggc ccgatcactt    3240
ggtgctggcc tgcacccgcg ctgagtttgg ctctagcgat gaagatacag attgaggtac    3300
tgaaatgtgt gggcgtggct taagggtggg aaagaatata taaggtgggg gtcttatgta    3360
gttttgtatc tgttttgcag cagccgccgc cgccatgagc accaactcgt ttgatggaag    3420
cattgtgagc tcatatttga caacgcgcat gccccatgg gccggggtgc gtcagaatgt    3480
gatgggctcc agcattgatg gtcgccccgt cctgcccgca aactctacta ccttgaccta    3540
cgagaccgtg tctggaacgc cgttggagac tgcagcctcc gccgccgctt cagccgctgc    3600
agccaccgcc cgcgggattg tgactgactt tgctttcctg agcccgcttg caagcagtgc    3660
agcttcccgt tcatccgccc gcgatgacaa gttgacggct cttttggcac aattggattc    3720
tttgaccccg gaacttaatg tcgtttctca gcagctgttg gatctgcgcc agcaggtttc    3780
tgccctgaag gcttcctccc ctcccaatgc ggtttaaaac ataaataaaa aaccagactc    3840
tgtttggatt tggatcaagc aagtgtcttg ctgtctttat ttaggggttt tgcgcgcgcg    3900
gtaggcccgg gaccagcggt ctcggtcgtt gagggtcctg tgtattttt ccaggacgtg    3960 gtaaaggtga ctctggatgt tcagatacat gggcataagc ccgtctctgg ggtggaggta    4020
gcaccactgc agagcttcat gctgcgggt ggtgttgtag atgatccagt cgtagcagga    4080
gcgctgggcg tggtgcctaa aaatgtcttt cagtagcaag ctgattgcca ggggcaggcc    4140
cttggtgtaa gtgtttacaa agcggttaag ctggatgggg tgcatacgtg gggatatgag    4200
atgcatcttg gactgtattt ttaggttggc tatgttccca gccatatccc tccggggatt    4260
catgttgtgc agaaccacca gcacagtgta tccggtgcac ttgggaaatt tgtcatgtag    4320
cttagaagga aatgcgtgga agaacttgga gacgcccttg tgacctccaa gatttttccat    4380
```

```
gcattcgtcc ataatgatgg caatgggccc acgggcggcg gcctgggcga agatatttct    4440
gggatcacta acgtcatagt tgtgttccag gatgagatcg tcataggcca ttttttacaaa    4500 gcgcgggcgg agggtgccag actgcggtat aatggttcca tccggcccag gggcgtagtt    4560
accctcacag atttgcattt cccacgcttt gagttcagat gggggatca tgtctacctg    4620 cggggcgatg aagaaaacgg tttccggggt aggggagatc agctgggaag aaagcaggtt    4680
cctgagcagc tgcgacttac cgcagccggt gggcccgtaa atcacaccta ttaccggctg    4740
caactggtag ttaagagagc tgcagctgcc gtcatccctg agcaggggg ccacttcgtt    4800 aagcatgtcc ctgactcgca tgttttccct gaccaaatcc gccagaaggc gctcgccgcc    4860
cagcgatagc agttcttgca aggaagcaaa gttttttcaac ggtttgagac cgtccgccgt    4920
aggcatgctt ttgagcgttt gaccaagcag ttccaggcgg tcccacagct cggtcacctg    4980
ctctacggca tctcgatcca gcatatctcc tcgtttcgcg ggttgggcg gctttcgctg    5040 tacggcagta gtcggtgctc gtccagacgg gccaggtca tgtctttcca cgggcgcagg    5100
gtcctcgtca gcgtagtctg ggtcacgtg aaggggtgcg ctccgggctg cgcgctggcc    5160
agggtgcgct tgaggctggt cctgctggtg ctgaagcgct gccggtcttc gccctgcgcg    5220
tcggccaggt agcatttgac catggtgtca tagtccagcc cctccgcggc gtggcccttg    5280
gcgcgcagct tgcccttgga ggaggcgccg cacgaggggc agtgcagact tttgagggcg    5340
tagagcttgg gcgcgagaaa taccgattcc ggggagtagg catccgcgcc gcaggccccg    5400
cagacggtct cgcattccac gagccaggtg agctctggcc gttcggggtc aaaaaccagg    5460
tttcccccat gcttttttgat gcgtttctta cctctggttt ccatgagccg gtgtccacgc    5520
tcggtgacga aaaggctgtc cgtgtccccg tatacagact tgagaggcct gtcctcgagc    5580
ggtgttccgc ggtcctcctc gtatagaaac tcggaccact ctgagacaaa ggctcgcgtc    5640
caggccagca cgaaggaggc taagtgggag gggtagcggt cgttgtccac tagggggtcc    5700
actcgctcca gggtgtgaag acacatgtcg ccctcttcgg catcaaggaa ggtgattggt    5760
ttgtaggtgt aggccacgtg accgggtgtt cctgaagggg ggctataaaa gggggtgggg    5820
gcgcgttcgt cctcactctc ttccgcatcg ctgtctgcga gggccagctg ttggggtgag    5880
tactccctct gaaaagcggg catgacttct gcgctaagat tgtcagtttc caaaaacgag    5940
gaggatttga tattcacctg gcccgcgtg atgcctttga gggtggccgc atccatctgg    6000
tcagaaaaga caatcttttt gttgtcaagc ttggtggcaa acgacccgta gagggcgttg    6060
gacagcaact tggcgatgga gcgcagggtt tggtttttgt cgcgatcggc gcgctccttg    6120
gccgcgatgt ttagctgcac gtattcgcgc gcaacgcacc gccattcggg aaagacggtg    6180
gtgcgctcgt cgggcaccag gtgcacgcgc caaccgcggt tgtgcagggt gacaaggtca    6240
acgctggtgg ctacctctcc gcgtaggcgc tcgttggtcc agcagaggcg gccgcccttg    6300
cgcgagcaga atggcggtag ggggtctagc tgcgtctcgt ccgggggtc tgcgtccacg    6360 gtaaagaccc cgggcagcag gcgcgcgtcg aagtagtcta tcttgcatcc ttgcaagtct    6420
agcgcctgct gccatgcgcg ggcggcaagc gcgcgctcgt atgggttgag tgggggaccc    6480
catggcatgg ggtgggtgag cgcggaggcg tacatgccgc aaatgtcgta acgtagagg    6540 ggctctctga gtattccaag atatgtaggg tagcatcttc caccgcggat gctggcgcgc    6600
acgtaatcgt atagttcgtg cgagggagcg aggaggtcgg gaccgaggtt gctacgggcg    6660
ggctgctctg ctcggaagac tatctgcctg aagatggcat gtgagttgga tgatatggtt    6720
ggacgctgga agacgttgaa gctggcgtct gtgagaccta ccgcgtcacg cacgaaggag    6780
```

```
gcgtaggagt cgcgcagctt gttgaccagc tcggcggtga cctgcacgtc tagggcgcag    6840
tagtccaggg tttccttgat gatgtcatac ttatcctgtc ccttttttt ccacagctcg    6900 cggttgagga caaactcttc gcggtctttc cagtactctt ggatcggaaa cccgtcggcc    6960
tccgaacggt aagagcctag catgtagaac tggttgacgg cctggtaggc gcagcatccc    7020
ttttctacgg gtagcgcgta tgcctgcgcg gccttccggc atgaccagca tgaagggcac    7080
gagctgcttc ccaaaggccc ccatccaagt ataggtctct acatcgtagg tgacaaagag    7140
acgctcggtg cgaggatgcg agccgatcgg gaagaactgg atctcccgcc accaattgga    7200
ggagtggcta ttgatgtggt gaaagtagaa gtccctgcga cgggccgaac actcgtgctg    7260
gcttttgtaa aaacgtgcgc agtactggca gcggtgcacg ggctgtacat cctgcacgag    7320
gttgacctga cgaccgcgca caaggaagca gagtgggaat ttgagcccct cgcctggcgg    7380
gtttggctgg tggtcttcta cttcggctgc ttgtccttga ccgtctggct gctcgagggg    7440
agttacggtg gatcggacca ccacgccgcg cgagcccaaa gtccagatgt ccgcgcgcgg    7500
cggtcggagc ttgatgacaa catcgcgcag atgggagctg tccatggtct ggagctcccg    7560
cggcgtcagg tcaggcggga gctcctgcag gtttacctcg catagacggg tcagggcgcg    7620
ggctagatcc aggtgatacc taatttccag gggctggttg gtggcggcgt cgatggcttg    7680
caagaggccg catccccgcg gcgcgactac ggtaccgcgc ggcgggcggt gggccgcggg    7740
ggtgtccttg gatgatgcat ctaaaagcgg tgacgcgggc gagcccccgg aggtagggg    7800 ggctccggac ccgccgggag aggggcagg ggcacgtcgg cgccgcgcgc gggcaggagc    7860
tggtgctgcg cgcgtaggtt gctggcgaac gcgacgacgc ggcggttgat ctcctgaatc    7920
tggcgcctct gcgtgaagac gacgggcccg gtgagcttga acctgaaaga gagttcgaca    7980
gaatcaattt cggtgtcgtt gacggcggcc tggcgcaaaa tctcctgcac gtctcctgag    8040
ttgtcttgat aggcgatctc ggccatgaac tgctcgatct cttcctcctg gagatctccg    8100
cgtccggctc gctccacggt ggcggcgagg tcgttggaaa tgcgggccat gagctgcgag    8160
aaggcgttga ggcctccctc gttccagacg cggctgtaga ccacgccccc ttcggcatcg    8220
cgggcgcgca tgaccacctg cgcgagattg agctccacgt gccgggcgaa gacggcgtag    8280
tttcgcaggc gctgaaagag gtagttgagg gtggtggcgg tgtgttctgc cacgaagaag    8340
tacataaccc agcgtcgcaa cgtggattcg ttgataattg ttgtgtaggt actccgccgc    8400
cgagggacct gagcgagtcc gcatcgaccg gatcggaaaa cctctcgaga aaggcgtcta    8460
accagtcaca gtcgcaaggt aggctgagca ccgtggcggg cggcagcggg cggcggtcgg    8520
ggttgtttct ggcggaggtg ctgctgatga tgtaattaaa gtaggcggtc ttgagacggc    8580
ggatggtcga cagaagcacc atgtccttgg gtccggcctg ctgaatgcgc aggcggtcgg    8640
ccatgcccca ggcttcgttt tgacatcggc gcaggtcttt gtagtagtct tgcatgagcc    8700
tttctaccgg cacttcttct tctccttcct cttgtcctgc atctcttgca tctatcgctg    8760
cggcggcggc ggagtttggc cgtaggtggc gccctcttcc tcccatgcgt gtgacccga    8820 agcccctcat cggctgaagc agggctaggt cggcgacaac gcgctcggct aatatggcct    8880
gctgcacctg cgtgagggta gactggaagt catccatgtc cacaaagcgg tggtatgcgc    8940
ccgtgttgat ggtgtaagtg cagttggcca taacggacca gttaacggtc tggtgacccg    9000
gctgcgagag ctcggtgtac ctgagacgcg agtaagccct cgagtcaaat acgtagtcgt    9060
tgcaagtccg caccaggtac tggtatccca ccaaaaagtg cggcggcggc tggcggtaga    9120
```

-continued

```
ggggccagcg tagggtggcc ggggctccgg ggcgagatc ttccaacata aggcgatgat    9180
atccgtagat gtacctggac atccaggtga tgccggcggc ggtggtggag gcgcgcggaa    9240
agtcgcggac gcggttccag atgttgcgca gcggcaaaaa gtgctccatg gtcgggacgc    9300
tctggccggt caggcgcgcg caatcgttga cgctctagcg tgcaaaagga gagcctgtaa    9360
gcgggcactc ttccgtggtc tggtggataa attcgcaagg gtatcatggc ggacgaccgg    9420
ggttcgagcc ccgtatccgg ccgtccgccg tgatccatgc ggttaccgcc cgcgtgtcga    9480
acccaggtgt gcgacgtcag acaacggggg agtgctcctt ttggcttcct tccaggcgcg    9540
gcggctgctg cgctagcttt tttggccact ggccgcgcgc agcgtaagcg gttaggctgg    9600
aaagcgaaag cattaagtgg ctcgctccct gtagccggag ggttattttc caagggttga    9660
gtcgcgggac ccccggttcg agtctcggac cggccggact gcggcgaacg ggggtttgcc    9720
tccccgtcat gcaagacccc gcttgcaaat tcctccggaa acagggacga gcccctttt    9780
tgcttttccc agatgcatcc ggtgctgcgg cagatgcgcc ccctcctca gcagcggcaa    9840
gagcaagagc agcggcagac atgcagggca ccctccccctc ctcctaccgc gtcaggaggg    9900
gcgacatccg cggttgacgc ggcagcagat ggtgattacg aaccccgcg gcgccgggcc    9960
cggcactacc tggacttgga ggagggcgag ggcctggcgc ggctaggagc gccctctcct   10020
gagcggcacc caagggtgca gctgaagcgt gatacgcgtg aggcgtacgt gccgcggcag   10080
aacctgtttc gcgaccgcga gggagaggag cccgaggaga tgcgggatcg aaagttccac   10140
gcagggcgcg agctgcggca tggcctgaat cgcgagcggt tgctgcgcga ggaggacttt   10200
gagcccgacg cgcgaaccgg gattagtccc gcgcgcgcac acgtggcggc cgccgacctg   10260
gtaaccgcat acgagcagac ggtgaaccag gagattaact ttcaaaaaag ctttaacaac   10320
cacgtgcgta cgcttgtggc gcgcgaggag gtggctatag gactgatgca tctgtgggac   10380
tttgtaagcg cgctggagca aaacccaaat agcaagccgc tcatggcgca gctgttcctt   10440
atagtgcagc acagcaggga caacgaggca ttcagggatg cgctgctaaa catagtagag   10500
cccgagggcc gctggctgct cgatttgata aacatcctgc agagcatagt ggtgcaggag   10560
cgcagcttga gcctggctga caaggtggcc gccatcaact attccatgct tagcctgggc   10620
aagtttttacg cccgcaagat ataccatacc ccttacgttc ccatagacaa ggaggtaaag   10680
atcgaggggt tctacatgcg catggcgctg aaggtgctta ccttgagcga cgacctgggc   10740
gtttatcgca acgagcgcat ccacaaggcc gtgagcgtga gccggcggcg cgagctcagc   10800
gaccgcgagc tgatgcacag cctgcaaagg gccctggctg gcacgggcag cggcgataga   10860
gaggccgagt cctactttga cgcgggcgct gacctgcgct gggcccaag ccgacgcgcc   10920
ctggaggcag ctggggccgg acctgggctg gcggtggcac ccgcgcgcgc tgcaacgtc    10980
ggcggcgtgg aggaatatga cgaggacgat gagtacgagc cagaggacgg cgagtactaa   11040
gcggtgatgt ttctgatcag atgatgcaag acgcaacgga cccggcggtg cgggcggcgc   11100
tgcagagcca gccgtccggc cttaactcca cggacgactg cgccaggtc atggaccgca    11160
tcatgtcgct gactgcgcgc aatcctgacg cgttccggca gcagccgcag gccaaccggc   11220
tctccgcaat tctggaagcg gtggtccggg cgcgcgcaaa ccccacgcac gagaaggtgc   11280
tggcgatcgt aaacgcgctg gccgaaaaca gggccatccg gcccgacgag gccggcctgg   11340
tctacgacgc gctgcttcag cgcgtggctc gttacaacag cggcaacgtg cagaccaacc   11400
tggaccggct ggtgggggat gtgcgcgagg ccgtggcgca gcgtgagcgc gcgcagcagc   11460
agggcaacct gggctccatg gttgcactaa acgccttcct gagtacacag cccgccaacg   11520
```

```
tgccgcgggg acaggaggac tacaccaact ttgtgagcgc actgcggcta atggtgactg    11580
agacaccgca aagtgaggtg taccagtctg ggccagacta tttttttccag accagtagac    11640 aaggcctgca gaccgtaaac ctgagccagg ctttcaaaaa cttgcagggg ctgtgggggg    11700
tgcgggctcc cacaggcgac cgcgcgaccg tgtctagctt gctgacgccc aactcgcgcc    11760
tgttgctgct gctaatagcg cccttcacgg acagtggcag cgtgtcccgg gacacatacc    11820
taggtcactt gctgacactg taccgcgagg ccataggtca ggcgcatgtg gacgagcata    11880
ctttccagga gattacaagt gtcagccgcg cgctgggca ggaggacacg gcagcctgg    11940 aggcaaccct aaactacctg ctgaccaacc ggcggcagaa gatccctcg ttgcacagtt    12000 taaacagcga ggaggagcgc attttgcgct acgtgcagca gagcgtgagc cttaacctga    12060
tgcgcgacgg ggtaacgccc agcgtggcgc tggacatgac cgcgcgcaac atggaaccgg    12120
gcatgtatgc ctcaaaccgg ccgtttatca accgcctaat ggactacttg catcgcgcgg    12180
ccgccgtgaa ccccgagtat ttcaccaatg ccatcttgaa cccgcactgg ctaccgcccc    12240
ctggtttcta caccggggga ttcgaggtgc ccgagggtaa cgatggattc ctctgggacg    12300
acatagacga cagcgtgttt tccccgcaac cgcagaccct gctagagttg caacagcgcg    12360
agcaggcaga ggcggcgctg cgaaaggaaa gcttccgcag gccaagcagc ttgtccgatc    12420
taggcgctgc ggccccgcgg tcagatgcta gtagcccatt tccaagcttg ataggggtctc    12480 ttaccagcac tcgcaccacc cgcccgcgcc tgctgggcga ggaggagtac ctaaacaact    12540
cgctgctgca gccgcagcgc gaaaaaaacc tgcctccggc atttcccaac aacgggatag    12600
agagcctagt ggacaagatg agtagatgga agacgtacgc gcaggagcac agggacgtgc    12660
caggcccgcg cccgcccacc cgtcgtcaaa ggcacgaccg tcagcggggt ctggtgtggg    12720
aggacgatga ctcggcagac gacagcagcg tcctggattt ggggagggagt ggcaacccgt    12780 ttgcgcacct tcgccccagg ctggggagaa tgttttaaaa aaaaaaagc atgatgcaaa    12840 ataaaaaact caccaaggcc atggcaccga gcgttggttt tcttgtattc cccttagtat    12900
gcggcgcgcg gcgatgtatg aggaaggtcc tcctccctcc tacgagagtg tggtgagcgc    12960
ggcgccagtg gcggcggcgc tgggttctcc cttcgatgct ccctggacc cgccgtttgt    13020 gcctccgcgg tacctgcggc ctaccggggg gagaaacagc atccgttact ctgagttggc    13080 accctattc gacaccaccc gtgtgtacct ggtggacaac aagtcaacgg atgtggcatc    13140
cctgaactac cagaacgacc acagcaactt tctgaccacg gtcattcaaa acaatgacta    13200
cagcccgggg gaggcaagca cacagaccat caatcttgac gaccggtcgc actgggcgg    13260 cgacctgaaa accatcctgc ataccaacat gccaaatgtg aacgagttca tgtttaccaa    13320
taagtttaag gcgcgggtga tggtgtcgcg cttgcctact aaggacaatc aggtggagct    13380
gaaatacgag tgggtggagt tcacgctgcc cgagggcaac tactccgaga ccatgaccat    13440
agaccttatg aacaacgcga tcgtggagca ctacttgaaa gtgggcagac agaacgggtg    13500
tctggaaagc gacatcgggg taaagtttga cacccgcaac ttcagactgg ggtttgaccc    13560
cgtcactggt cttgtcatgc ctggggtata tacaaacgaa gccttccatc cagacatcat    13620
tttgctgcca ggatgcgggg tggacttcac ccacagccgc ctgagcaact tgttgggcat    13680
ccgcaagcgg caaccctttc aggagggctt taggatcacc tacgatgatc tggagggtgg    13740
taacattccc gcactgttgg atgtggacgc ctaccaggcg agcttgaaag atgacaccga    13800
acagggcggg ggtggcgcag gcggcagcaa cagcagtggc agcggcgcgg aagagaactc    13860
```

```
caacgcggca gccgcggcaa tgcagccggt ggaggacatg aacgatcatg ccattcgcgg   13920
cgacaccttt gccacacggg ctgaggagaa gcgcgctgag gccgaagcag cggccgaagc   13980
tgccgccccc gctgcgcaac ccgaggtcga gaagcctcag aagaaaccgg tgatcaaacc   14040
cctgacagag gacagcaaga aacgcagtta caacctaata agcaatgaca gcaccttcac   14100
ccagtaccgc agctggtacc ttgcatacaa ctacggcgac cctcagaccg gaatccgctc   14160
atggaccctg ctttgcactc ctgacgtaac ctgcggctcg gagcaggtct actggtcgtt   14220
gccagacatg atgcaagacc ccgtgacctt ccgctccacg cgccagatca gcaactttcc   14280
ggtggtgggc gccgagctgt tgcccgtgca ctccaagagc ttctacaacg accaggccgt   14340
ctactcccaa ctcatccgcc agtttacctc tctgacccac gtgttcaatc gctttcccga   14400
gaaccagatt ttggcgcgcc cgccagcccc caccatcacc accgtcagtg aaaacgttcc   14460
tgctctcaca gatcacggga cgctaccgct gcgcaacagc atcggaggag tccagcgagt   14520
gaccattact gacgccagac gccgcacctg cccctacgtt tacaaggccc tgggcatagt   14580
ctcgccgcgc gtcctatcga gccgcacttt ttgagcaagc atgtccatcc ttatatcgcc   14640
cagcaataac acaggctggg gcctgcgctt cccaagcaag atgtttggcg gggccaagaa   14700
gcgctccgac caacacccag tgcgcgtgcg cgggcactac cgcgcgccct ggggcgcgca   14760
caaacgcggc cgcactgggc gcaccaccgt cgatgacgcc atcgacgcgg tggtggagga   14820
ggcgcgcaac tacacgccca cgccgccacc agtgtccaca gtggacgcgg ccattcagac   14880
cgtggtgcgc ggagcccggc gctatgctaa aatgaagaga cggcggaggc gcgtagcacg   14940
tcgccaccgc cgccgacccg gcactgccgc ccaacgcgcg gcgcggcccc tgcttaaccg   15000
cgcacgtcgc accggccgac gggcggccat gcgggccgct cgaaggctgg ccgcgggtat   15060
tgtcactgtg cccccaggt ccaggcgacg agcggccgcc gcagcagccg cggccattag   15120
tgctatgact cagggtcgca ggggcaacgt gtattggatg cgcgactcgg ttagcggcct   15180
gcgcgtgccc gtgcgcaccc gcccccgcg caactagatt gcaagaaaaa actactagaa   15240
ctcgtactgt tgtatgtatc cagcggcggc ggcgcgcaac gaagctatgt ccaagcgcaa   15300
aatcaaagaa gagatgctcc aggtcatcgc gccgagatc tatggccccc cgaagaagga   15360
agagcaggat tacaagcccc gaaagctaaa gcgggtcaaa aagaaaaaga aagatgatga   15420
tgatgaactt gacgacgagg tggaactgct gcacgctacc gcgcccaggc gacgggtaca   15480
gtggaaaggt cgacgcgtaa aacgtgttt gcgacccggc accaccgtag tctttacgcc   15540
cggtgagcgc tccacccgca cctacaagcg cgtgtatgat gaggtgtacg gcgacgagga   15600
cctgcttgag caggccaacg agcgcctcgg ggagtttgcc tacggaaagc ggcataagga   15660
catgctggcg ttgccgctgg acgagggcaa cccaacacct agcctaaagc ccgtaacact   15720
gcagcaggtg ctgcccgcgc ttgcaccgtc cgaagaaaag cgcggcctaa agcgcgagtc   15780
tggtgacttg gcacccaccg tgcagctgat ggtaccaag cgccagcgac tggaagatgt   15840
cttggaaaaa atgaccgtgg aacctgggct ggagcccgag gtccgcgtgc ggccaatcaa   15900
gcaggtggcg ccgggactgg gcgtgcagac cgtggacgtt cagatacca ctaccagtag   15960 caccagtatt gccaccgcca cagagggcat ggagacacaa acgtcccgg ttgcctcagc   16020 ggtggcggat gccgcggtgc aggcggtcgc tgcggccgcg tccaagacct ctacggaggt   16080
gcaaacggac ccgtggatgt ttcgcgtttc agcccccgg cgcccgcgcc gttcgaggaa   16140
gtacggcgcc gccagcgcgc tactgcccga atatgccta catccttcca ttgcgcctac   16200
ccccggctat cgtggctaca cctaccgccc cagaagacga gcaactaccc gacgccgaac   16260
```

```
caccactgga acccgccgcc gccgtcgccg tcgccagccc gtgctggccc cgatttccgt  16320
gcgcagggtg gctcgcgaag gaggcaggac cctggtgctg ccaacagcgc gctaccaccc  16380
cagcatcgtt taaaagccgg tctttgtggt tcttgcagat atggccctca cctgccgcct  16440
ccgtttcccg gtgccgggat tccgaggaag aatgcaccgt aggaggggca tggccggcca  16500
cggcctgacg ggcggcatgc gtcgtgcgca ccaccggcgg cggcgcgcgt cgcaccgtcg  16560
catgcgcggc ggtatcctgc ccctccttat tccactgatc gccgcggcga ttggcgccgt  16620
gcccggaatt gcatccgtgg ccttgcaggc gcagagacac tgattaaaaa caagttgcat  16680
gtggaaaaat caaataaaa agtctggact ctcacgctcg cttggtcctg taactatttt  16740
gtagaatgga agacatcaac tttgcgtctc tggccccgcg acacggctcg cgcccgttca  16800
tgggaaactg gcaagatatc ggcaccagca atatgagcgg tggcgccttc agctggggct  16860
cgctgtggag cggcattaaa aatttcggtt ccaccgttaa gaactatggc agcaaggcct  16920
ggaacagcag cacaggccag atgctgaggg ataagttgaa agagcaaaat ttccaacaaa  16980
aggtggtaga tggcctggcc tctggcatta gcggggtggt ggacctggcc aaccaggcag  17040
tgcaaaataa gattaacagt aagcttgatc cccgccctcc cgtagaggag cctccaccgg  17100
ccgtggagac agtgtctcca gaggggcgtg gcgaaaagcg tccgcgcccc gacagggaag  17160
aaactctggt gacgcaaata gacgagcctc cctcgtacga ggaggcacta aagcaaggcc  17220
tgcccaccac ccgtcccatc gcgcccatgg ctaccggagt gctgggccag cacacacccg  17280
taacgctgga cctgcctccc cccgccgaca cccagcagaa acctgtgctg ccaggcccga  17340
ccgccgttgt tgtaacccgt cctagccgcg cgtccctgcg ccgcgccgcc agcggtccgc  17400
gatcgttgcg gcccgtagcc agtggcaact ggcaaagcac actgaacagc atcgtgggtc  17460
tggggggtgca atccctgaag cgccgacgat gcttctgata gctaacgtgt cgtatgtgtg  17520
tcatgtatgc gtccatgtcg ccgccagagg agctgctgag ccgccgcgcg cccgcttttcc  17580
aagatggcta cccccttcgat gatgccgcag tggtcttaca tgcacatctc gggccaggac  17640
gcctcggagt acctgagccc cgggctggtg cagtttgccc gcgccaccga gacgtacttc  17700
agcctgaata acaagtttag aaaccccacg gtggcgccta cgcacgacgt gaccacagac  17760
cggtcccagc gtttgacgct gcggttcatc cctgtggacc gtgaggatac tgcgtactcg  17820
tacaaggcgc ggttcaccct agctgtgggt gataaccgtg tgctggacat ggcttccacg  17880
tactttgaca tccgcggcgt gctggacagg ggccctactt ttaagcccta ctctggcact  17940
gcctacaacg ccctggctcc caagggtgcc ccaaatcctt gcgaatggga tgaagctgct  18000
actgctcttg aaataaacct agaagaagag gacgatgaca acgaagacga agtagacgag  18060
caagctgagc agcaaaaaac tcacgtattt gggcaggcgc cttattctgg tataaatatt  18120
acaaaggagg gtattcaaat aggtgtcgaa ggtcaaacac ctaaatatgc cgataaaaca  18180
tttcaacctg aacctcaaat aggagaatct cagtggtacg aaacagaaat taatcatgca  18240
gctgggagag tcctaaaaaa gactaccccca atgaaaccat gttacggttc atatgcaaaa  18300
cccacaaatg aaaatggagg gcaaggcatt cttgtaaagc aacaaatgg aaagctagaa  18360
agtcaagtgg aaatgcaatt tttctcaact actgaggcag ccgcaggcaa tggtgataac  18420
ttgactccta aagtggtatt gtacagtgaa gatgtagata tagaaacccc agacactcat  18480
atttcttaca tgcccactat taaggaaggt aactcacgag aactaatggg ccaacaatct  18540
atgcccaaca ggcctaatta cattgctttt agggacaatt ttattggtct aatgtattac  18600
```

```
aacagcacgg gtaatatggg tgttctggcg ggccaagcat cgcagttgaa tgctgttgta   18660
gatttgcaag acagaaacac agagcttca taccagcttt tgcttgattc cattggtgat   18720
agaaccaggt acttttctat gtggaatcag gctgttgaca gctatgatcc agatgttaga   18780
attattgaaa atcatggaac tgaagatgaa cttccaaatt actgctttcc actgggaggt   18840
gtgattaata cagagactct taccaaggta aaacctaaaa caggtcagga aaatggatgg   18900
gaaaaagatg ctacagaatt ttcagataaa aatgaaataa gagttggaaa taattttgcc   18960
atggaaatca atctaaatgc caacctgtgg agaaatttcc tgtactccaa catagcgctg   19020
tatttgcccg acaagctaaa gtacagtcct tccaacgtaa aaatttctga taacccaaac   19080
acctacgact acatgaacaa gcgagtggtg gctcccgggc tagtggactg ctacattaac   19140
cttggagcac gctggtccct tgactatatg gacaacgtca acccatttaa ccaccaccgc   19200
aatgctggcc tgcgctaccg ctcaatgttg ctgggcaatg gtcgctatgt gcccttccac   19260
atccaggtgc ctcagaagtt ctttgccatt aaaaacctcc ttctcctgcc gggctcatac   19320
acctacgagt ggaacttcag gaaggatgtt aacatggttc tgcagagctc cctaggaaat   19380
gacctaaggg ttgacggagc cagcattaag tttgatagca tttgccttta cgccaccttc   19440
ttccccatgg cccacaacac cgcctccacg cttgaggcca tgcttagaaa cgacaccaac   19500
gaccagtcct ttaacgacta tctctccgcc gccaacatgc tctaccctat acccgccaac   19560
gctaccaacg tgcccatatc catccctcc cgcaactggg cggctttccg cggctgggcc   19620
ttcacgcgcc ttaagactaa ggaaacccca tcactgggct cgggctacga cccttattac   19680
acctactctg gctctatacc ctaccctagat ggaacctttt acctcaacca caccttaag   19740 aaggtggcca ttacctttga ctcttctgtc agctggcctg gcaatgaccg cctgcttacc   19800
cccaacgagt ttgaaattaa gcgctcagtt gacggggagg gttacaacgt tgcccagtgt   19860
aacatgacca agactggtt cctggtacaa atgctagcta actataacat tggctaccag   19920
ggcttctata tcccagagag ctacaaggac cgcatgtact ccttctttag aaacttccag   19980
cccatgagcc gtcaggtggt ggatgatact aaatacaagg actaccaaca ggtgggcatc   20040
ctacaccaac acaacaactc tggattttgtt ggctaccttg cccccaccat gcgcgaagga   20100
caggcctacc ctgctaactt ccctatccg cttataggca agaccgcagt tgacagcatt   20160
acccagaaaa agtttctttg cgatcgcacc ctttggcgca tcccattctc cagtaacttt   20220
atgtccatgg gcgcactcac agacctgggc caaaaccttc tctacgccaa ctccgcccac   20280
gcgctagaca tgactttttga ggtggatccc atggacgagc ccaccttct ttatgttttg   20340 tttgaagtct ttgacgtggt ccgtgtgcac cagccgcacc gcggcgtcat cgaaaccgtg   20400
tacctgcgca cgcccttctc ggccggcaac gccacaacat aaagaagcaa gcaacatcaa   20460
caacagctgc cgccatgggc tccagtgagc aggaactgaa agccattgtc aaagatcttg   20520
gttgtgggcc atatttttg ggcacctatg acaagcgctt ccaggctttt gtttctccac   20580
acaagctcgc ctgcgccata gtcaatacgg ccggtcgcga gactggggc gtacactgga   20640 tggcctttgc ctggaacccg cactcaaaaa catgctacct ctttgagccc tttggctttt   20700
ctgaccagcg actcaagcag gtttaccagt ttgagtacga gtcactcctg cgccgtagcg   20760
ccattgcttc ttcccccgac cgctgtataa cgctggaaaa gtccacccaa agcgtacagg   20820
ggcccaactc ggccgcctgt ggactattct gctgcatgtt tctccacgcc tttgccaact   20880 ggcccccaaac tccatggat cacaaccca ccatgaacct tattaccggg gtacccaact   20940
ccatgctcaa cagtcccag gtacagccca ccctgcgtcg caaccaggaa cagctctaca   21000
```

```
gcttcctgga gcgccactcg ccctacttcc gcagccacag tgcgcagatt aggagcgcca    21060 cttcttttg  tcacttgaaa aacatgtaaa aataatgtac tagagacact ttcaataaag    21120
gcaaatgctt ttatttgtac actctcgggt gattatttac ccccacccct gccgtctgcg    21180
ccgtttaaaa atcaaagggg ttctgccgcg catcgctatg cgccactggc agggacacgt    21240
tgcgatactg gtgtttagtg ctccacttaa actcaggcac aaccatccgc ggcagctcgg    21300
tgaagttttc actccacagg ctgcgcacca tcaccaacgc gtttagcagg tcgggcgccg    21360
atatcttgaa gtcgcagttg gggcctccgc cctgcgcgcg cgagttgcga tacacagggt    21420
tgcagcactg gaacactatc agcgccgggt ggtgcacgct ggccagcacg ctcttgtcgg    21480
agatcagatc cgcgtccagg tcctccgcgt tgctcagggc gaacggagtc aactttggta    21540
gctgccttcc caaaagggc  gcgtgcccag gctttgagtt gcactcgcac cgtagtggca    21600
tcaaaaggtg accgtgcccg gtctgggcgt taggatacag cgcctgcata aaagccttga    21660
tctgcttaaa agccacctga gcctttgcgc cttcagagaa gaacatgccg caagacttgc    21720
cggaaaactg attggccgga caggccgcgt cgtgcacgca gcaccttgcg tcggtgttgg    21780
agatctgcac cacatttcgg ccccaccggt tcttcacgat cttggccttg ctagactgct    21840
ccttcagcgc gcgctgcccg ttttcgctcg tcacatccat ttcaatcacg tgctccttat    21900
ttatcataat gcttccgtgt agacacttaa gctcgccttc gatctcagcg cagcggtgca    21960
gccacaacgc gcagcccgtg ggctcgtgat gcttgtaggt cacctctgca aacgactgca    22020
ggtacgcctg caggaatcgc cccatcatcg tcacaaaggt cttgttgctg gtgaaggtca    22080
gctgcaaccc gcggtgctcc tcgttcagcc aggtcttgca tacggccgcc agagcttcca    22140
cttggtcagg cagtagtttg aagttcgcct ttagatcgtt atccacgtgg tacttgtcca    22200
tcagcgcgcg cgcagcctcc atgcccttct cccacgcaga cacgatcggc acactcagcg    22260
ggttcatcac cgtaatttca ctttccgctt cgctgggctc ttcctcttcc tcttgcgtcc    22320
gcataccacg cgccactggg tcgtcttcat tcagccgccg cactgtgcgc ttacctcctt    22380
tgccatgctt gattagcacc ggtgggttgc tgaaacccac catttgtagc gccacatctt    22440
ctctttcttc ctcgctgtcc acgattacct ctggtgatgg cgggcgctcg ggcttgggag    22500
aagggcgctt cttttcttc  ttgggcgcaa tggccaaatc cgccgccgag gtcgatggcc    22560
gcgggctggg tgtgcgcggc accagcgcgt cttgtgatga gtcttcctcg tcctcggact    22620
cgatacgccg cctcatccgc ttttttgggg gcgcccgggg aggcggcggc gacggggacg    22680
gggacgacac gtcctccatg gttgggggac gtcgcgccgc accgcgtccg cgctcggggg    22740
tggtttcgcg ctgctcctct tcccgactgg ccatttcctt ctcctatagg cagaaaaga    22800 tcatggagtc agtcgagaag aaggacagcc taaccgcccc ctctgagttc gccaccaccg    22860
cctccaccga tgccgccaac gcgcctacca ccttccccgt cgaggcaccc ccgcttgagg    22920
aggaggaagt gattatcgag caggacccag gttttgtaag cgaagacgac gaggaccgct    22980
cagtaccaac agaggataaa aagcaagacc aggacaacgc agaggcaaac gaggaacaag    23040
tcgggcgggg ggacgaaagg catggcgact acctagatgt gggagacgac gtgctgttga    23100
agcatctgca gcgccagtgc gccattatct gcgacgcgtt gcaagagcgc agcgatgtgc    23160
ccctcgccat agcggatgtc agccttgcct acgaacgcca cctattctca ccgcgcgtac    23220
cccccaaacg ccaagaaaac ggcacatgcg agcccaaccc gcgcctcaac ttctaccccg    23280
tatttgccgt gccagaggtg cttgccacct atcacatctt tttccaaaac tgcaagatac    23340
```

```
ccctatcctg ccgtgccaac cgcagccgag cggacaagca gctggccttg cggcagggcg    23400
ctgtcatacc tgtatcgcc tcgctcaacg aagtgccaaa aatctttgag ggtcttggac    23460
gcgacgagaa gcgcgcggca aacgctctgc aacaggaaaa cagcgaaaat gaaagtcact    23520
ctggagtgtt ggtggaactc gagggtgaca acgcgcgcct agccgtacta aaacgcagca    23580
tcgaggtcac ccactttgcc tacccggcac ttaacctacc ccccaaggtc atgagcacag    23640
tcatgagtga gctgatcgtg cgccgtcgcg agcccctgga gagggatgca aatttgcaag    23700
aacaaacaga ggagggccta cccgcagttg gcgacgagca gctagcgcgc tggcttcaaa    23760
cgcgcgagcc tgccgacttg gaggagcgac gcaaactaat gatggccgca gtgctcgtta    23820
ccgtggagct tgagtgcatg cagcggttct ttgctgaccc ggagatgcag cgcaagctag    23880
aggaaacatt gcactacacc tttcgacagg gctacgtacg ccaggcctgc aagatctcca    23940
acgtggagct ctgcaacctg gtctcctacc ttggaatttt gcacgaaaac cgccttgggc    24000
aaaacgtgct tcattccacg ctcaagggcg aggcgcgccg cgactacgtc cgcgactgcg    24060
tttacttatt tctatgctac acctggcaga cggccatggg cgtttggcag cagtgcttgg    24120
aggagtgcaa cctcaaggag ctgcagaaac tgctaaagca aaacttgaag gacctatgga    24180
cggccttcaa cgagcgctcc gtggccgcgc acctggcgga catcattttc cccgaacgcc    24240
tgcttaaaac cctgcaacag ggtctgccag acttcaccag tcaaagcatg ttgcagaact    24300
ttaggaactt tatcctagag cgctcaggaa tcttgcccgc cacctgctgt gcacttccta    24360
gcgactttgt gcccattaag taccgcgaat gccctccgcc gctttggggc cactgctacc    24420
ttctgcagct agccaactac cttgcctacc actctgacat aatggaagac gtgagcggtg    24480
acggtctact ggagtgtcac tgtcgctgca acctatgcac cccgcaccgc tccctggttt    24540
gcaattcgca gctgcttaac gaaagtcaaa ttatcggtac ctttgagctg cagggtccct    24600
cgcctgacga aaagtccgcg gctccggggt tgaaactcac tccggggctg tggacgtcgg    24660
cttaccttcg caaatttgta cctgaggact accacgccca cgagattagg ttctacgaag    24720
accaatcccg cccgcctaat gcggagctta ccgcctgcgt cattacccag ggccacattc    24780
ttggccaatt gcaagccatc aacaaagccc gccaagagtt tctgctacga aagggacggg    24840
gggtttactt ggaccccag tccggcgagg agctcaaccc aatcccccg ccgccgcagc    24900 cctatcagca gcgccgcgg gcccttgctt cccaggatgg cacccaaaaa gaagctgcag    24960
ctgccgccgc cacccacgga cgaggaggaa tactgggaca gtcaggcaga ggaggttttg    25020
gacgaggagg aggaggacat gatggaagac tgggagagcc tagacgagga agcttccgag    25080
gtcgaagagg tgtcagacga aacaccgtca ccctcggtcg cattcccctc gccggcgccc    25140
cagaaatcgg caaccggttc cagcatggct acaacctccg ctcctcaggc gccgccggca    25200
ctgcccgttc gccgacccaa ccgtagatgg gacaccactg aaccagggc cggtaagtcc    25260 aagcagccgc cgccgttagc ccaagagcaa caacagcgcc aaggctaccg ctcatgcgc    25320 gggcacaaga acgccatagt tgcttgcttg caagactgtg ggggcaacat ctccttcgcc    25380
cgccgctttc ttctctacca tcacggcgtg gccttccccc gtaacatcct gcattactac    25440
cgtcatctct acagcccata ctgcaccggc ggcagcggca gcaacagcag cggccacaca    25500
gaagcaaagg cgaccggata gcaagactct gacaaagccc aagaaatcca cagcggcggc    25560
agcagcagga ggaggagcgc tgcgtctggc gcccaacgaa cccgtatcga cccgcgagct    25620
tagaaacagg atttttccca ctctgtatgc tatatttcaa cagagcaggg gccaagaaca    25680
agagctgaaa ataaaaaaca ggtctctgcg atccctcacc cgcagctgcc tgtatcacaa    25740
```

```
aagcgaagat cagcttcggc gcacgctgga agacgcggag gctctcttca gtaaatactg    25800
cgcgctgact cttaaggact agtttcgcgc cctttctcaa atttaagcgc gaaaactacg    25860
tcatctccag cggccacacc cggcgccagc acctgttgtc agcgccatta tgagcaagga    25920
aattcccacg ccctacatgt ggagttacca gccacaaatg ggacttgcgg ctggagctgc    25980
ccaagactac tcaacccgaa taaactacat gagcgcggga ccccacatga tatcccgggt    26040
caacggaata cgcgcccacc gaaaccgaat tctcctggaa caggcggcta ttaccaccac    26100
acctcgtaat aaccttaatc cccgtagttg gcccgctgcc ctggtgtacc aggaaagtcc    26160
cgctcccacc actgtggtac ttcccagaga cgcccaggcc gaagttcaga tgactaactc    26220
aggggcgcag cttgcgggcg gctttcgtca cagggtgcgg tcgcccgggc agggtataac    26280
tcacctgaca atcagagggc gaggtattca gctcaacgac gagtcggtga gctcctcgct    26340
tggtctccgt ccggacggga catttcagat cggcggcgcc ggccgctctt cattcacgcc    26400
tcgtcaggca atcctaactc tgcagacctc gtcctctgag ccgcgctctg gaggcattgg    26460
aactctgcaa tttattgagg agtttgtgcc atcggtctac tttaacccct tctcgggacc    26520
tcccggccac tatccggatc aatttattcc taactttgac gcggtaaagg actcggcgga    26580
cggctacgac tgaatgttaa gtggagaggc agagcaactg cgcctgaaac acctggtcca    26640
ctgtcgccgc cacaagtgct ttgcccgcga ctccggtgag ttttgctact ttgaattgcc    26700
cgaggatcat atcgagggcc cggcgcacgg cgtccggctt accgcccagg gagagcttgc    26760
ccgtagcctg attcgggagt ttacccagcg ccccctgcta gttgagcggg acaggggacc    26820
ctgtgttctc actgtgattt gcaactgtcc taaccctgga ttacatcaag atcctctagt    26880
taatgtcagg tcgcctaagt cgattaacta gagtacccgg ggatcttatt ccctttaact    26940
aataaaaaaa aataataaag catcacttac ttaaaatcag ttagcaaatt tctgtccagt    27000
ttattcagca gcacctcctt gccctcctcc cagctctggt attgcagctt cctcctggct    27060
gcaaactttc tccacaatct aaatggaatg tcagtttcct cctgttcctg tccatccgca    27120
cccactatct tcatgttgtt gcagatgaag cgcgcaagac cgtctgaaga taccttcaac    27180
cccgtgtatc catatgacac ggaaaccggt cctccaactg tgccttttct tactcctccc    27240
tttgtatccc ccaatgggtt tcaagagagt ccccctgggg tactctcttt gcgcctatcc    27300
gaacctctag ttacctccaa tggcatgctt gcgctcaaaa tgggcaacgg cctctctctg    27360
gacgaggccg gcaaccttac ctcccaaaat gtaaccactg tgagcccacc tctcaaaaaa    27420
accaagtcaa acataaacct ggaaatatct gcacccctca cagttacctc agaagcccta    27480
actgtggctg ccgccgcacc tctaatggtc gcgggcaaca cactcaccat gcaatcacag    27540
gccccgctaa ccgtgcacga ctccaaactt agcattgcca cccaaggacc cctcacagtg    27600
tcagaaggaa agctagccct gcaaacatca ggcccctca ccaccaccga tagcagtacc    27660
cttactatca ctgcctcacc ccctctaact actgccactg gtagcttggg cattgacttg    27720
aaagagccca tttatacaca aaatggaaaa ctaggactaa agtacggggc tcctttgcat    27780
gtaacagacg acctaaacac tttgaccgta gcaactggtc caggtgtgac tattaataat    27840
acttccttgc aaactaaagt tactggagcc ttgggttttg attcacaagg caatatgcaa    27900
cttaatgtag caggaggact aaggattgat tctcaaaaca gacgccttat acttgatgtt    27960
agttatccgt ttgatgctca aaaccaacta aatctaagac taggacaggg ccctcttttt    28020
ataaactcag cccacaactt ggatattaac tacaacaaag gcctttactt gtttacagct    28080
```

```
tcaaacaatt ccaaaaagct tgaggttaac ctaagcactg ccaaggggtt gatgtttgac    28140
gctacagcca tagccattaa tgcaggagat gggcttgaat ttggttcacc taatgcacca    28200
aacacaaatc ccctcaaaac aaaaattggc catggcctag aatttgattc aaacaaggct    28260
atggttccta aactaggaac tggccttagt tttgacagca caggtgccat tacagtagga    28320
aacaaaaata atgataagct aactttgtgg accacaccag ctccatctcc taactgtaga    28380
ctaaatgcag agaaagatgc taaactcact ttggtcttaa caaaatgtgg cagtcaaata    28440
cttgctacag tttcagtttt ggctgttaaa ggcagtttgg ctccaatatc tggaacagtt    28500
caaagtgctc atcttattat aagatttgac gaaaatggag tgctactaaa caattccttc    28560
ctggacccag aatattggaa ctttagaaat ggagatctta ctgaaggcac agcctataca    28620
aacgctgttg gatttatgcc taacctatca gcttatccaa atctcacgg taaaactgcc    28680 aaaagtaaca ttgtcagtca agtttactta aacggagaca aaactaaacc tgtaacacta    28740
accattacac taaacggtac acaggaaaca ggagacacaa ctccaagtgc atactctatg    28800
tcattttcat gggactggtc tggccacaac tacattaatg aaatatttgc cacatcctct    28860
tacacttttt catacattgc ccaagaataa agaatcgttt gtgttatgtt tcaacgtgtt    28920 tattttcaa ttgcagaaaa tttcaagtca tttttcattc agtagtatag ccccaccacc    28980
acatagctta tacagatcac cgtaccttaa tcaaactcac agaacctag tattcaacct    29040 gccacctccc tcccaacaca cagagtacac agtcctttct ccccggctgg ccttaaaaag    29100
catcatatca tgggtaacag acatattctt aggtgttata ttccacacgg tttcctgtcg    29160
agccaaacgc tcatcagtga tattaataaa ctccccgggc agctcactta agttcatgtc    29220
gctgtccagc tgctgagcca caggctgctg tccaacttgc ggttgcttaa cgggcggcga    29280
aggagaagtc cacgcctaca tgggggtaga gtcataatcg tgcatcagga tagggcggtg    29340
gtgctgcagc agcgcgcgaa taaactgctg ccgccgccgc tccgtcctgc aggaatacaa    29400
catggcagtg gtctcctcag cgatgattcg caccgcccgc agcataaggc gccttgtcct    29460
ccgggcacag cagcgcaccc tgatctcact taaatcagca cagtaactgc agcacagcac    29520
cacaatattg ttcaaaatcc cacagtgcaa ggcgctgtat ccaaagctca tggcggggac    29580
cacagaaccc acgtggccat cataccacaa gcgcaggtag attaagtggc gaccctcat    29640 aaacacgctg gacataaaca ttacctcttt tggcatgttg taattcacca cctcccggta    29700
ccatataaac ctctgattaa acatggcgcc atccaccacc atcctaaacc agctggccaa    29760
aacctgcccg ccggctatac actgcaggga accgggactg gaacaatgac agtgagagc    29820 ccaggactcg taaccatgga tcatcatgct cgtcatgata tcaatgttgg cacaacacag    29880
gcacacgtgc atacacttcc tcaggattac aagctcctcc cgcgttagaa ccatatccca    29940
gggaacaacc cattcctgaa tcagcgtaaa tcccacactg cagggaagac ctcgcacgta    30000
actcacgttg tgcattgtca aagtgttaca ttcgggcagc agcggatgat cctccagtat    30060
ggtagcgcgg gtttctgtct caaaaggagg tagacgatcc ctactgtacg gagtgcgccg    30120
agacaaccga gatcgtgttg gtcgtagtgt catgccaaat ggaacgccgg acgtagtcat    30180
atttcctgaa gcaaaccag gtgcgggcgt gacaaacaga tctgcgtctc cggtctcgcc    30240
gcttagatcg ctctgtgtag tagttgtagt atatccactc tctcaaagca tccaggcgcc    30300
ccctggcttc gggttctatg taaactcctt catgcgccgc tgccctgata acatccacca    30360
ccgcagaata agccacaccc agccaaccta cacattcgtt ctgcgagtca cacacggag    30420 gagcgggaag agctggaaga accatgtttt ttttttttatt ccaaaagatt atccaaaacc    30480
```

-continued

```
tcaaaatgaa gatctattaa gtgaacgcgc tcccctccgg tggcgtggtc aaactctaca   30540
gccaaagaac agataatggc atttgtaaga tgttgcacaa tggcttccaa aaggcaaacg   30600
gccctcacgt ccaagtggac gtaaaggcta aacccttcag ggtgaatctc ctctataaac   30660
attccagcac cttcaaccat gcccaaataa ttctcatctc gccaccttct caatatatct   30720
ctaagcaaat cccgaatatt aagtccggcc attgtaaaaa tctgctccag agcgccctcc   30780
accttcagcc tcaagcagcg aatcatgatt gcaaaaattc aggttcctca cagacctgta   30840
taagattcaa aagcggaaca ttaacaaaaa taccgcgatc ccgtaggtcc cttcgcaggg   30900
ccagctgaac ataatcgtgc aggtctgcac ggaccagcgc ggccacttcc ccgccaggaa   30960
ccatgacaaa agaacccaca ctgattatga cacgcatact cggagctatg ctaaccagcg   31020
tagccccgat gtaagcttgt tgcatggggcg gcgatataaa atgcaaggtg ctgctcaaaa   31080
aatcaggcaa agcctcgcgc aaaaagaaa gcacatcgta gtcatgctca tgcagataaa   31140
ggcaggtaag ctccggaacc accacagaaa aagacaccat ttttctctca aacatgtctg   31200
cgggtttctg cataaacaca aaataaaata acaaaaaaac atttaaacat tagaagcctg   31260
tcttacaaca ggaaaaacaa cccttataag cataagacgg actacggcca tgccggcgtg   31320
accgtaaaaa aactggtcac cgtgattaaa aagcaccacc gacagctcct cggtcatgtc   31380
cggagtcata atgtaagact cggtaaacac atcaggttga ttcacatcgg tcagtgctaa   31440
aaagcgaccg aaatagcccg ggggaataca tacccgcagg cgtagagaca acattacagc   31500
ccccatagga ggtataacaa aattaatagg agagaaaaac acataaacac ctgaaaaacc   31560
ctcctgccta ggcaaaatag caccctcccg ctccagaaca acatacagcg cttccacagc   31620
ggcagccata acagtcagcc ttaccagtaa aaaagaaaac ctattaaaaa aacaccactc   31680
gacacggcac cagctcaatc agtcacagtg taaaaaaggg ccaagtgcag agcgagtata   31740
tataggacta aaaatgacg taacggttaa agtccacaaa aaacccag aaaccgcac   31800 gcgaacctac gcccagaaac gaaagccaaa aaacccacaa cttcctcaaa tcgtcacttc   31860
cgttttccca cgttacgtca cttcccattt taagaaaact acaattccca acacatacaa   31920
gttactccgc cctaaaacct acgtcacccg ccccgttccc acgccccgcg ccacgtcaca   31980
aactccaccc cctcattatc atattggctt caatccaaaa taaggtatat tattgatgat   32040
```

<210> SEQ ID NO 15
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30

Glu Lys Gly Asp Pro Thr Glu Arg Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80
```

Gly Leu Asp Pro Asn Ala Met Tyr Ser Phe Leu Leu Asp Phe Val Ala
            85                  90                  95

Ala Asp Asn His Arg Trp Lys Tyr Val Asn Gly Glu Trp Val Pro Gly
        100                 105                 110

Gly Lys Pro Glu Pro Gln Ala Pro Ser Cys Val Tyr Ile His Pro Asp
    115                 120                 125

Ser Pro Asn Phe Gly Ala His Trp Met Lys Ala Pro Val Ser Phe Ser
130                 135                 140

Lys Val Lys Leu Thr Asn Lys Leu Asn Gly Gly Gln Ile Met Leu
145                 150                 155                 160

Asn Ser Leu His Lys Tyr Glu Pro Arg Ile His Ile Val Arg Val Gly
                165                 170                 175

Asp Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
        195                 200                 205

Lys Tyr Asn Pro Phe Ala Lys Ala Phe Leu Asp Ala Lys Glu Arg Ser
    210                 215                 220

Asp His Lys Glu Met Met Glu Glu Pro Gly Asp Ser Gln Gln Pro Gly
225                 230                 235                 240

Tyr Ser Gln Trp Gly Trp Leu Leu Pro Gly Thr Ser Thr Leu Cys Pro
                245                 250                 255

Pro Ala Asn Pro His Pro Gln Phe Gly Ala Leu Ser Leu Pro Ser
            260                 265                 270

Thr His Ser Cys Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
    290                 295                 300

Asp Asn Ser Pro Ala Cys Leu Ser Met Leu Gln Ser His Asp Asn Trp
305                 310                 315                 320

Ser Ser Leu Gly Met Pro Ala His Pro Ser Met Leu Pro Val Ser His
                325                 330                 335

Asn Ala Ser Pro Pro Thr Ser Ser Ser Gln Tyr Pro Ser Leu Trp Ser
            340                 345                 350

Val Ser Asn Gly Ala Val Thr Pro Gly Ser Gln Ala Ala Val Thr
    355                 360                 365

Asn Gly Leu Gly Ala Gln Phe Phe Arg Gly Ser Pro Ala His Tyr Thr
370                 375                 380

Pro Leu Thr His Pro Val Ser Ala Pro Ser Ser Gly Ser Pro Leu
385                 390                 395                 400

Tyr Glu Gly Ala Ala Ala Thr Asn Ile Val Asp Ser Gln Tyr Asp
                405                 410                 415

Ala Ala Ala Gln Gly Arg Leu Ile Ala Ser Trp Thr Pro Val Ser Pro
            420                 425                 430

Pro Ser Met
        435

<210> SEQ ID NO 16
<211> LENGTH: 31465
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
catcatcaat aatataccett attttggatt gaagccaata tgataatgag ggggtggagt   60
ttgtgacgtg gcgcggggcg tgggaacggg gcgggtgacg tagtagtgtg gcggaagtgt  120
gatgttgcaa gtgtggcgga acacatgtaa gcgacggatg tggcaaaagt gacgttttg   180
gtgtgcgccg gtgtacacag gaagtgacaa ttttcgcgcg gttttaggcg gatgttgtag  240
taaatttggg cgtaaccgag taagatttgg ccattttcgc gggaaaactg aataagagga  300
agtgaaatct gaataatttt gtgttactca tagcgcgtaa tactgtaata gtaatcaatt  360
acggggtcat tagttcatag cccatatatg gagttccgcg ttacataact tacggtaaat  420
ggcccgcctg gctgaccgcc caacgacccc cgcccattga cgtcaataat gacgtatgtt  480
cccatagtaa cgccaatagg gactttccat tgacgtcaat gggtggagta tttacggtaa  540
actgcccact tggcagtaca tcaagtgtat catatgccaa gtacgccccc tattgacgtc  600
aatgacggta aatggcccgc ctggcattat gcccagtaca tgaccttatg gactttcct  660
acttggcagt acatctacgt attagtcatc gctattacca tggtgatgcg gttttggcag  720
tacatcaatg ggcgtggata gcggtttgac tcacgggat ttccaagtct ccaccccatt  780
gacgtcaatg ggagtttgtt ttggcaccaa aatcaacggg actttccaaa atgtcgtaac  840
aactccgccc cattgacgca aatgggcggt aggcgtgtac ggtgggaggt ctatataagc  900
agagctggtt tagtgaaccg tcagatccgc tagagatctg gtaccgtcga cgcggccgct  960
cgagcctaag cttctagatg catgctcgag cggccgccag tgtgatggat atctgcagaa 1020
ttcgcccttg cttctagagc caccatgagc tcccctggca ccgagagcgc gggaaagagc 1080
ctgcagtacc gagtggacca cctgctgagc gccgtggaga atgagctgca ggcgggcagc 1140
gagaagggcg accccacaga gcgcgaactg cgcgtgggcc tggaggagag cgagctgtgg 1200
ctgcgcttca aggagctcac caatgagatg atcgtgacca gaacggcag gaggatgttt 1260
ccggtgctga aggtgaacgt gtctggcctg gaccccaacg ccatgtactc cttcctgctg 1320
gacttcgtgg cggcggacaa ccaccgctgg aagtacgtga cggggaatg ggtgccgggg 1380
ggcaagccgg agccgcaggc gcccagctgc gtctacatcc accccgactc gcccaacttc 1440
ggggcccact ggatgaaggc tcccgtctcc ttcagcaaag tcaagctcac caacaagctc 1500
aacggagggg gccagatcat gctgaactcc ttgcataagt atgagcctcg aatccacata 1560
gtgagagttg ggggtccaca gcgcatgatc accagccact gcttccctga cccagttc   1620
atagcggtga ctgctagaag tgatcacaaa gagatgatgg aggaacccgg agacagccag 1680
caacctgggt actcccaatg ggggtggctt cttcctggaa ccagcaccgt gtgtccacct 1740
gcaaatcctc atcctcagtt tggaggtgcc ctctccctcc cctccacgca cagctgtgac 1800
aggtacccaa ccctgaggag ccaccggtcc tcacctacc ccagccccta tgctcatcgg 1860
aacaattctc caacctattc tgacaactca cctgcatgtt tatccatgct gcaatcccat 1920
gacaattggt ccagccttgg aatgcctgcc catcccagca tgctccccgt gagccacaat 1980
gccagcccac ctaccagctc cagtcagtac cccagcctgt ggtctgtgag caacggcgcc 2040
gtcaccccgg gctcccaggc agcagccgtg tccaacgggc tgggggccca gttcttccgg 2100
ggctcccccg cgcactacac acccctcacc catccggtct cggcgccctc ttcctcggga 2160
tccccactgt acgaaggggc ggccgcggcc acagacatcg tggacagcca gtacgacgcc 2220
gcagcccaag gccgcctcat agcctcatgg acacctgtgt cgccaccttc catgtgagat 2280
atccgatcca ccggatctag ataactgatc ataatcagcc ataccacatt tgtagaggtt 2340
```

```
ttacttgctt taaaaaacct cccacacctc ccctgaacc tgaaacataa aatgaatgca    2400
attgttgttg ttaacttgtt tattgcagct tataatggtt acaaataaag caatagcatc    2460
acaaatttca caaataaagc attttttca ctgcattcta gttgtggttt gtccaaactc    2520
atcaatgtat cttaacgcgg atctggaagg tgctgaggta cgatgagacc cgcaccaggt    2580
gcagaccctg cgagtgtggc ggtaaacata ttaggaacca gcctgtgatg ctggatgtga    2640
ccgaggagct gaggcccgat cacttggtgc tggcctgcac ccgcgctgag tttggctcta    2700
gcgatgaaga tacagattga ggtactgaaa tgtgtgggcg tggcttaagg gtgggaaaga    2760
atatataagg tgggggtctt atgtagtttt gtatctgttt gcagcagcc gccgccgcca    2820 tgagcaccaa ctcgtttgat ggaagcattg tgagctcata tttgacaacg cgcatgcccc    2880
catgggccgg ggtgcgtcag aatgtgatgg gctccagcat tgatggtcgc cccgtcctgc    2940
ccgcaaactc tactaccttg acctacgaga ccgtgtctgg aacgccgttg gagactgcag    3000
cctccgccgc cgcttcagcc gctgcagcca ccgcccgcgg gattgtgact gactttgctt    3060
tcctgagccc gcttgcaagc agtgcagctt cccgttcatc cgcccgcgat gacaagttga    3120
cggctctttt ggcacaattg gattctttga cccgggaact taatgtcgtt tctcagcagc    3180
tgttggatct cgccagcag gtttctgccc tgaaggcttc ctcccctccc aatgcggttt    3240
aaaacataaa taaaaaacca gactctgttt ggatttggat caagcaagtg tcttgctgtc    3300
tttatttagg ggtttttgcgc gcgcggtagg cccgggacca gcggtctcgg tcgttgaggg    3360
tcctgtgtat tttttccagg acgtggtaaa ggtgactctg gatgttcaga tacatgggca    3420
taagcccgtc tctggggtgg aggtagcacc actgcagagc ttcatgctgc ggggtggtgt    3480
tgtagatgat ccagtcgtag caggagcgct gggcgtggtg cctaaaaatg tctttcagta    3540
gcaagctgat tgccaggggc aggccttgg tgtaagtgtt tacaaagcgg ttaagctggg    3600
atgggtgcat acgtggggat atgagatgca tcttggactg tattttaggg ttggctatgt    3660
tcccagccat atccctccgg ggattcatgt tgtgcagaac caccagcaca gtgtatccgg    3720
tgcacttggg aaatttgtca tgtagcttag aaggaaatgc gtggaagaac ttggagacgc    3780
ccttgtgacc tccaagattt tccatgcatt cgtccataat gatggcaatg gcccacgggg    3840
cggcggcctg ggcgaagata tttctgggat cactaacgtc atagttgtgt tccaggatga    3900
gatcgtcata ggccattttt acaaagcgcg ggcggagggt gccagactgc ggtataatgg    3960
ttccatccgg cccagggggcg tagttaccct cacagatttg catttcccac gctttgagtt    4020
cagatggggg gatcatgtct acctgcgggg cgatgaagaa acggttttcc ggggtagggg    4080
agatcagctg ggaagaaagc aggttcctga gcagctgcga cttaccgcag ccggtgggcc    4140
cgtaaatcac acctattacc ggctgcaact ggtagttaag agagctgcag ctgccgtcat    4200
ccctgagcag gggggccact tcgttaagca tgtccctgac tcgcatgttt tccctgacca    4260
aatccgccag aaggcgctcg ccgcccagcg atagcagttc ttgcaaggaa gcaaagtttt    4320
tcaacggttt gagaccgtcc gccgtaggca tgcttttgag cgtttgacca agcagttcca    4380
ggcggtccca cagctcggtc acctgctcta cggcatctcg atccagcata tctcctcgtt    4440 tcgcggggttg gggcggcttt cgctgtacgg cagtagtcgg tgctcgtcca gacgggccag    4500
ggtcatgtct ttccacgggc gcagggtcct cgtcagcgta gtctgggtca cggtgaaggg    4560
gtgcgctccg ggctgcgcgc tggccagggt gcgcttgagg ctggtcctgc tggtgctgaa    4620
gcgctgccga tcttcgccct gcgcgtcggc caggtagcat ttgaccatgg tgtcatagtc    4680
cagcccctcc gcggcgtggc ccttggcgcg cagcttgccc ttggaggagg cgccgcacga    4740
```

```
ggggcagtgc agactttga gggcgtagag cttgggcgcg agaaataccg attccgggga   4800
gtaggcatcc gcgccgcagg ccccgcagac ggtctcgcat tccacgagcc aggtgagctc   4860
tggccgttcg gggtcaaaaa ccaggttttcc cccatgcttt ttgatgcgtt tcttacctct   4920
ggtttccatg agccggtgtc cacgctcggt gacgaaaagg ctgtccgtgt ccccgtatac   4980
agacttgaga ggcctgtcct cgagcggtgt tccgcggtcc tcctcgtata gaaactcgga   5040
ccactctgag acaaaggctc gcgtccaggc cagcacgaag gaggctaagt gggagggta    5100
gcggtcgttg tccactaggg ggtccactcg ctccagggtg tgaagacaca tgtcgccctc   5160
ttcggcatca aggaaggtga ttggtttgta ggtgtaggcc acgtgaccgg tgttcctga    5220
agggggggcta taaaggggg tggggcgcg ttcgtcctca ctctcttccg catcgctgtc    5280
tgcgagggcc agctgttggg gtgagtactc cctctgaaaa gcgggcatga cttctgcgct   5340
aagattgtca gtttccaaaa acgaggagga tttgatattc acctggcccg cggtgatgcc   5400
tttgagggtg gccgcatcca tctggtcaga aaagacaatc ttttttgttgt caagcttggt   5460
ggcaaacgac ccgtagaggg cgttggacag caacttggcg atggagcgca gggtttggtt   5520
tttgtcgcga tcggcgcgct ccttggccgc gatgtttagc tgcacgtatt cgcgcgcaac   5580
gcaccgccat tcgggaaaga cggtggtgcg ctcgtcgggc accaggtgca cgcgccaacc   5640
gcggttgtgc agggtgacaa ggtcaacgct ggtggctacc tctccgcgta ggcgctcgtt   5700
ggtccagcag aggcggccgc ccttgcgcga gcagaatggc ggtaggggt ctagctgcgt    5760
ctcgtccggg gggtctgcgt ccacggtaaa gaccccgggc agcaggcgcg cgtcgaagta   5820
gtctatcttg catccttgca agtctagcgc ctgctgccat gcgcgggcgg caagcgcgcg   5880
ctcgtatggg ttgagtgggg gaccccatgg catgggtgg gtgagcgcgg aggcgtacat    5940
gccgcaaatg tcgtaaacgt agaggggctc tctgagtatt ccaagatatg tagggtagca   6000
tcttccaccg cggatgctgg cgcgcacgta atcgtatagt tcgtgcgagg gagcgaggag   6060
gtcgggaccg aggttgctac gggcgggctg ctctgctcgg aagactatct gcctgaagat   6120
ggcatgtgag ttggatgata tggttggacg ctggaagacg ttgaagctgg cgtctgtgag   6180
acctaccgcg tcacgcacga aggaggcgta ggagtcgcgc agcttgttga ccagctcggc   6240
ggtgacctgc acgtctaggg cgcagtagtc cagggtttcc ttgatgatgt catacttatc   6300
ctgtcccttt ttttttccaca gctcgcggtt gaggacaaac tcttcgcggt cttttccagta   6360
ctcttggatc ggaaacccgt cggcctccga acggtaagag cctagcatgt agaactggtt   6420
gacggcctgg taggcgcagc atcccttttc tacgggtagc gcgtatgcct gcgcggcctt   6480
ccggcatgac cagcatgaag ggcacgagct gcttcccaaa ggcccccatc caagtatagg   6540
tctctacatc gtaggtgaca aagagacgct cggtgcgagg atgcgagccg atcgggaaga   6600
actggatctc ccgccaccaa ttggaggagt ggctattgat gtggtgaaag tagaagtccc   6660
tgcgacgggc cgaacactcg tgctggcttt tgtaaaaacg tgcgcagtac tggcagcggt   6720
gcacgggctg tacatcctgc acgaggttga cctgacgacc gcgcacaagg aagcagagtg   6780
ggaatttgag cccctcgcct ggcgggtttg gctggtggtc ttctacttcg gctgcttgtc   6840
cttgaccgtc tggctgctcg aggggagtta cggtggatcg gaccaccacg ccgcgcgagc   6900
ccaaagtcca gatgtccgcg cggcgcggtc ggagcttgat gacaacatcg cgcagatggg   6960
agctgtccat ggtctggagc tcccgcgcgc tcaggtcagg cggagctcc tgcaggttta    7020
cctcgcatag acgggtcagg gcgcgggcta gatccaggtg atacctaatt tccagggggct  7080
```

```
ggttggtggc ggcgtcgatg gcttgcaaga ggccgcatcc ccgcggcgcg actacggtac   7140
cgcgcggcgg gcggtgggcc gcggggtgt ccttggatga tgcatctaaa agcggtgacg    7200
cgggcgagcc cccggaggta gggggggctc cggacccgcc gggagagggg gcagggcac    7260
gtcggcgccg cgcgcgggca ggagctggtg ctgcgcgcgt aggttgctgg cgaacgcgac   7320
gacgcggcgg ttgatctcct gaatctggcg cctctgcgtg aagacgacgg gcccggtgag   7380
cttgaacctg aaagagagtt cgacagaatc aatttcggtg tcgttgacgg cggcctggcg   7440
caaaatctcc tgcacgtctc ctgagttgtc ttgataggcg atctcggcca tgaactgctc   7500
gatctcttcc tcctggagat ctccgcgtcc ggctcgctcc acggtggcgg cgaggtcgtt   7560
ggaaatgcgg gccatgagct gcgagaaggc gttgaggcct ccctcgttcc agacgcggct   7620
gtagaccacg ccccccttcgg catcgcgggc gcgcatgacc acctgcgcga gattgagctc   7680
cacgtgccgg gcgaagacgg cgtagtttcg caggcgctga agaggtagt tgagggtggt    7740
ggcggtgtgt tctgccacga agaagtacat aacccagcgt cgcaacgtgg attcgttgat   7800
aattgttgtg taggtactcc gccgccgagg gacctgagcg agtccgcatc gaccggatcg   7860
gaaaacctct cgagaaaggc gtctaaccag tcacagtcgc aaggtaggct gagcaccgtg   7920
gcgggcggca gcgggcggcg gtcggggttg tttctggcgg aggtgctgct gatgatgtaa   7980
ttaaagtagg cggtcttgag acggcggatg gtcgacagaa gcaccatgtc cttgggtccg   8040
gcctgctgaa tgcgcaggcg gtcggccatg ccccaggctt cgttttgaca tcggcgcagg   8100
tctttgtagt agtcttgcat gagcctttct accggcactt cttcttctcc ttcctcttgt   8160
cctgcatctc ttgcatctat cgctgcgcg cggcggagt ttggccgtag gtggcgccct     8220
cttcctccca tgcgtgtgac cccgaagccc ctcatcggct gaagcagggc taggtcggcg   8280
acaacgcgct cggctaatat ggcctgctgc acctgcgtga gggtagactg gaagtcatcc   8340
atgtccacaa gcggtggta tgcgcccgtg ttgatggtgt aagtgcagtt ggccataacg    8400
gaccagttaa cggtctggtg acccggctgc gagagctcgg tgtacctgag acgcgagtaa   8460
gccctcgagt caaatacgta gtcgttgcaa gtccgcacca ggtactggta tcccaccaaa   8520
aagtgcggcg gcggctggcg gtagagggggc cagcgtaggg tggccggggc tccggggcg    8580
agatcttcca acataaggcg atgatatccg tagatgtacc tggacatcca ggtgatgccg    8640
gcggcggtgg tggaggcgcg cggaaagtcg cggacgcgt tccagatgtt gcgcagcggc    8700
aaaaagtgct ccatggtcgg gacgctctgg ccggtcaggc gcgcgcaatc gttgacgctc   8760
tagcgtgcaa aaggagagcc tgtaagcggg cactcttccg tggtctggtg gataaattcg   8820
caagggtatc atggcggacg accggggttc gagccccgta tccggccgtc cgccgtgatc   8880
catgcggtta ccgcccgcgt gtcgaaccca ggtgtgcgac gtcagacaac ggggagtgc    8940
tccttttggc ttccttccag gcgcggcggc tgctgcgcta gcttttttgg ccactggccg   9000
cgcgcagcgt aagcggttag gctggaaagc gaaagcatta agtggctcgc tccctgtagc   9060
cggagggtta ttttccaagg gttgagtcgc gggacccccg gttcgagtct cggaccggcc   9120
ggactgcggc gaacggggt ttgcctcccc gtcatgcaag accccgcttg caaattcctc    9180
cggaaacagg gacgagcccc tttttgctt ttcccagatg catccggtgc tgcggcagat    9240
gcgcccccct cctcagcagc ggcaagagca agagcagcgg cagacatgca gggcaccctc   9300
ccctcctcct accgcgtcag gaggggcgac atccgcggtt gacgcggcag cagatggtga   9360
ttacgaaccc ccgcggcgcc gggccggca ctacctggac ttggaggagg gcgagggcct    9420
ggcgcggcta ggagcgccct ctcctgagcg gcacccaagg gtgcagctga agcgtgatac   9480
```

```
gcgtgaggcg tacgtgccgc ggcagaacct gtttcgcgac cgcgaggag aggagcccga    9540
ggagatgcgg gatcgaaagt tccacgcagg gcgcgagctg cggcatggcc tgaatcgcga    9600
gcggttgctg cgcgaggagg actttgagcc cgacgcgcga accgggatta gtcccgcgcg    9660
cgcacacgtg gcggccgccg acctggtaac cgcatacgag cagacggtga accaggagat    9720
taactttcaa aaaagcttta acaaccacgt gcgtacgctt gtggcgcgcg aggaggtggc    9780
tataggactg atgcatctgt gggactttgt aagcgcgctg gagcaaaacc caaatagcaa    9840
gccgctcatg gcgcagctgt tccttatagt gcagcacagc agggacaacg aggcattcag    9900
ggatgcgctg ctaaacatag tagagcccga gggccgctgg ctgctcgatt tgataaacat    9960
cctgcagagc atagtggtgc aggagcgcag cttgagcctg gctgacaagg tggccgccat   10020
caactattcc atgcttagcc tgggcaagtt ttacgcccgc aagatatacc ataccccctta  10080
cgttcccata gacaaggagg taaagatcga ggggttctac atgcgcatgg cgctgaaggt   10140
gcttaccttg agcgacgacc tgggcgttta tcgcaacgag cgcatccaca aggccgtgag   10200
cgtgagccgg cggcgcgagc tcagcgaccg cgagctgatg cacagcctgc aaagggccct   10260
ggctggcacg ggcagcggcg atagagaggc cgagtcctac tttgacgcgg cgctgacct    10320
gcgctgggcc ccaagccgac gcgccctgga ggcagctggg gccggacctg ggctggcggt   10380
ggcacccgcg cgcgctggca acgtcggcgg cgtggaggaa tatgacgagg acgatgagta   10440
cgagccagag gacggcgagt actaagcggt gatgtttctg atcagatgat gcaagacgca   10500
acggacccgg cggtgcgggc ggcgctgcag agccagccgt ccggccttaa ctccacggac   10560
gactggcgcc aggtcatgga ccgcatcatg tcgctgactg cgcgcaatcc tgacgcgttc   10620
cggcagcagc cgcaggccaa ccggctctcc gcaattctgg aagcggtggt cccggcgcgc   10680
gcaaacccca cgcacgagaa ggtgctggcg atcgtaaacg cgctggccga aaacagggcc   10740
atccggcccg acgaggccgg cctggtctac gacgcgctgc ttcagcgcgt ggctcgttac   10800
aacagcggca acgtgcagac caacctggac cggctggtgg gggatgtgcg cgaggccgtg   10860
gcgcagcgtg agcgcgcgca gcagcagggc aacctgggct ccatggttgc actaaacgcc   10920
ttcctgagta cacagcccgc caacgtgccg cggggacagg aggactacac caactttgtg   10980
agcgcactgc ggctaatggt gactgagaca ccgcaaagtg aggtgtacca gtctgggcca   11040
gactattttt tccagaccag tagacaaggc ctgcagaccg taaacctgag ccaggctttc   11100
aaaaacttgc aggggctgtg gggggtgcgg gctcccacag gcgaccgcgc gaccgtgtct   11160
agcttgctga cgcccaactc gcgcctgttg ctgctgctaa tagcgcccct cacggacagt   11220
ggcagcgtgt cccgggacac ataccctaggt cacttgctga cactgtaccg cgaggccata   11280
ggtcaggcgc atgtggacga gcatactttc caggagatta caagtgtcag ccgcgcgctg   11340
gggcaggagg acacgggcag cctggaggca accctaaact acctgctgac caaccggcgg   11400
cagaagatcc cctcgttgca cagtttaaac agcgaggagg agcgcatttt gcgctacgtg   11460
cagcagagcg tgagccttaa cctgatgcgc gacggggtaa cgcccagcgt ggcgctggac   11520
atgaccgcgc gcaacatgga accgggcatg tatgcctcaa ccggccgtt tatcaaccgc   11580
ctaatggact acttgcatcg cgcggccgcc gtgaaccccg agtatttcac caatgccatc   11640
ttgaacccgc actggctacc gccccctggt ttctacaccg gggattcga ggtgcccgag    11700
ggtaacgatg gattcctctg gacgacata acgacagcg tgttttcccc gcaaccgcag    11760
accctgctag agttgcaaca gcgcgagcag gcagaggcgg cgctgcgaaa ggaaagcttc   11820
```

```
cgcaggccaa gcagcttgtc cgatctaggc gctgcggccc cgcggtcaga tgctagtagc    11880
ccatttccaa gcttgatagg gtctcttacc agcactcgca ccacccgccc gcgcctgctg    11940
ggcgaggagg agtacctaaa caactcgctg ctgcagccgc agcgcgaaaa aaacctgcct    12000
ccggcatttc ccaacaacgg gatagagagc ctagtggaca agatgagtag atggaagacg    12060
tacgcgcagg agcacaggga cgtgccaggc ccgcgcccgc ccacccgtcg tcaaaggcac    12120
gaccgtcagc ggggtctggt gtgggaggac gatgactcgg cagacgacag cagcgtcctg    12180
gatttgggag ggagtggcaa cccgtttgcg caccttcgcc ccaggctggg gagaatgttt    12240
taaaaaaaaa aaagcatgat gcaaaataaa aaactcacca aggccatggc accgagcgtt    12300
ggttttcttg tattccccctt agtatgcggc gcgcggcgat gtatgaggaa ggtcctcctc    12360
cctcctacga gagtgtggtg agcgcggcgc cagtggcggc ggcgctgggt tctcccttcg    12420
atgctcccct ggacccgccg tttgtgcctc cgcggtacct gcggcctacc gggggagaa    12480 acagcatccg ttactctgag ttggcacccc tattcgacac cacccgtgtg tacctggtgg    12540
acaacaagtc aacggatgtg gcatccctga actaccagaa cgaccacagc aactttctga    12600
ccacggtcat tcaaaacaat gactacagcc cggggaggc aagcacacag accatcaatc    12660
ttgacgaccg gtcgcactgg ggcggcgacc tgaaaaccat cctgcatacc aacatgccaa    12720
atgtgaacga gttcatgttt accaataagt ttaaggcgcg ggtgatggtg tcgcgcttgc    12780
ctactaagga caatcaggtg gagctgaaat acgagtgggt ggagttcacg ctgcccgagg    12840
gcaactactc cgagaccatg accatagacc ttatgaacaa cgcgatcgtg gagcactact    12900
tgaaagtggg cagacagaac ggggttctgg aaagcgacat cggggtaaag tttgacaccc    12960
gcaacttcag actggggttt gaccccgtca ctggtcttgt catgcctggg gtatatacaa    13020
acgaagcctt ccatccagac atcattttgc tgccaggatg cggggtggac ttcacccaca    13080
gccgcctgag caacttgttg ggcatccgca agcggcaacc cttccaggag ggctttagga    13140
tcacctacga tgatctggag ggtggtaaca ttccccgcact gttggatgtg gacgcctacc    13200
aggcgagctt gaaagatgac accgaacagg gcggggtgg cgcaggcggc agcaacagca    13260
gtggcagcgc cgcggaagag aactccaacg cggcagccgc ggcaatgcag ccggtggagg    13320
acatgaacga tcatgccatt cgcggcgaca cctttgccac acgggctgag gagaagcgcg    13380
ctgaggccga agcagcggcc gaagctgccg cccccgctgc gcaacccgag gtcgagaagc    13440
ctcagaagaa accggtgatc aaacccctga cagaggacag caagaaacgc agttacaacc    13500
taataagcaa tgcacagcacc ttcacccagt accgcagctg gtaccttgca tacaactacg    13560
gcgaccctca gaccggaatc cgctcatgga ccctgctttg cactcctgac gtaacctgcg    13620
gctcggagca ggtctactgg tcgttgccag acatgatgca agaccccgtg accttccgct    13680
ccacgcgcca gatcagcaac tttccggtgg tgggcgccga gctgttgccc gtgcactcca    13740
agagcttcta caacgaccag gccgtctact cccaactcat ccgccagttt acctctctga    13800
cccacgtgtt caatcgcttt cccgagaacc agatttttgc gcgcccgcca gcccccacca    13860
tcaccaccgt cagtgaaaac gttcctgctc tcacagatca cgggacgcta ccgctgcgca    13920
acagcatcgg aggagtccag cgagtgacca ttactgacgc cagacgccgc acctgcccct    13980
acgtttacaa ggccctgggc atagtctcgc cgcgcgtcct atcgagccgc acttttttgag    14040 caagcatgtc catccttata tcgcccagca ataacacagg ctggggcctg cgcttcccaa    14100
gcaagatgtt tggcggggcc aagaagcgct ccgaccaaca cccagtgcgc gtgcgcgggc    14160
actaccgcgc gccctggggc gcgcacaaac gcggccgcac tgggcgcacc accgtcgatg    14220
```

```
acgccatcga cgcggtggtg gaggaggcgc gcaactacac gcccacgccg ccaccagtgt   14280
ccacagtgga cgcggccatt cagaccgtgg tgcgcggagc ccggcgctat gctaaaatga   14340
agagacggcg gaggcgcgta gcacgtcgcc accgccgccg acccggcact gccgcccaac   14400
gcgcggcggc ggccctgctt aaccgcgcac gtcgcaccgg ccgacgggcg gccatgcggg   14460
ccgctcgaag gctggccgcg ggtattgtca ctgtgccccc caggtccagg cgacgagcgg   14520
ccgccgcagc agccgcggcc attagtgcta tgactcaggg tcgcaggggc aacgtgtatt   14580
gggtgcgcga ctcggttagc ggcctgcgcg tgcccgtgcg cacccgcccc ccgcgcaact   14640
agattgcaag aaaaaactac ttagactcgt actgttgtat gtatccagcg gcggcggcgc   14700
gcaacgaagc tatgtccaag cgcaaaatca agaagagat gctccaggtc atcgcgccgg   14760
agatctatgg ccccccgaag aaggaagagc aggattacaa gccccgaaag ctaaagcggg   14820
tcaaaaagaa aaagaaagat gatgatgatg aacttgacga cgaggtggaa ctgctgcacg   14880
ctaccgcgcc caggcgacgg gtacagtgga aggtcgacg cgtaaaacgt gttttgcgac   14940
ccggcaccac cgtagtcttt acgcccggtg agcgctccac ccgcacctac aagcgcgtgt   15000
atgatgaggt gtacgcgac gaggacctgc ttgagcaggc caacgagcgc ctcggggagt   15060
ttgcctacgg aaagcggcat aaggacatgc tggcgttgcc gctggacgag ggcaacccaa   15120
cacctagcct aaagcccgta acactgcagc aggtgctgcc cgcgcttgca ccgtccgaag   15180
aaaagcgcgg cctaaagcgc gagtctggtg acttggcacc caccgtgcag ctgatggtac   15240
ccaagcgcca gcgactggaa gatgtcttgg aaaaaatgac cgtggaacct gggctggagc   15300
ccgaggtccg cgtgcggcca atcaagcagg tggcgccggg actgggcgtg cagaccgtgg   15360
acgttcagat acccactacc agtagcacca gtattgccac cgccacagag ggcatggaga   15420
cacaaacgtc cccggttgcc tcagcggtgg cggatgccgc ggtgcaggcg gtcgctgcgg   15480
ccgcgtccaa gacctctacg gaggtgcaaa cggacccgtg gatgtttcgc gtttcagccc   15540
cccggcgccc gcgccgttcg aggaagtacg gcgccgccag cgcgctactg cccgaatatg   15600
ccctacatcc ttccattgcg cctaccccg gctatcgtgg ctacacctac cgccccagaa   15660
gacgagcaac tacccgacgc cgaaccacca ctggaacccg ccgccgccgt cgccgtcgcc   15720
agcccgtgct ggccccgatt tccgtgcgca gggtggctcg cgaaggaggc aggaccctgg   15780
tgctgccaac agcgcgctac caccccagca tcgtttaaaa gccggtcttt gtggttcttg   15840
cagatatggc cctcacctgc cgcctccgtt tcccggtgcc gggattccga ggaagaatgc   15900
accgtaggag gggcatggcc ggccacggcc tgacgggcgg catgcgtcgt gcgcaccacc   15960
ggcggcggcg cgcgtcgcac cgtcgcatgc gcggcggtat cctgcccctc cttattccac   16020
tgatcgccgc ggcgattggc gccgtgcccg gaattgcatc cgtggccttg caggcgcaga   16080
gacactgatt aaaaacaagt tgcatgtgga aaaatcaaaa taaaaagtct ggactctcac   16140
gctcgcttgg tcctgtaact attttgtaga atggaagaca tcaactttgc gtctctggcc   16200
ccgcgacacg gctcgcgccc gttcatggga aactggcaag atatcggcac cagcaatatg   16260
agcggtggcg ccttcagctg gggctcgctg tggagcggca ttaaaaattt cggttccacc   16320
gttaagaact atggcagcaa ggcctggaac agcagcacag gccagatgct gagggataag   16380
ttgaaagagc aaaatttcca acaaaaggtg gtagatggcc tggcctctgg cattagcggg   16440
gtggtggacc tggccaacca ggcagtgcaa aataagatta acagtaagct tgatccccgc   16500
cctcccgtag aggagcctcc accggccgtg gagacagtgt ctccagaggg gcgtggcgaa   16560
```

```
aagcgtccgc gccccgacag ggaagaaact ctggtgacgc aaatagacga gcctccctcg    16620
tacgaggagg cactaaagca aggcctgccc accacccgtc ccatcgcgcc catggctacc    16680
ggagtgctgg gccagcacac acccgtaacg ctggacctgc ctcccccgc cgacacccag     16740 cagaaacctg tgctgccagg cccgaccgcc gttgttgtaa cccgtcctag ccgcgcgtcc    16800
ctgcgccgcg ccgccagcgg tccgcgatcg ttgcggcccg tagccagtgg caactggcaa    16860
agcacactga acagcatcgt gggtctgggg gtgcaatccc tgaagcgccg acgatgcttc    16920
tgatagctaa cgtgtcgtat gtgtgtcatg tatgcgtcca tgtcgccgcc agaggagctg    16980
ctgagccgcc gcgcgcccgc tttccaagat ggctacccct tcgatgatgc cgcagtggtc    17040
ttacatgcac atctcgggcc aggacgcctc ggagtacctg agcccgggc tggtgcagtt     17100 tgcccgcgcc accgagacgt acttcagcct gaataacaag tttagaaacc ccacggtggc    17160
gcctacgcac gacgtgacca cagaccggtc ccagcgtttg acgctgcggt tcatccctgt    17220
ggaccgtgag gatactgcgt actcgtacaa ggcgcggttc accctagctg tgggtgataa    17280
ccgtgtgctg gacatggctt ccacgtactt tgacatccgc ggcgtgctgg acaggggccc    17340
tacttttaag ccctactctg gcactgccta caacgccctg gctcccaagg gtgccccaaa    17400
tccttgcgaa tgggatgaag ctgctactgc tcttgaaata aacctagaag aagaggacga    17460
tgacaacgaa gacgaagtag acgagcaagc tgagcagcaa aaaactcacg tatttgggca    17520
ggcgccttat tctggtataa atattacaaa ggagggtatt caaataggtg tcgaaggtca    17580
aacacctaaa tatgccgata aaacatttca acctgaacct caaataggag aatctcagtg    17640
gtacgaaaca gaaattaatc atgcagctgg gagagtccta aaaaagacta ccccaatgaa    17700
accatgttac ggttcatatg caaaacccac aaatgaaaat ggagggcaag gcattcttgt    17760
aaagcaacaa aatggaaagc tagaaagtca agtggaaatg caattttct caactactga     17820 ggcagccgca ggcaatggtg ataacttgac tcctaaagtg gtattgtaca gtgaagatgt    17880
agatatagaa accccagaca ctcatatttc ttacatgccc actattaagg aaggtaactc    17940
acgagaacta atgggccaac aatctatgcc caacaggcct aattacattg cttttaggga    18000 caatttatt ggtctaatgt attacaacag cacgggtaat atgggtgttc tggcgggcca     18060
agcatcgcag ttgaatgctg ttgtagattt gcaagacaga aacacagagc tttcatacca    18120
gcttttgctt gattccattg gtgatagaac caggtacttt tctatgtgga atcaggctgt    18180
tgacagctat gatccagatg ttagaattat tgaaaatcat ggaactgaag atgaacttcc    18240
aaattactgc tttccactgg gaggtgtgat taatacagag actcttacca aggtaaaacc    18300
taaaacaggt caggaaaatg gatgggaaaa agatgctaca gaattttcag ataaaaatga    18360
aataagagtt ggaaataatt ttgccatgga aatcaatcta aatgccaacc tgtggagaaa    18420
tttcctgtac tccaacatag cgctgtattt gcccgacaag ctaaagtaca gtccttccaa    18480
cgtaaaaatt tctgataacc caaacaccta cgactacatg aacaagcgag tggtggctcc    18540
cgggctagtg gactgctaca ttaaccttgg agcacgctgg tcccttgact atatggacaa    18600
cgtcaaccca tttaaccacc accgcaatgc tggcctgcgc taccgctcaa tgttgctggg    18660
caatggtcgc tatgtgccct ccacatccaa ggtgcctcag aagttctttg ccattaaaaa    18720
cctccttctc ctgccgggct catacaccta cgagtggaac ttcaggaagg atgttaacat    18780
ggttctgcag agctccctag gaaatgacct aagggttgac ggagccagca ttaagtttga    18840
tagcatttgc ctttacgcca ccttcttccc catggcccac aacaccgcct ccacgcttga    18900
ggccatgctt agaaacgaca ccaacgacca gtcctttaac gactatctct ccgccgccaa    18960
```

```
catgctctac cctatacccg ccaacgctac caacgtgccc atatccatcc cctcccgcaa   19020
ctgggcggct ttccgcggct gggccttcac gcgccttaag actaaggaaa ccccatcact   19080
gggctcgggc tacgacccct attacaccta ctctggctct ataccctacc tagatggaac   19140
cttttacctc aaccacacct ttaagaaggt ggccattacc tttgactctt ctgtcagctg   19200
gcctggcaat gaccgcctgc ttaccccccaa cgagtttgaa attaagcgct cagttgacgg   19260
ggagggttac aacgttgccc agtgtaacat gaccaaagac tggttcctgg tacaaatgct   19320
agctaactat aacattggct accagggctt ctatatccca gagagctaca aggaccgcat   19380
gtactccttc tttagaaaact tccagcccat gagccgtcag gtggtggatg atactaaata   19440
caaggactac caacaggtgg gcatcctaca ccaacacaac aactctggat tgttggcta    19500 ccttgccccc accatgcgcg aaggacaggc ctaccctgct aacttcccct atccgcttat   19560
aggcaagacc gcagttgaca gcattaccca gaaaaagttt ctttgcgatc gcaccctttg   19620
gcgcatccca ttctccagta actttatgtc catgggcgca ctcacagacc tgggccaaaa   19680
ccttctctac gccaactccg cccacgcgct agacatgact tttgaggtgg atcccatgga   19740
cgagcccacc cttctttatg ttttgtttga agtctttgac gtggtccgtg tgcaccagcc   19800
gcaccgcggc gtcatcgaaa ccgtgtacct gcgcacgccc ttctcggccg gcaacgccac   19860
aacataaaga agcaagcaac atcaacaaca gctgccgcca tgggctccag tgagcaggaa   19920
ctgaaagcca ttgtcaaaga tcttggttgt gggccatatt ttttgggcac ctatgacaag   19980
cgctttccag gctttgtttc tccacacaag ctcgcctgcg ccatagtcaa tacgccggt    20040 cgcgagactg ggggcgtaca ctggatggcc tttgcctgga acccgcactc aaaaacatgc   20100
tacctctttg agccctttgg cttttctgac cagcgactca agcaggttta ccagtttgag   20160
tacgagtcac tcctgcgccg tagcgccatt gcttcttccc ccgaccgctg tataacgctg   20220
gaaaagtcca cccaaagcgt acaggggccc aactcggccg cctgtggact attctgctgc   20280
atgtttctcc acgcctttgc caactggccc caaactccca tggatcacaa ccccaccatg   20340
aaccttatta ccggggtacc caactccatg ctcaacagtc cccaggtaca gcccaccctg   20400
cgtcgcaacc aggaacagct ctacagcttc ctggagcgcc actcgcccta cttccgcagc   20460
cacagtgcgc agattaggag cgccacttct ttttgtcact tgaaaaacat gtaaaaataa   20520
tgtactagag acactttcaa taaaggcaaa tgcttttatt tgtacactct cgggtgatta   20580
tttaccccca cccttgccgt ctgcgccgtt taaaaatcaa aggggttctg ccgcgcatcg   20640
ctatgcgcca ctggcaggga cacgttgcga tactggtgtt tagtgctcca cttaaactca   20700
ggcacaacca tccgcggcag ctcggtgaag ttttcactcc acaggctgcg caccatcacc   20760
aacgcgttta gcaggtcggg cgccgatatc ttgaagtcgc agttggggcc tccgccctgc   20820
gcgcgcgagt tgcgatacac agggttgcag cactggaaca ctatcagcgc cgggtggtgc   20880
acgctggcca gcacgctctt gtcggagatc agatccgcgt ccaggtcctc cgcgttgctc   20940
agggcgaacg gagtcaactt tggtagctgc cttcccaaaa agggcgcgtg cccaggcttt   21000
gagttgcact cgcaccgtag tggcatcaaa aggtgaccgt gccggtctg ggcgttagga    21060 tacagcgcct gcataaaagc cttgatctgc ttaaagcca cctgagcctt tgcgccttca    21120
gagaagaaca tgccgcaaga cttgccggaa aactgattgg ccggacaggc cgcgtcgtgc   21180
acgcagcacc ttgcgtcggt gttggagatc tgcaccacat tcggccccca ccggttcttc   21240
acgatcttgg ccttgctaga ctgctccttc agcgcgcgct gcccgttttc gctcgtcaca   21300
```

-continued

```
tccatttcaa tcacgtgctc cttatttatc ataatgcttc cgtgtagaca cttaagctcg    21360
ccttcgatct cagcgcagcg gtgcagccac aacgcgcagc ccgtgggctc gtgatgcttg    21420
taggtcacct ctgcaaacga ctgcaggtac gcctgcagga atcgccccat catcgtcaca    21480
aaggtcttgt tgctggtgaa ggtcagctgc aacccgcggt gctcctcgtt cagccaggtc    21540
ttgcatacgg ccgccagagc ttccacttgg tcaggcagta gtttgaagtt cgcctttaga    21600
tcgttatcca cgtggtactt gtccatcagc gcgcgcgcag cctccatgcc cttctcccac    21660
gcagacacga tcggcacact cagcgggttc atcaccgtaa tttcactttc cgcttcgctg    21720
ggctcttcct cttcctcttg cgtccgcata ccacgcgcca ctgggtcgtc ttcattcagc    21780
cgccgcactg tgcgcttacc tccttttgcca tgcttgatta gcaccggtgg gttgctgaaa    21840
cccaccattt gtagcgccac atcttctctt tcttcctcgc tgtccacgat tacctctggt    21900
gatggcgggc gctcgggctt gggagaaggg cgcttctttt tcttcttggg cgcaatggcc    21960
aaatccgccg ccgaggtcga tggccgcggg ctgggtgtgc gcggcaccag cgcgtcttgt    22020
gatgagtctt cctcgtcctc ggactcgata cgccgcctca tccgcttttt tgggggcgcc    22080
cggggaggcg gcggcgacgg ggacggggac gacacgtcct ccatggttgg gggacgtcgc    22140
gccgcaccgc gtccgcgctc ggggggtggtt tcgcgctgct cctcttcccg actggccatt    22200
tccttctcct ataggcagaa aaagatcatg gagtcagtcg agaagaagga cagcctaacc    22260 gcccctctg agttcgccac caccgcctcc accgatgccg ccaacgcgcc taccaccttc    22320
cccgtcgagg cacccccgct tgaggaggag gaagtgatta tcgagcagga cccaggtttt    22380
gtaagcgaag acgacgagga ccgctcagta ccaacagagg ataaaaagca agaccaggac    22440
aacgcagagg caaacgagga acaagtcggg cgggggacg aaaggcatgg cgactaccta    22500
gatgtgggag acgacgtgct gttgaagcat ctgcagcgcc agtgcgccat tatctgcgac    22560
gcgttgcaag agcgcagcga tgtgcccctc gccatagcgg atgtcagcct tgcctacgaa    22620
cgccacctat tctcaccgcg cgtacccccc aaacgccaag aaaacggcac atgcgagccc    22680
aacccgcgcc tcaacttcta ccccgtattt gccgtgccag aggtgcttgc cacctatcac    22740 atcttttttcc aaaactgcaa gataccccta tcctgccgtg ccaaccgcag ccgagcggac    22800
aagcagctgg ccttgcggca gggcgctgtc atacctgata tcgcctcgct caacgaagtg    22860
ccaaaaatct ttgagggtct tggacgcgac gagaagcgcg cggcaaacgc tctgcaacag    22920
gaaaacagcg aaaatgaaag tcactctgga gtgttggtgg aactcgaggg tgacaacgcg    22980
cgcctagccg tactaaaacg cagcatcgag gtcacccact ttgcctaccc ggcacttaac    23040 ctaccccca aggtcatgag cacagtcatg agtgagctga tcgtgcgccg tgcgcagccc    23100
ctggagaggg atgcaaattt gcaagaacaa acagaggagg gcctacccgc agttggcgac    23160
gagcagctag cgcgctggct tcaaacgcgc gagcctgccg acttggagga gcgacgcaaa    23220
ctaatgatgg ccgcagtgct cgttaccgtg gagcttgagt gcatgcagcg gttctttgct    23280
gacccggaga tgcagcgcaa gctagaggaa acattgcact acacctttcg acagggctac    23340
gtacgccagg cctgcaagat ctccaacgtg gagctctgca acctggtctc ctaccttgga    23400
attttgcacg aaaaccgcct tgggcaaaac gtgcttcatt ccacgctcaa gggcgaggcg    23460
cgccgcgact acgtccgcga ctgcgtttac ttatttctat gctacacctg gcagacggcc    23520
atgggcgttt ggcagcagtg cttggaggag tgcaacctca aggagctgca gaaactgcta    23580
aagcaaaact tgaaggacct atggacggcc ttcaacgagc gctccgtggc cgcgcacctg    23640
gcggacatca tttttccccga acgcctgctt aaaaaccctgc aacagggtct gccagacttc    23700
```

```
accagtcaaa gcatgttgca gaactttagg aactttatcc tagagcgctc aggaatcttg    23760
cccgccacct gctgtgcact tcctagcgac tttgtgccca ttaagtaccg cgaatgccct    23820
ccgccgcttt ggggccactg ctaccttctg cagctagcca actaccttgc ctaccactct    23880
gacataatgg aagacgtgag cggtgacggt ctactggagt gtcactgtcg ctgcaaccta    23940
tgcaccccgc accgctccct ggtttgcaat tcgcagctgc ttaacgaaag tcaaattatc    24000
ggtacctttg agctgcaggg tccctcgcct gacgaaaagt ccgcggctcc ggggttgaaa    24060
ctcactccgg ggctgtggac gtcggcttac cttcgcaaat ttgtacctga ggactaccac    24120
gcccacgaga ttaggttcta cgaagaccaa tcccgcccgc ctaatgcgga gcttaccgcc    24180
tgcgtcatta cccagggcca cattcttggc caattgcaag ccatcaacaa agcccgccaa    24240
gagtttctgc tacgaaaggg acggggggtt tacttggacc cccagtccgg cgaggagctc    24300
aacccaatcc ccccgccgcc gcagccctat cagcagcagc cgcgggccct tgcttcccag    24360
gatggcaccc aaaaagaagc tgcagctgcc gccgccaccc acggacgagg aggaatactg    24420
ggacagtcag gcagaggagg ttttggacga ggaggaggag gacatgatgg aagactggga    24480
gagcctagac gaggaagctt ccgaggtcga agaggtgtca gacgaaacac cgtcaccctc    24540
ggtcgcattc ccctcgccgg cgccccagaa atcggcaacc ggttccagca tggctacaac    24600
ctccgctcct caggcgccgc cggcactgcc cgttcgccga cccaaccgta gatgggacac    24660
cactggaacc agggccggta agtccaagca gccgccgccg ttagcccaag agcaacaaca    24720
gcgccaaggc taccgctcat ggcgcgggca caagaacgcc atagttgctt gcttgcaaga    24780
ctgtggggc aacatctcct tcgcccgccg ctttcttctc taccatcacg gcgtggcctt    24840
cccccgtaac atcctgcatt actaccgtca tctctacagc ccatactgca ccggcggcag    24900
cggcagcaac agcagcggcc acacagaagc aaaggcgacc ggatagcaag actctgacaa    24960
agcccaagaa atccacagcg gcggcagcag caggaggagg agcgctgcgt ctggcgccca    25020
acgaacccgt atcgacccgc gagcttagaa acaggatttt tcccactctg tatgctatat    25080
ttcaacagag caggggccaa gaacaagagc tgaaaataaa aaacaggtct ctgcgatccc    25140
tcacccgcag ctgcctgtat cacaaaagcg aagatcagct tcggcgcacg ctggaagacg    25200
cggaggctct cttcagtaaa tactgcgcgc tgactcttaa ggactagttt cgcgcccttt    25260
ctcaaattta agcgcgaaaa ctacgtcatc tccagcggcc acaccggcg ccagcacctg    25320
ttgtcagcgc cattatgagc aaggaaattc ccacgcccta catgtggagt taccagccac    25380
aaatgggact tgcggctgga gctgcccaag actactcaac ccgaataaac tacatgagcg    25440
cgggacccca catgatatcc cgggtcaacg gaatacgcgc ccaccgaaac cgaattctcc    25500
tggaacaggc ggctattacc accacacctc gtaataacct taatcccgt agttggcccg    25560
ctgccctggt gtaccaggaa agtcccgctc ccaccactgt ggtacttccc agagacgccc    25620
aggccgaagt tcagatgact aactcagggg cgcagcttgc gggcggcttt cgtcacaggg    25680
tgcggtcgcc cggcagggt ataactcacc tgacaatcag agggcgaggt attcagctca    25740
acgacgagtc ggtgagctcc tcgcttggtc tccgtccgga cgggacattt cagatcggcg    25800
gcgccggccg ctcttcattc acgcctcgtc aggcaatcct aactctgcag acctcgtcct    25860
ctgagccgcg ctctggaggc attggaactc tgcaatttat tgaggagttt gtgccatcgg    25920
tctactttaa ccccttctcg ggacctcccg gccactatcc ggatcaattt attcctaact    25980
ttgacgcggt aaaggactcg gcggacggct acgactgaat gttaagtgga gaggcagagc    26040
```

-continued

```
aactgcgcct gaaacacctg gtccactgtc gccgccacaa gtgctttgcc cgcgactccg    26100
gtgagttttg ctactttgaa ttgcccgagg atcatatcga gggcccggcg cacggcgtcc    26160
ggcttaccgc ccagggagag cttgcccgta gcctgattcg ggagtttacc cagcgccccc    26220
tgctagttga gcgggacagg ggaccctgtg ttctcactgt gatttgcaac tgtcctaacc    26280
ctggattaca tcaagatcct ctagttaatg tcaggtcgcc taagtcgatt aactagagta    26340
cccggggatc ttattccctt taactaataa aaaaaaataa taaagcatca cttacttaaa    26400
atcagttagc aaatttctgt ccagtttatt cagcagcacc tccttgccct cctcccagct    26460
ctggtattgc agcttcctcc tggctgcaaa ctttctccac aatctaaatg gaatgtcagt    26520
ttcctcctgt tcctgtccat ccgcacccac tatcttcatg ttgttgcaga tgaagcgcgc    26580
aagaccgtct gaagatacct tcaacccccgt gtatccatat gacacggaaa ccggtcctcc    26640
aactgtgcct tttcttactc ctcccttttgt atccccccaat gggtttcaag agagtccccc    26700
tggggtactc tctttgcgcc tatccgaacc tctagttacc tccaatggca tgcttgcgct    26760
caaaatgggc aacggcctct ctctggacga ggccggcaac cttacctccc aaaatgtaac    26820
cactgtgagc ccacctctca aaaaaaccaa gtcaaacata aacctggaaa tatctgcacc    26880
cctcacagtt acctcagaag ccctaactgt ggctgccgcc gcacctctaa tggtcgcggg    26940
caacacactc accatgcaat cacaggcccc gctaaccgtg cacgactcca aacttagcat    27000
tgccacccaa ggaccccctca cagtgtcaga aggaaagcta gccctgcaaa catcaggccc    27060
cctcaccacc accgatagca gtaccettac tatcactgcc tcaccccctc taactactgc    27120
cactggtagc ttgggcattg acttgaaaga gcccatttat acacaaaatg gaaaactagg    27180
actaaagtac ggggctccctt tgcatgtaac agacgaccta aacactttga ccgtagcaac    27240
tggtccaggt gtgactatta ataatacttc cttgcaaact aaagttactg gagccttggg    27300
ttttgattca caaggcaata tgcaacttaa tgtagcagga ggactaagga ttgattctca    27360
aaacagacgc cttatacttg atgttagtta tccgtttgat gctcaaaacc aactaaatct    27420
aagactagga cagggccctc ttttttataaa ctcagcccac aacttggata ttaactacaa    27480
caaaggcctt tacttgttta cagcttcaaa caattccaaa aagcttgagg ttaacctaag    27540
cactgccaag gggttgatgt tgacgctac agccatagcc attaatgcag gagatgggct    27600
tgaatttggt tcacctaatg caccaaacac aaatcccctc aaaacaaaaa ttggccatgg    27660
cctagaattt gattcaaaca aggctatggt tcctaaacta ggaactggcc ttagttttga    27720
cagcacaggt gccattacag taggaaacaa aaataatgat aagctaactt tgtgaccac    27780 accagctcca tctcctaact gtagactaaa tgcagagaaa gatgctaaac tcactttggt    27840
cttaacaaaa tgtggcagtc aaatacttgc tacagtttca gttttggctg ttaaaggcag    27900
tttggctcca atatctggaa cagttcaaag tgctcatctt attataagat tgacgaaaa    27960 tggagtgcta ctaaacaatt ccttcctgga cccagaatat tggaacttta gaaatggaga    28020
tcttactgaa ggcacagcct atacaaacgc tgttggattt atgcctaacc tatcagctta    28080
tccaaaatct cacggtaaaa ctgccaaaag taacattgtc agtcaagttt acttaaacgg    28140
agacaaaact aaacctgtaa cactaaccat tacactaaac ggtacacagg aaacaggaga    28200
cacaactcca agtgcatact ctatgtcatt ttcatgggac tggtctggcc acaactacat    28260
taatgaaata tttgccacat cctcttacac tttttcatac attgcccaag aataaagaat    28320
cgtttgtgtt atgtttcaac gtgttatttt ttcaattgca gaaaatttca gtcatttttt    28380
cattcagtag tatagcccca ccaccacata gcttatacag atcaccgtac cttaatcaaa    28440
```

```
ctcacagaac cctagtattc aacctgccac ctccctccca acacacagag tacacagtcc    28500
tttctccccg gctggcctta aaaagcatca tatcatgggt aacagacata ttcttaggtg    28560
ttatattcca cacggtttcc tgtcgagcca aacgctcatc agtgatatta ataaactccc    28620
cgggcagctc acttaagttc atgtcgctgt ccagctgctg agccacaggc tgctgtccaa    28680
cttgcggttg cttaacgggc ggcgaaggag aagtccacgc ctacatgggg gtagagtcat    28740
aatcgtgcat caggataggg cggtggtgct gcagcagcgc gcgaataaac tgctgccgcc    28800
gccgctccgt cctgcaggaa tacaacatgg cagtggtctc ctcagcgatg attcgcaccg    28860
cccgcagcat aaggcgcctt gtcctccggg cacagcagcg caccctgatc tcacttaaat    28920
cagcacagta actgcagcac agcaccacaa tattgttcaa aatcccacag tgcaaggcgc    28980
tgtatccaaa gctcatggcg gggaccacag aacccacgtg gccatcatac cacaagcgca    29040
ggtagattaa gtggcgaccc ctcataaaca cgctggacat aaacattacc tcttttggca    29100
tgttgtaatt caccacctcc cggtaccata taaacctctg attaaacatg gcgccatcca    29160
ccaccatcct aaaccagctg gccaaaacct gcccgccggc tatacactgc agggaaccgg    29220
gactggaaca atgacagtgg agagcccagg actcgtaacc atggatcatc atgctcgtca    29280
tgatatcaat gttggcacaa cacaggcaca cgtgcataca cttcctcagg attacaagct    29340
cctcccgcgt tagaaccata tcccagggaa caacccattc ctgaatcagc gtaaatccca    29400
cactgcaggg aagacctcgc acgtaactca cgttgtgcat tgtcaaagtg ttacattcgg    29460
gcagcagcgg atgatcctcc agtatggtag cgcgggtttc tgtctcaaaa ggaggtagac    29520
gatccctact gtacggagtg cgccgagaca accgagatcg tgttggtcgt agtgtcatgc    29580
caaatggaac gccggacgta gtcatatttc ctgaagcaaa accaggtgcg ggcgtgacaa    29640
acagatctgc gtctccggtc tcgccgctta gatcgctctg tgtagtagtt gtagtatatc    29700
cactctctca aagcatccag gcgcccctg gcttcgggtt ctatgtaaac tccttcatgc    29760
gccgctgccc tgataacatc caccaccgca gaataagcca cacccagcca acctacacat    29820
tcgttctgcg agtcacacac gggaggagcg ggaagagctg gaagaaccat gttttttttt    29880
ttattccaaa agattatcca aaacctcaaa atgaagatct attaagtgaa cgcgctcccc    29940
tccggtggcg tggtcaaact ctacagccaa agaacagata atggcatttg taagatgttg    30000
cacaatggct tccaaaaggc aaacggccct cacgtccaag tggacgtaaa ggctaaaccc    30060
ttcagggtga atctcctcta taaacattcc agcaccttca accatgccca ataattctc     30120
atctcgccac cttctcaata tatctctaag caaatcccga atattaagtc cggccattgt    30180
aaaaatctgc tccagagcgc cctccacctt cagcctcaag cagcgaatca tgattgcaaa    30240
aattcaggtt cctcacagac ctgtataaga ttcaaaagcg gaacattaac aaaaataccg    30300
cgatcccgta ggtcccttcg cagggccagc tgaacataat cgtgcaggtc tgcacggacc    30360
agcgcggcca cttccccgcc aggaaccatg acaaagaac ccacactgat tatgacacgc      30420
atactcggag ctatgctaac cagcgtagcc ccgatgtaag cttgttgcat gggcggcgat    30480
ataaatgca aggtgctgct caaaaaatca ggcaaagcct cgcgcaaaaa agaaagcaca     30540
tcgtagtcat gctcatgcag ataaaggcag gtaagctccg gaaccaccac agaaaaagac    30600
accattttc tctcaaacat gtctgcgggt ttctgcataa acacaaaata aaataacaaa     30660
aaacattta acattagaa gcctgtctta caacaggaaa acaacccctt ataagcataa      30720
gacggactac ggccatgccg gcgtgaccgt aaaaaaactg gtcaccgtga ttaaaaagca    30780
```

```
ccaccgacag ctcctcggtc atgtccggag tcataatgta agactcggta acacatcag    30840 gttgattcac atcggtcagt gctaaaaagc gaccgaaata gcccggggga atacataccc    30900
gcaggcgtag agacaacatt acagccccca taggaggtat aacaaaatta ataggagaga    30960
aaaacacata acacctgaaa aaccctcct gcctaggcaa aatagcaccc tcccgctcca     31020
gaacaacata cagcgcttcc acagcggcag ccataacagt cagccttacc agtaaaaaag    31080
aaaacctatt aaaaaacac cactcgacac ggcaccagct caatcagtca cagtgtaaaa     31140
aagggccaag tgcagagcga gtatatatag gactaaaaaa tgacgtaacg gttaaagtcc    31200
acaaaaaaca cccagaaaac cgcacgcgaa cctacgccca gaaacgaaag ccaaaaaacc    31260
cacaacttcc tcaaatcgtc acttccgttt tcccacgtta cgtcacttcc cattttaaga    31320
aaactacaat tcccaacaca tacaagttac tccgccctaa aacctacgtc acccgccccg    31380
ttcccacgcc ccgcgccacg tcacaaactc caccccctca ttatcatatt ggcttcaatc    31440
caaaataagg tatattattg atgat                                         31465
```

<210> SEQ ID NO 17
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Gly Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Ala Ala Ala Ala
145                 150                 155
```

<210> SEQ ID NO 18
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Met Pro Gly Asp Thr Pro Thr Leu His Glu Tyr Met Leu Asp Leu Gln
1               5                   10                  15
```

```
Pro Glu Thr Thr Asp Leu Tyr Gly Tyr Glu Gln Leu Asn Asp Ser Ser
             20                  25                  30

Glu Glu Glu Asp Glu Ile Asp Gly Pro Ala Gly Gln Ala Ala Pro Asp
         35                  40                  45

Arg Ala His Tyr Asn Ile Val Thr Phe Cys Cys Lys Cys Asp Ser Thr
     50                  55                  60

Leu Arg Arg Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                 85                  90                  95

Lys Pro
```

<210> SEQ ID NO 19
<211> LENGTH: 1147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
aagcagaggc tcgtttagtg aaccgtcaga tggtaccgtt taaactcgag gtcgacggta      60
tcgataagct tgatatcgaa ttcgagctcg gtaccccggg ttagtataaa agcagacatt     120
ttatgcacca aaagagaact gcaatgtttc aggacccaca ggagcgaccc agaaagttac     180
cacagttatg cacagagctg caaacaacta tacatgatat aatattagaa tgtgtgtact     240
gcaagcaaca gttactgcga cgtgaggtat atgactttgc ttttcgggat ggatgcatag     300
tatatagaga tgggaatcca tatgctgtat gtgataaatg tttaaagttt tattctaaaa     360
ttagtgagta tagacattat tgttatagtt tgtatggaac aacattagaa cagcaataca     420
acaaaccgtt gtgtgatttg ttaattaggt gtattaactg tcaaaagcca ctgtgtcctg     480
aagaaaagca aagacatctg acaaaaagc aaagattcca taatataagg ggtcggtgga     540
ccggtcgatg tatgtcttgt tgcagatcat caagaactcg tagagcagcc gcggcgtaat     600
catgcctgga gatacaccta cattgcatga atatatgtta gatttgcaac cagagacaac     660
tgatctctac ggttatgagc aattaaatga cagctcagag gaggaggatg aaatagatgg     720
tccagctgga caagcagcac cggacagagc ccattacaat attgtaacct tttgttgcaa     780
gtgtgactct acgcttcgga ggtgcgtaca aagcacacac gtagacattc gtactttgga     840
agacctgtta atgggcacac taggaattgt gtgccccatc tgttctcaga accataatc     900 taccatggct gatcctgcag catgcaagct ggggatccac tagttctaga gcggccgcca     960
cagcggggag atcagacatg atagatacat tgatgagttt ggacaaacca caactagaat    1020
gcagtgaaaa aatgctttat tgtgaaattg tgatgctatt gcttatttgt acattatagc    1080
tgcaataaac agttacaaca acaattgcat tcatttatgt tcaggtcagg gggaaggtgt    1140
ggaggtt                                                              1147
```

<210> SEQ ID NO 20
<211> LENGTH: 31361
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg      180 gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tactgtaata gtaatcaatt     360
acggggtcat tagttcatag cccatatatg gagttccgcg ttacataact tacggtaaat     420
ggcccgcctg gctgaccgcc caacgacccc cgcccattga cgtcaataat gacgtatgtt     480
cccatagtaa cgccaatagg gacttttccat tgacgtcaat gggtggagta tttacggtaa     540 actgccccact tggcagtaca tcaagtgtat catatgccaa gtacgccccc tattgacgtc     600
aatgacggta aatggcccgc ctggcattat gcccagtaca tgaccttatg ggactttcct     660
acttggcagt acatctacgt attagtcatc gctattacca tggtgatgcg gttttggcag     720
tacatcaatg ggcgtggata gcggtttgac tcacggggat ttccaagtct ccaccccatt     780
gacgtcaatg ggagtttgtt ttggcaccaa aatcaacggg actttccaaa atgtcgtaac     840
aactccgccc cattgacgca aatgggcggt aggcgtgtac ggtgggaggt ctatataagc     900
agagctggtt tagtgaaccg tcagatccgc tagagatctg gtaccgtcga cgcggccgct     960
cgagcctaag cttctagatg catgctcgag cggccgccag tgtgatggat atctgcagaa    1020
ttcgcccttg ctaagcagag gctcgtttag tgaaccgtca gatggtaccg tttaaactcg    1080
aggtcgacgg tatcgataag cttgatatcg aattcgagct cggtacccccc ggttagtata    1140 aaagcagaca ttttatgcac caaaagagaa ctgcaatgtt tcaggaccca caggagcgac    1200
ccagaaagtt accacagtta tgcacagagc tgcaaacaac tatacatgat ataatattag    1260
aatgtgtgta ctgcaagcaa cagttactgc gacgtgaggt atatgacttt gcttttcggg    1320
atggatgcat agtatataga gatgggaatc catatgctgt atgtgataaa tgtttaaagt    1380
tttattctaa aattagtgag tatagacatt attgttatag tttgtatgga acaacattag    1440
aacagcaata caacaaaccg ttgtgtgatt tgttaattag gtgtattaac tgtcaaaagc    1500
cactgtgtcc tgaagaaaag caaagacatc tggacaaaaa gcaagattc cataatataa    1560 ggggtcggtg gaccggtcga tgtatgtctt gttgcagatc atcaagaact cgtagagcag    1620
ccgcggcgta atcatgcctg gagatacacc tacattgcat gaatatatgt tagatttgca    1680
accagagaca actgatctct acggttatga gcaattaaat gacagctcag aggaggagga    1740
tgaaatagat ggtccagctg gacaagcagc accggacaga gcccattaca atattgtaac    1800
cttttgttgc aagtgtgact ctacgcttcg gaggtgcgta caaagcacac acgtagacat    1860
tcgtactttg gaagacctgt taatgggcac actaggaatt gtgtgcccca tctgttctca    1920
gaaaccataa tctaccatgg ctgatcctgc agcatgcaag ctggggatcc actagttcta    1980
gagcggccgc cacagcgggg agatcagaca tgatagatac attgatgagt ttggacaaac    2040
cacaactaga atgcagtgaa aaaatgcttt attgtgaaat tgtgatgcta ttgcttattt    2100
gtacattata gctgcaataa acagttacaa caacaattgc attcatttat gttcaggtca    2160
gggggaaggt gtggaggttc gatccaccgg atctagataa ctgatcataa tcagccatac    2220
cacatttgta gaggttttac ttgctttaaa aaacctccca cacctccccc tgaacctgaa    2280
acataaaatg aatgcaattg ttgttgttaa cttgttatt gcagcttata atggttacaa    2340
ataaagcaat agcatcacaa atttcacaaa taaagcattt ttttcactgc attctagttg    2400
```

```
tggtttgtcc aaactcatca atgtatctta acgcggatct ggaaggtgct gaggtacgat    2460
gagacccgca ccaggtgcag accctgcgag tgtggcggta acatattag gaaccagcct     2520 gtgatgctgg atgtgaccga ggagctgagg cccgatcact tggtgctggc ctgcacccgc    2580
gctgagtttg gctctagcga tgaagataca gattgaggta ctgaaatgtg tgggcgtggc    2640
ttaagggtgg gaaagaatat ataaggtggg ggtcttatgt agttttgtat ctgttttgca    2700
gcagccgccg ccgccatgag caccaactcg tttgatggaa gcattgtgag ctcatatttg    2760
acaacgcgca tgcccccatg ggccggggtg cgtcagaatg tgatgggctc cagcattgat    2820
ggtcgccccg tcctgcccgc aaactctact accttgacct acgagaccgt gtctggaacg    2880
ccgttggaga ctgcagcctc cgccgccgct tcagccgctg cagccaccgc ccgcgggatt    2940
gtgactgact ttgctttcct gagcccgctt gcaagcagtg cagcttcccg ttcatccgcc    3000
cgcgatgaca agttgacggc tcttttggca caattggatt ctttgacccg ggaacttaat    3060
gtcgtttctc agcagctgtt ggatctgcgc cagcaggttt ctgccctgaa ggcttcctcc    3120
cctcccaatg cggtttaaaa cataaataaa aaaccagact ctgtttggat ttggatcaag    3180
caagtgtctt gctgtctta tttagggggtt ttgcgcgcgc ggtaggcccg ggaccagcgg    3240
tctcggtcgt tgagggtcct gtgtatttt tccaggacgt ggtaaaggtg actctggatg    3300
ttcagataca tgggcataag cccgtctctg gggtggaggt agcaccactg cagagcttca    3360
tgctgcgggg tggtgttgta gatgatccag tcgtagcagg agcgctgggc gtggtgccta    3420
aaaatgtctt tcagtagcaa gctgattgcc aggggcaggc ccttggtgta agtgtttaca    3480
aagcggttaa gctgggatgg gtgcatacgt ggggatatga gatgcatctt ggactgtatt    3540
tttaggttgg ctatgttccc agccatatcc ctccggggat tcatgttgtg cagaaccacc    3600
agcacagtgt atccggtgca cttgggaaat ttgtcatgta gcttagaagg aaatgcgtgg    3660
aagaacttgg agacgccctt gtgacctcca agattttcca tgcattcgtc cataatgatg    3720
gcaatgggcc cacgggcggc ggcctgggcg aagatatttc tgggatcact aacgtcatag    3780
ttgtgttcca ggatgagatc gtcataggcc attttttacaa agcgcgggcg gagggtgcca   3840
gactgcggta taatggttcc atccggccca ggggcgtagt taccctcaca gatttgcatt    3900
tcccacgctt tgagttcaga tggggggatc atgtctacct gcgggcgat gaagaaaacg     3960 gtttccgggg taggggagat cagctgggaa gaaagcaggt tcctgagcag ctgcgactta    4020
ccgcagccgg tgggcccgta aatcacacct attaccggct gcaactggta gttaagagag    4080
ctgcagctgc cgtcatccct gagcaggggg gccacttcgt taagcatgtc cctgactcgc    4140 atgtttccc tgaccaaatc cgccagaagg cgctcgccgc ccagcgatag cagttcttgc    4200
aaggaagcaa agttttcaa cggtttgaga ccgtccgccg taggcatgct tttgagcgtt     4260
tgaccaagca gttccaggcg gtcccacagc tcggtcacct gctctacggc atctcgatcc    4320
agcatatctc ctcgtttcgc gggttgggc ggctttcgct gtacggcagt agtcggtgct     4380
cgtccagacg ggccagggtc atgtctttcc acgggcgcag ggtcctcgtc agcgtagtct    4440
gggtcacggt gaagggtgc gctccggct gcgcgctggc cagggtgcgc ttgaggctgg      4500
tcctgctggt gctgaagcgc tgccggtctt cgccctgcgc gtcggccagg tagcatttga    4560
ccatggtgtc atagtccagc ccctccgcgg cgtggccctt ggcgcgcagc ttgcccttgg    4620
aggaggcgcc gcacgagggg cagtgcagac ttttgagggc gtagagcttg ggcgcgagaa    4680
ataccgattc cggggagtag gcatccgcgc cgcaggcccc gcagacggtc tcgcattcca    4740
```

```
cgagccaggt gagctctggc cgttcggggt caaaaaccag gtttccccca tgcttttttga    4800
tgcgtttctt acctctggtt tccatgagcc ggtgtccacg ctcggtgacg aaaaggctgt    4860
ccgtgtcccc gtatacagac ttgagaggcc tgtcctcgag cggtgttccg cggtcctcct    4920
cgtatagaaa ctcggaccac tctgagacaa aggctcgcgt ccaggccagc acgaaggagg    4980
ctaagtggga ggggtagcgg tcgttgtcca ctaggggtc  cactcgctcc agggtgtgaa    5040
gacacatgtc gccctcttcg gcatcaagga aggtgattgg tttgtaggtg taggccacgt    5100
gaccgggtgt tcctgaaggg gggctataaa aggggggtgg ggcgcgttcg tcctcactct    5160
cttccgcatc gctgtctgcg agggccagct gttggggtga gtactccctc tgaaaagcgg    5220
gcatgacttc tgcgctaaga ttgtcagttt ccaaaaacga ggaggatttg atattcacct    5280
ggcccgcggt gatgcctttg agggtggccg catccatctg gtcagaaaag acaatctttt    5340
tgttgtcaag cttggtggca aacgacccgt agagggcgtt ggacagcaac ttggcgatgg    5400
agcgcagggt ttggtttttg tcgcgatcgg cgcgctcctt ggccgcgatg tttagctgca    5460
cgtattcgcg cgcaacgcac cgccattcgg gaaagacggt ggtgcgctcg tcgggcacca    5520
ggtgcacgcg ccaaccgcgg ttgtgcaggg tgacaaggtc aacgctggtg gctacctctc    5580
cgcgtaggcg ctcgttggtc cagcagaggc ggccgcccct tgcgcgagcag aatgccggta    5640
gggggtctag ctgcgtctcg tccgggggt  ctgcgtccac ggtaaagacc ccgggcagca    5700
ggcgcgcgtc gaagtagtct atcttgcatc cttgcaagtc tagcgcctgc tgccatgcgc    5760
gggcggcaag cgcgcgctcg tatgggttga gtggggacc  ccatggcatg gggtgggtga    5820
gcgcggaggc gtacatgccg caaatgtcgt aaacgtagag gggctctctg agtattccaa    5880
gatatgtagg gtagcatctt ccaccgcgga tgctggcgcg cacgtaatcg tatagttcgt    5940
gcgagggagc gaggaggtcg ggaccgaggt tgctacgggc gggctgctct gctcggaaga    6000
ctatctgcct gaagatggca tgtgagttgg atgatatggt tggacgctgg aagacgttga    6060
agctggcgtc tgtgagacct accgcgtcac gcacgaagga ggcgtaggag tcgcgcagct    6120
tgttgaccag ctcggcggtg acctgcacgt ctagggcgca gtagtccagg gtttccttga    6180
tgatgtcata cttatcctgt cccttttttt tccacagctc gcggttgagg acaaactctt    6240
cgcggtcttt ccagtactct tggatcggaa accgtcggc  ctccgaacgg taagagccta    6300
gcatgtagaa ctggttgacg gcctggtagg cgcagcatcc cttttctacg ggtagcgcgt    6360
atgcctgcgc ggccttccgg catgaccagc atgaagggca cgagctgctt cccaaaggcc    6420
cccatccaag tataggtctc tacatcgtag gtgacaaaga gacgctcggt gcgaggatgc    6480
gagccgatcg ggaagaactg gatctcccgc caccaattgg aggagtggct attgatgtgg    6540
tgaaagtaga agtccctgcg acgggccgaa cactcgtgct ggcttttgta aaaacgtgcg    6600
cagtactggc agcggtgcac gggctgtaca tcctgcacga ggttgacctg acgaccgcgc    6660
acaaggaagc agagtgggaa tttgagcccc tcgcctggcg ggtttggctg gtggtcttct    6720
acttcggctg cttgtccttg accgtctggc tgctcgaggg gagttacggt ggatcggacc    6780
accacgccgc gcgagcccaa agtccagatg tccgcgcgcg gcggtcggag cttgatgaca    6840
acatcgcgca gatgggagct gtccatggtc tggagctccc gcggcgtcag gtcaggcggg    6900
agctcctgca ggtttacctc gcatagacgg gtcagggcgc gggctagatc caggtgatac    6960
ctaatttcca ggggctggtt ggtggcggcg tcgatggctt gcaagaggcc gcatccccgc    7020
ggcgcgacta cggtaccgcg cggcgggcgg tgggccgcgg gggtgtcctt ggatgatgca    7080
tctaaaagcg gtgacgcggg cgagcccccg gaggtagggg gggctccgga cccgccggga    7140
```

```
gaggggggcag gggcacgtcg gcgccgcgcg cgggcaggag ctggtgctgc gcgcgtaggt    7200
tgctggcgaa cgcgacgacg cggcggttga tctcctgaat ctggcgcctc tgcgtgaaga    7260
cgacgggccc ggtgagcttg aacctgaaag agagttcgac agaatcaatt tcggtgtcgt    7320
tgacggcggc ctggcgcaaa atctcctgca cgtctcctga gttgtcttga taggcgatct    7380
cggccatgaa ctgctcgatc tcttcctcct ggagatctcc gcgtccggct cgctccacgg    7440
tggcggcgag gtcgttggaa atgcgggcca tgagctgcga gaaggcgttg aggcctccct    7500
cgttccagac gcggctgtag accacgcccc cttcggcatc gcgggcgcgc atgaccacct    7560
gcgcgagatt gagctccacg tgccgggcga agacggcgta gtttcgcagg cgctgaaaga    7620
ggtagttgag ggtggtggcg gtgtgttctg ccacgaagaa gtacataacc cagcgtcgca    7680
acgtggattc gttgataatt gttgtgtagg tactccgccg ccgagggacc tgagcgagtc    7740
cgcatcgacc ggatcggaaa acctctcgag aaaggcgtct aaccagtcac agtcgcaagg    7800
taggctgagc accgtggcgg gcggcagcgg gcggcggtcg gggttgtttc tggcggaggt    7860
gctgctgatg atgtaattaa agtaggcggt cttgagacgg cggatggtcg acagaagcac    7920
catgtccttg ggtccggcct gctgaatgcg caggcggtcg gccatgcccc aggcttcgtt    7980
ttgacatcgg cgcaggtctt tgtagtagtc ttgcatgagc ctttctaccg gcacttcttc    8040 ttctcccttcc tcttgtcctg catctcttgc atctatcgct gcggcggcgg cggagtttgg    8100
ccgtaggtgg cgccctcttc ctcccatgcg tgtgaccccg aagcccctca tcggctgaag    8160
cagggctagg tcgcgacaa cgcgctcggc taatatggcc tgctgcacct gcgtgagggt    8220
agactggaag tcatccatgt ccacaaagcg gtggtatgcg cccgtgttga tggtgtaagt    8280
gcagttggcc ataacggacc agttaacggt ctggtgaccc ggctgcgaga gctcggtgta    8340
cctgagacgc gagtaagccc tcgagtcaaa tacgtagtcg ttgcaagtcc gcaccaggta    8400
ctggtatccc accaaaaagt gcggcggcgg ctggcggtag aggggccagc gtaggtggc    8460 cggggctccg ggggcgagat cttccaacat aaggcgatga tatccgtaga tgtacctgga    8520
catccaggtg atgccggcgg cggtggtgga ggcgcgcgga aagtcgcgga cgcggttcca    8580
gatgttgcgc agcggcaaaa agtgctccat ggtcgggacg ctctgccgg tcaggcgcgc    8640 gcaatcgttg acgctctagc gtgcaaaagg agagcctgta agcgggcact cttccgtggt    8700
ctggtggata aattcgcaag ggtatcatgg cggacgaccg gggttcgagc cccgtatccg    8760
gccgtccgcc gtgatccatg cggttaccgc ccgcgtgtcg aacccaggtg tgcgacgtca    8820
gacaacgggg gagtgctcct tttggcttcc ttccaggcgc ggcggctgct gcgctagctt    8880
ttttggccac tggccgcgcg cagcgtaagc ggttaggctg gaaagcgaaa gcattaagtg    8940
gctcgctccc tgtagccgga gggttatttt ccaaggttg agtcgcggga ccccggttc    9000 gagtctcgga ccggccggac tgcggcgaac gggggtttgc ctccccgtca tgcaagaccc    9060
cgcttgcaaa ttcctccgga aacagggacg agccccttt ttgcttttcc cagatgcatc    9120
cggtgctgcg gcagatgcgc cccctcctc agcagcggca agagcaagag cagcggcaga    9180
catgcagggc accctcccct cctcctaccg cgtcaggagg ggcgacatcc gcggttgacg    9240
cggcagcaga tggtgattac gaaccccgc ggcgccgggc ccggcactac ctggacttgg    9300
aggagggcga gggcctggcg cggctaggag cgccctctcc tgagcggcac ccaagggtgc    9360
agctgaagcg tgatacgcgt gaggcgtacg tgccgcggca gaacctgttt cgcgaccgcg    9420
agggagagga gcccgaggag atgcgggatc gaaagttcca cgcagggcgc gagctgcggc    9480
```

```
atggcctgaa tcgcgagcgg ttgctgcgcg aggaggactt tgagcccgac gcgcgaaccg    9540
ggattagtcc cgcgcgcgca cacgtggcgg ccgccgacct ggtaaccgca tacgagcaga    9600
cggtgaacca ggagattaac tttcaaaaaa gctttaacaa ccacgtgcgt acgcttgtgg    9660
cgcgcgagga ggtggctata ggactgatgc atctgtggga cttgtaagc gcgctggagc    9720
aaaacccaaa tagcaagccg ctcatggcgc agctgttcct tatagtgcag cacagcaggg    9780
acaacgaggc attcagggat gcgctgctaa acatagtaga gcccgagggc cgctggctgc    9840
tcgatttgat aaacatcctg cagagcatag tggtgcagga gcgcagcttg agcctggctg    9900
acaaggtggc cgccatcaac tattccatgc ttagcctggg caagttttac gcccgcaaga    9960
tataccatac cccttacgtt cccatagaca aggaggtaaa gatcgagggg ttctacatgc   10020
gcatggcgct gaaggtgctt accttgagcg acgacctggg cgtttatcgc aacgagcgca   10080
tccacaaggc cgtgagcgtg agccggcggc gcgagctcag cgaccgcgag ctgatgcaca   10140
gcctgcaaag ggccctggct ggcacgggca cggcgatag agaggccgag tcctactttg   10200
acgcgggcgc tgacctgcgc tgggcccaa gccgacgcgc cctggaggca gctggggccg   10260
gacctgggct ggcggtggca cccgcgcgcg ctggcaacgt cggcggcgtg gaggaatatg   10320
acgaggacga tgagtacgag ccagaggacg gcgagtacta agcggtgatg tttctgatca   10380
gatgatgcaa gacgcaacgg acccggcggt gcgggcggcg ctgcagagcc agccgtccgg   10440
ccttaactcc acgacgact ggcgccaggt catggaccgc atcatgtcgc tgactgcgcg   10500
caatcctgac gcgttccggc agcagccgca ggccaaccgg ctctccgcaa ttctggaagc   10560
ggtggtcccg gcgcgcgcaa accccacgca cgagaaggtg ctggcgatcg taaacgcgct   10620
ggccgaaaac agggccatcc ggcccgacga ggccggcctg gtctacgacg cgctgcttca   10680
gcgcgtggct cgttacaaca gcggcaacgt gcagaccaac ctggaccggc tggtggggga   10740
tgtgcgcgag gccgtggcgc agcgtgagcg cgcgcagcag cagggcaacc tgggctccat   10800
ggttgcacta aacgccttcc tgagtacaca gcccgccaac gtgccgcggg acaggagga   10860
ctacaccaac tttgtgagcg cactgcggct aatggtgact gagacaccgc aaagtgaggt   10920
gtaccagtct gggccagact atttttttcca gaccagtaga caaggcctgc agaccgtaaa   10980
cctgagccag gctttcaaaa acttgcaggg gctgtggggg gtgcgggctc ccacaggcga   11040
ccgcgcgacc gtgtctagct tgctgacgcc caactcgcgc ctgttgctgc tgctaatagc   11100
gcccttcacg gacagtggca gcgtgtcccg ggacacatac ctaggtcact tgctgacact   11160
gtaccgcgag gccataggtc aggcgcatgt ggacgagcat actttccagg agattacaag   11220
tgtcagccgc gcgctgggc aggaggacac gggcagcctg gaggcaaccc taaactacct   11280
gctgaccaac cggcggcaga agatcccctc gttgcacagt ttaaacagcg aggaggagcg   11340
cattttgcgc tacgtgcagc agagcgtgag ccttaacctg atgcgcgacg gggtaacgcc   11400
cagcgtggcg ctggacatga ccgcgcgcaa catggaaccg gcatgtatg cctcaaaccg   11460
gccgtttatc aaccgcctaa tggactactt gcatcgcgcg gccgccgtga accccgagta   11520
tttcaccaat gccatcttga acccgcactg gctaccgccc ctggttttct acaccggggg   11580
attcgaggtg cccgagggta acgatggatt cctctgggac gacatagacg acagcgtgtt   11640
ttccccgcaa ccgcagaccc tgctagagtt gcaacagcgc gagcaggcag aggcggcgct   11700
gcgaaaggaa agcttccgca ggccaagcag cttgtccgat ctaggcgctg cggccccgcg   11760
gtcagatgct agtagcccat tccaagctt gatagggtct cttaccagca ctcgcaccac   11820
ccgcccgcgc ctgctgggcg aggaggagta cctaaacaac tcgctgctgc agccgcagcg   11880
```

```
cgaaaaaaac ctgcctccgg catttcccaa caacgggata gagagcctag tggacaagat   11940
gagtagatgg aagacgtacg cgcaggagca cagggacgtg ccaggcccgc gcccgcccac   12000
ccgtcgtcaa aggcacgacc gtcagcgggg tctggtgtgg gaggacgatg actcggcaga   12060
cgacagcagc gtcctggatt tgggagggag tggcaacccg tttgcgcacc ttcgccccag   12120
gctggggaga atgttttaaa aaaaaaaaag catgatgcaa aataaaaaac tcaccaaggc   12180
catggcaccg agcgttggtt ttcttgtatt ccccttagta tgcggcgcgc ggcgatgtat   12240
gaggaaggtc ctcctccctc ctacgagagt gtggtgagcg cggcgccagt ggcggcggcg   12300
ctgggttctc ccttcgatgc tccctggac ccgccgtttg tgcctccgcg gtacctgcgg    12360
cctaccgggg ggagaaacag catccgttac tctgagttgg caccctatt cgacaccacc    12420 cgtgtgtacc tggtgacaa caagtcaacg gatgtggcat ccctgaacta ccagaacgac    12480
cacagcaact ttctgaccac ggtcattcaa aacaatgact acagcccggg ggaggcaagc   12540
acacagacca tcaatcttga cgaccggtcg cactggggcg gcgacctgaa aaccatcctg   12600
cataccaaca tgccaaatgt gaacgagttc atgtttacca ataagtttaa ggcgcgggtg   12660
atggtgtcgc gcttgcctac taaggacaat caggtggagc tgaaatacga gtgggtggag   12720
ttcacgctgc ccgagggcaa ctactccgag accatgacca tagaccttat gaacaacgcg   12780
atcgtggagc actacttgaa agtgggcaga cagaacgggg ttctggaaag cgacatcggg   12840
gtaaagtttg acacccgcaa cttcagactg gggtttgacc ccgtcactgg tcttgtcatg   12900
cctggggtat atacaaacga agccttccat ccagacatca ttttgctgcc aggatgcggg   12960
gtggacttca cccacagccg cctgagcaac ttgttgggca tccgcaagcg gcaacccttc   13020
caggagggct ttaggatcac ctacgatgat ctggagggtg gtaacattcc cgcactgttg   13080
gatgtggacg cctaccaggc gagcttgaaa gatgacaccg aacagggcgg gggtggcgca   13140
ggcggcagca acagcagtgg cagcggcgcg gaagagaact ccaacgcggc agccgcggca   13200
atgcagccgg tggaggacat gaacgatcat gccattcgcg gcgacacctt tgccacacgg   13260
gctgaggaga agcgcgctga ggccgaagca gcggccgaag ctgccgcccc cgctgcgcaa   13320
cccgaggtcg agaagcctca gaagaaaccg gtgatcaaac ccctgacaga ggacagcaag   13380
aaacgcagtt acaacctaat aagcaatgac agcaccttca cccagtaccg cagctggtac   13440 cttcataca actacggcga ccctcagacc ggaatccgct catggaccct gctttgcact   13500
cctgacgtaa cctgcggctc ggagcaggtc tactggtcgt tgccagacat gatgcaagac   13560
cccgtgacct tccgctccac gcgccagatc agcaactttc cggtggtggg cgccgagctg   13620 ttgccgtgc actccaagag cttctacaac gaccaggccg tctactccca actcatccgc    13680
cagtttacct ctctgaccca cgtgttcaat cgctttcccg agaaccagat tttggcgcgc   13740
ccgccagccc ccaccatcac caccgtcagt gaaaacgttc ctgctctcac agatcacggg   13800
acgctaccgc tgcgcaacag catcggagga gtccagcgag tgaccattac tgacgccaga   13860
cgccgcacct gcccctacgt ttacaaggcc ctgggcatag tctcgccgcg cgtcctatcg   13920
agccgcactt tttgagcaag catgtccatc cttatatcgc ccagcaataa cacaggctgg   13980
ggcctgcgct tcccaagcaa gatgtttggc ggggccaaga agcgctccga ccaacaccca   14040
gtgcgcgtgc gcgggcacta ccgcgcgccc tgggcgcgc acaaacgcgg ccgcactggg    14100
cgcaccaccg tcgatgacgc catcgacgcg gtggtgaggg aggcgcgcaa ctacacgccc   14160
acgccgccac cagtgtccac agtggacgcg gccattcaga ccgtggtgcg cggagcccgg   14220
```

```
cgctatgcta aaatgaagag acggcggagg cgcgtagcac gtcgccaccg ccgccgaccc   14280
ggcactgccg cccaacgcgc ggcggcggcc ctgcttaacc gcgcacgtcg caccggccga   14340
cgggcggcca tgcgggccgc tcgaaggctg gccgcgggta ttgtcactgt gccccccagg   14400
tccaggcgac gagcggccgc cgcagcagcc gcggccatta gtgctatgac tcagggtcgc   14460
aggggcaacg tgtattgggt gcgcgactcg gttagcggcc tgcgcgtgcc cgtgcgcacc   14520
cgccccccgc gcaactagat tgcaagaaaa aactacttag actcgtactg ttgtatgtat   14580
ccagcggcgg cggcgcgcaa cgaagctatg tccaagcgca aaatcaaaga agagatgctc   14640
caggtcatcg cgccggagat ctatggcccc cgaagaagg aagagcagga ttacaagccc    14700
cgaaagctaa agcgggtcaa aagaaaaag aaagatgatg atgatgaact tgacgacgag    14760
gtggaactgc tgcacgctac cgcgcccagg cgacgggtac agtggaaagg tcgacgcgta   14820
aaacgtgttt tgcgacccgg caccaccgta gtctttacgc ccggtgagcg ctccacccgc   14880
acctacaagc gcgtgtatga tgaggtgtac ggcgacgagg acctgcttga gcaggccaac   14940
gagcgcctcg gggagtttgc ctacgaaaag cggcataagg acatgctggc gttgccgctg   15000
gacgagggca acccaacacc tagcctaaag cccgtaacac tgcagcaggt gctgcccgcg   15060
cttgcaccgt ccgaagaaaa gcgcggccta aagcgcgagt ctggtgactt ggcacccacc   15120
gtgcagctga tggtacccaa gcgccagcga ctggaagatg tcttggaaaa aatgaccgtg   15180
gaacctgggc tggagcccga ggtccgcgtg cggccaatca gcaggtggc gccgggactg     15240
ggcgtgcaga ccgtggacgt tcagataccc actaccagta gcaccagtat tgccaccgcc   15300
acagagggca tggagacaca aacgtccccg gttgcctcag cggtggcgga tgccgcggtg   15360
caggcggtcg ctgcggccgc gtccaagacc tctacggagg tgcaaacgga cccgtggatg   15420
tttcgcgttt cagccccccg gcgcccgcgc cgttcgagga agtacggcgc cgccagcgcg   15480
ctactgcccg aatatgccct acatccttcc attgcgccta cccccggcta tcgtggctac   15540
acctaccgcc ccagaagacg agcaactacc cgacgccgaa ccaccactgg aacccgccgc   15600
cgccgtcgcc gtcgccagcc cgtgctggcc ccgatttccg tgcgcagggt ggctcgcgaa   15660
ggaggcagga ccctggtgct gccaacagcg cgctaccacc ccagcatcgt ttaaaagccg   15720
gtctttgtgg ttcttgcaga tatggccctc acctgccgcc tccgtttccc ggtgccggga   15780
ttccgaggaa gaatgcaccg taggaggggc atggccggcc acggcctgac gggcggcatg   15840
cgtcgtgcgc accaccggcg gcggcgcgcg tcgcaccgtc gcatgcgcgg cggtatcctg   15900
cccctcctta ttccactgat cgccgcggcg attggcgccg tgcccggaat tgcatccgtg   15960
gccttgcagg cgcagagaca ctgattaaaa acaagttgca tgtggaaaaa tcaaaataaa   16020
aagtctggac tctcacgctc gcttggtcct gtaactattt tgtagaatgg aagacatcaa   16080
cttttgcgtct ctggccccgc gacacggctc gcgcccgttc atgggaaact ggcaagatat   16140
cggcaccagc aatatgagcg gtggcgcctt cagctgggc tcgctgtgga gcggcattaa     16200
aaatttcggt tccaccgtta agaactatgg cagcaaggcc tggaacagca gcacaggcca   16260
gatgctgagg gataagttga agagcaaaa tttccaacaa aggtggtag atggcctggc     16320
ctctggcatt agcggggtgg tggacctggc caaccaggca gtgcaaaata agattaacag   16380
taagcttgat ccccgccctc ccgtagagga gcctccaccg gccgtggaga cagtgtctcc   16440
agaggggcgt ggcgaaaagc gtccgcgccc cgacagggaa gaaactctgg tgacgcaaat   16500
agacgagcct ccctcgtacg aggaggcact aaagcaaggc ctgcccacca cccgtcccat   16560
cgcgcccatg gctaccggag tgctgggcca gcacacaccc gtaacgctgg acctgcctcc   16620
```

```
cccgccgac acccagcaga aacctgtgct gccaggcccg accgccgttg ttgtaacccg    16680
tcctagccgc gcgtccctgc gccgcgccgc cagcggtccg cgatcgttgc ggcccgtagc    16740
cagtggcaac tggcaaagca cactgaacag catcgtgggt ctgggggtgc aatccctgaa    16800
gcgccgacga tgcttctgat agctaacgtg tcgtatgtgt gtcatgtatg cgtccatgtc    16860
gccgccagag gagctgctga gccgccgcgc gcccgctttc caagatggct accccttcga    16920
tgatgccgca gtggtcttac atgcacatct cgggccagga cgcctcggag tacctgagcc    16980
ccgggctggt gcagtttgcc cgcgccaccg agacgtactt cagcctgaat aacaagttta    17040
gaaaccccac ggtggcgcct acgcacgacg tgaccacaga ccgtcccag cgtttgacgc    17100 tgcggttcat ccctgtggac cgtgaggata ctgcgtactc gtacaaggcg cggttcaccc    17160
tagctgtggg tgataaccgt gtgctggaca tggcttccac gtactttgac atccgcggcg    17220
tgctggacag gggccctact tttaagcccc actctggcac tgcctacaac gccctggctc    17280
ccaagggtgc cccaaatcct tgcgaatggg atgaagctgc tactgctctt gaaataaacc    17340
tagaagaaga ggacgatgac aacgaagacg aagtagacga gcaagctgag cagcaaaaaa    17400
ctcacgtatt tgggcaggcg ccttattctg gtataaatat tacaaaggag ggtattcaaa    17460
taggtgtcga aggtcaaaca cctaaatatg ccgataaaac atttcaacct gaacctcaaa    17520
taggagaatc tcagtggtac gaaacagaaa ttaatcatgc agctgggaga gtcctaaaaa    17580
agactacccc aatgaaacca tgttacggtt catatgcaaa acccacaaat gaaaatggag    17640
ggcaaggcat tcttgtaaag caacaaaatg gaaagctaga aagtcaagtg gaaatgcaat    17700
ttttctcaac tactgaggca gccgcaggca atggtgataa cttgactcct aaagtggtat    17760
tgtacagtga agatgtagat atagaaaccc cagacactca tatttcttac atgcccacta    17820
ttaaggaagg taactcacga gaactaatgg gccaacaatc tatgcccaac aggcctaatt    17880
acattgcttt tagggacaat tttattggtc taatgtatta caacagcacg ggtaatatgg    17940
gtgttctggc gggccaagca tcgcagttga atgctgttgt agatttgcaa gacagaaaca    18000
cagagctttc ataccagctt ttgcttgatt ccattggtga tagaaccagg tacttttcta    18060
tgtggaatca ggctgttgac agctatgatc cagatgttag aattattgaa atcatggaa    18120 ctgaagatga acttccaaat tactgctttc cactgggagg tgtgattaat acagagactc    18180
ttaccaaggt aaaacctaaa acaggtcagg aaaatggatg ggaaaaagat gctacagaat    18240
tttcagataa aaatgaaata agagttggaa ataattttgc catggaaatc aatctaaatg    18300
ccaacctgtg gagaaatttc ctgtactcca acatagcgct gtatttgccc gacaagctaa    18360
agtacagtcc ttccaacgta aaaatttctg ataacccaaa cacctacgac tacatgaaca    18420
agcgagtggt ggctcccggg ctagtggact gctacattaa ccttggagca cgctggtccc    18480
ttgactatat ggacaacgtc aacccattta ccaccaccg caatgctggc ctgcgctacc    18540
gctcaatgtt gctgggcaat ggtcgctatg tgcccttcca catccaggtg cctcagaagt    18600
tctttgccat taaaaacctc cttctcctgc cgggctcata cacctacgag tggaacttca    18660
ggaaggatgt taacatggtt ctgcagagct ccctaggaaa tgacctaagg gttgacggag    18720
ccagcattaa gtttgatagc atttgccttt acgccacctt cttccccatg gcccacaaca    18780
ccgcctccac gcttgaggcc atgcttagaa acgacaccaa cgaccagtcc tttaacgact    18840
atctctccgc cgccaacatg ctctacccta tacccgccaa cgctaccaac gtgcccatat    18900
ccatcccctc ccgcaactgg gcggctttcc gcggctgggc cttcacgcgc cttaagacta    18960
```

```
aggaaacccc atcactgggc tcgggctacg acccttatta cacctactct ggctctatac   19020
cctacctaga tggaaccttt tacctcaacc acacctttaa gaaggtggcc attacctttg   19080
actcttctgt cagctggcct ggcaatgacc gcctgcttac ccccaacgag tttgaaatta   19140
agcgctcagt tgacggggag ggttacaacg ttgcccagtg taacatgacc aaagactggt   19200
tcctggtaca aatgctagct aactataaca ttggctacca gggcttctat atcccagaga   19260
gctacaagga ccgcatgtac tccttcttta gaaacttcca gcccatgagc cgtcaggtgg   19320
tggatgatac taaatacaag gactaccaac aggtgggcat cctacaccaa cacaacaact   19380
ctggatttgt tggctacctt gcccccacca tgcgcgaagg acaggcctac cctgctaact   19440
tcccctatcc gcttataggc aagaccgcag ttgacagcat tacccagaaa aagtttcttt   19500
gcgatcgcac cctttggcgc atcccattct ccagtaactt tatgtccatg ggcgcactca   19560
cagacctggg ccaaaacctt ctctacgcca actccgccca cgcgctagac atgactttg   19620 aggtggatcc catggacgag cccacccttc tttatgtttt gtttgaagtc tttgacgtgg   19680
tccgtgtgca ccagccgcac cgcggcgtca tcgaaaccgt gtacctgcgc acgcccttct   19740
cggccggcaa cgccacaaca taaagaagca agcaacatca acaacagctg ccgccatggg   19800
ctccagtgag caggaactga aagccattgt caaagatctt ggttgtgggc catattttt   19860 gggcacctat gacaagcgct ttccaggctt tgtttctcca cacaagctcg cctgcgccat   19920
agtcaatacg gccggtcgcg agactggggg cgtacactgg atggcctttg cctggaaccc   19980
gcactcaaaa acatgctacc tctttgagcc ctttggcttt tctgaccagc gactcaagca   20040
ggtttaccag tttgagtacg agtcactcct gcgccgtagc gccattgctt cttcccccga   20100
ccgctgtata acgctggaaa agtccaccca aagcgtacag gggcccaact cggccgcctg   20160
tggactattc tgctgcatgt ttctccacgc ctttgccaac tggcccccaaa ctcccatgga   20220 tcacaaccc accatgaacc ttattaccgg ggtacccaac tccatgctca acagtcccca   20280
ggtacagccc accctgcgtc gcaaccagga acagctctac agcttcctgg agcgccactc   20340
gccctacttc cgcagccaca gtgcgcagat taggagcgcc acttcttttt gtcacttgaa   20400
aaacatgtaa aaataatgta ctagagacac tttcaataaa ggcaaatgct tttatttgta   20460
cactctcggg tgattattta ccccccaccct tgccgtctgc gccgtttaaa aatcaaaggg   20520
gttctgccgc gcatcgctat gcgccactgg cagggacacg ttgcgatact ggtgtttagt   20580
gctccactta aactcaggca caaccatccg cggcagctcg gtgaagtttt cactccacag   20640
gctgcgcacc atcaccaacg cgtttagcag gtcgggcgcc gatatcttga agtcgcagtt   20700
ggggcctccg ccctgcgcgc gcgagttgcg atacacaggg ttgcagcact ggaacactat   20760
cagcgccggg tggtgcacgc tggccagcac gctcttgtcg gagatcagat ccgcgtccag   20820
gtcctccgcg ttgctcaggg cgaacggagt caactttggt agctgccttc ccaaaaaggg   20880
cgcgtgccca ggctttgagt tgcactcgca ccgtagtggc atcaaaaggt gaccgtgccc   20940
ggtctgggcg ttaggataca gcgcctgcat aaaagccttg atctgcttaa agccaccctg   21000
agcctttgcg ccttcagaga agaacatgcc gcaagacttg ccggaaaact gattggccgg   21060
acaggccgcg tcgtgcacgc agcaccttgc gtcggtgttg gagatctgca ccacatttcg   21120
gccccaccgg ttcttcacga tcttggcctt gctagactgc tccttcagcg cgcgctgccc   21180
gttttcgctc gtcacatcca tttcaatcac gtgctcctta tttatcataa tgcttccgtg   21240
tagacactta agctcgcctt cgatctcagc gcagcggtgc agcacaacg cgcagcccgt   21300 gggctcgtga tgcttgtagg tcacctctgc aaacgactgc aggtacgcct gcaggaatcg   21360
```

```
ccccatcatc gtcacaaagg tcttgttgct ggtgaaggtc agctgcaacc cgcggtgctc   21420
ctcgttcagc caggtcttgc atacggccgc cagagcttcc acttggtcag gcagtagttt   21480
gaagttcgcc tttagatcgt tatccacgtg gtacttgtcc atcagcgcgc gcgcagcctc   21540
catgcccttc tcccacgcag acacgatcgg cacactcagc gggttcatca ccgtaatttc   21600
actttccgct tcgctgggct cttcctcttc ctcttgcgtc cgcataccac gcgccactgg   21660
gtcgtcttca ttcagccgcc gcactgtgcg cttacctcct tgccatgct tgattagcac    21720 cggtgggttg ctgaaaccca ccatttgtag cgccacatct tctctttctt cctcgctgtc   21780
cacgattacc tctggtgatg gcgggcgctc gggcttggga gaagggcgct tcttttcctt   21840
cttgggcgca atggccaaat ccgccgccga ggtcgatggc cgcgggctgg gtgtgcgcgg   21900
caccagcgcg tcttgtgatg agtcttcctc gtcctcggac tcgatacgcc gcctcatccg   21960
cttttttggg ggcgcccggg gaggcggcgg cgacggggac ggggacgaca cgtcctccat   22020
ggttggggga cgtcgcgccg caccgcgtcc gcgctcgggg gtggtttcgc gctgctcctc   22080
ttcccgactg gccatttcct tctcctatag gcagaaaaag atcatggagt cagtcgagaa   22140
gaaggacagc ctaaccgccc cctctgagtt cgccaccacc gcctccaccg atgccgccaa   22200
cgcgcctacc accttccccg tcgaggcacc cccgcttgag gaggaggaag tgattatcga   22260
gcaggaccca ggttttgtaa gcgaagacga cgaggaccgc tcagtaccaa cagaggataa   22320
aaagcaagac caggacaacg cagaggcaaa cgaggaacaa gtcgggcggg gggacgaaag   22380
gcatggcgac tacctagatg tgggagacga cgtgctgttg aagcatctgc agcgccagtg   22440
cgccattatc tgcgacgcgt tgcaagagcg cagcgatgtg cccctcgcca tagcggatgt   22500
cagccttgcc tacgaacgcc acctattctc accgcgcgta ccccccaaac gccaagaaaa   22560
cggcacatgc gagcccaacc cgcgcctcaa cttctacccc gtatttgccg tgccagaggt   22620
gcttgccacc tatcacatct ttttccaaaa ctgcaagata cccctatcct gccgtgccaa   22680
ccgcagccga gcggacaagc agctggcctt gcggcagggc gctgtcatac ctgatatcgc   22740
ctcgctcaac gaagtgccaa aaatctttga gggtcttgga cgcgacgaga agcgcgcggc   22800
aaacgctctg caacaggaaa acagcgaaaa tgaaagtcac tctggagtgt tggtggaact   22860
cgagggtgac aacgcgcgcc tagccgtact aaaacgcagc atcgaggtca cccactttgc   22920
ctacccggca cttaacctac cccccaaggt catgagcaca gtcatgagtg agctgatcgt   22980
gcgccgtgcg cagcccctgg agagggatgc aaatttgcaa gaacaaacag aggagggcct   23040
acccgcagtt ggcgacgagc agctagcgcg ctggcttcaa acgcgcgagc ctgccgactt   23100
ggaggagcga cgcaaactaa tgatggccgc agtgctcgtt accgtggagc ttgagtgcat   23160
gcagcggttc tttgctgacc cggagatgca gcgcaagcta gaggaaacat tgcactacac   23220
cttttgacag ggctacgtac gccaggcctg caagatctcc aacgtggagc tctgcaacct   23280
ggtctcctac cttggaattt tgcacgaaaa ccgccttggg caaaacgtgc ttcattccac   23340
gctcaagggc gaggcgcgcc gcgactacgt ccgcgactgc gtttacttat ttctatgcta   23400
cacctggcag acggccatgg gcgtttggca gcagtgcttg gaggagtgca acctcaagga   23460
gctgcagaaa ctgctaaagc aaaacttgaa ggacctatgg acggccttca acgagcgctc   23520
cgtggccgcg cacctggcgg acatcatttt ccccgaacgc ctgcttaaaa ccctgcaaca   23580
gggtctgcca gacttcacca gtcaaagcat gttgcagaac tttaggaact ttatcctaga   23640
gcgctcagga atcttgcccg ccacctgctg tgcacttcct agcgactttg tgcccattaa   23700
```

```
gtaccgcgaa tgccctccgc cgctttgggg ccactgctac cttctgcagc tagccaacta   23760
ccttgcctac cactctgaca taatggaaga cgtgagcggt gacggtctac tggagtgtca   23820
ctgtcgctgc aacctatgca ccccgcaccg ctccctggtt tgcaattcgc agctgcttaa   23880
cgaaagtcaa attatcggta cctttgagct gcagggtccc tcgcctgacg aaaagtccgc   23940
ggctccgggg ttgaaactca ctccggggct gtggacgtcg gcttaccttc gcaaatttgt   24000
acctgaggac taccacgccc acgagattag gttctacgaa gaccaatccc gcccgcctaa   24060
tgcggagctt accgcctgcg tcattaccca gggccacatt cttggccaat gcaagccat    24120 caacaaagcc cgccaagagt ttctgctacg aaagggacgg ggggtttact tggaccccca   24180
gtccggcgag gagctcaacc caatcccccc gccgccgcag ccctatcagc agcagccgcg   24240
ggcccttgct tcccaggatg gcacccaaaa agaagctgca gctgccgccg ccacccacgg   24300
acgaggagga atactgggac agtcaggcag aggaggtttt ggacgaggag gaggaggaca   24360
tgatggaaga ctgggagagc ctagacgagg aagcttccga ggtcgaagag gtgtcagacg   24420
aaacaccgtc accctcggtc gcattcccct cgccggcgcc ccagaaatcg gcaaccggtt   24480
ccagcatggc tacaacctcc gctcctcagg cgccgccggc actgcccgtt cgccgaccca   24540
accgtagatg ggacaccact ggaaccaggg ccggtaagtc caagcagccg ccgccgttag   24600
cccaagagca acaacagcgc caaggctacc gctcatggcg cgggcacaag aacgccatag   24660
ttgcttgctt gcaagactgt gggggcaaca tctccttcgc ccgccgcttt cttctctacc   24720
atcacggcgt ggccttcccc cgtaacatcc tgcattacta ccgtcatctc tacagcccat   24780
actgcaccgg cggcagcggc agcaacagca gcggccacac agaagcaaag gcgaccggat   24840
agcaagactc tgacaaagcc caagaaatcc acagcggcgg cagcagcagg aggaggagcg   24900
ctgcgtctgg cgcccaacga acccgtatcg acccgcgagc ttagaaacag gattttcccc   24960
actctgtatg ctatatttca acagagcagg ggccaagaac aagagctgaa aataaaaaac   25020
aggtctctgc gatccctcac ccgcagctgc ctgtatcaca aaagcgaaga tcagcttcgg   25080
cgcacgctgg aagacgcgga ggctctcttc agtaaatact gcgcgctgac tcttaaggac   25140
tagtttcgcg ccctttctca aatttaagcg cgaaaactac gtcatctcca gcggccacac   25200
ccggcgccag cacctgttgt cagcgccatt atgagcaagg aaattcccac gccctacatg   25260
tggagttacc agccacaaat gggacttgcg gctggagctg cccaagacta ctcaacccga   25320
ataaactaca tgagcgcggg accccacatg atatcccggg tcaacggaat acgcgcccac   25380
cgaaaccgaa ttctcctgga acaggcggct attaccacca cacctcgtaa taaccttaat   25440
ccccgtagtt ggcccgctgc cctggtgtac caggaaagtc ccgctcccac cactgtggta   25500
cttcccagag acgcccaggc cgaagttcag atgactaact caggggcgca gcttgcgggc   25560
ggctttcgtc acagggtgcg gtcgcccggg cagggtataa ctcacctgac aatcagaggg   25620
cgaggtattc agctcaacga cgagtcggtg agctcctcgc ttggtctccg tccggacggg   25680
acatttcaga tcgcggcgc cggccgctct tcattcacgc ctcgtcaggc aatcctaact   25740
ctgcagacct cgtcctctga gccgcgctct ggaggcattg gaactctgca atttattgag   25800
gagtttgtgc catcggtcta ctttaacccc ttctcgggac ctcccggcca ctatccggat   25860
caatttattc ctaactttga cgcggtaaag gactcggcgg acggctacga ctgaatgtta   25920
agtggagagg cagagcaact gcgcctgaaa cacctggtcc actgtcgccg ccacaagtgc   25980
tttgcccgcg actccggtga gttttgctac tttgaattgc ccgaggatca tatcgagggc   26040
ccggcgcacg gcgtccggct taccgcccag ggagagcttg cccgtagcct gattcgggag   26100
```

```
tttacccagc gcccctgct agttgagcgg gacagggac cctgtgttct cactgtgatt  26160
tgcaactgtc ctaaccctgg attacatcaa gatcctctag ttaatgtcag gtcgcctaag  26220
tcgattaact agagtacccg gggatcttat tcccttaac taataaaaaa aaataataaa  26280
gcatcactta cttaaaatca gttagcaaat ttctgtccag tttattcagc agcacctcct  26340
tgccctcctc ccagctctgg tattgcagct tcctcctggc tgcaaactt ctccacaatc  26400
taaatggaat gtcagtttcc tcctgttcct gtccatccgc acccactatc ttcatgttgt  26460
tgcagatgaa gcgcgcaaga ccgtctgaag ataccttcaa ccccgtgtat ccatatgaca  26520
cggaaaccgg tcctccaact gtgccttttc ttactcctcc ctttgtatcc cccaatgggt  26580
ttcaagagag tccccctggg gtactctctt tgcgcctatc cgaacctcta gttacctcca  26640
atggcatgct tgcgctcaaa atgggcaacg gcctctctct ggacgaggcc ggcaaccta  26700
cctcccaaaa tgtaaccact gtgagcccac ctctcaaaaa aaccaagtca acataaacc  26760
tggaaatatc tgcaccctc acagttacct cagaagccct aactgtggct gccgccgcac  26820
ctctaatggt cgcgggcaac acactcacca tgcaatcaca ggccccgcta accgtgcacg  26880
actccaaact tagcattgcc acccaaggac ccctcacagt gtcagaagga aagctagccc  26940
tgcaaacatc aggccccctc accaccaccg atagcagtac ccttactatc actgcctcac  27000
ccctctaac tactgccact ggtagcttgg gcattgactt gaagagccc atttatacac  27060
aaaatggaaa actaggacta aagtacgggg ctcctttgca tgtaacagac gacctaaaca  27120
ctttgaccgt agcaactggt ccaggtgtga ctattaataa tacttccttg caaactaag  27180
ttactggagc cttggttttt gattcacaag gcaatatgca acttaatgta gcaggaggac  27240
taaggattga ttctcaaaac agacgcctta tacttgatgt tagttatccg tttgatgctc  27300
aaaaccaact aaatctaaga ctaggacagg gccctctttt tataaactca gcccacaact  27360
tggatattaa ctacaacaaa ggcctttact tgttacagc ttcaaacaat tccaaaaagc  27420
ttgaggttaa cctaagcact gccaaggggt tgatgtttga cgctacagcc atagccatta  27480
atgcaggaga tgggcttgaa tttggttcac ctaatgcacc aaacacaaat ccctcaaaa  27540
caaaaattgg ccatggccta gaatttgatt caaacaaggc tatggttcct aaactaggaa  27600
ctggccttag ttttgacagc acaggtgcca ttacagtagg aaacaaaaat aatgataagc  27660
taactttgtg gaccacacca gctccatctc ctaactgtag actaaatgca gagaaagatg  27720
ctaaactcac tttggtctta acaaaatgtg gcagtcaaat acttgctaca gtttcagttt  27780
tggctgttaa aggcagtttg gctccaatat ctggaacagt tcaaagtgct catcttatta  27840
taagatttga cgaaaatgga gtgctactaa acaattcctt cctgacccca gaatattgga  27900
actttagaaa tggagatctt actgaaggca cagcctatac aaacgctgtt ggatttatgc  27960
ctaacctatc agcttatcca aaatctcacg gtaaaactgc caaaagtaac attgtcagtc  28020
aagtttactt aaacggagac aaaactaaac ctgtaacact aaccattaca ctaaacggta  28080
cacaggaaac aggagacaca actccaagtg catactctat gtcatttca tgggactggt  28140
ctggccacaa ctacattaat gaaatatttg ccacatcctc ttacttttt tcatacattg  28200
cccaagaata aagaatcgtt tgtgttatgt ttcaacgtgt ttattttca attgcagaaa  28260
atttcaagtc attttttcat cagtagtata gccccaccac cacatagctt atacagatca  28320
ccgtacctta atcaaactca cagaaccccta gtattcaacc tgccacctcc ctcccaacac  28380
acagagtaca cagtcctttc tccccggctg gccttaaaaa gcatcatatc atgggtaaca  28440
```

```
gacatattct taggtgttat attccacacg gtttcctgtc gagccaaacg ctcatcagtg   28500
atattaataa actccccggg cagctcactt aagttcatgt cgctgtccag ctgctgagcc   28560
acaggctgct gtccaacttg cggttgctta acgggcggcg aaggagaagt ccacgcctac   28620 atggggtag agtcataatc gtgcatcagg atagggcggt ggtgctgcag cagcgcgcga   28680
ataaactgct gccgccgccg ctccgtcctg caggaataca acatggcagt ggtctcctca   28740
gcgatgattc gcaccgcccg cagcataagg cgccttgtcc tccgggcaca gcagcgcacc   28800
ctgatctcac ttaaatcagc acagtaactg cagcacagca ccacaatatt gttcaaaatc   28860
ccacagtgca aggcgctgta tccaaagctc atggcgggga ccacagaacc cacgtggcca   28920
tcataccaca agcgcaggta gattaagtgg cgacccctca taaacacgct ggacataaac   28980
attacctctt ttggcatgtt gtaattcacc acctcccggt accatataaa cctctgatta   29040
aacatggcgc catccaccac catcctaaac cagctggcca aaacctgccc gccggctata   29100
cactgcaggg aaccgggact ggaacaatga cagtggagag cccaggactc gtaaccatgg   29160
atcatcatgc tcgtcatgat atcaatgttg gcacaacaca ggcacacgtg catacacttc   29220
ctcaggatta caagctcctc ccgcgttaga accatatccc agggaacaac ccattcctga   29280
atcagcgtaa atcccacact gcagggaaga cctcgcacgt aactcacgtt gtgcattgtc   29340
aaagtgttac attcgggcag cagcggatga tcctccagta tggtagcgcg ggtttctgtc   29400
tcaaaaggag gtagacgatc cctactgtac ggagtgcgcc gagacaaccg agatcgtgtt   29460
ggtcgtagtg tcatgccaaa tggaacgccg gacgtagtca tatttcctga agcaaaacca   29520
ggtgcgggcg tgacaaacag atctgcgtct ccggtctcgc cgcttagatc gctctgtgta   29580
gtagttgtag tatatccact ctctcaaagc atccaggcgc ccctggcttc gggttctat    29640 gtaaactcct tcatgcgccg ctgccctgat aacatccacc accgcagaat aagccacacc   29700
cagccaacct acacattcgt tctgcgagtc acacacggga ggagcgggaa gagctggaag   29760
aaccatgttt tttttttat tccaaaagat tatccaaaac ctcaaaatga agatctatta    29820
agtgaacgcg ctcccctccg gtggcgtggt caaactctac agccaaagaa cagataatgg   29880
catttgtaag atgttgcaca atggcttcca aaaggcaaac ggccctcacg tccaagtgga   29940
cgtaaaggct aaacccttca gggtgaatct cctctataaa cattccagca ccttcaacca   30000
tgcccaaata attctcatct cgccaccttc tcaatatatc tctaagcaaa tcccgaatat   30060
taagtccggc cattgtaaaa atctgctcca gagcgccctc caccttcagc ctcaagcagc   30120
gaatcatgat tgcaaaaatt caggttcctc acagacctgt ataagattca aaagcggaac   30180
attaacaaaa ataccgcgat cccgtaggtc ccttcgcagg gccagctgaa cataatcgtg   30240
caggtctgca cggaccagcg cggccacttc ccgccaggga accatgacaa agaacccac    30300 actgattatg acacgcatac tcggagctat gctaaccagc gtagcccgga tgtaagcttg   30360
ttgcatgggc ggcgatataa aatgcaaggt gctgctcaaa aaatcaggca aagcctcgcg   30420
caaaaaagaa agcacatcgt agtcatgctc atgcagataa aggcaggtaa gctccggaac   30480
caccacagaa aaagacacca tttttctctc aaacatgtct gcgggtttct gcataaacac   30540
aaaataaaat aacaaaaaaa catttaaaca ttagaagcct gtcttacaac aggaaaaaca   30600
acccttataa gcataagacg gactacggcc atgccggcgt gaccgtaaaa aaactggtca   30660
ccgtgattaa aaagcaccac cgacagctcc tcggtcatgt ccggagtcat aatgtaagac   30720
tcggtaaaca catcaggttg attcacatcg gtcagtgcta aaaagcgacc gaaatagccc   30780
gggggaatac atacccgcag gcgtagagac aacattacag cccccatagg aggtataaca   30840
```

```
aaattaatag gagagaaaaa cacataaaca cctgaaaaac cctcctgcct aggcaaaata   30900
gcaccctccc gctccagaac aacatacagc gcttccacag cggcagccat aacagtcagc   30960
cttaccagta aaaagaaaa cctattaaaa aaacaccact cgacacggca ccagctcaat    31020
cagtcacagt gtaaaaaagg gccaagtgca gagcgagtat atataggact aaaaaatgac   31080
gtaacggtta aagtccacaa aaaacaccca gaaaaccgca cgcgaaccta cgcccagaaa   31140
cgaaagccaa aaaacccaca acttcctcaa atcgtcactt ccgttttccc acgttacgtc   31200
acttcccatt ttaagaaaac tacaattccc aacacataca agttactccg ccctaaaacc   31260
tacgtcaccc gccccgttcc cacgcccgc gccacgtcac aaactccacc ccctcattat    31320
catattggct tcaatccaaa ataaggtata ttattgatga t                       31361
```

<210> SEQ ID NO 21
<211> LENGTH: 410
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
                20                  25                  30

Glu Lys Gly Asp Pro Thr Glu Arg Glu Leu Arg Val Gly Leu Glu Glu
            35                  40                  45

Ser Glu Leu Trp Leu Arg Phe Lys Glu Leu Thr Asn Glu Met Ile Val
        50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
130                 135                 140

Lys Val Lys Leu Thr Asn Lys Leu Asn Gly Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Arg Ser Asp His Lys Glu Met Met Glu Glu Pro
        195                 200                 205

Gly Asp Ser Gln Gln Pro Gly Tyr Ser Gln Trp Gly Trp Leu Leu Pro
    210                 215                 220

Gly Thr Ser Thr Val Cys Pro Pro Ala Asn His Pro Gln Phe Gly
225                 230                 235                 240

Gly Ala Leu Ser Leu Pro Ser Thr His Ser Cys Asp Arg Tyr Pro Thr
                245                 250                 255

Leu Arg Ser His Arg Ser Ser Pro Tyr Pro Ser Pro Tyr Ala His Arg

```
                    260                 265                 270
Asn Asn Ser Pro Thr Tyr Ser Asp Asn Ser Pro Ala Cys Leu Ser Met
            275                 280                 285

Leu Gln Ser His Asp Asn Trp Ser Ser Leu Gly Met Pro Ala His Pro
    290                 295                 300

Ser Met Leu Pro Val Ser His Asn Ala Ser Pro Pro Thr Ser Ser Ser
305                 310                 315                 320

Gln Tyr Pro Ser Leu Trp Ser Val Ser Asn Gly Ala Val Thr Pro Gly
                325                 330                 335

Ser Gln Ala Ala Ala Val Ser Asn Gly Leu Gly Ala Gln Phe Phe Arg
            340                 345                 350

Gly Ser Pro Ala His Tyr Thr Pro Leu Thr His Pro Val Ser Ala Pro
        355                 360                 365

Ser Ser Ser Gly Ser Pro Leu Tyr Glu Gly Ala Ala Ala Ala Thr Asp
        370                 375                 380

Ile Val Asp Ser Gln Tyr Asp Ala Ala Ala Gln Gly Arg Leu Ile Ala
385                 390                 395                 400

Ser Trp Thr Pro Val Ser Pro Pro Ser Met
                405                 410

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Trp Leu Leu Pro Gly Thr Ser Thr Val
1               5

<210> SEQ ID NO 23
<211> LENGTH: 702
<212> TYPE: PRT
<213> ORGANISM: Homo sapiens

<400> SEQUENCE: 23

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
```

-continued

```
145                 150                 155                 160
Asp Ala Val Ala Phe Thr Cys Glu Pro Glu Thr Gln Asp Ala Thr Tyr
                    165                 170                 175

Leu Trp Trp Val Asn Asn Gln Ser Leu Pro Val Ser Pro Arg Leu Gln
                    180                 185                 190

Leu Ser Asn Gly Asn Arg Thr Leu Thr Leu Phe Asn Val Thr Arg Asn
                    195                 200                 205

Asp Thr Ala Ser Tyr Lys Cys Glu Thr Gln Asn Pro Val Ser Ala Arg
210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                    245                 250                 255

Leu Ser Cys His Ala Ala Ser Asn Pro Pro Ala Gln Tyr Ser Trp Phe
                    260                 265                 270

Val Asn Gly Thr Phe Gln Gln Ser Thr Gln Glu Leu Phe Ile Pro Asn
                    275                 280                 285

Ile Thr Val Asn Asn Ser Gly Ser Tyr Thr Cys Gln Ala His Asn Ser
                    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                    325                 330                 335

Asp Glu Asp Ala Val Ala Leu Thr Cys Glu Pro Glu Ile Gln Asn Thr
                    340                 345                 350

Thr Tyr Leu Trp Trp Val Asn Asn Gln Ser Leu Pro Val Ser Pro Arg
                    355                 360                 365

Leu Gln Leu Ser Asn Asp Asn Arg Thr Leu Thr Leu Leu Ser Val Thr
                    370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                    405                 410                 415

Asp Pro Thr Ile Ser Pro Ser Tyr Thr Tyr Tyr Arg Pro Gly Val Asn
                    420                 425                 430

Leu Ser Leu Ser Cys His Ala Ala Ser Asn Pro Pro Ala Gln Tyr Ser
                    435                 440                 445

Trp Leu Ile Asp Gly Asn Ile Gln Gln His Thr Gln Glu Leu Phe Ile
                    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                    485                 490                 495

Ser Ala Glu Leu Pro Lys Pro Ser Ile Ser Ser Asn Asn Ser Lys Pro
                    500                 505                 510

Val Glu Asp Lys Asp Ala Val Ala Phe Thr Cys Glu Pro Glu Ala Gln
                    515                 520                 525

Asn Thr Thr Tyr Leu Trp Trp Val Asn Gly Gln Ser Leu Pro Val Ser
                    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                    565                 570                 575
```

```
Val Ser Ala Asn Arg Ser Asp Pro Val Thr Leu Asp Val Leu Tyr Gly
            580                 585                 590
Pro Asp Thr Pro Ile Ile Ser Pro Pro Asp Ser Ser Tyr Leu Ser Gly
            595                 600                 605
Ala Asn Leu Asn Leu Ser Cys His Ser Ala Ser Asn Pro Ser Pro Gln
            610             615                 620
Tyr Ser Trp Arg Ile Asn Gly Ile Pro Gln Gln His Thr Gln Val Leu
625                 630                 635                 640
Phe Ile Ala Lys Ile Thr Pro Asn Asn Asn Gly Thr Tyr Ala Cys Phe
                645                 650                 655
Val Ser Asn Leu Ala Thr Gly Arg Asn Asn Ser Ile Val Lys Ser Ile
            660                 665                 670
Thr Val Ser Ala Ser Gly Thr Ser Pro Gly Leu Ser Ala Gly Ala Thr
            675                 680                 685
Val Gly Ile Met Ile Gly Val Leu Val Gly Val Ala Leu Ile
            690                 695                 700
```